US009969689B2

(12) United States Patent
Dixon et al.

(10) Patent No.: US 9,969,689 B2
(45) Date of Patent: May 15, 2018

(54) ARYL ETHERS AND USES THEREOF

(71) Applicant: Peloton Therapeutics, Inc., Dallas, TX (US)

(72) Inventors: Darryl David Dixon, Somerset, NJ (US); Jonas Grina, Coppell, TX (US); John A. Josey, Dallas, TX (US); James P. Rizzi, Irving, TX (US); Stephen T. Schlachter, Dallas, TX (US); Eli M. Wallace, Richardson, TX (US); Bin Wang, Dallas, TX (US); Paul Wehn, Dallas, TX (US); Rui Xu, Dallas, TX (US); Hanbiao Yang, Coppell, TX (US)

(73) Assignee: PELOTON THERAPEUTICS, INC., Dallas, TX (US)

( * ) Notice: Subject to any disclaimer, the term of this patent is extended or adjusted under 35 U.S.C. 154(b) by 0 days. days.

(21) Appl. No.: 15/439,308

(22) Filed: Feb. 22, 2017

(65) Prior Publication Data
US 2017/0217891 A1    Aug. 3, 2017

Related U.S. Application Data

(63) Continuation of application No. 14/905,776, filed as application No. PCT/US2014/054375 on Sep. 5, 2014.

(60) Provisional application No. 61/978,421, filed on Apr. 11, 2014, provisional application No. 61/875,674, filed on Sep. 9, 2013.

(51) Int. Cl.
C07C 43/29 (2006.01)
C07C 43/275 (2006.01)
A61K 31/09 (2006.01)
C07D 213/85 (2006.01)
C07C 317/22 (2006.01)
C07D 213/65 (2006.01)

(52) U.S. Cl.
CPC .......... *C07D 213/85* (2013.01); *C07C 317/22* (2013.01); *C07D 213/65* (2013.01); *A61K 31/09* (2013.01); *C07C 43/275* (2013.01); *C07C 43/29* (2013.01); C07C 2602/08 (2017.05)

(58) Field of Classification Search
CPC ........ C07C 43/29; C07C 43/275; A61K 31/09
See application file for complete search history.

(56) References Cited

U.S. PATENT DOCUMENTS

| | | |
|---|---|---|
| 4,214,103 A | 7/1980 | Garman et al. |
| 4,426,385 A | 1/1984 | Cain |
| 4,505,929 A | 3/1985 | Markley et al. |
| 4,665,097 A | 5/1987 | Cain |
| 5,059,609 A | 10/1991 | Eggler et al. |
| 2005/0070474 A1 | 3/2005 | Krissansen et al. |
| 2005/0085541 A1 | 4/2005 | Shiohara et al. |
| 2006/0058361 A1 | 3/2006 | Fliri et al. |
| 2006/0128790 A1 | 6/2006 | Chu et al. |
| 2007/0088053 A1 | 4/2007 | Mirzadegan et al. |
| 2007/0155726 A1 | 7/2007 | Arnaiz et al. |
| 2007/0244071 A1 | 10/2007 | Dennis et al. |
| 2008/0312313 A1 | 12/2008 | Carballido et al. |
| 2009/0286812 A1 | 11/2009 | Erickson et al. |
| 2009/0325961 A1 | 12/2009 | Duan et al. |
| 2010/0029694 A1 | 2/2010 | Herold et al. |
| 2010/0048537 A1 | 2/2010 | Matsuoka et al. |
| 2010/0168110 A1 | 7/2010 | Chhipa et al. |
| 2011/0054173 A1 | 3/2011 | Brewster et al. |
| 2012/0295937 A1 | 11/2012 | Linehan et al. |
| 2013/0116275 A1 | 5/2013 | Van et al. |
| 2013/0137746 A1 | 5/2013 | Govek et al. |
| 2014/0073634 A1 | 3/2014 | Jones et al. |
| 2014/0148462 A1 | 5/2014 | Eckhardt et al. |
| 2014/0163025 A1 | 6/2014 | Eckhardt et al. |
| 2014/0200218 A1 | 7/2014 | Bellingham et al. |
| 2014/0371319 A1 | 12/2014 | Kazuta et al. |
| 2016/0250216 A1 | 9/2016 | Bruick et al. |
| 2016/0251307 A1 | 9/2016 | Dixon et al. |
| 2016/0362390 A1 | 12/2016 | Wehn et al. |
| 2016/0368893 A1 | 12/2016 | Dixon et al. |
| 2017/0217892 A1 | 8/2017 | Dixon et al. |

FOREIGN PATENT DOCUMENTS

| | | |
|---|---|---|
| CN | 101058535 A | 10/2007 |
| DE | 705530 C | 4/1941 |
| DE | 3239449 A1 | 5/1983 |
| DE | 3209878 A1 | 9/1983 |
| EP | 0027555 A1 | 4/1981 |
| FR | 1574139 A | 7/1969 |
| GB | 2017087 A | 10/1979 |
| JP | S58124758 A | 7/1983 |

(Continued)

OTHER PUBLICATIONS

Akincioglu, et al. Novel sulfamides as potential carbonic anhydrase isoenzymes inhibitors. Bioorg Med Chem. Mar. 15, 2013;21(6):1379-85. doi: 10.1016/j.bmc.2013.01.019. Epub Jan. 22, 2013.

Bertout, et al. HIF2alpha inhibition promotes p53 pathway activity, tumor cell death, and radiation responses. Proc Natl Acad Sci U S A. Aug. 25, 2009;106(34):14391-6. doi: 10.1073/pnas.0907357106. Epub Aug. 12, 2009.

Bhatt, et al. Hypoxia-inducible factor-2alpha: effect on radiation sensitivity and differential regulation by an mTOR inhibitor. BJU Int. Aug. 2008;102(3):358-63. doi: 10.1111/j.1464-410X.2008. 07558.x. Epub Apr. 3, 2008.

(Continued)

*Primary Examiner* — Theodore R. West
(74) *Attorney, Agent, or Firm* — Wilson Sonsini Goodrich & Rosati

(57) ABSTRACT

The present disclosure relates to HIF-2α inhibitors and methods of making and using them for treating cancer. Certain compounds were potent in HIF-2α scintillation proximity assay, luciferase assay, and VEGF ELISA assay, and led to tumor size reduction and regression in 786-O xenograft bearing mice in vivo.

20 Claims, 10 Drawing Sheets

(56) References Cited

FOREIGN PATENT DOCUMENTS

| JP | S6351363 A | 3/1988 |
|---|---|---|
| WO | WO-9324434 A1 | 12/1993 |
| WO | WO-9842671 A1 | 10/1998 |
| WO | WO-0116097 A1 | 3/2001 |
| WO | WO-2006027684 A1 | 3/2006 |
| WO | WO-2006083781 A1 | 8/2006 |
| WO | WO-2006125972 A1 | 11/2006 |
| WO | WO-2007071441 A1 | 6/2007 |
| WO | WO-2007099423 A1 | 9/2007 |
| WO | WO-2009093133 A1 | 7/2009 |
| WO | WO-2010068794 A2 | 6/2010 |
| WO | WO-2010103438 A1 | 9/2010 |
| WO | WO-2010137620 A1 | 12/2010 |
| WO | WO-2010141956 A2 | 12/2010 |
| WO | WO-2011105603 A1 | 9/2011 |
| WO | WO-2012123129 A1 | 9/2012 |
| WO | WO-2012170442 A1 | 12/2012 |
| WO | WO-2013011033 A1 | 1/2013 |
| WO | WO-2013040863 A1 | 3/2013 |
| WO | WO-2013057101 A1 | 4/2013 |
| WO | WO-2013064984 A1 | 5/2013 |
| WO | WO-2013110433 A1 | 8/2013 |
| WO | WO-2013133325 A1 | 9/2013 |
| WO | WO-2014078479 A2 | 5/2014 |
| WO | WO-2015035223 A1 | 3/2015 |

OTHER PUBLICATIONS

Cardoso, et al. Identification of Cys255 in HIF-1α as a novel site for development of covalent inhibitors of HIF-1a/ARNT PasB domain protein-protein interaction. Protein Sci. Dec. 2012;21(12):1885-96. doi: 10.1002/pro.2172. Epub Nov. 9, 2012.

Carew, et al. ELR510444 inhibits tumor growth and angiogenesis by abrogating HIF activity and disrupting microtubules in renal cell carcinoma. PLoS One. 2012;7(1):e31120. doi: 10.1371/journal.pone.0031120. Epub Jan. 25, 2012.

CAS Registry No. 81614-92-8 (Nov. 1984).

Giatromanolaki, et al. Relation of hypoxia inducible factor 1 alpha and 2 alpha in operable non-small cell lung cancer to angiogenic/molecular profile of tumours and survival. Br J Cancer. Sep. 14, 2001;85(6):881-90.

Gordon, et al. HIF-2alpha promotes hypoxic cell proliferation by enhancing c-myc transcriptional activity. Cancer Cell. Apr. 2007;11(4):335-47.

He, et al. Downregulating hypoxia-inducible factor-2α improves the efficacy of doxorubicin in the treatment of hepatocellular carcinoma. Cancer Sci. Mar. 2012;103(3):528-34. doi: 10.1111/j.1349-7006.2011.02177.x. Epub Jan. 13, 2012.

Holmquist-Mengelbier, et al. Recruitment of HIF-1alpha and HIF-2alpha to common target genes is differentially regulated in neuroblastoma: HIF-2alpha promotes an aggressive phenotype. Cancer Cell. Nov. 2006;10(5):413-23.

Hu, et al. Differential roles of hypoxia-inducible factor 1alpha (HIF-1alpha) and HIF-2alpha in hypoxic gene regulation. Mol Cell Biol. Dec. 2003;23(24):9361-74.

International search report and written opinion dated Jan. 27, 2015 for PCT/US2014/054375.

International search report and written opinion dated Apr. 15, 2015 for PCT/US2014/070346.

International search report and written opinion dated May 12, 2016 for PCT/US2016/021060.

International search report and written opinion dated May 17, 2016 for PCT/US2016/021846.

International search report and written opinion dated May 20, 2016 for PCT/US2016/021061.

International search report and written opinion dated May 31, 2016 for PCT/US2016/021492.

International search report and written opinion dated Jun. 20, 2016 for PCT/US2016/021510.

International search report and written opinion dated Jul. 26, 2016 for PCT/US2016/027611.

Karoor, et al. Alveolar hypoxia promotes murine lung tumor growth through a VEGFR-2/EGFR-dependent mechanism. Cancer Prev Res (Phila). Aug. 2012;5(8):1061-71. doi: 10.1158/1940-6207.CAPR-12-0069-T. Epub Jun. 14, 2012.

Keith, et al. HIF1α and HIF2α: sibling rivalry in hypoxic tumour growth and progression. Nat Rev Cancer. Dec. 15, 2011;12(1):9-22. doi: 10.1038/nrc3183.

Key, et al. Principles of ligand binding within a completely buried cavity in HIF2alpha PAS-B. J Am Chem Soc. Dec. 9, 2009;131(48):17647-54. doi: 10.1021/ja9073062.

Kim, et al. HIF2alpha cooperates with RAS to promote lung tumorigenesis in mice. J Clin Invest. Aug. 2009;119(8):2160-70.

King, F.D., Biososteres, Conformational restriction, and pro-drugs-case history: An example of a conformational restriction approach. Med. Chem., Principle and Practice (1994), pp. 206-208.

Kondo, et a. Inhibition of HIF2alpha is sufficient to suppress pVHL-defective tumor growth. PLoS Biol. Dec. 2003;1(3):E83, 439-444. Epub Dec. 22, 2003.

Kondo, et al. Inhibition of HIF is necessary for tumor suppression by the von Hippel-Lindau protein. Cancer Cell. Apr. 2002;1(3):237-46.

Koshiji, et al. HIF-1alpha induces cell cycle arrest by functionally counteracting Myc. EMBO J. May 5, 2004;23(9):1949-56. Epub Apr. 8, 2004.

Lee, et al. Acriflavine inhibits HIF-1 dimerization, tumor growth, and vascularization. Proc Natl Acad Sci U S A. Oct. 20, 2009;106(42)17910-5. doi: 10.1073/pnas.0909353106. Epub Oct. 1, 2009.

Li, et al. Hypoxia-inducible factors regulate tumorigenic capacity of glioma stem cells. Cancer Cell. Jun. 2, 2009;15(6):501-13. doi: 10.1016/j.ccr.2009.03.018.

Maher, et al. von Hippel-Lindau disease: a clinical and scientific review. Eur J Hum Genet. Jun. 2011;19(6):617-23. doi: 10.1038/ejhg.2010.175. Epub Mar. 9, 2011.

Mandriota, et al. HIF activation identifies early lesions in VHL kidneys: evidence for site-specific tumor suppressor function in the nephron. Cancer Cell. Jun. 2002;1(5):459-68.

Maranchie, et al. The contribution of VHL substrate binding and HIF1-alpha to the phenotype of VHL loss in renal cell carcinoma. Cancer Cell. Apr. 2002;1(3):247-55.

Mazumdar, et al. HIF-2alpha deletion promotes Kras-driven lung tumor development. Proc Natl Acad Sci U S A. Aug. 10, 2010;107(32):14182-7. doi: 10.1073/pnas.1001296107. Epub Jul. 21, 2010.

Miranda, et al. A cyclic peptide inhibitor of HIF-1 heterodimerization that inhibits hypoxia signaling in cancer cells. J Am Chem Soc. Jul. 17, 2013;135(28):10418-25. doi: 10.1021/ja402993u. Epub Jul. 9, 2013.

Morrison and Boyd, Isotope Effects. Org. Chem., 3rd ed., (1974), pp. 353-356.

Nguyen, et al. Epigenetic regulation of hypoxia inducible factor in diseases and therapeutics. Arch Pharm Res. Mar. 2013;36(3):252-63. doi: 10.1007/s12272-013-0058-x. Epub Feb. 26, 2013.

Office Action dated Nov. 21, 2016 for US Appl. No. 15/037,047.

Office Action dated Dec. 16, 2016 for U.S. Appl. No. 14/905,776.

Owens, et al. Smooth muscle cell hypertrophy versus hyperplasia in hypertension. Proc Natl Acad Sci U S A. Dec. 1981;78(12):7759-63.

Percy, et al. A gain-of-function mutation in the HIF2A gene in familial erythrocytosis. N Engl J Med. Jan. 10, 2008;358(2):162-8. doi: 10.1056/NEJMoa073123.

Percy, et al. Two new mutations in the HIF2A gene associated with erythrocytosis. Am J Hematol. Apr. 2012;87(4):439-42. doi: 10.1002/ajh.23123. Epub Feb. 24, 2012.

PubChem. Compound Summary for CID 21110550. 1-10. Create Date: Dec. 5, 2007 [retrieved on Jan. 20, 2015]. Retrieved from the Internet.< URL:http://pubchem.ncbi.nlm.nih.gov/compound/21110550>. entire document.

PubChem. Compound Summary for CID 825455. 1-11. Create Date: Jul. 9, 2005. [retrieved on Jan. 20, 2015]. Retrieved from the Internet.<URL:http://pubchem.ncbi.nlm.nih.gov/compound/825455>. entire document.

(56) References Cited

OTHER PUBLICATIONS

Raval, et al. Contrasting properties of hypoxia-inducible factor 1 (HIF-1) and HIF-2 in von Hippel-Lindau-associated renal cell carcinoma. Mol Cell Biol. Jul. 2005;25(13):5675-86.
Rogers, et al. Development of inhibitors of the PAS-B domain of the HIF-2α transcription factor. J Med Chem. Feb. 28, 2013;56(4):1739-47. doi: 10.1021/jm301847z. Epub Feb. 18, 2013.
Sakairi, et al. Synthesis and SAR studies of bicyclic amine series GPR119 agonists. Bioorganic & Medicinal Chemistry Letters. 2012; 22:5123-5128.
Scheuermann, et al. Allosteric inhibition of hypoxia inducible factor-2 with small molecules. Nat Chem Biol. Apr. 2013;9(4):271-6. doi: 10.1038/nchembio.1185. Epub Feb. 24, 2013.
Scheuermann, et al. Artificial ligand binding within the HIF2alpha Pas-B domain of the HIF2 transcription factor. Proc Natl Acad Sci U S A. Jan. 13, 2009;106(2):450-5. doi: 10.1073/pnas.0808092106. Epub Jan. 7, 2009.
Semenza. Hypoxia-inducible factors: mediators of cancer progression and targets for cancer therapy. Trends Pharmacol Sci. Apr. 2012;33(4):207-14. doi: 10.1016/j.tips.2012.01.005. Epub Mar. 6, 2012.
Shen, et al. The VHL/HIF axis in clear cell renal carcinoma. Semin Cancer Biol. Feb. 2013;23(1):18-25. doi: 10.1016/j.semcancer. 2012.06.001. Epub Jun. 13, 2012.
Song et al., Synthesis and Biochemical Evaluation of Thiochromanone Thiosemicarbazone Analogues as Inhibitors of Cathepsin L ACS Med. Chem. Lett.. (2012), vol. 3(6), pp. 450-453.
Talks, et al. The expression and distribution of the hypoxia-inducible factors HIF-1alpha and HIF-2alpha in normal human tissues, cancers, and tumor-associated macrophages. Am J Pathol. Aug. 2000;157(2):411-21.
Tan, et al. Identification of a novel small-molecule inhibitor of the hypoxia-inducible factor 1 pathway. Cancer Res. Jan. 15, 2005;65(2):605-12.
Vanharanta, et al. Epigenetic expansion of VHL-HIF signal output drives multiorgan metastasis in renal cancer. Nat Med. Jan. 2013;19(1):50-6. doi: 10.1038/nm.3029. Epub Dec. 9, 2012.
Xue, et al. Hypoxia-inducible factor-2α activation promotes colorectal cancer progression by dysregulating iron homeostasis. Cancer Res. May 1, 2012;72(9):2285-93. doi: 10.1158/0008-5472. CAN-11-3836. Epub Mar. 14, 2012.
Xue, et al. Hypoxia-inducible factor-2α is essential in activating the COX2/mPGES-1/PGE2 signaling axis in colon cancer. Carcinogenesis. Jan. 2013;34(1):163-9. doi: 10.1093/carcin/bgs313. Epub Oct. 5, 2012.

Zhuang, et al. Somatic HIF2A gain-of-function mutations in paraganglioma with polycythemia. N Engl J Med. Sep. 6, 2012;367(10):922-30. doi: 10.1056/NEJMoa1205119.
Zimmer, et al. Inhibition of hypoxia-inducible factor is sufficient for growth suppression of VHL-/-tumors. Mol Cancer Res. Feb. 2004;2(2):89-95.
Zimmer, et al. Small-molecule inhibitors of HIF-2a translation link its 5'UTR iron-responsive element to oxygen sensing. Mol Cell. Dec. 26, 2008;32(6):838-48. doi: 10.1016/j.molcel.2008.12.004.
CAS Registry No. 1050878-94-8 (Sep. 2008).
CAS Registry No. 1062399-04-05 (Oct. 2008).
CAS Registry No. 1090604-08-2 (Dec. 2008).
CAS Registry No. 1119387-77-7 (Mar. 2009).
CAS Registry No. 1147778-06-0 (May 2009).
CAS Registry No. 1386280-55-2 (Aug. 2012).
CAS Registry No. 879353-79-4 (Apr. 2006).
CAS Registry No. 903274-78-2 (Aug. 2006).
CAS Registry No. 950051-37-3 (Oct. 2007).
European Search Report dated Mar. 29, 2017 for EP Application No. 14871152.6.
Office Action dated Apr. 28, 2017 for U.S. Appl. No. 14/905,776.
Svensson, et al., Bromination of bicyclic phenols with SO2 heterocyclic annelated rings, ACTA Pharmaceutica Suecica, Royal Pharmaceutical Institute, Sweden, vol. 12, No. 5-6, Jan. 1, 1975: pp. 401-406.
CAS Registry No. 21081-71-0, Database Registry, Chemical Abstracts Services, [retrieved on Mar. 23, 2017], Published 1968.
Co-pending U.S. Appl. No. 15/439,494, filed Feb. 22, 2017.
European Search Report dated Mar. 8, 2017 for EP Application No. 14842085.4.
Lin, et al., Efficient in silico assay of inhibitors of hepatitis c virus RNA-dependent RNA polymerase by structure-based virtual screening and in vitro evaluation. Assay and drug development technologies. 9(3): Jun. 2011; pp. 290-298. XP55350132.
Notice of Allowance dated Apr. 6, 2017 for U.S. Appl. No. 15/177,166.
Office Action dated Mar. 24, 2017 for U.S. Appl. No. 15/037,047.
Co-pending U.S. Appl. No. 15/553,570, filed Aug. 24, 2017.
Co-pending U.S. Appl. No. 15/556,153, filed Sep. 6, 2017.
Co-pending U.S. Appl. No. 15/556,248, filed Sep. 6, 2017.
Co-pending U.S. Appl. No. 15/556,607, filed Sep. 7, 2017.
Co-pending U.S. Appl. No. 15/556,609, filed Sep. 7, 2017.
Co-pending U.S. Appl. No. 15/564,348, filed Oct. 4, 2017.
Notice of Allowance dated Sep. 7, 2017 for U.S. Appl. No. 15/177,166.
Office Action dated Aug. 16, 2017 for U.S. Appl. No. 15/037,047.
Office Action dated Sep. 8, 2017 for U.S. Appl. No. 14/905,776.

ARYL ETHERS AND USES THEREOF

The present application claims the benefit and is a Continuation Application of U.S. application Ser. No. 14/905,776, filed Jan. 15, 2016, which is a 371 of International Patent Application PCT/US2014/054375, filed Sep. 5, 2014, which claims priority to U.S. Provisional Application Ser. No. 61/875,674, filed Sep. 9, 2013, and 61/978,421, filed Apr. 11, 2014, the entire contents of each application being hereby incorporated by reference.

This invention was in part funded by a grant from Cancer Prevention Research Institute of Texas (Grant number R1009).

Intratumoral hypoxia is a driving force in cancer progression and is closely linked to poor patient prognosis and resistance to chemotherapy and radiation treatment. Progress over the past several decades in mapping the molecular mechanisms that enable cellular adaptation to chronic oxygen deprivation has intensified interest in identifying drugs that effectively block the hypoxic response pathway in tumors. Hypoxia-Inducible Factors (HIF-1α and HIF-2α) are transcription factors that play central roles in this pathway, and thus represent attractive targets for therapeutic intervention. The half-life of HIF-α proteins is tightly regulated by the oxidative status within the cell. Under normoxic conditions, specific proline residues on the HIF proteins are hydroxylated by the oxygen sensitive HIF-specific prolyl-hydroxylases (PHD). The tumor suppressor von Hippel-Lindau (VHL) protein binds to the specific hydroxylated proline residues and recruits E3 ubiquition-ligase complex that targets HIF-α proteins for proteasomal degradation. Because PHDs require oxygen to function, under hypoxic conditions, HIF-α proteins accumulate and enter the nucleus to activate gene expression. Genetic mutations of the VHL gene that result in loss of function lead to constitutively active HIF-α proteins regardless of oxygen levels. Upon activation, these transcription factors stimulate the expression of genes that coordinately regulate anaerobic metabolism, angiogenesis, cell proliferation, cell survival, extracellular matrix remodeling, pH homeostasis, amino acid and nucleotide metabolism, and genomic instability. While many gene products involved in the hypoxic response have been explored individually as therapeutic targets for cancer, broad inhibition of the pathway through direct targeting of HIF-α proteins offers an exciting opportunity to attack tumors on multiple fronts (Keith, et al. *Nature Rev. Cancer* 12: 9-22, 2012).

Both HIF-1α and HIF-2α form a dimeric complex with HIF-1β (or ARNT: aryl hydrocarbon receptor nuclear translocator) and subsequently bind to hypoxia response elements (HRE) in target genes. Because the level of HIF-1β is unaffected by oxygen levels or VHL, transcriptional activity of the complex is largely driven by the availability of the HIF-α proteins. While HIF-1α and HIF-2α share significant sequence homology, they differ in tissue distribution, sensitivity to hypoxia, timing of activation and target gene specificity (Hu, et al. *Mol. Cell Biol.* 23: 9361-9374, 2003 and Keith, et al. *Nature Rev. Cancer* 12: 9-22, 2012). Whereas HIF-1α mRNA is ubiquitously expressed, the expression of HIF-2α mRNA is found primarily in kidney fibroblasts, hepatocytes and intestinal lumen epithelial cells. Consistent with the tight regulation of the HIF-α proteins under normal physiology, neither is detected in normal tissue with the exception of HIF-2α in macrophages (Talks, et al. *Am. J. Pathol.* 157: 411-421, 2000). However, HIF-2α protein has been detected in various human tumors of the bladder, breast, colon, liver, ovaries, pancreas, prostate and kidney as well as tumor-associated macrophages (Talks, et al. *Am. J. Pathol.* 157: 411-421, 2000). HIF-1α has been reported to give a transient, acute transcriptional response to hypoxia while HIF-2α provides more prolonged transcriptional activity. Furthermore, HIF-2α has greater transcriptional activity than HIF-1α under moderately hypoxic conditions like those encountered in end capillaries (Holmquist-Mengelbier, et al. *Cancer Cell* 10: 413-423, 2006). Whereas some hypoxia-regulated genes are controlled by both HIF-1α and HIF-2α, some are only responsive to specific HIF-α proteins. For example, lactate dehydrogenase A (LDHA), phosphoglycerate kinase (PGK) and pyruvate dehydrogenase kinase 1 (PDK1) are uniquely controlled by HIF-1α whereas Oct-4 and erythropoietin (EPO) by HIF-2α. Often the relative contributions of the HIF-α proteins to gene transcription are cell type-, and disease-specific. More importantly, the HIF-α proteins may play contrasting roles in tumorigenesis. For example, the oncogene MYC is a transcription factor that controls cell cycle G1/S transition. MYC is overexpressed in 40% of human cancer. It has been shown that HIF-2α activity increases MYC transcription activity whereas HIF-1α inhibits MYC activity. As a result, in MYC driven tumors, HIF-2α inhibition reduced proliferation whereas HIF-1α inhibition increased growth (Gordan, et al. *Cancer Cell* 11: 335-347, 2007 and Koshiji et al. *EMBO J.* 23: 1949-1956, 2004).

Therefore, the identification of effective small molecules to modulate the activity of HIF-2α is desirable.

SUMMARY

In one aspect, the present disclosure provides a compound of Formula I

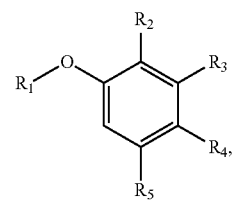

or a pharmaceutically acceptable salt thereof, wherein:

$R_1$ is aryl or heteroaryl;

$R_2$ is nitro, carboxaldehyde, carboxylic acid, ester, amido, cyano, halo, sulfonyl, alkyl or heteroalkyl;

$R_3$ is hydrogen, halo, cyano, alkyl, heteroalkyl, alkenyl, alkynyl, alkylamino, carboxaldehyde, carboxylic acid, oxime, ester, amido or acyl, or $R_2/R_3$ and atoms they are attached to form a 5- or 6-membered carbocycle with at least one $sp^3$ hybridized carbon;

$R_4$ is nitro, halo, cyano, alkyl, sulfinyl, sulfonamide, sulfonyl or sulfoximinyl; and $R_5$ is hydrogen, halo or alkyl.

In another aspect, the present disclosure provides a pharmaceutical composition comprising a compound described herein and a pharmaceutically acceptable carrier or excipient. The compound may exist in an amorphous form, a crystalline form, or as a salt, solvate or hydrate.

In another aspect, the present disclosure provides a method of treating renal cell carcinoma by administrating a therapeutically effective amount of a compound described herein or a pharmaceutical composition thereof to a subject in need of such treatment. In some embodiments, the subject is a human.

In another aspect, the present disclosure provides a method of inhibiting the activities of HIF-2α in a cell, comprising contacting the cell with an effective amount of a compound described herein.

In another aspect, the present disclosure provides a kit comprising a pharmaceutical composition comprising a compound described herein and a pharmaceutically acceptable carrier or excipient and an instruction for using the composition to treat a subject suffering from cancer. In some embodiments, the cancer is renal cell carcinoma.

BRIEF DESCRIPTION OF FIGURES

FIG. 1 shows that Compound 15 treatment of renal cell carcinoma 786-O xenograft bearing mice reduced the mRNA levels of HIF-2α and HIF-2α-regulated genes (PAI-1, CCND1, VEGFA, and GLUT1) in tumor. Compound 15 had no significant effect on the mRNA level of HIF-1α or non-HIF-2α-regulated genes (PGK1 and PDK1).

FIG. 2 shows that Compound 163 treatment of renal cell carcinoma 786-O xenograft bearing mice reduced the mRNA levels of HIF-2α and HIF-2α-regulated genes (PAI-1 and CCND1) in tumor. Compound 163 had no significant effect on the mRNA levels of HIF-1α and non-HIF-2α-regulated genes (PGK1 and PDK1).

FIG. 3 shows that Compound 15 treatment of 786-O xenograft bearing mice reduced HIF-2α-regulated EPO gene expression in mouse kidney, but had no significant effect on the expression of HIF-1α-regulated PGK1 gene.

FIG. 4 shows that Compound 15 treatment of 786-O xenograft bearing mice reduced the levels of HIF-2α and CyclinD1 proteins in tumor.

FIG. 5 shows that Compound 15 treatment of 786-0 xenograft bearing mice reduced the plasma level of human VEGFA.

FIG. 6 shows that Compound 163 treatment of 786-O xenograft bearing mice reduced the plasma level of human VEGFA.

FIG. 7 shows that Compound 15 treatment of 786-O xenograft bearing mice as a single agent led to tumor size reduction and regression.

FIG. 8 shows that Compound 163 treatment of 786-O xenograft bearing mice as a single agent led to tumor size reduction and regression.

DETAILED DESCRIPTION OF THE INVENTION

Figure 1:
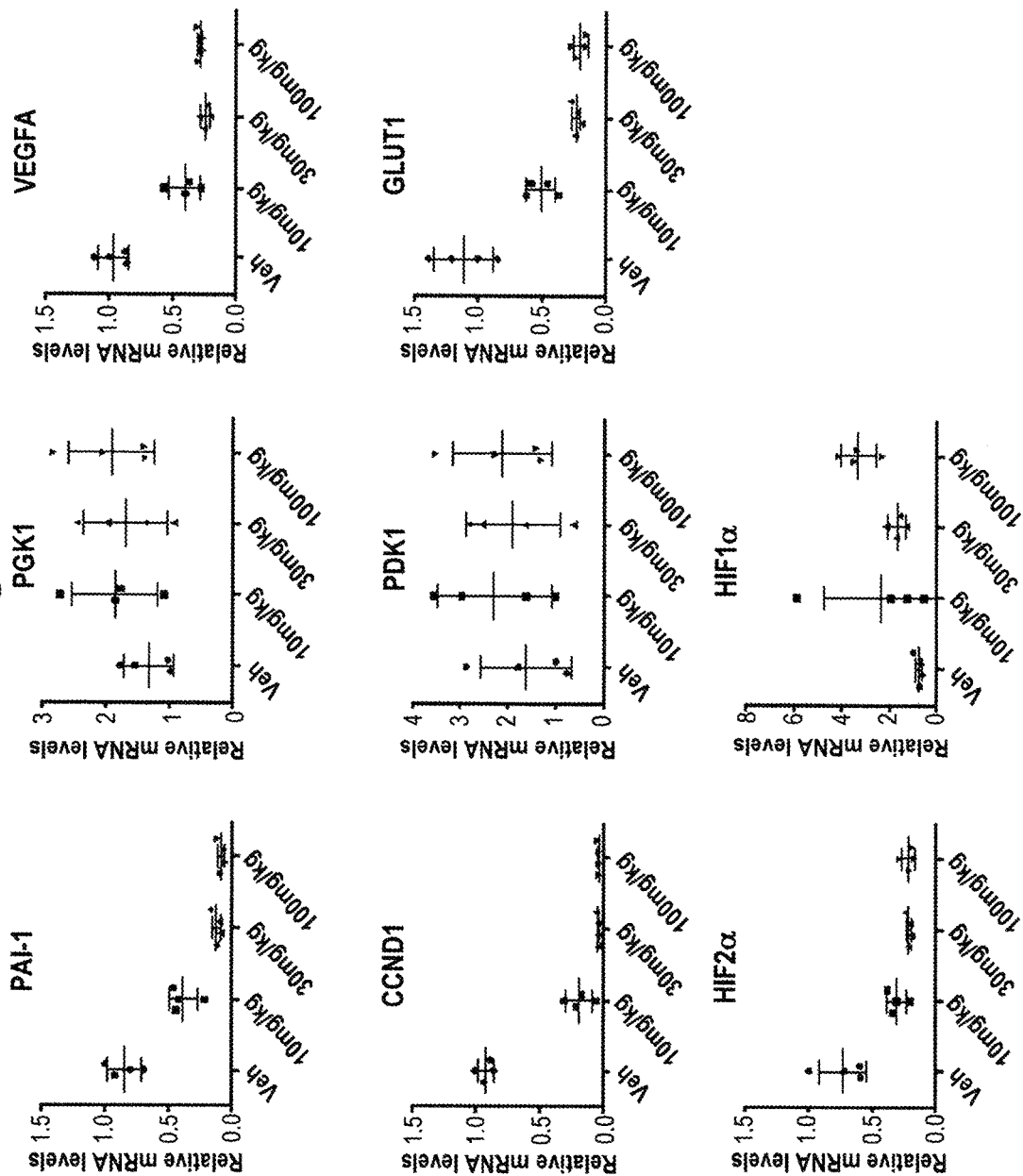
FIG. 1 shows treatment of renal cell carcinoma 786-O xenograft bearing mice at 0 mg/kg (denoted as "Veh"), 10 mg/kg, 30 mg/kg, and 100 mg/kg of Compound 15 three times each at 12 hour intervals.

For purposes of interpreting this disclosure, the following definitions will apply.

The term "HIF-2α" refers to a monomeric protein that contains several conserved structured domains: basic helix-loop-helix (bHLH), and two Per-ARNT-Sim (PAS) domains designated PAS-A and PAS-B, in addition to C-terminal regulatory regions. "HIF-2α" is also alternatively known by several other names in the scientific literature, including Endothelial PAS Domain Protein 1 (EPAS1), HIF2A, PASD2, HIF-2-Alpha, HIF2-Alpha, HLF, Hypoxia-Inducible Factor 2-Alpha, HIF-1alpha-Like Factor, and MOP2. As a member of the bHLH/PAS family of transcription factors, "HIF-2α" forms an active heterodimeric transcription factor complex by binding to the ARNT (also known as HIF-1β) protein through non-covalent interactions.

The term "subject" includes, but is not limited to, humans of any age group, e.g., a pediatric subject (e.g., infant, child or adolescent) or adult subject (e.g., young adult, middle-aged adult or senior adult)) and/or other primates (e.g., cynomolgus monkeys or rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

The term "scintillation proximity assay" (SPA) refers to a homogenous assay in which light is emitted when a radio-labeled ligand is brought into close proximity to a radio-sensitive bead. The assay typically contains a target protein that contains a tag (e.g., His Tag, Glutathione S-transferase Tag). The tag on the protein is used to bind the target protein to the scintillation bead. Radio-labeled ligand (e.g., labeled with tritium) that binds to the protein is now in close proximity to the bead, and when the radio-label (e.g., tritium) decays, the high energy particle hits the bead resulting in the emission of light that is detected by a detector, such as photomultiplier tube or CCD camera. When unlabeled ligands or compounds that bind to the protein are used in the assay, they displace the radio-labeled ligand, resulting in loss of signal. For a general reference describing the assay, see Park, et al. *Analytical Biochemistry* 269: 94-104, 1999.

HIF-2α activity as used herein has its ordinary meaning in the art. HIF-2α activity, for example, includes activation of gene transcription mediated by HIF-2α.

The term "inhibiting HIF-2α activity", as used herein, refers to slowing, reducing, altering, as well as completely eliminating and/or preventing HIF-2α activity.

As used herein, the terms "treatment", "treating", "palliating" and "ameliorating" are used interchangeably herein. These terms refer to an approach for obtaining beneficial or desired results including, but are not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compositions can be administered to a patient at risk of developing a particular disease, or to a patient reporting one or more of the physiological symptoms of a disease, even though a diagnosis of this disease may not have been made.

The term "alkyl" refers to a straight or branched hydrocarbon chain radical comprising carbon and hydrogen atoms, containing no unsaturation, and having from one to ten carbon atoms (i.e., C1-C10 alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a C1-C4 alkyl group. Typical alkyl groups include, but are in no way limited to, methyl, ethyl, n-propyl, isopropyl, n-butyl, isobutyl, sec-butyl, tert-butyl, pentyl, isopentyl, neopentyl, hexyl, septyl, and the like. The alkyl is attached to the rest of the molecule by a single bond. Unless stated otherwise specifically in the specification, an alkyl group is optionally substituted by one or more of the following substituents: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)—R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, heteroalkyl, cycloalkyl, heterocycloalkyl, aryl or heteroaryl.

The term "aromatic" or "aryl" refers to an aromatic radical with six to ten ring atoms (i.e., C6-C10 aromatic or C6-C10 aryl) which has at least one ring having a conjugated pi electron system which is carbocyclic (e.g., phenyl, fluorenyl, and naphthyl). Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently alkyl, heteroalkyl, alkenyl, allynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)—R$^a$, —OC(=O)OR$^a$, —OC(=O)N(R$^a$)$_2$, —N(R$^a$)$_2$, —C(=O)R$^a$, —C(=O)OR$^a$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$N(R$^a$)$_2$ (where t is 1 or 2), —N(R$^a$)S(=O)$_t$R$^a$ (where t is 1 or 2), —S(=O)$_t$R$^a$ (where t is 1 or 2), —S(=O)$_t$N(R$^a$)$_2$ (where t is 1 or 2), or —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, heteroalkyl, cycloalkyl, heterocycloalkyl, aryl or heteroaryl.

The term "heteroaryl" or, alternatively, "heteroaromatic" refers to a 5- to 18-membered aromatic radical (i.e., C5-C18 heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group may consist of 5 ring atoms, 6 ring atoms, etc., up to and including 18 ring atoms. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical, e.g., nitrogen or sulfur, is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl, benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7, 8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —SR$^a$, —OC(=O)—R$^a$, —OC(=O)OR$^a$, —N(R$^a$)$_2$, —C(=O)OR$^a$, —OC(=O)N(R$^a$)$_2$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, heteroalkyl, cyclolalkyl, heterocycloalkyl, aryl or heteroaryl. Examples of monocylic heteroaryls include, but are not limited to, imidazolyl, pyridinyl, pyrrolyl, pyrazinyl, pyrimidinyl, thiazolyl, furanyl and thienyl.

The term "acyl" refers to a —C(=O)R radical, wherein R is alkyl, cycloalkyl, aryl, heteroaryl, heteroalkyl, or heterocycloalkyl, which are as described herein. The R group is joined to the carbonyl through a carbon-carbon single bond. In some embodiments, it is a C1-C10 acyl radical which refers to the total number of chain or ring atoms of the alkyl, cycloalkyl, aryl, heteroalkyl, heteroaryl or heterocycloalkyl portion of the acyl group plus the carbonyl carbon of acyl, i.e. ring or chain atoms plus carbonyl. If the R radical is heteroaryl or heterocycloalkyl, the hetero ring or chain atoms contribute to the total number of chain or ring atoms. Unless stated otherwise specifically in the specification, the R of an acyl group is optionally substituted by one or more substituents which independently are: alkyl, heteroalkyl, alkenyl, alkynyl, cycloalkyl, heterocycloalkyl, aryl, heteroaryl, hydroxy, halo, cyano, trifluoromethyl, trifluoromethoxy, nitro, trimethylsilanyl, —OR$^a$, —SR$^a$, —OC(=O)—R$^a$, —OC(=O)OR$^a$, —N(R$^a$)$_2$, —C(=O)R$^a$, —C(=O)OR$^a$, —OC(=O)N(R$^a$)$_2$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), or —P(=O)(OR$^a$)$_2$, wherein each of R$^a$ is independently hydrogen, alkyl, heteroalkyl, cycloalkyl, heterocycloalkyl, aryl or heteroaryl.

The term "halo", "halide", or alternatively, "halogen" means fluoro, chloro, bromo or iodo. The terms "haloalkyl" refers to alkyl structures that are substituted with one or more halo groups or combinations thereof. The terms "haloalkoxy" refers to alkoxy structures that are substituted with one or more halo groups or combinations thereof. The terms "fluoroalkyl" and "fluoroalkoxy" refer to haloalkyl and haloalkoxy groups, respectively, in which the halo is fluoro. Examples of fluoroalkyl include, but are not limited to, —CH$_2$F, —CHF$_2$, —CF$_3$, —CF$_2$CH$_3$, —CH$_2$CF$_3$, and —CF$_2$CF$_3$.

The term "cyano" refers to a —CN radical.

The term "alkoxy" refers to an —O-alkyl radical, wherein alkyl is as described herein and contains 1 to 10 carbons (i.e., C1-C10 alkoxy). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms. In some embodiments, it is a C1-C4 alkoxy group. Unless stated otherwise specifically in the specification, an alkoxy moiety may be substituted by one or more of the substituents described as suitable substituents for an alkyl radical.

The term "sp$^3$ hybridized carbon" refers to a carbon atom that is bonded to four other atoms. sp$^3$ hybridization results from the combination of the s orbital and all three p orbitals in the second energy level of carbon. It results in four equivalent orbitals and the geometric arrangement of those four orbitals is tetrahedral.

The term "sulfonyl" refers to a —S(=O)$_2$—R radical, wherein R is selected from the group consisting of alkyl, cycloalkyl, aryl, heteroalkyl, heteroaryl (bonded through a ring carbon) and heterocycloalkyl (bonded through a ring carbon). Unless stated otherwise specifically in the specification, the R group may be substituted by one or more of the substituents described as suitable substituents for an alkyl, an aryl or a heteroaryl radical.

The term "sulfoximinyl" refers to a —S(=O)(=NR$^a$)—R$^b$ radical, wherein R$^a$ is selected from the group consisting of hydrogen, alkyl, cycloalkyl, aryl, cyano, carbamoyl, acyl, heteroaryl (bonded through a ring carbon) and heterocycloalkyl (bonded through a ring carbon) and R$^b$ is independently selected from the group consisting of alkyl, cycloalkyl, aryl, heteroalkyl, heteroaryl (bonded through a ring carbon) and heterocycloalkyl (bonded through a ring carbon). Unless stated otherwise specifically in the specification, the R$^a$ and R$^b$ group may be substituted by one or more of the substituents described as suitable substituents for an alkyl, an aryl or a heteroaryl radical.

The term "sulfonamide" refers to a —S(=O)$_2$—N(R$^a$) radical, wherein each R$^a$ is independently hydrogen, alkyl, heteroalkyl, cycloalkyl or heterocycloalkyl, and at least one R$^a$ is hydrogen.

The term "cycloalkyl" refers to a monocyclic or polycyclic non-aromatic radical that contains carbon and hydrogen, and may be saturated, or partially unsaturated. Cycloalkyl groups include groups having from 3 to 10 ring atoms (i.e., C3-C10 cycloalkyl). Whenever it appears herein, a numerical range such as "3 to 10" refers to each integer in the given range; e.g., "3 to 10 carbon atoms" means that the cycloalkyl group may consist of 3 carbon ring atoms, 4 carbon ring atoms, 5 carbon ring atoms, etc., up to and including 10 carbon ring atoms. In some embodiments, it is a C3-C5 cycloalkyl radical. Illustrative examples of cycloalkyl groups include, but are not limited to the following moieties: cyclopropyl, cyclobutyl, cyclopentyl, cyclohexyl, cycloseptyl, cyclooctyl, cyclononyl, cyclodecyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)—R$^a$, —OC(=O)OR$^a$, —OC(=O)N(R$^a$)$_2$, —N(R$^a$)$_2$, —C(=O)R$^a$, —C(=O)OR$^a$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, heteroalkyl, cycloalkyl, heterocycloalkyl, aryl or heteroaryl.

The term "heterocyclyl" or "heterocycloalkyl" refers to a stable and not fully aromatic 3- to 18-membered ring (i.e., C3-C18 heterocycloalkyl) radical that comprises two to twelve ring carbon atoms and from one to six ring heteroatoms selected from nitrogen, oxygen and sulfur. Whenever it appears herein, a numerical range such as "3 to 18" refers to each integer in the given range; e.g., "3 to 18 ring atoms" means that the heterocycloalkyl group may consist of 3 ring atoms, 4 ring atoms, etc., up to and including 18 ring atoms. In some embodiments, it is a C5-C10 heterocycloalkyl. In some embodiments, it is a C4-C10 heterocycloalkyl. In some embodiments, it is a C3-C10 heterocycloalkyl. Unless stated otherwise specifically in the specification, the heterocycloalkyl radical may be a monocyclic, bicyclic, tricyclic or tetracyclic ring system, which may include fused or bridged ring systems. The heteroatoms in the heterocycloalkyl radical may be optionally oxidized. One or more nitrogen atoms, if present, may optionally be quaternized.

The heterocycloalkyl radical may be partially or fully saturated. The heterocycloalkyl may be attached to the rest of the molecule through any atom of the ring(s). Examples of such heterocycloalkyl radicals include, but are not limited to, 6,7-dihydro-5H-cyclopenta[b]pyridine, dioxolanyl, thienyl [1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxothiomorpholinyl, and 1,1-dioxo-thiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)—R$^a$, —OC(=O)OR$^a$, —OC(=O)N(R$^a$)$_2$, —N(R$^a$)$_2$, —C(=O)R$^a$, —C(=O)OR$^a$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, heteroalkyl, cycloalkyl, heterocycloalkyl, aryl or heteroaryl.

The terms "heteroalkyl", "heteroalkenyl" and "heteroalkynyl" include optionally substituted alkyl, alkenyl and alkynyl radicals, which respectively have one or more skeletal chain atoms selected from an atom other than carbon, e.g., oxygen, nitrogen, sulfur, phosphorus or combinations thereof. A numerical range, which refers to the chain length in total, may be given. For example, C3-C4 heteroalkyl has a chain length of 3-4 atoms. For example, a —CH$_2$OCH$_2$CH$_3$ radical is referred to as a "C4 heteroalkyl", which includes the heteroatom in the atom chain length description. Connection to the rest of the molecule is through a carbon in the heteroalkyl chain. A heteroalkyl may be a substituted alkyl. The same definition applies to heteroalkenyl or heteroalkynyl. Unless otherwise stated in the specification, a heteroalkyl group may be substituted with one or more substituents which independently are: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)—R$^a$, —OC(=O)OR$^a$, —OC(=O)N(R$^a$)$_2$, —N(R$^a$)$_2$, —C(=O)R$^a$, —C(=O)OR$^a$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$R$_a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, heteroalkyl, cycloalkyl, heterocycloalkyl, aryl or heteroaryl.

The term "amino" or "amine" refers to a —NH$_2$ radical group,

The term "acyloxy" refers to a R(C=O)O— radical wherein R is alkyl, cycloalkyl, aryl, heteroalkyl, heteroaryl or heterocycloalkyl, which are as described herein. In some embodiments, it is a C2-C4 acyloxy radical, wherein the C2-C4 refers to the total number, i.e., 1-3 of the chain or ring atoms of the alkyl, cycloalkyl, aryl, heteroalkyl, heteroaryl or heterocycloalkyl portion of the acyloxy group plus the carbonyl carbon of acyl, i.e., the ring or chain atoms plus carbonyl. If the R radical is heteroaryl or heterocycloalkyl, the hetero ring or chain atoms contribute to the total number of chain or ring atoms. Unless stated otherwise specifically in the specification, the R of an acyloxy group is optionally substituted by one or more of the following substituents: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)—R$^a$, —OC(=O)OR$^a$, —OC(=O)N(R$^a$)$_2$, —N(R$^a$)$_2$, —C(=O)R$^a$, —C(=O)OR$^a$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each of R$^a$ is independently hydrogen, alkyl, heteroalkyl, cycloalkyl, heterocycloalkyl, aryl or heteroaryl.

The term "alkenyl" refers to a straight or branched hydrocarbon chain radical group comprising carbon and hydrogen atoms, containing at least one double bond, and having from two to ten carbon atoms (i.e., C2-C10 alkenyl). Whenever it appears herein, a numerical range such as "2 to 10" refers to each integer in the given range; e.g., "2 to 10 carbon atoms" means that the alkenyl group may contain 2 carbon atoms, 3 carbon atoms, etc., up to and including 10 carbon atoms. In certain embodiments, an alkenyl comprises two to eight carbon atoms (i.e., C2-C8 alkenyl). In other embodiments, an alkenyl comprises two to five carbon atoms (i.e., C2-C5 alkenyl). The alkenyl is attached to the rest of the molecule by a single bond, for example, ethenyl (i.e., vinyl), prop-1-enyl, but-1-enyl, pent-1-enyl, penta-1,4-dienyl, and the like. Unless stated otherwise specifically in the specification, an alkenyl group is optionally substituted by one or more of the following substituents: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)—R$^a$, —OC(=O)OR$^a$, —OC(=O)N(R$^a$)$_2$, —N(R$^a$)$_2$, —C(=O)R$^a$, —C(=O)OR$^a$, —C(=O)N(R$^a$)$_2$, —N(R$^a$)C(=O)R$^a$, —N(R$^a$)C(=O)OR$^a$, —N(R$^a$)C(=O)N(R$^a$)$_2$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each of R$^a$ is independently hydrogen, alkyl, heteroalkyl, cycloalkyl, heterocycloalkyl, aryl or heteroaryl.

The term "alkynyl" refers to a straight or branched hydrocarbon chain radical group comprising carbon and hydrogen atoms, containing at least one triple bond, and having from two to ten carbon atoms (i.e., C2-C10 alkynyl). In some embodiments, an alkynyl group may contain one or more double bonds. Whenever it appears herein, a numerical range such as "2 to 10" refers to each integer in the given range; e.g., "2 to 10 carbon atoms" means that the alkynyl group may contain 2 carbon atoms, 3 carbon atoms, etc., up to and including 10 carbon atoms. In certain embodiments, an alkynyl comprises two to eight carbon atoms (i.e., C2-C8 alkynyl). In other embodiments, an alkynyl has two to five carbon atoms (i.e., C2-C5 alkynyl). The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)—R$^a$, —OC(=O)OR$^a$, —OC(=O)N(R$^a$)$_2$, —N(R$^a$)$_2$, —C(=O)R$^a$, —C(=O)OR$^a$, —C(=O)N(R$^a$)$_2$, —N(R$^a$)C(=O)OR$^a$, —N(R$^a$)C(=O)R$^a$, —N(R$^a$)C(=O)N(R$^a$)$_2$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, heteroalkyl, cycloalkyl, heterocycloalkyl, aryl or heteroaryl.

The term "alkylamino" refers to a chemical moiety with formula —N(R$^a$)$_2$, wherein each R$^a$ is independently hydrogen, alkyl, heteroalkyl, cycloalkyl, or heterocycloalkyl, and at least one R$^a$ is not hydrogen. Two R$^a$s may optionally form a 3-8 membered ring.

The term "amide" or "amido" refers to a chemical moiety with formula —C(=O)N(R$^a$)$_2$ or —NR$^a$C(=O)R$^a$, wherein each of R$^a$ is independently selected from the group consisting of hydrogen, alkyl, cycloalkyl, aryl, heteroaryl (bonded through a ring carbon) and heterocycloalkyl. Two R$^a$s, together with the atoms they are attached to, optionally form a 5-10 membered ring. In some embodiments, it is a C1-C4 amido or amide radical, which includes the amide carbonyl in the total number of carbons in the radical. Unless stated otherwise specifically in the specification, an amido group is optionally substituted independently by one or more of the substituents as described herein for alkyl, cycloalkyl, aryl, heteroaryl, or heterocycloalkyl. An amino acid or a peptide molecule may be attached to a compound having an amine or a carboxylic acid moiety, thereby forming a prodrug. The procedures and specific groups to make such amides are known to those of skilled in the art and can readily be found in reference sources such as Greene and Wuts, *Protective Groups in Organic Synthesis*, 3rd Ed., John Wiley & Sons, New York, N.Y., 1999.

"Carboxaldehyde" refers to a —(C=O)H radical.

"Carboxylic acid" refers to a —(C=O)OH radical.

"Ester" refers to a chemical radical of formula —C(=O)OR, where R is selected from the group consisting of alkyl, cycloalkyl, aryl, heteroaryl (bonded through a ring carbon) and heteroalkyl (bonded through a ring carbon). A hydroxy or carboxylic acid moiety on the compounds described herein may be esterified. The procedures and specific groups to make such esters are known to those skilled in the art and can readily be found in reference sources such as Greene and Wuts, *Protective Groups in Organic Synthesis*, 3rd Ed., John Wiley & Sons, New York, N.Y., 1999. Unless stated otherwise specifically in the specification, an ester group is optionally substituted by one or more substituents which independently are: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)—R$^a$, —OC(=O)OR$^a$, —OC(=O)N(R$^a$)$_2$, —N(R$^a$)$_2$, —C(=O)R$^a$, —C(=O)OR$^a$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$OR$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each of R$^a$ is independently hydrogen, alkyl, heteroalkyl, cycloalkyl, heterocycloalkyl, aryl, or heteroaryl.

"Imino" refers to a =N—R$^a$ radical, wherein R$^a$ is hydrogen, alkyl, heteroalkyl, cycloalkyl, cyano, aryl, heterocycloalkyl or heteroaryl.

"Isocyanato" refers to a —NCO radical.

"Isothiocyanato" refers to a —NCS radical.

"Mercaptyl" refers to an (alkyl)S- or (H)S-radical.

"Moiety" refers to a specific segment or functional group of a molecule. Chemical moieties are often recognized chemical entities embedded in or appended to a molecule.

"Hydroxy" refers to a —OH radical.

"Oxa" refers to a —O— radical.

"Oxo" refers to a =O radical.

"Nitro" refers to a —NO$_2$ radical.

"Oxime" refers to a —C(=N—OH)—R radical, where R is hydrogen or alkyl.

"Sulfinyl" refers to a —S(=O)—R radical, where R is selected from the group consisting of alkyl, cycloalkyl, aryl, heteroalkyl, heteroaryl (bonded through a ring carbon) and heterocyclyl (bonded through a ring carbon). In some embodiments, R is fluoroalkyl.

"Sulfoxyl" refers to a —S(=O)$_2$OH radical.

"Sulfonate" refers to a —S(=O)$_2$—OR radical, where R is selected from the group consisting of alkyl, cycloalkyl, aryl, heteroalkyl, heteroaryl (bonded through a ring carbon) and heteroalkyl (bonded through a ring carbon). The R group is optionally substituted by one or more of the substituents described for alkyl, heteroalkyl, cycloalkyl, heterocycloalkyl, aryl, and heteroaryl respectively.

"Thiocyanato" refers to a —CNS radical.

"Thioxo" refers to a =S radical.

"Substituted" means that the referenced group may be substituted with one or more additional group(s) individually and independently selected from acyl, alkyl, heteroalkyl, cycloalkyl, heterocycloalkyl, aryl, heteroaryl, hydroxy, alkoxy, mercapto, alkylthio, arylthio, cyano, halo, carbonyl, ester, thiocarbonyl, isocyanato, thiocyanato, isothiocyanato, nitro, perhaloalkyl, perfluoroalkyl, phosphate, silyl, sulfinyl, sulfonyl, sulfonamide, sulfoximinyl, alkylamino, and amino, and the protected derivatives thereof. The substituents themselves may be substituted, for example, a cycloalkyl substituent may have a halide substituted at one or more ring carbons, and the like. The protecting groups that may form the protective derivatives of the above substituents are known to those of skill in the art and may be found in references such as Greene and Wuts cited herein.

The term "optional" or "optionally" means that the subsequently described event or circumstance may or may not occur, and includes instances where the event or circumstance occurs and instances in which it does not. For example, "alkyl optionally substituted with" encompasses both "alkyl" and "alkyl" substituted with groups as defined herein. It will be understood by those skilled in the art, with respect to any group containing one or more substituents, that such groups are not intended to introduce any substitution or substitution patterns which would be deemed unacceptable by one of ordinary skill in the art.

The methods and formulations described herein include the use of N-oxides, crystalline forms (also known as polymorphs), or pharmaceutically acceptable salts of compounds having the structure of formulae described herein, as well as active metabolites of these compounds having the same type of activity. In addition, the compounds described herein can exist in unsolvated as well as solvated forms with pharmaceutically acceptable solvents such as water, ethanol, and the like. The solvated forms of the compounds presented herein are also considered to be disclosed herein.

The compounds described herein may exhibit their natural isotopic abundance, or one or more of the atoms may be artificially enriched in a particular isotope having the same atomic number, but an atomic mass or mass number different from the atomic mass or mass number predominantly found in nature. The present invention is meant to include all suitable isotopic variations of the compounds described herein. For example, hydrogen has three naturally occurring isotopes, denoted $^1$H (protium), $^2$H (deuterium), and $^3$H (tritium). Protium is the most abundant isotope in nature. Enriching for deuterium may afford certain therapeutic advantages, such as increased in vivo half-life and/or exposure, or may provide a compound useful for investigating in vivo routes of drug elimination and metabolism. Isotopically-enriched compounds may be prepared by conventional techniques well known to those skilled in the art or by processes analogous to those described in the Schemes and Examples herein using appropriate isotopically-enriched reagents and/or intermediates. See Pleiss and Voger, *Synthesis and Applications of Isotopically Labeled Compounds*, Vol. 7, Wiley, ISBN-10: 0471495018, published on Mar. 14, 2001.

Unless otherwise specified, chemical entities described herein may include, but are not limited to, when possible, their optical isomers, such as enantiomers and diastereomers, mixtures of enantiomers, including racemates, mixtures of diastereomers, and other mixtures thereof, to the extent they can be made by one of ordinary skill in the art by routine experimentation. In those situations, the single enantiomers or diastereomers, i.e., optically active forms, can be obtained by asymmetric synthesis or by resolution of the racemates or mixtures of diastereomers. Resolution of the racemates or mixtures of diastereomers, if needed, can be accomplished, for example, by conventional methods such as crystallization in the presence of a resolving agent, or chromatography, using, for example, a chiral high-pressure liquid chromatography (HPLC) column. In addition, chemical entities having carbon-carbon double bonds or carbon-nitrogen double bonds may exist in Z- or E-form (or cis- or trans-form). Furthermore, some chemical entities may exist in various tautomeric forms. Unless otherwise specified, chemical entities described herein are intended to include all Z-, E- and tautomeric forms as well.

The term "pharmaceutically acceptable" means that a chemical entity, such as a compound, a carrier, an additive or a salt, is acceptable for being administered to a subject.

The term "pharmaceutically acceptable salts" refers to salts prepared from pharmaceutically acceptable bases or acids including inorganic or organic bases and inorganic or organic acids. Salts derived from inorganic bases may be selected, for example, from aluminum, ammonium, calcium, copper, ferric, ferrous, lithium, magnesium, manganic, manganous, potassium, sodium, and zinc salts. Further, for example, the pharmaceutically acceptable salts derived from inorganic bases may be selected from ammonium, calcium, magnesium, potassium, and sodium salts. Salts derived from pharmaceutically acceptable organic bases may be selected, for example, from salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and tromethamine.

When chemical entities disclosed herein are basic, salts may be prepared using at least one pharmaceutically acceptable acid, selected from inorganic and organic acids. Such acid may be selected, for example, from acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, trifluoroacetic acid, and p-toluenesulfonic acids. In some embodiments, such acid may be selected, for example, from citric, hydrobromic, hydrochloric, maleic, phosphoric, sulfuric, fumaric, and tartaric acids.

The term "pharmaceutically acceptable carrier" as used herein means a diluent, excipient, encapsulating material or formulation auxiliary, which may be non-toxic, and inert, which may not have undesirable effect on a subject, preferably a mammal, more preferably a human, or which may be suitable for delivering an active agent to the target site without affecting the activity of the agent.

The term "enantiomeric excess," as used herein, is the percent excess of one enantiomer compared to that of the other enantiomer in a mixture, and can be calculated using the following equation: enantiomeric excess=((R−S)/(R+S))×100=% (R*)−% (S*), wherein R and S are the number of moles of each enantiomer in the mixture, and R* and S* are the respective mole fractions of the enantiomers in the mixture. For example, for a mixture with 87% R enantiomer and 13% S enantiomer, the enantiomeric excess is 74%.

The term "effective amount" or "therapeutically effective amount" refers to an amount of a compound or pharmaceutical composition described herein that is sufficient to effect the intended application including, but not limited to, disease treatment, as illustrated below. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The specific dose will vary depending on, for example, the particular compounds chosen, the dosing regimen to be followed, whether it is administered in combination with other agents, timing of administration, the tissue to which it is administered, and the physical delivery system in which it is carried.

The term "about" refers to ±10% of a stated number or value.

The following abbreviations and terms have the indicated meanings throughout:

DAST=Diethylaminosulfur trifluoride
DCM=Dichloromethane
MTBE=Methyl t-butyl ether
HATU=O-(7-azabenzotriazol-1-yl)-N,N,N',N'-tetramethyluronium hexafluorophosphate
NBS=N-Bromosuccinimide
NMP=N-Methyl-2-pyrrolidone
e.e. or ee=Enantiomeric excess
PPTS=Pyridinium p-toluenesulfonate
DMAP=4-Dimethylaminopyridine
DMF=N,N-Dimethylformamide Compounds When " ⌇ " is drawn across a bond, it denotes where a bond disconnection or attachment occurs. For example, in the chemical structure shown below,

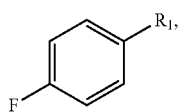

$R_1$ group is attached to the para position of a fluorophenyl ring through a single bond. When $R_1$ is phenyl, it can also be drawn as

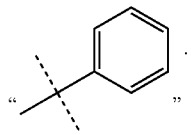

The waved line " ~ " means a bond with undefined stereochemistry. For example,

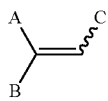

represents a mixture of

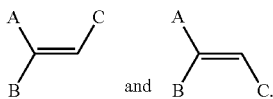

When a bond is drawn across a ring, it means substitution at a non-specific ring atom or position. For example, in the structure shown below,

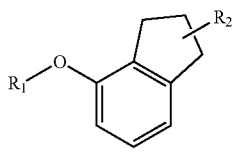

$R_2$ may be attached to any one of the —CH$_2$— in the five-membered ring.

In one aspect, the present disclosure provides a compound having the structure of Formula I

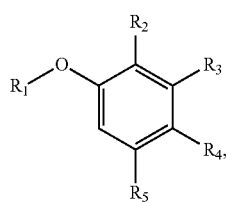

or a pharmaceutically acceptable salt thereof, wherein:
$R_1$ is aryl or heteroaryl;
$R_2$ is nitro, carboxaldehyde, carboxylic acid, ester, amido, cyano, halo, sulfonyl or alkyl;

$R_3$ is hydrogen, halo, cyano, alkyl, heteroalkyl, alkenyl, alkynyl, alkylamino, carboxaldehyde, carboxylic acid, oxime, ester, amido or acyl, or $R_2/R_3$ and atoms they are attached to form a 5- or 6-membered carbocycle with at least one sp$^a$ hybridized carbon;

$R_4$ is nitro, halo, cyano, alkyl, sulfinyl, sulfonamide, sulfonyl or sulfoximinyl; and $R_5$ is hydrogen, halo or alkyl.

In some embodiments, $R_1$ is phenyl or monocyclic heteroaryl. In some further embodiments, $R_1$ is phenyl or pyridyl, optionally substituted with one or more substituents selected from the group consisting of halo, alkyl, alkoxy, and cyano. In a further embodiment, the substituent(s) is selected from the group consisting of halo, C1-C4 alkyl, C1-C4 alkoxy, and cyano.

In some embodiments, $R_1$ is

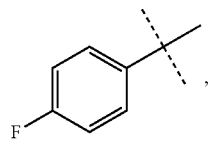

wherein the aryl ring may optionally be substituted with one or more substituents selected from the group consisting of cyano, halo, alkyl and alkoxy. In a further embodiment, the substituent(s) is selected from the group consisting of halo, C1-C4 alkyl, C1-C4 alkoxy, and cyano.

In some embodiments, $R_1$ is

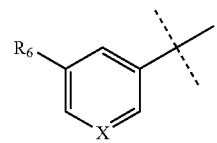

wherein X is N or CR$_7$, $R_6$ is cyano, halo, alkyl or alkoxy, and $R_7$ is hydrogen, cyano, halo, alkyl or alkoxy. In a further embodiment, $R_6$ is cyano, halo, C1-C4 alkyl or C1-C4 alkoxy, and $R_7$ is hydrogen, cyano, halo, C1-C4 alkyl or C1-C4 alkoxy.

In some embodiments, $R_1$ is pyridyl N-oxide. In a further embodiment, the pyridyl N-oxide is substituted with one or more substituents selected from the group consisting of halo, C1-C4 alkyl, C1-C4 alkoxy, and cyano.

In some embodiments, $R_1$ is bicyclic heteroaryl. In a further embodiment, the bicyclic heteroaryl is substituted with one or more substituents selected from the group consisting of halo, C1-C4 alkyl, C1-C4 alkoxy, and cyano.

In some embodiments, $R_1$ is selected from the group consisting of:

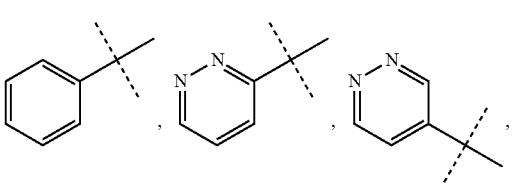

-continued

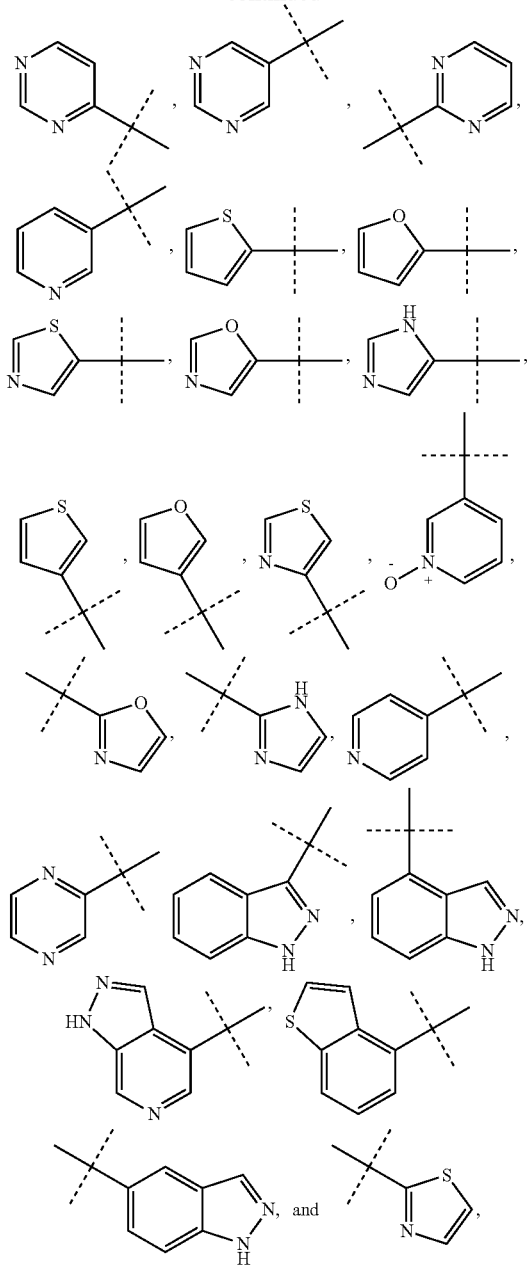

and the rings specified for $R_1$ may optionally be substituted by one or more substituents described for aryl and heteroaryl. In a further embodiment, the substituent(s) is selected from the group consisting of halo, C1-C4 alkyl, C1-C4 alkoxy, and cyano.

In some embodiments, $R_2$ is cyano, halo or alkyl. In some embodiments, $R_2$ is halo or alkyl. In some embodiments, $R_2$ is fluoro, chloro, bromo or iodo. In some embodiments, $R_2$ is fluoroalkyl. In some further embodiments, $R_2$ is —$CH_2F$, —$CHF_2$, or —$CF_3$.

In some embodiments, $R_3$ is hydrogen, halo, cyano, alkyl, heteroalkyl or acyl; or $R_2/R_3$ and atoms they are attached to may optionally form a 5- or 6-membered carbocycle with at least one sp$^3$ hybridized carbon. In a further embodiment, $R_3$ is halo, cyano or alkyl. In yet a further embodiment, $R_3$ is —$(CH_2)_nOH$, wherein n is 1, 2, or 3. In still a further embodiment, n is 1.

In some embodiments, $R_2/R_3$ and atoms they are attached to form a 5- or 6-membered carbocycle with at least one sp$^3$ carbon. Representative compounds with the carbocycle include, but are not limited to, the following:

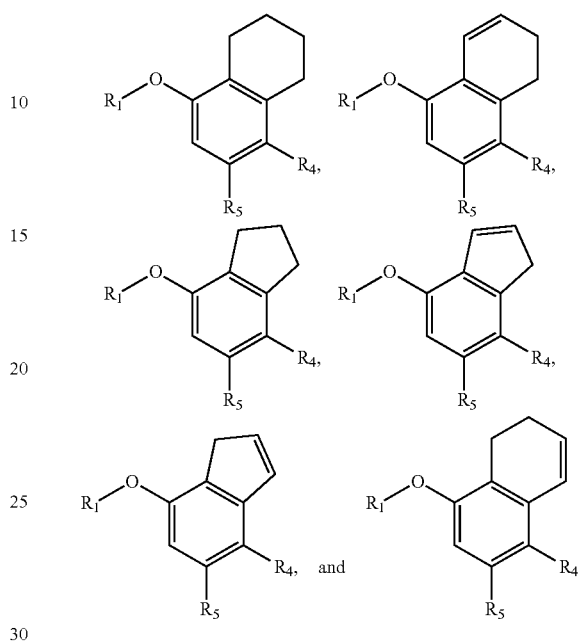

wherein the carbocycle formed by linking $R_2$ and $R_3$ may be optionally substituted with fluoro, chloro, hydroxy, alkyl, or heteroalkyl. In a further embodiment, the substituent(s) is selected from the group consisting of halo, C1-C4 alkyl, C1-C4 alkoxy, and cyano.

In some embodiments, $R_3$ is hydrogen, $R_4$ is —S(=O)$_2R_a$ or —S(=O)(=N$R_b$)$R_c$, wherein $R_a$ is fluoroalkyl, $R_b$ is hydrogen, cyano or alkyl and $R_c$ is alkyl. In a further embodiment, $R_1$ is selected from the group consisting of

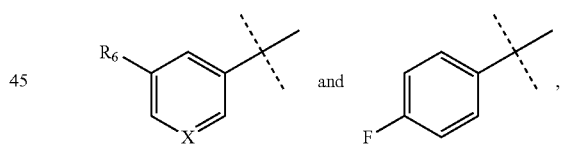

wherein:
X is N or C$R_7$, $R_6$ is cyano, halo, alkyl or alkoxy, and $R_7$ is hydrogen, cyano, halo, alkyl or alkoxy; and

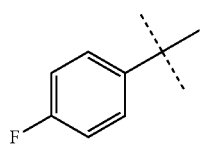

may optionally be substituted with one or more substituents selected from the group consisting of cyano, halo, alkyl and alkoxy. In a further embodiment, the alkyl is C1-C4 alkyl. In another further embodiment, the alkoxy is C1-C4 alkoxy.

In some embodiments, $R_4$ is halo, cyano, fluoroalkyl, sulfinyl, sulfonamide, sulfonyl or sulfoximinyl. In some embodiments, $R_4$ is cyano, fluoroalkyl, sulfonamide, sulfinyl, sulfonyl or sulfoximinyl. In some embodiments, $R_4$ is fluoroalkyl, sulfonamide, sulfonyl or sulfoximinyl.

In some embodiments, $R_4$ is —S(=O)$_2$R$_a$, wherein $R_a$ is alkyl or cycloalkyl. In a further embodiment, $R_a$ is C1-C4 alkyl, optionally substituted with one or more fluorines. Suitable examples of fluorine-substituted C1-C4 alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$, and —CF$_2$CH$_3$. In still a further embodiment, $R_a$ is methyl, optionally substituted with one or more fluorines.

In some embodiments, $R_4$ is —S(=O)(=NR$_b$)R$_a$, wherein $R_a$ is alkyl or cycloalkyl and $R_b$ is hydrogen, cyano, or alkyl. In a further embodiment, $R_a$ is C1-C4 alkyl, optionally substituted with one or more fluorines. Suitable examples of fluorine-substituted C1-C4 alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$, and —CF$_2$CH$_3$.

In some embodiments, $R_4$ is —S(=O)$_2$—N(R$_a$)$_2$, wherein each $R_a$ is independently hydrogen, alkyl, heteroalkyl, cycloalkyl or heterocycloalkyl, and at least one $R_a$ is hydrogen. In a further embodiment, both $R_a$s are hydrogen. In another further embodiment, one $R_a$ is hydrogen and the other $R_a$ is C1-C4 alkyl.

In some embodiments, $R_4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$, and —S(=O)(=N—CN)CF$_3$.

In some embodiments, $R_5$ is hydrogen. In some other embodiments, $R_5$ is C1-C4 alkyl. In a further embodiment, $R_5$ is methyl.

In some embodiments, each of $R_2$ and $R_3$ is independently alkyl and $R_4$ is cyano, fluoroalkyl, sulfonamide, sulfinyl, sulfonyl or sulfoximinyl.

In some embodiments, $R_3$ is —CH$_2$OH. In a further embodiment, $R_4$ is cyano, fluoroalkyl, sulfonamide, sulfinyl, sulfonyl or sulfoximinyl and $R_5$ is hydrogen. In still a further embodiment, $R_2$ is cyano, halo, or alkyl.

In some embodiments, $R_1$ is phenyl or monocyclic heteroaryl; $R_2$ is nitro, halo, cyano or alkyl; $R_3$ is halo, cyano or alkyl; $R_4$ is cyano, fluoroalkyl, sulfonamide, sulfinyl, sulfonyl or sulfoximinyl. In a further embodiment, $R_4$ is selected from the group consisting of —CN, —CF$_3$, —S(=O)CH$_3$, —S(=O)$_2$CH$_3$, —S(=O)$_2$CH$_2$F, —S(O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$, and —S(=O)(=N—CN)CF$_3$. In still a further embodiment, $R_5$ is hydrogen.

In some embodiments, $R_1$ is bicyclic heteroaryl; $R_2$ is nitro, halo, cyano or alkyl; $R_3$ is halo, cyano or alkyl; $R_4$ is cyano, fluoroalkyl, sulfonamide, sulfinyl, sulfonyl or sulfoximinyl; and $R_5$ is hydrogen.

In some embodiments, $R_1$ is phenyl, monocyclic heteroaryl, or bicyclic heteroaryl; $R_2$ is halo, cyano or alkyl; $R_3$ is halo, cyano or alkyl; $R_4$ is cyano, fluoroalkyl, sulfonamide, sulfinyl, sulfonyl or sulfoximinyl; $R_5$ is hydrogen; and $R_3$ is —CH$_2$OH.

In some embodiments, $R_2$ and $R_3$ and the atoms they are attached to form a 5- or 6-membered carbocycle with at least one sp$^3$ carbon; $R_4$ is cyano, fluoroalkyl, sulfonamide, sulfinyl, sulfonyl or sulfoximinyl; and $R_5$ is hydrogen. In a further embodiment, $R_1$ is phenyl or monocyclic heteroaryl. In another further embodiment, $R_1$ is bicyclic heteroaryl.

In another aspect, the present invention provides a compound having the structure of Formula IIa

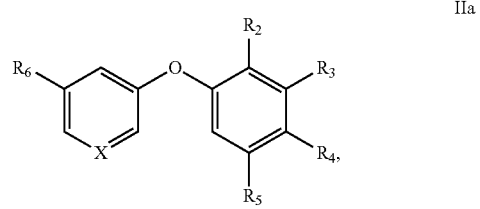

or a pharmaceutically acceptable salt thereof, wherein:

$R_2$ is nitro, carboxaldehyde, carboxylic acid, ester, amido, cyano, halo, sulfonyl or alkyl;

$R_3$ is hydrogen, halo, cyano, oxime, alkyl, heteroalkyl, alkenyl, alkynyl, alkylamino or acyl, or $R_2/R_3$ and atoms they are attached to form a 5- or 6-membered carbocycle with at least one sp$^3$ hybridized carbon;

$R_4$ is nitro, halo, cyano, alkyl, sulfinyl, sulfonamide, sulfonyl, or sulfoximinyl;

$R_5$ is hydrogen, halo or alkyl.

X is N or CR$_7$;

$R_6$ is cyano, halo, alkyl, or alkoxy; and $R_7$ is hydrogen, cyano, halo, alkyl, or alkoxy.

In some embodiments, $R_2$ is cyano, halo, or alkyl. In some embodiments, $R_2$ is halo or alkyl. In some embodiments, $R_2$ is fluoro, chloro, bromo, or iodo. In some embodiments, $R_2$ is fluoroalkyl. In some further embodiments, $R_2$ is —CH$_2$F, —CHF$_2$, or —CF$_3$.

In some embodiments, $R_3$ is hydrogen, halo, cyano, alkyl, heteroalkyl, or acyl; or $R_2/R_3$ and atoms they are attached to may optionally form a 5- or 6-membered carbocycle with at least one sp$^3$ hybridized carbon.

In some embodiments, $R_3$ is halo, cyano, or alkyl. In a further embodiment, $R_3$ is —(CH$_2$)$_n$OH, wherein n is 1, 2 or 3.

In some embodiments, $R_2/R_3$ and atoms they are attached to form a 5- or 6-membered carbocycle with at least one sp$^3$ carbon. Representative compounds with the carbocycle include, but are not limited to, the following:

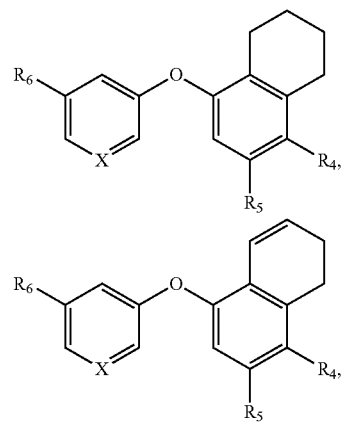

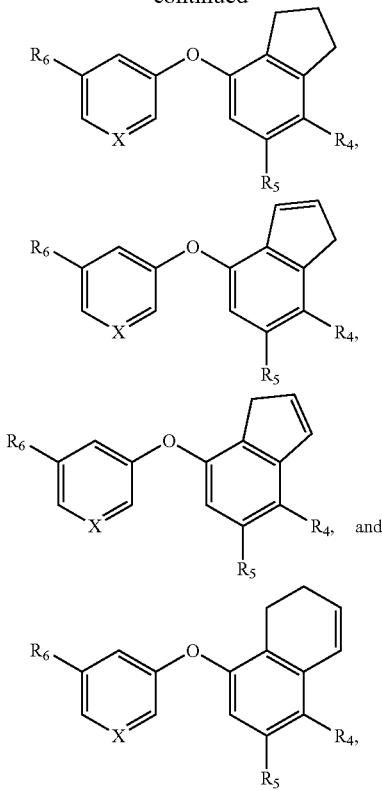

wherein the carbocycle formed by linking $R_2$ and $R_3$ may be optionally substituted with fluoro, chloro, hydroxy, alkyl, or heteroalkyl. In a further embodiment, the substituent(s) is selected from the group consisting of halo, C1-C4 alkyl, C1-C4 alkoxy, and cyano.

In some embodiments, $R_3$ is hydrogen, $R_4$ is —S(=O)$_2$R$_a$ or —S(=O)(=NR$_b$)R$_a$, wherein R$_a$ is fluoroalkyl and R$_b$ is hydrogen, cyano, or alkyl.

In some embodiments, $R_4$ is halo, cyano, fluoroalkyl, sulfinyl, sulfonamide, sulfonyl or sulfoximinyl. In some embodiments, $R_4$ is cyano, fluoroalkyl, sulfonamide, sulfinyl, sulfonyl, or sulfoximinyl. In some embodiments, $R_4$ is fluoroalkyl, sulfonamide, sulfonyl, or sulfoximinyl.

In some embodiments, $R_4$ is —S(=O)$_2$R$_a$, wherein R$_a$ is alkyl or cycloalkyl. In a further embodiment, R$_a$ is C1-C4 alkyl, optionally substituted with one or more fluorines. Suitable examples of fluorine-substituted C1-C4 alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$, and —CF$_2$CH$_3$. In still a further embodiment, R$_a$ is methyl, optionally substituted with one or more fluorines.

In some embodiments, $R_4$ is —S(=O)(=NR$_b$)R$_a$, wherein R$_a$ is alkyl or cycloalkyl and R$_b$ is hydrogen, cyano, or alkyl. In a further embodiment, R$_a$ is C1-C4 alkyl, optionally substituted with one or more fluorines. Suitable examples of fluorine-substituted C1-C4 alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$, and —CF$_2$CH$_3$.

In some embodiments, $R_4$ is —S(=O)$_2$—N(R$_a$)$_2$, wherein each R$_a$ is independently hydrogen, alkyl, heteroalkyl, cycloalkyl, or heterocycloalkyl, and at least one R$_a$ is hydrogen. In a further embodiment, both R$_a$s are hydrogen. In another further embodiment, one R$_a$ is hydrogen and the other R$_a$ is C1-C4 alkyl.

In some embodiments, $R_4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$, and —S(=O)(=N—CN)CF$_3$.

In some embodiments, $R_5$ is hydrogen. In some other embodiments, $R_5$ is C1-C4 alkyl. In a further embodiment, $R_5$ is methyl.

In some embodiments, $R_6$ is cyano, halo, C1-C4 alkyl, or C1-C4 alkoxy.

In some embodiments, $R_7$ is hydrogen, cyano, halo, C1-C4 alkyl, or C1-C4 alkoxy.

In some embodiments, $R_2$/$R_3$ and atoms they are attached to form a 5- or 6-membered carbocycle with at least one sp$^a$ carbon and $R_4$ is cyano, fluoroalkyl, sulfonamide, sulfinyl, sulfonyl, or sulfoximinyl.

In some embodiments, $R_3$ is —CH$_2$OH and $R_4$ is cyano, fluoroalkyl, sulfonamide, sulfonyl, or sulfoximinyl. In a further embodiment, $R_2$ is halo, cyano, or alkyl. In still a further embodiment, $R_5$ is hydrogen.

In some embodiments, $R_2$ is halo, cyano or alkyl; $R_3$ is —CH$_2$OH; $R_4$ is cyano, fluoroalkyl, sulfonamide, sulfonyl, or sulfoximinyl; $R_5$ is hydrogen; X is N or CR$_7$; $R_7$ is halo, cyano or C1-C4 alkyl; and $R_6$ is halo, cyano or C1-C4 alkyl. In a further embodiment, $R_4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$, and —S(=O)(=N—CN)CF$_3$.

In another aspect, the present invention provides a compound having the structure of Formula IIb

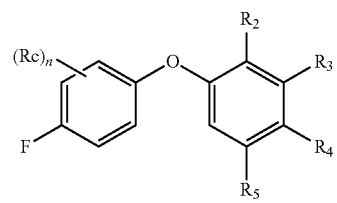

or a pharmaceutically acceptable salt thereof, wherein:

$R_2$ is nitro, carboxaldehyde, carboxylic acid, ester, amido, cyano, halo, sulfonyl, or alkyl;

$R_3$ is hydrogen, halo, cyano, oxime, alkyl, heteroalkyl, alkenyl, alkynyl, alkylamino, or acyl; or $R_2$/$R_3$ and atoms they are attached to form a 5- or 6-membered carbocycle with at least one sp$^3$ hybridized carbon;

$R_4$ is nitro, halo, cyano, alkyl, sulfinyl, sulfonamide, sulfonyl, or sulfoximinyl;

$R_5$ is hydrogen, halo or alkyl;

n is 1, 2, 3, or 4; and

Rc is hydrogen, cyano, halo, alkyl or alkoxy.

In some embodiments, $R_2$ is cyano, halo, or alkyl. In some embodiments, $R_2$ is halo or alkyl. In some embodiments, $R_2$ is fluoro, chloro, bromo, or iodo. In some embodiments, $R_2$ is fluoroalkyl. In some further embodiments, $R_2$ is —CH$_2$F, —CHF$_2$ or —CF$_3$.

In some embodiments, $R_3$ is hydrogen, halo, cyano, alkyl, heteroalkyl, or acyl; or $R_2/R_3$ and atoms they are attached to may optionally form a 5- or 6-membered carbocycle with at least one sp$^3$ hybridized carbon. In a further embodiment, $R_3$ is halo, cyano or alkyl. In yet a further embodiment, $R_3$ is —(CH$_2$)$_n$OH, wherein n is 1, 2 or 3.

In some embodiments, $R_2/R_3$ and atoms they are attached to form a 5- or 6-membered carbocycle with at least one sp$^3$ carbon. Representative compounds with the carbocycle include, but are not limited to, the following:

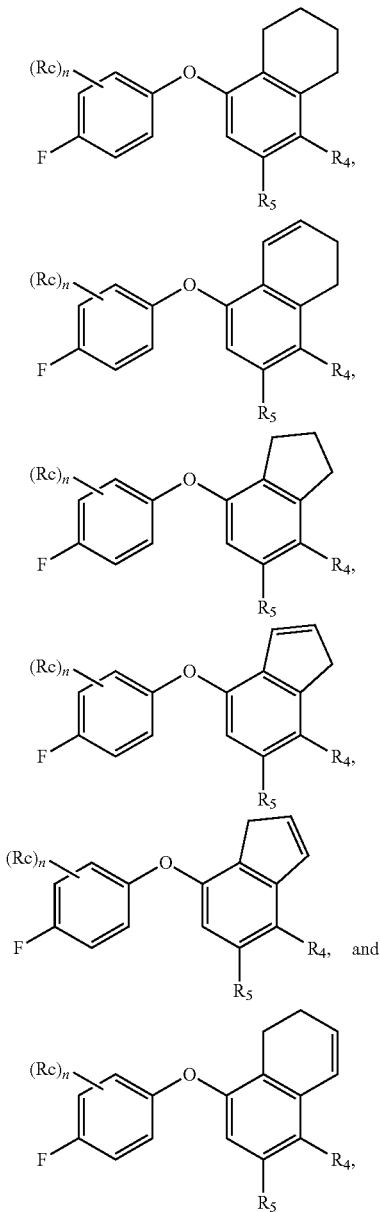

wherein the carbocycle formed by linking $R_2$ and $R_3$ may be optionally substituted with fluoro, chloro, hydroxy, alkyl or heteroalkyl. In a further embodiment, the substituent(s) is selected from the group consisting of halo, C1-C4 alkyl, C1-C4 alkoxy, and cyano.

In some embodiments, $R_3$ is hydrogen, $R_4$ is —S(=O)$_2$R$_a$ or —S(=O)(=NR$_b$)R$_d$, wherein R$_a$ is fluoroalkyl, R$_b$ is hydrogen, cyano or alkyl and R$_d$ is alkyl.

In some embodiments, $R_4$ is halo, cyano, fluoroalkyl, sulfinyl, sulfonamide, sulfonyl or sulfoximinyl. In some embodiments, $R_4$ is cyano, fluoroalkyl, sulfonamide, sulfinyl, sulfonyl or sulfoximinyl. In some embodiments, $R_4$ is fluoroalkyl, sulfonamide, sulfonyl or sulfoximinyl.

In some embodiments, $R_4$ is —S(=O)$_2$R$_a$, wherein R$_a$ is alkyl or cycloalkyl. In a further embodiment, R$_a$ is C1-C4 alkyl, optionally substituted with one or more fluorines. Suitable examples of fluorine-substituted C1-C4 alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$, and —CF$_2$CH$_3$. In still a further embodiment, R$_a$ is methyl, optionally substituted with one or more fluorines.

In some embodiments, $R_4$ is —S(=O)(=NR$_b$)R$_a$, wherein R$_a$ is alkyl or cycloalkyl and R$_b$ is hydrogen, cyano, or alkyl. In a further embodiment, R$_a$ is C1-C4 alkyl, optionally substituted with one or more fluorines. Suitable examples of fluorine-substituted C1-C4 alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$, and —CF$_2$CH$_3$.

In some embodiments, $R_4$ is —S(=O)$_2$—N(R$_a$)$_2$, wherein each R$_a$ is independently hydrogen, alkyl, heteroalkyl, cycloalkyl, or heterocycloalkyl; and at least one R$_a$ is hydrogen. In a further embodiment, both R$_a$s are hydrogen. In another further embodiment, one R$_a$ is hydrogen and the other R$_a$ is C1-C4 alkyl.

In some embodiments, $R_4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$, and —S(=O)(=N—CN)CF$_3$.

In some embodiments, $R_5$ is hydrogen. In some other embodiments, $R_5$ is C1-C4 alkyl. In a further embodiment, $R_5$ is methyl.

In some embodiments, $R_3$ is —CH$_2$OH and $R_4$ is fluoroalkyl, sulfonamide, sulfonyl, sulfinyl, or sulfoximinyl. In a further embodiment, $R_2$ is halo, cyano, or alkyl. In still a further embodiment, $R_5$ is hydrogen.

In some embodiments, $R_2$ is halo, cyano, or alkyl; $R_3$ is —CH$_2$OH; $R_4$ is fluoroalkyl, sulfonamide, sulfinyl, sulfonyl, or sulfoximinyl; $R_5$ is hydrogen; and R$_c$ is halo, cyano, or alkyl. In a further embodiment, $R_4$ is selected from the group consisting of —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$, and —S(=O)(=N—CN)CF$_3$.

In some embodiments, $R_2/R_3$ and atoms they are attached to form a 5- or 6-membered carbocycle with at least one sp$^a$ carbon and $R_4$ is cyano, fluoroalkyl, sulfonamide, sulfinyl, sulfonyl, or sulfoximinyl. In a further embodiment, $R_4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$, and —S(=O)(=N—CN)CF$_3$. In still a further embodiment, $R_5$ is hydrogen.

In some embodiments, Rc is cyano, halo, C1-C4 alkyl or C1-C4 alkoxy.

In another aspect, the present invention provides a compound having the structure of Formula III

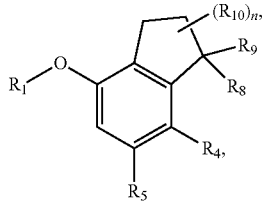

or a pharmaceutically acceptable salt thereof, wherein:
n is 1, 2, 3 or 4;
$R_1$ is aryl or heteroaryl;
$R_4$ is nitro, halo, cyano, alkyl, sulfinyl, sulfonamide, sulfonyl, or sulfoximinyl;
$R_5$ is hydrogen, halo or alkyl;
$R_8$ is hydrogen, hydroxy, alkoxy, alkylamino, or amino;
$R_9$ is hydrogen, alkyl, alkenyl, or alkynyl, or $R_8$ and $R_9$ in combination form oxo or oxime; and
each of $R_{10}$ is independently selected from the group consisting of hydrogen, fluoro, chloro, hydroxy, alkyl, and heteroalkyl with the proviso that when $R_{10}$ is hydroxy, n is 1 or 2; or two $R_{10}$ and the carbon atom(s) they are attached to form a 3- to 8-membered cycloalkyl or heterocycloalkyl.

In some embodiments, $R_1$ is phenyl or monocyclic heteroaryl. In some further embodiments, $R_1$ is phenyl or pyridyl, optionally substituted with one or more substituents selected from the group consisting of halo, alkyl, alkoxy, and cyano. In a further embodiment, $R_1$ is

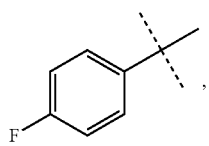

wherein the aryl ring is optionally substituted with one or more substituents selected from the group consisting of cyano, halo, alkyl, and alkoxy. In another further embodiment, $R_1$ is

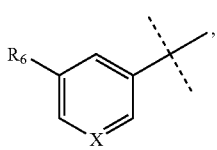

wherein X is N or $CR_7$, $R_6$ is cyano, halo, alkyl, or alkoxy, and $R_7$ is hydrogen, cyano, halo, alkyl, or alkoxy.

In some embodiments, $R_1$ is bicyclic heteroaryl.
In some embodiments, $R_1$ is selected from the group consisting of:

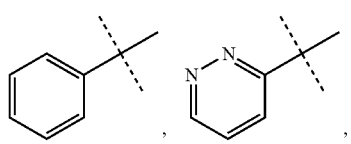

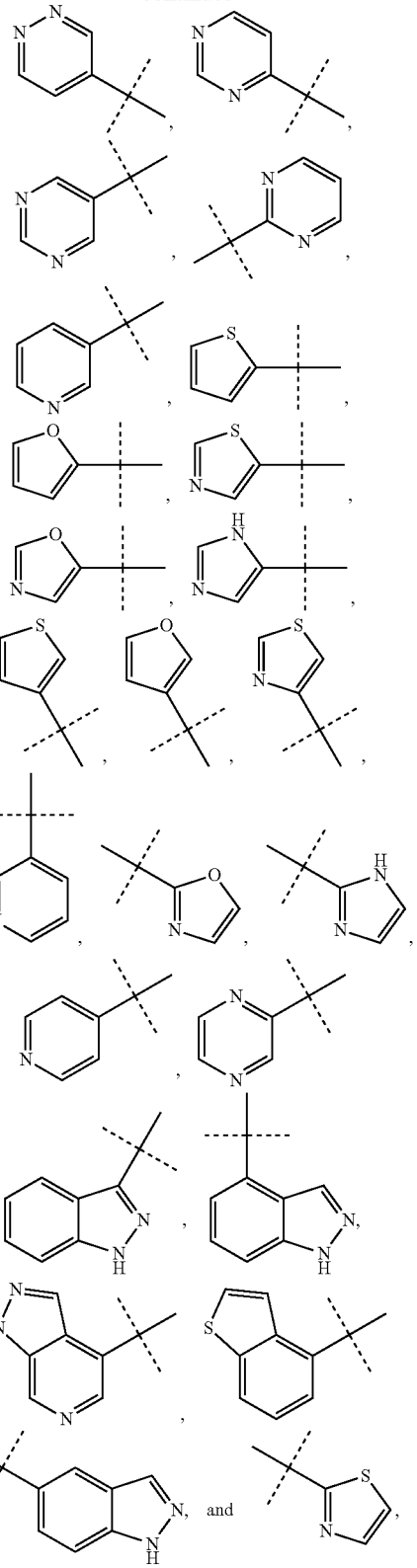

and the rings specified for $R_1$ may optionally be substituted with one or more substituents described for aryl and heteroaryl. In a further embodiment, the substituent(s) is selected from the group consisting of halo, C1-C4 alkyl, C1-C4 alkoxy, and cyano.

In some embodiments, $R_4$ is cyano, fluoroalkyl, sulfinyl, sulfonamide, sulfonyl, or sulfoximinyl. In a further embodiment, $R_4$ is fluoroalkyl, sulfonamide, sulfinyl, sulfonyl, or sulfoximinyl.

In some embodiments, $R_4$ is —S(=O)$_2$R$_a$, wherein $R_a$ is alkyl or cycloalkyl. In a further embodiment, $R_a$ is C1-C4 alkyl, optionally substituted with one or more fluorines. Suitable examples of fluorine-substituted C1-C4 alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$, and —CF$_2$CH$_3$. In still a further embodiment, $R_a$ is methyl, optionally substituted with one or more fluorines.

In some embodiments, $R_4$ is —S(=O)(=NR$_b$)R$_a$, wherein $R_a$ is alkyl or cycloalkyl and $R_b$ is hydrogen, cyano, or alkyl. In a further embodiment, $R_a$ is C1-C4 alkyl, optionally substituted with one or more fluorines. Suitable examples of fluorine-substituted C1-C4 alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$, and —CF$_2$CH$_3$.

In some embodiments, $R_4$ is —S(=O)$_2$—N(R$_a$)$_2$, wherein each of $R_a$ is independently hydrogen, alkyl, heteroalkyl, cycloalkyl, or heterocycloalkyl, and at least one $R_a$ is hydrogen. In a further embodiment, both $R_a$s are hydrogen. In another further embodiment, one $R_a$ is hydrogen and the other $R_a$ is C1-C4 alkyl.

In some embodiments, $R_4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$, and —S(=O)(=N—CN)CF$_3$.

In some embodiments, $R_5$ is hydrogen or alkyl. In some other embodiments, $R_5$ is alkyl. In a further embodiment, $R_5$ is C1-C4 alkyl.

In some embodiments, $R_8$ is hydroxy or amino. In a further embodiment, $R_8$ is hydroxy. In another further embodiment, $R_8$ is amino.

In some embodiments, $R_{10}$ is fluoro. In a further embodiment, n is 1, 2 or 3.

In some embodiments, $R_1$ is monocyclic aryl or monocyclic heteroaryl and $R_8$ is hydroxy or amino. In a further embodiment, $R_{10}$ is fluoro. In still a further embodiment, n is 1, 2 or 3.

In some embodiments, $R_1$ is phenyl or monocyclic heteroaryl, $R_8$ is hydroxy or amino, $R_{10}$ is fluoro, n is 1, 2 or 3 and $R_5$ is hydrogen.

In some embodiments, $R_1$ is bicyclic heteroaryl and $R_8$ is hydroxy or amino. In a further embodiment, $R_{10}$ is fluoro. In still a further embodiment, n is 1, 2 or 3.

In some embodiments, $R_1$ is bicyclic heteroaryl, $R_8$ is hydroxy or amino, $R_{10}$ is fluoro, n is 1, 2 or 3, and $R_5$ is hydrogen.

In some embodiments, $R_4$ is cyano, fluoroalkyl, sulfonamide, sulfinyl, sulfonyl, or sulfoximinyl, and $R_8$ is hydroxy or amino. In a further embodiment, $R_9$ is hydrogen. In another further embodiment, $R_{10}$ is fluoro. In still a further embodiment, n is 1, 2 or 3.

In some embodiments, $R_4$ is cyano, fluoroalkyl, sulfonamide, sulfonyl, sulfinyl, or sulfoximinyl; $R_8$ is hydroxy or amino; $R_{10}$ is fluoro; n is 1, 2 or 3; and $R_5$ is hydrogen. In a further embodiment, $R_9$ is hydrogen.

In some embodiments, $R_8$ is hydroxy or amino and $R_9$ is hydrogen. In a further embodiment, $R_{10}$ is fluoro. In still a further embodiment, n is 1, 2 or 3.

In some embodiments, $R_8$ is hydroxy or amino, $R_9$ is hydrogen, $R_{10}$ is fluoro, n is 1, 2 or 3, and $R_5$ is hydrogen. In a further embodiment, $R_4$ is selected from the group consisting of —CN, —CF$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$, and —S(=O)(=N—CN)CF$_3$.

In another aspect, the present invention provides a compound having the structure of Formula IVa, IVb, IVc or IVd:

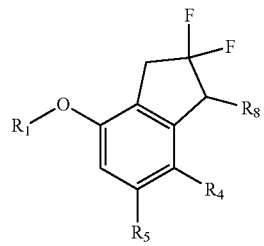

IVa

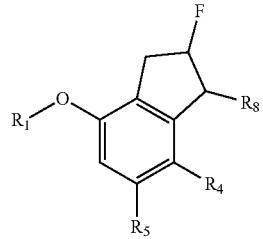

IVb

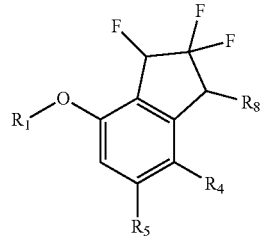

IVc

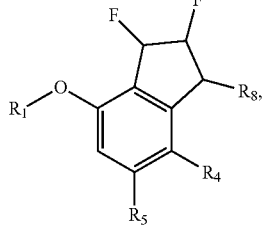

IVd or a pharmaceutically acceptable salt thereof,
wherein:
$R_1$ is aryl or heteroaryl;
$R_4$ is nitro, halo, cyano, alkyl, sulfinyl, sulfonamide, sulfonyl, or sulfoximinyl;
$R_5$ is hydrogen, halo or alkyl; and
$R_8$ is hydrogen, hydroxy, alkoxy, alkylamino or amino.

In some embodiments, $R_1$ is monocyclic aryl or monocyclic heteroaryl. In some further embodiments, $R_1$ is phenyl or pyridyl, optionally substituted with one or more substituents selected from the group consisting of halo, alkyl, alkoxy, and cyano. In a further embodiment, $R_1$ is

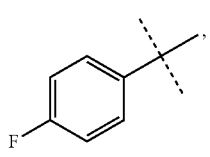

wherein the aryl ring may optionally be substituted with one or more substituents selected from the group consisting of cyano, halo, alkyl, and alkoxy. In another further embodiment, $R_1$ is

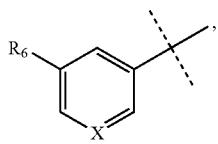

wherein X is N or $CR_7$, $R_6$ is cyano, halo, alkyl or alkoxy, and $R_7$ is hydrogen, cyano, halo, alkyl, or alkoxy.

In some embodiments, $R_1$ is bicyclic heteroaryl having at least one N atom.

In some embodiments, $R_1$ is selected from the group consisting of:

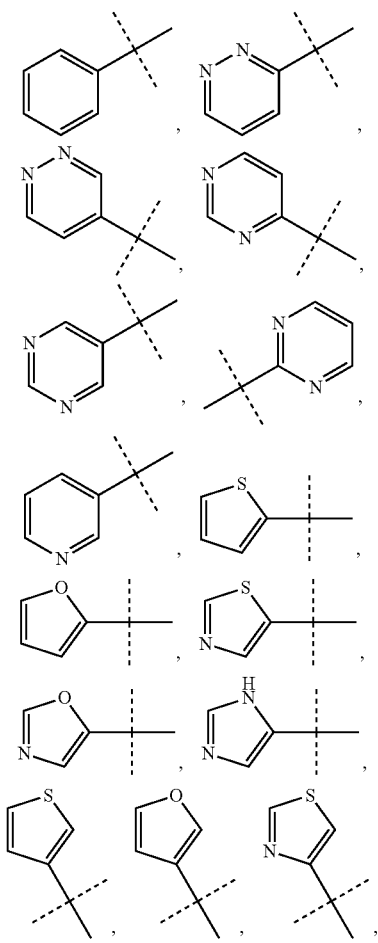

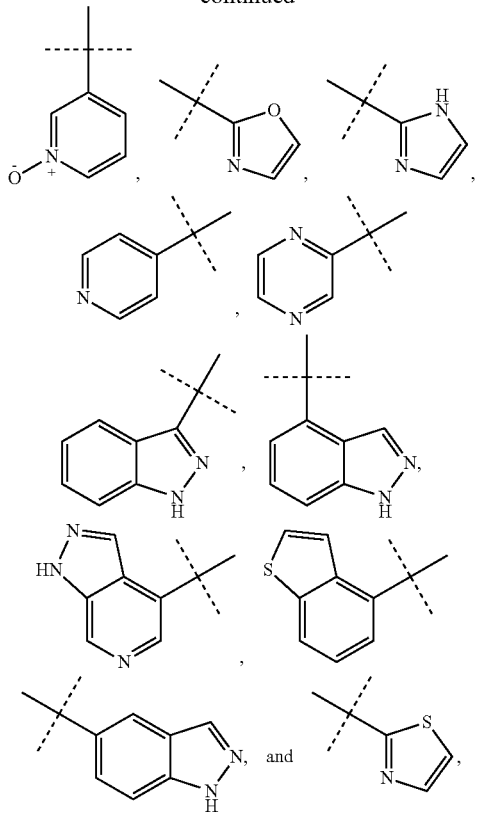

and the rings specified for $R_1$ may optionally be substituted by one or more substituents described for aryl and heteroaryl. In a further embodiment, the substituent(s) is selected from the group consisting of halo, C1-C4 alkyl, C1-C4 alkoxy, and cyano.

In some embodiments, $R_4$ is cyano, fluoroalkyl, sulfinyl, sulfonamide, sulfonyl, or sulfoximinyl. In a further embodiment, $R_4$ is fluoroalkyl, sulfonamide, sulfinyl, sulfonyl, or sulfoximinyl.

In some embodiments, $R_4$ is —S(=O)$_2R_a$, wherein $R_a$ is alkyl or cycloalkyl. In a further embodiment, $R_a$ is C1-C4 alkyl, optionally substituted with one or more fluorines. Suitable examples of fluoroalkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$, and —CF$_2$CH$_3$. In still a further embodiment, $R_a$ is methyl, optionally substituted with one or more fluorines.

In some embodiments, $R_4$ is —S(=O)(=NR$_b$)R$_a$, wherein $R_a$ is alkyl or cycloalkyl and $R_b$ is hydrogen, cyano, or alkyl. In a further embodiment, $R_a$ is C1-C4 alkyl, optionally substituted with one or more fluorines. Suitable examples of fluoroalkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$, and —CF$_2$CH$_3$.

In some embodiments, $R_4$ is —S(=O)$_2$—N(R$_a$)$_2$, wherein each $R_a$ is independently hydrogen, alkyl, heteroalkyl, cycloalkyl, or heterocycloalkyl, and at least one $R_a$ is hydrogen. In a further embodiment, both $R_a$s are hydrogen. In another further embodiment, one $R_a$ is hydrogen and the other $R_a$ is C1-C4 alkyl.

In some embodiments, $R_4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH₂F, —S(=O)(=NH)CHF₂, —S(=O)(=NH)CF₃, —S(=O)(=N—CN)CH₃, —S(=O)(=N—CN)CH₂F, —S(=O)(=N—CN)CHF₂, and —S(=O)(=N—CN)CF₃.

In some embodiments, R₅ is hydrogen or alkyl. In some other embodiments, R₅ is alkyl. In a further embodiments, R₅ is C1-C4 alkyl.

In some embodiments, R₈ is hydroxy. In some other embodiments, R₈ is amino.

In some embodiments, R₁ is bicyclic heteroaryl and R₄ is cyano, fluoroalkyl, sulfonamide, sulfinyl, sulfonyl, or sulfoximinyl. In a further embodiment, R₅ is hydrogen. In another further embodiment, R₄ is selected from the group consisting of —CN, —CF₃, —S(=O)CH₃, —S(=O)₂CH₃, —S(=O)₂CH₂F, —S(=O)₂CHF₂, —S(=O)₂CF₃, —S(=O)₂NH₂, —S(=O)₂NHCH₃, —S(=O)(=NH)CH₃, —S(=O)(=NH)CH₂F, —S(=O)(=NH)CHF₂, —S(=O)(=NH)CF₃, —S(=O)(=N—CN)CH₃, —S(=O)(=N—CN)CH₂F, —S(=O)(=N—CN)CHF₂, and —S(=O)(=N—CN)CF₃.

In some embodiments, R₁ is bicyclic heteroaryl; R₄ is cyano, fluoroalkyl, sulfonamide, sulfonyl, sulfinyl, or sulfoximinyl; R₈ is hydroxy or amino; and R₅ is hydrogen. In a further embodiment, R₈ is hydroxy. In another further embodiment, R₄ is selected from the group consisting of —CN, —CF₃, —S(=O)CH₃, —S(=O)₂CH₃, —S(=O)₂CH₂F, —S(=O)₂CHF₂, —S(=O)₂CF₃, —S(=O)₂NH₂, —S(=O)₂NHCH₃, —S(=O)(=NH)CH₃, —S(=O)(=NH)CH₂F, —S(=O)(=NH)CHF₂, —S(=O)(=NH)CF₃, —S(=O)(=N—CN)CH₃, —S(=O)(=N—CN)CH₂F, —S(=O)(=N—CN)CHF₂, and —S(=O)(=N—CN)CF₃.

In some embodiments, R₁ is phenyl, or monocyclic heteroaryl and R₄ is cyano, fluoroalkyl, sulfonamide, sulfinyl, sulfonyl, or sulfoximinyl. In a further embodiment, R₅ is hydrogen. In another further embodiment, R₄ is selected from the group consisting of —CN, —CF₃, —S(=O)CH₃, —S(=O)₂CH₃, —S(=O)₂CH₂F, —S(=O)₂CHF₂, —S(=O)₂CF₃, —S(=O)₂NH₂, —S(=O)₂NHCH₃, —S(=O)(=NH)CH₃, —S(=O)(=NH)CH₂F, —S(=O)(=NH)CHF₂, —S(=O)(=NH)CF₃, —S(=O)(=N—CN)CH₃, —S(=O)(=N—CN)CH₂F, —S(=O)(=N—CN)CHF₂, and —S(=O)(=N—CN)CF₃.

In some embodiments, R₁ is phenyl or monocyclic heteroaryl; R₄ is cyano, fluoroalkyl, sulfonamide, sulfinyl, sulfonyl or sulfoximinyl; R₈ is hydroxy or amino; and R₅ is hydrogen. In a further embodiment, R₈ is hydroxy. In another further embodiment, R₄ is selected from the group consisting of —CN, —CF₃, —S(=O)CH₃, —S(=O)₂CH₃, —S(=O)₂CH₂F, —S(=O)₂CHF₂, —S(=O)₂CF₃, —S(=O)₂NH₂, —S(=O)₂NHCH₃, —S(=O)(=NH)CH₃, —S(=O)(=NH)CH₂F, —S(=O)(=NH)CHF₂, —S(=O)(=NH)CF₃, —S(=O)(=N—CN)CH₃, —S(=O)(=N—CN)CH₂F, —S(=O)(=N—CN)CHF₂, and —S(=O)(=N—CN)CF₃.

In some embodiments, R₁ is phenyl or monocyclic heteroaryl and R₈ is hydroxy or amino. In a further embodiment, R₅ is hydrogen. In another further embodiment, R₅ is alkyl. In still a further embodiment, R₅ is C1-C4 alkyl.

In some embodiments, R₁ is bicyclic heteroaryl and R₈ is hydroxy or amino. In a further embodiment, R₅ is hydrogen. In another further embodiment, R₅ is alkyl. In still a further embodiment, R₅ is C1-C4 alkyl.

In another aspect, the present invention provides a compound having the structure of Formula Va, Vb, Vc or Vd:

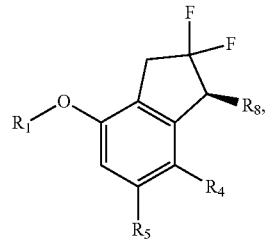
Va

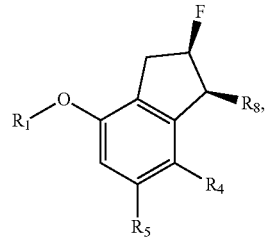
Vb

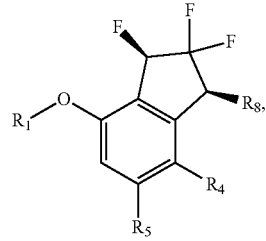
Vc

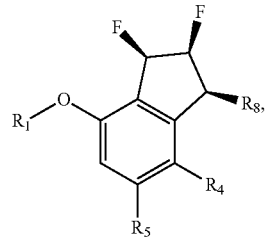
Vd or a pharmaceutically acceptable salt thereof,
wherein:
R₁ is aryl or heteroaryl;
R₄ is halo, cyano, alkyl, sulfonamide, sulfinyl, sulfonyl or sulfoximinyl;
R₅ is hydrogen, halo or alkyl; and
R₈ is hydroxy or amino.

In some embodiments, R₁ is phenyl or monocyclic heteroaryl. In some further embodiments, R₁ is phenyl or pyridyl, optionally substituted with one or more substituents selected from the group consisting of halo, alkyl, alkoxy, and cyano. In a further embodiment,

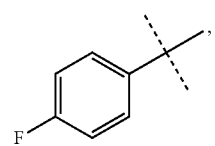

wherein the aryl ring may optionally be substituted with one or more substituents selected from the group consisting of cyano, halo, alkyl, or alkoxy. In another further embodiment, R₁ is

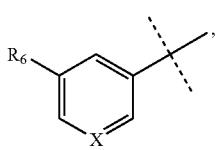

wherein X is N or $CR_7$, $R_6$ is cyano, halo, alkyl, or alkoxy, and $R_7$ is hydrogen, cyano, halo, alkyl, or alkoxy.

In some embodiments, $R_1$ is bicyclic heteroaryl.

In some embodiments, $R_1$ is selected from the group consisting of:

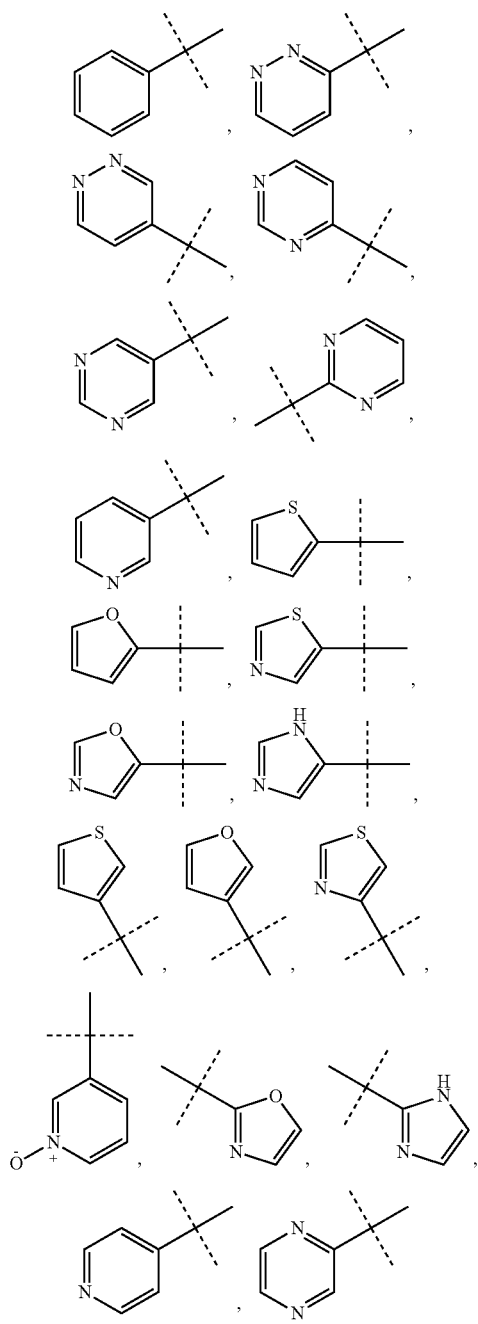

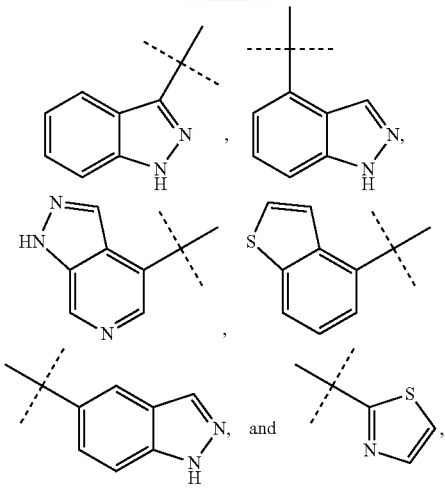

and the rings specified for $R_1$ may optionally be substituted by one or more substituents described for aryl and heteroaryl. In a further embodiment, the substituent(s) is selected from the group consisting of halo, C1-C4 alkyl, C1-C4 alkoxy, and cyano.

In some embodiments, $R_4$ is cyano, fluoroalkyl, sulfonamide, sulfonyl, sulfinyl, or sulfoximinyl.

In some embodiments, $R_4$ is —S(=O)$_2R_a$, wherein $R_a$ is alkyl or cycloalkyl. In a further embodiment, $R_a$ is C1-C4 alkyl, optionally substituted with one or more fluorines. Suitable examples of fluorine-substituted C1-C4 alkyl include, but are not limited to, —$CH_2F$, —$CHF_2$, —$CF_3$, —$CH_2CF_3$, —$CH_2CHF_2$, —$CH_2CH_2F$, —$CHFCH_3$, and —$CF_2CH_3$. In still a further embodiment, $R_a$ is methyl, optionally substituted with one or more fluorines.

In some embodiments, $R_4$ is —S(=O)(=$NR_b$)$R_a$, wherein $R_a$ is alkyl or cycloalkyl and $R_b$ is hydrogen, cyano, or alkyl. In a further embodiment, $R_a$ is C1-C4 alkyl, optionally substituted with one or more fluorines. Suitable examples of fluorine-substituted C1-C4 alkyl include, but are not limited to, —$CH_2F$, —$CHF_2$, —$CF_3$, —$CH_2CF_3$, —$CH_2CHF_2$, —$CH_2CH_2F$, —$CHFCH_3$, and —$CF_2CH_3$.

In some embodiments, $R_4$ is —S(=O)$_2$—N($R_a$)$_2$, wherein each $R_a$ is independently hydrogen, alkyl, heteroalkyl, cycloalkyl, or heterocycloalkyl, and at least one $R_a$ is hydrogen. In a further embodiment, both $R_a$s are hydrogen. In another further embodiment, one $R_a$ is hydrogen and the other $R_a$ is C1-C4 alkyl.

In some embodiments, $R_4$ is selected from the group consisting of —CN, —$CF_3$, —S(=O)$CH_3$, —S(=O)$_2CH_3$, —S(=O)$_2CH_2F$, —S(=O)$_2CHF_2$, —S(=O)$_2CF_3$, —S(=O)$_2NH_2$, —S(=O)$_2NHCH_3$, —S(=O)(=NH)$CH_3$, —S(=O)(=NH)$CH_2F$, —S(=O)(=NH)$CHF_2$, —S(=O)(=NH)$CF_3$, —S(=O)(=N—CN)$CH_3$, —S(=O)(=N—CN)$CH_2F$, —S(=O)(=N—CN)$CHF_2$, and —S(=O)(=N—CN)$CF_3$.

In some embodiments, $R_5$ is hydrogen or alkyl. In some other embodiments, $R_5$ is alkyl. In a further embodiments, $R_5$ is C1-C4 alkyl.

In some embodiments, $R_8$ is hydroxy. In some other embodiments, $R_8$ is amino.

In some embodiments, $R_1$ is bicyclic heteroaryl and $R_4$ is cyano, fluoroalkyl, sulfonamide, sulfonyl, sulfinyl, or sulfoximinyl. In a further embodiment, $R_5$ is hydrogen. In still a further embodiment, $R_4$ is selected from the group consisting of —CN, —$CF_3$, —S(=O)$CH_3$, —S(=O)$_2CH_3$, —S(=O)₂CH₂F, —S(=O)₂CHF₂, —S(=O)₂CF₃, —S(=O)₂NH₂, —S(=O)₂NHCH₃, —S(=O)(=NH)CH₃, —S(=O)(=NH)CH₂F, —S(=O)(=NH)CHF₂, —S(=O)(=NH)CF₃, —S(=O)(=N—CN)CH₃, —S(=O)(=N—CN)CH₂F, —S(=O)(=N—CN)CHF₂, and —S(=O)(=N—CN)CF₃.

In some embodiments, R₁ is bicyclic heteroaryl; R₄ is cyano, fluoroalkyl, sulfonamide, sulfonyl, sulfinyl, or sulfoximinyl; R₈ is hydroxy or amino; and R₅ is hydrogen. In a further embodiment, R₈ is hydroxy. In still a further embodiments, R₄ is selected from the group consisting of —CN, —CF₃, —S(=O)CH₃, —S(=O)₂CH₃, —S(=O)₂CH₂F, —S(=O)₂CHF₂, —S(=O)₂CF₃, —S(=O)₂NH₂, —S(=O)₂NHCH₃, —S(=O)(=NH)CH₃, —S(=O)(=NH)CH₂F, —S(=O)(=NH)CHF₂, —S(=O)(=NH)CF₃, —S(=O)(=N—CN)CH₃, —S(=O)(=I\T-CN)CH₂F, —S(=O)(=N—CN)CHF₂, and —S(=O)(=N—CN)CF₃.

In some embodiments, R₁ is phenyl or monocyclic heteroaryl and R₄ is cyano, fluoroalkyl, sulfonamide, sulfonyl, sulfinyl, or sulfoximinyl. In a further embodiment, R₅ is hydrogen. In still a further embodiments, R₄ is selected from the group consisting of —CN, —CF₃, —S(=O)CH₃, —S(=O)₂CH₃, —S(=O)₂CH₂F, —S(=O)₂CHF₂, —S(=O)₂CF₃, —S(=O)₂NH₂, —S(=O)₂NHCH₃, —S(=O)(=NH)CH₃, —S(=O)(=NH)CH₂F, —S(=O)(=NH)CHF₂, —S(=O)(=NH)CF₃, —S(=O)(=N—CN)CH₃, —S(=O)(=N—CN)CH₂F, —S(=O)(=N—CN)CHF₂, and —S(=O)(=N—CN)CF₃.

In some embodiments, R₁ is phenyl or monocyclic heteroaryl; R₄ is cyano, fluoroalkyl, sulfonamide, sulfonyl, sulfinyl, or sulfoximinyl; R₈ is hydroxy or amino; and R₅ is hydrogen. In a further embodiment, R₈ is hydroxy. In still a further embodiments, R₄ is selected from the group consisting of —CN, —CF₃, —S(=O)CH₃, —S(=O)₂CH₃, —S(=O)₂CH₂F, —S(=O)₂CHF₂, —S(=O)₂CF₃, —S(=O)₂NH₂, —S(=O)₂NHCH₃, —S(=O)(=NH)CH₃, —S(=O)(=NH)CH₂F, —S(=O)(=NH)CHF₂, —S(=O)(=NH)CF₃, —S(=O)(=N—CN)CH₃, —S(=O)(=N—CN)CH₂F, —S(=O)(=N—CN)CHF₂, and —S(=O)(=N—CN)CF₃.

In some embodiments, R₁ is phenyl or monocyclic heteroaryl and R₈ is hydroxy or amino. In a further embodiment, R₅ is hydrogen. In another further embodiment, R₅ is alkyl. In still a further embodiment, R₅ is C1-C4 alkyl.

In some embodiments, R₁ is bicyclic heteroaryl and R₈ is hydroxy or amino. In a further embodiment, R₅ is hydrogen. In another further embodiment, R₅ is alkyl. In still a further embodiment, R₅ is C1-C4 alkyl.

In some embodiments, a compound of any one of Formulae Va-Vd has enantiomeric excess of at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or even higher. In some embodiments, a compound of any one of Formulae Va-Vd has enantiomeric excess of about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%.

In another aspect, the present disclosure provides a compound or pharmaceutically acceptable salt selected from the group consisting of the following compounds:

| Example Number | Structure |
|---|---|
| 1 | 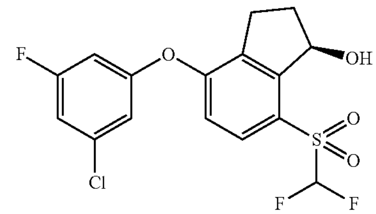 [SMILES: O=S(=O)(c1ccc(Oc2cc(F)cc(Cl)c2)c2c1[C@H](O)CC2)C(F)F] |
| 2 | 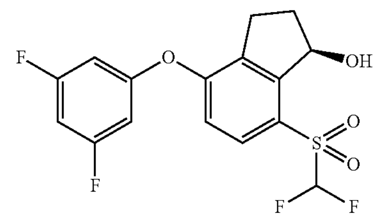 [SMILES: O=S(=O)(c1ccc(Oc2cc(F)cc(F)c2)c2c1[C@H](O)CC2)C(F)F] |
| 6 | 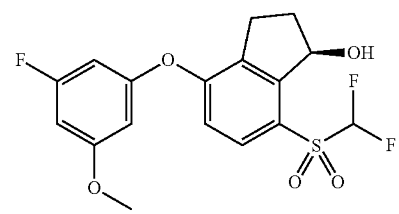 [SMILES: COc1cc(F)cc(Oc2ccc(S(=O)(=O)C(F)F)c3c2CC[C@H]3O)c1] |
| 8 | 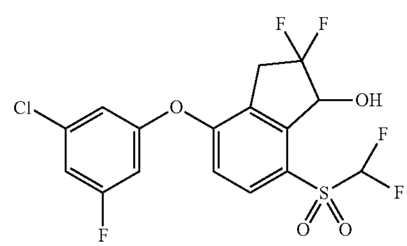 [SMILES: O=S(=O)(c1ccc(Oc2cc(F)cc(Cl)c2)c2c1C(O)C(F)(F)C2)C(F)F] |
| 9 | 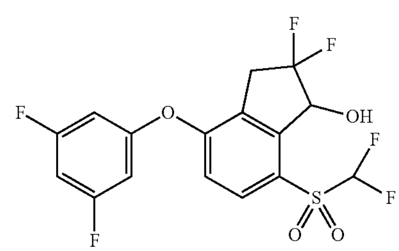 [SMILES: O=S(=O)(c1ccc(Oc2cc(F)cc(F)c2)c2c1C(O)C(F)(F)C2)C(F)F] |
| 11 | 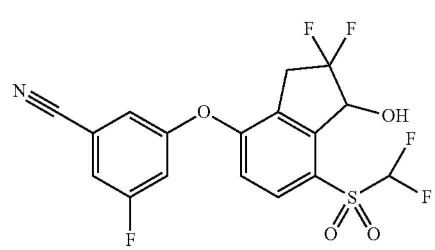 [SMILES: N#Cc1cc(F)cc(Oc2ccc(S(=O)(=O)C(F)F)c3c2CC(F)(F)C3O)c1] |

-continued
| Example Number | Structure |
|---|---|
| 15 | |
| 17 | |
| 25 | |
| 26 | |
| 27 | |
| 55 | |
-continued
| Example Number | Structure |
|---|---|
| 56 | 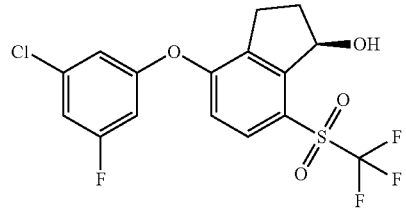 [SMILES: O=S(=O)(c1ccc(Oc2cc(F)cc(Cl)c2)c2c1[C@H](O)CC2)C(F)(F)F] |
| 57 | 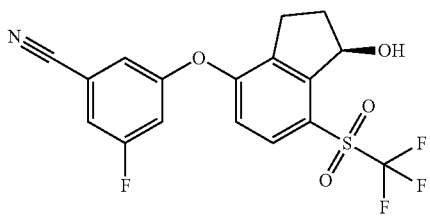 [SMILES: N#Cc1cc(F)cc(Oc2ccc(S(=O)(=O)C(F)(F)F)c3c2CC[C@H]3O)c1] |
| 58 | 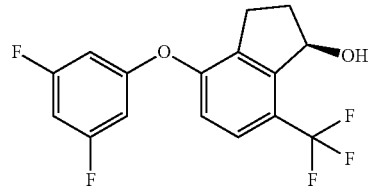 [SMILES: O[C@@H]1CCc2c(Oc3cc(F)cc(F)c3)ccc(C(F)(F)F)c21] |
| 59 | 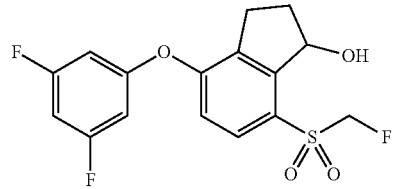 [SMILES: O=S(=O)(CF)c1ccc(Oc2cc(F)cc(F)c2)c2c1C(O)CC2] |
| 60 | 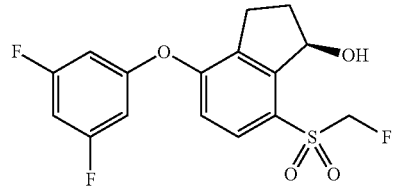 [SMILES: O=S(=O)(CF)c1ccc(Oc2cc(F)cc(F)c2)c2c1[C@H](O)CC2] |
| 61 | 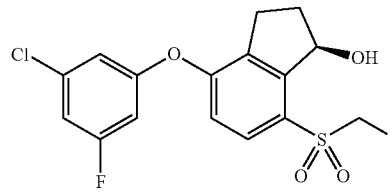 |
| 62 | 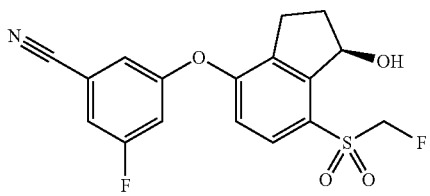 [SMILES: N#Cc1cc(F)cc(Oc2ccc(S(=O)(=O)CF)c3c2CC[C@H]3O)c1] |

| Example Number | Structure |
|---|---|
| 63 | 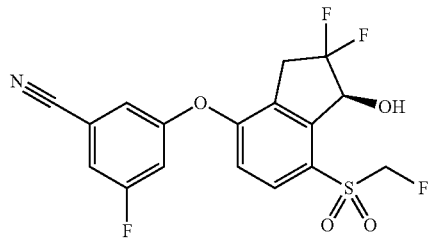 [SMILES: N#Cc1cc(F)cc(Oc2ccc(S(=O)(=O)CF)c3c2CC(F)(F)[C@H]3O)c1] |
| 64 | 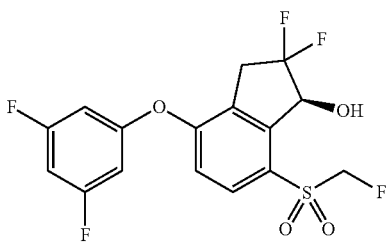 [SMILES: O=S(=O)(CF)c1ccc(Oc2cc(F)cc(F)c2)c2c1[C@H](O)C(F)(F)C2] |
| 65 | 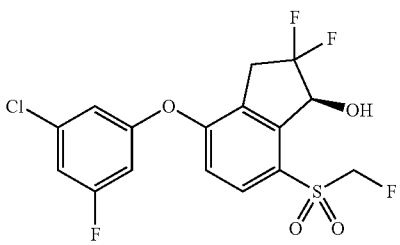 [SMILES: O=S(=O)(CF)c1ccc(Oc2cc(F)cc(Cl)c2)c2c1[C@H](O)C(F)(F)C2] |
| 67 | 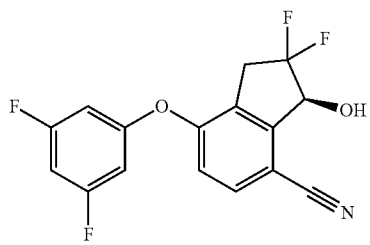 [SMILES: N#Cc1ccc(Oc2cc(F)cc(F)c2)c2c1[C@H](O)C(F)(F)C2] |
| 115 | 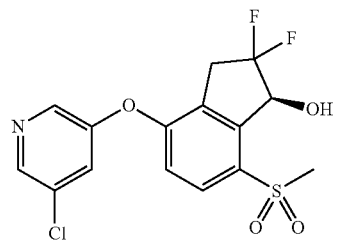 [SMILES: CS(=O)(=O)c1ccc(Oc2cncc(Cl)c2)c2c1[C@H](O)C(F)(F)C2] |
| 155 | 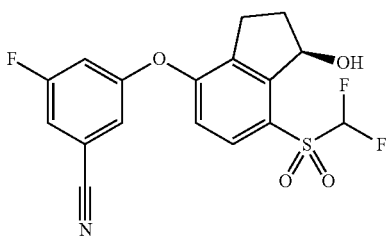 [SMILES: N#Cc1cc(F)cc(Oc2ccc(S(=O)(=O)C(F)F)c3c2CC[C@H]3O)c1] |
| Example Number | Structure |
|---|---|
| 158 | 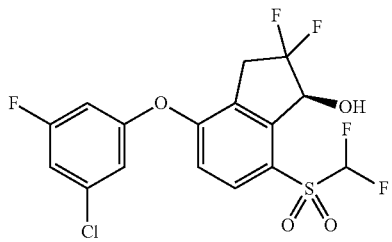 [SMILES: O=S(=O)(c1ccc(Oc2cc(F)cc(Cl)c2)c2c1[C@H](O)C(F)(F)C2)C(F)F] |
| 159 | 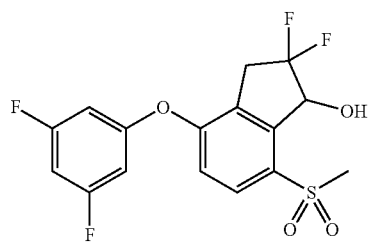 [SMILES: CS(=O)(=O)c1ccc(Oc2cc(F)cc(F)c2)c2c1C(O)C(F)(F)C2] |
| 160 | 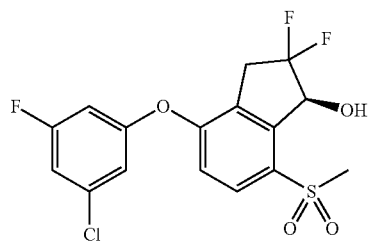 [SMILES: CS(=O)(=O)c1ccc(Oc2cc(F)cc(Cl)c2)c2c1[C@H](O)C(F)(F)C2] |
| 161 | 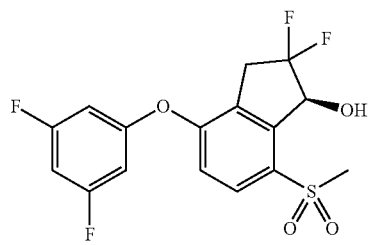 [SMILES: CS(=O)(=O)c1ccc(Oc2cc(F)cc(F)c2)c2c1[C@H](O)C(F)(F)C2] |
| 162 | 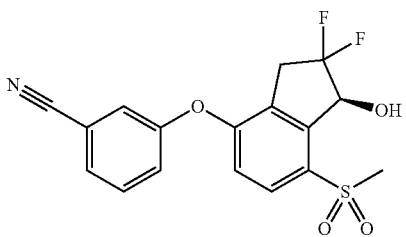 [SMILES: CS(=O)(=O)c1ccc(Oc2cccc(C#N)c2)c2c1[C@H](O)C(F)(F)C2] |
| 163 | 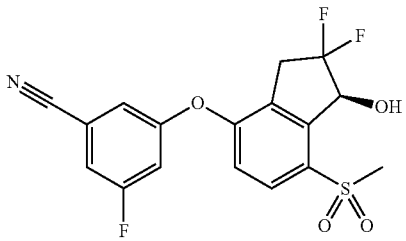 |

| Example Number | Structure |
|---|---|
| 165 | 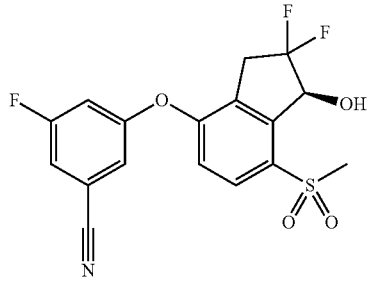 [SMILES: CS(=O)(=O)c1ccc(Oc2cc(F)cc(C#N)c2)c2c1[C@H](O)C(F)(F)C2] |
| 166 | 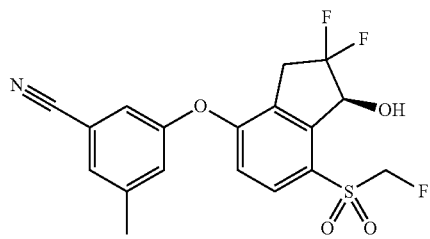 [SMILES: Cc1cc(C#N)cc(Oc2ccc(S(=O)(=O)CF)c3c2CC(F)(F)[C@H]3O)c1] |
| 167 | 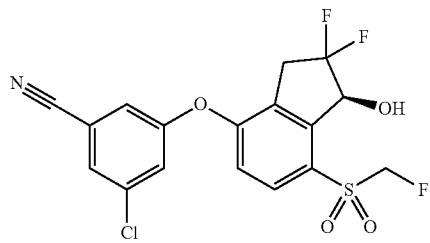 [SMILES: N#Cc1cc(Cl)cc(Oc2ccc(S(=O)(=O)CF)c3c2CC(F)(F)[C@H]3O)c1] |
| 185 | 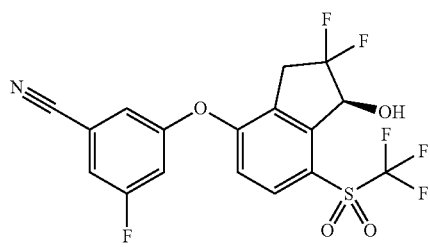 [SMILES: N#Cc1cc(F)cc(Oc2ccc(S(=O)(=O)C(F)(F)F)c3c2CC(F)(F)[C@H]3O)c1] |
| 186 | 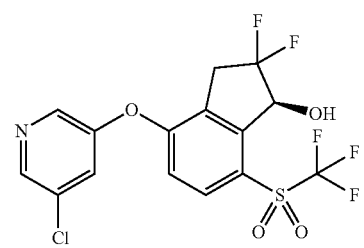 [SMILES: O=S(=O)(c1ccc(Oc2cncc(Cl)c2)c2c1[C@H](O)C(F)(F)C2)C(F)(F)F] |
| 187 | 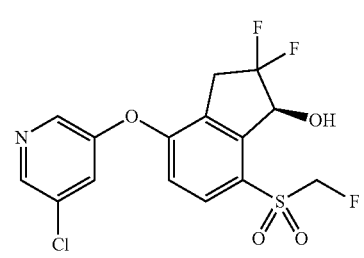 [SMILES: O=S(=O)(CF)c1ccc(Oc2cncc(Cl)c2)c2c1[C@H](O)C(F)(F)C2] |
| Example Number | Structure |
|---|---|
| 188 | 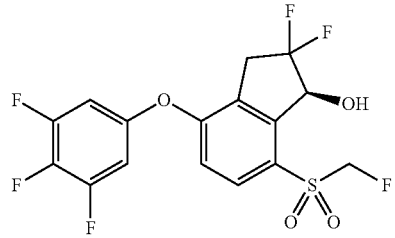 [SMILES: O=S(=O)(CF)c1ccc(Oc2cc(F)c(F)c(F)c2)c2c1[C@H](O)C(F)(F)C2] |
| 191 | 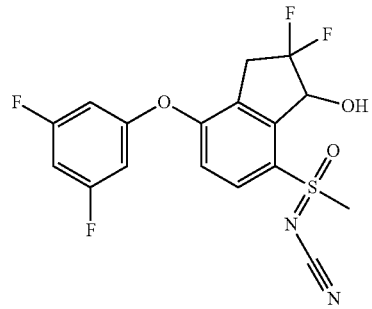 [SMILES: CS(=O)(=NC#N)c1ccc(Oc2cc(F)cc(F)c2)c2c1C(O)C(F)(F)C2] |
| 192 | 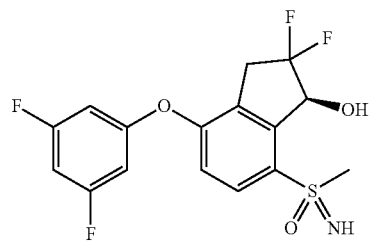 [SMILES: CS(=N)(=O)c1ccc(Oc2cc(F)cc(F)c2)c2c1[C@H](O)C(F)(F)C2] |
| 196 | 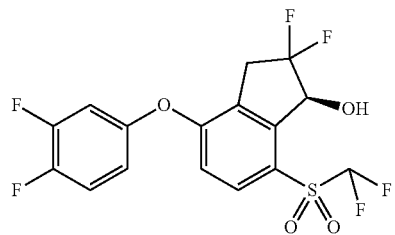 [SMILES: O=S(=O)(c1ccc(Oc2ccc(F)c(F)c2)c2c1[C@H](O)C(F)(F)C2)C(F)F] |
| 198 | 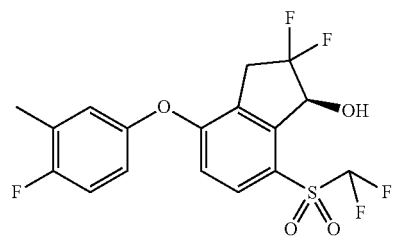 [SMILES: Cc1cc(Oc2ccc(S(=O)(=O)C(F)F)c3c2CC(F)(F)[C@H]3O)ccc1F] |
| 200 | 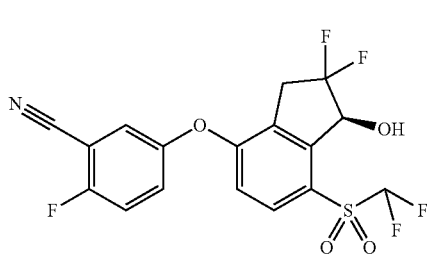 [SMILES: N#Cc1cc(Oc2ccc(S(=O)(=O)C(F)F)c3c2CC(F)(F)[C@H]3O)ccc1F] |

| Example Number | Structure |
|---|---|
| 206 | 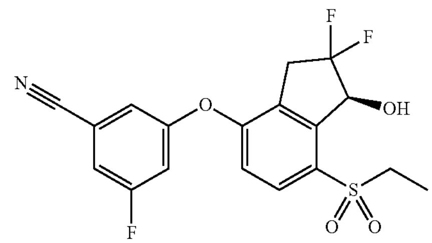 [SMILES: CCS(=O)(=O)c1ccc(Oc2cc(F)cc(C#N)c2)c2c1[C@H](O)C(F)(F)C2] |
| 215 | 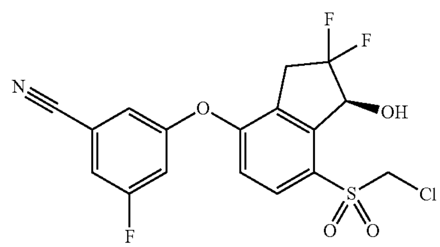 [SMILES: N#Cc1cc(F)cc(Oc2ccc(S(=O)(=O)CCl)c3c2CC(F)(F)[C@H]3O)c1] |
| 221 | 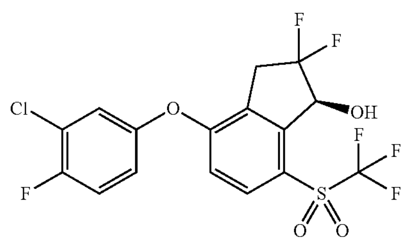 [SMILES: O=S(=O)(c1ccc(Oc2ccc(F)c(Cl)c2)c2c1[C@H](O)C(F)(F)C2)C(F)(F)F] |
| 223 | 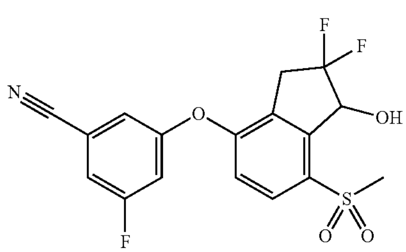 [SMILES: CS(=O)(=O)c1ccc(Oc2cc(F)cc(C#N)c2)c2c1C(O)C(F)(F)C2] |
| 224 | 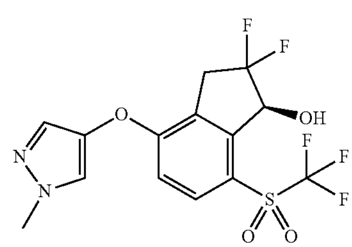 [SMILES: Cn1cc(Oc2ccc(S(=O)(=O)C(F)(F)F)c3c2CC(F)(F)[C@H]3O)cn1] |
| 225 | 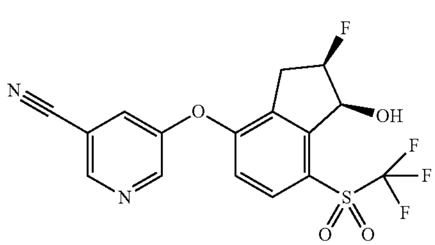 [SMILES: N#Cc1cncc(Oc2ccc(S(=O)(=O)C(F)(F)F)c3c2C[C@@H](F)[C@H]3O)c1] |

| Example Number | Structure |
|---|---|
| 227 | 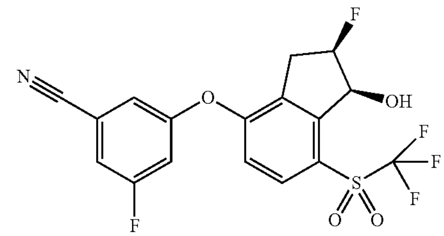 [SMILES: N#Cc1cc(F)cc(Oc2ccc(S(=O)(=O)C(F)(F)F)c3c2C[C@@H](F)[C@H]3O)c1] |
| 228 | 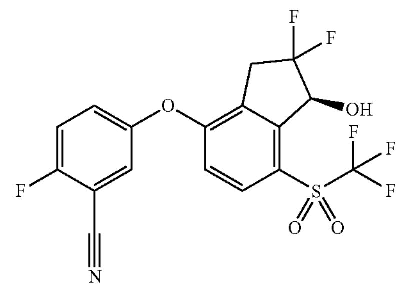 [SMILES: N#Cc1cc(Oc2ccc(S(=O)(=O)C(F)(F)F)c3c2CC(F)(F)[C@H]3O)ccc1F] |
| 229 | 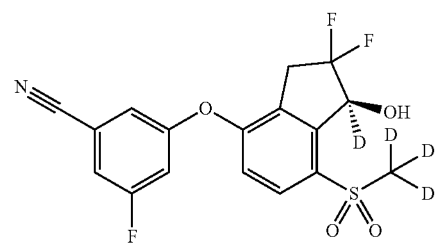 [SMILES: [2H]C([2H])([2H])S(=O)(=O)c1ccc(Oc2cc(F)cc(C#N)c2)c2c1[C@]([2H])(O)C(F)(F)C2] |
| 230 | 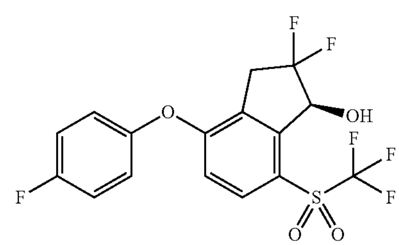 [SMILES: O=S(=O)(c1ccc(Oc2ccc(F)cc2)c2c1[C@H](O)C(F)(F)C2)C(F)(F)F] |
| 231 | 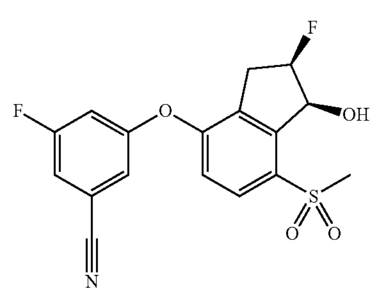 [SMILES: CS(=O)(=O)c1ccc(Oc2cc(F)cc(C#N)c2)c2c1[C@H](O)[C@H](F)C2] |
| 232 | 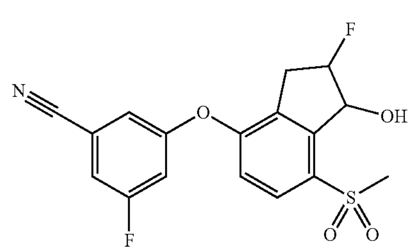 [SMILES: CS(=O)(=O)c1ccc(Oc2cc(F)cc(C#N)c2)c2c1C(O)C(F)C2] |

-continued

| Example Number | Structure |
|---|---|
| 233 | 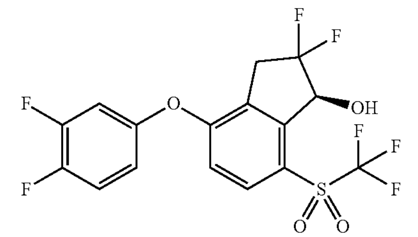 [SMILES: O=S(=O)(c1ccc(Oc2ccc(F)c(F)c2)c2c1[C@H](O)C(F)(F)C2)C(F)(F)F] |
| 234 | 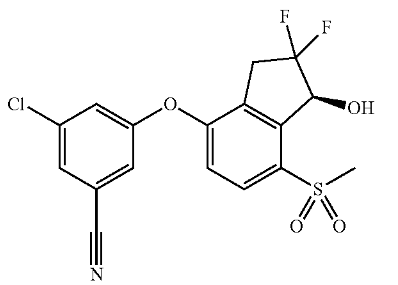 [SMILES: CS(=O)(=O)c1ccc(Oc2cc(Cl)cc(C#N)c2)c2c1[C@H](O)C(F)(F)C2] |
| 235 | 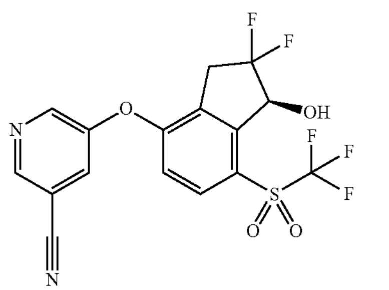 [SMILES: N#Cc1cncc(Oc2ccc(S(=O)(=O)C(F)(F)F)c3c2CC(F)(F)[C@H]3O)c1] |
| 236 | 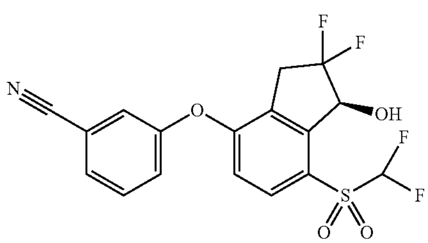 [SMILES: N#Cc1cccc(Oc2ccc(S(=O)(=O)C(F)F)c3c2CC(F)(F)[C@H]3O)c1] |
| 237 | 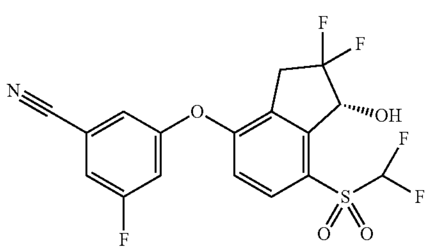 [SMILES: N#Cc1cc(F)cc(Oc2ccc(S(=O)(=O)C(F)F)c3c2CC(F)(F)[C@@H]3O)c1] |
| 240 | 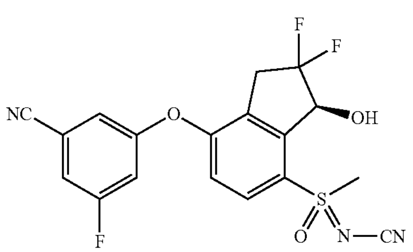 [SMILES: CS(=O)(=NC#N)c1ccc(Oc2cc(F)cc(C#N)c2)c2c1[C@H](O)C(F)(F)C2] |

-continued

| Example Number | Structure |
|---|---|
| 241 | 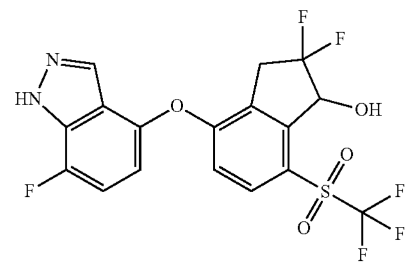 [SMILES: O=S(=O)(c1ccc(Oc2ccc(F)c3[nH]ncc23)c2c1C(O)C(F)(F)C2)C(F)(F)F] |
| 245 | 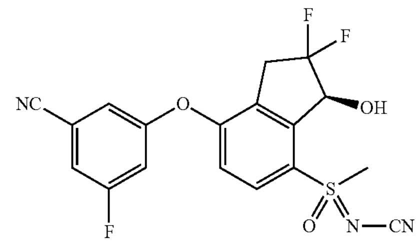 [SMILES: CS(=O)(=NC#N)c1ccc(Oc2cc(F)cc(C#N)c2)c2c1[C@H](O)C(F)(F)C2] |
| 247 | 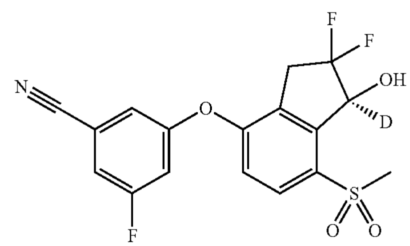 [SMILES: [2H][C@]1(O)c2c(S(C)(=O)=O)ccc(Oc3cc(F)cc(C#N)c3)c2CC1(F)F] |
| 251 | 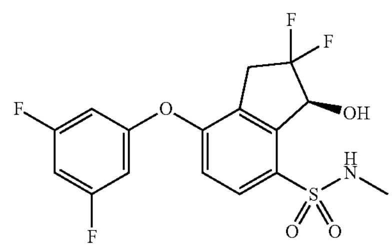 [SMILES: CNS(=O)(=O)c1ccc(Oc2cc(F)cc(F)c2)c2c1[C@H](O)C(F)(F)C2] |
| 252 | 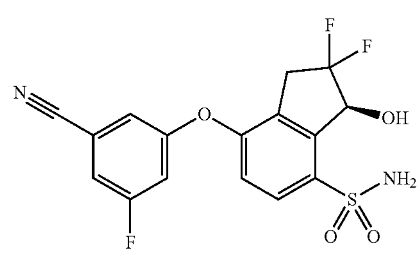 [SMILES: N#Cc1cc(F)cc(Oc2ccc(S(N)(=O)=O)c3c2CC(F)(F)[C@H]3O)c1] |
| 254 | 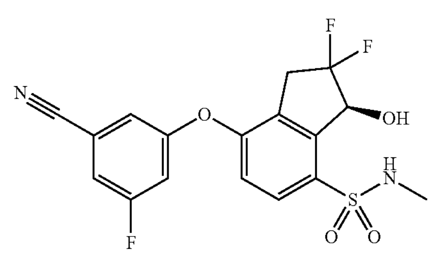 [SMILES: CNS(=O)(=O)c1ccc(Oc2cc(F)cc(C#N)c2)c2c1[C@H](O)C(F)(F)C2] |

-continued

| Example Number | Structure |
|---|---|
| 256 | 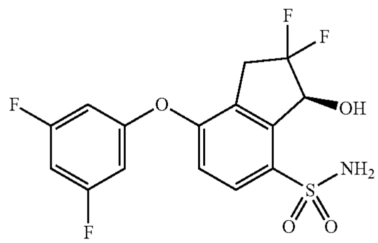 [SMILES: NS(=O)(=O)c1ccc(Oc2cc(F)cc(F)c2)c2c1[C@H](O)C(F)(F)C2] |
| 260 | 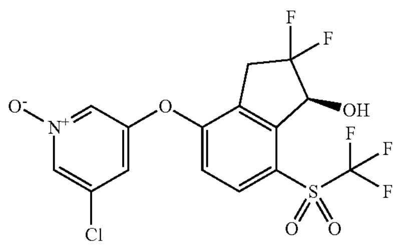 [SMILES: O=S(=O)(c1ccc(Oc2cc(Cl)c[n+]([O-])c2)c2c1[C@H](O)C(F)(F)C2)C(F)(F)F] |
| 266 | 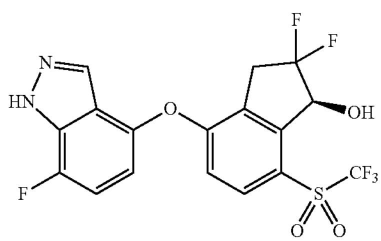 [SMILES: O=S(=O)(c1ccc(Oc2ccc(F)c3[nH]ncc23)c2c1[C@H](O)C(F)(F)C2)C(F)(F)F] |
| 267 | 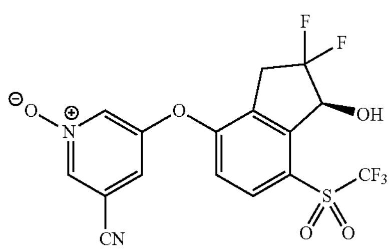 [SMILES: N#Cc1cc(Oc2ccc(S(=O)(=O)C(F)(F)F)c3c2CC(F)(F)[C@H]3O)c[n+]([O-])c1] |
| 270 | 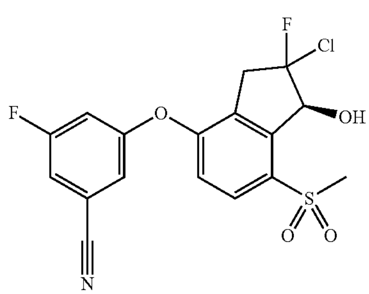 [SMILES: CS(=O)(=O)c1ccc(Oc2cc(F)cc(C#N)c2)c2c1[C@H](O)C(F)(Cl)C2] |
| 273 | 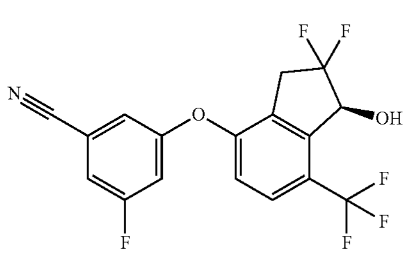 [SMILES: N#Cc1cc(F)cc(Oc2ccc(C(F)(F)F)c3c2CC(F)(F)[C@H]3O)c1] |

-continued

| Example Number | Structure |
|---|---|
| 274 | 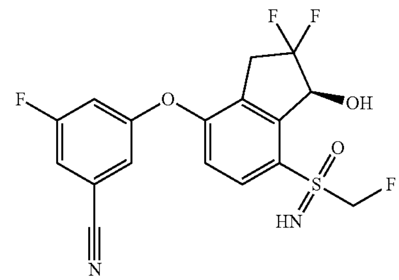 [SMILES: N#Cc1cc(F)cc(Oc2ccc(S(=N)(=O)CF)c3c2CC(F)(F)[C@H]3O)c1] |
| 275 | 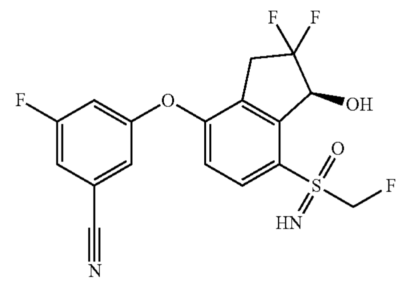 [SMILES: N#Cc1cc(F)cc(Oc2ccc(S(=N)(=O)CF)c3c2CC(F)(F)[C@H]3O)c1] |
| 276 | 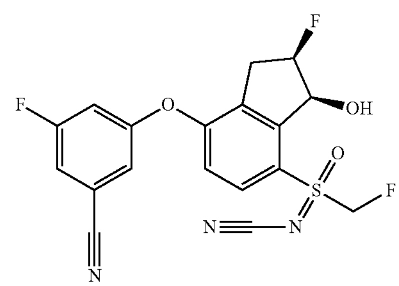 [SMILES: N#CN=S(=O)(CF)c1ccc(Oc2cc(F)cc(C#N)c2)c2c1[C@H](O)[C@H](F)C2] |
| 277 | 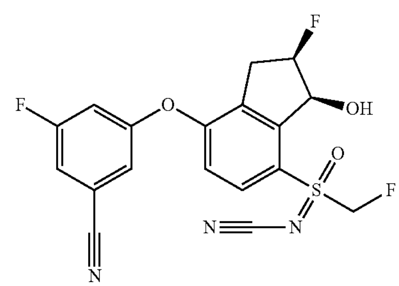 [SMILES: N#CN=S(=O)(CF)c1ccc(Oc2cc(F)cc(C#N)c2)c2c1[C@H](O)[C@H](F)C2] |
| 285 | 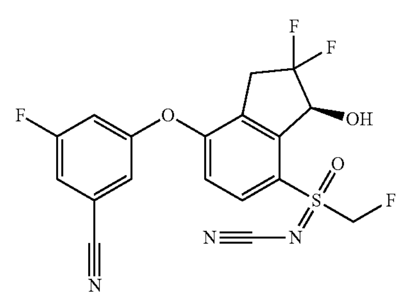 [SMILES: N#CN=S(=O)(CF)c1ccc(Oc2cc(F)cc(C#N)c2)c2c1[C@H](O)C(F)(F)C2] |

49
-continued
| Example Number | Structure |
|---|---|
| 286 | 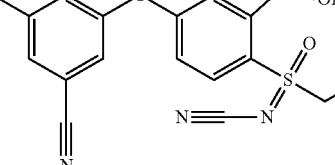 |
| 289 | 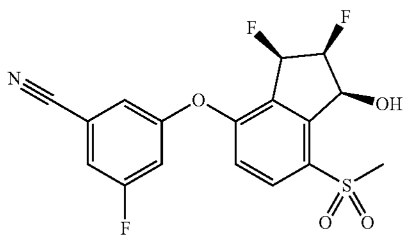 [SMILES: CS(=O)(=O)c1ccc(Oc2cc(F)cc(C#N)c2)c2c1[C@H](O)[C@H](F)[C@@H]2F] |
| 290 | 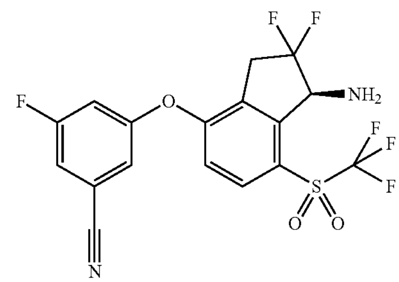 [SMILES: N#Cc1cc(F)cc(Oc2ccc(S(=O)(=O)C(F)(F)F)c3c2CC(F)(F)[C@H]3N)c1] |
| 292 | 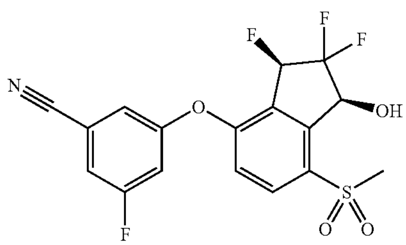 [SMILES: CS(=O)(=O)c1ccc(Oc2cc(F)cc(C#N)c2)c2c1[C@H](O)C(F)(F)[C@@H]2F] |
| 302 | 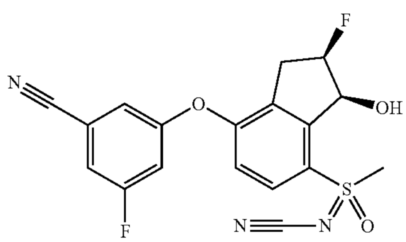 [SMILES: CS(=O)(=NC#N)c1ccc(Oc2cc(F)cc(C#N)c2)c2c1[C@H](O)[C@H](F)C2] |
| 303 | 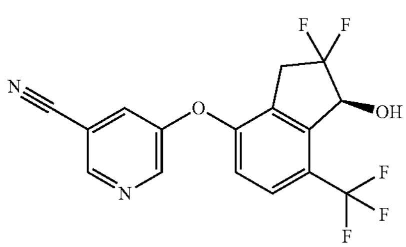 [SMILES: N#Cc1cncc(Oc2ccc(C(F)(F)F)c3c2CC(F)(F)[C@H]3O)c1] |
50
-continued
| Example Number | Structure |
|---|---|
| 304 | 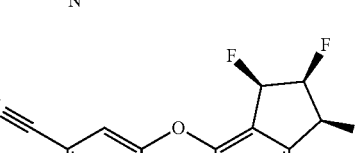 |
| 305 | 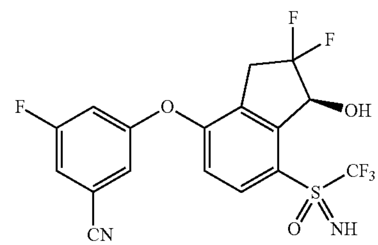 [SMILES: N#Cc1cc(F)cc(Oc2ccc(S(=N)(=O)C(F)(F)F)c3c2CC(F)(F)[C@H]3O)c1] |
| 306 | 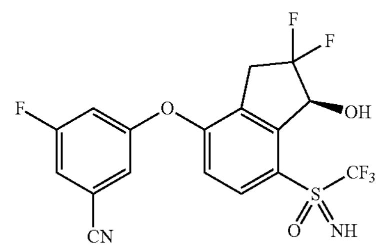 [SMILES: N#Cc1cc(F)cc(Oc2ccc(S(=N)(=O)C(F)(F)F)c3c2CC(F)(F)[C@H]3O)c1] |
| 309 | 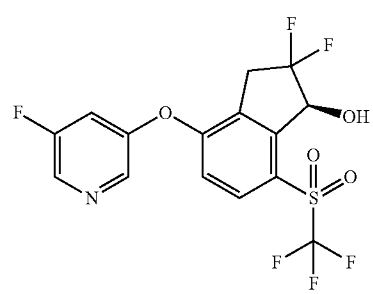 [SMILES: O=S(=O)(c1ccc(Oc2cncc(F)c2)c2c1[C@H](O)C(F)(F)C2)C(F)(F)F] |
| 310 | 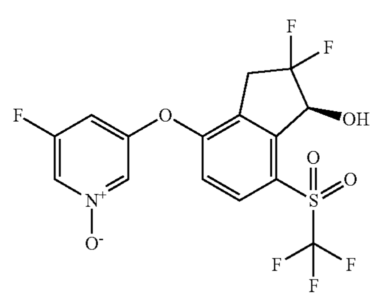 [SMILES: O=S(=O)(c1ccc(Oc2cc(F)c[n+]([O-])c2)c2c1[C@H](O)C(F)(F)C2)C(F)(F)F] |

| Example Number | Structure |
|---|---|
| 314 | 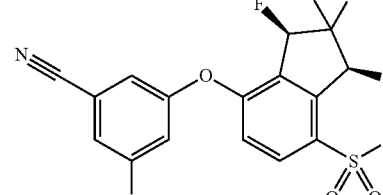 |
| 315 | 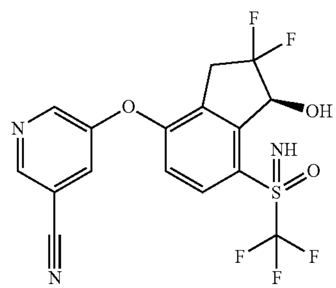 [SMILES: N#Cc1cncc(Oc2ccc(S(=N)(=O)C(F)(F)F)c3c2CC(F)(F)[C@H]3O)c1] |
| 316 | 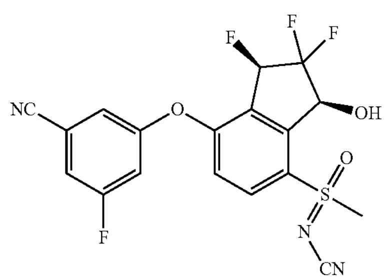 [SMILES: CS(=O)(=NC#N)c1ccc(Oc2cc(F)cc(C#N)c2)c2c1[C@H](O)C(F)(F)[C@@H]2F] |
| 317 | 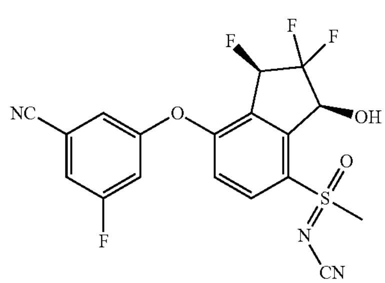 [SMILES: CS(=O)(=NC#N)c1ccc(Oc2cc(F)cc(C#N)c2)c2c1[C@H](O)C(F)(F)[C@@H]2F] |
| 336 | 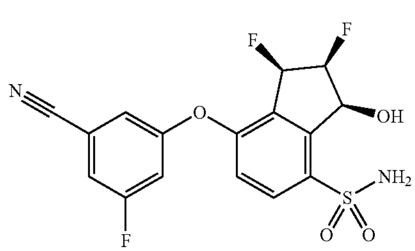 [SMILES: N#Cc1cc(F)cc(Oc2ccc(S(N)(=O)=O)c3c2[C@@H](F)[C@@H](F)[C@H]3O)c1] |

| Example Number | Structure |
|---|---|
| 338 | 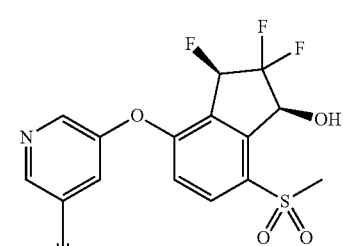 |
| 342 | 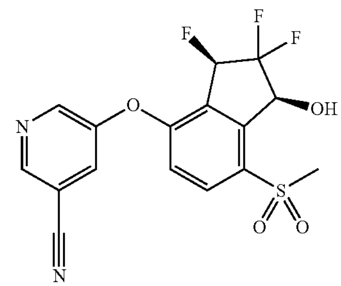 [SMILES: CS(=O)(=O)c1ccc(Oc2cncc(C#N)c2)c2c1[C@H](O)C(F)(F)[C@@H]2F] |

Method of Use

The chemical entities described herein are useful for the treatment, or in the preparation of a medicament for the treatment of HIF-2α mediated diseases, including but are not limited to, cancer. A role of HIF-2α in tumorigenesis and tumor progression has been implicated in many human cancers. One of the strongest links between HIF-2α activity and disease is in renal cell carcinoma (RCC), including clear cell renal cell carcinoma (ccRCC) (reviewed in Shen and Kaelin, *Seminars in Cancer Biology* 23: 18-25, 2013). Greater than eighty percent of ccRCC have defective VHL either through deletion, mutation or post-translational modification. Defective VHL in ccRCC results in constitutively active HIF-α proteins regardless of the oxygen level. A series of studies using gain-of-function and loss-of-function approaches in xenograft mouse models have clearly demonstrated that HIF-2α is the key oncogenic substrate of VHL (Kondo, et al. *Cancer Cell* 1: 237-246, 2002; Kondo, et al. *PLoS Biology* 1: 439-444, 2002; Maranchi, et al. *Cancer Cell* 1: 247-255, 2002; Zimmer, et al. *Mol. Cancer Res* 2: 89-95, 2004). In these studies, biological knockdown of HIF-2α in VHL-null tumors inhibited tumor formation in a manner analogous to reintroduction of VHL. And, overexpression of HIF-2α overcame the tumor suppressive role of VHL. In addition, single nucleotide polymorphism in HIF-2α that rendered HIF-2α refractory to PHD-mediated degradation have been linked to increased risk of kidney cancer. Furthermore, immunohistochemical analyses of morphologically normal renal tubular cells show HIF activation, thereby supporting an early, dominant pathologic role in the disease (Mandriota, et al. *Cancer Cell* 1: 459-468, 2002; Raval, et al. *Mol. Cell. Biol.* 25: 5675-5686, 2005). In addition to their role in tumor initiation, the VHL-HIF-2α axis has been implicated in ccRCC tumor metastasis (Vanharanta et al. *Nature Medicine* 19: 50-59, 2013). Genetic studies on HIF-1α have led to the hypothesis that HIF-1α acts as a tumor suppressor in kidney cancer. HIF-1α resides on a frequently deleted chromosome in ccRCC and deletion of HIF-1α increased tumor growth in mice (reviewed in Shen and Kaelin, *Seminars in Cancer Biology* 23: 18-25, 2013). Taken together, these data overwhelmingly support the potential therapeutic utility of HIF-2α targeted agents for the treatment of ccRCC.

VHL disease is an autosomal dominant syndrome that not only predisposes patients to kidney cancer (~70% lifetime risk), but also to hemangioblastomas, pheochromocytoma and pancreatic neuroendocrine tumors. VHL disease results in tumors with constitutively active HIF-α proteins with the majority of these dependent on HIF-2a activity (Maher, et al. *Eur. J. Hum. Genet.* 19: 617-623, 2011). HIF-2α has been linked to cancers of the retina, adrenal gland and pancreas through both VHL disease and activating mutations. Recently, gain-of-function HIF-2α mutations have been identified in erythrocytosis and paraganglioma with polycythemia (Zhuang, et al. *NEJM* 367: 922-930, 2012; Percy, et al. *NEJM* 358: 162-168, 2008; and Percy, et al. *Am. J. Hematol.* 87: 439-442, 2012). Notably, a number of known HIF-2α target gene products (e.g., VEGF, PDGF, and cyclin D1) have been shown to play pivotal roles in cancers derived from kidney, liver, colon, lung, and brain. In fact, therapies targeted against one of the key HIF-2α regulated gene products, VEGF, have been approved for the treatment of these cancers.

Due to poor vascularization, intratumor environment of rapidly growing tumors are normally hypoxic, a condition that activates HIF-α which supports tumor cell survival and proliferation. Studies have demonstrated a correlation between HIF-2a overexpression and poor prognosis in multiple cancers including astrocytoma, breast, cervical, colorectal, glioblastoma, glioma, head and neck, hepatocellular, non-small cell lung, melanoma, neuroblastoma, ovarian, and prostate, thereby providing support for HIF-2α as a therapeutic target for these diseases (reviewed in Keith, et al. *Nature Rev. Cancer* 12: 9-22, 2012). Also, epigenetic inactivation of VHL expression and thus constitutive activation of HIF-α proteins has been found in many cancers including RCC, multiple myeloma, retinoblastoma, NSCLC, pancreatic endocrine tumors, squamous cell carcinoma, acute myeloid leukemia, myelodysplastic syndrome, and esophageal squamous cell carcinoma (reviewed in Nguyen, et al. *Arch. Pharm. Res* 36: 252-263, 2013).

Specifically, HIF-2α has been demonstrated to play an important role in APC mutant colorectal cancer through control of genes involved in proliferation, iron utilization and inflammation (Xue, et al. *Cancer Res* 72: 2285-2293, 2012; and Xue and Shah, *Carcinogenesis* 32: 163-169, 2013). In hepatocellular carcinoma (HCC), knock-down of HIF-2a in preclinical models reduced the expression of VEGF and cyclin D1 genes both in vitro and in vivo, resulting in inhibition of cell proliferation and tumor growth (He, et al. *Cancer Sci.* 103: 528-534, 2012). Additionally, fifty percent of NSCLC patients have overexpression of HIF-2α protein, which correlates strongly with VEGF expression and most importantly poor overall survival. HIF-1α is also overexpressed in many lung cancer patients. However, in contrast to HIF-2a, HIF-1α expression does not correlate with reduced overall survival (Giatromanolaki, et al. *Br. J Cancer* 85: 881-890, 2001). In mice engineered with both non-degradable HIF-2α and mutant KRAS tumors, increased tumor burden and decreased survival were observed when compared to mice with only mutant KRAS expression (Kim, et al. *Clin. Invest.* 119: 2160-2170, 2009). This research demonstrates that HIF-2α contributes to tumor growth and progression in lung cancer and suggests a relationship with clinical prognosis in NSCLC. Furthermore, HIF-2α activity has been linked to the progression of chronic obstructive pulmonary disease (COPD) and lung cancer in mouse models (Karoor, et al. *Cancer Prev. Res.* 5: 1061-1071, 2012). However, genetic deletion of HIF-2α in a KRAS mutant mouse model increased tumor growth through the reduction of Scgb3a1 tumor suppressor gene (Mazumdar, et al. *PNAS* 107: 14182-14187, 2010). In total, these studies implicate HIF-2α in lung cancer progression but suggest that maintenance of the basal HIF-2a level maybe beneficial. HIF-2α activity has also been demonstrated to be important in central nervous system cancers (Holmquist-Mengelbier, et al. *Cancer Cell* 10: 413-423, 2006 and Li, et al. *Cancer Cell* 15: 501-513, 2009). In preclinical animal models of neuroblastoma, HIF-2α knockdown reduced tumor growth. Additionally, high protein levels of HIF-2α were correlated with advanced disease, poor prognosis and high VEGF levels. Similarly, poor survival in glioma correlated with HIF-2α expression. And, inhibition of HIF-2α in glioma stem cells reduced cell proliferation, and survival in vitro and tumor initiation in vivo. Interestingly, while HIF-1α is expressed in both neural progenitors and brain tumor stem cells, HIF-2α is only expressed in the latter. Moreover, glioma survival is correlated to HIF-2α but not HIF-1α levels.

Approximately 50% of cancer patients receive radiation treatment, either alone or in combination with other therapies. Tumor hypoxia has long been associated with resistance to radiation therapy. Therefore, inhibition of HIF-2α could improve radiation response of cancer/tumor cells. Bhatt and co-workers showed that decreasing levels of HIF-2a leads to increased sensitivity to ionizing radiation in renal cell carcinoma cell lines (Bhatt, et al. *BJU Int.* 102: 358-363, 2008). Furthermore, Bertout and co-workers demonstrated that HIF-2α inhibition enhances effectiveness of radiation through increased p53-dependent apoptosis (Bertout, et al. *PNAS* 106: 14391-14396, 2009).

Multiple groups have reported attempts to discover inhibitors of HIF-α activity. These efforts include irreversible inhibitors, small molecules, cyclic peptides and natural products (Cardoso, et al. *Protein Sci.* 21: 1885-1896, 2012, Miranda, et al. 2013, Mooring, et al. *J. Am. Chem. Soc.* 135: 10418-10425, 2011, Tan, et al. *Cancer Res.* 65: 605-612, 2005, and WO2013011033 and WO2013057101). Some indirect, non-specific approaches to block HIF-α protein activity have also been described (Zimmer, et al. *Mole Cell* 32: 838-848, 2008 and Carew, et al. *PLoS ONE* 7: e31120, 2012). The reported molecular mechanisms of these approaches include decreased HIF-1α mRNA levels, decreased HIF-1α protein synthesis, increased HIF-1α degradation, decreased HIF subunit heterodimerization, decreased HIF binding to DNA, and decreased HIF transcriptional activity. For example, acriflavine, an antibacterial agent, is reported to bind directly to the PAS-B domain of HIF-1α and HIF-2a and block their interaction with HIF-1β, thereby blocking HIF-dependent gene transcription and leading to impaired tumor growth and vascularization (Lee, et al. *PNAS* 106: 17910-17915, 2009). Furthermore, HIF-1α protein synthesis has reported to be blocked by various molecules including rapamycin, temsirolimus, everolimus, cardiac glycosides, microtubule targeting agents (taxotere), and topoisomerase inhibitors (topotecan). Drugs that induce degradation of HIF-1α include HSP90 inhibitors, e.g., 17-allylamino-17-demethoxygeldanamycin, and antioxidants, such as ascorbate. Anthracyclines, such as doxorubicin and daunorubicin, bind to DNA and block the binding of HIF-1α and HIF-2α in cultured cells and also block HIF-1α-dependent expression of angiogenic growth factors, leading to impaired tumor growth (Semenza, *Trends Pharmacol. Sci.*

33: 207-214, 2012). However, attempts to identify selective molecules that directly interfere with HIF-2α function have been met with little success, evidenced by the current paucity of clinical (or pre-clinical) programs targeting this transcription factor.

Recent work from Professors Kevin Gardner and Richard Bruick at the University of Texas Southwestern Medical Center has revealed a unique ligand-binding pocket in a select domain of HIF-2α that is required for HIF-2α transcriptional activity. High-resolution structural data gathered against one of the isolated HIF-2α PAS domains, both alone and in complexes, revealed a large internal hydrated cavity (280 $A^3$)—highly unusual for a protein of this size (Scheuermann et al. *PNAS* 106: 450-455, 2009 and Key et al. *J. Am. Chem. Soc.*, 131: 17647-17654, 2009). Furthermore, small molecule HIF-2α PAS B domain binders have been identified (Rogers, et al. *J. Med. Chem.* 56: 1739-1747, 2013). Binding of these ligands leads to inhibition of HIF-2α transcriptional activity in cells (Scheuermann, et al. *Nat Chem Biol.* 9: 271-276, 2013).

In one aspect, the compounds or their pharmaceutical compositions described herein are useful as inhibitors of HIF-2α. Thus, without wishing to be bound by any particular theory, the compounds or their pharmaceutical compositions described herein are particularly useful for treating or lessening the severity of a disease, condition, or disorder where activation of HIF-2α and/or one or more downstream processes associated with the activation or over activation of HIF-2α are implicated in the disease, condition, or disorder. Accordingly, the present invention provides a method for treating or lessening the severity of a disease, condition, or disorder where activation or over activation of HIF-2α is implicated in the disease state.

In another aspect, the present disclosure provides a method of treating renal cell carcinoma of a subject with a compound described herein or a pharmaceutically acceptable salt thereof. RCC is one of the most common forms of kidney cancer arising from the proximal convoluted tubule. RCC is also known as hypernephroma. Initial treatment is commonly a radical or partial nephrectomy and remains the mainstay of curative treatment. Where the tumor is confined to the renal parenchyma, the 5-year survival rate is 60-70%, but this is lowered considerably where metastasis have spread. RCC is generally resistant to radiation therapy and chemotherapy, although some cases respond to immunotherapy. Targeted cancer therapies such as sunitinib, temsirolimus, bevacizumab, axitinib, pazopanib, interferon-alpha, and sorafenib have improved the outlook for RCC (progression-free survival), although they have not yet demonstrated improved survival rate. Subtypes of RCC include, but are not limited to, clear cell renal cell carcinoma, papillary renal cell carcinoma, and chromophobe renal cell carcinoma.

Pharmaceutical Compositions and Dosage Forms

A compound or a pharmaceutically acceptable salt thereof may be formulated as a pharmaceutical composition prior to being administered to a subject. The pharmaceutical composition may comprise additional additives such as pharmaceutically acceptable excipients, carriers, and vehicles. Suitable pharmaceutically acceptable excipients, carriers, and vehicles include but are not limited to processing agents and drug delivery modifiers, for example, ethylene glycol, calcium phosphate, magnesium stearate, talc, monosaccharides, disaccharides, starch, gelatin, cellulose, methyl cellulose, hydroxypropyl cellulose, sodium carboxymethyl cellulose, dextrose, hydroxypropyl-β-cyclodextrin, polyvinylpyrrolidine, low melting waxes, ion exchange resins, and the like, as well as combinations of any two or more thereof.

A pharmaceutical composition comprising a compound or a pharmaceutically acceptable salt thereof may be administered enterally, orally, parenterally, sublingually, rectally, or topically in a unit dosage containing pharmaceutically acceptable excipients, carriers, or vehicles. Generally, the unit dosage is a dose sufficient for the compound or its pharmaceutically acceptable salt to achieve desired therapeutic effect. Suitable modes of administration include oral, subcutaneous, intra-arterial, intramuscular, intraperitoneal, intranasal, intraocular, subdural, vaginal, gastrointestinal, and the like. The compound or its salt can also be administered as prodrugs, wherein the prodrugs undergo transformation in the body of the treated subject to form a therapeutically active ingredient.

A pharmaceutical composition comprising a compound or a pharmaceutically acceptable salt described herein may be in any form suitable for the intended purpose of administration, including, for example, a solid or a liquid dosage form. The liquid dosage form may include solution, suspension, softgel, syrup, elixir, or emulsion. Liquid carriers are typically used in preparing solutions, suspensions, and emulsions. Liquid carriers contemplated for use in the practice of the present invention include, for example, water, saline, ethylene glycol, propylene glycol, pharmaceutically acceptable organic solvents, pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, sunflower oil, and the like. For parenteral administration, the carrier can also be an oily ester such as isopropyl myristate, and the like. Compositions of the present invention may also be in the form of nanoparticles, microparticles, microcapsules, liposomal encapsulates, and the like, as well as combinations of any two or more thereof. Solid dosage forms for oral administration may include capsule, tablet, pill, powder, and granule. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

In cases of a solid dosage form, examples of daily dosages of the compounds described herein which can be used are an effective amount within the dosage range of about 0.001 mg to about 2 mg per kilogram of body weight, about 0.001 mg to about 5 mg per kilogram of body weight, about 0.001 mg to about 10 mg per kilogram of body weight, about 0.001 mg to about 20 mg per kilogram of body weight, about 0.001 mg to about 50 mg per kilogram of body weight, about 0.001 mg to about 100 mg per kilogram of body weight, about 0.001 mg to about 200 mg per kilogram of body weight, or about 0.001 mg to about 300 mg per kilogram of body weight. When administered orally or by inhalation, examples of daily dosages are an effective amount within the dosage range of about 0.1 mg to about 10 mg, or about 0.1 mg to about 20 mg, or about 0.1 mg to about 30 mg, or about 0.1 mg to about 40 mg, or about 0.1 mg to about 50 mg, or about 0.1 mg to about 60 mg, or about 0.1 mg to about 70 mg, or about 0.1 mg to about 80 mg, or about 0.1 mg to about 90 mg, or about 0.1 mg to about 100 mg, or about 0.1 mg to about 200 mg, or about 0.1 mg to about 300 mg, or about 0.1 mg to about 400 mg, or about 0.1 mg to about 500 mg, or about 0.1 mg to about 600 mg, or about 0.1 mg to about 700 mg, or about 0.1 mg to about 800 mg, or about 0.1 mg to about 900 mg, or about 0.1 mg to about 1 g, or about 20 mg to 300 mg, or about 20 mg to 500 mg, or about 20 mg to 700 mg, or about 20 mg to 1000 mg, or about 50 mg to 1500 mg, or about 50 mg to 2000 mg. Preferred fixed daily doses include about 1 mg, about 2 mg, about 3 mg, about 4 mg, about 5 mg, about 6 mg, about 7 mg, about 8 mg, about 9 mg, about 10 mg, about 12 mg, about 15 mg, about 18 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, about 1000 mg, about 1200 mg, about 1500 mg, or about 2000 mg, independently of body weight. However, it is understood that pediatric patients may require smaller dosages, and depending on the severity of the disease and condition of the patient, dosages may vary. The compound will preferably be administered once daily, but may be administered two, three or four times daily, or every other day, or once or twice per week.

When formulated as a liquid, the concentration of the compounds described herein may be about 0.01 mg/ml to about 0.1 mg/ml or about 0.1 mg/ml to about 1 mg/ml, but can also be about 1 mg/ml to about 10 mg/ml or about 10 mg/ml to about 100 mg/ml. The liquid formulation could be a solution or a suspension. When formulated as a solid, for example as a tablet or as a powder for inhalation, the concentration, expressed as the weight of a compound divided by total weight, will typically be about 0.01% to about 0.1%, about 0.1% to about 1%, about 1% to about 10%, about 10% to about 20%, about 20% to about 40%, about 40% to about 60%, about 60% to about 80%, or about 80% to about 100%.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., "Methods in Cell Biology", Volume XIV, ISBN: 978-0-12-564114-2, Academic Press, New York, N.W., p. 33 (1976) and Medina, Zhu, and Kairemo, "Targeted liposomal drug delivery in cancer", *Current Pharm. Des.* 10: 2981-2989, 2004. For additional information regarding drug formulation and administration, see "Remington: The Science and Practice of Pharmacy," Lippincott Williams & Wilkins, Philadelphia, ISBN-10: 0781746736, 21$^{st}$ Edition (2005).

Method of Making

Compounds disclosed herein may be prepared by routes described below. Materials used herein are either commercially available or prepared by synthetic methods generally known in the art. These schemes are not limited to the compounds listed or by any particular substituents, which are employed for illustrative purposes. Although various steps are described and depicted in Schemes 1-12, the steps in some cases may be performed in a different order than the order shown. Various modifications to these synthetic reaction schemes may be made and will be suggested to one skilled in the art having referred to the disclosure contained in this application. Numberings or R groups in each scheme do not necessarily correspond to that of claims or other schemes or tables.

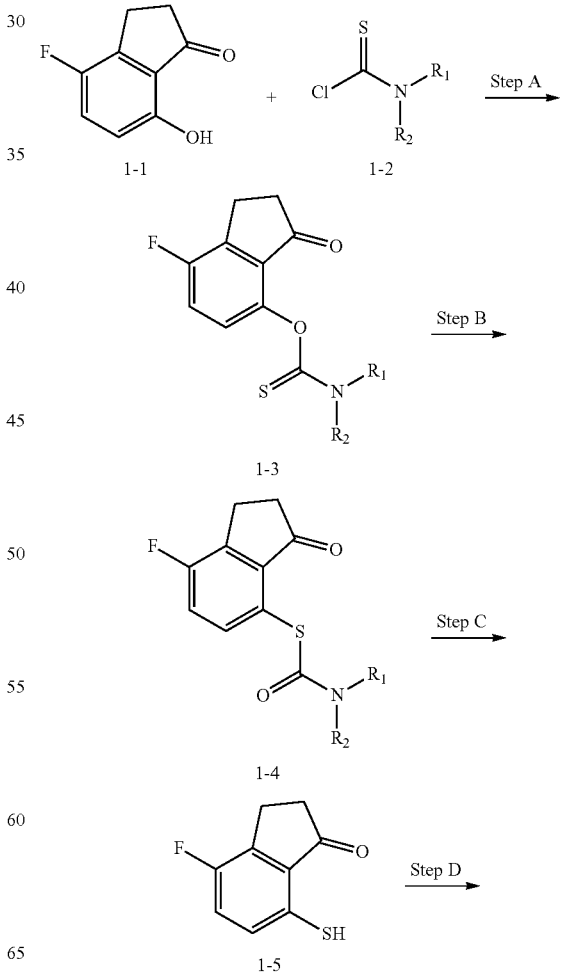

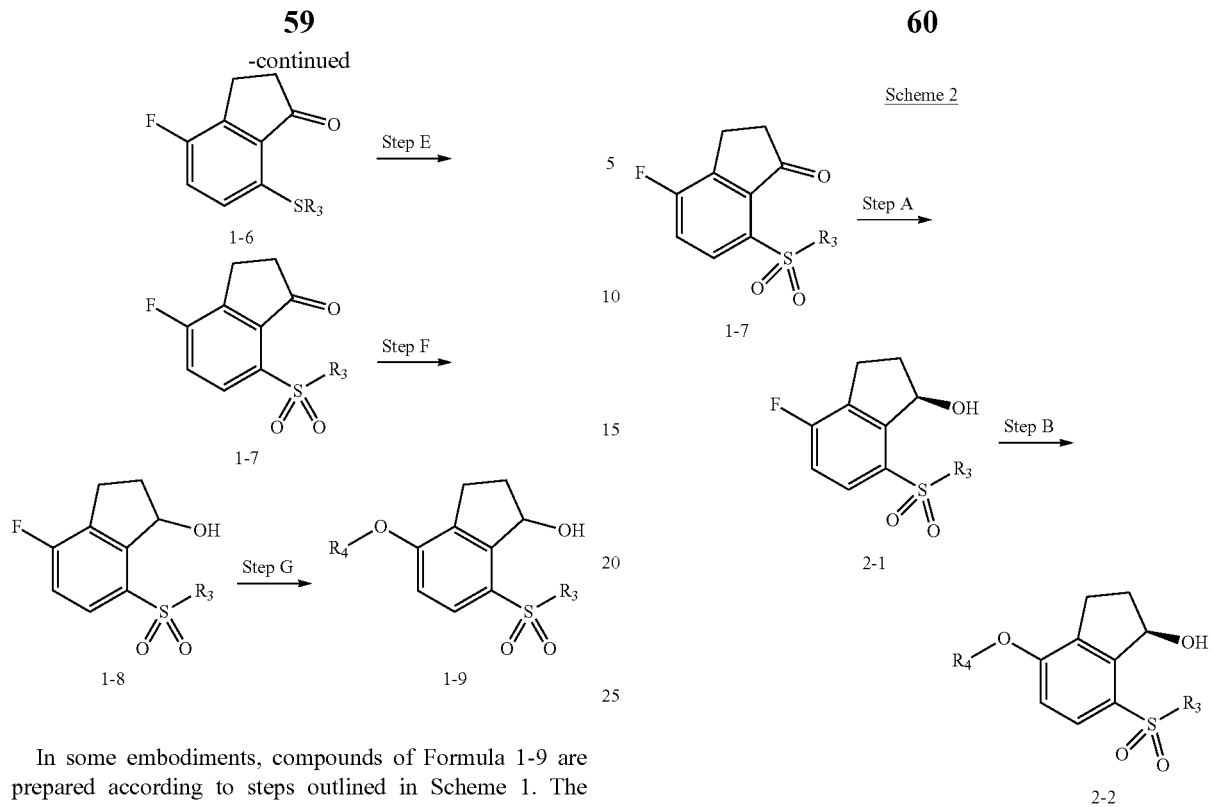

In some embodiments, compounds of Formula 1-9 are prepared according to steps outlined in Scheme 1. The synthesis starts with phenol 1-1. Reaction of 1-1 with chloride 1-2 (wherein $R_1$ and $R_2$ are independently alkyl) provides intermediate 1-3. The reaction may be carried out in a suitable organic solvent in the presence of a base. Suitable bases for the reaction include, but are not limited to, organic bases, for example, triethylamine, N,N-diisopropylethylamine, 1,4-diazabicyclo[2.2.2]octane, and inorganic bases, for example, sodium hydroxide, cesium carbonate, cesium bicarbonate, sodium carbonate, and potassium carbonate. Compound 1-3 is then subjected to a rearrangement reaction to give compound 1-4. Elevated temperature may be needed for the rearrangement to occur. The temperature may be in a range of 100° C. to 300° C. In some embodiments, the temperature is in a range of 180° C. to 240° C. Hydrolysis of compound 1-4 provides thiophenol 1-5, which is alkylated to provide compound 1-6. A variety of alkyl group may be introduced. In some embodiments, $R_3$ is a C1-C4 alkyl. In a further embodiment, $R_3$ is a C1-C4 fluoroalkyl. Oxidation of compound 1-6 may be accomplished by a variety of methods known in the art, including but are not limited to, $RuCl_3$ catalyzed oxidation in the presence of $NaIO_4$, oxidation with m-chloroperbenzoic acid (mCPBA) and oxidation with Oxone®. The ketone in 1-7 is then reduced to give alcohol 1-8, which then undergoes a nucleophilic aromatic substitution (SNAr) reaction with a suitable substrate $R_4OH$ (wherein $R_4$ is aryl or heteroaryl) to give compounds of Formula 1-9. Temperature for carrying out the SNAr reaction may depend on the reactivity of both $R_4OH$ and/or compound 1-8. The reaction may be carried out in a temperature range from room temperature to 200° C. In some embodiments, the temperature range is from room temperature to 60° C. In some other embodiments, the temperature range is from 60° C. to 100° C. In some other embodiments, the temperature range is from 100° C. to 200° C.

In some other embodiments, compounds of Formula 1-9 are prepared asymmetrically to give compounds of Formula 2-2 (Scheme 2). For example, direct asymmetric reduction of ketone 1-7 (Step A) may be accomplished chemically or enzymatically. For a recent review on enzymatic reduction of ketones, see Moore, et al. *Acc. Chem. Res.* 40: 1412-1419, 2007. Examples of chemical asymmetric reduction of ketone include, but are not limited to, Corey-Bakshi-Shibata (CBS) reduction, asymmetric hydrogenation, and asymmetric transfer hydrogenation. In some embodiments, the asymmetric transfer hydrogenation is catalyzed by ruthenium. For examples of methods and catalysts for ruthenium catalyzed transfer hydrogenation, see U.S. Pat. Nos. 6,184,381 and 6,887,820. Exemplary catalysts for asymmetric transfer hydrogenation include, but are not limited to, the following (shown as the R, R configuration):

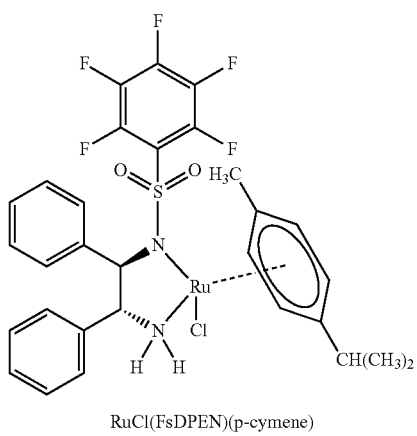

RuCl(FsDPEN)(p-cymene)

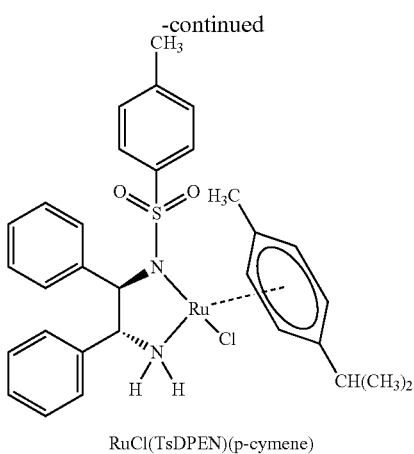

RuCl(TsDPEN)(p-cymene)

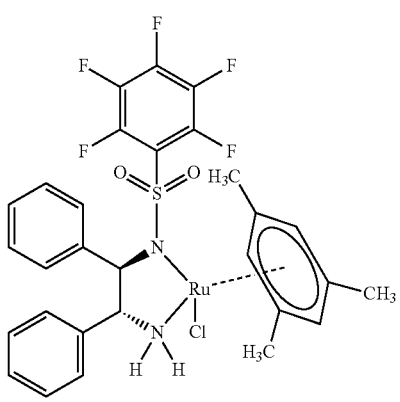

RuCl(TsDPEN)(mesitylene)

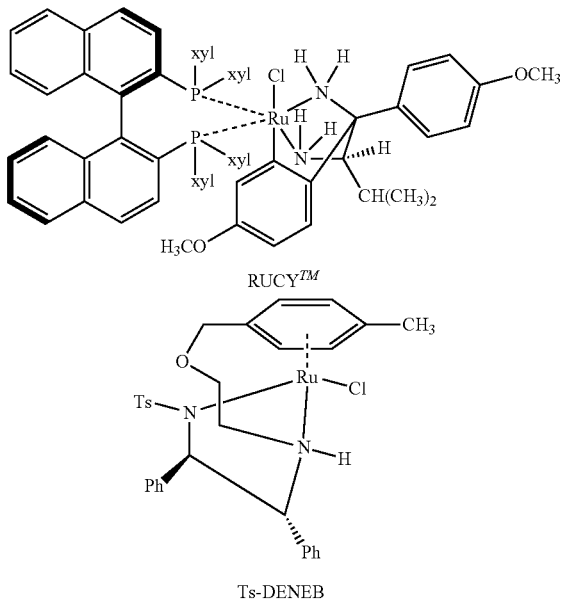

RUCY™

Ts-DENEB

The asymmetric transfer hydrogenation may be carried out at or below room temperature. In some embodiments, the asymmetric transfer hydrogenation is carried out at about 4° C. The alcohol product may have an enantiomeric excess of at least 90%, at least 91%, at least 92%, at least 93%, at least 94%, at least 95%, at least 96%, at least 97%, or even higher. It is well understood by one skilled in the art that changing the catalyst configuration will lead to a product with the opposite configuration. The chiral alcohol 2-1 can be coupled with a suitable substrate, for example a phenol, to give compounds of Formula 2-2 without significant loss of enantiomeric excess. The loss of enantiomeric excess (ee) in the coupling step for 2-2 may be less than about 1%, less than about 2%, less than about 3%, less than about 4%, less than about 5%, less than about 6%, or less than about 8%.

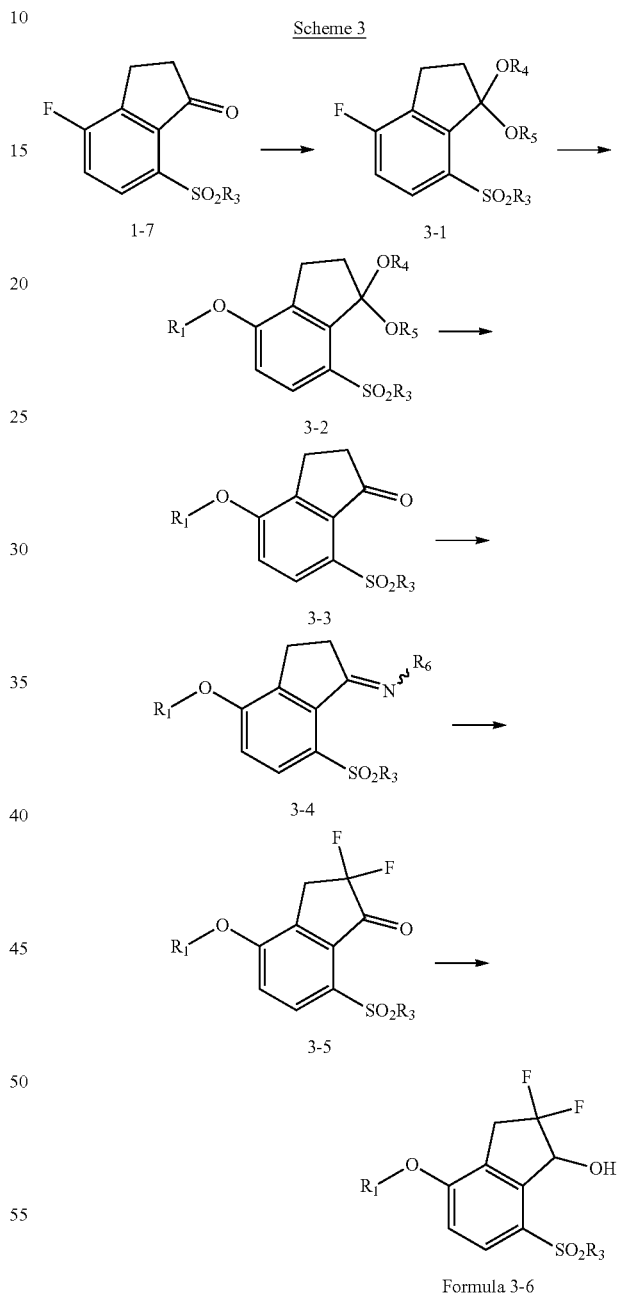

Scheme 3

In some embodiments, compounds of Formula 3-6 are prepared according to Scheme 3. The ketone in 1-7 is protected as a ketal to give compound 3-1, wherein each of $R_4$ and $R_5$ is independently an alkyl group. In addition, $R_4$ and $R_5$ may optionally be connected to form a cyclic ketal. Exemplary structures of ketal 3-1 include, but are not limited to, the following:

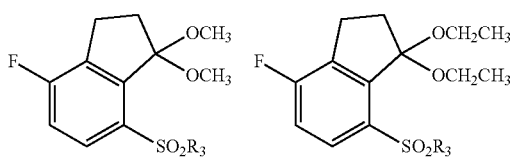

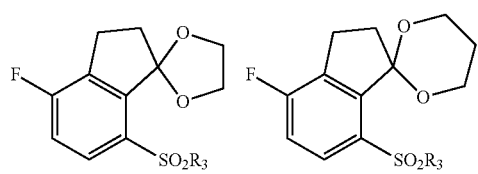

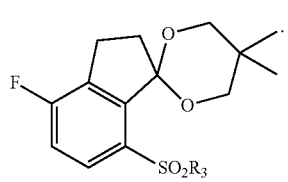

Ketal 3-1 and a suitable a suitable substrate R₁OH (wherein R₁ is aryl or heteroaryl) may undergo a nucleophilic aromatic substitution reaction (SNAr) to give biaryl ether 3-2. Similarly to the SNAr reaction described in Step G of Scheme 1, the reaction temperature may depend on the reactivity of ketal 3-1 and/or R₁OH. Following deprotection of the ketal in 3-2, the resulting ketone 3-3 is condensed with an amine to form imine 3-4, wherein R₆ is alkyl. The imine functional group in 3-4 may exist as a mixture of E, Z isomers. Fluorination of 3-4 can be accomplished with a fluorinating reagent, for example, 1-(chloromethyl)-4-fluoro-1,4-diazoniabicyclo[2.2.2]octane ditetrafluoroborate, to give difluoroketone 3-5 after acid hydrolysis. Finally, reduction of the ketone in 3-5 with a hydride donor gives compounds of Formula 3-6.

Scheme 4

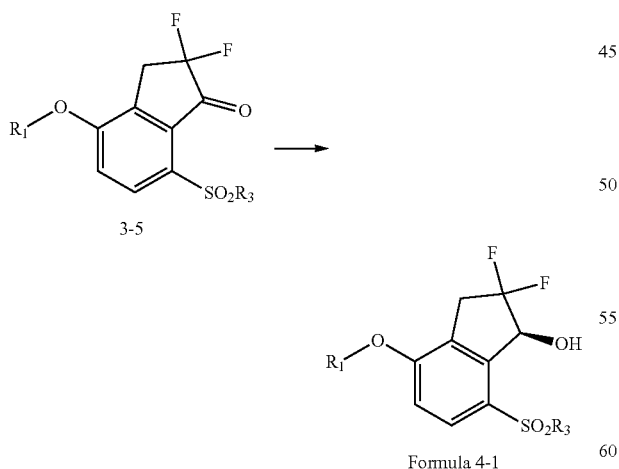

Similarly, compounds of Formula 4-1 can be prepared in asymmetric fashion by asymmetric reduction as outlined in Scheme 2. In some embodiments, the asymmetric reduction gives compounds of Formula 4-1 with an enantiomeric excess of at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or even higher. The enantiomeric excess of compounds of Formulae 2-2 and 4-1 may be determined by chrial HPLC or Mosher ester analysis. For determination of ee with Mosher ester, see Hoye, et al. *Natural Protocol*, 2: 2451, 2007.

Scheme 5

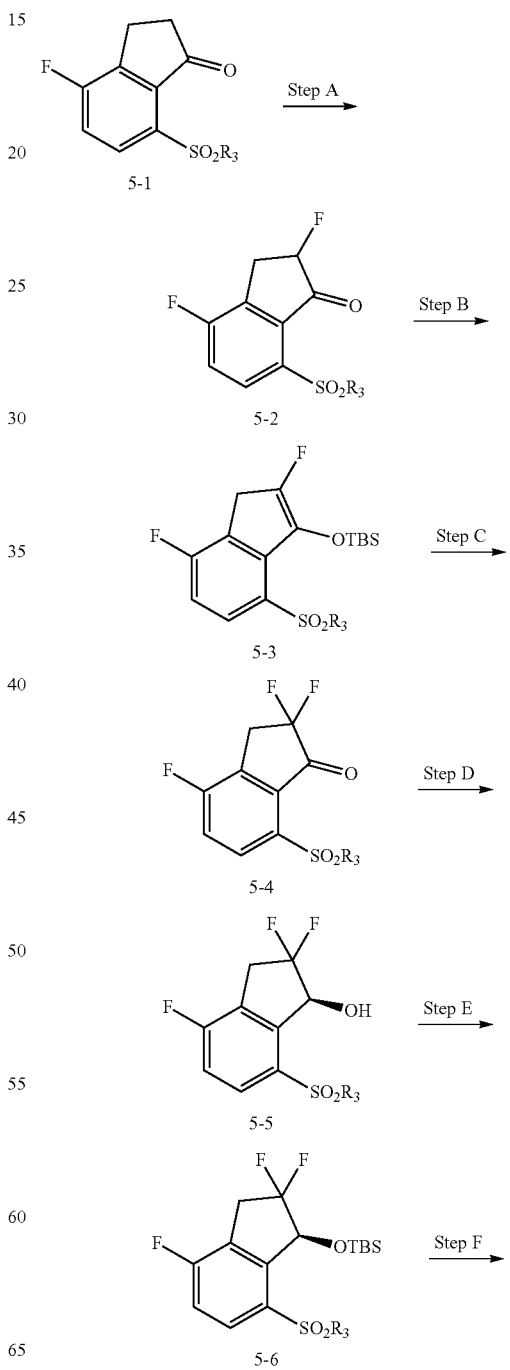

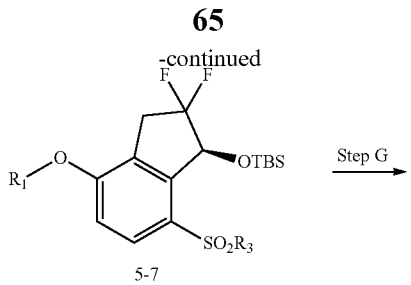

5-7

Step G →

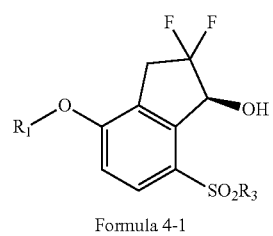

Formula 4-1

Alternatively, compounds of Formula 4-1 are prepared according to Scheme 5. The ketone in 5-1 is fluorinated to give monofluoroketone 5-2, which is then converted to a silylenol ether, e.g., TBS enol ether 5-3. Other silyl protecting groups, for example, triisopropylsilyl or diphenyl-t-butylsilyl, may also be used. The resulting enol ether is further fluorinated to give difluoroketone 5-4, which undergoes an asymmetric reduction, such as asymmetric transfer hydrogenation as described herein, to give chiral alcohol 5-5. Protection of the hydroxy moiety, followed by SNAr reaction and then deprotection provides compounds of Formula 4-1.

Scheme 6

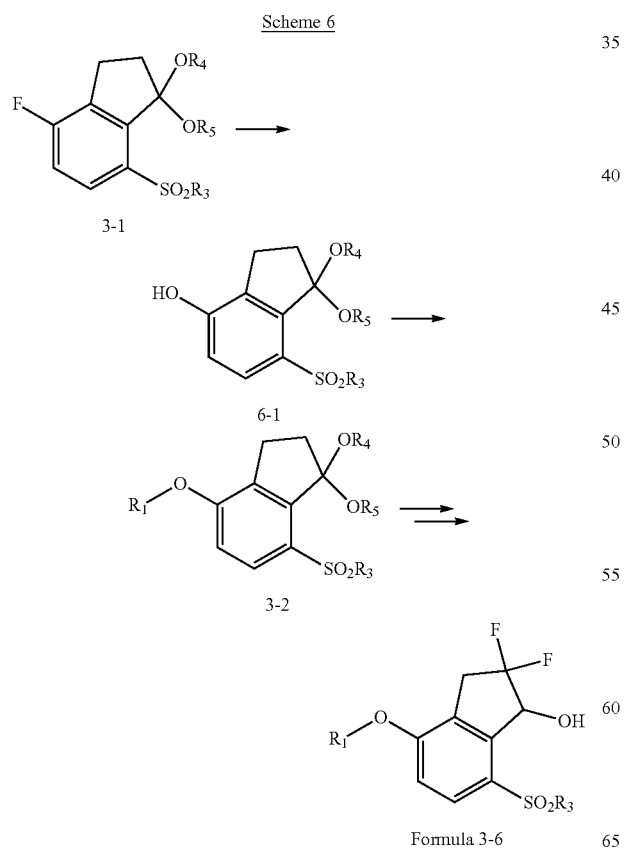

Alternatively, compounds of Formula 3-6 are prepared according to Scheme 6. Treatment of aryl fluoro 3-1 with a hydroxide source gives phenol 6-1. Suitable hydroxide sources include, but are not limited to, sodium hydroxide and potassium hydroxide. Suitable solvents for the reaction include, but are not limited to, DMSO, DMA, DMF or EtOH. The phenol 6-1 can react with an aryl or heteroaryl halide via a SNAr reaction to give biaryl ether 3-2, which can be converted to compounds of Formula 3-6 as described in Scheme 3.

Scheme 7

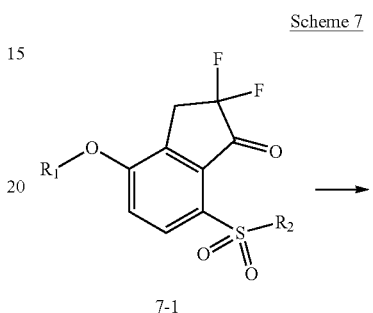

Compounds of Formula 7-3 and 7-4 may be prepared according to Scheme 7. For example, condensation of $NH_2R_3$ with difluoroketone 7-1, wherein $R_1$ is aryl or heteroaryl and $R_2$ is aryl, heteroaryl, alkyl, heteroalkyl, heterocycle, or cycloalkyl, gives intermediate 7-2. In some embodiments, $R_3$ is a chiral auxiliary. Exemplary chiral auxiliaries include but are not limited to the following:

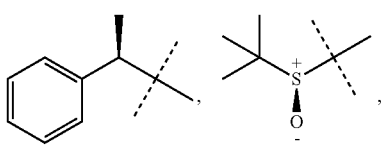

and their enantiomers thereof. Hydride reduction of intermediate 7-2 yields 7-3. At this stage, the chiral auxiliary may be cleaved under appropriate conditions, e.g., hydrogenation or acid treatment, to give chiral secondary amine 7-4. In some other embodiments, when compounds of Formula 7-3 are desirable, wherein $R_3$ is not hydrogen, asymmetric hydrogenation or asymmetric transfer hydrogenation is applied on intermediate 7-2 to give compounds of Formula 7-3. For a review on asymmetric hydrogenation and asymmetric transfer hydrogenation, see Iwao Ojima ed. *Catalytic Asymmetric Synthesis*, Wiley-VCH, Inc., 2000, ISBN 0-471-29805-0.

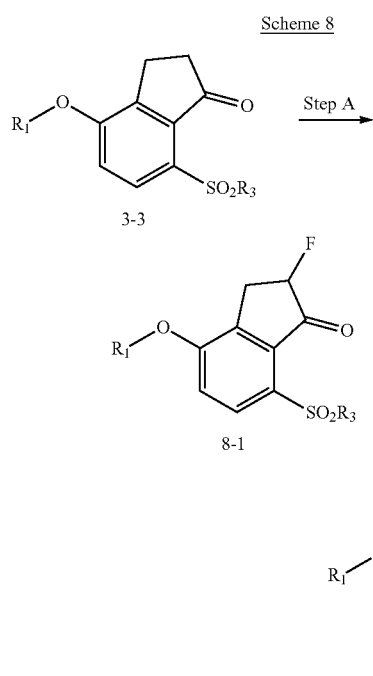

In some embodiments, compounds of Formula 8-2 are prepared according to Scheme 8. For example, ketones of Formula 3-3 is monofluorinated to give monofluoroketones of Formula 8-1. The monofluorination can be achieved with a variety of fluorinating reagents, e.g., N-Fluoro-o-benzenedisulfonimide, acetyl hypofluorite, Accufluor®, Selectfluor®, Selectfluor® II, or N-Fluorobenzenesulfonimide, in the presence or absence of a base. The compounds of Formula 8-1 are reduced to give compounds of Formula 8-2. In some cases, the reduction is highly diasteroselective to give compounds of Formula 8-2 with greater than 80%, greater than 82%, greater than 84%, greater than 86%, greater than 88%, greater than 90%, greater than 92%, greater than 94%, greater than 96%, or even greater than 96% diasteroselectivity. In some cases, the reduction is highly enantioselective to give compounds of Formula 8-2 with greater than 80%, greater than 82%, greater than 84%, greater than 86%, greater than 88%, greater than 90%, greater than 92%, greater than 94%, greater than 96%, or even greater than 96% enantioselectivity. Reduction conditions to achieve high enantioselectivity include, but are not limited to, asymmetric transfer hydrogenation and enzymatic reduction as described herein.

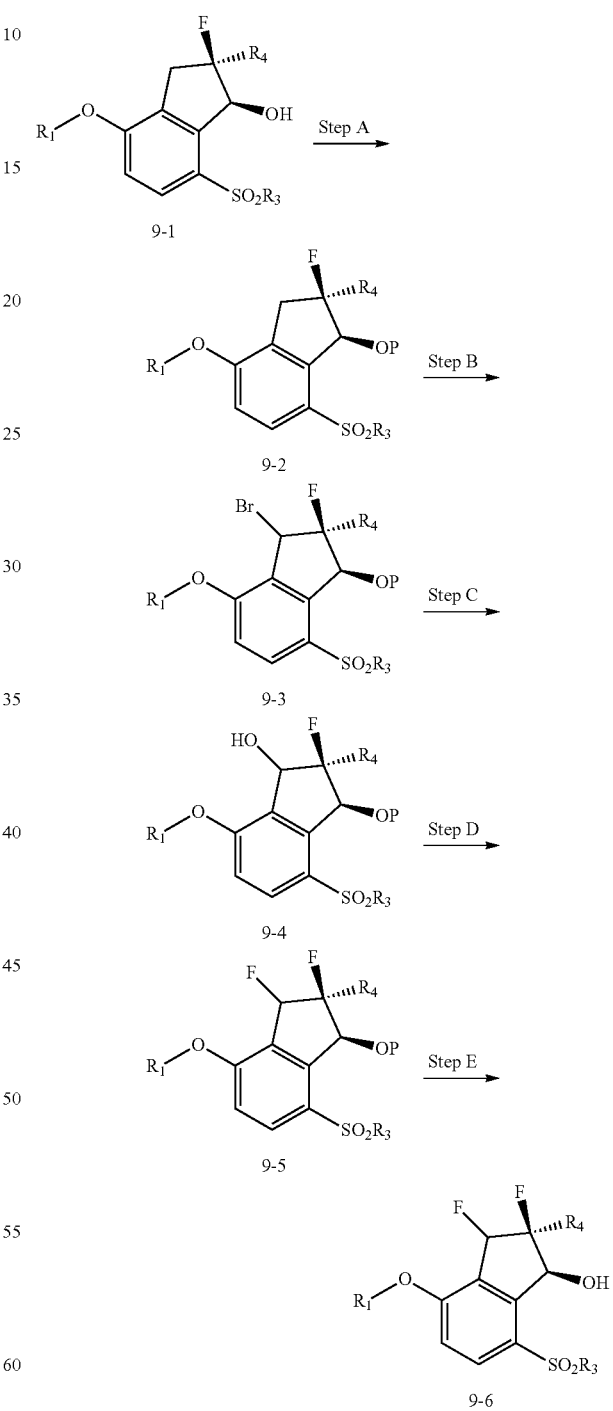

In some embodiments, compounds of Formula 9-6 are prepared according to scheme 9, wherein $R_4$ is hydrogen, alkyl or fluoro. The hydroxy group in compounds of Formula 9-1 may be protected with, e.g., acyl or methoxymethyl ether (MOM), to give compounds of Formula 9-2. Benzylic bromination in Step B may be carried out with a bromide source, e.g., N-bromosuccinimide, in the presence of a radical initiator, e.g., 2,2'-azobis(2-methylpropionitrile) (AIBN) or benzyol peroxide. The bromide in compounds of Formula 9-3 can be replaced with a hydroxy group in a solvent comprising water in the presence of a silver salt, e.g., $Ag_2CO_3$ or $AgClO_4$ or $AgBF_4$. Finally, fluorination of the hydroxy group in Formula 9-4 followed by deprotection gives compounds of Formula 9-6. In some cases, direct benzylic oxidation may be used for converting compounds of Formula 9-2 to compounds of Formula 9-4, thus bypassing an intermediate bromination step.

Scheme 10

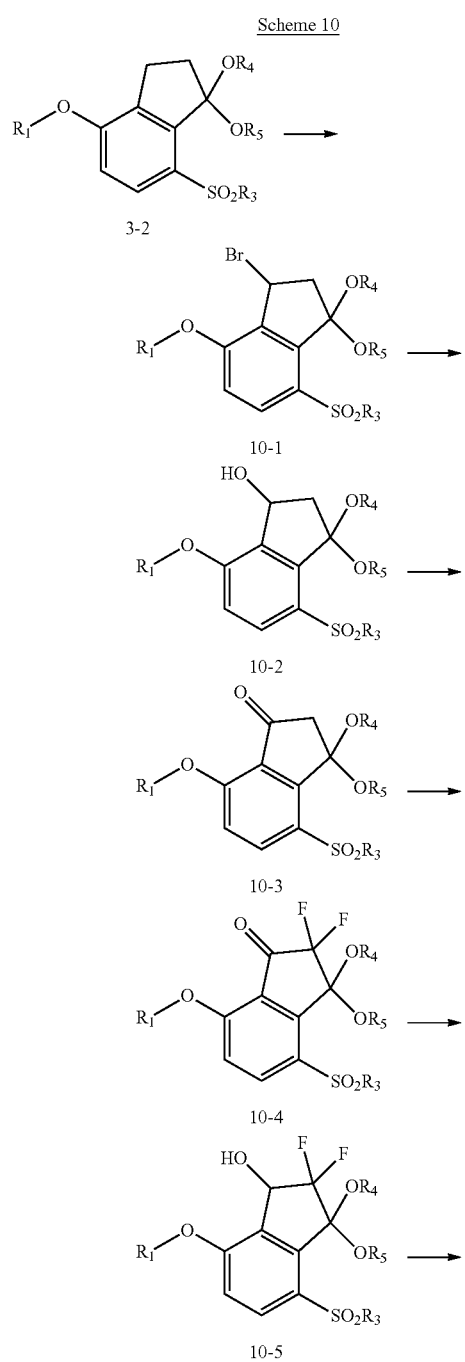

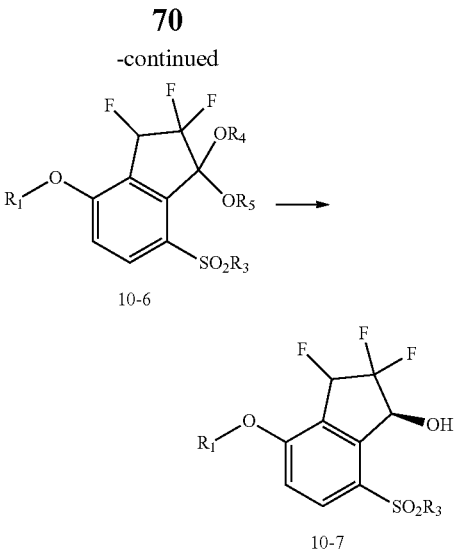

In some embodiments, compounds of Formula 10-7 is prepared according to Scheme 10. For example, compounds of Formula 10-3 may be prepared from compounds of Formula 3-2 by following a similar sequence as outlined in Scheme 9. Further functional group manipulations lead to compounds of Formula 10-7.

Scheme 11

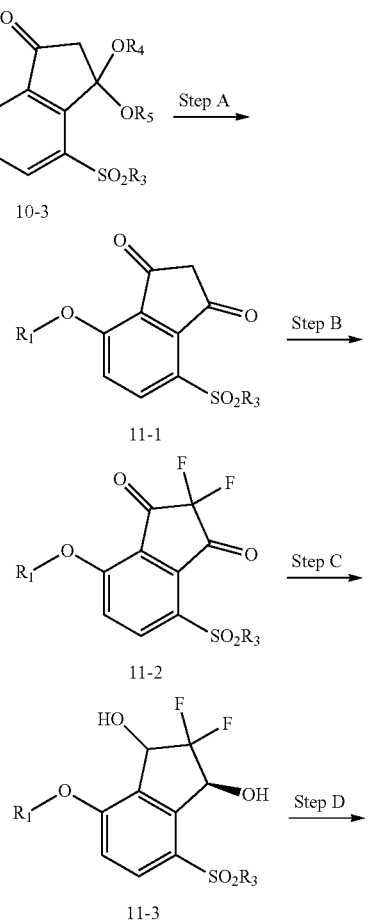

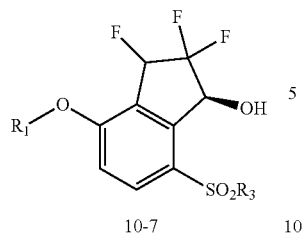

Alternatively, compounds of Formula 10-3 is deprotected to give diketone 11-1, which is fluorinated to give difluoro diketone 11-2. Asymmetric reduction of 11-2 provides diol 11-2. In some embodiments, one of the hydroxy groups is selectively fluorinated to give compounds of Formula 10-7.

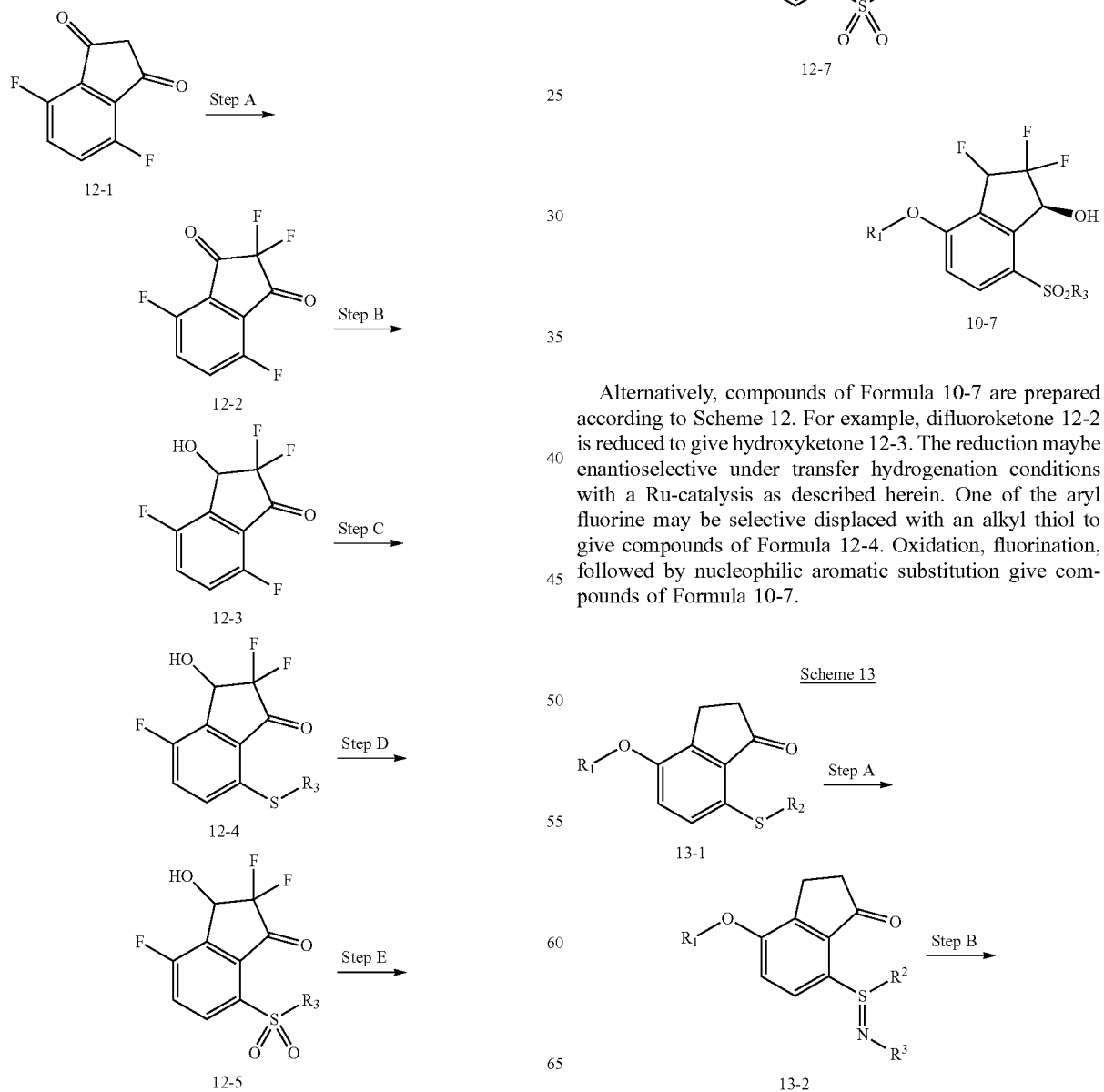

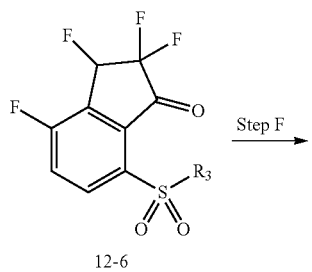

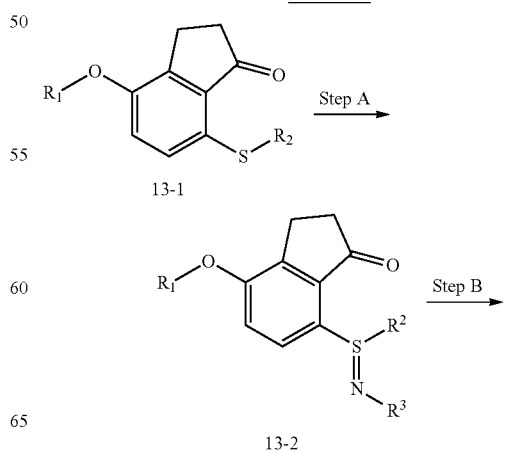

Alternatively, compounds of Formula 10-7 are prepared according to Scheme 12. For example, difluoroketone 12-2 is reduced to give hydroxyketone 12-3. The reduction maybe enantioselective under transfer hydrogenation conditions with a Ru-catalysis as described herein. One of the aryl fluorine may be selective displaced with an alkyl thiol to give compounds of Formula 12-4. Oxidation, fluorination, followed by nucleophilic aromatic substitution give compounds of Formula 10-7.

-continued

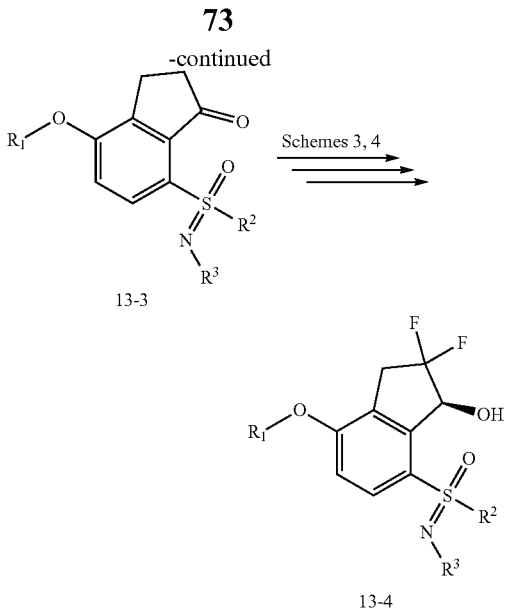

13-3

13-4

In some embodiments, compounds of Formula 13-4 are prepared according to Scheme 13. Aryl sulfides 13-1 are treated with $H_2N-R_3$ and an oxidant, e.g., diacetoxyiodobenzene or dipivaloyloxyiodobenzene, in a suitable solvent, such as acetoniltrile, to obtain aryl sulfinimides 13-2. In some embodiments, for compounds of Formula 13-1 with fluoroalkyl $R_2$ substituents, the presence of rhodium(II) acetate or $Rh_2(esp)_2$ catalyst, along with magnesium oxide, is helpful. Oxidation of the aryl sulfinimides 13-2 to substituted sulfoximines 13-3 may be accomplished with catalytic ruthenium(III) chloride and sodium periodate in a suitable solvent, such as a mixture of water, acetonitrile, and carbon tetrachloride. Substituted sulfoximines 13-3 are then manipulated similarly as described in Schemes 3 and 4 to afford sulfoximines of Formula 13-4 as a diastereomeric mixture. The diastereomers may be separated by column chromatography.

Experiments

The examples below are intended to be purely exemplary and should not be considered to be limiting in any way. Efforts have been made to ensure accuracy with respect to numbers used (for example, amounts, temperature, etc.) but some experimental errors and deviations should be taken into account.

$^1H$ and $^{19}F$ NMR analysis of intermediates and exemplified compounds were performed on an Agilent Technologies 400/54 magnet system (operating at 399.85 MHz or 376.24 MHz). Vnmrj VERSION 3.2 software Pulse sequences were selected from the default experiment set. Reference frequency was set using TMS as an internal standard. Typical deuterated solvents were utilized as indicated in the individual examples.

LCMS analysis of intermediates and exemplified compounds was performed on an Agilent Technologies 1200 Series HPLC system coupled to an Agilent Technologies 6150 Quadrapole LC/MS detector. Analytes were detected by UV absorbance at 220 and 254 nm. Analyte ions were detected by mass spectrometry in both negative and positive modes (110-800 amu scan range, API-ES ionization). A long HPLC method was run on a Phenomenex® Kinetex 2.6 µm C18 100 Å, 30×3.00 mm column. The column temperature was set at 40° C. UV absorptions were detected at 220 and 254 nm. Samples were prepared as a solution in about 1:1 (v/v) acetonitrile:water mixture. Flow rate was about 0.80 mL/minute. Elution solvents were acetonitrile and water each containing 0.1% formic acid. In a typical run, a linear gradient starting with 5% acetonitrile and 95% water and ending with 95% acetonitrile and 5% water over 12 minutes was carried out. At the end of each run, the column was washed with 95% acetonitrile and 5% water for 2 minutes.

Enantiomeric excess was determined by Mosher ester analysis or with chiral HPLC. The chiral HPLC analysis was performed on an Agilent Technologies 1200 Series HPLC system. Analytes were detected by UV absorbance at 220 and 254 nm. A detailed description of the analytical method is provided below:

Column: Lux® 5 u Cellulose-4 5.0 µm 1000 Å, 150×4.60 mm
Flow rate: 1.5 mL/min
Mobile phase A: 0.1% Formic acid in water
Mobile phase B: 0.1% Formic acid in Acetonitrile
Strong needle wash: 90% Acetonitrile, 10% Water
Weak needle wash: 10% Water, 90% Acetonitrile
Injection volume: 2 µL
Column temperature: 40° C.
Autosampler temperature: Room temperature
Run time: 5.0 min
Gradient: 60% mobile phase A and 40% mobile phase B Routine chromatographic purification was performed using Biotage Isolera One automated systems running Biotage Isolera One 2.0.6 software (Biotage LLC, Charlotte, N.C.). Flow rates were the default values specified for the particular column in use. Reverse phase chromatography was performed using elution gradients of water and acetonitrile on KP-C18-HS Flash+ columns (Biotage LLC) of various sizes. Typical loading was between 1:50 and 1:1000 crude sample:RP $SiO_2$ by weight. Normal phase chromatography was performed using elution gradients of various solvents (e.g. hexane, ethyl acetate, methylene chloride, methanol, acetone, chloroform, MTBE, etc.). The columns were SNAP Cartridges containing KP-SIL or SNAP Ultra (25 µm spherical particles) of various sizes (Biotage LLC). Typical loading was between 1:10 to 1:150 crude sample:$SiO_2$ by weight.

Compound names were generated with ChemBioDraw ultra 13.0.0.3015 or OpenEye Scientific Software's mol2nam application.

Example 1

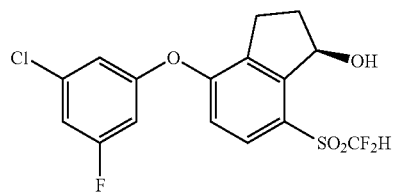

(R)-4-(3-chloro-5-fluorophenoxy)-7-((difluoromethyl)sulfonyl)-2,3-dihydro-1H-inden-1-ol (Compound 1)

Step A: Preparation of O-(7-fluoro-3-oxo-indan-4-yl)-N,N-dimethylcarbamothioate

A mixture of 4-fluoro-7-hydroxy-indan-1-one (17.0 g, 102 mmol), DMF (340 mL), N,N-dimethylcarbamothioyl chloride (37.9 g, 307 mmol), and 1,4-diazabicyclo[2.2.2]octane (34.4 g, 307 mmol) was stirred at ambient temperature for 2 hours. The reaction was poured into cold water and extracted with EtOAc. The combined organic layers were washed with water and brine, dried and concentrated. The resulting solid was recrystallized from 1:1 hexane:EtOAc (240 mL) to give O-(7-fluoro-3-oxo-indan-4-yl)-N,N-dimethylcarbamothioate as a white solid (12.0 g). The mother liquid was concentrated and purified by flash chromatography on silica gel (0-1% EtOAc in dichloromethane) to give a solid, which was triturated with 4:1 hexane:EtOAc to give additional O-(7-fluoro-3-oxo-indan-4-yl)-N,N-dimethylcarbamothioate (6.9 g, combined yield 18.9 g, 73%). LCMS ESI (+) m/z 254 (M+H).

Step B: Preparation of S-(7-fluoro-3-oxo-indan-4-yl)-N,N-dimethylcarbamothioate

A mixture of O-(7-fluoro-3-oxo-indan-4-yl)-N,N-dimethylcarbamothioate (18.9 g, 74.6 mmol) and diphenyl ether (200 mL) was heated at 220° C. under nitrogen for 30 minutes. After cooling, the reaction mixture was diluted with hexane. The mixture was passed through a short silica gel pad eluting with hexane to remove diphenyl ether. Further elution with EtOAc afforded the crude product, which was purified by flash chromatography on silica gel (15-40% EtOAc/hexane) to afford S-(7-fluoro-3-oxo-indan-4-yl)-N,N-dimethylcarbamothioate (18.0 g, 95%) as a solid. LCMS ESI (+) m/z 254 (M+H).

Step C: Preparation of 4-fluoro-7-sulfanyl-indan-1-one

A stirred mixture of S-(7-fluoro-3-oxo-indan-4-yl)-N,N-dimethylcarbamothioate (25.0 g, 98.7 mmol), 95% ethanol (490 mL) and 3N NaOH (173 mL, 691 mmol) was heated under nitrogen at reflux for 30 minutes. After cooling, the reaction mixture was cooled to 0° C. using an ice bath. 3N HCl was added dropwise to adjust the pH to 4-5. Most ethanol was evaporated under reduced pressure. The precipitated solid was collected by filtration, washed with water and dried to give 4-fluoro-7-sulfanyl-indan-1-one (17.0 g, 95%), which was used in the next step without further purification.

Step D: Preparation of 7-(difluoromethylsulfanyl)-4-fluoro-indan-1-one

To a stirred solution of 4-fluoro-7-sulfanyl-indan-1-one (crude from Step C, 17.0 g, 93.3 mmol) in acetonitrile (490 mL) was added a solution of KOH (104.7 g, 1866 mmol) in water (490 mL). The reaction mixture was purged with nitrogen and then cooled to −78° C. Bromodifluoromethyl diethylphosphonate (33.2 mL, 187 mmol) was added all in once. The resulting mixture was allowed to warm to ambient temperature and vigorously stirred for 2 hours. The reaction mixture was partitioned between EtOAc and water. The aqueous layer was extracted with EtOAc. The combined organics were washed with water and brine, dried over $Na_2SO_4$, filtered, and concentrated to dryness. The residue was purified by passing through a short silica gel pad eluting with 10% EtOAc in hexane to give 7-(difluoromethylsulfanyl)-4-fluoro-indan-1-one (18.3 g, 84%), which was used in the next step without further purification. LCMS ESI (+) m/z 233 (M+H).

Step E: Preparation of 7-((difluoromethyl)sulfonyl)-4-fluoro-2,3-dihydro-1H-inden-1-one Sodium periodate (41.9 g, 196 mmol) was added all at once to 7-(difluoromethylsulfanyl)-4-fluoro-indan-1-one (18.2 g, 78.4 mmol) and ruthenium(III) chloride (0.41 g, 2.0 mmol) in acetonitrile (392 mL)/carbon tetrachloride (392 mL)/water (392 mL). The reaction mixture was stirred at ambient temperature for 5 hours. Solids were removed by filtration through Celite and rinsed with $CH_2Cl_2$. The organic layer was separated. The aqueous layer was extracted with $CH_2Cl_2$. The combined organics were washed with brine, dried over $Na_2SO_4$, filtered and concentrated in vacuo. The crude product was passed through a short silica gel pad eluting with 30% EtOAc/hexane to give 7-(difluoromethylsulfonyl)-4-fluoro-indan-1-one (18.8 g, 91%) as a white solid. LCMS ESI (+) m/z 265 (M+H).

Step F: Preparation of (1R)-7-(difluoromethylsulfonyl)-4-fluoro-indan-1-ol

A pear-shaped flask was charged with 7-(difluoromethylsulfonyl)-4-fluoro-indan-1-one (992 mg, 3.75 mmol), formic acid (0.178 mL, 4.69 mmol), triethylamine (0.576 mL, 4.13 mmol), and dichloromethane (25 mL). The reaction mixture was backfilled with nitrogen. RuCl(p-cymene)[(R,R)-Ts-DPEN] (48 mg, 0.08 mmol) was added in one portion, and the reaction mixture was stirred at ambient temperature overnight. The reaction was concentrated under reduced pressure. The residue was purified by flash chromatography on silica gel (5-20% EtOAc in hexanes) to give (1R)-7-(difluoromethylsulfonyl)-4-fluoro-indan-1-ol (990 mg, 99%) as a solid. The ee was determined to be 98% by $^{19}F$ NMR analysis of the corresponding Mosher ester. LCMS ESI (+) m/z 267 (M+H); ESI (−) m/z 311 (M−H+46).

Step G: Preparation of (R)-4-(3-chloro-5-fluorophenoxy)-7-((difluoromethyl)sulfonyl)-2,3-dihydro-1H-inden-1-ol (Compound 1)

A solution of 3-chloro-5-fluoro-phenol (24 mg, 0.17 mmol) and (1R)-7-(difluoromethylsulfonyl)-4-fluoro-indan-1-ol (40 mg, 0.15 mmol) in NMP (1 mL) at ambient temperature was treated with $NaHCO_3$ (37 mg, 0.45 mmol). The reaction mixture was stirred at 90° C. under nitrogen for 4 hours. After cooling, the reaction mixture was partitioned between EtOAc and water. The aqueous layer was extracted with EtOAc. The combined organic layers were washed with water and brine, dried and concentrated. The residue was purified by C18 reverse phase flash chromatography (Biotage Isolera One unit, C18 Flash 12+M column, 10-60% $CH_3CN$/water) to give Compound 1 (25 mg, 42%). The ee was determined to be 98% by $^{19}F$ NMR analysis of the corresponding Mosher ester. LCMS ESI (+) m/z 393 (M+H); ESI (−) m/z 437, 439 (M−H+46); $^1H$ NMR (400 MHz, $CDCl_3$): δ 7.81 (d, 1H), 7.00-6.89 (m, 3H), 6.73-6.71 (m, 1H), 6.35 (t, 1H), 5.66-5.65 (m, 1H), 3.19-3.13 (m, 2H), 2.96-2.90 (m, 1H), 2.50-2.40 (m, 1H), 2.30-2.24 (m, 1H).

Alternative Synthesis of 4-fluoro-7-sulfanyl-indan-1-one

Step A: A solution of (7-fluoro-3-oxo-indan-4-yl) trifluoromethanesulfonate (237.0 mg, 0.79 mmol) and Xantphos (50.6 mg, 0.09 mmol) in 1,4-Dioxane (3 mL) was sparged with nitrogen for 3 mins. The reaction mixture was then treated sequentially with S-Potassium Thioacetate (136.1 mg, 1.19 mmol) and Tris(dibenzylideneacetone)dipalladium (0) (36.4 mg, 0.04 mmol) under continuous nitrogen stream. The vessel was sealed and heated to 100° C. for 4 hours. The reaction mixture was filtered to remove insolubles with $CH_2Cl_2$ used as a rinse. The filtrate was concentrated and purification was achieved by chromatography on silica using 10%-30% EtOAc/hexane to give S-(7-fluoro-3-oxo-indan-4-yl) ethanethioate (99 mg, 0.44 mmol, 46% yield). LCMS ESI (+) m/z 225 (M+H).

Step B: To a round bottom flask containing S-(7-fluoro-3-oxo-indan-4-yl) ethanethioate (99.0 mg, 0.4400 mmol) dissolved in 4.4 mL of degassed THF (sparged with nitrogen for 5 min) was added ammonium hydroxide (620 μL, 4.45 mmol). The resulting reaction mixture stirred for 40 minutes under nitrogen atmosphere. TLC indicates consumption of starting material and LCMS identifies the desired product. The reaction mixture was concentrated to remove excess THF and then poured into 1 mL of 1 M NaOH and 15 mL of water and rinsed with 2×20 mL of $CH_2Cl_2$. The remaining aqueous phase was acidified with 10 mL of 1 M HCl and extracted with 3×20 mL of $CH_2Cl_2$. The combined organic extracts were dried with $MgSO_4$, filtered, and concentrated to dryness. The product was used without further purification to give 4-fluoro-7-sulfanyl-indan-1-one (44 mg, 0.24 mmol, 55% yield).

Example 2

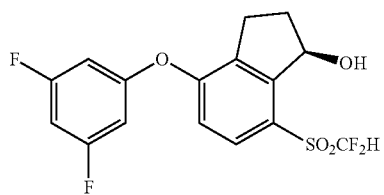

(R)-7-((Difluoromethyl)sulfonyl)-4-(3,5-difluorophenoxy)-2,3-dihydro-1H-inden-1-ol (Compound 2)

Prepared similarly as described in Example 1 using 3,5-difluorophenol in place of 3-chloro-5-fluoro-phenol in Step G. LCMS ESI (+) m/z 377 (M+H); ESI (−) m/z 421 (M−H+46); $^1$H NMR (400 MHz, $CDCl_3$): δ 7.81 (d, 1H), 6.96 (d, 1H), 6.73-6.68 (m, 1H), 6.62-6.61 (m, 2H), 6.36 (t, 1H), 5.66-5.65 (m, 1H), 3.22-3.10 (m, 2H), 2.96-2.90 (m, 1H), 2.50-2.40 (m, 1H), 2.29-2.24 (m, 1H).

Example 3

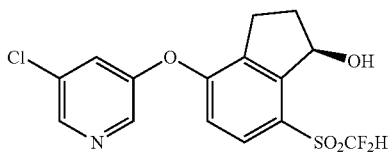

(R)-4-((5-chloropyridin-3-yl)oxy)-7-((difluoromethyl)sulfonyl)-2,3-dihydro-1H-inden-1-ol (Compound 3)

Prepared similarly as described in Example 1 using 5-chloropyridin-3-ol in place of 3-chloro-5-fluoro-phenol in Step G. LCMS ESI (+) m/z 376, 378 (M+H); $^1$H NMR (400 MHz, $CDCl_3$): δ 8.49 (s, 1H), 8.36 (s, 1H), 7.81 (d, 1H), 7.44-7.43 (m, 1H), 6.89 (d, 1H), 6.36 (t, 1H), 5.67-5.66 (m, 1H), 3.23-3.16 (m, 2H), 2.99-2.92 (m, 1H), 2.51-2.42 (m, 1H), 2.32-2.25 (m, 1H).

Example 4

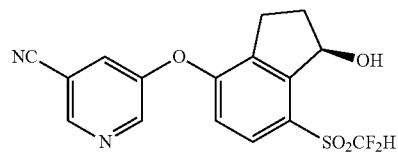

(R)-5-((7-((Difluoromethyl)sulfonyl)-1-hydroxy-2,3-dihydro-1H-inden-4-yl)oxy)nicotinonitrile (Compound 4)

Prepared similarly as described in Example 1 using 5-hydroxynicotinonitrile in place of 3-chloro-5-fluoro-phenol in Step G. LCMS ESI (+) m/z 367 (M+H); $^1$H NMR (400 MHz, $CDCl_3$): δ 8.76 (s, 1H), 8.66 (s, 1H), 7.86 (d, 1H), 7.65-7.64 (m, 1H), 6.93 (d, 1H), 6.38 (t, 1H), 5.71-5.65 (m, 1H), 3.20-3.16 (m, 2H), 2.96-2.90 (m, 1H), 2.50-2.42 (m, 1H), 2.37-2.24 (m, 1H).

Example 5

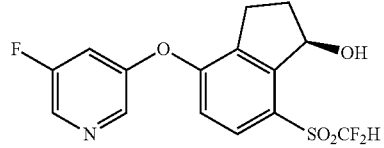

(R)-7-((difluoromethyl)sulfonyl)-4-((5-fluoropyridin-3-yl)oxy)-2,3-dihydro-1H-inden-1-ol (Compound 5)

Prepared similarly as described in Example 1 using 5-fluoropyridin-3-ol in place of 3-chloro-5-fluoro-phenol in Step G. LCMS ESI (+) m/z 360 (M+H); $^1$H NMR (400 MHz, $CDCl_3$): δ 8.41 (s, 1H), 8.32 (s, 1H), 7.82 (d, 1H), 7.22-7.17 (m, 1H), 6.92 (d, 1H), 6.37 (t, 1H), 5.70-5.60 (m, 1H), 3.23-3.18 (m, 2H), 2.99-2.97 (m, 1H), 2.54-2.40 (m, 1H), 2.34-2.22 (m, 1H).

Example 6

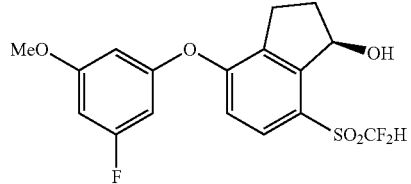

(R)-7-((difluoromethyl)sulfonyl)-4-(3-fluoro-5-methoxyphenoxy)-2,3-dihydro-1H-inden-1-ol (Compound 6)

Prepared similarly as described in Example 1 using 3-fluoro-5-methoxyphenol in place of 3-chloro-5-fluorophenol in Step G. LCMS ESI (−) m/z 433 (M−H+46); $^1$H NMR (400 MHz, CDCl$_3$): δ 7.77 (d, 1H), 6.91 (d, 1H), 6.54-6.50 (m, 1H), 6.42-6.38 (m, 2H), 6.39 (t, 1H), 5.67-5.63 (m, 1H), 3.80 (s, 3H), 3.23-3.15 (m, 2H), 2.99-2.92 (m, 1H), 2.50-2.45 (m, 1H), 2.30-2.23 (m, 1H).

Example 7

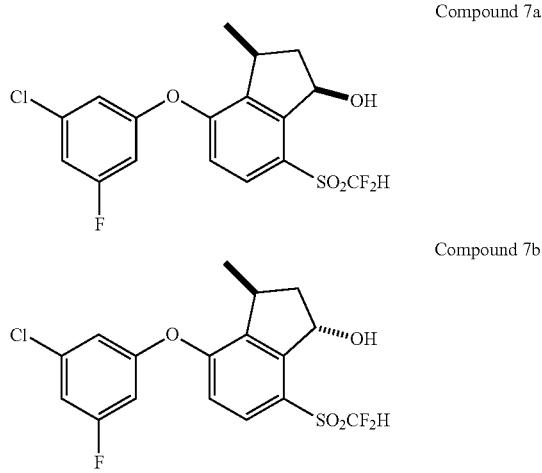

Compound 7a

Compound 7b

Step A: Preparation of 7-((difluoromethyl)sulfonyl)-4-fluoro-3-methyl-2,3-dihydro-1H-inden-1-ol To a solution of 7-(difluoromethylsulfonyl)-4-fluoro-3-methyl-indan-1-one (55 mg, 0.2 mmol, prepared similarly as described in Example 1 using 4-fluoro-7-hydroxy-3-methyl-2, 3-dihydro-1H-inden-1-one in place of 4-fluoro-7-hydroxy-2,3-dihydro-1H-inden-1-one in Step A) in methanol (5 mL) at room temperature was added sodium borohydride (15 mg, 0.4 mmol) portion wise. The reaction was stirred at room temperature until starting material disappeared by TLC analysis. The reaction mixture was diluted with brine and extracted with EtOAc. The combined extract was dried over MgSO$_4$, filtered and concentrated. The crude product was used in the next step without further purification.

Step B: A mixture of 7-(difluoromethylsulfonyl)-4-fluoro-3-methyl-indan-1-ol (55 mg, 0.2 mmol, crude from step A), 3-chloro-5-fluoro-phenol (57 mg, 0.39 mmol), and cesium bicarbonate (76 mg, 0.39 mmol) in 1-methyl-2-pyridone (2 mL) was heated under N$_2$ at 90° C. for 1 hour. LCMS indicated the presence of both product and starting material in the reaction mixture. The flask was resealed and heated at 100° C. for 2 hours. The reaction mixture was cooled to room temperature, diluted with brine and extracted with EtOAc. The combined organic extracts were dried over MgSO$_4$, filtered and concentrated. Purification with preparative TLC with EtOAc/hexane (10%) followed by reverse phase column chromatography with water/acetonitrile (10% to 90%) gave racemic Compound 7a (2.4 mg, 3% from step A) and racemic Compound 7b (0.7 mg, 1% from step A).

LCMS ESI (+) m/z 254 (M+H). Characterization for 7a: LCMS ESI (+) m/z 429, 431 (M+Na); $^1$H NMR (400 MHz, CDCl$_3$): δ 7.81 (d, 1H), 7.01-6.98 (m, 1H), 6.91-6.89 (m, 2H), 6.75-6.71 (m, 1H), 6.34 (t, 1H), 5.58-5.53 (m, 1H), 3.48-3.40 (m, 1H), 3.22 (d, 1H), 2.66-2.59 (m, 1), 1.98-1.93 (m, 1H), 1.46 (d, 3H). Characterization for 7b: LCMS ESI (+) m/z 429, 431 (M+Na); $^1$H NMR (400 MHz, CDCl$_3$): δ 7.81 (d, 1H), 7.01-6.97 (m, 1H), 6.92 (d, 1H), 6.89-6.88 (m, 1H), 6.73-6.69 (m, 1H), 6.38 (t, 1H), 5.70-5.67 (m, 1H), 3.71-3.64 (m, 1H), 3.25 (d, 1H), 2.47-2.41 (m, 1H), 2.14-2.06 (m, 1H), 1.36 (d, 3H).

Example 8

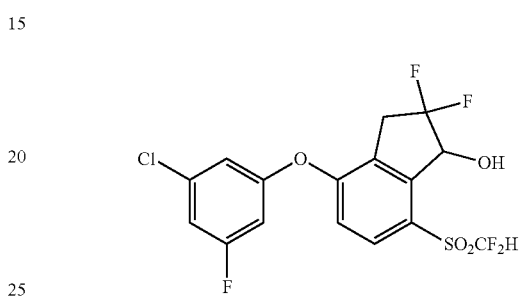

Step A: Preparation of 7-((difluoromethyl)sulfonyl)-4-fluoro-2,3-dihydrospiro[indene-1,2'-[1,3]dioxolane](Compound 8)

A mixture of 7-(difluoromethylsulfonyl)-4-fluoro-indan-1-one (114 mg, 0.43 mmol), ethylene glycol (4 mL, 0.43 mmol), p-toluenesulfonic acid monohydrate (4 mg, 0.02 mmol) and toluene (20 mL) was refluxed with azotropic removal of H$_2$O using a Dean-Stark trap. The reaction was monitored by LCMS and ethylene glycol was added twice (4 mL each time). After refluxing for about 6 hours, LCMS indicated about 50% conversion. The mixture was cooled to room temperature, diluted with saturated aqueous NaHCO$_3$, and extracted with EtOAc. The organic layer was dried over Na$_2$SO$_4$, filtered, and concentrated. The residue was purified by C18 reverse phase flash chromatography (Biotage Isolera One unit, 10-50% CH$_3$CN/water) to give incomplete separation of starting material and product. Fractions containing starting material and product were combined and used in the next step. LCMS ESI (+) m/z 309 (M+H).

Step B: Preparation of 4-(3-chloro-5-fluorophenoxy)-7-((difluoromethyl)sulfonyl)-2,3-dihydrospiro [indene-1,2'-[1,3]dioxolane]

Prepared analogously to Step B of Example 7 using 7-((difluoromethyl)sulfonyl)-4-fluoro-2,3-dihydrospiro[indene-1,2'[1,3]dioxolane] in place of 7-((difluoromethyl)sulfonyl)-4-fluoro-3-methyl-2,3-dihydro-1H-inden-1-ol. LCMS ESI (+) m/z 435/437 (M+H).

Step C: Preparation of 4-(3-chloro-5-fluoro-phenoxy)-7-(difluoromethylsulfonyl)indan-1-one To a solution of 4-(3-chloro-5-fluorophenoxy)-7-((difluoromethyl)sulfonyl)-2,3-dihydrospiro[indene-1,2'-[1,3]dioxolane] (5 mg, 0.012 mmol) in acetone (1 mL) at room temperature was added pyridinium p-toluenesulfonate (PPTS, 3 small crystals) and water (0.2 mL). The reaction was heated at 85° C. in a sealed tube for 1 hour. LCMS indicated a clean reaction with about 1:1 mixture of product: starting material. Additional 4-(3-chloro-5-fluorophenoxy)-7-((difluoromethyl)sulfonyl)-2,3-dihydrospiro[indene-1,2'-[1,3]dioxolane] (45 mg) in acetone (3 mL) was added, followed by PPTS (20 mg, 0.08 mmol) and water (0.3 mL). The reaction mixture was heated at 90° C. for 4 hours, concentrated, and purified by C18 reverse phase flash chromatography (Biotage Isolera One unit, 10-90% CH$_3$CN/water) to give 4-(3-chloro-5-fluoro-phenoxy)-7-(difluoromethylsulfonyl)indan-1-one (42 mg, 0.11 mmol, 94% yield). LCMS ESI (+) m/z 391/393 (M+H).

Step D: Preparation of (E,Z)—N-butyl-4-(3-chloro-5-fluorophenoxy)-7-((difluoromethyl)sulfonyl)-2,3-dihydro-1H-inden-1-imine A mixture of 4-(3-chloro-5-fluoro-phenoxy)-7-(difluoromethylsulfonyl)indan-1-one (42 mg, 0.11 mmol), 4 Å molecule sieves (300 mg, 0.11 mmol), trifluoroacetic acid (5 drops) and butan-1-amine (840 mg, 11.5 mmol) in benzene (1.2 mL) was heated under nitrogen in a sealed tube at 80° C. for 2 hours.

The reaction was not complete by $^1$H NMR analysis. The reaction mixture was transferred to a round bottom flask. Additional benzene (20 mL) and butane-1-amine (0.5 mL) were added. The reaction mixture was refluxed with azeotropic removal of water using a Dean-Stark trap. After one hour, additional benzene (10 mL) and butane-1-amine (0.5 mL) were added. The procedure was repeated one more time. After refluxing for two additional hours, the reaction mixture was concentrated and then dissolved in t-butyl ethyl ether. The organic layer was washed with saturated aqueous NaHCO$_3$ and then brine, dried over Na$_2$SO$_4$, filtered, and concentrated. The crude imine (E,Z)—N-butyl-4-(3-chloro-5-fluorophenoxy)-7-((difluoromethyl)sulfonyl)-2,3-dihydro-1H-inden-1-imine was used in the next step without further purification.

Step E: Preparation of 4-(3-chloro-5-fluoro-phenoxy)-7-(difluoromethylsulfonyl)-2,2-difluoro-indan-1-one A mixture of (E,Z)—N-butyl-4-(3-chloro-5-fluoro-phenoxy)-7-(difluoromethylsulfonyl)indan-1-imine (48 mg, 0.11 mmol, crude from Step D), sodium sulfate (200 mg, 0.11 mmol) and Selectfluor® (95 mg, 0.27 mmol) in anhydrous acetonitrile (10 mL) was heated at 85° C. under N$_2$ for 4 hours. After the reaction mixture was cooled to room temperature, HCl (37%, 1 mL) was added. The reaction mixture was stirred at room temperature for 15 minutes, and concentrated. The residue was diluted with EtOAc, washed with saturated NaHCO$_3$ and brine, dried over Na$_2$SO$_4$, filtered, and concentrated. The crude product was used in the next step without further purification. LCMS ESI (+) m/z 444/446 (M+NH4).

Step F: Preparation of 4-(3-chloro-5-fluoro-phenoxy)-7-(difluoromethylsulfonyl)-2,2-difluoro-indan-1-ol (Compound 8)

To a solution of 4-(3-chloro-5-fluoro-phenoxy)-7-(difluoromethylsulfonyl)-2,2-difluoro-indan-1-one (crude from Step E) in methanol (4 mL) was added sodium borohydride (100 mg, 2.64 mmol). The reaction was stirred at room temperature for 20 minutes. The reaction mixture was poured into brine, extracted with EtOAc, dried over MgSO$_4$, filtered, and concentrated. The residue was purified twice by preparative TLC with EtOAc/hexane (15%) to give Compound 8 (14 mg, 30% from Step E). LCMS ESI (+) m/z 429, 431 (M+H). $^1$H NMR (400 MHz, CDCl$_3$): δ 7.90 (d, 1H), 7.06-7.03 (m, 1H), 6.98 (d, 1H), 6.94-6.92 (m, 1H), 6.78-6.74 (m, 1H), 6.42 (t, 1H), 5.50 (d, 1H), 3.61-3.43 (m, 2H), 3.24 (s, 1H).

Example 9

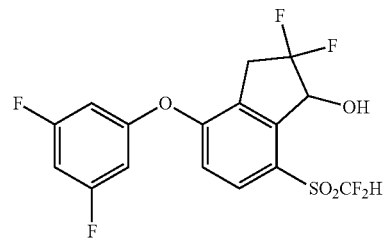

7-(difluoromethylsulfonyl)-4-(3,5-difluorophenoxy)-2,2-difluoro-indan-1-ol (Compound 9)

Prepared analogously to the procedure for Compound 8 in Example 8. LCMS ESI (+) m/z 413 (M+H); $^1$H NMR (400 MHz, CDCl$_3$): δ 7.90 (d, 1H), 7.01 (d, 1H), 6.80-6.73 (m, 1H), 6.70-6.63 (m, 2H), 6.43 (t, 1H), 5.50 (m, 1H), 3.60-3.43 (m, 2H), 3.30 (d, 1H).

Example 10

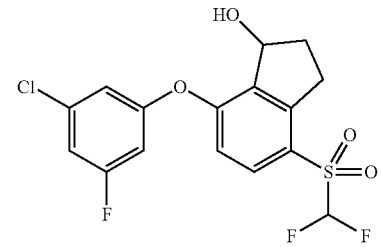 [SMILES: O=S(=O)(c1ccc(Oc2cc(F)cc(Cl)c2)c2c1CCC2O)C(F)F]

7-(3-chloro-5-fluoro-phenoxy)-4-(difluoromethylsulfonyl)indan-1-ol (Compound 10)

Step A: Preparation of 4-bromo-7-(3-chloro-5-fluoro-phenoxy)indan-1-one

A mixture of 4-bromo-7-fluoro-indan-1-one (50 mg, 0.22 mmol), 3-chloro-5-fluoro-phenol (48 mg, 0.33 mmol) and cesium bicarbonate (50.8 mg, 0.26 mmol) in 1-methyl-2-pyrrolidone (1.5 mL) was heated at 100° C. for 2 hours. LCMS indicated about 40% conversion. The reaction mixture was heated for another 2 hours at 110° C. and directly purified by C18 reverse phase flash chromatography (Biotage Isolera One unit, 10-80% CH$_3$CN/water) to give 4-bromo-7-(3-chloro-5-fluoro-phenoxy)indan-1-one (27 mg, 0.08 mmol, 35% yield). LCMS ESI (+) m/z 355, 357, 359 (M+H).

Step B: Preparation of S-[7-(3-chloro-5-fluoro-phenoxy)-1-oxo-indan-4-yl] ethanethioate A mixture of 4-bromo-7-(3-chloro-5-fluoro-phenoxy)indan-1-one (22 mg, 0.06 mmol), Pd$_2$(dba)$_3$ (2.8 mg), xantphos (3.58 mg, 0.01 mmol) and S-potassium thioacetate (17.7 mg, 0.15 mmol) was heated in a microwave at 150° C. under N₂ for 30 minutes. The reaction mixture was concentrated under reduced pressure and purified by flash chromatography with EtOAc/hexane (0% to 30%) to give S-[7-(3-chloro-5-fluoro-phenoxy)-1-oxo-indan-4-yl] ethanethioate (8.3 mg, 0.02 mmol, 38% yield). LCMS ESI (+) m/z 351, 353 (M+H).

Step C: Preparation of 7-(3-chloro-5-fluoro-phenoxy)-4-sulfanyl-indan-1-one

To a solution of S-[7-(3-chloro-5-fluoro-phenoxy)-1-oxo-indan-4-yl] ethanethioate (8.3 mg, 0.02 mmol) in tetrahydrofuran (6 mL) at room temperature under nitrogen was added ammonium hydroxide (0.2 mL). The reaction mixture was stirred at room temperature for 1.5 hours and then concentrated. The residue was dissolved in EtOAc and washed with 1 N HCl, dried over MgSO₄, filtered, and concentrated. The crude product was used in the next step without further purification. LCMS ESI (−) m/z 307, 309 (M−H).

Step D: Preparation of 7-(3-chloro-5-fluoro-phenoxy)-4-(difluoromethylsulfanyl)indan-1-one To a mixture of KOH (13.27 mg, 0.24 mmol) and 7-(3-chloro-5-fluoro-phenoxy)-4-sulfanyl-indan-1-one (7.3 mg, 0.02 mmol) in a mixture of water (0.4 mL) and acetonitrile (1.5 mL) at −5° C. was added bromodifluoromethyl diethylphosphonate (0.01 mL, 0.07 mmol). The reaction mixture was stirred at room temperature for 3 hours, diluted with brine, and extracted with EtOAc. The organic layer was dried over MgSO₄, filtered, and concentrated. The residue was purified by flash column chromatography with EtOAc/hexane (0% to 40%) to give 7-(3-chloro-5-fluoro-phenoxy)-4-(difluoromethylsulfanyl)indan-1-one (3.5 mg, 0.01 mmol, 41% yield). LCMS ESI (+) m/z 359, 361 (M+H).

Step E: Preparation of 7-(3-chloro-5-fluoro-phenoxy)-4-(difluoromethylsulfonyl)indan-1-one A mixture of 7-(3-chloro-5-fluoro-phenoxy)-4-(difluoromethylsulfanyl)indan-1-one (3.5 mg, 0.01 mmol), ruthenium trichloride (0.1 mg), and sodium periodate (6.3 mg, 0.03 mmol) in a mixture of acetonitrile (1 mL), carbon tetrachloride (1 mL), and water (2 mL) was stirred at room temperature for 3 hours. The reaction mixture was diluted with brine, extracted with EtOAc. The organic layer was dried over MgSO₄, filtered, and concentrated. The residue was purified by flash column chromatography with EtOAc/hexane (0% to 60%) to give 7-(3-chloro-5-fluoro-phenoxy)-4-(difluoromethylsulfanyl)indan-1-one (3.5 mg, 0.01 mmol, quant.). LCMS ESI (+) m/z 391, 393 (M+H).

Step F: Preparation of 7-(3-chloro-5-fluoro-phenoxy)-4-(difluoromethylsulfonyl)indan-1-ol (Compound 10)

To a solution of 7-(3-chloro-5-fluoro-phenoxy)-4-(difluoromethylsulfonyl)indan-1-one (4 mg, 0.01 mmol) in methanol (1 mL) at room temperature was added sodium borohydride (10 mg, 0.26 mmol) portion wise. The reaction mixture was stirred at room temperature for 30 minutes and directly purified by preparative TLC with EtOAc/hexane (35%) to give Compound 10 (2.8 mg, 0.007 mmol, 70% yield). LCMS ESI (+) m/z 375, 377 (M−OH). ¹H NMR (400 MHz, CDCl₃): δ 7.85 (d, 1H), 7.04-7.00 (m, 1H), 6.97-6.95 (m, 1H), 6.84-6.77 (m, 2H), 6.18 (t, 1H), 5.58-5.53 (m, 1H), 3.59-3.50 (m, 1H), 3.34-3.26 (m, 1H), 2.60-2.50 (m, 1H), 2.31 (d, 1H), 2.21-2.13 (m, 1H).

Example 11

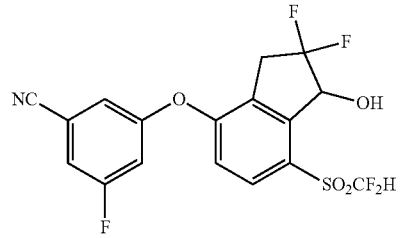

3-[7-(difluoromethylsulfonyl)-2,2-difluoro-1-hydroxy-indan-4-yl]oxy-5-fluoro-benzonitrile (Compound 11)

Prepared analogously to the procedure for Compound 8. LCMS ESI (+) m/z 437 (M+NH₄); ¹H NMR (400 MHz, CDCl₃): δ 7.94 (d, 1H), 7.33-7.29 (m, 1H), 7.23-7.21 (m, 1H), 7.13-7.09 (m, 1H), 7.00 (d, 1H), 6.43 (t, 1H), 5.51 (d, 1H), 3.60-3.43 (m, 2H), 3.30 (br s, 1H).

Example 12

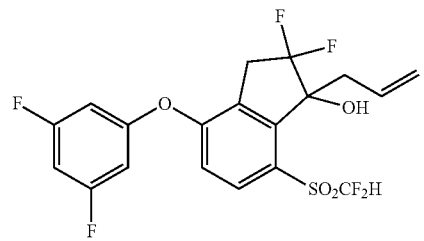

1-allyl-7-(difluoromethylsulfonyl)-4-(3,5-difluorophenoxy)-2,2-difluoro-indan-1-ol (Compound 12)

A mixture of 7-(difluoromethylsulfonyl)-4-(3,5-difluorophenoxy)-2,2-difluoro-indan-1-one (prepared analogously to the procedures in Example 8, 24 mg, 0.06 mmol), 3-iodoprop-1-ene (0.05 mL, 0.58 mmol), and indium (67 mg, 0.58 mmol) in N,N-dimethylformamide (2 mL) was stirred at room temperature overnight. The reaction mixture was diluted with 1:1 water/brine and extracted with EtOAc. The organic layer was dried over MgSO₄, filtered, and concentrated. The residue was purified by flash column chromatography with EtOAc/hexane (30%) to give Compound 12 (9.7 mg, 0.02 mmol, 37% yield). LCMS ESI (−) m/z 451 (M−H); ¹H NMR (400 MHz, CDCl₃): δ 8.01 (d, 1H), 6.97 (d, 1H), 6.82-6.55 (m, 4H), 5.76-5.64 (m, 1H), 5.35-5.26 (m, 2H), 3.54-3.44 (m, 2H), 3.31-3.18 (m, 1H), 3.06-2.96 (m, 2H).

Example 13

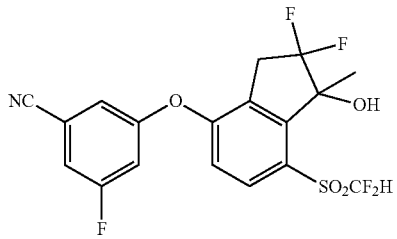

3-[7-(difluoromethylsulfonyl)-2,2-difluoro-1-hydroxy-1-methyl-indan-4-yl]oxy-5-fluoro-benzonitrile (Compound 13)

To a solution of 3-[7-(difluoromethylsulfonyl)-2,2-difluoro-1-oxo-indan-4-yl]oxy-5-fluoro-benzonitrile (4.8 mg, 0.01 mmol) in tetrahydrofuran (4 mL) at room temperature was added dimethylzinc (0.01 mL, 0.01 mmol). The reaction was heated to 80° C. for 1 hour. The reaction mixture was directly purified by preparative TLC with EtOAc/hexane (30%) to give Compound 13 (2.1 mg, 0.005 mmol, 42% yield). LCMS ESI (+) m/z 451 (M+NH$_4$); $^1$H NMR (400 MHz, CDCl$_3$): δ 8.0 (d, 1H), 7.33-7.30 (m, 1H), 7.23-7.21 (m, 1H), 7.13-7.09 (m, 1H), 6.92 (d, 1H), 6.62 (m, 1H), 3.58-3.49 (m, 2H), 3.34-3.20 (m, 1H), 1.84-1.82 (m, 3H).

Example 14

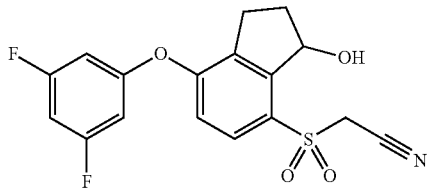 [SMILES: N#CCS(=O)(=O)c1ccc(Oc2cc(F)cc(F)c2)c2c1C(O)CC2]

2-[7-(3,5-difluorophenoxy)-3-hydroxy-indan-4-yl]sulfonylacetonitrile (Compound 14)

Step A: Preparation of 2-(7-fluoro-3-oxo-indan-4-yl)sulfanylacetonitrile

A mixture of 4-fluoro-7-sulfanyl-indan-1-one (prepared from 1 g of S-(7-fluoro-3-oxo-indan-4-yl)-N,N-dimethylcarbamothioate according to Step C of Example 1), sodium carbonate (1 g, 9.43 mmol) and bromoacetonitrile (719.7 mg, 6 mmol) was heated at 60° C. overnight. The reaction mixture was concentrated under reduced pressure. The residue was purified by flash column chromatography with EtOAc/hexane (0% to 30%) to give 980 mg of 2-(7-fluoro-3-oxo-indan-4-yl)sulfanylacetonitrile as a brown solid (quant. yield).

Steps B-F: 2-[7-(3,5-Difluorophenoxy)-3-hydroxy-indan-4-yl]sulfonylacetonitrile (Compound 14) was prepared analogously to the procedures in Example 1. LCMS ESI (−) m/z 364 (M−H); $^1$H NMR (400 MHz, CDCl$_3$): δ 7.9 (d, 1H), 6.97 (d, 1H), 6.73-6.67 (m 1H), 6.64-6.58 (m, 1H), 5.83-5.79 (m, 1H), 6.57-6.53 (m, 1H), 4.22 (d, 1H), 3.20-3.10 (m, 1H), 2.95-2.85 (m, 2H), 2.60-2.50 (m, 1H), 2.25-2.16 (m, 1H).

Example 15

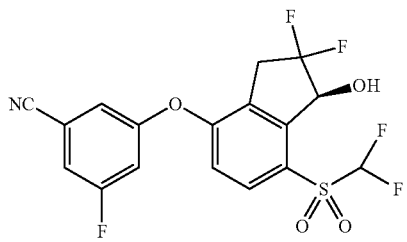 [SMILES: N#Cc1cc(F)cc(Oc2ccc(S(=O)(=O)C(F)F)c3c2CC(F)(F)[C@H]3O)c1]

3-[(1S)-7-(difluoromethylsulfonyl)-2,2-difluoro-1-hydroxy-indan-4-yl]oxy-5-fluoro-benzonitrile (Compound 15)

Step A: Preparation of 3-((7-((difluoromethyl)sulfonyl)-2,3-dihydrospiro[indene-1,2'-[1,3]dioxolan]-4-yl)oxy)-5-fluorobenzonitrile A mixture of 3-fluoro-5-hydroxy-benzonitrile (1.33 g, 9.7 mmol), 7'-(difluoromethylsulfonyl)-4'-fluoro-spiro[1,3-dioxolane-2,1'-indane] (1.0 g, 3.24 mmol), and cesium bicarbonate (1.26 g, 6.5 mmol) in 1-methyl-2-pyrrolidone (1.8 mL) was heated under N$_2$ at 110° C. (microwave) for 1 hour and 5 minutes. The reaction was repeated ten times. The reaction mixtures were combined, diluted with EtOAc, and washed twice with 1 N NaOH. The combined aqueous layer was extracted with EtOAc. The EtOAc extracts were combined and washed with brine, dried over Na$_2$SO$_4$, filtered, and concentrated to about 100 mL to give a suspension. The suspension was filtered to give 3-((7-((difluoromethyl)sulfonyl)-2,3-dihydrospiro[indene-1,2'-[1,3]dioxolan]-4-yl)oxy)-5-fluorobenzonitrile as an off-white solid (6.25 g). The filtrate was diluted with EtOAc, washed with brine (3×), dried over Na$_2$SO$_4$, filtered, and concentrated. The residue was purified by flash column chromatography on silica gel with EtOAc/hexane (0% to 40%) to give additional 3-((7-((difluoromethyl)sulfonyl)-2,2-difluoro-2,3-dihydrospiro[indene-1,2'-[1,3]dioxolan]-4-yl)oxy)-5-fluorobenzonitrile (3.3 g, 69% combined yield) as a white solid. LCMS ESI (+) m/z 426 (M+H).

Step B: Preparation of 3-((7-((difluoromethyl)sulfonyl)-1-oxo-2,3-dihydro-1H-inden-4-yl)oxy)-5-fluorobenzonitrile A mixture of 3-((7-((difluoromethyl)sulfonyl)-2,3-dihydrospiro[indene-1,2'[1,3]dioxolan]-4-yl)oxy)-5-fluorobenzonitrile (10.9 g, 25.6 mmol) and PPTS (667 mg, 2.66 mmol) in acetone (100 mL)/water (15 mL) was heated at 82° C. for 5 hours and then 75° C. overight. The reaction mixture was cooled to room temperature, concentrated under reduced pressure, diluted with EtOAc, washed with saturated aqueous NaHCO$_3$, dried over MgSO$_4$, filtered, and concentrated. The residue was filtered and washed with water. The solid obtained was briefly dried under vacuum at 50° C. and then triturated with EtOAc/hexane to give 3-((7-((difluoromethyl)sulfonyl)-1-oxo-2,3-dihydro-1H-inden-4-yl)oxy)-5-fluorobenzonitrile (8 g). Flash column chromatography of the mother liquor on silica gel with EtOAc/hexane (0% to 80%) provided additional 3-((7-((difluoromethyl)sulfonyl)-1-oxo-2,3-dihydro-1H-inden-4-yl)oxy)-5-fluorobenzonitrile (1.3 g, combined 9.3 g, quant. yield). LCMS ESI (+) m/z 382 (M+H).

Step C: Preparation of (E,Z)-3-((1-(butylimino)-7-((difluoromethyl)sulfonyl)-2,3-dihydro-1H-inden-4-yl)oxy)-5-fluorobenzonitrile A mixture of 3-((7-((difluoromethyl)sulfonyl)-1-oxo-2,3-dihydro-1H-inden-4-yl)oxy)-5-fluorobenzonitrile (1.42 g, 3.72 mmol), butylamine (6.0 mL) and 5 drops of trifluoroacetic acid (~0.1 mL) in benzene (40 mL) was refluxed overnight with removal of water using a Dean-Stark trap. The reaction mixture was concentrated under reduced pressure, diluted with methyl tert-butyl ether, washed with saturated aqueous NaHCO$_3$ and brine, dried over Na$_2$SO$_4$, filtered, and concentrated. The residue was used in the next step without further purification.

Step D: Preparation of 3-((7-((difluoromethyl)sulfonyl)-2,2-difluoro-1-oxo-2,3-dihydro-1H-inden-4-yl)oxy)-5-fluorobenzonitrile A mixture of (E,Z)-3-((1-(butylimino)-7-((difluoromethyl)sulfonyl)-2,3-dihydro-1H-inden-4-yl)oxy)-5-fluorobenzonitrile (1.29 g, 3 mmol, crude from step C), Selectfluor® (2.62 g, 7.4 mmol) and sodium sulfate (4 g, 28.2 mmol) under N$_2$ was heated at 82° C. for 4 hours. After cooling to room temperature, concentrated HCl (37%, 3 mL) was added. The mixture was stirred at room temperature for 15 minutes and then concentrated under reduced pressure. The residue was diluted with methyl t-butyl ether, washed with half saturated aqueous NaHCO$_3$ and then brine, dried over Na$_2$SO$_4$, filtered, and triturated with EtOAc/hexane to give 3-((7-((difluoromethyl)sulfonyl)-2,2-difluoro-1-oxo-2,3-dihydro-1H-inden-4-yl)oxy)-5-fluorobenzonitrile as an off-white solid (0.5 g). The mother liquor was purified by flash column chromatography with EtOAc/hexane (5% to 40%) to give additional 3-((7-((difluoromethyl)sulfonyl)-2,2-difluoro-1-oxo-2,3-dihydro-1H-inden-4-yl)oxy)-5-fluorobenzonitrile (0.13 g, 51% combined yield). LCMS ESI (+) m/z 418 (M+H) and 435 (M+NH$_4$).

Step E: Preparation of (S)-3-((7-((difluoromethyl)sulfonyl)-2,2-difluoro-1-hydroxy-2,3-dihydro-1H-inden-4-yl)oxy)-5-fluorobenzonitrile (Compound 15)

An ice cold solution of RuCl(p-cymene)[(R,R)-Ts-DPEN] (0.6 mg) in dichloromethane (0.2 mL) was added by syringe under nitrogen to an ice cold solution of 3-[7-(difluoromethylsulfonyl)-2,2-difluoro-1-oxo-indan-4-yl]oxy-5-fluoro-benzonitrile (28 mg, 0.07 mmol), triethylamine (18.7 µL, 0.13 mmol) and formic acid (7.6 µL, 0.2 mmol) in dichloromethane (0.5 mL) and then placed in a refrigerator at 4° C. overnight. The reaction mixture was directly purified on preparative TLC with EtOAc/hexane (40%) to give Compound 15 (23.4 mg, 0.06 mmol, 83% yield). The ee was determined to be greater than 95% by $^{19}$F NMR analysis of the corresponding Mosher ester. LCMS ESI (+) m/z 420 (M+H); $^1$H NMR (400 MHz, CDCl$_3$): δ 7.94 (d, 1H), 7.33-6.98 (m, 4H), 6.44 (t, 1H), 5.51 (d, 1H), 3.61-3.45 (m, 2H).

Example 16

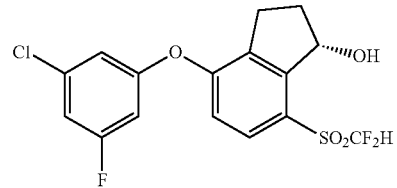

(S)-4-(3-chloro-5-fluorophenoxy)-7-((difluoromethyl)sulfonyl)-2,3-dihydro-1H-inden-1-ol (Compound 16)

Prepared similarly as described in Example 1 using RuCl (p-cymene)[(S,S)-Ts-DPEN] in place of RuCl(p-cymene)[(R,R)-Ts-DPEN] in Step F. The e.e. was determined to be 96% by $^{19}$F NMR analysis of the corresponding Mosher ester. LCMS ESI (+) m/z 393 (M+H); ESI (−) m/z 437/439 (M−H+46); $^1$H NMR (400 MHz, CDCl$_3$): δ 7.81 (d, 1H), 7.00-6.98 (m, 1H), 6.94 (d, 1H), 6.89-6.88 (m, 1H), 6.74-6.71 (m, 1H), 6.35 (t, 1H), 5.67-5.65 (m, 1H), 3.21-3.13 (m, 2H), 2.96-2.89 (m, 1H), 2.50-2.41 (m, 1H), 2.30-2.23 (m, 1H).

Example 17

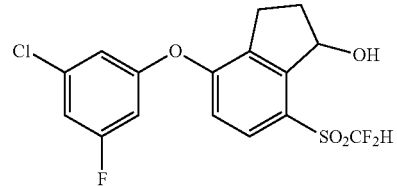

4-(3-chloro-5-fluorophenoxy)-7-((difluoromethyl)sulfonyl)-2,3-dihydro-1H-inden-1-ol (Compound 17)

Step A: Preparation of 7-(difluoromethylsulfonyl)-4-fluoro-indan-1-ol

To a stirred solution of 7-(difluoromethylsulfonyl)-4-fluoro-indan-1-one (110 mg, 0.42 mmol) in methanol (4 mL) was added sodium borohydride (24 mg, 0.62 mmol). The reaction mixture was stirred at ambient temperature for 1 hour. Saturated aqueous NH$_4$Cl solution was added dropwise. The mixture was extracted with EtOAc. The combined organic layers were washed with water and brine, dried and concentrated in vacuo to give 7-(difluoromethylsulfonyl)-4-fluoro-indan-1-ol (100 mg, 90%), which was used in the next step without further purification. LCMS ESI (+) m/z 267 (M+H); ESI (−) m/z 311 (M−H+46).

Step B: Preparation of 4-(3-chloro-5-fluorophenoxy)-7-((difluoromethyl)sulfonyl)-2,3-dihydro-1H-inden-1-ol (Compound 17)

Prepared similarly as described in Example 1 Step G using 7-(difluoromethylsulfonyl)-4-fluoro-indan-1-ol in place of (1R)-7-(difluoromethylsulfonyl)-4-fluoro-indan-1-ol. LCMS ESI (+) m/z 393 (M+H); ESI (−) m/z 437, 439 (M−H+46).

Example 18

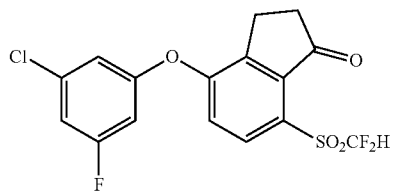

4-(3-chloro-5-fluorophenoxy)-7-((difluoromethyl)sulfonyl)-2,3-dihydro-1H-inden-1-one (Compound 18)

To a stirred solution of 4-(3-chloro-5-fluoro-phenoxy)-7-(difluoromethylsulfonyl)indan-1-ol Compound 17 (23 mg, 0.06 mmol) in dichloromethane (1 mL) was added Dess-Martin periodinane (37 mg, 0.09 mmol). The reaction mixture was stirred at ambient temperature for 3 hours. The reaction mixture was partitioned between EtOAc and water. The aqueous layer was extracted with EtOAc. The combined organic layers were washed with water and brine, dried and concentrated. The residue was purified by flash chromatography on silica gel (5-20% EtOAc in hexane) to give Compound 18 (20 mg, 87%) as a white solid. LCMS ESI (+) m/z 391, 393 (M+H); $^1$H NMR (400 MHz, CDCl$_3$): δ 8.15 (d, 1H), 7.14 (d, 1H), 7.12 (t, 1H), 7.07-7.04 (m, 1H), 6.96-6.93 (m, 1H), 6.80-6.76 (m, 1H), 3.23-3.20 (m, 2H), 2.90-2.87 (m, 2H).

Example 19

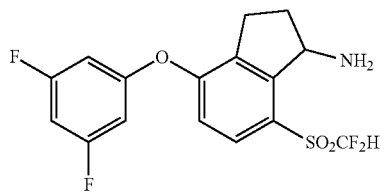

7-((difluoromethyl)sulfonyl)-4-(3,5-difluorophenoxy)-2,3-dihydro-1H-inden-1-amine (Compound 19)

Step A: Preparation of 7-((difluoromethyl)sulfonyl)-4-(3,5-difluorophenoxy)-2,3-dihydro-1H-inden-1-one Prepared as described in Example 18 using (R)-7-((difluoromethyl)sulfonyl)-4-(3,5-difluorophenoxy)-2,3-dihydro-1H-inden-1-ol (Compound 2) in place of 4-(3-chloro-5-fluoro-phenoxy)-7-(difluoromethylsulfonyl)indan-1-ol (Compound 17). LCMS ESI (+) m/z 375 (M+H).

Step B: Preparation of 7-((difluoromethyl)sulfonyl)-4-(3,5-difluorophenoxy)-2,3-dihydro-1H-inden-1-amine (Compound 19)

A mixture of 7-((difluoromethyl)sulfonyl)-4-(3,5-difluorophenoxy)-2,3-dihydro-1H-inden-1-one (25 mg, 0.07 mmol) and NH$_4$OAc (51 mg, 0.67 mmol) in i-PrOH (0.77 mL) was stirred at ambient temperature for 1 hour. NaBH$_3$CN (17 mg, 0.27 mmol) was added. The mixture was heated at reflux for 1 hour. After cooling, the reaction was quenched by the addition of saturated aqueous NaHCO$_3$ solution. The aqueous layer was extracted with dichloromethane. The combined organic layers were washed with brine, dried and concentrated. The residue was purified by flash chromatography on silica gel (2-12% MeOH in dichloromethane) to give Compound 19, which was converted to HCl salt by treatment with 4N HCl in dioxane (4 mg, 16% yield). LCMS ESI (+) m/z 376 (M+H). $^1$H NMR for free base (400 MHz, CDCl$_3$): δ 7.81 (d, 1H), 6.92 (d, 1H), 6.72-6.67 (m, 1H), 6.62 (t, 1H), 6.63-6.59 (m, 2H), 4.96-4.94 (m, 1H), 3.18-3.10 (m, 1H), 2.99-2.92 (m, 1H), 2.51-2.41 (m, 1H), 2.30-2.00 (m, 3H).

Example 20

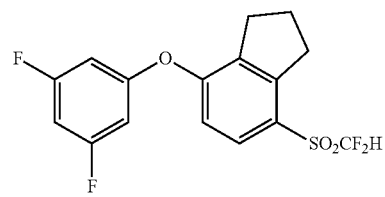

4-((Difluoromethyl)sulfonyl)-7-(3,5-difluorophenoxy)-2,3-dihydro-1H-indene (Compound 20)

To a mixture of ((1R)-7-(difluoromethylsulfonyl)-4-(3,5-difluorophenoxy)indan-1-ol (Compound 2) (25 mg, 0.07 mmol), triethylsilane (0.13 mL, 0.80 mmol), and EtOH (0.7 mL) was added Pd(OH)$_2$/C (20% load on carbon, 5 mg). The reaction mixture was heated at reflux overnight. After cooling, the reaction mixture was filtered through Celite. The filtrate was concentrated. The residue was purified by C18 reverse phase flash chromatography (Biotage Isolera One unit, C18 Flash 12+M column, 30-95% CH$_3$CN/water) to afford Compound 20 (10 mg, 42%) as a white solid. LCMS ESI (+) m/z 361 (M+H); $^1$H NMR (400 MHz, CDCl$_3$): δ 7.76 (d, 1H), 6.87 (d, 1H), 6.69-6.63 (m, 1H), 6.60-6.55 (m, 2H), 6.18 (t, 1H), 3.37 (t, 2H), 2.93 (t, 2H), 2.20-2.17 (m, 2H).

Example 21

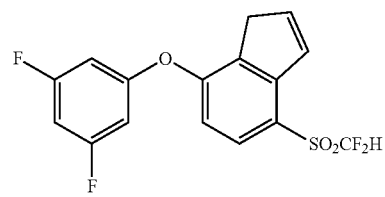

4-((Difluoromethyl)sulfonyl)-7-(3,5-difluorophenoxy)-1H-indene (Compound 21)

A mixture of 7-(difluoromethylsulfonyl)-4-(3,5-difluorophenoxy)indan-1-ol (60 mg, 0.16 mmol), p-toluenesulfonic acid monohydrate (9.1 mg, 0.05 mmol) and toluene (1.6 mL) was heated at 100° C. for 5 hours. After cooling, the reaction mixture was concentrated. The residue was purified by C18 reverse phase flash chromatography (Biotage Isolera One unit, C18 Flash 12+M column, 20-60% $CH_3CN$/water) to afford Compound 21 (50 mg, 88% yield) as a solid. LCMS ESI (+) m/z 359 (M+H); $^1$H NMR (400 MHz, $CDCl_3$): δ 7.88 (d, 1H), 7.47-7.45 (m, 1H), 6.93-6.90 (m, 2H), 6.71-6.60 (m, 3H), 6.22 (t, 1H), 3.49-3.48 (m, 1H).

Example 22

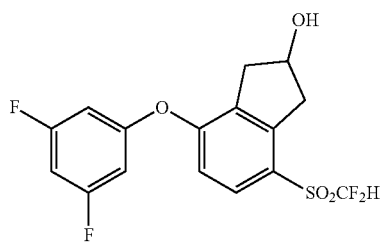

4-((Difluoromethyl)sulfonyl)-7-(3,5-difluorophenoxy)-2,3-dihydro-1H-inden-2-ol (Compound 22)

Step A: Preparation of 2-((difluoromethyl)sulfonyl)-5-(3,5-difluorophenoxy)-1a,6a-dihydro-6H-indeno[1,2-b]oxirene To a stirred solution of 4-(difluoromethylsulfonyl)-7-(3,5-difluorophenoxy)-1H-indene (Compound 21) (30 mg, 0.08 mmol) in dichloromethane (0.4 mL) was added 3-chloroperbenzoic acid (38 mg, 0.17 mmol). The reaction mixture was stirred for 40 hours at ambient temperature. The reaction mixture then diluted with dichloromethane, washed with 20% sodium carbonate, dried over anhydrous sodium sulfate and concentrated under reduced pressure. The crude product was purified by column chromatography on silica gel (15% EtOAc in hexane) to afford 2-((difluoromethyl)sulfonyl)-5-(3,5-difluorophenoxy)-1a,6a-dihydro-6H-indeno[1,2-b]oxirene (24 mg, 77%). LCMS ESI (−) m/z 357 (M−H−16).

Step B: Preparation of 4-((difluoromethyl)sulfonyl)-7-(3,5-difluorophenoxy)-2,3-dihydro-1H-inden-2-ol (Compound 22)

To a stirred solution of 2-((difluoromethyl)sulfonyl)-5-(3,5-difluorophenoxy)-1a,6a-dihydro-6H-indeno[1,2-b]oxirene (24 mg, 0.06 mmol) in 1,2-dichloroethane (0.6 mL) was added diiodozinc (31 mg, 0.1 mmol) and sodium cyanoborohydride (8.1 mg, 0.13 mmol). The reaction mixture was heated to reflux for 16 hours. After cooling, the reaction was quenched by the addition of 1N HCl. The mixture was extracted with dichloromethane. The combined organic layers were washed with brine, dried and concentrated. The residue was purified by flash chromatography on silica gel (10-30% EtOAc in hexane) to give Compound 22 (7 mg, 29%). LCMS ESI (−) m/z 421 (M−H+46); $^1$H NMR (400 MHz, $CDCl_3$): δ 7.79 (d, 1H), 6.90 (d, 1H), 6.72-6.66 (m, 1H), 6.64-6.57 (m, 2H), 6.19 (t, 1H), 4.85-4.81 (m, 1H), 3.60-3.44 (m, 3H), 3.21-2.99 (m, 2H).

Example 23

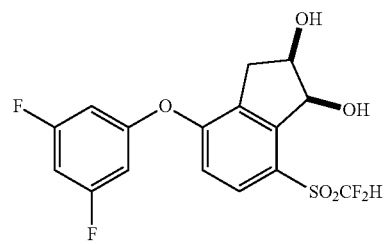

cis-(±)7-((Difluoromethyl)sulfonyl)-4-(3,5-difluorophenoxy)-2,3-dihydro-1H-indene-1,2-diol (Compound 23)

Two diols were isolated as a mixture of two diastereomers from Example 22 Step B by further elution of the silica gel column with 50% EtOAc in hexane. The mixture was further purified by C18 reverse phase flash chromatography (Biotage Isolera One unit, C18 Flash 12+M column, 20-50% $CH_3CN$/water) to give Compound 23 (4 mg, 16%) as a solid. LCMS ESI (−) m/z 437 (M−H+46); $^1$H NMR (400 MHz, $CDCl_3$): δ 7.83 (d, 1H), 6.98 (d, 1H), 6.74-6.69 (m, 1H), 6.64-6.62 (m, 2H), 6.36 (t, 1H), 5.37 (brs, 1H), 4.65-4.63 (m, 1H), 3.45-3.39 (m, 2H), 2.92-2.88 (m, 1H).

Example 24

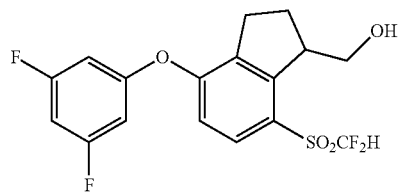

(7-((Difluoromethyl)sulfonyl)-4-(3,5-difluorophenoxy)-2,3-dihydro-1H-inden-1-yl)methanol (Compound 24)

Step A: Preparation of 7-((difluoromethyl)thio)-4-fluoro-2,3-dihydro-1H-indene-1-carbaldehyde Lithium bis(trimethylsilyl)amide (1.0 M solution in THF, 0.32 mL, 0.32 mmol) was added dropwise to a stirred suspension of (methoxy methyl)triphenylphosphonium chloride (103 mg, 0.30 mmol) in dry THF (1 mL) at 0° C. under nitrogen. The mixture was stirred at 0° C. for 1 hour. A solution of 7-(difluoromethylsulfanyl)-4-fluoro-indan-1-one (50 mg, 0.22 mmol) in THF (1 mL) was added dropwise. The mixture was stirred at 0° C. for 1 hour and at ambient temperature overnight. Water was added and the mixture was partitioned between EtOAc and brine. The aqueous layer was extracted with EtOAc. The combined organic layers were washed with brine, dried and concentrated. The crude was dissolved in tetrahydrofuran (2 mL). Concentrated HCl (0.11 mL) was added. The reaction mixture was stirred at ambient temperature for 4 hours, and then extracted with EtOAc. The combined organic layers were washed with brine, dried and concentrated. The residue was purified by flash chromatography on silica gel (10-50% EtOAc/hexane) to give 7-((difluoromethyl)thio)-4-fluoro-2,3-dihydro-1H-indene-1-carbaldehyde (24 mg, 45%). LCMS ESI (−) m/z 245 (M−H).

Step B: Preparation of (7-((difluoromethyl)thio)-4-fluoro-2,3-dihydro-1H-inden-1-yl)methanol To a stirred solution of 7-((difluoromethyl)thio)-4-fluoro-2,3-dihydro-1H-indene-1-carbaldehyde (24 mg, 0.10 mmol) in MeOH (1 mL) was added sodium borohydride (5.5 mg, 0.15 mmol). The reaction mixture was stirred at ambient temperature for 30 minutes. Water was added dropwise to quench the reaction. The mixture was extracted with EtOAc. The combined organic layers were washed with water and brine, dried and concentrated. The residue was purified by flash chromatography on silica gel (10-50% EtOAc/hexane) to give (7-((difluoromethyl)thio)-4-fluoro-2,3-dihydro-1H-inden-1-yl)methanol (17 mg, 70% yield). LCMS ESI (−) m/z 247 (M−H).

Step C: Preparation of (7-((difluoromethyl)sulfonyl)-4-fluoro-2,3-dihydro-1H-inden-1-yl)methanol To a stirred solution of (7-((difluoromethyl)thio)-4-fluoro-2,3-dihydro-1H-inden-1-yl)methanol (17 mg, 0.07 mmol) in dichloromethane (0.7 mL) was added 3-chloroperbenzoic acid (35 mg, 0.21 mmol). The reaction mixture was stirred at ambient temperature overnight. The reaction was quenched by the addition of saturated aqueous NaHCO$_3$ solution and saturated aqueous Na$_2$S$_2$O$_3$ solution and then extracted twice with EtOAc. The combined organic layers were washed with water and brine, dried and concentrated. The residue was purified by flash chromatography on silica gel (10-30% EtOAc/hexane) to give (7-((difluoromethyl)sulfonyl)-4-fluoro-2,3-dihydro-1H-inden-1-yl)methanol (14 mg, 73%). LCMS ESI (+) m/z 281 (M+H).

Step D: Preparation of (7-((difluoromethyl)sulfonyl)-4-(3,5-difluorophenoxy)-2,3-dihydro-1H-inden-1-yl)methanol (Compound 24)

Prepared similarly as described in Example 1 Step G using (7-((difluoromethyl)sulfonyl)-4-fluoro-2,3-dihydro-1H-inden-1-yl)methanol in place of (1R)-7-(difluoromethylsulfonyl)-4-fluoro-indan-1-ol. LCMS ESI (+) 391 m/z (M+H); $^1$H NMR (400 MHz, CDCl$_3$): δ 7.77 (d, 1H), 6.90 (d, 1H), 6.71-6.65 (m, 1H), 6.62-6.36 (m, 2H), 6.23 (t, 1H), 3.94-3.71 (m, 3H), 2.97-2.89 (m, 2H), 2.84 (s, 1H), 2.40-2.22 (m, 2H).

Example 25

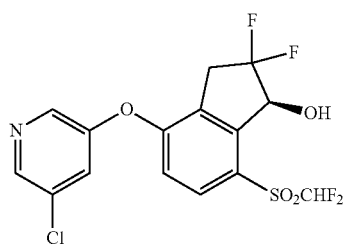

(S)-4-((5-chloropyridin-3-yl)oxy)-7-((difluoromethyl)sulfonyl)-2,2-difluoro-2,3-dihydro-1H-inden-1-ol (Compound 25)

Step A: Preparation of 3-chloro-5-((7-((difluoromethyl)sulfonyl)-2,3-dihydrospiro[indene-1,2'[1,3]dioxolan]-4-yl)oxy)pyridine 7-((Difluoromethyl)sulfonyl)-4-fluoro-2,3-dihydrospiro[indene-1,2'[1,3]dioxolane] (3.0 g, 9.7 mmol) was combined with 5-chloropyridin-3-ol (1.89 g, 14.6 mmol) and sodium bicarbonate (2.45 g, 29.2 mmol) then the solids were suspended in N-methylpyrrolidinone (28.5 mL). The mixture was heated to 90° C. for 14 hours then stirred at ambient temperature for 34 hours. The reaction mixture was diluted with ethyl acetate and water and the layers were separated. The aqueous was washed with ethyl acetate and the combined organic layers were washed five times with water, saturated NaCl, dried over Na$_2$SO$_4$ and concentrated in vacuo to a cream-colored solid (4.36 g). LCMS ESI (+) m/z (M+H) 418, 420.

Step B: Preparation of 4-((5-chloropyridin-3-yl)oxy)-7-((difluoromethyl)sulfonyl)-2,3-dihydro-1H-inden-1-one 3-Chloro-5-((7-((difluoromethyl)sulfonyl)-2,3-dihydrospiro[indene-1,2'-[1,3]dioxolan]-4-yl)oxy)pyridine (5.07 g, 12.1 mmol) was dissolved in 6:1 acetone/water (100 mL) and treated with pyridinium p-toluenesulfonate (304 mg, 1.21 mmol). The mixture was heated to 82° C. for 22 hours then stirred at ambient temperature for 38 hours. The reaction mixture was treated with additional pyridinium p-toluenesulfonate (304 mg, 1.21 mmol) and reheated to 90° C. for 24 hours. The reaction was cooled and concentrated in vacuo. The remaining aqueous was treated with saturated NaHCO$_3$ and ethyl acetate then separated. The aqueous was washed with ethyl acetate and the combined organics were washed with saturated NaHCO$_3$, saturated NaCl, dried over Na$_2$SO$_4$ and concentrated in vacuo to a tan solid (4.25 g). LCMS ESI (+) m/z (M+H) 374, 376.

Step C: Preparation of N-butyl-4-((5-chloropyridin-3-yl)oxy)-7-((difluoromethyl)sulfonyl)-2,3-dihydro-1H-inden-1-imine 4-((5-Chloropyridin-3-yl)oxy)-7-((difluoromethyl)sulfonyl)-2,3-dihydro-1H-inden-1-one (4.25 g, 11.4 mmol) was suspended in benzene (250 mL) and treated with butylamine (45 mL, 454 mmol) and trifluoroacetic acid (0.44 mL, 5.7 mmol). The reaction flask was heated through a Dean-Stark trap while monitoring the reaction by $^1$H NMR. After 3.5 hours, the reaction mixture was cooled and concentrated in vacuo then the residue was redissolved in MTBE and water. After separation, the organic layer was washed three times with water, saturated NaHCO$_3$, saturated NaCl, dried over Na$_2$SO$_4$ and concentrated in vacuo to a tan solid (4.8 g).

Step D: Preparation of 4-((5-chloropyridin-3-yl)oxy)-7-((difluoromethyl)sulfonyl)-2,2-difluoro-2,3-dihydro-1H-inden-1-one N-Butyl-4-((5-chloropyridin-3-yl)oxy)-7-((difluoromethyl)sulfonyl)-2,3-dihydro-1H-inden-1-imine (4.8 g, 11.2 mmol) was dissolved in dry acetonitrile (110 mL) and treated with Selectfluor® (9.9 g, 28 mmol) and sodium sulfate (16 g, 112 mmol). The mixture was heated to 100° C.

for 8 hours then stirred for 3 hours at ambient temperature. The mixture was treated with concentrated aqueous HCl (14 mL, 169 mmol) and stirred for 10 minutes. The mixture was concentrated in vacuo then the resulting suspension was diluted with water (250 mL) and ethyl acetate. After separation, the aqueous was washed twice with ethyl acetate and the combined organic layer was washed with saturated NaHCO$_3$, saturated NaCl, dried over Na$_2$SO$_4$ and concentrated in vacuo to a dark semi-solid. The crude product was redissolved in methylene chloride and chromatographed on SiO$_2$ eluting with a gradient of ethyl acetate/hexane. The desired material was collected and concentrated in vacuo to a cream-colored solid (1.76 g). LCMS ESI (+) m/z (M+H) 409.9/411.9.

Step E: Preparation of (S)-4-((5-chloropyridin-3-yl)oxy)-7-((difluoromethyl)sulfonyl)-2,2-difluoro-2,3-dihydro-1H-inden-1-ol (Compound 25)

4-((5-Chloropyridin-3-yl)oxy)-7-((difluoromethyl)sulfonyl)-2,2-difluoro-2,3-dihydro-1H-inden-1-one (1.76 g, 4.3 mmol) was dissolved in methylene chloride (46 mL), treated with triethylamine (1.2 mL, 8.6 mmol) and formic acid (0.49 mL, 12.9 mmol) then cooled to 0° C. The solution was treated with solid RuCl(p-cymene)[(R,R)-Ts-DPEN] (27 mg, 0.04 mmol). The homogeneous reaction mixture was transferred to the refrigerator and allowed to stand at 4° C. for 14 hours. The mixture was concentrated in vacuo and chromatographed on SiO$_2$ eluting with a gradient of ethyl acetate and hexanes. After chromatography, the desired product was concentrated in vacuo. The remaining oil was dissolved in Et$_2$O, concentrated in vacuo, and dried under high vacuum to give Compound 25 as a white foam (1.64 g). LCMS ESI (+) m/z (M+H) 410, 412. $^1$H NMR (400 MHz, CDCl$_3$) δ 8.55-8.54 (m, 1H), 8.40-8.39 (m, 1H), 7.91 (d, 1H), 7.52-7.49 (m, 1H), 6.93 (d, 1H), 6.44 (t, 1H), 5.53-5.49 (m, 1H), 3.64-3.48 (m, 2H), 3.35 (d, 1H).

Alternative synthesis of 4-((5-chloropyridin-3-yl)oxy)-7-((difluoromethyl)sulfonyl)-2,3-dihydro-1H-inden-1-one Preparation of 4-((5-chloropyridin-3-yl)oxy)-7-((difluoromethyl)sulfonyl)-2,3-dihydro-1H-inden-1-one Prepared similarly as described in Example 18 using (R)-4-((5-chloropyridin-3-yl)oxy)-7-((difluoromethyl)sulfonyl)-2,3-dihydro-1H-inden-1-ol (Compound 3) in place of 4-(3-chloro-5-fluoro-phenoxy)-7-(difluoromethylsulfonyl)indan-1-ol (Compound 17). LCMS ESI (+) m/z 374, 376 (M+H).

Example 26

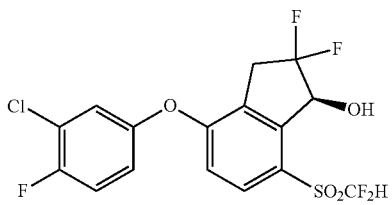

(S)-4-(3-Chloro-4-fluorophenoxy)-7-((difluoromethyl)sulfonyl)-2,2-difluoro-2,3-dihydro-1H-inden-1-ol (Compound 26)

Step A: Preparation of 7-((difluoromethyl)sulfonyl)-2,4-difluoro-2,3-dihydro-1H-inden-1-one A mixture of 7-(difluoromethylsulfonyl)-4-fluoro-indan-1-one (100 mg, 0.38 mmol), methanol (4 mL) and Accufluor® (50% on aluminum oxide, 158 mg, 0.490 mmol) was heated at reflux for 5 hours. After cooling, the solvent was removed under reduced pressure. The residue was taken up in dichloromethane and filtered. The filtrate was washed with water and brine, dried and concentrated. The residue was purified by flash chromatography on silica gel (10-25% EtOAc/hexane) to give 7-((difluoromethyl)sulfonyl)-2,4-difluoro-2,3-dihydro-1H-inden-1-one (55 mg, 51%). LCMS ESI (+) m/z 283 (M+H).

Step B: Preparation of tert-butyl((4-((difluoromethyl)sulfonyl)-2,7-difluoro-1H-inden-3-yl)oxy)dimethylsilane To a stirred solution of 7-((difluoromethyl)sulfonyl)-2,4-difluoro-2,3-dihydro-1H-inden-1-one (352 mg, 1.25 mmol) and triethylamine (1.04 mL, 7.48 mmol) in dichloromethane (10 mL) was added dropwise [tert-butyl(dimethyl)silyl] trifluoromethanesulfonate (0.43 mL, 1.87 mmol) at 0° C. under nitrogen. The reaction mixture was allowed to warm to ambient temperature and stir for 3 hours. The reaction mixture was diluted with EtOAc, washed with saturated aqueous NaHCO$_3$ solution and brine, dried and concentrated. The crude was used in the next step without further purification. LCMS ESI (+) m/z 397 (M+H).

Step C: Preparation of 7-((difluoromethyl)sulfonyl)-2,2,4-trifluoro-2,3-dihydro-1H-inden-1-one To a stirred solution of tert-butyl((4-((difluoromethyl)sulfonyl)-2,7-difluoro-1H-inden-3-yl)oxy)dimethylsilane (crude, 494 mg, 1.25 mmol) in acetonitrile (12 mL) was added Selectfluor® (574 mg, 1.62 mmol). The resulting mixture was stirred at ambient temperature for 3 hours. The solvent was evaporated in vacuo. The residue was partitioned between EtOAc and water. The aqueous layer was extracted with EtOAc. The combined organics were washed with water and brine, dried over Na$_2$SO$_4$, filtered, and concentrated to dryness. The residue was purified by flash chromatography on silica gel (8-28% EtOAc in hexane) to give 7-((difluoromethyl)sulfonyl)-2,2,4-trifluoro-2,3-dihydro-1H-inden-1-one (315 mg, 84%). LCMS ESI (+) m/z 301 (M+H).

Step D: Preparation of (S)-7-((difluoromethyl)sulfonyl)-2,2,4-trifluoro-2,3-dihydro-1H-inden-1-ol Prepared analogously to the procedure for in Example 1 Step F. LCMS ESI (−) m/z 347 (M−H+46).

Step E: Preparation of (S)-tert-butyl((7-((difluoromethyl)sulfonyl)-2,2,4-trifluoro-2,3-dihydro-1H-inden-1-yl)oxy)dimethylsilane To a stirred solution of (S)-7-((difluoromethyl)sulfonyl)-2,2,4-trifluoro-2,3-dihydro-1H-inden-1-ol (140 mg, 0.46 mmol) in dichloromethane (5 mL) was added 2,6-dimethylpyridine (0.21 mL, 1.9 mmol) under nitrogen. The reaction was cooled to −78° C. [tert-Butyl(dimethyl)silyl]trifluoromethanesulfonate (0.27 mL, 1.2 mmol) was added dropwise. The resulting mixture was allowed to warm to ambient temperature and stirred for 3 hours. The reaction mixture was partitioned between EtOAc and water. The aqueous layer was extracted with EtOAc. The combined organics were washed with water and brine, dried over Na$_2$SO$_4$, filtered, and concentrated to dryness. The residue was purified by flash column chromatography on silica gel (2-10% EtOAc in hexane) to give (S)-tert-butyl((7-((difluoromethyl)sulfonyl)-2,2,4-trifluoro-2,3-dihydro-1H-inden-1-yl)oxy)dimethylsilane (155 mg, 80%). LCMS ESI (+) m/z 417 (M+H).

Step F

Preparation of (S)-tert-butyl((4-(3-chloro-4-fluorophenoxy)-7-((difluoromethyl)sulfonyl)-2,2-difluoro-2,3-dihydro-1H-inden-1-yl)oxy)dimethylsilane: A mixture of (S)-tert-butyl((7-((difluoromethyl)sulfonyl)-2,2,4-trifluoro-2,3-dihydro-1H-inden-1-yl)oxy)dimethylsilane (100 mg, 0.24 mmol), 3-chloro-4-fluoro-phenol (70 mg, 0.48 mmol) and sodium hydrogen carbonate (61 mg, 0.72 mmol) in 1-methyl-2-pyrrolidone (0.8 mL) was heated at 70° C. under nitrogen for 3 hours. After cooling, the reaction mixture was partitioned between EtOAc and water. The aqueous layer was extracted with EtOAc. The combined organic layers were washed with water and brine, dried over Na$_2$SO$_4$, and concentrated. The residue was purified by flash chromatography on silica gel (3-15% EtOAc/hexane) affording (S)-tert-butyl((4-(3-chloro-4-fluorophenoxy)-7-((difluoromethyl)sulfonyl)-2,2-difluoro-2,3-dihydro-1H-inden-1-yl)oxy)dimethylsilane (41 mg, 31%). LCMS ESI (−) m/z 541, 543 (M−H).

Step G: Preparation of (S)-4-(3-chloro-4-fluorophenoxy)-7-((difluoromethyl)sulfonyl)-2,2-difluoro-2,3-dihydro-1H-inden-1-ol (Compound 26)

To a stirred solution of (S)-tert-butyl((4-(3-chloro-4-fluorophenoxy)-7-((difluoromethyl)sulfonyl)-2,2-difluoro-2,3-dihydro-1H-inden-1-yl)oxy)dimethylsilane (41 mg, 0.08 mmol) in tetrahydrofuran (0.8 mL) was added tetrabutylammonium fluoride (1.0 M solution in THF, 0.08 mL, 0.08 mmol). The reaction mixture was stirred at ambient temperature for 1 hour. The reaction mixture was then partitioned between EtOAc and water. The aqueous layer was extracted with EtOAc. The combined organic layers were washed with water and brine, dried and concentrated. The residue was purified by C18 reverse phase flash chromatography (Biotage Isolera One unit, C18 Flash 12+M column, 20-95% CH$_3$CN/water) to give Compound 26 (17 mg, 53%) as a white solid. The ee was determined to be >95% by $^{19}$F NMR analysis of the corresponding Mosher ester. LCMS ESI (−) m/z 473, 475 (M−H+46); $^1$H NMR (400 MHz, CDCl$_3$): δ 7.86 (d, 1H), 7.26-7.22 (m, 2H), 7.05-6.95 (m, 1H), 6.86 (d, 1H), 6.41 (t, 1H), 5.51-5.47 (m, 1H), 3.58-3.51 (m, 2H), 3.26 (brd s, 1H).

Example 27

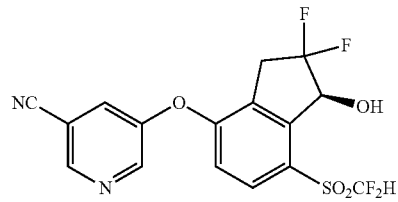

(S)-5-((7 #Difluoromethyl)sulfonyl)-2,2-difluoro-1-hydroxy-2,3-dihydro-1H-inden-4-yl)oxy)nicotinonitrile (Compound 27)

Prepared similarly as described in Example 26 using 5-hydroxynicotinonitrile in place of 3-chloro-4-fluoro-phenol in Step F. LCMS ESI (+) m/z 403 (M+H); $^1$H NMR (400 MHz, CDCl$_3$): δ 8.82 (s, 1H), 8.71 (s, 1H), 7.95 (d, 1H), 7.73-7.71 (m, 1H), 6.95 (d, 1H), 6.44 (t, 1H), 5.55-5.50 (m, 1H), 3.60-3.51 (m, 2H), 3.29 (d, 1H).

Example 28

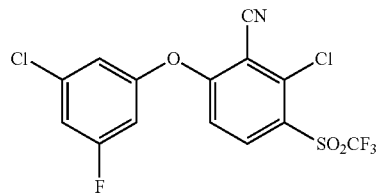

2-Chloro-6-(3-chloro-5-fluorophenoxy)-3-((trifluoromethyl)sulfonyl)benzonitrile (Compound 28)

Step A: Preparation of 2-bromo-3-chloro-4-((trifluoromethyl)thio)aniline

To a stirred solution of 3-chloro-4-((trifluoromethyl)thio)aniline (3.0 g, 13.2 mmol) in DMF (60 mL) was added dropwise a solution of NBS (2.7 g, 15.2 mmol) in DMF (30 mL) at 0° C. under nitrogen. The reaction mixture was stirred at ambient temperature overnight. The reaction mixture was poured into water and extracted with EtOAc. The combined organic layers were washed with water and brine, dried and concentrated. The residue was purified by column chromatography on silica gel (1-5% EtOAc in hexane) to give 2-bromo-3-chloro-4-((trifluoromethyl)thio)aniline (1.10 g, 27%). LCMS ESI (−) m/z 304, 306, 308 (M−H).

Step B: Preparation of (3-bromo-2,4-dichlorophenyl)(trifluoromethyl)sulfane

To a stirred solution of 2-bromo-3-chloro-4-((trifluoromethyl)thio)aniline (0.80 g, 2.61 mmol) in acetic acid (8 mL) was added concentrated HCl (4 mL) dropwise. The reaction mixture was stirred for 10 minutes. A solution of NaNO$_2$ (0.216 g, 3.13 mmol) in water (2 mL) was added dropwise. In a separate flask, a solution of CuCl (388 mg, 3.92 mmol) in concentrated HCl (4 mL) was prepared. The reaction mixture of the diazonium salt prepared beforehand was then quickly added dropwise to the solution of the copper salt. The resulting reaction mixture was stirred at ambient temperature for 2 hours. The reaction mixture was then poured into ice-cooled water and the aqueous phase was extracted twice with EtOAc. The combined organic layers were dried, filtered and then evaporated. The resulting crude product was purified by column chromatography on silica gel (1-3% EtOAc in hexane) to yield (3-bromo-2,4-dichlorophenyl)(trifluoromethyl)sulfane (0.38 g, 47%). LCMS ESI (−) m/z 319, 321, 323 (M−H).

Step C: Preparation of 2,6-dichloro-3-((trifluoromethyl)thio)benzonitrile

To a solution of (3-bromo-2,4-dichlorophenyl)(trifluoromethyl)sulfane (68 mg, 0.21 mmol) in NMP (1 mL) in a microwave reaction vessel was added CuCN (22 mg, 0.25 mmol). The reaction mixture was heated at 190° C. in a microwave reactor for 30 minutes. After cooling, the reaction mixture was partitioned between EtOAc and water. The aqueous layer was extracted with EtOAc. The combined organic layers were washed with water and brine, dried and concentrated. The crude was purified by flash chromatography on silica gel (2-5% EtOAc/hexane) to give 2,6-dichloro-3-((trifluoromethyl)thio)benzonitrile (25 mg, 44%).

Step D: Preparation of 2,6-dichloro-3-((trifluoromethyl)sulfonyl)benzonitrile

To a stirred mixture of 2,6-dichloro-3-((trifluoromethyl)thio)benzonitrile (35 mg, 0.13 mmol), acetonitrile (3 mL), CCl$_4$ (3 mL) and water (6 mL) were added NaIO$_4$ (69 mg, 0.32 mmol) and RuCl$_3$ (1 mg, 0.003 mmol). The reaction mixture was stirred at ambient temperature for 3 hours. The reaction mixture was partitioned between EtOAc and water. The aqueous layer was extracted with EtOAc. The combined organic layers were washed with water and brine, dried and concentrated. The residue was purified by flash chromatography on silica gel (2-10% EtOAc/hexane) to give 2,6-dichloro-3-((trifluoromethyl)sulfonyl)benzonitrile (25 mg, 64%). $^1$H NMR (400 MHz, CDCl$_3$): δ 8.31 (d, 1H), 7.75 (d, 1H).

Step E: Preparation of 2-chloro-6-(3-chloro-5-fluorophenoxy)-3-((trifluoromethyl)sulfonyl)benzonitrile (Compound 28)

To a pear-shaped flask were added 2,6-dichloro-3-((trifluoromethyl)sulfonyl)benzonitrile (25 mg, 0.082 mmol), 3-chloro-5-fluorophenol (12 mg, 0.08 mmol) and NMP (1 mL). Cs$_2$CO$_3$ (16 mg, 0.05 mmol) was added. The reaction mixture was stirred at ambient temperature for 3 hours and then partitioned between EtOAc and water. The aqueous layer was extracted with EtOAc. The combined organic layers were washed with brine, dried and concentrated. The residue was purified by C18 reverse phase flash chromatography (Biotage Isolera One unit, C18 Flash 12+M column, 20-100% CH$_3$CN/water) to give Compound 28 (18 mg, 53%) as a white solid. LCMS ESI (−) m/z 412, 414 (M−H); $^1$H NMR (400 MHz, CDCl$_3$): δ 8.27 (d, 1H), 7.17-7.14 (m, 1H), 7.03-7.02 (m, 1H), 6.97 (d, 1H), 6.88-6.85 (m, 1H).

Example 29

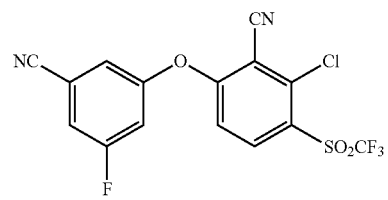

2-Chloro-6-(3-cyano-5-fluorophenoxy)-3-((trifluoromethyl)sulfonyl)benzonitrile (Compound 29): Prepared similarly as described in Example 28 using 3-fluoro-5-hydroxybenzonitrile in place of 3-chloro-5-fluorophenol in Step E. LCMS ESI (−) m/z 403/405 (M−H); $^1$H NMR (400 MHz, CDCl$_3$): δ 8.31 (d, 1H), 7.44-7.41 (m, 1H), 7.32-7.31 (m, 1H), 7.24-7.20 (m, 1H), 6.97 (d, 1H).

Example 30

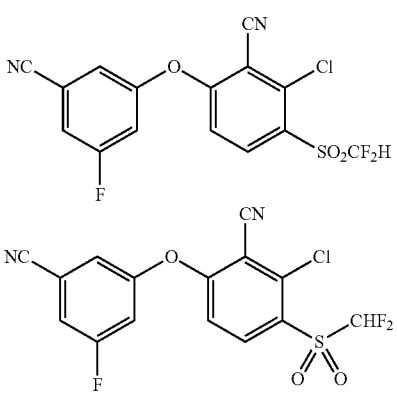

2-Chloro-6-(3-cyano-5-fluorophenoxy)-3-((difluoromethyl)sulfonyl)benzonitrile (Compound 30)

Step A: Preparation of 3-bromo-2,4-dichlorobenzenethiol

To a stirred solution of triphenylphosphine (2.43 g, 9.25 mmol) in dichloromethane (8 mL) and DMF (0.5 mL) was added dropwise a solution of 3-bromo-2,4-dichlorobenzene-1-sulfonyl chloride (1.00 g, 3.08 mmol) in dichloromethane (8 mL) at 0° C. The reaction mixture was allowed to gradually warm to ambient temperature over 2 hours. The reaction mixture was concentrated. To the residue was added 1 N NaOH solution and extracted with ether. The aqueous layer was acidified with 3 N HCl and extracted with EtOAc. The combined organic layers were washed with brine, dried (MgSO$_4$), filtered and concentrated in vacuo. The residue was purified by flash chromatography on silica gel affording 3-bromo-2,4-dichlorobenzenethiol (0.207 g, 26%) as a white solid. LCMS ESI (−) m/z 255, 257, 259 (M−H).

Step B: Preparation of (3-bromo-2,4-dichlorophenyl)(trifluoromethyl)sulfane

Prepared similarly as described in Example 1 Step D using 3-bromo-2,4-dichlorobenzenethiol in place of 4-fluoro-7-sulfanyl-indan-1-one. $^1$H NMR (400 MHz, CDCl$_3$): δ 7.57 (d, 1H), 7.41 (d, 1H), 6.90 (t, 1H).

Step C: Preparation of (2-chloro-6-(3-cyano-5-fluorophenoxy)-3-((difluoromethyl)sulfonyl)benzonitrile (Compound 30)

Prepared analogously to the procedures for Compound 28 in Example 28 Step C to Step E. LCMS ESI (−) m/z 385, 387 (M−H); $^1$H NMR (400 MHz, CDCl$_3$): δ 8.28 (d, 1H), 7.42-7.40 (m, 1H), 7.31-7.26 (m, 1H), 7.22-7.19 (m, 1H), 6.97 (d, 1H), 6.45 (t, 1H).

Example 31

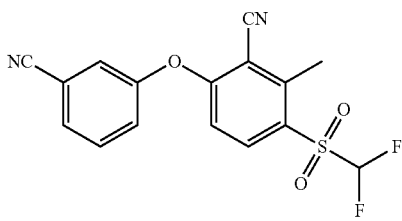 [SMILES: Cc1c(S(=O)(=O)C(F)F)ccc(Oc2cccc(C#N)c2)c1C#N]

6-(3-Cyanophenoxy)-3-((difluoromethyl)sulfonyl)-2-methylbenzonitrile (Compound 31)

Step A: 3-Bromo-6-fluoro-2-methyl-benzonitrile

2-Fluoro-6-methyl-benzonitrile (1000 mg, 7.4 mmol) was added to trifluoromethanesulfonic acid (4.98 mL, 56.2 mmol) cooled in ice. The resulting cold solution was treated with N-bromosuccinimide (1380 mg, 7.8 mmol). The mixture was allowed to stir at ambient temperature. After 30 min, the reaction mixture was poured into ice water and extracted with 2 portions dichloromethane. The combined dichloromethane layers were washed with brine, dried over MgSO$_4$, filtered, and evaporated to yield 3-bromo-6-fluoro-2-methyl-benzonitrile (1560 mg, 7.3 mmol, 98% yield) as a light brown oil that solidified.

Step B: S-(3-Cyano-4-fluoro-2-methyl-phenyl) ethanethioate

To a solution of 3-bromo-6-fluoro-2-methyl-benzonitrile (1500 mg, 7.0 mmol) in 1,4-dioxane (35 mL) was added acetylsulfanylpotassium (840 mg, 7.4 mmol). The mixture was sparged with nitrogen and then (5-diphenylphosphanyl-9,9-dimethyl-xanthen-4-yl)-diphenyl-phosphane (487 mg, 0.8 mmol) and tris(dibenzylideneacetone)dipalladium(0) (3523 mg, 0.4 mmol) were added. The sparging was stopped, and the flask was heated at reflux under nitrogen. After 4.5 hours, the reaction mixture was diluted with EtOAc and brine, filtered, and partitioned. The EtOAc was washed with brine, dried over MgSO$_4$, filtered and evaporated.

The residue was chromatographed on a Biotage 50 g SNAP column with a 10% to 60% EtOAc:hexane gradient. The product containing fractions were combined to afford S-(3-cyano-4-fluoro-2-methyl-phenyl) ethanethioate (441 mg, 2.1 mmol, 30% yield).

Step C: 6-Fluoro-2-methyl-3-sulfanyl-benzonitrile

Lithium hydroxide monohydrate (265 mg, 6.3 mmol) was added to a degassed (N$_2$) solution of S-(3-cyano-4-fluoro-2-methyl-phenyl) ethanethioate (441 mg, 2.1 mmol) in methanol (12 mL) and water (3 mL). The mixture was stirred at ambient temperature under nitrogen. After 45 minutes, the reaction mixture was evaporated, the aqueous residue was neutralized with 10% HCl, and the mixture was extracted with EtOAc. The EtOAc was washed with brine, dried over MgSO$_4$, filtered, and evaporated to afford 6-fluoro-2-methyl-3-sulfanyl-benzonitrile (370 mg, 2.2 mmol, 100% yield).

Step D: 3-(Difluoromethylsulfanyl)-6-fluoro-2-methyl-benzonitrile

Potassium hydroxide (1862 mg, 33 mmol) was added to a degassed frozen slurry of 6-fluoro-2-methyl-3-sulfanyl-benzonitrile (370 mg, 2.2 mmol) and bromodifluoromethyl diethylphosphonate (886 mg, 3.3 mmol) in acetonitrile (6 mL) and water (6 mL) cooled in dry ice/acetone under nitrogen. The mixture was allowed to warm to ambient temperature. After 20 minutes, the reaction mixture was partitioned between MTBE and brine. The MTBE was washed with brine, dried over MgSO$_4$, filtered, and evaporated to yield a yellow oil. This was chromatographed on a Biotage 50 g SNAP column with a 0% to 40% EtOAc:hexane gradient. 3-(Difluoromethylsulfanyl)-6-fluoro-2-methyl-benzonitrile was obtained as a pale yellow oil (239 mg, 1.1 mmol, 50% yield).

Step E: 3-(Difluoromethylsulfonyl)-6-fluoro-2-methyl-benzonitrile

3-Chloroperbenzoic acid (740 mg, 3.3 mmol) was added to a solution of 3-(difluoromethylsulfanyl)-6-fluoro-2-methyl-benzonitrile (239 mg, 1.1 mmol) in dichloromethane (10 mL). The reaction mixture was stirred at ambient temperature overnight. Additional 3-chloroperbenzoic acid (246 mg, 1.1 mmol) was added and the mixture was heated at reflux for 24 hours. The reaction mixture was concentrated, diluted with EtOAc, washed twice with a mixture of saturated aqueous NaHCO$_3$ and aqueous sodium thiosulfate (1 M), water, brine, dried over MgSO$_4$, filtered, and evaporated to afford a white solid. This was chromatographed on a Biotage 25 g SNAP column with a 20% to 60% EtOAc:hexane gradient. 3-(Difluoromethylsulfonyl)-6-fluoro-2-methyl-benzonitrile was obtained as a white solid (138 mg, 0.6 mmol, 50% yield).

Step F: 6-(3-Cyanophenoxy)-3-((difluoromethyl)sulfonyl)-2-methylbenzonitrile (Compound 31)

3-Hydroxybenzonitrile (7.17 mg, 0.06 mmol) was added to a solution of 3-(difluoromethylsulfonyl)-6-fluoro-2-methyl-benzonitrile (15 mg, 0.06 mmol) and sodium hydrogen carbonate (10 mg, 0.12 mmol) in DMF (0.5 mL) in a vial. The vial was sealed and heated at 50° C. After 50 minutes, the reaction mixture was partitioned between EtOAc and water. The EtOAc was washed with water, brine, dried over MgSO$_4$, filtered, and evaporated. The residue was chromatographed on a Biotage 10 g SNAP column with a 20% to 80% EtOAc:hexane gradient to give Compound 31 as a white solid (18.4 mg, 0.05 mmol, 88% yield). $^1$H NMR (400 MHz, CDCl$_3$): δ 8.14 (d, 1H), 7.67-7.61 (m, 2H), 7.48-7.47 (m, 1H), 6.80 (d, 1H), 6.24 (t, 1H), 2.98 (s, 3H). m/z (ES-API-neg) [M−H]=374.

Example 32

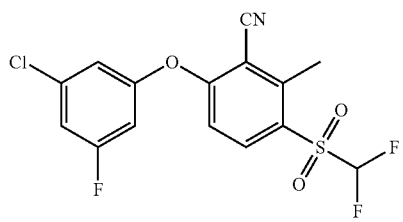 [SMILES: Cc1c(S(=O)(=O)C(F)F)ccc(Oc2cc(F)cc(Cl)c2)c1C#N]

6-(3-Chloro-5-fluorophenoxy)-3-((difluoromethyl)sulfonyl)-2-methylbenzonitrile (Compound 32)

Prepared similarly according to Example 31, Step F, substituting 3-chloro-5-fluorophenol for 3-hydroxybenzonitrile. $^1$H NMR (400 MHz, CDCl$_3$): δ 8.15 (d, 1H), 7.12-7.08 (m, 1H), 7.01-6.99 (m, 1H), 6.89 (d, 1H), 6.85-6.81 (m, 1H), 6.24 (t, 1H), 2.97 (s, 3H). m/z (ES-API-neg) [M−1]=374

Example 33

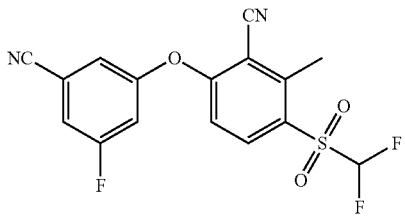 [SMILES: Cc1c(S(=O)(=O)C(F)F)ccc(Oc2cc(F)cc(C#N)c2)c1C#N]

6-(3-Cyano-5-fluorophenoxy)-3-((difluoromethyl)sulfonyl)-2-methylbenzonitrile (Compound 33)

Prepared similarly according to Example 31, Step F, substituting 3-fluoro-5-hydroxybenzonitrile for 3-hydroxybenzonitrile. $^1$H NMR (400 MHz, CDCl$_3$): δ 8.20 (d, 1H), 7.39-7.35 (m, 1H), 7.29-7.27 (m, 1H), 7.20-7.16 (m, 1H), 6.90 (d, 1H), 6.26 (t, 1H), 2.90 (s, 3H). m/z (ES-API-neg) [M−1]=365.

Example 34

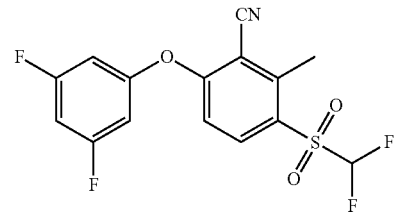 [SMILES: Cc1c(S(=O)(=O)C(F)F)ccc(Oc2cc(F)cc(F)c2)c1C#N]

3-((Difluoromethyl)sulfonyl)-6-(3,5-difluorophenoxy)-2-methylbenzonitrile (Compound 34)

Prepared similarly according to Example 31, Step F, substituting 3,5-difluorophenol for 3-hydroxybenzonitrile. $^1$H NMR (400 MHz, CDCl$_3$): δ 8.15 (d, 1H), 6.91 (d, 1H), 6.85-6.79 (m, 1H), 6.77-6.70 (m, 2H), 6.24 (t, 1H), 2.97 (s, 3H). m/z (ES-API-neg) [M−1]=358.

Example 35

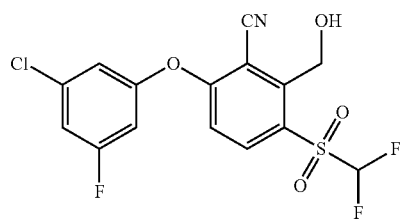 [SMILES: N#Cc1c(Oc2cc(F)cc(Cl)c2)ccc(S(=O)(=O)C(F)F)c1CO]

6-(3-Chloro-5-fluorophenoxy)-3-((difluoromethyl)sulfonyl)-2-(hydroxymethyl)benzonitrile (Compound 35)

Step A: 2-(Bromomethyl)-6-(3-chloro-5-fluoro-phenoxy)-3-(difluoromethylsulfonyl)benzonitrile N-Bromosuccinimide (24 mg, 0.14 mmol) was added to a solution of 6-(3-chloro-5-fluoro-phenoxy)-3-(difluoromethylsulfonyl)-2-methylbenzonitrile Compound 32 (50.8 mg, 0.14 mmol) in carbon tetrachloride (3 mL). The suspension was treated with AIBN (1.1 mg, 0.01 mmol) and heated at reflux for 9 days, with additional N-bromosuccinimide and AIBN being added as needed to drive the reaction to completion. Finally, the reaction mixture was diluted with dichloromethane, washed with water, brine, dried over MgSO$_4$, filtered, and evaporated to yield a colorless glass. This was chromatographed on a Biotage 10 g SNAP column with a 10% to 60% EtOAc:hexane gradient. 2-(Bromomethyl)-6-(3-chloro-5-fluoro-phenoxy)-3-(difluoromethylsulfonyl)benzonitrile was obtained as a white solid (26.4 mg, 0.06 mmol, 43% yield).

Step B: [3-(3-Chloro-5-fluoro-phenoxy)-2-cyano-6-(difluoromethylsulfonyl)phenyl]methyl acetate 2-(Bromomethyl)-6-(3-chloro-5-fluoro-phenoxy)-3-(difluoromethylsulfonyl)benzonitrile (12 mg, 0.03 mmol) in DMF (0.50 mL) was treated with potassium acetate (13.2 mg, 0.13 mmol). The solution was stirred at ambient temperature. After 30 minutes, the reaction mixture was partitioned between EtOAc and water. The EtOAc was washed with water, brine, dried over MgSO$_4$, filtered, and evaporated to afford a residue. This was chromatographed on a Biotage 10 g SNAP column with a 10% to 60% EtOAc:hexane gradient to give [3-(3-Chloro-5-fluoro-phenoxy)-2-cyano-6-(difluoromethylsulfonyl)phenyl]methyl acetate (4.4 mg, 0.01 mmol, 38% yield). m/z (ES-API-pos) [M+H]=451.

Step C: 6-(3-Chloro-5-fluorophenoxy)-3-((difluoromethyl)sulfonyl)-2-(hydroxymethyl)benzonitrile (Compound 35)

Lithium hydroxide hydrate (0.85 mg, 0.02 mmol) was added to a solution of [3-(3-chloro-5-fluoro-phenoxy)-2- cyano-6-(difluoromethylsulfonyl)phenyl]methyl acetate (4.4 mg, 0.01 mmol) in methanol (0.80 mL) and water (0.40 mL). After 15 minutes, the reaction mixture was treated with a few drops of 1M HCl and evaporated. The residue was partitioned between EtOAc and water. The EtOAc was washed with brine, dried over MgSO$_4$, filtered, and evaporated to afford a white film. This was chromatographed on a Biotage 10 g SNAP column with a 10% to 60% EtOAc:hexane gradient. Further purification was completed using a 2 mm preparative TLC plate and developed 4 times with 4:1 dichloromethane:hexane to give Compound 35 (1.0 mg, 0.003 mmol, 25% yield) as a white solid. $^1$H NMR (400 MHz, CDCl$_3$): δ 8.07 (d, 1H), 7.13-7.05 (m, 1H), 7.04-6.95 (m, 2H), 6.89-6.85 (m, 1H), 6.26 (t, 1H), 5.60 (s, 2H). m/z (ES-API-neg) [M−1]=391.

Example 36

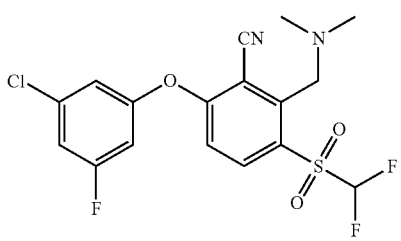 [SMILES: CN(C)Cc1c(S(=O)(=O)C(F)F)ccc(Oc2cc(F)cc(Cl)c2)c1C#N]

6-(3-Chloro-5-fluorophenoxy)-3-((difluoromethyl) sulfonyl)-2-((dimethylamino)methyl)benzonitrile (Compound 36)

N,N-Dimethylamine in THF (1.0 M, 0.02 mL, 0.02 mmol) was added to an ice cold solution of 2-(bromomethyl)-6-(3-chloro-5-fluoro-phenoxy)-3-(difluoromethylsulfonyl)benzonitrile (10 mg, 0.02 mmol) and triethylamine (0.01 mL, 0.07 mmol) in tetrahydrofuran (1 mL). The mixture was allowed to warm to ambient temperature. After 1 hour, the reaction mixture was evaporated. The residue was partitioned between EtOAc and water. The EtOAc was washed with brine, dried over MgSO$_4$, filtered, and evaporated to afford a residue. This was chromatographed on a Biotage 10 g SNAP column with a 10% to 60% EtOAc:hexane gradient to give Compound 36 (4.1 mg, 0.01 mmol, 45% yield) as a white solid. $^1$H NMR (400 MHz, CDCl$_3$): δ 8.29 (d, 1H), 7.13-7.09 (m, 1H), 7.02 (t, 1H), 7.01-6.99 (m, 1H), 6.96 (d, 1H), 6.86-6.82 (m, 1H), 4.11 (s, 2H), 2.34 (s, 6H). m/z (ES-API-pos) [M+H]=419.

Example 37

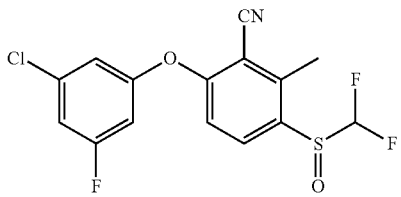 [SMILES: Cc1c(S(=O)C(F)F)ccc(Oc2cc(F)cc(Cl)c2)c1C#N]

6-(3-Chloro-5-fluorophenoxy)-3-((difluoromethyl) sulfinyl)-2-methylbenzonitrile (Compound 37)

Step A: (3-Cyano-4-fluoro-2-methyl-phenyl)-(difluoromethyl)-oxido-sulfonium

3-Chloroperbenzoic acid (740 mg, 3.3 mmol) was added to a solution of 3-(difluoromethylsulfanyl)-6-fluoro-2-methyl-benzonitrile (239 mg, 1.1 mmol) in dichloromethane (10 mL). The reaction mixture was stirred at ambient temperature overnight. Additional 3-chloroperbenzoic acid (246 mg, 1.1 mmol) was added and the mixture was heated at reflux for 24 hours. The reaction mixture was concentrated, diluted with EtOAc, washed twice with a mixture of saturated aqueous NaHCO$_3$ and aqueous sodium thiosulfate (1 M), water, brine, dried over MgSO$_4$, filtered, and evaporated to afford a white solid. This was chromatographed on a Biotage 25 g SNAP column with a 20% to 60% EtOAc:hexane gradient to give 3-(difluoromethylsulfonyl)-6-fluoro-2-methyl-benzonitrile (138 mg, 0.55 mmol, 50% yield) as a white solid and (3-cyano-4-fluoro-2-methyl-phenyl)-(difluoromethyl)-oxido-sulfonium (28.7 mg, 0.12 mmol, 11% yield) as a colorless glass.

Step B: 6-(3-Chloro-5-fluorophenoxy)-3-((difluoromethyl)sulfinyl)-2-methylbenzonitrile (Compound 37)

3-Chloro-5-fluoro-phenol (0.0022 mL, 0.0200 mmol) was added to a solution of (3-cyano-4-fluoro-2-methyl-phenyl)-(difluoromethyl)-oxido-sulfonium (5.0 mg, 0.02 mmol) and potassium carbonate (4.4 mg, 0.03 mmol) in DMF (0.5 mL) in a vial. The vial was sealed and heated at 50° C. After 75 min, the reaction mixture was partitioned between EtOAc and water. The EtOAc was washed with water, brine, dried over MgSO$_4$, filtered, and evaporated. The residue was chromatographed on a Biotage 10 g SNAP column with a 10% to 60% EtOAc:hexane gradient to give Compound 37 (6.8 mg, 0.02 mmol, 88% yield) as a colorless glass. $^1$H NMR (400 MHz, CDCl$_3$): δ 8.07 (d, 1H), 7.07-7.03 (m, 1H), 7.01 (d, 1H), 6.96-6.94 (m, 1H), 6.81-6.77 (m, 1H), 6.15 (t, 1H), 2.68 (s, 3H). m/z (ES-API-neg) [M−H]=358.

Example 38

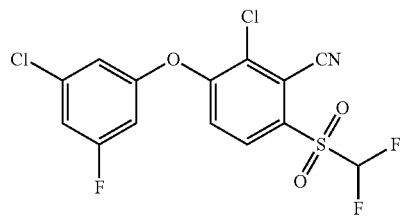 [SMILES: N#Cc1c(S(=O)(=O)C(F)F)ccc(Oc2cc(F)cc(Cl)c2)c1Cl]

2-Chloro-3-(3-chloro-5-fluorophenoxy)-6-((difluoromethyl)sulfonyl)benzonitrile (Compound 38)

Step A: 2-Chloro-3-fluoro-6-sulfanyl-benzonitrile

A flask containing a solution of 2-chloro-3,6-difluorobenzonitrile (2.0 g, 11.5 mmol) in DMF (10 mL) was sparged with nitrogen, cooled in ice, and treated with sodiosulfanylsodium (944 mg, 12.1 mmol). The yellow suspension was stirred and slowly allowed to warm to ambient temperature. After 45 min, the reaction mixture was diluted with 1M NaOH, washed with 2 portions of dichloromethane, acidified to pH 2 with conc. HCl, and extracted with 2 portions of dichloromethane. The dichloromethane was washed with two portions of brine, dried over MgSO₄, filtered, and evaporated to yield 2-chloro-3-fluoro-6-sulfanyl-benzonitrile (1.44 g, 7.7 mmol, 67% yield) as a waxy pale yellow solid. m/z (ES-API-neg) [M−H]=186.

Step B: 2-Chloro-6-(difluoromethylsulfanyl)-3-fluoro-benzonitrile

Bromodifluoromethyl diethylphosphonate (384 mg, 1.44 mmol) was added to a degassed frozen slurry of 2-chloro-3-fluoro-6-sulfanyl-benzonitrile (180 mg, 0.96 mmol) and potassium hydroxide (807 mg, 14.4 mmol) in acetonitrile (4 mL) and water (4 mL) cooled in dry ice/acetone under nitrogen. The mixture was allowed to warm to ambient temperature. After 20 min, the reaction mixture was partitioned between MTBE and brine. The MTBE was washed with brine, dried over MgSO₄, filtered, and evaporated to yield a yellow oil. This was chromatographed on a Biotage 25 g SNAP column with a 10% to 60% EtOAc:hexane gradient to give 2-chloro-6-(difluoromethylsulfanyl)-3-fluoro-benzonitrile (77 mg, 0.33 mmol, 34% yield) as a colorless oil.

Step C: 2-Chloro-6-(difluoromethylsulfonyl)-3-fluoro-benzonitrile

A solution of 2-chloro-6-(difluoromethylsulfanyl)-3-fluoro-benzonitrile (77 mg, 0.33 mmol) and 3-chloroperbenzoic acid (197 mg, 1.14 mmol) in dichloromethane (10 mL) was heated at reflux overnight. An additional 100 mg 3-chloroperbenzoic acid was added and refluxing continued overnight. The reaction mixture was concentrated, diluted with EtOAc, washed twice with a mixture of saturated aqueous NaHCO₃ and 1M sodium thiosulfate, water, brine, dried over MgSO₄, filtered, and evaporated to afford a white solid. This was chromatographed on a Biotage 10 g SNAP column with a 20% to 80% EtOAc:hexane gradient to give 2-chloro-6-(difluoromethylsulfonyl)-3-fluoro-benzonitrile (68 mg, 0.25 mmol, 76% yield) as a waxy white solid. m/z (ES-API-neg) [M−H]=266.

Step D: (2-Chloro-3-(3-chloro-5-fluorophenoxy)-6-((difluoromethyl)sulfonyl)phenyl)methanol (Compound 38)

As solution of 2-chloro-6-(difluoromethylsulfonyl)-3-fluoro-benzonitrile (10 mg, 0.04 mmol) and 3-chloro-5-fluoro-phenol (0.004 mL, 0.04 mmol) in acetonitrile (0.5 mL) was treated with sodium hydrogen carbonate (6 mg, 0.07 mmol). The mixture was heated at 50° C. After 3 hours, the reaction mixture was partitioned between EtOAc and water. The EtOAc was washed with water, brine, dried over MgSO₄, filtered, and evaporated. The residue was chromatographed on a Biotage 10 g SNAP column with a 10% to 60% EtOAc:hexane gradient to give Compound 38 (6.8 mg, 0.02 mmol, 46% yield) as a colorless glass. ¹H NMR (400 MHz, CDCl₃): δ 8.03 (d, 1H), 7.24 (d, 1H), 7.12-7.08 (m, 1H), 6.96-6.94 (m, 1H), 6.81-6.77 (m, 1H), 6.41 (t, 1H). m/z (ES-API-neg) [M−H+18]=413.

Example 39

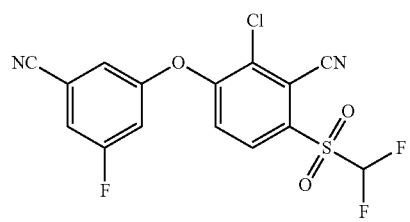 [SMILES: N#Cc1cc(F)cc(Oc2ccc(S(=O)(=O)C(F)F)c(C#N)c2Cl)c1]

2-Chloro-3-(3-cyano-5-fluorophenoxy)-6-((difluoromethyl)sulfonyl)benzonitrile (Compound 39)

Prepared similarly according to Example 38, Step D, substituting 3-fluoro-5-hydroxy-benzonitrile for 3-chloro-5-fluoro-phenol. ¹H NMR (400 MHz, CDCl₃): δ 8.09 (d, 1H), 7.37-7.34 (m, 1H), 7.29 (d, 1H), 7.22-7.21 (m, 1H), 7.14-7.10 (m, 1H), 6.43 (t, 1H). m/z (ES-API-neg) [M−H+18]=404.

Example 40

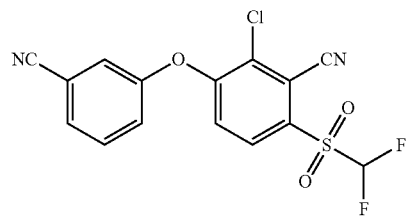 [SMILES: N#Cc1cccc(Oc2ccc(S(=O)(=O)C(F)F)c(C#N)c2Cl)c1]

2-Chloro-3-(3-cyanophenoxy)-6-((difluoromethyl)sulfonyl)benzonitrile (Compound 40)

Prepared similarly according to Example 38, Step D, substituting 3-hydroxy-benzonitrile for 3-chloro-5-fluoro-phenol. ¹H NMR (400 MHz, CDCl₃): δ 8.03 (d, 1H), 7.68-7.62 (m, 2H), 7.45-7.43 (m, 1H), 7.40-7.36 (m, 1H), 7.17 (d, 1H), 6.41 (t, 1H). m/z (ES-API-neg) [M−H+18]=386.

Example 41

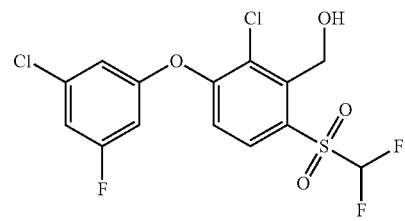

(2-Chloro-3-(3-chloro-5-fluorophenoxy)-6-((difluoromethyl)sulfonyl)phenyl)methanol (Compound 41)

Step A: 2-Chloro-6-(difluoromethylsulfanyl)-3-fluoro-benzaldehyde

Diisobutylaluminum hydride solution (1.18 mL, 1.18 mmol, 1M in heptane) was added to an ice cold solution of 2-chloro-6-(difluoromethylsulfanyl)-3-fluoro-benzonitrile (200 mg, 0.84 mmol) in dichloromethane (5 mL). After 1 hour, the reaction mixture was treated with ~2 mL methanol, then 2 mL 10% HCl. This was stirred for 1 h. The mixture was concentrated and the aqueous residue was partitioned between EtOAc and water. The EtOAc was washed with brine, dried over $MgSO_4$, filtered, and evaporated to afford a pale yellow oil. This was chromatographed on a Biotage 25 g SNAP column with a 10% to 60% EtOAc:hexane gradient to give 2-chloro-6-(difluoromethylsulfanyl)-3-fluoro-benzaldehyde (124 mg, 0.5 mmol, 61% yield) as a colorless glass.

Step B: [2-chloro-6-(difluoromethylsulfanyl)-3-fluoro-phenyl]methanol

Sodium borohydride (29 mg, 0.77 mmol) was added to an ice cold solution of 2-chloro-6-(difluoromethylsulfanyl)-3-fluoro-benzaldehyde (124 mg, 0.52 mmol) in methanol (10 mL). The reaction mixture was allowed to slowly warm to ambient temperature. After 1.5 hours, the reaction was quenched with saturated aqueous $NH_4Cl$ and concentrated. The aqueous slurry was partitioned between EtOAc and water. The EtOAc was washed with brine, dried over $MgSO_4$, filtered, and evaporated to yield [2-chloro-6-(difluoromethylsulfanyl)-3-fluoro-phenyl]methanol (110 mg, 0.45 mmol, 88% yield) as a colorless oil.

Step D: [2-chloro-6-(difluoromethylsulfonyl)-3-fluoro-phenyl]methanol

3-Chloroperbenzoic acid (235 mg, 1.36 mmol) was added to a solution of [2-chloro-6-(difluoromethylsulfanyl)-3-fluoro-phenyl]methanol (110 mg, 0.45 mmol) in dichloromethane (10 mL). The vial was sealed and heated at 45° C. After 4.5 hours, the reaction mixture was concentrated, diluted with EtOAc, washed twice with a mixture of saturated aqueous $NaHCO_3$ and 1M sodium thiosulfate, then with water, brine, dried over $MgSO_4$, filtered, and evaporated to afford a colorless oil that solidified. This was chromatographed on a Biotage 10 g SNAP column with a 10% to 80% EtOAc:hexane gradient to give [2-chloro-6-(difluoromethylsulfonyl)-3-fluoro-phenyl]methanol (94 mg, 0.34 mmol, 76% yield) as a waxy white solid.

Step E: (2-Chloro-3-(3-chloro-5-fluorophenoxy)-6-((difluoromethyl)sulfonyl)phenyl)methanol (Compound 41)

3-Chloro-5-fluoro-phenol (0.004 mL, 0.04 mmol) was added to a solution of [2-chloro-6-(difluoromethylsulfonyl)-3-fluoro-phenyl]methanol (10 mg, 0.04 mmol) and sodium hydrogen carbonate (6.12 mg, 0.07 mmol) in DMF (0.5 mL) in a vial. The vial was sealed and heated at 80° C. After 3 hours, the reaction mixture was partitioned between EtOAc and saturated aqueous $NaHCO_3$. The EtOAc was washed with water, brine, dried over $MgSO_4$, filtered, and evaporated. The residue was chromatographed on a Biotage 10 g SNAP column with a 10% to 60% EtOAc:hexane gradient to give Compound 41 (8.8 mg, 0.02 mmol, 60% yield) as a white solid. $^1H$ NMR (400 MHz, $CDCl_3$): δ 8.01 (d, 1H), 7.06 (d, 1H), 7.04-7.01 (m, 1H), 6.91-6.88 (m, 1H), 6.76-6.71 (m, 1H), 6.47 (t, 1H), 5.21 (d, 2H), 2.69 (t, 1H). m/z (ES-API-neg) [M−H+46]=445.

Example 42

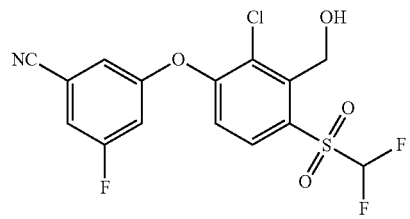 [SMILES: N#Cc1cc(F)cc(Oc2ccc(S(=O)(=O)C(F)F)c(CO)c2Cl)c1]

3-(2-Chloro-4-((difluoromethyl)sulfonyl)-3-(hydroxymethyl)phenoxy)-5-fluorobenzonitrile (Compound 42)

Prepared similarly according to Example 41, Step E, substituting 3-fluoro-5-hydroxy-benzonitrile for 3-chloro-5-fluoro-phenol. $^1H$ NMR (400 MHz, $CDCl_3$): δ 8.06 (d, 1H), 7.28-7.25 (m, 1H), 7.15-7.12 (m, 2H), 7.07-7.03 (m, 1H), 6.50 (t, 1H), 5.21 (d, 2H), 2.70 (t, 1H). m/z (ES-API-neg) [M−H+46]=436.

Example 43

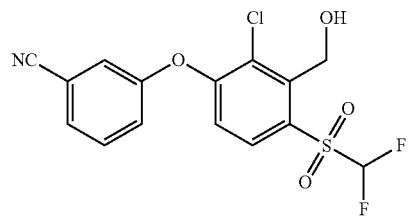 [SMILES: N#Cc1cccc(Oc2ccc(S(=O)(=O)C(F)F)c(CO)c2Cl)c1]

3-(2-Chloro-4-((difluoromethyl)sulfonyl)-3-(hydroxymethyl)phenoxy)benzonitrile (Compound 43)

Prepared similarly according to Example 41, Step E, substituting 3-hydroxy-benzonitrile for 3-chloro-5-fluoro-phenol. $^1H$ NMR (400 MHz, $CDCl_3$): δ 8.00 (d, 1H), 7.59-7.56 (m, 1H), 7.38-7.37 (m, 1H), 7.36-7.31 (m, 1H), 7.00 (d, 1H), 6.48 (t, 1H), 5.22 (d, 2H), 2.71 (t, 1H). m/z (ES-API-neg) [M−H+46]=418.

Example 44

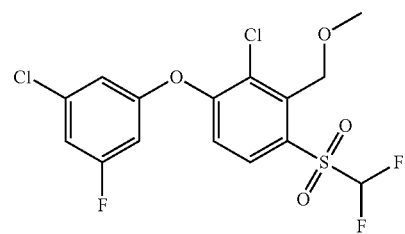 [SMILES: COCc1c(S(=O)(=O)C(F)F)ccc(Oc2cc(F)cc(Cl)c2)c1Cl]

2-Chloro-1-(3-chloro-5-fluorophenoxy)-4-((difluoromethyl)sulfonyl)-3-(methoxymethyl)benzene (Compound 44)

Step A: 2-Chloro-3-(3-chloro-5-fluoro-phenoxy)-6-(difluoromethylsulfonyl)phenyl]methyl methanesulfonate Methanesulfonyl chloride (0.0039 mL, 0.05 mmol) was added to an ice cold solution of [2-chloro-3-(3-chloro-5-fluoro-phenoxy)-6-(difluoromethylsulfonyl)phenyl]methanol (Compound 41, 16.9 mg, 0.04 mmol) and triethylamine (0.01 mL, 0.11 mmol) in dichloromethane (2 mL). The mixture was allowed to slowly warm to ambient temperature. After 2 hours, the reaction mixture was diluted with dichloromethane, washed with water, brine, dried over MgSO$_4$, filtered, and evaporated to afford [2-chloro-3-(3-chloro-5-fluoro-phenoxy)-6-(difluoromethylsulfonyl)phenyl]methyl methanesulfonate as a colorless film.

Step B: 2-Chloro-1-(3-chloro-5-fluorophenoxy)-4-((difluoromethyl)sulfonyl)-3-(methoxymethyl)benzene (Compound 44)

A solution of 25% sodium methanolate in methanol (0.01 mL, 0.04 mmol) was added to a solution of [2-chloro-3-(3-chloro-5-fluoro-phenoxy)-6-(difluoromethylsulfonyl)phenyl]methyl methanesulfonate (20 mg, 0.04 mmol) in methanol (1 mL). The mixture was heated at 50° C. Another equivalent of 25% sodium methoxide in methanol was added. After 2 hours, the reaction mixture was evaporated and the residue was partitioned between EtOAc and dilute brine. The EtOAc was washed with brine, dried over MgSO$_4$, filtered, and evaporate. The residue was chromatographed on a Biotage 10 g SNAP column with a 10% to 60% EtOAc:hexane gradient to give Compound 44 as a colorless film (0.9 mg, 0.002 mmol, 5% yield). $^1$H NMR (400 MHz, CDCl$_3$): δ 8.01 (d, 1H), 7.06 (d, 1H), 7.04-7.01 (m, 1H), 6.91-6.88 (m, 1H), 6.76-6.71 (m, 1H), 6.47 (t, 1H), 5.21 (d, 2H), 2.69 (t, 1H). m/z (ES-API-neg) [M−H+46]=445.

Example 45

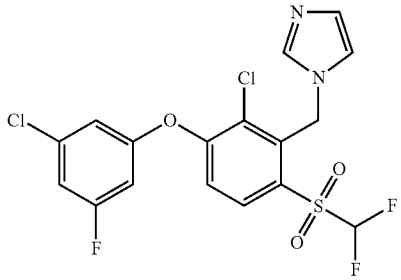 [SMILES: O=S(=O)(c1ccc(Oc2cc(F)cc(Cl)c2)c(Cl)c1Cn1ccnc1)C(F)F]

1-(2-Chloro-3-(3-chloro-5-fluorophenoxy)-6-((difluoromethyl)sulfonyl)benzyl)-1H-imidazole (Compound 45)

Imidazole (15.8 mg, 0.23 mmol) was added to a solution of crude [2-chloro-3-(3-chloro-5-fluoro-phenoxy)-6-(difluoromethylsulfonyl)phenyl]methyl methanesulfonate (37 mg, 0.08 mmol) in tetrahydrofuran (2 mL). The mixture was heated at 80° C. for 1 hour. The reaction mixture was partitioned between EtOAc and water. The EtOAc was washed with brine, dried over MgSO$_4$, filtered, and evaporated. The residue was chromatographed on a Biotage 10 g SNAP column with a 10% to 100% EtOAc:hexane gradient. Desired fractions containing 1-(2-chloro-3-(3-chloro-5-fluorophenoxy)-6-((difluoromethyl)sulfonyl)benzyl)-1H-imidazole were concentrated to give Compound 45 as a colorless glass (18.8 mg, 0.04 mmol, 54% yield). $^1$H NMR (400 MHz, CDCl$_3$): δ 8.06 (d, 1H), 7.67 (s, 1H), 7.12-7.03 (m, 4H), 6.93 (s, 1H), 6.77 (br d, 1H), 5.92 (t, 1H), 5.76 (d, 2H). m/z (ES-API-pos) [M+H]=451.

Example 46

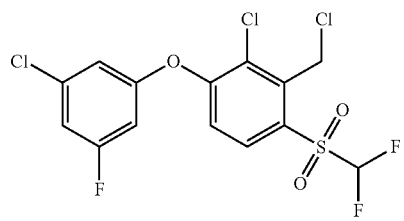 [SMILES: O=S(=O)(c1ccc(Oc2cc(F)cc(Cl)c2)c(Cl)c1CCl)C(F)F]

2-Chloro-1-(3-chloro-5-fluorophenoxy)-3-(chloromethyl)-4-((difluoromethyl)sulfonyl)benzene (Compound 46)

Isolated as a by-product of Example 45. Compound 46 was obtained as a colorless glass (1.7 mg, 0.004 mmol, 5% yield). $^1$H NMR (400 MHz, CDCl$_3$): δ 8.03 (d, 1H), 7.07 (d, 1H), 7.06-7.03 (m, 1H), 6.93-6.91 (m, 1H), 6.78-6.74 (m, 1H), 6.42 (t, 1H), 5.26 (d, 2H). m/z (ES-API-neg) [M−H+46]=463.

Example 47

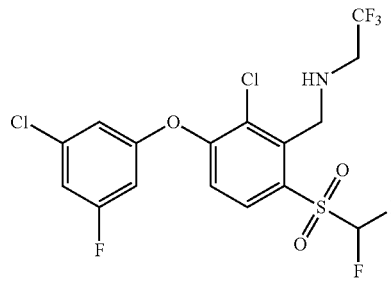

N-(2-Chloro-3-(3-chloro-5-fluorophenoxy)-6-((difluoromethyl)sulfonyl)benzyl)-2,2,2-trifluoroethan-1-amine (Compound 47)

2,2,2-Trifluoroethylamine (8.68 mg, 0.09 mmol) was added to a solution of [2-chloro-3-(3-chloro-5-fluoro-phenoxy)-6-(difluoromethylsulfonyl)phenyl]methyl methanesulfonate (28 mg, 0.06 mmol) and triethylamine (0.02 mL, 0.12 mmol) in tetrahydrofuran (1 mL) in a vial. The mixture was heated at 80° C. overnight. After cooling, the reaction mixture was partitioned between EtOAc and water. The EtOAc was washed with brine, dried over MgSO$_4$, filtered, and evaporated. The residue was chromatographed on a Biotage 10 g SNAP column with a 10% to 60% EtOAc:hexane gradient to give Compound 47 (28 mg, 0.06 mmol) as a colorless glass. $^1$H NMR (400 MHz, CDCl$_3$): δ 8.04 (d, 1H), 7.05-7.01 (m, 2H), 6.90-6.89 (m, 1H), 6.75-6.71 (m, 1H), 6.67 (s, 1H), 6.43 (t, 1H), 4.50 (br s, 2H) 3.40-3.30 (m, 2H). m/z (ES-API-pos) [M+H]=482.

Example 48

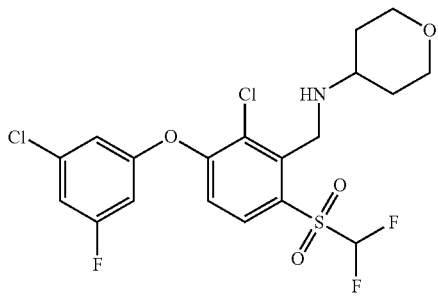 [SMILES: O=S(=O)(c1ccc(Oc2cc(F)cc(Cl)c2)c(Cl)c1CNC1CCOCC1)C(F)F]

N-(2-Chloro-3-(3-chloro-5-fluorophenoxy)-6-((difluoromethyl)sulfonyl)benzyl)tetrahydro-2H-pyran-4-amine (Compound 48)

4-Aminotetrahydropyran (0.02 mL, 0.2 mmol) was added to a solution of [2-chloro-3-(3-chloro-5-fluoro-phenoxy)-6-(difluoromethylsulfonyl)phenyl]methyl methanesulfonate (23.8 mg, 0.05 mmol) in DMF (1 mL). The mixture was heated at 60° C. After 1.5 hours, the reaction mixture was partitioned between EtOAc and dilute aqueous NaCl. The EtOAc was washed with water, brine, dried over MgSO$_4$, filtered, and evaporated to afford a colorless glass. This was chromatographed on a Biotage 10 g SNAP column with a 20% to 80% EtOAc:hexane gradient to give Compound 48 (15 mg, 0.03 mmol, 62% yield) as a colorless glass. $^1$H NMR (400 MHz, CDCl$_3$): δ 8.04 (d, 1H), 7.07 (t, 2H), 7.03-6.99 (m, 2H), 6.89-6.87 (m, 1H), 6.74-6.70 (m, 1H), 4.40 (s, 2H), 4.05-3.98 (m, 2H) 3.48-3.40 (m, 2H), 2.89-2.81 (m, 1H), 1.97-1.90 (m, 2H), 1.52-1.41 (m, 3H). m/z (ES-API-pos) [M+H]=484.

Example 49

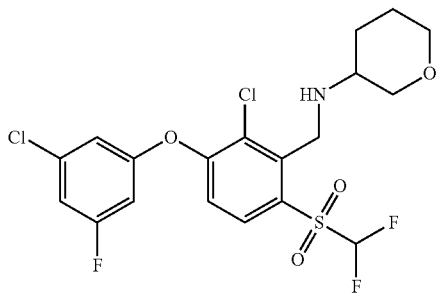 [SMILES: O=S(=O)(c1ccc(Oc2cc(F)cc(Cl)c2)c(Cl)c1CNC1CCCOC1)C(F)F]

N-(2-Chloro-3-(3-chloro-5-fluorophenoxy)-6-((difluoromethyl)sulfonyl)benzyl)tetrahydro-2H-pyran-3-amine (Compound 49)

[2-Chloro-3-(3-chloro-5-fluorophenoxy)-6-(difluoromethylsulfonyl)phenyl]methyl methanesulfonate (20 mg, 0.04 mmol) was added to a solution of crude tetrahydropyran-3-ylamine (17 mg, 0.17 mmol) in DMF (0.5 mL). The mixture was allowed to stir at 50° C. for 2 hours. The reaction mixture was partitioned between EtOAc and water. The EtOAc was washed with water, brine, dried over MgSO$_4$, filtered, and evaporated to afford a colorless glass. This was chromatographed on a Biotage 10 g SNAP column with a 10% to 60% EtOAc:hexane gradient to give Compound 49 (14 mg, 0.03 mmol, 69% yield) as a colorless glass. $^1$H NMR (400 MHz, CDCl$_3$): δ 8.04 (d, 1H), 7.09 (t, 2H), 7.03-7.00 (m, 2H), 6.89-6.88 (m, 1H), 6.74-6.70 (m, 1H), 4.40 (s, 2H), 3.94-3.89 (m, 1H) 3.78-3.71 (m, 1H), 3.56-3.49 (m, 1H), 3.39-3.33 (m, 1H), 2.86-2.79 (m, 1H), 2.06-1.97 (m, 1H), 1.80-1.72 (m, 1H), 1.66-1.46 (m, 3H). m/z (ES-API-pos) [M+H]=484.

Example 50

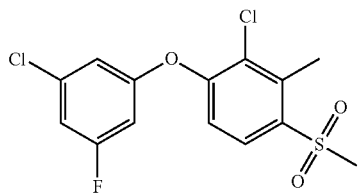 [SMILES: Cc1c(S(C)(=O)=O)ccc(Oc2cc(F)cc(Cl)c2)c1Cl]

6-(3-Chloro-5-fluorophenoxy)-2-methyl-3-(methylsulfonyl)benzonitrile (Compound 50)

Step A:
6-Fluoro-2-methyl-3-methylsulfanyl-benzonitrile

Dimethyl sulfate (0.13 mL, 1.38 mmol) was added to a mixture of potassium carbonate (273 mg, 1.97 mmol) and 6-fluoro-2-methyl-3-sulfanyl-benzonitrile (220 mg, 1.32 mmol) in DMF (5 mL). This was stirred at ambient temperature for 10 minutes. The mixture was partitioned between EtOAc and water. The EtOAc was washed with water, brine, dried over MgSO$_4$, filtered, and evaporated to afford 6-fluoro-2-methyl-3-methylsulfanyl-benzonitrile (220 mg, 1.2 mmol, 92% yield) as a tan solid.

Step B:
6-Fluoro-2-methyl-3-methylsulfonyl-benzonitrile

3-Chloroperbenzoic acid (628 mg, 3.64 mmol) was added to a solution of 6-fluoro-2-methyl-3-methylsulfanyl-benzonitrile (220 mg, 1.2 mmol) in dichloromethane (20 mL). The solution was stirred at ambient temperature overnight. The reaction mixture was concentrated, diluted with EtOAc, washed twice with a mixture of saturated aqueous NaHCO$_3$ and 1M sodium thiosulfate, then with water, brine, dried over MgSO$_4$, filtered, and evaporated to afford 6-fluoro-2-methyl-3-methylsulfonyl-benzonitrile (250 mg, 1.17 mmol, 97% yield) as a white solid.

Step C: 6-(3-Chloro-5-fluorophenoxy)-2-methyl-3-(methylsulfonyl)benzonitrile (Compound 50)

3-Chloro-5-fluorophenol (0.01 mL, 0.05 mmol) was added to a solution of sodium hydrogen carbonate (7.9 mg, 0.09 mmol) and 6-fluoro-2-methyl-3-methylsulfonyl-benzonitrile (10 mg, 0.05 mmol) in DMF (0.5 mL) in a vial. The vial was sealed and heated at 50° C. After 3 hours, the reaction mixture was partitioned between EtOAc and saturated aqueous NaHCO₃. The EtOAc was washed with brine, dried over MgSO₄, filtered, and evaporated. The residue was chromatographed on a Biotage 10 g SNAP column with a 10% to 60% EtOAc:hexane gradient to give Compound 50 (7.7 mg, 0.02 mmol, 48% yield). ¹H NMR (400 MHz, CDCl₃): δ 8.20 (d, 1H), 7.08-7.04 (m, 1H), 6.96-6.94 (m, 1H), 6.87 (d, 1H), 6.81-6.77 (m, 1H), 3.12 (s, 3H), 2.97 (s, 3H). m/z (ES-API-neg) [M−H]=338.

Example 51

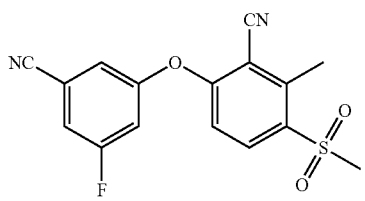 [SMILES: Cc1c(S(C)(=O)=O)ccc(Oc2cc(F)cc(C#N)c2)c1C#N]

6-(3-Cyano-5-fluorophenoxy)-2-methyl-3-(methylsulfonyl)benzonitrile (Compound 51)

Prepared similarly according to Example 50, Step C, substituting 3-fluoro-5-hydroxybenzonitrile for 3-chloro-5-fluoro-phenol. ¹H NMR (400 MHz, CDCl₃): δ 8.25 (d, 1H), 7.33-7.30 (m, 1H), 7.22-7.20 (m, 1H), 7.16-7.12 (m, 1H), 6.93-6.89 (m, 1H), 3.13 (s, 3H), 2.98 (s, 3H). m/z (ES-API-neg) [M−H]=329.

Example 52

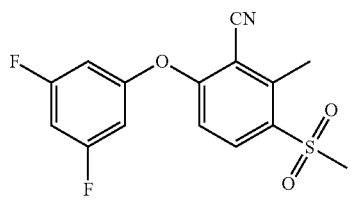 [SMILES: Cc1c(S(C)(=O)=O)ccc(Oc2cc(F)cc(F)c2)c1C#N]

6-(3,5-Difluorophenoxy)-2-methyl-3-(methylsulfonyl)benzonitrile (Compound 52)

Prepared similarly according to Example 50, Step C, substituting 3,5-difluorophenol for 3-chloro-5-fluorophenol. ¹H NMR (400 MHz, CDCl₃): δ 8.20 (d, 1H), 6.91-6.88 (m, 1H), 6.81-6.75 (m, 1H), 6.72-6.65 (m, 2H), 3.12 (s, 3H), 2.97 (s, 3H). m/z (ES-API-neg) [M−H]=322.

Example 53

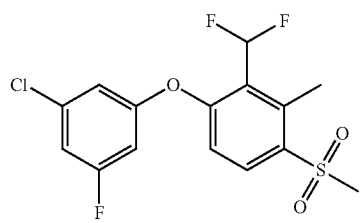 [SMILES: Cc1c(S(C)(=O)=O)ccc(Oc2cc(F)cc(Cl)c2)c1C(F)F]

1-(3-Chloro-5-fluorophenoxy)-2-(difluoromethyl)-3-methyl-4-(methylsulfonyl)benzene (Compound 53)

Step A: 6-(3-Chloro-5-fluoro-phenoxy)-2-methyl-3-methylsulfonyl-benzaldehyde

1M DIBAL in heptane (0.45 mL, 0.45 mmol) was added to an ice cold solution of 6-(3-chloro-5-fluoro-phenoxy)-2-methyl-3-methylsulfonyl-benzonitrile Compound 50 (109 mg, 0.32 mmol) in dichloromethane (5 mL). After 30 min, the reaction mixture was treated with 1.5 mL methanol, then 1.5 mL 10% HCl. After stirring for 1 h, the mixture was concentrated and the aqueous residue was partitioned between EtOAc and water. The EtOAc was washed with brine, dried over MgSO₄, filtered, and evaporated to afford 6-(3-chloro-5-fluoro-phenoxy)-2-methyl-3-methylsulfonyl-benzaldehyde (99.1 mg, 0.3 mmol, 90% yield) as a white solid. m/z (ES-API-pos) [M+H]=444.

Step B: 1-(3-Chloro-5-fluorophenoxy)-2-(difluoromethyl)-3-methyl-4-(methylsulfonyl)benzene (Compound 53)

Diethylaminosulfur trifluoride (0.084 mL, 0.64 mmol) was added to a solution of 6-(3-chloro-5-fluoro-phenoxy)-2-methyl-3-methylsulfonyl-benzaldehyde (99.1 mg, 0.29 mmol) in dichloromethane (10 mL). After addition, ethanol (0.001 mL, 0.01 mmol) was added. The reaction mixture was stirred at ambient temperature overnight. Additional diethylaminosulfur trifluoride was added over 2 days until the starting aldehyde was consumed, as determined by LC/MS. The reaction mixture was diluted with dichloromethane and treated with saturated aqueous NaHCO₃. The dichloromethane layer was washed with water, brine, dried over MgSO₄, filtered, and evaporated. The residue was chromatographed on a Biotage 10 g SNAP column with a 10% to 60% EtOAc:hexane gradient to give Compound 53 (65 mg, 0.18 mmol, 62% yield). ¹H NMR (400 MHz, CDCl₃): δ 8.18 (br d, 1H), 7.26 (t, 1H), 7.01-6.97 (m, 1H), 6.89-6.84 (m, 2H), 6.71-6.67 (m, 1H), 3.15 (s, 3H), 2.95 (t, 3H). m/z (ES-API-neg) [M−H]=363.

Example 54

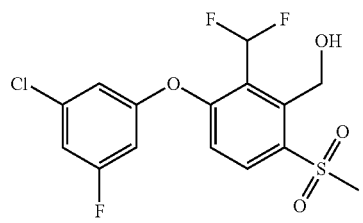 [SMILES: CS(=O)(=O)c1ccc(Oc2cc(F)cc(Cl)c2)c(C(F)F)c1CO]

(3-(3-Chloro-5-fluorophenoxy)-2-(difluoromethyl)-6-(methylsulfonyl)phenyl)methanol (Compound 54)

Step A: 3-(Bromomethyl)-1-(3-chloro-5-fluoro-phenoxy)-2-(difluoromethyl)-4-methylsulfonylbenzene Benzoyl peroxide (1.84 mg, 0.01 mmol) was added to a solution of 1-(3-chloro-5-fluoro-phenoxy)-2-(difluoromethyl)-3-methyl-4-methylsulfonyl-benzene Compound 53 (55.5 mg, 0.15 mmol) and N-bromosuccinimide (27 mg, 0.15 mmol) in carbon tetrachloride (4 mL). The mixture was heated at reflux overnight, with additional benzoyl peroxide and N-bromosuccinimide added until the starting material was consumed. The reaction mixture was evaporated and the residue was partitioned between EtOAc and water. The EtOAc was washed with brine, dried over MgSO₄, filtered, and evaporated to afford a colorless oil. The residue was chromatographed on a Biotage 10 g SNAP column with a 10% to 60% EtOAc:hexane gradient to give 3-(bromomethyl)-1-(3-chloro-5-fluoro-phenoxy)-2-(difluoromethyl)-4-methylsulfonylbenzene (40.2 mg, 0.09 mmol, 60% yield) as a colorless glass.

Step B: [3-(3-chloro-5-fluoro-phenoxy)-2-(difluoromethyl)-6-methylsulfonyl-phenyl]methyl acetate 3-(Bromomethyl)-1-(3-chloro-5-fluoro-phenoxy)-2-(difluoromethyl)-4-methylsulfonyl-benzene (40.2 mg, 0.09 mmol) in DMF (1.5 mL) was treated with potassium acetate (44 mg, 0.45 mmol). The solution was stirred at ambient temperature for 20 minutes. The reaction mixture was partitioned between EtOAc and water. The EtOAc was washed with water, brine, dried over MgSO₄, filtered, and evaporated to afford [3-(3-chloro-5-fluoro-phenoxy)-2-(difluoromethyl)-6-methylsulfonyl-phenyl]methyl acetate (38 mg, 0.09 mmol, 100% yield). m/z (ES-API-neg) [M−H]=421.

Step C: (3-(3-Chloro-5-fluorophenoxy)-2-(difluoromethyl)-6-(methylsulfonyl)phenyl)methanol (Compound 54)

Lithium hydroxide hydrate (11.3 mg, 0.27 mmol) was added to a solution of [3-(3-chloro-5-fluoro-phenoxy)-2-(difluoromethyl)-6-methylsulfonyl-phenyl]methyl acetate (38 mg, 0.09 mmol) in methanol (4 mL) and water (1 mL). The mixture was stirred at ambient temperature for 10 minutes. The reaction mixture was evaporated and the residue was partitioned between EtOAc and water. The EtOAc was washed with brine, dried over MgSO₄, filtered, and evaporated. The residue was chromatographed on a Biotage 10 g SNAP column with a 10% to 60% EtOAc:hexane gradient to give Compound 54 (25.2 mg, 0.07 mmol, 74% yield) and as a colorless glass. ¹H NMR (400 MHz, CDCl₃): δ 8.21 (d, 1H), 7.31 (t, 1H), 7.03-6.98 (m, 2H), 6.89-6.87 (m, 1H), 6.74-6.70 (m, 1H), 5.27 (d, 2H), 3.30 (s, 3H), 2.96-2.91 (m, 1H). m/z (ES-API-neg) [M−H+46]=425.

Example 55

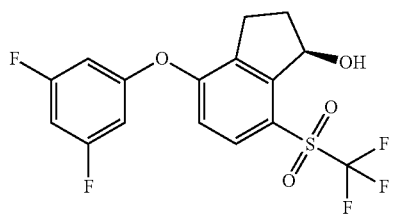 [SMILES: O=S(=O)(c1ccc(Oc2cc(F)cc(F)c2)c2c1[C@H](O)CC2)C(F)(F)F]

(R)-4-(3,5-Difluorophenoxy)-7-((trifluoromethyl)sulfonyl)-2,3-dihydro-1H-inden-1-ol (Compound 55)

Step A:
4-Fluoro-7-(trifluoromethylsulfanyl)indan-1-one

Methyl viologen dichloride hydrate (22.6 mg, 0.09 mmol) and 4-fluoro-7-sulfanyl-indan-1-one (320 mg, 1.76 mmol) were dissolved in DMF (3 mL) in a vial. The solution was cooled in dry ice/acetone and trifluoromethyl iodide gas (688 mg, 3.5 mmol) was condensed into the cooled solution. Triethylamine (0.34 mL, 2.46 mmol) was added and the vial was sealed. This was stirred at ambient temperature overnight. The reaction mixture was partitioned between EtOAc and water. The EtOAc was washed with water, brine, dried over MgSO₄, filtered, and evaporated. The residue was chromatographed on a Biotage 50 g SNAP column with a 10% to 60% EtOAc:hexane gradient to give 4-fluoro-7-(trifluoromethylsulfanyl)indan-1-one (130 mg, 0.52 mmol, 30% yield) as a colorless glass. m/z (ES-API-neg) [M−H]= 281.

Step B:
4-Fluoro-7-(trifluoromethylsulfonyl)indan-1-one

Sodium periodate (457.8 mg, 2.14 mmol) was added to a mixture of 4-fluoro-7-sulfanyl-indan-1-one (130 mg, 0.71 mmol) and ruthenium(III) chloride (4.44 mg, 0.02 mmol) in carbon tetrachloride (2 mL), acetonitrile (2 mL), and water (4 mL). The mixture was stirred at ambient temperature for 2 hours. The reaction mixture was partitioned between dichloromethane and water. The dichloromethane was washed with brine, dried over MgSO₄, filtered, and evaporated. The residue was chromatographed on a Biotage 25 g SNAP column with a 10% to 60% EtOAc:hexane gradient to give 4-fluoro-7-(trifluoromethylsulfonyl)indan-1-one (127 mg, 0.45 mmol, 63% yield) as a white solid.

Step C: (1R)-4-Fluoro-7-(trifluoromethylsulfonyl)indan-1-ol

To a solution of 4-fluoro-7-(trifluoromethylsulfonyl)indan-1-one (127 mg, 0.45 mmol) in dichloromethane (5 mL) was added formic acid (0.02 mL, 0.56 mmol) and triethylamine (0.07 mL, 0.5 mmol). The reaction mixture was sparged with nitrogen and RuCl(p-cymene)[(R,R)-Ts-DPEN] (5.7 mg, 0.01 mmol) was added in one portion. The reaction mixture was stirred at room temperature overnight under nitrogen. The reaction mixture was evaporated and the residue was chromatographed on a Biotage 25 g SNAP column with a 10% to 60% EtOAc:hexane gradient to give (1R)-4-fluoro-7-(trifluoromethylsulfonyl)indan-1-ol (115 mg, 0.4 mmol, 90% yield) as a colorless oil. ¹⁹F NMR (CDCl₃) showed e.e. >93% based on Mosher ester CF₃ resonances.

Step D: (R)-4-(3,5-Difluorophenoxy)-7-((trifluoromethyl)sulfonyl)-2,3-dihydro-1H-inden-1-ol (Compound 55)

3,5-Difluorophenol (8.66 mg, 0.07 mmol) was added to a solution of (1R)-4-fluoro-7-(trifluoromethylsulfonyl)indan-1-ol (17.2 mg, 0.06 mmol) and sodium hydrogen carbonate (10.17 mg, 0.12 mmol) in DMF (0.5 mL). This was heated at 80° C. After 2 hours, the reaction mixture was partitioned between EtOAc and water. The EtOAc was washed with water, brine, dried over MgSO₄, filtered, and evaporated. The residue was chromatographed on a Biotage 10 g SNAP column with a 5% to 40% EtOAc:hexane gradient to give an impure product. This was rechromatographed on a Biotage 10 g SNAP column with a 40% to 100% dichloromethane:hexane gradient to give a product with a small amount of impurity. This was rechromatographed on a Biotage 10 g SNAP column with a 5% to 35% EtOAc:hexane gradient to give Compound 55 (6.5 mg, 0.02 mmol, 27% yield) as a colorless oil. ¹H NMR (400 MHz, CDCl₃): δ 7.84 (d, 1H), 6.95 (d, 1H), 6.76-6.70 (m, 1H), 6.66-6.60 (m, 2H), 5.65-5.60 (m, 1H), 3.25-3.15 (m, 2H), 3.00-2.92 (m, 1H) 2.47-2.28 (m, 2H). m/z (ES-API-neg) [M−H]=393.

Example 56

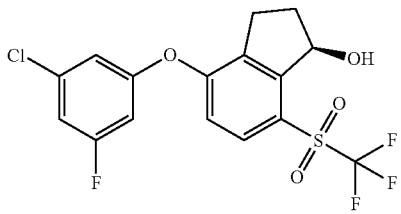 [SMILES: O=S(=O)(c1ccc(Oc2cc(F)cc(Cl)c2)c2c1[C@H](O)CC2)C(F)(F)F]

(R)-4-(3-Chloro-5-fluorophenoxy)-7-((trifluoromethyl)sulfonyl)-2,3-dihydro-1H-inden-1-ol (Compound 56)

Prepared similarly according to Example 55, Step D substituting 3-chloro-5-fluorophenol for 3,5-difluorophenol. ¹HNMR (400 MHz, CDCl₃): δ 7.84 (d, 1H), 7.03-6.99 (m, 1H), 6.93 (d, 1H), 6.92-6.90 (m, 1H), 6.75-6.71 (m, 1H), 5.65-5.61 (m, 1H), 3.24-3.15 (m, 2H), 3.01-2.92 (m, 1H) 2.47-2.28 (m, 2H). m/z (ES-API-neg) [M−H+46]=455.

Example 57

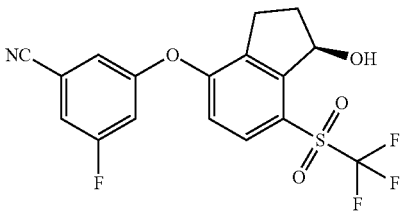 [SMILES: N#Cc1cc(F)cc(Oc2ccc(S(=O)(=O)C(F)(F)F)c3c2CC[C@H]3O)c1]

(R)-3-Fluoro-5-((1-hydroxy-7-((trifluoromethyl)sulfonyl)-2,3-dihydro-1H-inden-4-yl)oxy)benzonitrile (Compound 57):

Prepared similarly according to Example 55, Step D substituting 3-fluoro-5-hydroxybenzonitrile for 3,5-difluorophenol. ¹H NMR (400 MHz, CDCl₃): δ 7.88 (d, 1H), 7.28-7.25 (m, 2H), 7.19-7.17 (m, 1H), 7.09-7.05 (m, 1H), 6.96 (d, 1H), 5.66-5.62 (m, 1H), 3.23-3.13 (m, 2H), 2.99-2.90 (m, 1H) 2.47-2.29 (m, 2H). m/z (ES-API-neg) [M−H+46]=446.

Example 58

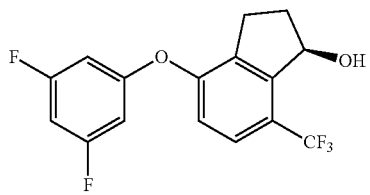 [SMILES: O[C@@H]1CCc2c(Oc3cc(F)cc(F)c3)ccc(C(F)(F)F)c21]

(R)-4-(3,5-Difluorophenoxy)-7-(trifluoromethyl)-2,3-dihydro-1H-inden-1-ol (Compound 58)

Step A: 4-Fluoro-7-(trifluoromethyl)indan-1-one

A solution of 7-bromo-4-fluoro-indan-1-one (1.00 g, 4.37 mmol) in DMF (15 mL) in a microwave vial was treated with copper(I) iodide (1.66 g, 8.73 mmol) and methyl 2,2-difluoro-2-fluorosulfonyl-acetate (2.78 mL, 21.8 mmol). The vial was sealed and heated in a heating bath at 100° C. overnight. CAUTION: Pressure buildup from released CO₂ is likely. Additional aliquots of methyl 2,2-difluoro-2-sulfonylacetate and CuI were added, the vial was resealed, and heating continued for another 24 hours. The reaction mixture was diluted with water and EtOAc, filtered through celite, and the layers separated. The EtOAc was washed with water, brine, dried over MgSO₄, filtered, and evaporated. The residue was chromatographed on a Biotage 50 g SNAP column with a 10% to 60% dichloromethane:hexane gradient to give 4-fluoro-7-(trifluoromethyl)indan-1-one (209 mg, 0.96 mmol, 22% yield) as a tan solid.

Step B: (1R)-4-fluoro-7-(trifluoromethyl)indan-1-ol

To a solution of 4-fluoro-7-(trifluoromethyl)indan-1-one (209 mg, 0.96 mmol) in dichloromethane (7 mL) was added formic acid (0.05 mL, 1.2 mmol) and triethylamine (0.15 mL, 1.05 mmol). The reaction mixture was sparged with nitrogen and RuCl(p-cymene)[(R,R)-Ts-DPEN] (12.2 mg, 0.02 mmol) was added in one portion. The reaction mixture was stirred at room temperature overnight under nitrogen. The solvent was evaporated and the residue was chromatographed on a Biotage 25 g SNAP column with a 5% to 30% EtOAc:hexane gradient to give (1R)-4-fluoro-7-(trifluoromethyl)indan-1-ol (169 mg, 0.77 mmol, 80% yield) as a tan solid. Mosher ester analysis ¹H NMR (CDCl₃)) of the methoxy signal integrations indicated a 90% enantiomeric excess.

Step C: (R)-4-(3,5-Difluorophenoxy)-7-(trifluoromethyl)-2,3-dihydro-1H-inden-1-ol (Compound 58)

3,5-Difluorophenol (13 mg, 0.10 mmol) was added to a mixture of (1R)-4-fluoro-7-(trifluoromethyl)indan-1-ol (21 mg, 0.10 mmol) and cesium carbonate (46.6 mg, 0.14 mmol) in DMF (0.5 mL) in a vial. The vial was sealed and heated at 135° C. for 24 hours. The reaction mixture was partitioned between EtOAc and 0.3 M aqueous NaOH. The EtOAc was washed with dilute aqueous NaOH, water, brine, dried over MgSO₄, filtered, and evaporated. The residue was chromatographed on a Biotage 10 g SNAP column with a 5% to 40% EtOAc:hexane gradient to give an impure product. This was rechromatographed on a Biotage 10 g SNAP column with a 5% to 30% EtOAc:hexane gradient followed by re-chromatographing on a Biotage 12M RP column with a 20% to 90% acetonitrile:water gradient to give Compound 58 (2.4 mg, 0.007 mmol, 8% yield) as a colorless oil. ¹H NMR (400 MHz, CDCl₃): δ 7.53-7.49 (m, 1H), 6.98-6.95 (m, 1H), 6.62-6.55 (m, 1H), 6.53-6.46 (m, 2H), 5.53 (br s, 1H), 3.11-3.01 (m, 1H), 2.84-2.76 (m, 1H), 2.41-2.31 (m, 1H) 2.25-2.18 (m, 1H), 2.04 (br s, 1H). m/z (ES-API-neg) [M−H]=329.

Example 59

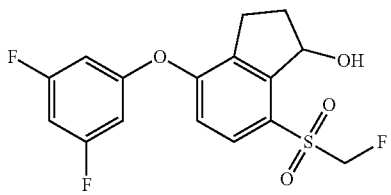 [SMILES: O=S(=O)(CF)c1ccc(Oc2cc(F)cc(F)c2)c2c1C(O)CC2]

(R)-4-(3,5-Difluorophenoxy)-7-((fluoromethyl)sulfonyl)-2,3-dihydro-1H-inden-1-ol (Compound 59)

Step A: 4-Fluoro-7-methylsulfinyl-indan-1-one

3-Chloroperbenzoic acid (37 mg, 0.15 mmol) was added to an ice-cold solution of 4-fluoro-7-methylsulfanyl-indan-1-one (30 mg, 0.15 mmol) in dichloromethane (5 mL). After 5 minutes, the reaction mixture was concentrated, diluted with EtOAc, washed twice with a mixture of saturated aqueous $NaHCO_3$ and 1M sodium thiosulfate, water, brine, dried over $MgSO_4$, filtered, and evaporated to afford 4-fluoro-7-methylsulfinyl-indan-1-one (26 mg, 0.12 mmol, 80% yield) as a white solid. m/z (ES-API-pos) [M+H]=213.

Step B:
4-Fluoro-7-(fluoromethylsulfanyl)indan-1-one

Diethylaminosulfur trifluoride (5.5 mL, 41.9 mmol) was added dropwise to an ice cold solution of 4-fluoro-7-methylsulfinyl-indan-1-one (1480 mg, 7 mmol) and trichlorostibane (795 mg, 3.5 mmol) in dichloromethane (140 mL). The mixture was stirred at ambient temperature. After 3 hours the reaction mixture was quenched with dropwise addition of saturated aqueous $NaHCO_3$. The mixture was diluted with dichloromethane and washed with saturated aqueous $NaHCO_3$, brine, dried over $MgSO_4$, filtered, and evaporated to yield 4-fluoro-7-(fluoromethylsulfanyl)indan-1-one (1550 mg, 7.24 mmol, 100% yield).

Step C:
4-Fluoro-7-(fluoromethylsulfonyl)indan-1-one

3-Chloroperbenzoic acid (5.35 g, 21.7 mmol) was added to a solution of 4-fluoro-7-(fluoromethylsulfanyl)indan-1-one (1550 mg, 7.24 mmol) in dichloromethane (145 mL). After 4.5 hours, additional 3-chloroperbenzoic acid (5.35 g, 21.7 mmol) was added. After 6.5 hours, the reaction mixture was concentrated, diluted with EtOAc, washed with 2 portions of a mixture of 1M $Na_2S_2O_3$ and saturated aqueous $NaHCO_3$, brine, dried over $MgSO_4$, filtered, and evaporated to afford a tan solid. This was chromatographed on a Biotage 100 g SNAP column with a 20% to 80% EtOAc:hexane gradient to give 4-fluoro-7-(fluoromethylsulfonyl)indan-1-one (700 mg, 2.84 mmol, 39% yield) as a white solid. m/z (ES-API-pos) [M+H]=247.

Step D:
4-Fluoro-7-(fluoromethylsulfonyl)indan-1-ol

4-Fluoro-7-(fluoromethylsulfonyl)indan-1-one (17.9 mg, 0.07 mmol) was added to a solution of sodium borohydride (4.13 mg, 0.11 mmol) in methanol (2 mL). The reaction mixture was allowed to stir at ambient temperature. After 1.25 hours, the reaction was quenched with saturated aqueous $NH_4Cl$ and concentrated. The aqueous slurry was partitioned between EtOAc and water. The EtOAc was washed with brine, dried over $MgSO_4$, filtered, and evaporated to yield 4-fluoro-7-(fluoromethylsulfonyl)indan-1-ol (15.3 mg, 0.06 mmol, 85% yield).

Step E: 4-(3,5-Difluorophenoxy)-7-((fluoromethyl)sulfonyl)-2,3-dihydro-1H-inden-1-ol (Compound 59)

3,5-Difluorophenol (12.0 mg, 0.09 mmol) was added to a mixture of 4-fluoro-7-(fluoromethylsulfonyl)indan-1-ol (15.3 mg, 0.06 mmol) and cesium hydrogen carbonate (23.9 mg, 0.12 mmol) in DMF (1 mL). The mixture was stirred at 80° C. for a total of 6 hours. The reaction mixture was partitioned between EtOAc and dilute NaOH. The EtOAc was washed with water, brine, dried over $MgSO_4$, filtered, and evaporated. The residue was chromatographed on a Biotage 10 g SNAP column with a 10% to 40% EtOAc:hexane gradient to give an impure product. This was rechromatographed on a Biotage 12M RP column with a 20% to 90% ACN:water gradient to give Compound 59 (1.7 mg, 0.005 mmol, 8% yield) as a colorless glass. $^1$H NMR (400 MHz, $CDCl_3$): δ 7.81 (d, 1H), 6.97 (d, 1H), 6.70-6.64 (m, 1H), 6.61-6.55 (m, 2H), 5.70-5.66 (m, 1H), 5.41-5.14 (m, 2H), 3.29 (d, 1H), 3.18-3.09 (m, 1H), 2.92-2.83 (m, 1H), 2.51-2.42 (m, 1H) 2.27-2.19 (m, 1H). m/z (ES-API-neg) [M−H+46]=403.

Example 60

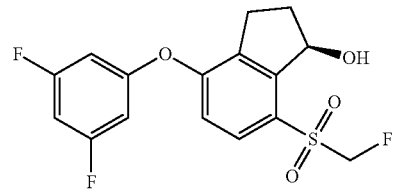 [SMILES: O=S(=O)(CF)c1ccc(Oc2cc(F)cc(F)c2)c2c1[C@H](O)CC2]

(R)-4-(3,5-Difluorophenoxy)-7-((fluoromethyl)sulfonyl)-2,3-dihydro-1H-inden-1-ol (Compound 60)

Step A:
(1R)-4-fluoro-7-(fluoromethylsulfonyl)indan-1-ol

To a solution of 4-fluoro-7-(fluoromethylsulfonyl)indan-1-one (227 mg, 0.92 mmol) in dichloromethane (10 mL) was added formic acid (0.04 mL, 1.15 mmol) and triethylamine (0.14 mL, 1 mmol). The reaction mixture was sparged with nitrogen and RuCl(p-cymene)[(R,R)-Ts-DPEN] (11.7 mg, 0.02 mmol) was added in one portion. The reaction mixture was stirred at room temperature overnight under nitrogen. The reaction mixture was evaporated and the residue was chromatographed on a Biotage 25 g SNAP column with a 10% to 80% EtOAc:hexane gradient to give (1R)-4-fluoro-7-(fluoromethylsulfonyl)indan-1-ol (230 mg, 0.93 mmol, 100% yield) as a colorless oil that solidified on standing. m/z (ES-API-neg) [M−H+46]=293.0. $^{19}$FNMR ($CDCl_3$) showed an enantiomeric excess of >90% based on the Mosher ester trifluoromethyl resonances.

Step B: (R)-4-(3,5-Difluorophenoxy)-7-((fluoromethyl)sulfonyl)-2,3-dihydro-1H-inden-1-ol (Compound 60)

3,5-Difluorophenol (15.7 mg, 0.12 mmol) was added to a mixture of (1R)-4-fluoro-7-(fluoromethylsulfonyl)indan-1-ol (20 mg, 0.08 mmol) and sodium hydrogen carbonate (20.3 mg, 0.24 mmol) in DMF (1 mL). The mixture was stirred and heated at 80° C. overnight, then at 100° C. for 24 hours. The reaction mixture was partitioned between EtOAc and dilute NaOH. The EtOAc was washed with water, brine, dried over MgSO$_4$, filtered, and evaporated. The residue was chromatographed on a Biotage 10 g SNAP column with a 10% to 50% EtOAc:hexane gradient to give Compound 60 (10.5 mg, 0.03 mmol, 36% yield). $^1$H NMR (400 MHz, CDCl$_3$): δ 7.81 (d, 1H), 6.97 (d, 1H), 6.70-6.64 (m, 1H), 6.61-6.55 (m, 2H), 5.70-5.66 (m, 1H), 5.42-5.13 (m, 2H), 3.30 (d, 1H), 3.18-3.09 (m, 1H), 2.92-2.83 (m, 1H), 2.51-2.42 (m, 1H) 2.27-2.19 (m, 1H). m/z (ES-API-neg) [M−H+46]=403.

Example 61

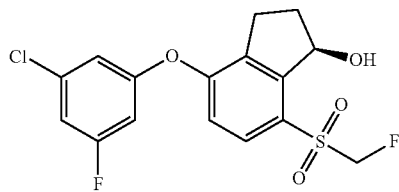 [SMILES: O=S(=O)(CF)c1ccc(Oc2cc(F)cc(Cl)c2)c2c1[C@H](O)CC2]

(R)-4-(3-Chloro-5-fluorophenoxy)-7-((fluoromethyl)sulfonyl)-2,3-dihydro-1H-inden-1-ol (Compound 61)

Prepared similarly according to Example 60, Step B, substituting 3-chloro-5-fluorophenol for 3,5-difluorophenol. $^1$H NMR (400 MHz, CDCl$_3$): δ 7.81 (d, 1H), 6.97-6.93 (m, 2H), 6.87-6.85 (m, 1H), 6.71-6.67 (m, 1H), 5.71-5.66 (m, 1H), 5.42-5.13 (m, 2H), 3.30 (d, 1H), 3.18-3.09 (m, 1H), 2.92-2.84 (m, 1H), 2.51-2.41 (m, 1H) 2.28-2.19 (m, 1H). m/z (ES-API-neg) [M−H+46]=419.

Example 62

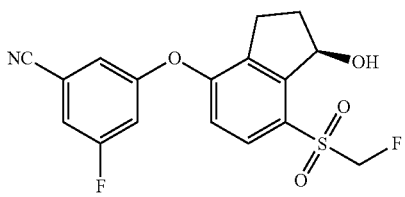 [SMILES: N#Cc1cc(F)cc(Oc2ccc(S(=O)(=O)CF)c3c2CC[C@H]3O)c1]

(R)-3-Fluoro-5-((7-((fluoromethyl)sulfonyl)-1-hydroxy-2,3-dihydro-1H-inden-4-yl)oxy)benzonitrile (Compound 62)

Prepared similarly according to Example 60, Step B, substituting 3-fluoro-5-hydroxybenzonitrile for 3,5-difluorophenol. $^1$H NMR (400 MHz, CDCl$_3$): δ 7.85 (d, 1H), 7.23-7.19 (m, 2H), 7.13-7.11 (m, 1H), 7.04-7.00 (m, 1H), 6.98 (d, 1H), 5.72-5.67 (m, 1H), 5.44-5.12 (m, 2H), 3.29 (d, 1H), 3.16-3.07 (m, 1H), 2.90-2.81 (m, 1H), 2.52-2.42 (m, 1H), 2.29-2.20 (m, 1H). m/z (ES-API-neg) [M−H+46]=410.

Example 63

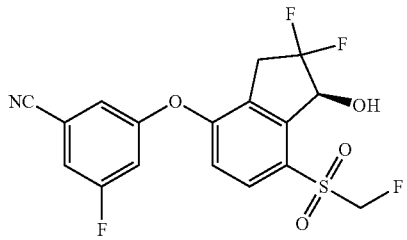 [SMILES: N#Cc1cc(F)cc(Oc2ccc(S(=O)(=O)CF)c3c2CC(F)(F)[C@H]3O)c1]

(S)-3-((2,2-difluoro-7-((fluoromethyl)sulfonyl)-1-hydroxy-2,3-dihydro-1H-inden-4-yl)oxy)-5-fluorobenzonitrile (Compound 63)

Step A: 4'-Fluoro-7'-(fluoromethylsulfonyl)spiro[1,3-dioxolane-2,1'-indane]

Trimethylsilyl trifluoromethanesulfonate (0.1 mL, 0.570 mmol) was added to a solution of 4-fluoro-7-(fluoromethylsulfonyl)indan-1-one (700 mg, 2.8 mmol) and trimethyl (2-trimethylsilyloxyethoxy)silane (1.4 mL, 5.7 mmol) in dichloromethane (50 mL) cooled to −78° C. The reaction mixture was allowed to warm to ambient temperature. After 5.5 hours, the reaction mixture was quenched with triethylamine (1.58 mL, 11.4 mmol) and evaporated. The residue was partitioned between EtOAc and dilute NaCl. The EtOAc was washed with water, brine, dried over MgSO$_4$, filtered, and evaporated to afford 4'-fluoro-7'-(fluoromethylsulfonyl) spiro[1,3-dioxolane-2,1'-indane] (630 mg, 2.2 mmol, 76% yield).

Step B: 3-Fluoro-5-[7'-(fluoromethylsulfonyl)spiro[1,3-dioxolane-2,1'-indane]-4'-yl]oxy-benzonitrile A solution of sodium hydrogen carbonate (108.5 mg, 1.29 mmol), 3-fluoro-5-hydroxy-benzonitrile (85.0 mg, 0.62 mmol), and 4'-fluoro-7'-(fluoromethylsulfonyl)spiro[1,3-dioxolane-2,1'-indane] (150 mg, 0.52 mmol) in DMF (3 mL) in a vial were heated at 110° C. overnight. The reaction mixture was partitioned between EtOAc and dilute NaOH. The EtOAc was washed with water, brine, dried over MgSO$_4$, filtered, and evaporated. The residue was chromatographed on a Biotage 25 g SNAP column with a 10% to 60% EtOAc:hexane gradient to give 3-fluoro-5-[7'-(fluoromethylsulfonyl)spiro[1,3-dioxolane-2,1'-indane]-4'-yl]oxy-benzonitrile (101 mg, 0.25 mmol, 48% yield) as a colorless glass.

Step C: 3-Fluoro-5-[7-(fluoromethylsulfonyl)-1-oxo-indan-4-yl]oxy-benzonitrile

3-Fluoro-5-[7'-(fluoromethylsulfonyl)spiro[1,3-dioxolane-2,1'-indane]-4'-yl]oxy-benzonitrile (101 mg, 0.25 mmol) was added to a solution of 4-methylbenzenesulfonate pyridin-1-ium (62.3 mg, 0.25 mmol) in acetone (6 mL) and water (0.75 mL) in a vial. The vial was sealed and the mixture was heated at 85° C. After 2.5 hours, the reaction mixture was evaporated and the residue was partitioned between EtOAc and water. The EtOAc was washed with brine, dried over MgSO₄, filtered, and evaporated to yield 3-fluoro-5-[7-(fluoromethylsulfonyl)-1-oxo-indan-4-yl]oxy-benzonitrile (84.5 mg, 0.23 mmol, 94% yield). m/z (ES-API-pos) [M+H]=364.

Step D: 3-[(E,Z)-1-Butylimino-7-(fluoromethylsulfonyl)indan-4-yl]oxy-5-fluoro-benzonitrile Trifluoroacetic acid (0.0036 mL, 0.05 mmol) was added to a solution of 3-fluoro-5-[7-(fluoromethylsulfonyl)-1-oxo-indan-4-yl]oxy-benzonitrile (84.5 mg, 0.23 mmol) and butan-1-amine (2.3 mL, 23.3 mmol) in benzene (10 mL). The mixture was heated at reflux for 5 hours with a Dean-Stark trap attached. The reaction mixture was evaporated and the residue was partitioned between EtOAc and saturated aqueous NaHCO₃. The EtOAc was washed with brine, dried over MgSO₄, filtered, and evaporated to yield 3-[(E,Z)-1-butylimino-7-(fluoromethylsulfonyl)indan-4-yl]oxy-5-fluoro-benzonitrile (99 mg, 0.24 mmol, 100% yield).

Step E: 3-[2,2-Difluoro-7-(fluoromethylsulfonyl)-1-oxo-indan-4-yl]oxy-5-fluoro-benzonitrile 1-(Chloromethyl)-4-fluoro-1,4-diazoniabicyclo[2.2.2]octane ditetrafluoroborate (209 mg, 0.59 mmol) was added to a solution of 3-[(E,Z)-1-butylimino-7-(fluoromethylsulfonyl)indan-4-yl]oxy-5-fluoro-benzonitrile (99 mg, 0.240 mmol) and sodium sulfate (33.6 mg, 0.24 mmol) in acetonitrile (6 mL) in a vial. The vial was sealed and heated at 100° C. for 6 hours. The reaction mixture was treated with ~1 mL 6 M HCl and stirred for 5 minutes. The reaction mixture was partitioned between EtOAc and water. The EtOAc was washed with brine, dried over MgSO₄, filtered, and evaporated. The residue was chromatographed on a Biotage 10 g SNAP column with a 10% to 60% EtOAc:hexane gradient to give 3-[2,2-difluoro-7-(fluoromethylsulfonyl)-1-oxo-indan-4-yl]oxy-5-fluoro-benzonitrile (37.2 mg, 0.09 mmol, 39% yield) as a white solid.

Step F: (S)-3-((2,2-difluoro-7-((fluoromethyl)sulfonyl)-1-hydroxy-2,3-dihydro-1H-inden-4-yl)oxy)-5-fluorobenzonitrile (Compound 63)

RuCl(p-cymene)[(R,R)-Ts-DPEN] (1.19 mg, 0.002 mmol) was added to a nitrogen-sparged solution of 3-[2,2-difluoro-7-(fluoromethylsulfonyl)-1-oxo-indan-4-yl]oxy-5-fluoro-benzonitrile (37.2 mg, 0.09 mmol), formic acid (0.0044 mL, 0.12 mmol), and triethylamine (0.014 mL, 0.10 mmol) in dichloromethane (6 mL). This was stirred at ambient temperature for 3.5 hours. The reaction mixture was evaporated and the residue was chromatographed on a Biotage 10 g SNAP column with a 10% to 40% EtOAc:hexane gradient to give Compound 63 (30.8 mg, 0.08 mmol, 82% yield). ¹H NMR (400 MHz, CDCl₃): δ 7.93 (d, 1H), 7.30-7.26 (m, 1H), 7.20-7.19 (m, 1H), 7.10-7.07 (m, 1H), 7.00 (d, 1H), 5.59-5.13 (m, 3H), 3.58-3.38 (m, 1H). m/z (ES-API-neg) [M–H+46]=446. ¹⁹F NMR (CDCl₃) showed an e.e. of 89% based on the Mosher ester analysis of the trifluoromethyl resonance.

Example 64

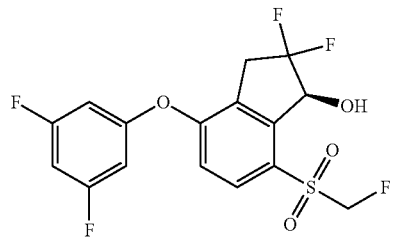 [SMILES: O=S(=O)(CF)c1ccc(Oc2cc(F)cc(F)c2)c2c1[C@H](O)C(F)(F)C2]

(S)-4-(3,5-Difluorophenoxy)-2,2-difluoro-7-((fluoromethyl)sulfonyl)-2,3-dihydro-1H-inden-1-ol (Compound 64)

Prepared similarly according to Example 63, Steps B-F, substituting 3,5-difluorophenol for 3-fluoro-5-hydroxy-benzonitrile. ¹H NMR (400 MHz, CDCl₃): δ 7.90 (d, 1H), 7.01 (d, 1H), 6.77-6.71 (m, 1H), 6.67-6.60 (m, 2H), 5.58-5.12 (m, 3H), 3.58-3.38 (m, 3H). m/z (ES-API-neg) [M–H+46]=439. Enantiomeric excess>93%.

Example 65

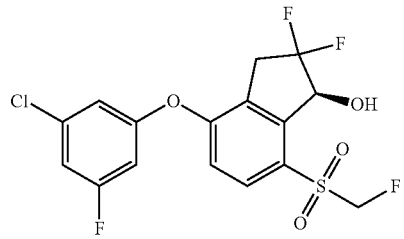 [SMILES: O=S(=O)(CF)c1ccc(Oc2cc(F)cc(Cl)c2)c2c1[C@H](O)C(F)(F)C2]

(S)-4-(3-Chloro-5-fluorophenoxy)-2,2-difluoro-7-((fluoromethyl)sulfonyl)-2,3-dihydro-1H-inden-1-ol (Compound 65)

Prepared similarly according to Example 63, Steps B-F, substituting 3-chloro-5-difluorophenol for 3-fluoro-5-hydroxy-benzonitrile. ¹H NMR (400 MHz, CDCl₃): δ 7.90 (d, 1H), 7.03-7.00 (m, 1H), 6.98 (d, 1H), 6.91-6.90 (m, 1H), 6.76-6.72 (m, 1H), 5.58-5.12 (m, 3H), 3.59-3.39 (m, 3H). m/z (ES-API-neg) [M–H+46]=455. Enantiomeric excess determined by Mosher ester analysis: 86%.

Example 66

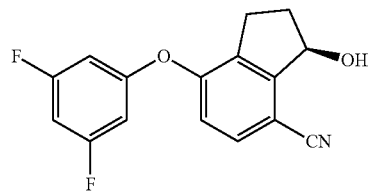 [SMILES: N#Cc1ccc(Oc2cc(F)cc(F)c2)c2c1[C@H](O)CC2]

(R)-7-(3,5-Difluorophenoxy)-3-hydroxy-2,3-dihydro-1H-indene-4-carbonitrile (Compound 66)

Step A: 7-Fluoro-3-oxo-indane-4-carbonitrile

A mixture of 7-bromo-4-fluoro-indan-1-one (500 mg, 2.2 mmol) and copper cyanide (254 mg, 2.8 mmol) in 1-methyl-2-pyrrolidone (11 mL) was heated at 190° C. for 45 minutes in a microwave. The reaction mixture was partitioned between water and EtOAc, filtered through celite, and the EtOAc layer was washed with 2 portions of water, brine, dried over $MgSO_4$, filtered, and evaporated to yield 7-fluoro-3-oxo-indane-4-carbonitrile (300 mg, 1.7 mmol, 79% yield).

Step B: 7-(3,5-Difluorophenoxy)-3-oxo-indane-4-carbonitrile 3,5-Difluorophenol (48.0 mg, 0.370 mmol) was added to a mixture of sodium hydrogen carbonate (51.6 mg, 0.61 mmol) and 7-fluoro-3-oxo-indane-4-carbonitrile (53.8 mg, 0.310 mmol) in DMF (2 mL). The mixture was stirred at 100° C. overnight. The reaction mixture was partitioned between EtOAc and dilute aqueous NaCl. The EtOAc was washed with dilute aqueous NaOH, brine, dried over $MgSO_4$, filtered, and evaporated. The residue was chromatographed on a Biotage 10 g SNAP column with a 10% to 60% EtOAc:hexane gradient to give 7-(3,5-difluorophenoxy)-3-oxo-indane-4-carbonitrile (32.2 mg, 0.11 mmol, 37% yield).

Step C: (R)-7-(3,5-Difluorophenoxy)-3-hydroxy-2,3-dihydro-1H-indene-4-carbonitrile Compound 66

RuCl(p-cymene)[(R,R)-Ts-DPEN] (13.4 mg, 0.020 mmol) was added to a nitrogen-sparged solution of 7-(3,5-difluorophenoxy)-3-oxo-indane-4-carbonitrile (30 mg, 0.11 mmol), triethylamine (0.02 mL, 0.12 mmol), and formic acid (0.005 mL, 0.13 mmol) in dichloromethane (5 mL). The mixture was stirred at ambient temperature under nitrogen for 4 hours and evaporated. The residue was chromatographed on a Biotage 10 g SNAP column with a 20% to 80% EtOAc:hexane gradient to give Compound 66 (27.2 mg, 0.09 mmol, 90% yield). $^1$H NMR (400 MHz, $CDCl_3$): δ 7.55-7.52 (m, 1H), 6.90 (d, 1H), 6.65-6.60 (m, 1H), 6.55-6.49 (m, 2H), 5.56-5.51 (m, 1H), 3.08-3.00 (m, 1H), 2.80-2.71 (m, 1H), 2.68-2.64 (m, 1H) 2.60-2.50 (m, 1H), 2.17-2.08 (m, 1H). m/z (ES-API-neg) [M−H]=286. $^{19}$F NMR ($CDCl_3$) showed an e.e. of 95% based on analysis of the Mosher ester trifluoromethyl resonance.

Example 67

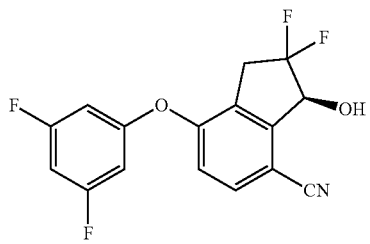 [SMILES: N#Cc1ccc(Oc2cc(F)cc(F)c2)c2c1[C@H](O)C(F)(F)C2]

(S)-7-(3,5-Difluorophenoxy)-2,2-difluoro-3-hydroxy-2,3-dihydro-1H-indene-4-carbonitrile (Compound 67)

Step A: (E,Z)-3-Butylimino-7-(3,5-difluorophenoxy)indane-4-carbonitrile

A solution of 7-(3,5-difluorophenoxy)-3-oxo-indane-4-carbonitrile (82.7 mg, 0.29 mmol), butan-1-amine (2.87 mL, 29 mmol), and trifluoroacetic acid (0.0044 mL, 0.058 mmol) in benzene (20 mL) was heated at reflux for 9 hours with a Dean-Stark trap attached. The reaction mixture was evaporated and the residue was partitioned between EtOAc and dilute $NaHCO_3$. The EtOAc was washed with brine, dried over $MgSO_4$, filtered, and evaporated to afford (E,Z)-3-butylimino-7-(3,5-difluorophenoxy)indane-4-carbonitrile (92 mg, 0.27 mmol, 93% yield).

Step B: 7-(3,5-Difluorophenoxy)-2,2-difluoro-3-oxo-indane-4-carbonitrile 1-(Chloromethyl)-4-fluoro-1,4-diazoniabicyclo[2.2.2]octane ditetrafluoroborate (239 mg, 0.68 mmol) was added to a solution of (E,Z)-3-butylimino-7-(3,5-difluorophenoxy)indane-4-carbonitrile (92 mg, 0.27 mmol) and sodium sulfate (38.4 mg, 0.270 mmol) in acetonitrile (6 mL) in a vial. The vial was sealed and heated at 100° C. for 6 hours. After cooling, the reaction mixture was treated with ~1 mL 6 M HCl and stirred for 15 minutes. The reaction mixture was partitioned between EtOAc and water. The EtOAc was washed with brine, dried over $MgSO_4$, filtered, and evaporated. The residue was chromatographed on a Biotage 10 g SNAP column with a 10% to 60% EtOAc:hexane gradient to give 7-(3,5-difluorophenoxy)-2,2-difluoro-3-oxo-indane-4-carbonitrile (29.8 mg, 0.09 mmol, 34% yield) as a white solid. m/z (ES-API-pos) [M+H+18]=339.

Step C: (S)-7-(3,5-Difluorophenoxy)-2,2-difluoro-3-hydroxy-2,3-dihydro-1H-indene-4-carbonitrile (Compound 67)

RuCl(p-cymene)[(R,R)-Ts-DPEN] (1.2 mg, 0.002 mmol) was added to a nitrogen-sparged solution of 7-(3,5-difluorophenoxy)-2,2-difluoro-3-oxo-indane-4-carbonitrile (29.8 mg, 0.09 mmol), formic acid (0.004 mL, 0.12 mmol), and triethylamine (0.014 mL, 0.100 mmol) in dichloromethane (6 mL). The mixture was stirred at ambient temperature for 3.5 hours. The reaction mixture was evaporated and the residue was chromatographed on a Biotage 10 g SNAP column with a 10% to 60% EtOAc:hexane gradient to give Compound 67 (24.5 mg, 0.08 mmol, 82% yield) as a waxy white crystalline solid. $^1$H NMR (400 MHz, $CDCl_3$): δ 7.62 (d, 1H), 6.94 (d, 1H), 6.72-6.67 (m, 1H), 6.61-6.54 (m, 2H), 5.36-5.30 (m, 1H), 3.54-3.30 (m, 2H), 3.13-3.10 (m, 1H). m/z (ES-API-neg) [M−H+46]=368. $^{19}$F NMR ($CDCl_3$) showed an e.e. of 50% based on the Mosher ester analysis of the trifluoromethyl resonance.

Example 68

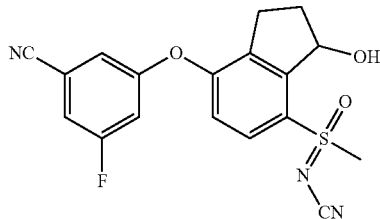 [SMILES: CS(=O)(=NC#N)c1ccc(Oc2cc(F)cc(C#N)c2)c2c1C(O)CC2]

(N-((7-(3-Cyano-5-fluorophenoxy)-3-hydroxy-2,3-dihydro-1H-inden-4-yl)(methyl)(oxo)$\lambda^6$-sulfanylidene)cyanamide (Compound 68)

Step A: N-((7-fluoro-3-oxo-2,3-dihydro-1H-inden-4-yl)(methyl)-$\lambda^4$-sulfanylidene)cyanamide (Diacetoxyiodo)benzene (902 mg, 2.8 mmol) was added to an ice-cold solution of 4-fluoro-7-methylsulfanyl-indan-1-one (500 mg, 2.55 mmol) and cyanamide (128 mg, 3.1 mmol) in acetonitrile (25 mL). The reaction mixture was stirred at ice-bath temperature for 40 minutes, and allowed to warm to ambient temperature. After 6 hours, the reaction mixture was evaporated. The residue was partitioned between EtOAc and water. The EtOAc was washed with brine, dried over MgSO$_4$, filtered, and evaporated to afford the desired product (600 mg, 2.5 mmol, 100% yield). m/z (LCMS ESI-pos) [M+H]=237.

Step B: N-((7-fluoro-3-oxo-2,3-dihydro-1H-inden-4-yl)(methyl)(oxo)-$\lambda^6$-sulfanylidene)cyanamide Sodium periodate (271 mg, 1.27 mmol) was added to a mixture of (E,Z)—N-((7-fluoro-3-oxo-2,3-dihydro-1H-inden-4-yl)(methyl)-$\lambda^4$-sulfanylidene)cyanamide (100 mg, 0.42 mmol) and ruthenium(III) chloride (2.63 mg, 0.013 mmol) in carbon tetrachloride (4 mL), acetonitrile (4 mL), and water (8 mL). The mixture was stirred overnight at ambient temperature. The reaction mixture was partitioned between dichloromethane and water. The dichloromethane was washed with brine, dried over MgSO$_4$, filtered, and evaporated to afford the desired product (100 mg; 0.4 mmol; 94% yield). m/z (LCMS ESI-pos) [M+H]=253.

Step C: N-((7-(3-cyano-5-fluorophenoxy)-3-oxo-2,3-dihydro-1H-inden-4-yl)(methyl)(oxo)-$\lambda^6$-sulfanylidene)cyanamide: Sodium hydrogen carbonate (60 mg, 0.71 mmol) was added to a vial containing a solution of 3-fluoro-5-hydroxy-benzonitrile (65 mg, 0.48 mmol) and N-((7-fluoro-3-oxo-2,3-dihydro-1H-inden-4-yl)(methyl)(oxo)-$\lambda^6$-sulfanylidene)cyanamide (60 mg, 0.48 mmol) in DMF (1.5 mL). The sealed vial was heated at 70° C. overnight. The reaction mixture was partitioned between EtOAc and dilute NaCl. The EtOAc was washed with water, brine, dried over MgSO$_4$, filtered, and evaporated. The residue was chromatographed on a Biotage 10 g SNAP column with a 30% to 100% EtOAc:hexane gradient to give the desired product (3.0 mg; 0.008 mmol; 3% yield). m/z (LCMS ESI-pos) [M+H]=370.

Step D: N-((7-(3-Cyano-5-fluorophenoxy)-3-hydroxy-2,3-dihydro-1H-inden-4-yl)(methyl)(oxo)-$\lambda^6$-sulfanylidene)cyanamide (Compound 68)

Sodium borohydride (0.4 mg, 0.007 mmol) was added to an ice-cold solution of N-((7-(3-cyano-5-fluorophenoxy)-3-oxo-2,3-dihydro-1H-inden-4-yl)(methyl)(oxo)-$\lambda^6$-sulfanylidene)cyanamide (2.6 mg, 0.007 mmol) in methanol (1 mL). The mixture was stirred at ambient temperature overnight. The reaction mixture was quenched with saturated aqueous NH$_4$Cl and evaporated. The residue was chromatographed on a Biotage 10 g SNAP column with a 20% to 80% EtOAc:hexane gradient to give Compound 68 (1.2 mg, 0.003 mmol, 46% yield). m/z (LCMS ESI-pos) [M+H]=372; $^1$H NMR (400 MHz, CDCl$_3$): δ 7.87 (d, 1H), 7.25-7.22 (m, 1H), 7.15-7.13 (m, 1H), 7.08-6.97 (m, 2H), 5.86-5.80 (m, 1H), 3.51 (s, 3H), 3.19-3.06 (m, 2H), 2.95-2.78 (m, 1H), 2.65-2.55 (m, 1H), 2.27-2.14 (m, 1H).

Example 69

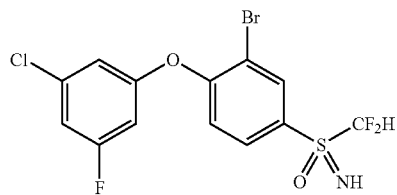 [SMILES: N=S(=O)(c1ccc(Oc2cc(F)cc(Cl)c2)c(Br)c1)C(F)F]

2-bromo-1-(3-chloro-5-fluorophenoxy)-4-((difluoromethyl)sulfonimidoyl)benzene (Compound 69)

Step A: 2-bromo-4-((difluoromethyl)sulfinyl)-1-fluorobenzene

To a solution of (3-bromo-4-fluorophenyl)(difluoromethyl)sulfane (530 mg, 2.06 mmol) in MeOH (10 mL) cooled to 0° C. was added OXONE® (633.7 mg, 1.03 mmol) as a solution in 8 mL of water. The OXONE® solution was added in 2 portions each 15 minutes apart. The resulting suspension was allowed to warm to room temperature over 2 hours. One milliliter of 1 M sodium thiosulfate solution was added to quench any left over oxidant, then the volatiles were removed by concentration under reduced pressure. The leftover residue was solutbilized with 90 mL of water and extracted with 3×40 mL EtOAc. The combined organics were rinsed with 20 mL of brine, dried with MgSO$_4$, filtered, and concentrated to dryness. Purification was achieved by chromatography on silica gel using 0-30% EtOAC/hexane as eluent to give the desired product (100 mg, 18% yield).

Step B: 2-bromo-4-(S-(difluoromethyl)sulfonimidoyl)-1-fluorobenzene

A suspension of 2-bromo-4-((difluoromethyl)sulfinyl)-1-fluorobenzene (100 mg, 0.37 mmol), 2,2,2-trifluoroacetamide (83 mg, 0.73 mmol), bis(rhodium(α,α,α',α'-tetramethyl-1,3-benezenedipropionic acid)) (11 mg, 4 mol %), and magnesium oxide (74 mg, 1.83 mmol) in 1.7 mL of dichloromethane was treated with diacetoxy iodobenzene (236 mg, 0.73 mmol) and left to stir overnight. The reaction mixture was filtered through celite, concentrated to dryness, and then redissolved in 4 mL of MeOH. The resulting reaction mixture was treated with K$_2$CO$_3$ (5 mg) and stirred for 2 hours at room temperature. The reaction mixture was concentrated to dryness and the residue purified by chromatography on silica 50-100% CH$_2$Cl$_2$/hexane as eluent to give 2-bromo-4-(S-(difluoromethyl)sulfonimidoyl)-1-fluorobenzene (73 mg, 0.25 mmol, 69% yield). LCMS ESI (+) m/z 288, 290 (M+H).

Step C: 2-bromo-1-(3-chloro-5-fluorophenoxy)-4-((difluoromethyl)sulfonimidoyl)benzene (Compound 69)

2-Bromo-4-(S-(difluoromethyl)sulfonimidoyl)-1-fluorobenzene (35 mg, 0.12 mmol) and 3-chloro-5-fluorophenol (23 mg, 0.16 mmol) were dissolved in 0.5 mL of DMF and treated with cesium carbonate (48 mg, 0.146 mmol). The reaction was heated to 90° C. for 1.5 hours. The reaction mixture was poured into 60 mL of water and extracted with 3×20 mL Et$_2$O. The combined organics were rinsed with 20 mL of brine, dried with MgSO$_4$, filtered, and concentrated to dryness. The crude residue was purified on silica using 0-30% EtOAc/hexane as eluent to give Compound 69 (29 mg, 0.70 mmol, 58% yield) as a clear oil. LCMS ESI (+) m/z 414, 416, 418 (M+H); $^1$H NMR (400 MHz, CDCl$_3$): δ 8.34 (d, 1H), 7.96 (m, 1H), 7.08 (d, 1H), 6.99 (m, 1H), 6.86 (m, 1H), 6.70 (m, 1H), 6.16 (t, 1H), 3.35 (br s, 1H).

Example 70

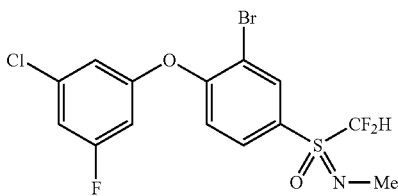 [SMILES: CN=S(=O)(c1ccc(Oc2cc(F)cc(Cl)c2)c(Br)c1)C(F)F]

N-methyl-2-bromo-1-(3-chloro-5-fluorophenoxy)-4-(S-(difluoromethyl)sulfonimidoyl)benzene (Compound 70)

A flask containing 2-bromo-1-(3-chloro-5-fluorophenoxy)-4-((difluoromethyl)sulfonimidoyl)benzene (20 mg, 0.20 mmol) dissolved in DMF (0.5 mL) was treated sequentially with potassium carbonate (8.0 mg, 0.24 mmol) and iodomethane (4 µL, 0.236 mmol). The resulting suspension stirred overnight at room temperature. The crude residue was applied directly to a reversed-phase column for purification using 10-100% CH$_3$CN/Water to give Compound 70 (1.0 mg, 5% yield) as a clear oil. LCMS ESI (+) m/z 428, 430, 432 (M+H); $^1$H NMR (400 MHz, CDCl$_3$): δ 8.26 (d, 1H), 7.87 (m, 1H), 7.07 (d, 1H), 6.98 (m, 1H), 6.86 (m, 1H), 6.70 (m, 1H), 6.22 (t, 1H), 2.98 (s, 3H).

Example 71

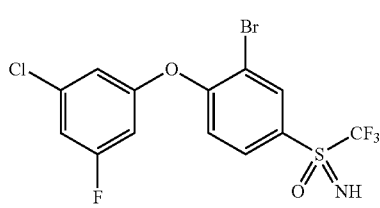 [SMILES: N=S(=O)(c1ccc(Oc2cc(F)cc(Cl)c2)c(Br)c1)C(F)(F)F]

2-bromo-1-(3-chloro-5-fluorophenoxy)-4-((trifluoromethyl)sulfonimidoyl)benzene (Compound 71)

Step A: 1-fluoro-2-bromo-4-((trifluoromethyl)sulfinyl)benzene

To a solution of (3-bromo-4-fluorophenyl)(trifluoromethyl)sulfane (530 mg, 1.93 mmol) in MeOH (10 mL) at 25° C. was added OXONE® (592 mg, 0.96 mmol) as a solution in 8 mL of water. The OXONE® solution was added in 2 portions each 15 minutes apart. The reaction mixture was heated to 50° C. and left to stir overnight. One milliliter of 1 M sodium thiosulfate solution was added to quench any leftover oxidant. Volatile solvents were removed by concentration under reduced pressure. The residue was solubilized with 60 mL of water and extracted with 3×30 mL EtOAc. The combined organics were rinsed with 20 mL of brine, dried with MgSO$_4$, filtered, and concentrated to dryness. The crude residue was purified on silica gel using 0-20% EtOAC/hexane as eluent (90 mg, 16%).

Step B: (3-bromo-4-fluorophenyl)(imino)(trifluoromethyl)-λ$^6$-sulfanone

A sample of 1-fluoro-2-bromo-4-((trifluoromethyl)sulfinyl)benzene (88 mg, 0.30 mmol) was dissolved in 0.6 mL of fuming sulfuric acid (20% SO$_3$), cooled to 0° C., and treated with sodium azide (21 mg, 0.32 mmol). The sample was heated to 70° C. for 1.5 hours (CAUTION: explosion potential, use appropriate caution and protective apparatus). Due to incomplete conversion as judged by LCMS, the reaction mixture was cooled back to 0° C. and treated with an additional portion of sodium azide (21 mg, 0.32 mmol) and reheated. The reaction mixture was cooled to room temperature, poured onto ice, and extracted with 3×20 mL Et$_2$O. The combined organics were rinsed with 20 mL saturated aqueous sodium bicarbonate, rinsed with 20 mL of brine, dried with MgSO$_4$, filtered, and concentrated to dryness. The crude residue was purified on silica using 0-40% EtOAc/hexane as eluent. (3-Bromo-4-fluorophenyl)(imino)(trifluoromethyl)-λ$^6$-sulfanone was isolated as a biege oil (54.6 mg, 0.18 mmol, 59% yield). LCMS ESI (−) m/z 304, 306 (M−H).

Step C: 2-bromo-1-(3-chloro-5-fluorophenoxy)-4-((trifluoromethyl)sulfonimidoyl)benzene Prepared analogously as described in step C of the preparation for Compound 69. Purified by chromatography on silica using 0-15% EtOAc/hexane as eluent to give Compound 71 as a clear oil (45 mg, 0.10 mmol, 58% yield). LCMS ESI (−) m/z 430, 432, 434 (M−H); $^1$H NMR (400 MHz, CDCl$_3$): δ 8.42 (d, 1H), 8.03 (m, 1H), 7.07 (d, 1H), 7.01 (m, 1H), 6.89 (m, 1H), 6.73 (m, 1H), 3.65 (br s, 1H).

Example 72

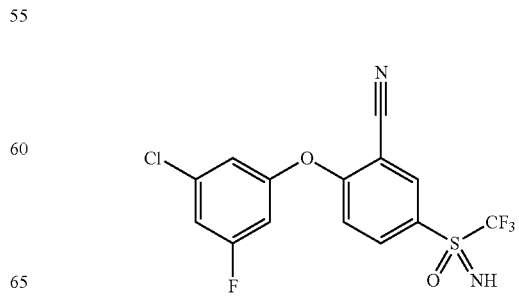

2-(3-chloro-5-fluorophenoxy)-5-((trifluoromethyl)sulfonimidoyl)benzonitrile (Compound 72)

2-Bromo-1-(3-chloro-5-fluorophenoxy)-4-((trifluoromethyl)sulfonimidoyl)benzene (23 mg, 0.05 mmol), palladium (II) chloride (dppf) methylene chloride adduct (16 mg, 0.02 mmol) and dicyanozinc (5 mg, 0.05 mmol) were dissolved in 0.4 mL of DMF. The resulting mixture was heated to 170° C. by microwace irradiation for 30 minutes. The resulting suspension was purified directly by injection onto a reverse phase column as solution in DMF using 30-90% ACN/Water as eluent to give Compound 72 as a biege oil (6.1 mg, 31%). LCMS ESI (−) m/z 377, 379 (M−H); $^1$H NMR (400 MHz, CDCl$_3$): δ 8.47 (d, 1H), 8.23 (m, 1H), 7.12 (m, 1H), 7.07 (d, 1H), 7.00 (m, 1H), 6.84 (m, 1H), 3.74 (br s, 1H).

Example 73

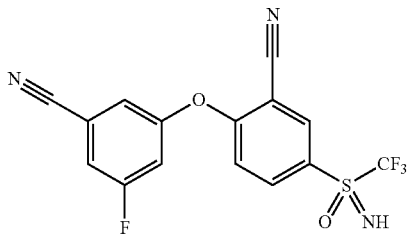 [SMILES: N#Cc1cc(F)cc(Oc2ccc(S(=N)(=O)C(F)(F)F)cc2C#N)c1]

2-(3-cyano-5-fluorophenoxy)-5-((trifluoromethyl)sulfonimidoyl)benzonitrile (Compound 73)

2-Bromo-1-(3-chloro-5-fluorophenoxy)-4-((trifluoromethyl)sulfonimidoyl)benzene (22.7 mg, 0.05 mmol), palladium (II) chloride (dppf) methylene chloride adduct (16.3 mg, 0.020 mmol) and dicyanozinc (5 mg, 0.05 mmol) were dissolved in 0.4 mL of DMF. The resulting mixture was heated to 170° C. by microwace irradiation for 30 minutes. The resulting suspension was purified directly by injection onto a reverse phase column as solution in DMF using 30-90% ACN/Water as eluent to give Compound 73 as a biege oil (5.2 mg, 27%). LCMS ESI (−) m/z 368 (M−H); $^1$H NMR (400 MHz, CDCl$_3$): δ 8.50 (d, 1H), 8.28 (m, 1H), 7.38 (m, 1H), 7.30 (m, 1H), 7.20 (m, 1H), 7.09 (d, 1H), 3.78 (br s, 1H).

Example 74

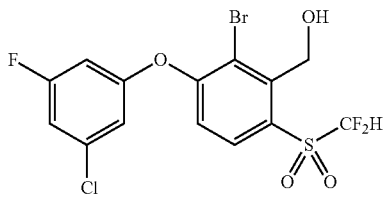 [SMILES: O=S(=O)(c1ccc(Oc2cc(F)cc(Cl)c2)c(Br)c1CO)C(F)F]

(2-bromo-3-(3-chloro-5-fluorophenoxy)-6-((difluoromethyl)sulfonyl)phenyl)methanol (Compound 74)

Prepared by an analogous set of procedures delineated in the preparation of Compound 102. The reaction mixture was purified directly on reverse phase by injection of the DMF reaction solution. 40%-80% CH$_3$CN/Water was used as eluent to give Compound 74 (22.3 mg, 0.05 mmol, 49% yield) as a white solid. LCMS ESI (+) m/z 462, 464, 466 (M+NH$_4$); $^1$H NMR (400 MHz, CDCl$_3$): δ 8.06 (d, 1H), 7.04-6.99 (m, 2H), 6.90 (m, 1H), 6.73 (m, 1H), 6.48 (t, 1H), 5.25 (d, 2H), 2.69 (t, 1H).

Example 75

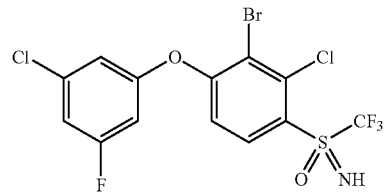 [SMILES: N=S(=O)(c1ccc(Oc2cc(F)cc(Cl)c2)c(Br)c1Cl)C(F)(F)F]

(3-bromo-2-chloro-4-(3-chloro-5-fluorophenoxy)phenyl)(imino)(trifluoromethyl)-λ$^6$-sulfanone (Compound 75)

Step A: 2-bromo-1,3-dichloro-4-((trifluoromethyl)sulfinyl)benzene

A solution of 2-bromo-1,3-dichloro-4-(trifluoromethylsulfanyl)benzene (135 mg, 0.41 mmol) in dichloromethane (4.1 mL) at 25° C. was treated with 3-chloroperbenzoic acid (92.8 mg, 0.41 mmol) and stirred at 25° C. overnight. After stirring overnight, an additional 3-chloroperbenzoic acid (30.9 mg, 0.33 equivalent) was added and the reaction was left to stir for 2 more days. The reaction mixture was poured into 10 mL of 1 N NaOH and extracted with 3×10 mL of CH$_2$Cl$_2$. The combined organics were rinsed with 10 mL of brine, dried with MgSO$_4$, filtered, and concentrated to dryness. The product was used without further purification.

Step B: (3-bromo-2,4-dichlorophenyl)(imino)(trifluoromethyl)-λ$^6$-sulfanone

See step B from the preparation for Compound 71. The crude residue was purified on silica using 0→25% EtOAc/hexane as eluent to give the desired product (24.8 mg, 0.07 mmol, 17% yield). LCMS ESI (+) m/z: 356, 358, 360.

Step C: (3-bromo-2-chloro-4-(3-chloro-5-fluorophenoxy)phenyl)(imino)(trifluoromethyl)-λ$^6$-sulfanone A solution of 3-chloro-5-fluoro-phenol (10.2 mg, 0.070 mmol) and (3-bromo-2,4-dichlorophenyl)(imino)(trifluoromethyl)-λ$^6$-sulfanone (24.8 mg, 0.07 mmol) in DMF (0.7 mL) at room temperature was treated with potassium carbonate (325 mesh, 9.6 mg, 0.07 mmol) and stirred at 85° C. until complete by LCMS (~1 hour). The reaction mixture was purified directly on reverse phase by injection of the DMF reaction solution. 30%-100% CH$_3$CN/Water was used as eluent. Repurification was achieved by chromatography on silica using 40%-100% CH$_2$Cl$_2$/hexane to give Compound 75 as glassy solid (1.6 mg, 5% yield). LCMS ESI (−) m/z 464, 466, 468 (M−H); $^1$H NMR (400 MHz, CDCl$_3$): δ 8.33 (d, 1H), 7.03 (m, 1H), 6.98 (d, 1H), 6.90 (m, 1H), 6.74 (m, 1H), 3.88 (br s, 1H).

Example 76

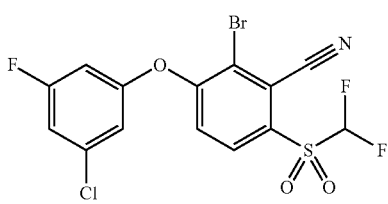 [SMILES: N#Cc1c(S(=O)(=O)C(F)F)ccc(Oc2cc(F)cc(Cl)c2)c1Br]

2-bromo-3-(3-chloro-5-fluorophenoxy)-6-((difluoromethyl)sulfonyl)benzonitrile (Compound 76)

Prepared by an analogous set of procedures delineated in the preparation of Compound 98. LCMS ESI (+) m/z 441, 443, 445 (M+H); $^1$H NMR (400 MHz, CDCl$_3$): δ 8.00 (d, 1H), 7.36 (d, 1H), 7.03 (m, 1H), 6.87 (m, 1H), 6.72 (m, 1H), 6.33 (t, 1H).

Example 77

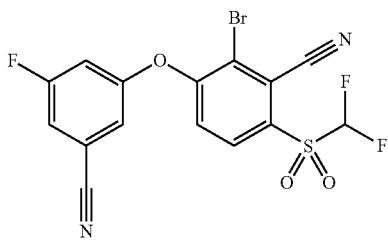 [SMILES: N#Cc1cc(F)cc(Oc2ccc(S(=O)(=O)C(F)F)c(C#N)c2Br)c1]

2-Bromo-3-(3-cyano-5-fluorophenoxy)-6-((difluoromethyl)sulfonyl)benzonitrile (Compound 77)

Prepared by an analogous set of procedures delineated in the preparation of Compound 98. LCMS ESI (+) m/z 432, 434 (M+H); $^1$H NMR (400 MHz, CDCl$_3$): δ 8.06 (d, 1H), 7.42 (d, 1H), 7.28 (m, 1H), 7.12 (m, 1H), 7.03 (m, 1H), 6.36 (t, 1H).

Example 78

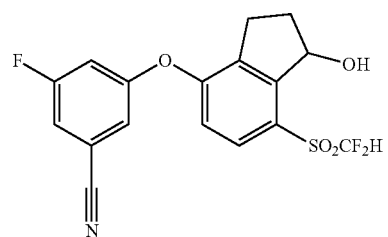

3-((7-((Difluoromethyl)sulfonyl)-1-hydroxy-2,3-dihydro-1H-inden-4-yl)oxy)-5-fluorobenzonitrile (Compound 78)

Prepared similarly according to step G in the synthesis of Compound 1 using 3-fluoro-5-hydroxy-benzonitrile as the phenol component. LCMS ESI (+) m/z 401 (M+NH$_4$); $^1$H NMR (400 MHz, CDCl$_3$): δ 7.86 (d, 1H), 7.16 (m, 1H), 7.04 (m, 1H), 6.97 (d, 1H), 6.37 (t, 1H), 5.69-5.65 (m, 1H), 3.21-3.11 (m, 2H), 2.92 (m, 1H), 2.51-2.41 (m, 1H), 2.32-2.23 (m, 1H).

Example 79

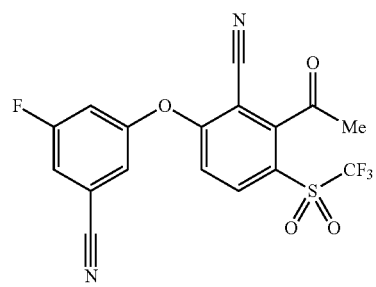 [SMILES: CC(=O)c1c(S(=O)(=O)C(F)(F)F)ccc(Oc2cc(F)cc(C#N)c2)c1C#N]

2-Acetyl-6-(3-cyano-5-fluorophenoxy)-3-((trifluoromethyl)sulfonyl)benzonitrile (Compound 79)

A solution of 2-chloro-6-(3-cyano-5-fluoro-phenoxy)-3-(trifluoromethylsulfonyl)benzonitrile (10 mg, 0.025 mmol) and bis(di-tert-butyl(4-dimethylaminophenyl)phosphine)dichloropalladium(II) (1.8 mg, 0.003 mmol) in DMF (0.25 mL) was treated with tributyl(1-ethoxyvinyl)stannane (16.7 μL, 0.05 mmol) and heated to 160° C. for 15 minutes by microwave irradiation. The reaction mixture was poured into 10 mL of water and extracted with 3×15 mL Et$_2$O. The combined organics were rinsed with 10 mL of brine, dried with MgSO$_4$, filtered, and concentrated to dryness. The crude residue was dissolved in 2 mL of dioxane and treated with 10% HCl (1 mL). Concentrated HCl (1.5 mL) was added to drive the reaction to completion. The reaction mixture was quenched by the careful addition of saturated NaHCO$_3$. The reaction mixture was poured into 20 mL of brine and extracted with 3×20 mL EtOAc. The combined organics were rinsed with 10 mL of brine, dried with MgSO$_4$, filtered, and concentrated to dryness. Purification was achieved by chromatography on silica using 10%-30% EtOAc/hexane as eluent to give Compound 79 as a beige oil (1.1 mg, 11%). $^1$H NMR (400 MHz, CDCl$_3$): δ 8.16 (d, 1H), 7.43 (m, 1H), 7.34-7.32 (m, 1H), 7.24-7.21 (m, 1H), 7.06 (d, 1H), 2.79 (s, 3H).

Example 80

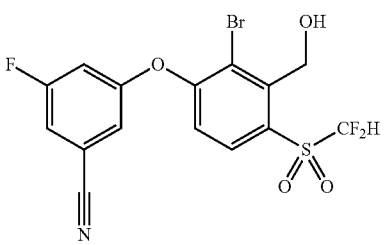 [SMILES: N#Cc1cc(F)cc(Oc2ccc(S(=O)(=O)C(F)F)c(CO)c2Br)c1]

3-(2-Bromo-4-((difluoromethyl)sulfonyl)-3-(hydroxymethyl)phenoxy)-5-fluorobenzonitrile (Compound 80)

Prepared by an analogous set of procedures delineated in the preparation of Compound 102. 3-fluoro-5-hydroxy-benzonitrile was used as the phenol component in place of 3-chloro-5-fluoro-phenol. LCMS ESI (+) m/z 453, 455 (M+NH$_4$); $^1$H NMR (400 MHz, CDCl$_3$): δ 8.11 (d, 1H), 7.28-7.23 (m, 1H), 7.15-7.13 (m, 1H), 7.09 (d, 1H), 7.05 (m, 1H), 6.50 (t, 1H), 5.25 (d, 2H), 2.69 (t, 1H).

Example 81

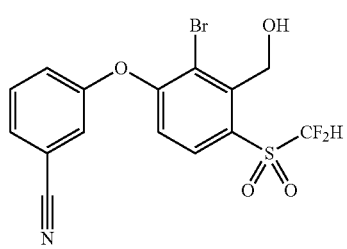 [SMILES: N#Cc1cccc(Oc2ccc(S(=O)(=O)C(F)F)c(CO)c2Br)c1]

3-(2-Bromo-4-((difluoromethyl)sulfonyl)-3-(hydroxymethyl)phenoxy)benzonitrile (Compound 81)

Prepared by an analogous set of procedures delineated in the preparation of Compound 102. 3-Hydroxy-benzonitrile was used as the phenol component in place of 3-chloro-5-fluoro-phenol. LCMS ESI (+) m/z 435, 437 (M+NH$_4$); $^1$H NMR (400 MHz, CDCl$_3$): δ 8.05 (d, 1H), 7.59-7.56 (m, 2H), 7.39-7.37 (m, 1H), 7.36-7.31 (m, 1H), 6.95 (d, 1H), 6.48 (t, 1H), 5.26 (d, 2H), 2.70 (t, 1H).

Example 82

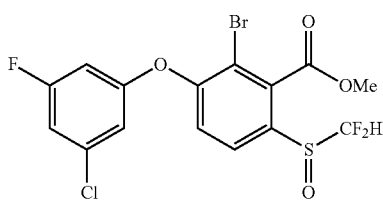 [SMILES: COC(=O)c1c(S(=O)C(F)F)ccc(Oc2cc(F)cc(Cl)c2)c1Br]

Methyl 2-bromo-3-(3-chloro-5-fluorophenoxy)-6-((difluoromethyl)sulfinyl)benzoate (Compound 82)

Step A: Methyl 2-bromo-6-((difluoromethyl)sulfinyl)-3-fluorobenzoate

Prepared by an analogous set of procedures delineated in the preparation of Compound 96. Purification was achieved on silica using 5%-25% EtOAc/hexane as eluent (88 mg, 53% yield).

Step B: Methyl 2-bromo-3-(3-chloro-5-fluorophenoxy)-6-((difluoromethyl)sulfinyl)benzoate See step C from the preparation of Compound 69. Purified by chromatography on silica using 5%-25% EtOAc/hexane as eluent to give Compound 82 as a colorless oil (13.2 mg, 11% yield). LCMS ESI (+) m/z 457, 459, 461 (M+H); $^1$H NMR (400 MHz, CDCl$_3$): δ 8.05 (d, 1H), 7.28 (d, 1H), 6.96 (m, 1H), 6.83-6.81 (m, 1H), 6.66 (m, 1H), 6.58 (m, 1H), 4.04 (t, 3H).

Example 83

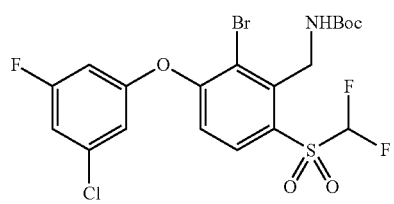 [SMILES: CC(C)(C)OC(=O)NCc1c(S(=O)(=O)C(F)F)ccc(Oc2cc(F)cc(Cl)c2)c1Br]

tert-Butyl (2-bromo-3-(3-chloro-5-fluorophenoxy)-6-((difluoromethyl)sulfonyl)benzyl)carbamate (Compound 83)

Step A: Preparation of tert-butyl (2-bromo-6-((difluoromethyl)thio)-3-fluorobenzyl)carbamate 2-Bromo-6-((difluoromethyl)thio)-3-fluorobenzonitrile was prepared by an analogous set of procedures delineated in the preparation of Compound 98. A solution of 2-bromo-6-(difluoromethylsulfanyl)-3-fluoro-benzonitrile (45 mg, 0.16 mmol) in tetrahydrofuran (1 mL) was treated with dimethylsulfonioboranuide (46.6 µL, 0.48 mmol) and stirred at 60° C. for 4 hours. The reaction mixture was quenched by the addition of 1 mL of MeOH and 0.8 mL of 4 M HCl in dioxane. The resulting mixture stirred for 15 minutes at room temperature and 30 minutes at 50° C. The reaction mixture was quenched by the addition of 2 mL of saturated NaHCO$_3$ and then concentrated under reduced pressure. The residue was solubilized with 10 mL of 1:1 CH$_2$Cl$_2$/water. The biphasic mixture was treated with tert-butoxycarbonyl tert-butyl carbonate (34.8 mg, 0.16 mmol) and left to stir for 1 hour. The reaction mixture was extracted with 3×15 mL 30% iso-propyl alcohol in CHCl$_3$. The combined organics were rinsed with 20 mL of brine, dried with MgSO$_4$, filtered, and concentrated to dryness. Purification was achieved by chromatography on silica using 5%-30% EtOAc/hexane as eluent to give the desired product (56 mg, 91% yield). LCMS ESI (+) m/z 286, 288 [MH$^+$—CO$_2$—C$_4$H$_8$].

Step B: Preparation of tert-butyl-(2-bromo-6-((difluoromethyl)sulfonyl)-3-fluorobenzyl)carbamate A procedure similar to Step E in Example 1 was followed. LCMS ESI (+) m/z 362, 364 [MH$^+$—C$_4$H$_8$].

Step C: Preparation of tert-butyl-(2-bromo-3-(3-chloro-5-fluorophenoxy)-6-((difluoromethyl)sulfonyl)benzyl)carbamate A procedure similar to Step F in Example 1 was followed. Purification was achieved by chromatography on silica using 5%-30% EtOAc/hexane to give Compound 83 as a clear film (51 mg, 51% yield). LCMS ESI (+) m/z 488, 490, 492 [MH$^+$—C$_4$H$_8$]; $^1$H NMR (400 MHz, CDCl$_3$): δ 8.04 (d, 1H), 7.02 (m, 1H), 6.99 (d, 1H), 6.90-6.88 (m, 1H), 6.73 (m, 1H), 6.62 (br t, 1H), 5.22 (br s, 1H), 4.95 (d, 2H), 1.45 (s, 9H).

Example 84

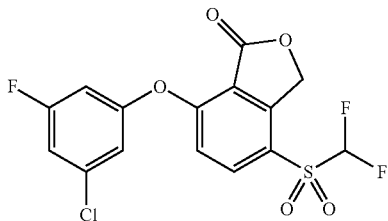 [SMILES: O=C1OCc2c(S(=O)(=O)C(F)F)ccc(Oc3cc(F)cc(Cl)c3)c21]

7-(3-Chloro-5-fluorophenoxy)-4-((difluoromethyl)
sulfonyl)isobenzofuran-1(3H)-one (Compound 84)

Step A: Preparation of [2-bromo-6-(difluoromethyl-
sulfanyl)-3-fluoro-phenyl]methanol A procedure similar to Step D in Example 1 was followed. LCMS ESI (+) m/z 269, 271 (M+H−16).

Step B: Preparation of 4-(difluoromethylsulfanyl)-
7-fluoro-3H-isobenzofuran-1-one A solution of [2-bromo-6-(difluoromethylsulfanyl)-3-fluoro-phenyl]methanol (51 mg, 0.18 mmol) in 1-methyl-2-pyrrolidone (0.8 mL) was treated with copper(I) cyanide (19.1 mg, 0.21 mmol) and stirred at 160° C. by microwave irradiation for 35 minutes. The reaction mixture was purified directly on reverse phase by injection of the reaction solution. 10%-70% CH$_3$CN/Water was used as eluent to give 4-(difluoromethylsulfanyl)-7-fluoro-3H-isobenzofuran-1-one (18 mg, 0.08 mmol, 43% yield). LCMS ESI (+) m/z 235 (M+H).

Step C: Preparation of 4-((difluoromethyl)sulfonyl)-
7-fluoroisobenzofuran-1(3H)-one A solution of 3-chloroperbenzoic acid (60.3 mg, 0.27 mmol) in dichloromethane (2 mL) at 0° C. was treated with 4-(difluoromethylsulfanyl)-7-fluoro-3H-isobenzofuran-1-one (18 mg, 0.08 mmol) and left to stir 2 days at room temperature. The reaction mixture was poured into 10 mL of 1 M NaOH and extracted with 3×20 mL CH$_2$Cl$_2$. The combined organics were rinsed with 20 mL of brine, dried with MgSO$_4$, filtered, and concentrated to dryness. Purification was achieved by chromatography on silica using 10%-40% EtOAc/hexane provided 4-((difluoromethyl)sulfonyl)-7-fluoroisobenzofuran-1(3H)-one (19 mg, 0.07 mmol, 92% yield). LCMS ESI (−) m/z 265 (M−H).

Step D: Preparation of 7-(3-chloro-5-fluorophe-
noxy)-4-((difluoromethyl)sulfonyl)isobenzofuran-1
(3H)-one A procedure similar to Step F of Example 1 was followed. Sodium bicarbonate was used in place potassium carbonate. Purification was achieved by chromatography on silica using 5%-30% EtOAc/hexane to give Compound 84 as a white solid (21.7 mg, 78% yield). LCMS ESI (+) m/z 393, 395 (M+H); $^1$H NMR (400 MHz, CDCl$_3$): δ 8.07 (d, 1H), 7.11 (m, 1H), 7.04-6.99 (m, 2H), 6.87 (m, 1H), 6.26 (t, 1H), 5.61 (d, 2H).

Example 85

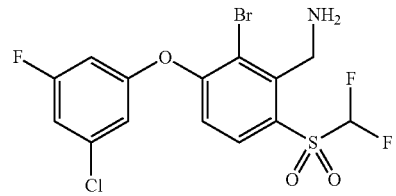 [SMILES: NCc1c(S(=O)(=O)C(F)F)ccc(Oc2cc(F)cc(Cl)c2)c1Br]

(2-Bromo-3-(3-chloro-5-fluorophenoxy)-6-((difluo-
romethyl)sulfonyl)phenyl)methanamine (Compound
85)

A solution of tert-butyl (2-bromo-3-(3-chloro-5-fluorophenoxy)-6-((difluoromethyl)sulfonyl)benzyl)carbamate (49 mg, 0.09 mmol) in dichloromethane (1 mL) at 25° C. was treated with 0.5 mL of TFA. The reaction mixture was left to stir for 1 hour. Volatiles were removed by concentration under reduced pressure. The residue was solubilized with 15 mL of 30% isopropyl alcohol/CHCl$_3$ and poured into 10 mL of saturated NaHCO$_3$. The organic phase was separated and the aqueous extracted further with 3×10 mL 30% iso-propyl alcohol/CHCl$_3$. The combined organics were rinsed with 20 mL of brine, dried with MgSO$_4$, filtered, and concentrated to dryness to give Compound 85 as a clear film (35 mg, 87% yield). LCMS ESI (+) m/z 444, 446, 448 (M+H); $^1$H NMR (400 MHz, CDCl$_3$): δ 8.04 (d, 1H), 7.02 (m, 1H), 6.97 (d, 1H), 6.89 (m, 1H), 6.73 (m, 1H), 6.66 (t, 1H), 4.45 (br s, 2H).

Example 86

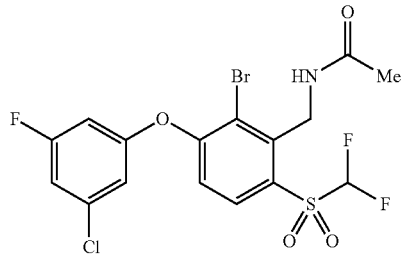 [SMILES: CC(=O)NCc1c(S(=O)(=O)C(F)F)ccc(Oc2cc(F)cc(Cl)c2)c1Br]

N-(2-Bromo-3-(3-chloro-5-fluorophenoxy)-6-((dif-
luoromethyl)sulfonyl)benzyl)acetamide (Compound
86)

A solution of (2-bromo-3-(3-chloro-5-fluorophenoxy)-6-((difluoromethyl)sulfonyl)phenyl)methanamine (15.4 mg, 0.03 mmol) and triethylamine (9.6 μL, 0.07 mmol) in dichloromethane (1 mL) at 25° C. was treated with acetic anhydride (4.0 μL, 0.04 mmol) and stirred at 25° C. until complete by LCMS (~1 hour). The reaction mixture was poured into 10 mL of saturated NaHCO$_3$ and extracted with 3×10 mL 30% iso-propyl alcohol/CHCl$_3$. The combined organics were rinsed with 10 mL of brine, dried with MgSO$_4$, filtered, and concentrated to dryness to give Compound 86 as a white solid (16.7 mg, 99% yield). LCMS ESI (+) m/z 486, 488, 490 (M+H); $^1$H NMR (400 MHz, CDCl$_3$):

δ 8.04 (d, 1H), 7.03 (m, 1H), 6.99 (d, 1H), 6.90 (m, 1H), 6.74 (m, 1H), 6.66 (t, 1H), 6.11 (br s, 1H), 5.05 (d, 2H), 2.00 (s, 3H).

Example 87

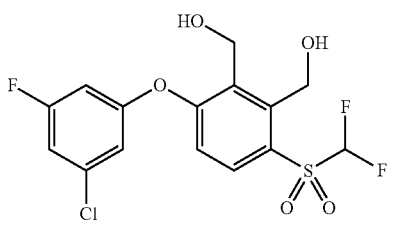 [SMILES: O=S(=O)(c1ccc(Oc2cc(F)cc(Cl)c2)c(CO)c1CO)C(F)F]

(3-(3-Chloro-5-fluorophenoxy)-6-((difluoromethyl) sulfonyl)-1,2-phenylene)dimethanol (Compound 87)

A solution of 7-(3-chloro-5-fluorophenoxy)-4-((difluoromethyl)sulfonyl)isobenzofuran-1(31-1)-one (20 mg, 0.05 mmol) in tetrahydrofuran (2 mL) at 0° C. was treated with lithium aluminum hydride (1.0 M in THF, 0.1 mL, 0.10 mmol) and stirred at 0° C. for 2 hours. Workup was achieved by adding 20% sodium potassium tartrate solution (1 mL), stirring for 20 min, and then concentrating the reaction mixture to remove THF. The leftover reaction mixture was poured into 20 mL of water and extracted with 3×10 mL iso-propyl alcohol/CHCl$_3$. The combined organics were rinsed with 10 mL of brine, dried with MgSO4, filtered, and concentrated to dryness. Purification was achieved by chromatography on silica using 10%-50% EtOAc/hexane to give Compound 87 as a white solid (10 mg, 49% yield). LCMS ESI (+) m/z 379, 381 (M+H−16); $^1$H NMR (400 MHz, CDCl$_3$): δ 8.07 (d, 1H), 7.02 (d, 1H), 7.00 (m, 1H), 6.90-6.88 (m, 1H), 6.75-6.71 (m, 1H), 6.46 (t, 1H), 5.18 (d, 2H), 5.01 (d, 2H), 3.01 (t, 1H), 2.76 (t, 1H).

Example 88

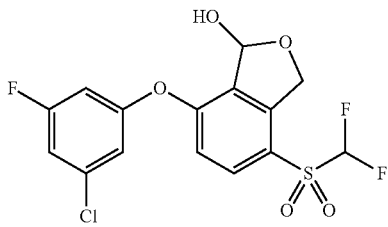 [SMILES: O=S(=O)(c1ccc(Oc2cc(F)cc(Cl)c2)c2c1COC2O)C(F)F]

7-(3-Chloro-5-fluorophenoxy)-4-((difluoromethyl) sulfonyl)-1,3-dihydroisobenzofuran-1-ol (Compound 88)

A solution of 7-(3-chloro-5-fluorophenoxy)-4-((difluoromethyl)sulfonyl)isobenzofuran-1(31-1)-one (20 mg, 0.05 mmol) in tetrahydrofuran (2 mL) at 0° C. was treated with lithium aluminum hydride (1.0 M in THF, 0.1 mL, 0.10 mmol) and stirred at 0° C. for 2 hours. Workup was achieved by adding 20% sodium potassium tartrate solution (1 mL), stirring for 20 minutes, and then concentrating the reaction mixture to remove THF. The leftover reaction mixture was poured into 20 mL of water and extracted with 3×10 mL iso-propanol/CHCl$_3$. The combined organics were rinsed with 10 mL of brine, dried with MgSO$_4$, filtered, and concentrated to dryness. Purification was achieved by chromatography on silica using 10%-50% EtOAc/hexane to give Compound 88 as a clear solid (0.8 mg, 4% yield). LCMS ESI (+) m/z 377, 379 (M+H−16); $^1$H NMR (400 MHz, CDCl$_3$): δ 7.89 (d, 1H), 7.03 (m, 1H), 6.97-6.94 (m, 2H), 6.80 (m, 1H), 6.67 (m, 1H), 6.20 (t, 1H), 5.57 (m, 1H), 5.39 (d, 1H), 3.33 (d, 1H).

Example 89

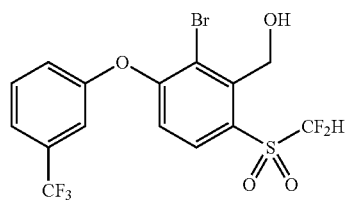 [SMILES: O=S(=O)(c1ccc(Oc2cccc(C(F)(F)F)c2)c(Br)c1CO)C(F)F]

(2-Bromo-6-((difluoromethyl)sulfonyl)-3-(3-(trifluoromethyl)phenoxy)phenyl)methanol (Compound 89)

Prepared by an analogous set of procedures delineated in the preparation of Compound 102. LCMS ESI (+) m/z 478, 480 (M+NH$_4$); $^1$H NMR (400 MHz, CDCl$_3$): δ 8.01 (d, 1H), 7.63-7.55 (m, 2H), 7.41-7.38 (m, 1H), 7.28 (m, 1H), 6.90 (d, 1H), 6.47 (t, 1H), 5.26 (d, 2H), 2.73 (t, 1H).

Example 90

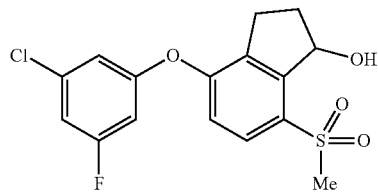 [SMILES: CS(=O)(=O)c1ccc(Oc2cc(F)cc(Cl)c2)c2c1C(O)CC2]

4-(3-Chloro-5-fluorophenoxy)-7-(methylsulfonyl)-2, 3-dihydro-1H-inden-1-ol (Compound 90)

Step A: 4-fluoro-7-(methylthio)-2,3-dihydro-1H-inden-1-ol

A solution of 4-fluoro-7-methylsulfanyl-indan-1-one (88 mg, 0.45 mmol) in methanol (2.2 mL) at 25° C. was treated with sodium borohydride (25 mg, 0.67 mmol) and stirred at 25° C. for 30 minutes. The reaction mixture was quenched by the addition of 1 mL of water. Volatiles were removed by concentration under reduced pressure. The reaction mixture was poured into 10 mL of water and extracted with 3×20 mL EtOAc. The combined organics were rinsed with 10 mL of brine, dried with MgSO$_4$, filtered, and concentrated to dryness. The resulting product was used immediately without further purification. LCMS ESI (+) m/z 181 (M+H−16).

Step B: 4-fluoro-7-(methylsulfonyl)-2,3-dihydro-1H-inden-1-ol

4-Fluoro-7-(methylthio)-2,3-dihydro-1H-inden-1-ol (0.45 mmol) was dissolved in dichloromethane (2.2 mL) and treated with 3-chloroperbenzoic acid (301.5 mg, 1.35 mmol). The reaction mixture was left to stir at 25° C. overnight. The reaction mixture was poured into 10 mL of 1 N NaOH and extracted with 3×20 mL CH$_2$Cl$_2$. The combined organics were rinsed with 10 mL of brine, dried with MgSO$_4$, filtered, and concentrated to dryness (35 mg, 34% yield). The resulting product was used immediately without further purification. LCMS ESI (+) m/z 213 (M+H−16).

Step C: 4-(3-chloro-5-fluorophenoxy)-7-(methylsulfonyl)-2,3-dihydro-1H-inden-1-ol A suspension of 4-fluoro-7-(methylsulfonyl)-2,3-dihydro-1H-inden-1-ol (12 mg, 0.05 mmol), 3-chloro-5-fluoro-phenol (7.6 mg, 0.05 mmol), and cesium bicarbonate (11.1 mg, 0.06 mmol) in 1-methyl-2-pyrrolidone (0.5 mL) was heated to 145° C. for 4 hours. The reaction mixture was poured into 20 mL of water and extracted with 3×10 mL Et$_2$O. The combined organics were rinsed with 10 mL of brine, dried with MgSO$_4$, filtered, and concentrated to dryness. Purification was achieved by chromatography on silica using 20%-60% EtOAc/hexane to give Compound 90 as a thin film (4.9 mg, 26% yield). LCMS ESI (+) m/z 339, 341 (M+H−16); $^1$H NMR (400 MHz, CDCl$_3$): δ 7.80 (d, 1H), 6.95 (d, 1H), 6.93 (m, 1H), 6.84-6.82 (m, 1H), 6.66 (m, 1H), 5.68 (m, 1H), 3.64 (d, 1H), 3.20 (s, 3H), 3.15-3.06 (m, 1H), 2.83 (m, 1H), 2.53-2.43 (m, 1H), 2.27-2.18 (m, 1H).

Example 91

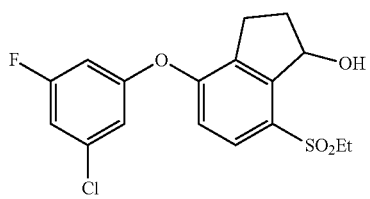

4-(3-Chloro-5-fluorophenoxy)-7-(ethylsulfonyl)-2,3-dihydro-1H-inden-1-ol (Compound 91)

An analogous set of procedures for the preparation of Compound 90 was followed. In step A, iodomethane was replaced with iodoethane. In step F, the reaction mixture was purified directly on reverse phase by injection of the reaction solution. 20%-80% CH$_3$CN/Water was used as eluent. LCMS ESI (+) m/z 353, 355 (M-OH); $^1$H NMR (400 MHz, CDCl$_3$): δ 7.74 (d, 1H), 6.95-6.92 (m, 2H), 6.84-6.82 (m, 1H), 6.66 (m, 1H), 5.65-5.60 (m, 1H), 3.70 (d, 1H), 3.35-3.19 (m, 2H), 3.15-3.06 (m, 1H), 2.83 (m, 1H), 2.49-2.39 (m, 1H), 2.27-2.19 (m, 1H), 1.34 (t, 3H).

Example 92

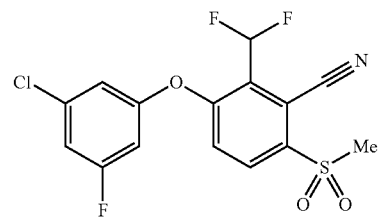 [SMILES: CS(=O)(=O)c1ccc(Oc2cc(F)cc(Cl)c2)c(C(F)F)c1C#N]

3-(3-Chloro-5-fluorophenoxy)-2-(difluoromethyl)-6-(methylsulfonyl)benzonitrile (Compound 92)

Step A: 2-bromo-3-(difluoromethyl)-1,4-difluoro-benzene

A solution of 2-bromo-3,6-difluoro-benzaldehyde (5 g, 22.6 mmol) in dichloromethane (113 mL) at 0° C. was treated with diethylaminosulfur trifluoride (7.17 mL, 54.3 mmol). The ice bath was removed from the resulting reaction mixture and it stirred for 2 hours at room temperature. The reaction mixture was cooled to 0° C. and quenched by the careful addition of 60 mL of saturated aqueous NaHCO$_3$ (CO$_2$ evolution occured). The reaction mixture was vigorously stirred for 30 minutes. An additional portion of 30 mL of saturated aqueous NaHCO$_3$ was added and the reaction stirred for a further 30 minutes. The reaction mixture was extracted with 3×40 mL CH$_2$Cl$_2$. The combined organics were rinsed with 20 mL of brine, dried with MgSO$_4$, filtered, and concentrated to dryness to give 2-bromo-3-(difluoromethyl)-1,4-difluoro-benzene. The product was used without further purification.

Step B: 2-(difluoromethyl)-3,6-difluorobenzonitrile

A solution of 2-bromo-3-(difluoromethyl)-1,4-difluoro-benzene (5.12 g, 21.1 mmol) in 1-methyl-2-pyrrolidone (42 mL) was treated with copper(I) cyanide (2.45 g, 27.4 mmol) and stirred at 180° C. for 1 hour and 45 minutes. The reaction mixture was cooled to room temperature and diluted with 200 mL of ether. The resulting suspension was filtered through celite. The filtrate was poured into 500 mL of water, separated, and extracted further with 3×70 mL Et$_2$O. The combined organics were rinsed with 50 mL of brine, dried with MgSO$_4$, filtered, and concentrated to dryness. Purification was achieved by chromatography on silica using 20%-70% CH$_2$Cl$_2$/hexane. Product is a white solid that can sublime under prolonged exposure to high vacuum (3.0 g, 15.9 mmol, 76% yield).

Step C: 2-(difluoromethyl)-3-fluoro-6-methylsulfanyl-benzonitrile

To a solution of 2-(difluoromethyl)-3,6-difluoro-benzonitrile (5.27 g, 27.9 mmol) in tetrahydrofuran (120 mL) was added methylsulfanylsodium (2.05 g, 29.3 mmol) at 0° C. After addition, the reaction mixture was stirred at 0° C. for 8 hours and then warmed to ambient temperature overnight. Water (50 mL) and MTBE (100 mL) were added. The organic layer was separated, washed with brine, dried (sodium sulfate), filtered and concentrated under reduced pressure to give 2-(difluoromethyl)-3-fluoro-6-methylsulfanyl-benzonitrile (6 g, 27.6 mmol, 99% yield) as yellow solid, which was used directly in the next step without purification. Alternatively, purification was achieved by chromatography on silica using 10%-35% EtOAc/hexane. LCMS ESI (+) m/z 218 (M+H).

Step D: 2-(difluoromethyl)-3-fluoro-6-methylsulfonyl-benzonitrile

A suspension of 2-(difluoromethyl)-3-fluoro-6-methylsulfanyl-benzonitrile (6.3 g, 29 mmol), Oxone® (53.56 g, 87.01 mmol) in acetonitrile (70 mL) and water (35 mL) was stirred at 56° C. for 3 hours. After cooling to ambient temperature, solid was removed by filtration and washed with MTBE (200 mL). The volatile solvent was removed under reduced pressure from the filtrate. The resulting solution was extracted with MTBE (400 mL), washed with brine, dried (sodium sulfate), filtered and concentrated under reduced pressure. The resulting solid was suspended in 2:1 hexane/MTBE (150 mL) and stirred for 10 minutes. The resulting white solid was collected by filtration and dried to give 2-(difluoromethyl)-3-fluoro-6-methylsulfonyl-benzonitrile (4.46 g, 17.9 mmol, 62% yield). LCMS ESI (+) m/z 250 (M+H).

Step E: 3-(3-chloro-5-fluorophenoxy)-2-(difluoromethyl)-6-(methylsulfonyl)benzonitrile A solution of 2-(difluoromethyl)-3-fluoro-6-methylsulfonyl-benzonitrile (150 mg, 0.6 mmol), 3-chloro-5-fluorophenol (88.2 mg, 0.6 mmol), and cesium bicarbonate (116.7 mg, 0.6 mmol) in DMF (1.5 mL) was stirred at 50° C. for 6 hours. The reaction mixture was poured into 50 mL of water containing 1 mL of 1 M NaOH and extracted with 3×20 mL Et$_2$O. The combined organics were rinsed with 20 mL of brine, dried with MgSO$_4$, filtered, and concentrated to dryness. Purification was achieved by chromatography on silica using 10%-40% EtOAc/hexane as eluent to give Compound 92 as a white solid (121 mg, 53% yield). LCMS ESI (+) m/z 393, 395 (M+NH$_4$); $^1$H NMR (400 MHz, CDCl$_3$): δ 8.29-8.25 (m, 1H), 7.27-7.23 (m, 1H), 7.22 (t, 1H), 7.10-7.06 (m, 1H), 6.93-6.91 (m, 1H), 6.76 (m, 1H), 3.35 (s, 3H).

Example 93

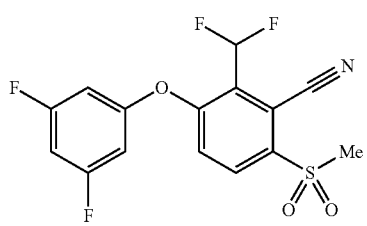 [SMILES: CS(=O)(=O)c1ccc(Oc2cc(F)cc(F)c2)c(C(F)F)c1C#N]

2-(Difluoromethyl)-3-(3,5-difluorophenoxy)-6-(methylsulfonyl)benzonitrile (Compound 93)

The product was prepared similarly according to step E in the synthesis for Compound 92 using 3,5-difluorophenol as the phenol component. LCMS ESI (+) m/z 377 (M+NH$_4$); $^1$H NMR (400 MHz, CDCl$_3$): δ 8.29-8.25 (m, 1H), 7.29-7.25 (m, 1H), 7.22 (t, 1H), 6.80 (tt, 1H), 6.69-6.63 (m, 2H), 3.35 (s, 3H).

Example 94

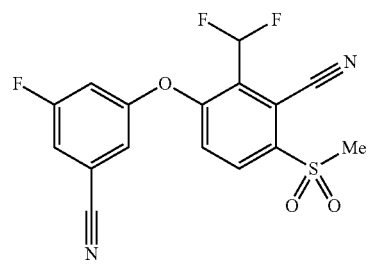 [SMILES: CS(=O)(=O)c1ccc(Oc2cc(F)cc(C#N)c2)c(C(F)F)c1C#N]

3-(3-Cyano-5-fluorophenoxy)-2-(difluoromethyl)-6-(methylsulfonyl)benzonitrile (Compound 94)

The product was prepared similarly according to step E in the synthesis for Compound 92 using 3-fluoro-5-hydroxy-benzonitrile as the phenol component. LCMS ESI (+) m/z 384 (M+NH$_4$); $^1$H NMR (400 MHz, CDCl$_3$): δ 8.34-8.30 (m, 1H), 7.35-7.32 (m, 1H), 7.29-7.25 (m, 1H), 7.21 (t, 1H), 7.21-7.18 (m, 1H), 7.11 (m, 1H), 3.36 (s, 3H).

Example 95

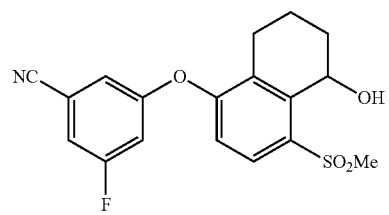 [SMILES: CS(=O)(=O)c1ccc(Oc2cc(F)cc(C#N)c2)c2c1C(O)CCC2]

3-Fluoro-5-((5-hydroxy-4-(methylsulfonyl)-5,6,7,8-tetrahydronaphthalen-1-yl)oxy)benzonitrile (Compound 95)

Step A: 8-bromo-5-hydroxy-tetralin-1-one:
Glassware was flame dried prior to the reaction A solution of 8-bromo-5-methoxy-tetralin-1-one (510.2 mg, 2 mmol) in 1,2-dichloroethane (10 mL) was treated with aluminum trichloride (1173.4 mg, 8.8 mmol) and the resulting suspension was stirred at 85° C. for 3.5 hours. The reaction mixture was carefully poured into 34 mL of 10% HCl and stirred for 2 hours. The reaction mixture was diluted with 22 mL of CH$_2$Cl$_2$ and vigorously stirred. The mixture was filtered through celite to remove black-colored insoluble materials to give 8-bromo-5-hydroxy-tetralin-1-one (198 mg crude product), which was used without further purification. LCMS ESI (+) m/z 241, 243 (M+H).

Step B: 3-(8-bromo-1-oxo-tetralin-5-yl)oxy-5-fluoro-benzonitrile

A suspension of 3,5-difluorobenzonitrile (211.2 mg, 1.52 mmol), 8-bromo-5-hydroxy-tetralin-1-one (183 mg, 0.76 mmol), and cesium bicarbonate (161.9 mg, 0.83 mmol) in 1-methyl-2-pyrrolidone (3.0 mL) was stirred at 150° C. by microwave irradiation for 30 minutes. The reaction mixture was poured into 40 mL of water and extracted with 3×20 mL Et$_2$O. The combined organics were rinsed with 10 mL of brine, dried with MgSO$_4$, filtered, and concentrated to dryness to give 3-(8-bromo-1-oxo-tetralin-5-yl)oxy-5-fluoro-benzonitrile (71.5 mg crude product). The product was isolated as a mixture of bromo and des-bromo derivatives and used without further purification. LCMS ESI (+) m/z 360, 362 (M+H).

Step C: 3-fluoro-5-((4-(methylsulfonyl)-5-oxo-5,6,7,8-tetrahydronaphthalen-1-yl)oxy)benzonitrile A solution of 3-(8-bromo-1-oxo-tetralin-5-yl)oxy-5-fluoro-benzonitrile (51.5 mg, 0.14 mmol), methanesulfinic acid sodium salt (16.1 mg, 0.16 mmol) and copper(I) iodide (136.2 mg, 0.7 mmol) in dimethyl sulfoxide (1 mL) was heated to 100° C. for 30 minutes. The reaction mixture, while vigorously stirred, was diluted with 4 mL of Et$_2$O and then diluted with 2 mL of water. The resulting suspension was filtered through celite and the filter cake rinsed extensively with Et$_2$O. The filtrate was poured into 20 mL of water and extracted with 3×10 mL Et$_2$O. The combined organics were rinsed with 10 mL of brine, dried with MgSO$_4$, filtered, and concentrated to dryness. Purification was achieved by chromatography on silica using 10%-50% EtOAc/hexane to give 3-fluoro-5-((4-(methylsulfonyl)-5-oxo-5,6,7,8-tetrahydronaphthalen-1-yl)oxy)benzonitrile (31.8 mg, 0.15 mmol, 62% yield). LCMS ESI (+) m/z 360 (M+H).

Step D: 3-fluoro-5-((5-hydroxy-4-(methylsulfonyl)-5,6,7,8-tetrahydronaphthalen-1-yl)oxy)benzonitrile A procedure similar to step C of Example 90 was followed. Purification was achieved by chromatography on silica using 20%-60% EtOAc/hexane to give Compound 95 as a thin film (10 mg, 84% yield). LCMS ESI (+) m/z 379 (M+NH$_4$); $^1$H NMR (400 MHz, CDCl$_3$): δ 7.98 (d, 1H), 7.17 (m, 1H), 7.05-7.03 (m, 1H), 6.97 (m, 1H), 6.95 (d, 1H), 5.44-5.39 (m, 1H), 3.72 (m, 1H), 3.25 (s, 3H), 3.04-2.95 (m, 1H), 2.58-2.47 (m, 1H), 2.29-2.22 (m, 1H), 2.16-2.03 (m, 1H), 1.91-1.73 (m, 2H).

Example 96

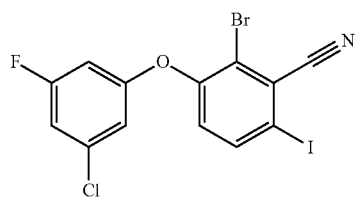 [SMILES: N#Cc1c(I)ccc(Oc2cc(F)cc(Cl)c2)c1Br]

2-Bromo-3-(3-chloro-5-fluorophenoxy)-6-iodobenzonitrile (Compound 96)

Step A: Preparation of 2-bromo-3-fluoro-6-iodobenzoic acid

2-Bromo-3-fluoro-benzoic acid (7.5 g, 34.3 mmol) was combined with palladium (II) acetate (384 mg, 1.7 mmol), iodine (8.7 g, 34.3 mmol), diacetoxy iodobenzene (11.0 g, 34.3 mmol) and DMF (165 mL). The resulting suspension was heated to 120° C. for 28 hours then stirred at ambient temperature for 40 hours. The reaction was concentrated to remove most of the DMF then the residue was poured into 0.1 M HCl (resultant pH<3) and extracted with Et$_2$O. Solid Na$_2$S$_2$O$_3$ was added to dissipate some of the iodine color. After separation, the aqueous was washed three times with Et$_2$O (100 mL each) then the combined organic layers were washed with 1M Na$_2$S$_2$O$_3$ to remove the remaining purple color. The organic layer was washed with saturated NaCl, dried over Na$_2$SO$_4$ and concentrated in vacuo. The crude product solidified after standing under vacuum (8 g, 67%).

Step B: Preparation of 2-bromo-3-fluoro-6-iodobenzamide

2-Bromo-3-fluoro-6-iodobenzoic acid (2.33 g, 6.76 mmol) was dissolved in THF (20 mL) and cooled to 0° C. The solution was treated with DMF (10 drops) followed by dropwise addition of thionyl chloride (1.0 mL, 10.1 mmol) then stirred for 10 minutes. The reaction was warmed to ambient temperature and stirred for 2 hours. The mixture was recooled to 0° C. and treated with concentrated ammonium hydroxide (5 mL) and the mixture was allowed to warm to ambient temperature with the bath and stirred overnight. The mixture was concentrated in vacuo then redissolved in saturated NaHCO$_3$ and ethyl acetate. The layers were separated and the organic phase was washed with saturated NaHCO$_3$, saturated NaCl, dried over Na$_2$SO$_4$ and concentrated in vacuo to give a white solid (2.20 g, 94%).

Step C: Preparation of 2-bromo-3-fluoro-6-iodobenzonitrile

2-Bromo-3-fluoro-6-iodobenzamide (10 g, 29 mmol) was suspended in phosphorus oxychloride (41 mL), treated with triethylamine (12.2 mL, 87.2 mmol) then the mixture was heated to 75° C. for 3 hours. The reaction was cooled to ambient temperature with the bath and stirred overnight. The mixture was concentrated in vacuo to remove excess POCl$_3$ then the semi-dry residue was treated with ice and some water. The mixture was stirred until the ice melted and the beige solid was collected by filtration, washed with water and air-dried (8.04 g, quant.).

Step D: Preparation of 2-bromo-3-(3-chloro-5-fluorophenoxy)-6-iodobenzonitrile (Compound 96)

2-Bromo-3-fluoro-6-iodobenzonitrile (25.2 mg, 0.08 mmol) was combined with 3-chloro-5-fluorophenol (11 mg, 0.08 mmol) and 325-mesh potassium carbonate (13 mg, 0.09 mmol) in acetonitrile (0.25 mL). The mixture was heated to 210° C. in an Initiator® microwave reactor for 30 minutes. After cooling, the reaction was diluted with Et$_2$O and water then separated. The aqueous phase was washed with Et$_2$O and the combined organic layers were washed twice with 10% Na$_2$CO$_3$, saturated NaHCO$_3$, saturated NaCl, dried over Na$_2$SO$_4$ and concentrated in vacuo. The crude product was chromatographed on reversed-phase SiO$_2$ eluting with a gradient of MeCN/water. The first material to elute from the column was concentrated in vacuo then the residue was partitioned between water and ethyl acetate. The organic layer was washed with saturated NaCl, dried over Na$_2$SO$_4$ and concentrated in vacuo to give Compound 96 (10 mg, 27%). $^1$H NMR (400 MHz, CDCl$_3$): δ 7.85 (d, 1H), 6.94 (d, 1H), 6.93-6.90 (m, 1H), 6.74-6.73 (m, 1H), 6.61-6.57 (m, 1H).

Example 97

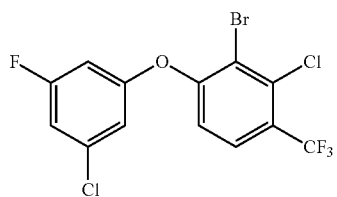 [SMILES: Fc1cc(Cl)cc(Oc2ccc(C(F)(F)F)c(Cl)c2Br)c1]

2-Bromo-3-chloro-1-(3-chloro-5-fluorophenoxy)-4-(trifluoromethyl)benzene (Compound 97)

Step A: Preparation of 2-chloro-4-(3-chloro-5-fluorophenoxy)-3-nitro-1-(trifluoromethyl)benzene 1,3-Dichloro-2-nitro-4-(trifluoromethyl)benzene (0.50 g, 1.9 mmol) was treated with cesium carbonate (1.25 g, 3.9 mmol) and slurried in NMP (4 mL). The suspension was cooled to 0° C. and treated with 3-fluoro-5-chlorophenol (282 mg, 1.9 mmol) dissolved in NMP (2 mL). The mixture was stirred while the ice bath warmed to ambient temperature for 14 hours. The reaction mixture was diluted with water and Et₂O then separated. The aqueous was washed with Et₂O and the combined organic layers were washed twice with 10% Na₂CO₃, saturated NaCl, dried over Na₂SO₄ and concentrated in vacuo. The material was chromatographed on SiO₂ eluting with a gradient of ethyl acetate/hexane and the fractions containing the desired material were concentrated in vacuo to a white solid (125 mg, 17%).

Step B: Preparation of 2-chloro-6-(3-chloro-5-fluorophenoxy)-3-(trifluoromethyl)aniline 2-Chloro-4-(3-chloro-5-fluorophenoxy)-3-nitro-1-(trifluoromethyl)benzene (110 mg, 0.30 mmol) was dissolved in 95% ethanol (2 mL) and treated with tin (II) chloride pentahydrate (335 mg, 1.2 mmol). The mixture was heated to reflux for 5 hours then stirred at ambient temperature for 55 hours. The mixture was concentrated in vacuo then redissolved in ethyl acetate. The organic layer was washed three times with 10% NaOH, water, saturated NaHCO₃, saturated NaCl, dried over Na₂SO₄ and concentrated in vacuo to a light oil (105 mg, quant.).

Step C: Preparation of 2-bromo-3-chloro-1-(3-chloro-5-fluorophenoxy)-4-(trifluoromethyl)benzene (Compound 97)

2-Chloro-6-(3-chloro-5-fluorophenoxy)-3-(trifluoromethyl)aniline (102 mg, 0.30 mmol)) was dissolved in dioxane (0.7 mL), diluted with concentrated HCl (0.7 mL) then cooled to 0° C. A solution of sodium nitrite (21 mg, 0.30 mmol) in water (50 pt) was added dropwise then stirred 15 minutes after the addition. The diazonium intermediate was treated with a cooled (0° C.) solution of copper (I) bromide (52 mg, 0.36 mmol) dissolved in 6N HCl (0.34 mL). The mixture was stirred for 15 minutes then warmed to 60° C. for 16 hours. The reaction was quenched with water and ethyl acetate and the aqueous layer was separated from the dark organic layer. The organic layer was washed several times with saturated NH₄Cl, saturated NaCl, dried over Na₂SO₄ and concentrated in vacuo. The crude product was chromatographed on SiO₂ eluting with a gradient of ethyl acetate/hexane to give Compound 97 as a colorless oil (55 mg, 45%). ¹H NMR (400 MHz, CDCl₃): δ 7.68 (d, 1H), 6.99-6.94 (m, 2H), 6.85-6.84 (m, 1H), 6.71-6.67 (m, 1H).

Example 98

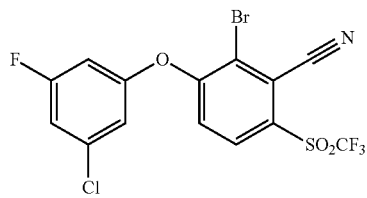

2-Bromo-3-(3-chloro-5-fluorophenoxy)-6-((trifluoromethyl)sulfonyl)benzonitrile (Compound 98)

Step A: Preparation of S-(3-bromo-2-cyano-4-fluorophenyl) ethanethioate

2-Bromo-3-fluoro-6-iodobenzonitrile [Compound 96, Step C] (6.5 g, 19.9 mmol) and Xantphos (1.38 g, 2.39 mmol) were suspended in 2:1 toluene/acetone (80 mL). The mixture was sparged with argon then treated with tris (dibenzylideneacetone)dipalladium (1.0 g, 1.1 mmol) and potassium ethanethioate (2.84 g, 24.9 mmol). The mixture was sealed under argon and heated to 70° C. for 3 hours then stirred at ambient temperature overnight. The reaction was filtered through celite, the retained solids were washed with methylene chloride and the filtrate was concentrated in vacuo. The crude product was chromatographed on SiO₂ eluting with a gradient of ethyl acetate and hexane. All fractions (including higher and lower R_f materials) containing the desired material were collected and concentrated to a crude dark brown solid (4.0 g, 73%). This material was used without further purification.

Step B: Preparation of 2-bromo-3-fluoro-6-mercaptobenzonitrile

S-(3-Bromo-2-cyano-4-fluorophenyl) ethanethioate (4.0 g, 14.6 mmol) was dissolved in THF (130 mL) and the solution was sparged with argon gas for 10 minutes. Concentrated ammonium hydroxide (15M, 18 mL) was added and the resultant solution was sparged for an additional 5 minutes then stirred for 40 minutes. The reaction mixture was concentrated in vacuo then redissolved in Et₂O and some water plus 10% NH₄OH to adjust to pH 10. The aqueous layer was separated and washed twice with Et₂O. The aqueous layer was adjusted to pH 2 with 1M KHSO₄ then extracted three times with Et₂O. The combined organics were washed with water, saturated NaCl, dried over Na₂SO₄ and concentrated in vacuo to a tan solid (1.92 g, 56%).

Step C: Preparation of 2-bromo-3-fluoro-6-((trifluoromethyl)thio)benzonitrile

2-Bromo-3-fluoro-6-mercaptobenzonitrile (1.92 g, 8.3 mmol) was dissolved in DMF (11 mL) and treated with methyl viologen dichloride (213 mg, 0.83 mmol) and triethylamine (2.9 mL, 20.7 mmol). This solution was cooled to −78° C. and excess trifluoromethyliodide gas (18.5 g) was condensed into the solution. The reaction vessel was sealed, warmed directly to ambient temperature and stirred for 18 hours. The reaction was cooled to −78° C., opened carefully and the volatile reagents were removed with vigorous nitrogen flow through the solution. The mixture was poured into saturated NaCl, diluted with Et$_2$O and separated. The aqueous phase was washed three times with Et$_2$O and the combined organics were washed with saturated NaCl, dried over Na$_2$SO$_4$ and concentrated in vacuo. The crude product was purified on SiO$_2$ eluting with a gradient of ethyl acetate and hexane to give 2-bromo-3-fluoro-6-((trifluoromethyl)thio)benzonitrile (2.46 g, quant.).

Step D: Preparation of 2-bromo-3-fluoro-6-((trifluoromethyl)sulfonyl)benzonitrile 2-Bromo-3-fluoro-6-((trifluoromethyl)thio)benzonitrile (145 mg, 0.48 mmol) was dissolved in a mixture of MeCN, CCl$_4$ and water (1:1:2, 4.8 mL) then ruthenium (III) chloride (3 mg, 0.01 mmol) and sodium periodate (310 mg, 1.45 mmol) were added. The suspension was stirred at ambient temperature for 4 hours. The mixture was diluted with methylene chloride and filtered through a pad of celite. The filtrate was separated and the aqueous layer was washed with fresh methylene chloride. The combined organic extracts were passed through a small pad of Florisil® (pre-wetted with methylene chloride). The filter media was washed with methylene chloride then the combined filtrates were concentrated in vacuo to a white solid (145 mg, quant.).

Step E: Preparation of 2-bromo-3-(3-chloro-5-fluorophenoxy)-6-((trifluoromethyl)sulfonyl)benzonitrile (Compound 98)

2-Bromo-3-fluoro-6-((trifluoromethyl)sulfonyl)benzonitrile (26 mg, 0.08 mmol) was combined with sodium bicarbonate (13 mg, 0.16 mmol) in acetonitrile (0.25 mL) and the suspension was cooled to 0° C. A solution of 3-chloro-5-fluorophenol (11 mg, 0.08 mmol) in acetonitrile (0.25 mL) was added dropwise to the cold suspension. The mixture was stirred at 0° C. for 30 minutes then warmed to ambient temperature for 6 hours. The mixture was diluted with ethyl acetate and water then separated. The organic layer was washed twice with saturated NaHCO$_3$, saturated NaCl, dried over Na$_2$SO$_4$ and concentrated in vacuo. The crude product was chromatographed on SiO$_2$ eluting with a gradient of ethyl acetate/hexane to give Compound 98 as a free-flowing white solid (22.7 mg, 62%). LCMS ESI (−) m/z (M−H) 456, 458; $^1$H NMR (400 MHz, CDCl$_3$): δ 8.12 (d, 1H), 7.18 (d, 1H), 7.14-7.11 (m, 1H), 6.97-6.96 (m, 1H), 6.82-6.79 (m, 1H).

Example 99

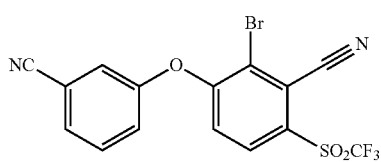

2-Bromo-3-(3-cyanophenoxy)-6-((trifluoromethyl)sulfonyl)benzonitrile (Compound 99)

Prepared similarly as described in Compound 98, Step E utilizing 3-hydroxybenzonitrile (52%). LCMS ESI (+) m/z (M+NH$_4$) 448, 450; $^1$H NMR (400 MHz, CDCl$_3$): δ 8.12 (d, 1H), 7.69-7.63 (m, 2H), 7.46-7.45 (m, 1H), 7.41-7.38 (m, 1H), 7.11 (d, 1H).

Example 100

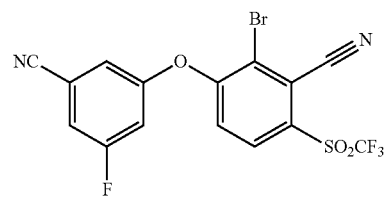

2-Bromo-3-(3-cyano-5-fluorophenoxy)-6-((trifluoromethyl)sulfonyl)benzonitrile (Compound 100)

Prepared similarly as described in Example 98, Step E utilizing 3-fluoro-5-hydroxybenzonitrile (>90%). LCMS ESI (+) m/z (M+NH$_4$) 466, 468; $^1$H NMR (400 MHz, CDCl$_3$): δ 8.17 (d, 1H), 7.39-7.36 (m, 1H), 7.24-7.23 (m, 1H), 7.22 (d, 1H), 7.16-7.13 (m, 1H).

Example 101

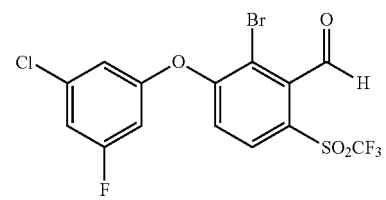

2-Bromo-3-(3-chloro-5-fluorophenoxy)-6-((trifluoromethyl)sulfonyl)benzaldehyde (Compound 101)

Step A: Preparation of 2-bromo-3-fluoro-6-((trifluoromethyl)sulfonyl)benzaldehyde 2-Bromo-3-fluoro-6-(trifluoromethylsulfonyl)benzonitrile (500 mg, 1.5 mmol) [Compound 98, Step D] was dissolved in dichloromethane (8 mL) and cooled to 0° C. The solution was treated slowly with a solution of diisobutylaluminum hydride (1M in heptane, 1.81 mL, 1.81 mmol) and the mixture was stirred at 0° C. for 5 hours. Additional diisobutylaluminum hydride (1M in heptane, 0.3 mL, 0.3 mmol) was added dropwise and the reaction mixture was stirred at 0° C. for an additional 2 hours. The reaction was quenched at 0° C. by addition of cold 1N HCl (8 mL). The suspension was warmed to ambient temperature and stirred for 1 hour. The mixture was neutralized by addition of solid NaHCO₃ and the resultant precipitate was filtered and washed with ethyl acetate. The filtrate was separated, the aqueous was washed with ethyl acetate and the combined organics were washed with saturated NaHCO₃, saturated NaCl, dried over Na₂SO₄ and concentrated in vacuo to give the desired product (458 mg, 90%).

Step B: Preparation of 2-bromo-3-(3-chloro-5-fluorophenoxy)-6-((trifluoromethyl)sulfonyl)benzaldehyde 2-Bromo-3-fluoro-6-(trifluoromethylsulfonyl)benzaldehyde (458 mg, 1.37 mmol) was treated with sodium bicarbonate (230 mg, 2.73 mmol) and 3-chloro-5-fluoro-phenol (210 mg, 1.44 mmol) and the solids were slurried in acetonitrile (4 mL) then the mixture was stirred at 50° C. for 20 hours. The reaction was concentrated in a stream of nitrogen gas then diluted with water and ethyl acetate. The layers were separated and the aqueous was washed three times with ethyl acetate. The combined organic layers were washed three times with 10% K₂CO₃, saturated NaHCO₃, saturated NaCl, dried over Na₂SO₄ and concentrated in vacuo to a light yellow oil. The crude material was chromatographed on SiO₂ eluting with a gradient of hexane/ethyl acetate to give Compound 101 as a colorless oil (525 mg, 83%). ¹H NMR (400 MHz, CDCl₃): δ 10.31 (s, 1H), 7.99 (d, 1H), 7.10 (d, 1H), 7.10-7.07 (m, 1H), 6.96-6.94 (m, 1H), 6.81-6.77 (m, 1H).

Example 102

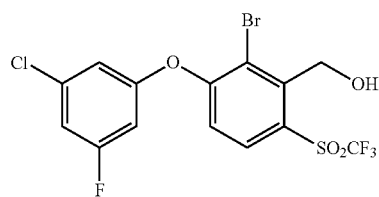

(2-Bromo-3-(3-chloro-5-fluorophenoxy)-6-((trifluoromethyl)sulfonyl)phenyl)methanol (Compound 102)

2-Bromo-3-(3-chloro-5-fluoro-phenoxy)-6-(trifluoromethylsulfonyl)benzaldehyde [Compound 101] (16.5 mg, 0.04 mmol) was dissolved in 95% EtOH (0.5 mL) and treated with sodium borohydride (2.7 mg, 0.07 mmol) in a single portion. The mixture was stirred at ambient temperature for 3 hours, quenched with 1N HCl (0.5 mL), and stirred at ambient temperature for 30 minutes. The mixture was diluted with Et₂O and separated. The aqueous was washed with Et₂O and the combined organics were washed twice with water, saturated NaHCO₃, saturated NaCl, dried over Na₂SO₄ and concentrated in vacuo. The crude solid was triturated in hexanes/methylene chloride and the resulting solid was filtered, washed with hexane and air-dried to give Compound 102 (8 mg, 43%). ¹H NMR (400 MHz, CDCl₃): δ 7.77 (d, 1H), 7.16 (d, 1H), 7.00-6.97 (m, 1H), 6.83-6.82 (m, 1H), 6.70-6.67 (m, 1H), 5.43 (s, 2H).

Example 103

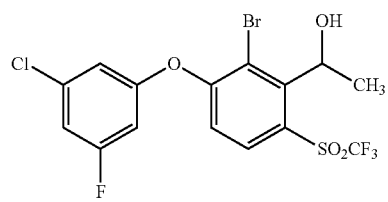

1-(2-Bromo-3-(3-chloro-5-fluorophenoxy)-6-((trifluoromethyl)sulfonyl)phenyl)ethan-1-ol (Compound 103)

2-Bromo-3-(3-chloro-5-fluoro-phenoxy)-6-(trifluoromethylsulfonyl)benzaldehyde [Compound 101] (23 mg, 0.05 mmol) was dissolved in THF (0.2 mL), cooled to 0° C. and treated dropwise with a solution of dimethylzinc (1M in heptane, 0.22 mL, 0.22 mmol). The mixture was heated to 80° C. for 25 hours. After cooling to ambient temperature, the mixture was added to cold 1N HCl (1 mL). After stirring for several minutes, the aqueous layer was adjusted to pH 8-9 with saturated NaHCO₃. The aqueous suspension was extracted three times with Et₂O. The combined organics were washed with saturated NaHCO₃, saturated NaCl, dried over Na₂SO₄ and concentrated in vacuo. The crude material was chromatographed on SiO₂ eluting with 20:1 hexane/ethyl acetate to give Compound 103 as a white solid (8.7 mg, 36%). LCMS ESI (−) m/z (M−H) 475, 477; ¹H NMR (400 MHz, CDCl₃): δ 8.11 (d, 1H), 7.06-7.03 (m, 1H), 6.95 (d, 1H), 6.92-6.91 (m, 1H), 6.77-6.74 (m, 1H), 5.88 (m, 1H), 3.38 (d, 1H), 1.81 (d, 3H).

Example 104

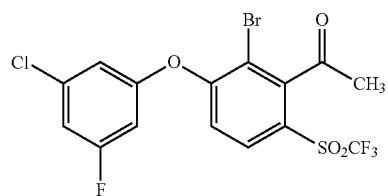

1-(2-Bromo-3-(3-chloro-5-fluorophenoxy)-6-((trifluoromethyl)sulfonyl)phenyl)ethan-1-one (Compound 104)

1-[2-Bromo-3-(3-chloro-5-fluorophenoxy)-6-(trifluoromethylsulfonyl)phenyl]ethan-1-ol (10 mg, 0.02 mmol) [Compound 103] was dissolved in methylene chloride (0.2 mL) and treated with Dess-Martin periodinane (11.5 mg, 0.03 mmol) and the solution was stirred at ambient temperature for 45 minutes. The reaction was diluted with saturated NaHCO₃ and 10% aqueous sodium thiosulfate then stirred for 10 minutes. The aqueous was washed three times with Et₂O and the combined organics were washed with saturated NaHCO₃, saturated NaCl, dried over Na₂SO₄ and concentrated in vacuo to give Compound 104 as a semi-solid (11 mg, quant.). LCMS ESI (−) m/z (M−H) 473, 475; LCMS ESI (+) m/z (M+H) 474.8/476.7; ¹H NMR (400 MHz, CDCl$_3$): δ 7.97-7.94 (m, 1H), 7.10-7.07 (m, 1H), 7.01 (d, 1H), 6.80-6.77 (m, 1H), 2.71 (s, 3H).

Example 105

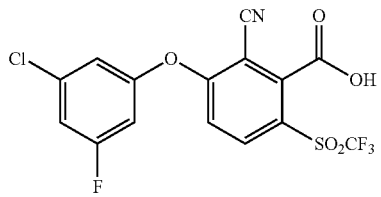

3-(3-Chloro-5-fluorophenoxy)-2-cyano-6-((trifluoromethyl)sulfonyl)benzoic acid (Compound 105)

2-Bromo-3-(3-chloro-5-fluoro-phenoxy)-6-(trifluoromethylsulfonyl)benzaldehyde (44 mg, 0.10 mmol) [Compound 101] was combined with copper (I) cyanide (8.6 mg, 0.1 mmol) in NMP (0.5 mL), purged with bubbling argon gas, then the mixture was heated to 190° C. for 60 minutes in the Initiator® microwave reactor. After cooling, most of the NMP was removed in a stream of nitrogen gas. The residue was dissolved in ethyl acetate and water. The layers were separated and the organic layer was washed five times with water, saturated NaCl, dried over Na$_2$SO$_4$ and concentrated in vacuo. The crude product was chromatographed on SiO$_2$ eluting with a gradient of ethyl acetate/hexane to give Compound 105 as a tan solid (45% yield). LCMS ESI (+) m/z (M+H) 424, 426; $^1$H NMR (400 MHz, CDCl$_3$): δ 8.35 (d, 1H), 7.84 (brd s, 1H), 7.26 (d, 1H), 7.15-7.12 (m, 1H), 7.04-7.03 (m, 1H), 6.89-6.86 (m, 1H).

Example 106

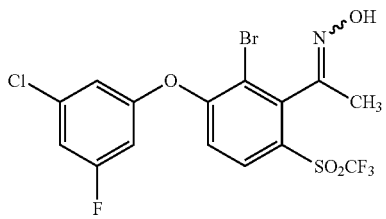

1-(2-Bromo-3-(3-chloro-5-fluorophenoxy)-6-((trifluoromethyl)sulfonyl)phenyl)ethan-1-one oxime (Compound 106)

Hydroxylamine hydrochloride (16 mg, 0.23 mmol) was combined with sodium acetate (18.6 mg, 0.23 mmol) and a solution of 1-[2-bromo-3-(3-chloro-5-fluoro-phenoxy)-6-(trifluoromethylsulfonyl)phenyl]ethanone [Compound 104] (45 mg, 0.09 mmol) dissolved in 95% EtOH (0.9 mL) was added then the resultant mixture was stirred at ambient temperature for 16 hours. The solvent was removed using a stream of nitrogen gas and the residue was diluted with 1M Na$_2$CO$_3$ and ethyl acetate. The phases were separated and the aqueous was washed with ethyl acetate. The combined organic layers were washed with saturated NaHCO$_3$, saturated NaCl, dried over Na$_2$SO$_4$ and concentrated in vacuo to a colorless film to give Compound 106 as a light yellow oil (44 mg, quant.). LCMS ESI (+) m/z (M+H) 492, 494; $^1$H NMR (400 MHz, CDCl$_3$): δ 7.95-7.94 (m, 1H), 7.09-7.06 (m, 1H), 7.01 (d, 1H), 6.96-6.95 (m, 1H), 6.80-6.77 (m, 1H), 2.70 (s, 3H).

Example 107

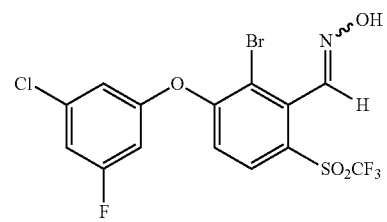

2-Bromo-3-(3-chloro-5-fluorophenoxy)-6-((trifluoromethyl)sulfonyl)benzaldehyde oxime (Compound 107)

Hydroxylamine hydrochloride (5.8 mg, 0.08 mmol) was added to a suspension of sodium acetate (6.8 mg, 0.08 mmol) and 2-bromo-3-(3-chloro-5-fluoro-phenoxy)-6-(trifluoromethylsulfonyl)benzaldehyde [Compound 101] (16 mg, 0.03 mmol) in 95% EtOH (0.5 mL). The mixture was stirred at ambient temperature for 2 hours. The reaction mixture was concentrated in a stream of nitrogen gas then diluted with 1M Na$_2$CO$_3$ and ethyl acetate. After separation of the layers, the aqueous was washed with ethyl acetate and the combined organic layers were washed with saturated NaHCO$_3$, saturated NaCl, dried over Na$_2$SO$_4$ and concentrated in vacuo to give Compound 107 as a colorless film (23 mg, quant.). LCMS ESI (+) m/z (M+H) 476, 478; $^1$H NMR (400 MHz, CDCl$_3$): δ 8.39 (s, 1H), 8.07 (d, 1H), 7.07 (d, 1H), 7.07-7.04 (m, 1H), 6.94-6.93 (m, 1H), 6.79-6.76 (m, 1H).

Example 108

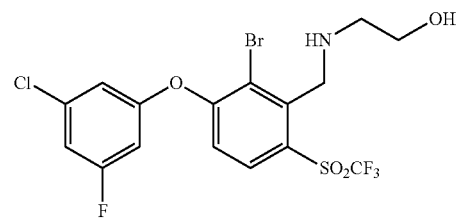

2-((2-Bromo-3-(3-chloro-5-fluorophenoxy)-6-((trifluoromethyl)sulfonyl)benzyl)amino)ethan-1-ol (Compound 108)

2-Bromo-3-(3-chloro-5-fluoro-phenoxy)-6-(trifluoromethylsulfonyl)benzaldehyde [Compound 101] (10 mg, 0.02 mmol) was dissolved in 1,2-dichloroethane (0.1 mL) and treated with ethanolamine (1.4 μL, 0.02 mmol) and sodium triacetoxyborohydride (14 mg, 0.06 mmol). The solution was stirred at ambient temperature for 18 hours. The mixture was quenched by dropwise addition of 10% HCl until the mixture remained acidic (pH<2). This mixture was stirred for 1 hour then readjusted to pH 8-9 with saturated NaHCO$_3$ and diluted with Et$_2$O and water. After separation, the aqueous was washed twice with Et$_2$O. The combined organic layers were washed with water, saturated NaHCO$_3$, saturated NaCl, dried over Na$_2$SO$_4$ and concentrated in vacuo. The crude material was chromatographed on SiO$_2$ eluting with a gradient of ethyl acetate/hexane to give Compound 108 as colorless oil (3 mg, 29%). LCMS ESI (+) m/z (M+H) 506, 508; $^1$H NMR (400 MHz, CDCl$_3$): δ 8.07 (d, 1H), 7.06-7.03 (m, 1H), 6.98 (d, 1H), 6.93-6.92 (m, 1H), 6.78-6.74 (m, 1H), 4.32 (s, 2H), 3.72 (t, 2H), 2.97 (t, 2H).

Example 109

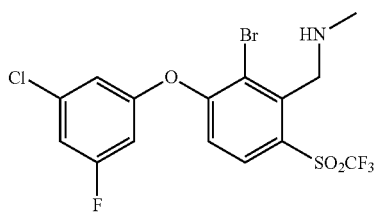

1-(2-Bromo-3-(3-chloro-5-fluorophenoxy)-6-((trifluoromethyl)sulfonyl)phenyl)-N-methylmethanamine (Compound 109)

2-Bromo-3-(3-chloro-5-fluoro-phenoxy)-6-(trifluoromethylsulfonyl)benzaldehyde (30 mg, 0.06 mmol) [Compound 101] was dissolved in trimethyl orthoformate (0.3 mL) and treated with methylamine hydrochloride (4.4 mg, 0.07 mmol) and N,N-diisopropylethylamine (17 µL, 0.06 mmol). The solution was stirred at ambient temperature for 18 hours. The mixture was treated with MeOH (0.25 mL) and sodium triacetoxyborohydride (41 mg, 0.19 mmol) and stirred for 3 days. The reaction was treated with sodium borohydride (10 mg) and stirred overnight at ambient temperature. The mixture was cooled to 0° C. and quenched by dropwise addition of 10% HCl until the mixture remained acidic (pH<2). This mixture was stirred for 1 hour, readjusted to pH 8-9 with saturated NaHCO$_3$ then diluted with Et$_2$O and water. After separation, the aqueous was washed twice with Et$_2$O. The combined organic layers were washed with water, saturated NaHCO$_3$, saturated NaCl, dried over Na$_2$SO$_4$ and concentrated in vacuo. The crude material was chromatographed on SiO$_2$ eluting with a gradient of hexane/ethyl acetate to give Compound 109 as colorless oil (2 mg, 7%). LCMS ESI (+) m/z (M+H) 476, 478; $^1$H NMR (400 MHz, CDCl$_3$): δ 8.06 (d, 1H), 7.05-7.02 (m, 1H), 6.97 (d, 1H), 6.91-6.90 (m, 1H), 6.76-6.72 (m, 1H), 4.25 (s, 2H), 2.57 (s, 3H).

Example 110

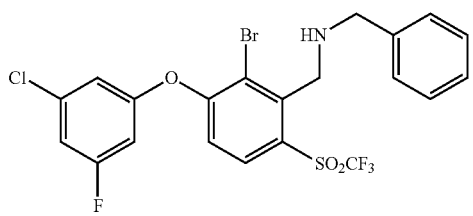

N-Benzyl-1-(2-bromo-3-(3-chloro-5-fluorophenoxy)-6-((trifluoromethyl)sulfonyl)phenyl)methanamine (Compound 110)

2-Bromo-3-(3-chloro-5-fluoro-phenoxy)-6-(trifluoromethylsulfonyl)benzaldehyde (44 mg, 0.10 mmol) [Compound 101] was dissolved in 1,2-dichloroethane (0.4 mL) and treated with benzylamine (11 µL, 0.10 mmol) and sodium triacetoxyborohydride (61 mg, 0.29 mmol). The solution was stirred at ambient temperature for 18 hours and the solvent was removed using a stream of nitrogen gas. The crude product was chromatographed on SiO$_2$ eluting with a gradient of ethyl acetate/hexane to give Compound 110 as a white solid (14.8 mg, 27%). LCMS ESI (+) m/z (M+H) 552, 554; $^1$H NMR (400 MHz, CDCl$_3$): δ 8.04 (d, 1H), 7.39-7.31 (m, 4H), 7.28-7.23 (m, 1H), 7.05-7.02 (m, 1H), 6.94 (d, 1H), 6.91-6.89 (m, 1H), 6.75-6.72 (m, 1H), 4.30 (s, 2H), 3.96 (s, 2H).

Example 111

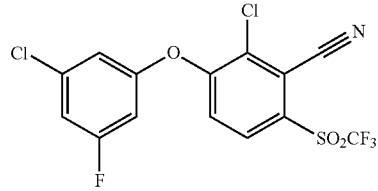

2-Chloro-3-(3-chloro-5-fluorophenoxy)-6-((trifluoromethyl)sulfonyl)benzonitrile Compound 111)

Step A: Preparation of 2-chloro-3-fluoro-6-mercaptobenzonitrile

2-Chloro-3,6-difluoro-benzonitrile (7.35 g, 42.4 mmol) in DMF (38 mL) was sparged with nitrogen gas for 5 minutes, cooled to 0° C., and treated with sodium sulfide (3.47 g, 44.5 mmol). The yellow suspension was stirred at 0° C. for 45 minutes. The reaction was diluted with methylene chloride and 1M NH$_4$OH. After separation, the aqueous was washed with methylene chloride. The aqueous was adjusted to pH 2 with 10% KHSO$_4$ then extracted twice with methylene chloride. The combined organics were washed with water, saturated NaCl, dried over Na$_2$SO$_4$ and concentrated in vacuo to light yellow oil (6.1 g, 75%).

Step B: Preparation of 2-chloro-3-fluoro-6-((trifluoromethyl)thio)benzonitrile

2-Chloro-3-fluoro-6-mercaptobenzonitrile (6.1 g, 32 mmol) was dissolved in DMF (42 mL) and treated with methyl viologen dichloride (0.42 g, 1.6 mmol). This suspension was cooled to −78° C. treated with triethylamine (11.3 mL, 81 mmol) then trifluoromethyliodide gas (5.2 g) was condensed into the solution. The reaction vessel was sealed and the mixture was warmed directly to ambient temperature and stirred for 14 hours. The reaction vessel was opened carefully then the volatile reagents were removed with vigorous nitrogen flow into the solution. The mixture was poured into saturated NaCl, diluted with Et$_2$O and separated. The aqueous phase was washed three times with Et$_2$O and the combined organic layers were washed with saturated NaCl, dried over Na$_2$SO$_4$ and concentrated in vacuo to dark oil (4.9 g). The crude product was chromatographed on SiO₂, eluting with a gradient of ethyl acetate/hexane. The desired product was obtained as a light yellow oil (3.0 g, 37%).

Step C: Preparation of 2-chloro-3-fluoro-6-((trifluoromethyl)sulfonyl)benzonitrile 2-Chloro-3-fluoro-6-((trifluoromethyl)thio)benzonitrile (0.38 g, 1.5 mmol) was dissolved in a mixture of MeCN, CCl₄ and water (volumn ratio 1:1:2, 15 mL) and ruthenium (III) chloride (9.1 mg, 0.04 mmol) was added. Sodium periodate (0.94 g, 4.4 mmol) was added in a single portion and the mixture was stirred at ambient temperature for 4 hours. The mixture was diluted with methylene chloride and filtered through a pad of celite. The filtrate was separated and the aqueous was washed with fresh methylene chloride. The combined extracts were passed through a pad of Florisil® (pre-wetted with methylene chloride). The pad was washed with methylene chloride then the combined colorless filtrates were gently concentrated in vacuo to a dark oil. The crude product was chromatographed on SiO₂, eluting with a gradient of ethyl acetate/hexane. The product was obtained as a light oil which formed a white solid on standing (145 mg, 33%).

Step D: Preparation of 2-chloro-3-(3-chloro-5-fluorophenoxy)-6-((trifluoromethyl)sulfonyl)benzonitrile 2-Chloro-3-fluoro-6-((trifluoromethyl)sulfonyl)benzonitrile (1.08 g, 3.75 mmol) was combined with sodium bicarbonate (573 mg, 6.82 mmol) in acetonitrile (10 mL) and the suspension was cooled to 0° C. 3-Chloro-5-fluoro-phenol (0.5 g, 3.4 mmol) was added to the suspension and the mixture was allowed to warm to ambient temperature and stirred for 60 hours. The reaction was diluted with 10% Na₂CO₃ and ethyl acetate then separated. The organic layer was washed three times with 10% Na₂CO₃, saturated NaHCO₃, dried over Na₂SO₄ and concentrated in vacuo. The crude material was chromatographed on SiO₂ eluting with a gradient of ethyl acetate/hexane to give Compound 111 as colorless oil (339 mg, 21%). LCMS ESI (+) m/z (M+NH₄) 431, 433; ¹H NMR (400 MHz, CDCl₃): δ 8.08 (d, 1H), 7.23 (d, 1H), 7.14-7.11 (m, 1H), 6.98-6.96 (m, 1H), 6.83-6.79 (m, 1H).

Example 112

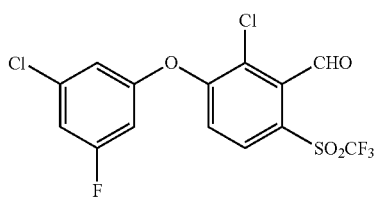

2-Chloro-3-(3-chloro-5-fluorophenoxy)-6-((trifluoromethyl)sulfonyl)benzaldehyde (Compound 112)

2-Chloro-3-(3-chloro-5-fluorophenoxy)-6-((trifluoromethyl)sulfonyl)benzonitrile [Compound 111] (339 mg, 0.82 mmol) was dissolved in dichloromethane (5 mL) and cooled to −20° C. The solution was treated dropwise with 1M diisobutylaluminum hydride in heptanes (0.9 mL, 0.9 mmol) and stirred at −20° C. for 90 minutes, then warmed to 0° C. and stirred for 90 minutes. The reaction was quenched at 0° C. by gradual addition of 10% HCl (ca. 3 mL) then the mixture was stirred at 0° C. for 30 minutes. The mixture was diluted with methylene chloride and water then separated. The aqueous was washed with methylene chloride and the combined organic layers were washed with water, one-half saturated NaHCO₃, dried over Na₂SO₄ and concentrated in vacuo. The crude material was chromatographed on SiO₂ eluting with a gradient of hexane/ethyl acetate. The early eluting product was collected and concentrated to give Compound 112 as a colorless oil (67 mg, 19%). ¹H NMR (400 MHz, CDCl₃): δ 10.43 (s, 1H), 7.96 (d, 1H), 7.15 (d, 1H), 7.09-7.07 (m, 1H), 6.95-6.94 (m, 1H), 6.80-6.77 (m, 1H).

Example 113

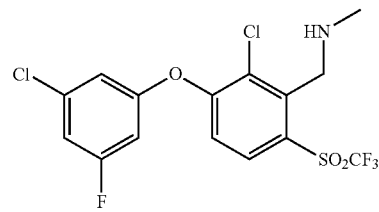

1-(2-Chloro-3-(3-chloro-5-fluorophenoxy)-6-((trifluoromethyl)sulfonyl)phenyl)-N-methylmethanamine (Compound 113)

2-Chloro-3-(3-chloro-5-fluorophenoxy)-6-((trifluoromethyl)sulfonyl)benzaldehyde [Compound 112] (20 mg, 0.05 mmol) was dissolved in 1,2-dichloroethane (0.15 mL) and treated with methylamine hydrochloride (3.6 mg, 0.05 mmol), N,N-diisopropylethylamine (9.2 µL, 0.05 mmol), and sodium triacetoxyborohydride (30 mg, 0.14 mmol). The solution was stirred at ambient temperature for 18 hours. The mixture was quenched with 10% HCl and stirred for 20 minutes. The acid was neutralized with saturated NaHCO₃, then the suspension was diluted with methylene chloride and water. After separation, the aqueous was washed twice with methylene chloride and the combined organic layers were washed with one-half saturated NaHCO₃, water, dried over Na₂SO₄ and concentrated in vacuo. The residue was chromatographed on SiO₂, eluting with a stepped gradient of hexane/ethyl acetate to give Compound 113 as a colorless oil (9 mg, 41%). LCMS ESI (+) m/z (M+H) 432, 434; ¹H NMR (400 MHz, CDCl₃): δ 8.02 (d, 1H), 7.05-7.02 (m, 1H), 7.01 (d, 1H), 6.91-6.90 (m, 1H), 6.76-6.72 (m, 1H), 4.22 (s, 2H), 2.56 (s, 3H).

Example 114

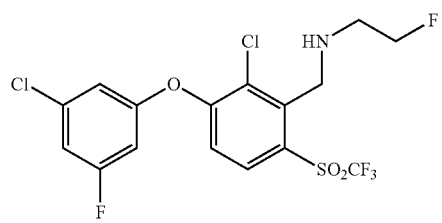

N-(2-Chloro-3-(3-chloro-5-fluorophenoxy)-6-((trifluoromethyl)sulfonyl)benzyl)-2-fluoroethan-1-amine (Compound 114)

2-Chloro-3-(3-chloro-5-fluorophenoxy)-6-((trifluoromethyl)sulfonyl)benzaldehyde [Compound 112] (20 mg, 0.05 mmol) was dissolved in 1,2-dichloroethane (0.15 mL) and treated with 2-fluoroethylamine hydrochloride (5.2 µL, 0.05 mmol) and sodium triacetoxyborohydride (30 mg, 0.14 mmol). The solution was stirred at ambient temperature for 18 hours. The mixture was quenched with 10% HCl and stirred for 20 minutes. The acid was neutralized with saturated NaHCO$_3$ then diluted with methylene chloride and water. After separation, the aqueous was washed twice with methylene chloride and the combined organic layers were washed with one-half saturated NaHCO$_3$, water, dried over Na$_2$SO$_4$ and concentrated in vacuo. The residue was chromatographed on SiO$_2$, eluting with a stepped gradient of hexane/ethyl acetate to give Compound 114 as a colorless oil (5.9 mg, 25%). LCMS ESI (+) m/z (M+H) 464, 466; $^1$H NMR (400 MHz, CDCl$_3$): δ 8.02 (d, 1H), 7.06-7.03 (m, 1H), 7.01 (d, 1H), 6.92 (m, 1H), 6.77-6.73 (m, 1H), 4.64 (t, 1H), 4.52 (t, 1H), 4.34 (s, 2H), 3.11-3.09 (m, 1H), 3.04-3.02 (m, 1H).

Example 115

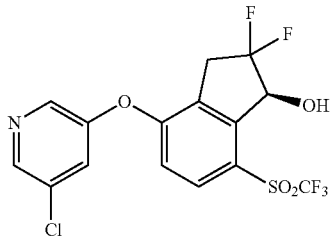

(S)-4-((5-Chloropyridin-3-yl)oxy)-2,2-difluoro-7-(methylsulfonyl)-2,3-dihydro-1H-inden-1-ol (Compound 115)

Step A: Preparation of 4-((5-chloropyridin-3-yl)oxy)-7-(methylsulfonyl)-2,3-dihydro-1H-inden-1-one 3-Chloro-5-((7-(methylsulfonyl)-2,3-dihydrospiro[indene-1,2'-[1,3]dioxolan]-4-yl)oxy)pyridine [Prepared similarly as described in Example 8, Step B utilizing 3-chloro-5-hydroxypyridine.] (340 mg, 0.89 mmol) was dissolved in 6:1 acetone/water (4.4 mL) and treated with pyridinium p-toluenesulfonate (22.4 mg, 0.090 mmol). The mixture was heated to 82° C. in a sealed bottle for 18 hours. The reaction was cooled and concentrated in a stream of nitrogen gas. The resulting solid was redissolved in ethyl acetate and the organic phase was washed twice with saturated NaHCO$_3$, saturated NaCl, dried over Na$_2$SO$_4$ and concentrated in vacuo to a white solid (300 mg, quant.).

Step B: Preparation of (E,Z)—N-butyl-4-((5-chloropyridin-3-yl)oxy)-7-(methylsulfonyl)-2,3-dihydro-1H-inden-1-imine 4-((5-Chloropyridin-3-yl)oxy)-7-(methylsulfonyl)-2,3-dihydro-1H-inden-1-one (300 mg, 0.89 mmol) was dissolved in benzene (10 mL) and treated with butylamine (1.67 mL, 16.9 mmol) and trifluoroacetic acid (0.03 mL, 0.44 mmol) then the mixture was refluxed through a Dean-Stark trap for 2.5 hours. The progress of the reaction was followed by $^1$H NMR. The reaction mixture was cooled and concentrated in vacuo. The residue was redissolved in ethyl acetate and saturated NaHCO$_3$ then separated. The organic layer was washed with saturated NaHCO$_3$, saturated NaCl, dried over Na$_2$SO$_4$ and concentrated in vacuo to a sticky residue (355 mg). $^1$H NMR of this material showed both imine isomers were present.

Step C: Preparation of 4-((5-chloropyr, quant.idin-3-yl)oxy)-2,2-difluoro-7-(methylsulfonyl)-2,3-dihydro-1H-inden-1-one (E,Z)—N-butyl-4-((5-chloropyridin-3-yl)oxy)-7-(methylsulfonyl)-2,3-dihydro-1H-inden-1-imine (150 mg, 0.38 mmol) was treated with sodium sulfate (542 mg, 3.8 mmol) then dissolved in dry MeCN (4.8 mL). The suspension was treated with Selectfluor® (338 mg, 0.95 mmol). The flask and condenser were flushed with argon and heated to 82° C. for 5.5 hours under argon then stirred for 9 hours at ambient temperature. The mixture was treated with concentrated hydrochloric acid (0.95 mL, 11.4 mmol) and stirred for 20 minutes at ambient temperature. The whole mixture was concentrated in vacuo to remove volatile solvents. The resulting suspension was diluted with ethyl acetate and water then separated. The organic layer was washed with water, saturated NaHCO$_3$, saturated NaCl, dried over Na$_2$SO$_4$ and concentrated in vacuo to a solid. The crude material was purified on SiO$_2$ eluting with a gradient of ethyl acetate/hexane. The desired material was collected and concentrated to a white solid (91 mg, 63%).

Step D: Preparation of (S)-4-((5-chloropyridin-3-yl)oxy)-2,2-difluoro-7-(methylsulfonyl)-2,3-dihydro-1H-inden-1-ol 4-((5-Chloropyridin-3-yl)oxy)-2,2-difluoro-7-(methylsulfonyl)-2,3-dihydro-1H-inden-1-one (89 mg, 0.24 mmol) was dissolved in methylene chloride (1.1 mL), treated with triethylamine (0.07 mL, 0.48 mmol) and formic acid (0.03 mL, 0.7 mmol) then cooled to 0° C. The solution was treated with a cold solution of RuCl(p-cymene)[(R,R)-Ts-DPEN] (1.5 mg) dissolved in methylene chloride (1.1 mL). The reaction mixture was transferred to the refrigerator and allowed to stand at 4° C. for 60 hours. The mixture was concentrated in vacuo and chromatographed on SiO$_2$ eluting with a gradient of ethyl acetate/hexane. The product was concentrated in vacuo to a colorless oil. The oil was dissolved in methylene chloride and hexane and re-concentrated to give Compound 115 as a white solid (64 mg, 70%). The stereopurity was >95% ee, as determined by Mosher ester analysis. LCMS ESI (+) m/z (M+H) 376, 378; $^1$H NMR (400 MHz, CDCl$_3$): δ 8.50-8.49 (m, 1H), 8.36-8.35 (m, 1H), 7.89 (d, 1H), 7.43 (t, 1H), 6.93 (d, 1H), 5.62-5.58 (m, 1H), 3.62-3.40 (m, 3H), 3.22 (s, 3H).

Example 116

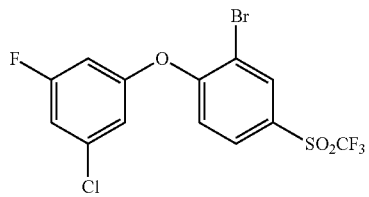

2-Bromo-1-(3-chloro-5-fluorophenoxy)-4-((trifluoromethyl)sulfonyl)benzene (Compound 116)

Step A: Preparation of (3-bromo-4-fluorophenyl)(trifluoromethyl)sulfane

Trifluoromethyliodide (2.84 g, 14.5 mmol) was condensed into a solution containing 3-bromo-4-fluorobenzenethiol (1.00 g, 4.8 mmol), methyl viologen dichloride (118 mg, 0.48 mmol) and Et$_3$N (1.68 mL, 12.1 mmol) in DMF (6.4 mL) at −78° C. The sealed tube was quickly capped with a threaded Teflon cap and tightly sealed. The reaction mixture was then warmed to room temperature and stirred for 39 hours. The reaction mixture was cooled to −78° C. and opened carefully, poured into brine (20 mL), extracted with Et$_2$O (5×40 mL), washed with brine (20 mL), dried (Na$_2$SO$_4$) and concentrated in vacuo. The crude product was purified on silica gel (50 g SNAP, 16 CV, 1-20% EtOAc/hexanes) affording (3-bromo-4-fluorophenyl)(trifluoromethyl)sulfane (1.2 g, 90% yield) as a clear, colorless oil.

Step B: Preparation of 2-bromo-1-fluoro-4-((trifluoromethyl)sulfonyl)benzene

Sodium periodate (2.80 g, 13.1 mmol) was added all at once to (3-bromo-4-fluorophenyl)(trifluoromethyl)sulfane (1.20 g, 4.4 mmol) and RuCl$_3$ (22.6 mg, 0.11 mmol) in MeCN (10 mL)/CCl$_4$ (10 mL)/H$_2$O (20 mL) at room temperature and stirred for 2 hours. The reaction mixture was extracted with EtOAc (3×50 mL), washed with brine (30 mL), dried (Na$_2$SO$_4$), filtered and concentrated in vacuo. The crude product was purified on silica gel (25 g SNAP, 14 CV, 2-20% EtOAc/hexane) affording 2-bromo-1-fluoro-4-((trifluoromethyl)sulfonyl)benzene (1.14 g, 85%) as a clear, colorless oil which became a white solid upon standing.

Step C: Preparation of 2-bromo-1-(3-chloro-5-fluorophenoxy)-4-((trifluoromethyl)sulfonyl)benzene (Compound 116)

Cesium carbonate (358 mg, 1.1 mmol) was added all at once to 2-bromo-1-fluoro-4-((trifluoromethyl)sulfonyl)benzene (307 mg, 1.0 mmol) and 3-chloro-5-fluorophenol (161 mg, 1.1 mmol) in NMP (3.0 mL) then warmed to 50° C. and stirred for 1.5 hours. The mixture was cooled to room temperature and purified directly on reverse phase silica gel (25+M, 14 CV, 20-100% MeCN/water) affording Compound 116 (389 mg, 90% yield) as a white solid. LCMS ESI (−) m/z 431 (M−H). $^1$H-NMR (400 MHz, CDCl$_3$): δ 8.30 (d, 1H), 7.93 (m, 1H), 7.08-7.02 (m, 2H), 6.93-6.91 (m, 1H), 6.78-6.74 (m, 1H).

Example 117

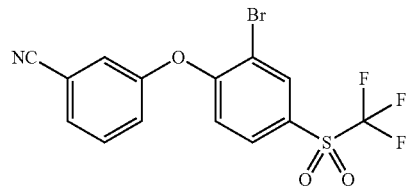 [SMILES: N#Cc1cccc(Oc2ccc(S(=O)(=O)C(F)(F)F)cc2Br)c1]

3-(2-Bromo-4-((trifluoromethyl)sulfonyl)phenoxy)benzonitrile (Compound 117)

Cesium carbonate (38.0 mg, 0.12 mmol) was added to 2-bromo-1-fluoro-4-((trifluoromethyl)sulfonyl)benzene (30.0 mg, 0.10 mmol) and 3-hydroxybenzonitrile (14.0 mg, 0.12 mmol) in NMP (0.5 mL) and then warmed to 50° C. for 5 hours. Purified directly on reverse phase silica gel (12+M, 14 CV) eluting with 20-100% MeCN/water affording Compound 117 (35.6 mg, 0.09 mmol, 90% yield) as a white oil. LCMS ESI (−) m/z 404 (M−H).

Example 118

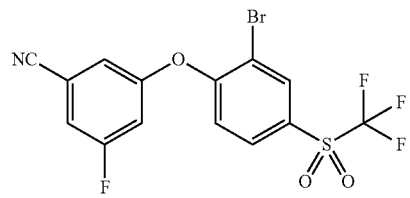 [SMILES: N#Cc1cc(F)cc(Oc2ccc(S(=O)(=O)C(F)(F)F)cc2Br)c1]

3-(2-Bromo-4-((trifluoromethyl)sulfonyl)phenoxy)-5-fluorobenzonitrile (Compound 118)

Cesium carbonate (46.0 mg, 0.14 mmol) was added all at once to 2-bromo-1-fluoro-4-((trifluoromethyl)sulfonyl)benzene (40.0 mg, 0.13 mmol) and 3-fluoro-5-hydroxybenzonitrile (20.0 mg, 0.14 mmol) in NMP (0.5 mL) and then warmed to 50° C. and stirred for 1.5 hours. The reaction mixture was cooled to room temperature and purified directly on reverse phase silica gel (12+M, 14 CV, 30-100% MeCN/water) affording Compound 118 (50 mg, 0.12 mmol, 91% yield) as a white solid. LCMS ESI (−) m/z 422 (M−H).

Example 119

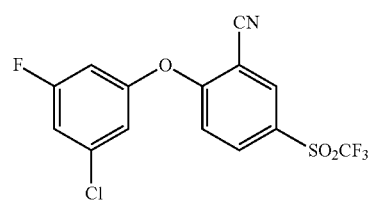

2-(3-Chloro-5-fluorophenoxy)-5-((trifluoromethyl)sulfonyl)benzonitrile (Compound 119)

Pd(PPh$_3$)$_4$ (14.4 mg, 0.013 mmol) was added all at once to Zn(CN)$_2$ (8.8 mg, 0.08 mmol) and 2-bromo-1-(3-chloro-5-fluorophenoxy)-4-((trifluoromethyl)sulfonyl)benzene (54.0 mg, 0.13 mmol) in NMP (1.0 mL) under nitrogen then evacuated and back-filled with nitrogen five times. The reaction mixture was then warmed to 100° C. for 4 hours. The reaction mixture was cooled to room temperature, diluted with water (5 mL), extracted with Et$_2$O (4×10 mL), washed with brine (10 mL), dried (Na$_2$SO$_4$), filtered and concentrated in vacuo. The crude product was purified on silica gel (10 g SNAP, 14 CV) eluting with 1-24% EtOAc/hexane affording Compound 119 (28.4 mg, 0.08 mmol, 60%) as a clear oil. LCMS ESI (−) m/z 379 (M−H); $^1$H-NMR (400 MHz, CDCl$_3$): δ 8.35 (d, 1H), 8.13 (m, 1H), 7.16-7.13 (m, 1H), 7.11 (d, 1H), 7.03-7.01 (m, 1H), 6.88-6.85 (m, 1H).

Example 120

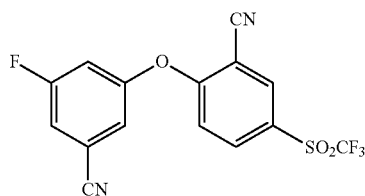

2-(3-Cyano-5-fluorophenoxy)-5-((trifluoromethyl)sulfonyl)benzonitrile (Compound 120)

Tetrakis(triphenylphosphine)palladium(0) (12.8 mg, 0.01 mmol) was added all at once to Zn(CN)$_2$ (7.8 mg, 0.07 mmol) and 3-(2-bromo-4-((trifluoromethyl)sulfonyl)phenoxy)-5-fluorobenzonitrile (47 mg, 0.11 mmol) in NMP (1.0 mL) under nitrogen then evacuated and back-filled with nitrogen five times. The reaction mixture was then warmed to 100° C. for 6 hours. The reaction mixture was cooled to room temperature, diluted with water (5 mL), extracted with Et$_2$O (4×10 mL), washed with brine (10 mL), dried (Na$_2$SO$_4$), filtered and concentrated in vacuo. The crude product was purified on reverse phase silica gel (12+M, 20-100% MeCN/water, 14 CV) then silica gel (10 g SNAP, 5-40% EtOAc/hexane, 14 CV) affording Compound 120 (10 mg, 0.03 mmol, 24% yield) as a clear oil that formed a white solid upon standing. LCMS ESI (−) m/z 369 (M−H).

Example 121

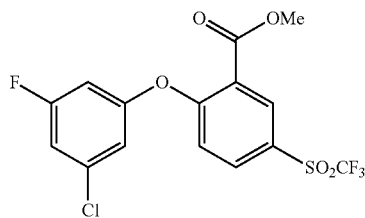

Methyl 2-(3-chloro-5-fluorophenoxy)-5-((trifluoromethyl)sulfonyl)benzoate (Compound 121)

Triethylamine (106 µL, 0.76 mmol) was added dropwise to a mixture of 2-bromo-1-(3-chloro-5-fluorophenoxy)-4-((trifluoromethyl)sulfonyl)benzene (110 mg, 0.25 mmol), Pd(OAc)$_2$ (5.7 mg, 0.025 mmol) and 1,3-bis(diphenylphosphino)propane (10.5 mg, 0.025 mmol) in DMF (1.5 mL) and MeOH (1.0 mL) that had been saturated with carbon monoxide. The reaction mixture was then warmed to 80° C. under a balloon of carbon monoxide for 3.5 hours. The reaction mixture was cooled to room temperature and directly purified on reverse phase silica gel (25+M, 20-100% MeCN/water, 16 CV) affording Compound 121 (47 mg, 45% yield) as a clear, colorless oil. LCMS ESI (−) m/z 411 (M−H); $^1$H NMR (400 MHz, CDCl$_3$): δ 8.58 (d, 1H), 8.10-8.07 (m, 1H), 7.14 (d, 1H), 7.03-7.00 (m, 1H), 6.91-6.90 (m, 1H), 6.77-6.73 (m, 1H), 3.94 (s, 3H).

Example 122

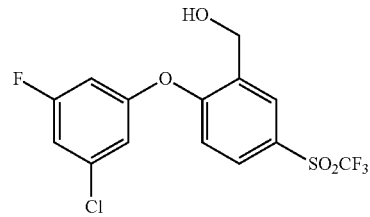

(2-(3-Chloro-5-fluorophenoxy)-5-((trifluoromethyl)sulfonyl)phenyl)methanol (Compound 122)

DIBAL (1 M in heptanes, 174 µL, 0.17 mmol) was added dropwise to methyl 2-(3-chloro-5-fluorophenoxy)-5-((trifluoromethyl)sulfonyl)benzoate (24 mg, 0.06 mmol) in CH$_2$Cl$_2$ (0.5 mL) at 0° C. and stirred for 1 hour. Excess DIBAL was quenched by the careful addition of acetone (0.5 mL). The mixture was diluted with water (2 mL), extracted with dichloromethane (3×5 mL), washed with brine (5 mL), dried (Na$_2$SO$_4$), filtered and concentrated. The crude product was purified on silica gel (10 g SNAP, 14 CV, 20-55% EtOAc/hexane) affording Compound 122 (16 mg, 0.04 mmol, 72% yield) as a clear oil. LCMS ESI (−) m/z 383 (M−H).

Example 123

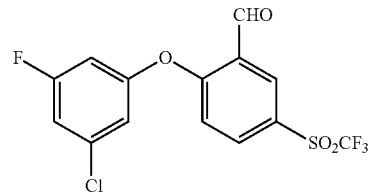

2-(3-Chloro-5-fluorophenoxy)-5-((trifluoromethyl)sulfonyl)benzaldehyde (Compound 123)

Dess-Martin periodinane (20 mg, 0.05 mmol, 1.5 equivalent) was added all at once to (2-(3-chloro-5-fluorophenoxy)-5-((trifluoromethyl)sulfonyl)phenyl)methanol (12 mg, 0.03 mmol, 1.0 equiv) dissolved in ice cold CH$_2$Cl$_2$ (0.5 mL) and stirred for 40 minutes. The reaction was quenched with 1:1 saturated NaHCO$_3$/Na$_2$S$_2$O$_3$ (2 mL), extracted with CH$_2$Cl$_2$ (2×5 mL), dried (Na$_2$SO$_4$), filtered and concentrated. The residue was purified on silica gel (10 g SNAP, 14 CV, 7-60% EtOAc/hexane) affording Compound 123 (11 mg, 92% yield) as a clear oil.

Example 124

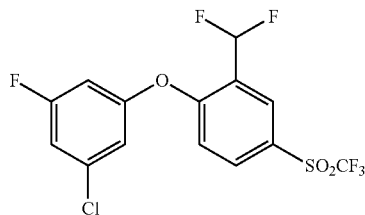

1-(3-Chloro-5-fluorophenoxy)-2-(difluoromethyl)-4-((trifluoromethyl)sulfonyl)benzene (Compound 124)

(Diethylamino)sulfur trifluoride (10 mg, 0.08 mmol) was added to 2-(3-chloro-5-fluorophenoxy)-5-((trifluoromethyl)sulfonyl)benzaldehyde (5.0 mg, 0.01 mmol) in dichloromethane (0.2 mL) at room temperature and stirred for 4.5 days in a sealed flask. The reaction was quenched with saturated NaHCO$_3$ (1 mL), extracted with MTBE (3×3 mL), washed with brine (3 mL), dried (MgSO$_4$), filtered and concentrated. The crude product was purified on silica gel (10 g SNAP, 14 CV, 2-20% EtOAc/hexane) affording Compound 124 (4.0 mg, 0.01 mmol, 75% yield) as a clear oil. $^1$HNMR (400 MHz, CDCl$_3$): δ 8.35-8.34 (m, 1H), 8.09-8.05 (m, 1H), 7.17-6.90 (m, 4H), 6.82-6.78 (m, 1H).

Example 125

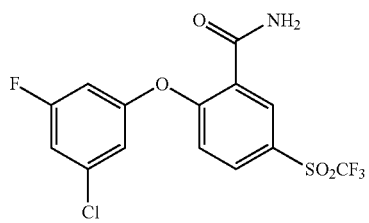

2-(3-Chloro-5-fluorophenoxy)-5-((trifluoromethyl)sulfonyl)benzamide (Compound 125)

Step A: Preparation of 2-(3-chloro-5-fluorophenoxy)-5-((trifluoromethyl)sulfonyl)benzoic acid Lithium hydroxide monohydrate (46 mg, 1.1 mmol, 10 equivalent) added all at once to methyl 2-(3-chloro-5-fluorophenoxy)-5-((trifluoromethyl)sulfonyl)benzoate (45 mg, 0.11 mmol, 1.0 equiv) in 4:1 THF/water (1.25 mL) and stirred at room temperature for 6 hours. The mixture was diluted with 4 N HCl (4 mL), extracted with EtOAc (3×10 mL), washed with brine (10 mL), dried (MgSO$_4$), filtered and concentrated. The residue was purified on reverse phase column (12+M, 14 CV, 20-100% MeCN/water) to afford 2-(3-chloro-5-fluorophenoxy)-5-((trifluoromethyl)sulfonyl)benzoic acid (27.8 mg, 64% yield) as a sticky white foam.

Step B: Preparation of 2-(3-chloro-5-fluorophenoxy)-5-((trifluoromethyl)sulfonyl)benzamide (Compound 125)

N-[(Dimethylamino)-1H-1,2,3-triazolo-[4,5-b]pyridin-1-ylmethylene]-N-methylmethanaminium hexafluorophosphate N-oxide, (HATU) (42.0 mg, 0.11 mmol) was added all at once to a solution of 2-(3-chloro-5-fluorophenoxy)-5-((trifluoromethyl)sulfonyl)benzoic acid (22.0 mg, 0.055 mmol), NH$_4$Cl (6.0 mg, 0.11 mmol) and N,N-diisopropylethylamine (29 µL, 0.165 mmol) in DMF (0.5 mL) at room temperature then stirred for 16 hours in a sealed reaction vial. Purification directly on reverse phase column (12+M, 14 CV, 20-100% MeCN/water) affording Compound 125 (15.4 mg, 70% yield). LCMS ESI (−) m/z 396 (M−H); $^1$H-NMR (400 MHz, CDCl$_3$): δ 8.95 (d, 1H), 8.07-8.04 (m, 1H), 7.21 (br s, 1H), 7.15-7.12 (m, 1H), 7.05 (d, 1H), 7.02-7.01 (m, 1H), 6.86-6.83 (m, 1H), 6.01 (br s, 1H).

Example 126

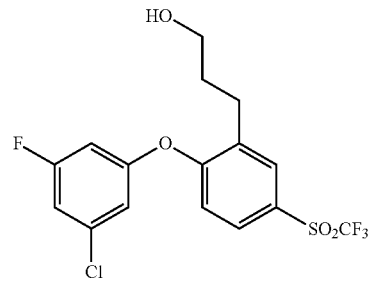

3-[2-(3-Chloro-5-fluoro-phenoxy)-5-(trifluoromethylsulfonyl)phenyl]propan-1-ol (Compound 126)

Step A: Preparation of 2-allyl-1-(3-chloro-5-fluorophenoxy)-4-(trifluoromethylsulfonyl)benzene Allyl(tributyl)stannane (0.13 mL, 0.43 mmol) was added by syringe to a degassed mixture of 2-bromo-1-(3-chloro-5-fluoro-phenoxy)-4-(trifluoromethylsulfonyl)benzene (116 mg, 0.27 mmol) and tetrakis(triphenylphosphine)palladium (0) (30.9 mg, 0.03 mmol) in DMF (2 mL) at room temperature to a microwave vial equipped with a septum under nitrogen. The septa was quickly replaced with a microwave cap and sealed under a blanket of nitrogen. The reaction mixture was then warmed to 160° C. for 30 minutes in a microwave reactor. After cooling to room temperature, the mixture was filtered through Celite, washed with MTBE (10 mL) then stirred with saturated KF (10 mL) for 30 minutes. The phases were separated, the aqueous extracted with MTBE (3×10 mL), then the combined organics were washed with brine (20 mL), dried (Na$_2$SO$_4$), filtered and concentrated in vacuo. The crude product was purified on silica gel (10 g SNAP, 14 CV, 0-25% EtOAc/hexane) affording 2-allyl-1-(3-chloro-5-fluoro-phenoxy)-4-(trifluoromethylsulfonyl)benzene (95 mg, 0.24 mmol, 90% yield) as a clear oil.

Step B: Preparation of 3-[2-(3-chloro-5-fluoro-phenoxy)-5-(trifluoromethylsulfonyl)phenyl]propan-1-ol (Compound 126)

9-Borabicyclo[3.3.1]nonane (0.4 M in THF, 0.25 mL, 0.10 mmol) was added dropwise to 2-allyl-1-(3-chloro-5-fluoro-phenoxy)-4-(trifluoromethylsulfonyl)benzene (26.0 mg, 0.07 mmol) in tetrahydrofuran (0.50 mL) at room temperature and stirred for 18 hours. The reaction mixture was cooled to −10° C. followed by the addition of 1 N NaOH (1 mL) and 30% $H_2O_2$ (100 µL) and stirred for 1 hour. The reaction was extracted with EtOAc (3×5 mL), washed with brine (5 mL), dried ($Na_2SO_4$), filtered and concentrated in vacuo. The crude product was purified on silica gel (10 g SNAP, 14 CV, 12-100% EtOAc/hexane) affording Compound 126 (6.0 mg, 0.015 mmol, 22% yield) as a colorless oil. LCMS ESI (−) m/z 457 (M+$HCO_2^-$); $^1$H-NMR (400 MHz, $CDCl_3$): δ 7.96 (d, 1H), 7.84 (m, 1H), 7.02-6.98 (m, 2H), 6.88-6.87 (m, 1H), 6.73-6.69 (m, 1H), 3.74-3.60 (m, 2H), 2.91-2.87 (m, 2H), 1.97-1.90 (m, 2H), 1.40-1.37 (m, 1H).

Example 127

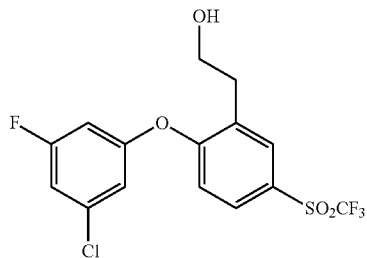

2-[2-(3-Chloro-5-fluoro-phenoxy)-5-(trifluoromethylsulfonyl)phenyl]ethanol (Compound 127)

Step A: Preparation of 1-(3-chloro-5-fluoro-phenoxy)-4-(trifluoromethylsulfonyl)-2-vinyl-benzene Tributyl(vinyl)stannane (0.05 mL, 0.17 mmol) was added to a degassed mixture of 2-bromo-1-(3-chloro-5-fluoro-phenoxy)-4-(trifluoromethylsulfonyl)benzene (64 mg, 0.15 mmol) and tetrakis(triphenylphosphine)palladium(0) (17 mg, 0.01 mmol) in DMF (1 mL) in a microwave vial at room temperature under nitrogen. The septum was quickly replaced with a crimp cap and the reaction vial was sealed. The reaction mixture was then warmed to 160° C. for 45 minutes in a microwave reactor. The crude mixture was purified directly on reverse phase column (25+M, 14 CV, 20-100% MeCN/water) affording 1-(3-chloro-5-fluoro-phenoxy)-4-(trifluoromethylsulfonyl)-2-vinyl-benzene (40 mg, 0.1 mmol, 67% yield) as a yellow oil.

Step B: Preparation of 2-[2-(3-chloro-5-fluoro-phenoxy)-5-(trifluoromethylsulfonyl)phenyl]ethanol (Compound 127)

9-Borabicyclo[3.3.1]nonane (0.4 M in THF, 0.8 mL, 0.32 mmol) was added dropwise to 1-(3-chloro-5-fluoro-phenoxy)-4-(trifluoromethylsulfonyl)-2-vinyl-benzene (38.0 mg, 0.10 mmol) in tetrahydrofuran (0.20 mL) at room temperature. The reaction mixture was stirred for 20 hours. The reaction mixture was then added carefully to ice water (10 mL), MTBE (10 mL), 3 N NaOH (0.5 mL) and 30% $H_2O_2$ (100 µL) and stirred for 30 minutes. The mixture was extracted with MTBE (3×10 mL), washed with brine (20 mL), dried over $MgSO_4$, filtered and concentrated. The crude product was purified on silica gel (10 g SNAP, 14 CV, 2-40% EtOAc/hexane) affording Compound 127 (9.0 mg, 0.02 mmol, 22% yield) as a clear, colorless oil. LCMS ESI (−) m/z 397 (M−H); $^1$H-NMR (400 MHz, $CDCl_3$): δ 8.02 (d, 1H), 7.86 (m, 1H), 7.02-6.99 (m, 2H), 6.89-6.87 (m, 1H), 6.74-6.70 (m, 1H), 3.98-3.93 (m, 2H), 3.06 (t, 2H), 1.50-1.47 (m, 1H).

Example 128

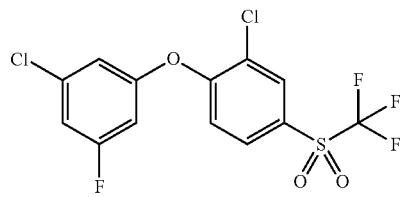 [SMILES: O=S(=O)(c1ccc(Oc2cc(F)cc(Cl)c2)c(Cl)c1)C(F)(F)F]

2-Chloro-1-(3-chloro-5-fluorophenoxy)-4-((trifluoromethyl)sulfonyl)benzene (Compound 128)

Step A: Preparation of (3-chloro-4-fluorophenyl)(trifluoromethyl)sulfane

Trifluoromethyliodide (2.17 g, 11.1 mmol) was condensed into a solution of 3-chloro-4-fluorobenzenethiol (0.6 g, 3.7 mmol, 1.0 equiv), methyl viologen dichloride (95 mg, 0.37 mmol, 0.1 equiv) and $Et_3N$ (1.3 mL, 9.2 mmol, 2.5 equiv) in DMF (5.0 mL) at −78° C. The septum was quickly replaced with a threaded Teflon cap and tightly sealed. The reaction mixture was then warmed to room temperature and stirred for 60 hours. The reaction mixture was cooled to −78° C. and opened carefully, poured into brine (20 mL), extracted with $Et_2O$ (5×20 mL), washed with brine (20 mL), dried ($Na_2SO_4$) and concentrated in vacuo using a low temperature water bath. The crude product was purified on silica gel (25 g SNAP, 14 CV, 1-10% EtOAc/hexane) affording (3-chloro-4-fluorophenyl)(trifluoromethyl)sulfane (600 mg) as a clear, colourless oil which was used in the next reaction immediately.

Step B: Preparation of 2-bromo-1-fluoro-4-((trifluoromethyl)sulfonyl)benzene Sodium periodate (1.80 g, 8.4 mmol, 3.23 equiv) was added all at once to (3-chloro-4-fluorophenyl)(trifluoromethyl)sulfane (600 mg, 2.6 mmol, 1.0 equiv) and $RuCl_3$ (13.5 mg, 0.065 mmol, 0.025 equiv) in MeCN (6 mL)/$CCl_4$ (6 mL)/$H_2O$ (12 mL) at room temperature and stirred for 2 hours. The reaction mixture was filtered, the filter cake rinsed with $CH_2Cl_2$ (30 mL), then extracted with $CH_2Cl_2$ (3×30 mL), washed with brine (20 mL), dried ($Na_2SO_4$), filtered and concentrated in vacuo. The crude product was purified on silica gel (25 g SNAP, 14 CV) eluting with 1-20% EtOAc/hexane affording 2-bromo-1-fluoro-4-((trifluoromethyl)sulfonyl)benzene (530 mg, 55% yield over 2 steps) as a clear, colorless oil which turned into a white solid upon cooling to −78° C.

Step C: Preparation of 2-chloro-1-(3-chloro-5-fluorophenoxy)-4-((trifluoromethyl)sulfonyl)benzene (Compound 128)

Cesium carbonate (41.0 mg, 0.126 mmol) was added all at once to 2-chloro-1-fluoro-4-((trifluoromethyl)sulfonyl)benzene (30.0 mg, 0.11 mmol) and 3-fluoro-5-chlorophenol (18.0 mg, 0.13 mmol) in NMP (0.5 mL) then warmed to 50° C. and stirred for 1.5 hours. After cooling to room temperature, the mixture was purified directly on reverse phase column (12+M, 14 CV, 30-100% MeCN/water) affording Compound 128 (41.6 mg, 0.13 mmol, 94% yield) as a clear oil. LCMS ESI (−) m/z 387 (M−H).

Example 129

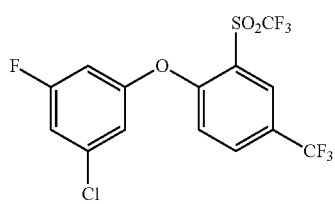

1-(3-Chloro-5-fluorophenoxy)-4-(trifluoromethyl)-2-((trifluoromethyl)sulfonyl)benzene (Compound 129)

Step A: Preparation of (2-chloro-5-(trifluoromethyl)phenyl)(trifluoromethyl)sulfane To a pressure vessel equipped with a septum, stir bar and methyl viologen dichloride (60 mg, 0.24 mmol, 0.1 equiv) under Ar was added DMF (3.0 mL), 2-chloro-5-(trifluoromethyl)benzenethiol (500 mg, 2.4 mmol, 1.0 equiv) and Et$_3$N (819 μL, 5.9 mmol, 2.5 equiv) at room temperature. The reaction mixture was then cooled to −78° C. where CF$_3$I (1.38 g, 7.1 mmol) was added through tygon tubing equipped with a needle along the cooled wall of the vessel (vented to a bubbler). The septum was then quickly replaced with a threaded Teflon cap and the reaction vessel was tightly sealed and warmed to room temperature where it was stirred for 18 hours. The reaction mixture was cooled to −78° C. and opened carefully. The contents of the vessel were then poured into water (10 mL), extracted with Et$_2$O (5×10 mL), washed with brine (20 mL), dried (Na$_2$SO$_4$), filtered and concentrated. The crude product was purified on silica gel (25 g SNAP, 14 CV) eluting with 5-40% EtOAc/hexane affording (2-chloro-5-(trifluoromethyl)phenyl)(trifluoromethyl)sulfane (450 mg, 68% yield) as a pale yellow liquid.

Step B: Preparation of 1-chloro-4-(trifluoromethyl)-2-((trifluoromethyl)sulfonyl)benzene Sodium periodate (1.03 g, 4.8 mmol, 3.0 equiv) was added all at once to (2-chloro-5-(trifluoromethyl)phenyl)(trifluoromethyl)sulfone (450 mg, 1.6 mmol, 1.0 equiv) and RuCl$_3$ (3.3 mg, 0.02 mmol, 0.01 equiv) in 1/1/2 MeCN/CCl$_4$/H$_2$O (8 mL) at room temperature and stirred vigorously for 15 hours. The reaction mixture was diluted with water (20 mL), extracted with CH$_2$Cl$_2$ (3×20 mL), washed with brine (20 mL), dried (Na$_2$SO$_4$), filtered and concentrated. The crude product was purified on silica gel (10 g SNAP, 14 CV) eluting with 2-30% EtOAc/hexane affording 1-chloro-4-(trifluoromethyl)-2-((trifluoromethyl)sulfonyl)benzene (426 mg, 85% yield) as a white solid.

Step C: Preparation of 1-(3-chloro-5-fluorophenoxy)-4-(trifluoromethyl)-2-((trifluoromethyl)sulfonyl)benzene (Compound 129)

Potassium carbonate (31 mg, 0.221 mmol, 1.5 equiv) was added to 1-chloro-4-(trifluoromethyl)-2-((trifluoromethyl)sulfonyl)benzene (46 mg, 0.147 mmol, 1.0 equiv) and 3-chloro-5-fluorophenol (32 mg, 0.221 mmol, 1.5 equiv) in benzene (2.0 mL) then warmed to reflux overnight. The reaction was cooled to room temperature and concentrated in vacuo. Purification on reverse phase column (12+M, 14 CV, 30-100% MeCN/water) yielded Compound 129 (39.4 mg, 63% yield) as a white solid. LCMS ESI (−) m/z 421 (M−H); $^1$H-NMR (400 MHz, CDCl$_3$): δ 8.39-8.38 (m, 1H), 7.98-7.95 (m, 1H), 7.15 (d, 1H), 7.08-7.05 (m, 1H), 6.95-6.94 (m, 1H), 6.80-6.77 (m, 1H).

Example 130

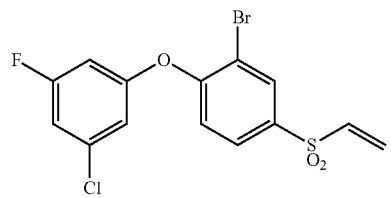 [SMILES: C=CS(=O)(=O)c1ccc(Oc2cc(F)cc(Cl)c2)c(Br)c1]

2-Bromo-1-(3-chloro-5-fluorophenoxy)-4-(vinylsulfonyl)benzene (Compound 130)

Step A: Preparation of 2-((3-bromo-4-fluorophenyl)thio)ethyl acetate

Sodium bicarbonate (609 mg, 7.24 mmol, 3.0 equiv) was added all at once to 3-bromo-4-fluorobenzenethiol (500 mg, 2.42 mmol, 1.0 equiv) and 2-bromoethyl acetate (807 mg, 4.83 mmol, 2.0 equiv) in 1:1 dioxane/water (14.0 mL) at room temperature then stirred for 62 hours under nitrogen. The reaction mixture was diluted with water (20 mL), extracted with EtOAc (3×25 mL), washed with brine (25 mL), dried (MgSO$_4$), filtered and concentrated. Crude 2-((3-bromo-4-fluorophenyl)thio)ethyl acetate was used without purification in the next reaction.

Step B: Preparation of 2-((3-bromo-4-fluorophenyl)sulfonyl)ethyl acetate

Crude 2-((3-bromo-4-fluorophenyl)thio)ethyl acetate (709 mg, 2.4 mmol, 1.0 equiv) in MeOH (12.0 mL) was added dropwise to Oxone® (3.28 g, 5.3 mmol, 2.2 equiv) in water (12.0 mL) by addition funnel over 10 minutes, then stirred an additional 2 hours. The reaction mixture was filtered, extracted with MTBE (4×25 mL), washed with brine (25 mL), dried (MgSO$_4$), filtered and concentrated. The crude product was purified on silica gel (25 g SNAP, 14 CV, 10-100% EtOAc/hexane) affording 2-((3-bromo-4-fluorophenyl)sulfonyl)ethyl acetate (530 mg, 67% over 2 steps) as a clear oil that slowly became a white solid upon standing.

Step C: Preparation of 2-bromo-1-(3-chloro-5-fluorophenoxy)-4-(vinylsulfonyl)benzene (Compound 130)

Cesium carbonate (48 mg, 0.15 mmol, 1.2 equiv) was added all at once to 2-((3-bromo-4-fluorophenyl)sulfonyl) ethyl acetate (40 mg, 0.12 mmol, 1.0 equiv) and 3-chloro-5-fluorophenol (22 mg, 0.15 mmol, 1.2 equiv) in NMP (0.5 mL) then warmed to 50° C. and stirred for 16 hours. The reaction mixture Cooled to room temperature and purified directly on reverse phase silica gel (12+M, 14 CV, 20-100% MeCN/water) then silica gel (10 g SNAP, 14 CV, 7-60% EtOAc/hexanes) affording Compound 130 (9.5 mg, 20% yield) as a clear oil. LCMS ESI (−) m/z 389 (M−H); $^1$H-NMR (400 MHz, CDCl$_3$): δ 8.18 (d, 1H), 7.83-7.80 (m, 1H), 7.07 (d, 1H), 6.97-6.94 (m, 1H), 6.82-6.81 (m, 1H), 6.70-6.64 (m, 2H), 6.54-6.50 (m, 1H), 6.13-6.11 (m, 1H).

Example 131

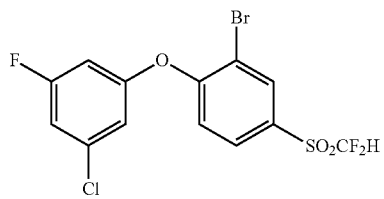

2-Bromo-1-(3-chloro-5-fluorophenoxy)-4-((difluoromethyl)sulfonyl)benzene (Compound 131)

Step A: Preparation of (3-bromo-4-fluorophenyl)(difluoromethyl)sulfane

Diethyl (bromodifluoromethyl)phosphonate (2.58 g, 9.66 mmol) was added all at once by syringe to a degassed mixture of 3-bromo-5-fluorobenzenethiol (1.00 g, 4.8 mmol) and KOH (5.42 g, 96.6 mmol) in MeCN (24.0 mL) and water (24.0 mL) at −78° C. under nitrogen The cooling bath was removed immediately and the mixture was stirred at room temperature for 30 minutes. The reaction was diluted with water (20 mL), extracted with MTBE (4×50 mL), washed with brine (50 mL), dried (Na$_2$SO$_4$), filtered and concentrated in vacuo. Crude (3-bromo-4-fluorophenyl)(difluoromethyl)sulfane (1.24 g) was used directly in the following reaction. $^1$HNMR (400 MHz, CDCl$_3$): δ 7.82-7.80 (m, 1H), 7.54-7.50 (m, 1H), 7.15 (t, 1H), 6.80 (t, 1H).

Step B: Preparation of 2-bromo-1-fluoro-4-((trifluoromethyl)sulfonyl)benzene Sodium periodate (2.58 g, 12.06 mmol) was added all at once to (3-bromo-4-fluorophenyl)(difluoromethyl)sulfane (1.24 g, 4.83 mmol) and RuCl$_3$ (25 mg, 0.12 mmol) in MeCN (10 mL)/CCl$_4$ (10 mL)/H$_2$O (20 mL) at room temperature and stirred for 2 hours. The reaction mixture was filtered, the filter cake washed with dichloromethane, then the organic filtrate was washed with brine (30 mL), dried (Na$_2$SO$_4$), filtered and concentrated in vacuo. The crude product was purified on silica gel (25 g SNAP, 14 CV, 5-40% EtOAc/hexanes) affording 2-bromo-1-fluoro-4-((trifluoromethyl)sulfonyl)benzene (1.16 g, 83% yield over 2 steps) as a clear, colorless oil which became a white solid upon standing.

Step C: Preparation of 2-bromo-1-(3-chloro-5-fluorophenoxy)-4-((difluoromethyl)sulfonyl)benzene (Compound 131)

Cesium carbonate (358 mg, 1.1 mmol) was added all at once to 2-bromo-4-((difluoromethyl)sulfonyl)-1-fluorobenzene (289 mg, 1.0 mmol) and 3-chloro-5-fluorophenol (161 mg, 1.1 mmol) in NMP (3.0 mL) then warmed to 50° C. and stirred for 2 hours and 45 minutes. The mixture was cooled to room temperature and purified directly on reverse phase silica gel (25+M, 14 CV, 20-100% MeCN/water) affording Compound 131 (369 mg, 89% yield) as a white solid. LCMS ESI (−) m/z 413 (M−H); $^1$H-NMR (400 MHz, CDCl$_3$): δ 8.26 (d, 1H), 7.89-7.87 (m, 1H), 7.07 (d, 1H), 7.04-7.00 (m, 1H), 6.90-6.89 (m, 1H), 6.75-6.72 (m, 1H), 6.21 (t, 1H).

Example 132

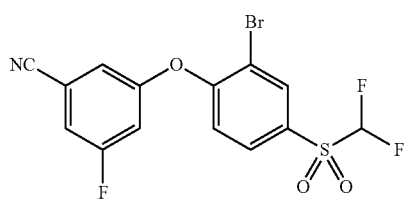 [SMILES: N#Cc1cc(F)cc(Oc2ccc(S(=O)(=O)C(F)F)cc2Br)c1]

3-(2-Bromo-4-((difluoromethyl)sulfonyl)phenoxy)-5-fluorobenzonitrile (Compound 132)

Preparation of 3-(2-bromo-4-((difluoromethyl)sulfonyl)phenoxy)-5-fluorobenzonitrile (Compound 132)

Cesium carbonate (76.0 mg, 0.23 mmol) was added all at once to 2-bromo-4-((difluoromethyl)sulfonyl)-1-fluorobenzene (61.0 mg, 0.21 mmol) and 3-fluoro-5-hydroxybenzonitrile (32.0 mg, 0.23 mmol) in NMP (0.5 mL) then warmed to 50° C. and stirred for 2.5 hours. The mixture was cooled to room temperature and purified directly on reverse phase silica gel (12+M, 14 CV, 20-100% MeCN/water) affording Compound 132 (76 mg, 0.19 mmol, 88% yield) as a white solid. LCMS ESI (−) m/z 404 (M−H); $^1$HNMR (400 MHz, CDCl$_3$): δ 8.30 (d, 1H), 7.95-7.93 (m, 1H), 7.27-7.25 (m, 1H), 7.15-7.13 (m, 2H), 7.06-7.03 (m, 1H), 6.24 (t, 1H).

Example 133

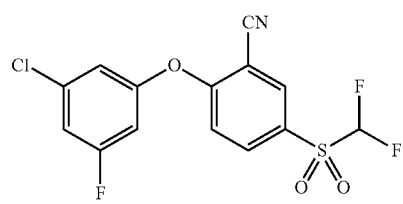 [SMILES: N#Cc1cc(S(=O)(=O)C(F)F)ccc1Oc1cc(F)cc(Cl)c1]

2-(3-Chloro-5-fluorophenoxy)-5-((difluoromethyl)sulfonyl)benzonitrile (Compound 133)

Tetrakis(triphenylphosphine)palladium(0) (15.6 mg, 0.014 mmol) was added all at once to Zn(CN)$_2$ (9.5 mg, 0.08 mmol) and 2-bromo-1-(3-chloro-5-fluorophenoxy)-4-((difluoromethyl)sulfonyl)benzene (56.0 mg, 0.14 mmol) in NMP (0.6 mL) under nitrogen. The flask was evacuated and back-filled with nitrogen five times. The reaction mixture was then warmed to 100° C. for 22 hours. The reaction mixture was cooled to room temperature, diluted with water (5 mL), extracted with Et$_2$O (4×10 mL), washed with brine (10 mL), dried (Na$_2$SO$_4$), filtered and concentrated in vacuo. The crude product was purified on reverse phase silica gel (12+M, 15-100% MeCN/water, 14 CV) affording Compound 133 (4.6 mg, 0.01 mmol, 9% yield) as a pale yellow solid. LCMS ESI (−) m/z 360 (M−H); $^1$HNMR (400 MHz, CDCl$_3$): δ 8.34 (d, 1H), 8.15-8.12 (m, 1H), 7.40-7.37 (m, 1H), 7.31-7.29 (m, 1H), 7.22-7.19 (m, 1H), 7.10 (d, 1H), 6.26 (t, 1H).

Example 134

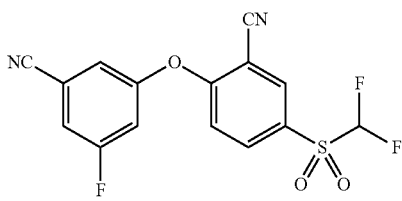 [SMILES: N#Cc1cc(F)cc(Oc2ccc(S(=O)(=O)C(F)F)cc2C#N)c1]

2-(3-Cyano-5-fluorophenoxy)-5-((difluoromethyl)sulfonyl)benzonitrile (Compound 134)

Step A: Preparation of 2-fluoro-5-mercaptobenzonitrile

3-Cyano-4-fluorobenzene-1-sulfonyl chloride (5.00 g, 22.77 mmol, 1.0 equiv) in CH$_2$Cl$_2$ (24.0 mL) was added dropwise by addition funnel over 20 minutes to an ice cold solution of PPh$_3$ (17.91 g, 68.30 mmol, 3.0 equiv) in CH$_2$Cl$_2$ (24.0 mL) and DMF (1.3 mL) then stirred at room temperature for 60 hours. The mixture was diluted with 1 N HCl (50 mL), extracted with CH$_2$Cl$_2$ (3×50 mL) then concentrated. MTBE (200 mL) was added, Ph$_3$PO was removed by filtration, the filter cake rinsed with MTBE (150 mL), and the organics were combined and concentrated. Purification on silica gel (100 g SNAP, 14 CV, 12-80% CH$_2$Cl$_2$/hexanes) afforded 2-fluoro-5-mercaptobenzonitrile (2.90 g, 83% yield) as a fluffy white solid.

Step B: Preparation of 5-((difluoromethyl)thio)-2-fluorobenzonitrile

Diethyl (bromodifluoromethyl)phosphonate (1.66 g, 6.2 mmol, 2.0 equiv) was added all at once by syringe to a degassed mixture of 2-fluoro-5-mercaptobenzonitrile (475 mg, 3.1 mmol, 1.0 equiv) and KOH (3.48 g, 62 mmol, 20.0 equiv) in MeCN (15.0 mL) and water (15.0 mL) at −78° C. under nitrogen. The reaction was immediately removed from the cooling bath and stirred at room temperature for 30 minutes. The mixture was diluted with water (10 mL), extracted with MTBE (4×20 mL), washed with brine (30 mL), dried (Na$_2$SO$_4$), filtered and concentrated in vacuo. Crude 5-((difluoromethyl)thio)-2-fluorobenzonitrile (630 mg) was used directly in the following reaction.

Step C: Preparation of 5-((difluoromethyl)sulfonyl)-2-fluorobenzonitrile

Sodium periodate (1.66 g, 7.8 mmol, 2.5 equiv) was added all at once to 5-((difluoromethyl)thio)-2-fluorobenzonitrile (630 mg, 3.1 mmol, 1.0 equiv) and RuCl$_3$ (16 mg, 0.078 mmol, 0.025 equiv) in 1:1:2 MeCN/CCl$_4$/water (30 mL) at room temperature and stirred for 1 hour. The reaction was filtered, washed the filter cake with CH$_2$Cl$_2$ (30 mL), extracted with CH$_2$Cl$_2$ (2×25 mL), washed with brine (25 mL), dried (Na$_2$SO$_4$), filtered through a 3 cm pad of Florisil® and concentrated. The crude product was purified on silica gel (10 g SNAP, 14 CV, 7-60% EtOAc/hexane affording 5-((difluoromethyl)sulfonyl)-2-fluorobenzonitrile (528 mg, 72% yield over 2 steps) as a white solid.

Step D: Preparation of 2-(3-cyano-5-fluorophenoxy)-5-((difluoromethyl)sulfonyl)benzonitrile (Compound 134)

Cesium carbonate (70.0 mg, 0.22 mmol) was added all at once to 2-bromo-4-((difluoromethyl)sulfonyl)-1-fluorobenzene (46.0 mg, 0.20 mmol) and 5-((difluoromethyl)sulfonyl)-2-fluorobenzonitrile (30.0 mg, 0.22 mmol) in NMP (0.5 mL) then warmed to 50° C. and stirred for 1.5 hours. The mixture was cooled to room temperature and purified directly on reverse phase silica gel (12+M, 14 CV, 20-100% MeCN/water) affording Compound 134 (44.8 mg, 0.13 mmol, 65% yield) as a white solid. LCMS ESI (−) m/z 351 (M−H). $^1$HNMR (400 MHz, CDCl$_3$): δ 8.34 (d, 1H), 8.15-8.12 (m, 1H), 7.40-7.37 (m, 1H), 7.31-7.29 (m, 1H), 7.22-7.19 (m, 1H), 7.10 (d, 1H), 6.26 (t, 1H).

Example 135

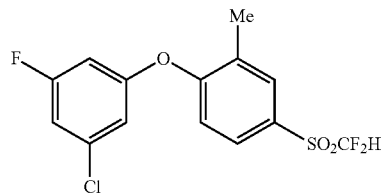

1-(3-Chloro-5-fluoro-phenoxy)-4-(difluoromethylsulfonyl)-2-methyl-benzene (Compound 135)

Step A: Preparation of 4-(difluoromethylsulfanyl)-1-fluoro-2-methyl-benzene

Bromodifluoromethyl diethylphosphonate (1.88 g, 7.0 mmol) was added by syringe to a degassed mixture of 4-fluoro-3-methyl-benzenethiol (500.0 mg, 3.5 mmol) and potassium hydroxide (3.95 g, 70.33 mmol) in acetonitrile (15 mL) and water (15 mL) at −78° C. under nitrogen. The reaction mixture was then immediately warmed to room temperature and stirred vigorously for 30 minutes. The mixture was extracted with EtOAc (3×20 mL), washed with brine (20 mL), dried (Na$_2$SO$_4$), filtered and concentrated in vacuo. Crude 4-(difluoromethylsulfanyl)-1-fluoro-2-methyl-benzene was used as is in the next reaction.

Step B: Preparation of 4-(difluoromethylsulfonyl)-1-fluoro-2-methyl-benzene

Sodium periodate (1.51 g, 7.0 mmol) was added all at once to 4-(difluoromethylsulfanyl)-1-fluoro-2-methyl-benzene (676 mg, 3.52 mmol) and ruthenium(III) chloride (18.25 mg, 0.09 mmol) in carbon tetrachloride (8 mL)/acetonitrile (8 mL)/water (16 mL) at room temperature and stirred for 3 hours. The mixture was filtered, diluted with water (20 mL), washed with CH$_2$Cl$_2$ (3×20 mL), washed with brine (20 mL), dried (Na$_2$SO$_4$), filtered and concentrated in vacuo affording 4-(difluoromethylsulfonyl)-1-fluoro-2-methyl-benzene (480 mg, 2.14 mmol, 61% yield).

Step C: Preparation of 1-(3-chloro-5-fluoro-phenoxy)-4-(difluoromethylsulfonyl)-2-methyl-benzene (Compound 135)

Cesium carbonate (80 mg, 0.25 mmol) was added all at once to 4-(difluoromethylsulfonyl)-1-fluoro-2-methyl-benzene (50 mg, 0.22 mmol) and 3-chloro-5-fluoro-phenol (36 mg, 0.25 mmol) in 1-methyl-2-pyrrolidone (1.0 mL) at room temperature then the reaction vial was sealed with a threaded cap. The reaction mixture was then warmed to 50° C. and continued to stir at this temperature until completion as judged by LC-MS. The mixture was cooled to room temperature then purified directly on reverse phase column (25+M, 14 CV, 20-100% MeCN/water) affording Compound 135 (43.6 mg, 0.12 mmol, 53% yield) as a brown oil. LCMS ESI (−) m/z 349 (M−H). $^1$HNMR (400 MHz, CDCl$_3$): δ 7.86 (d, 1H), 7.80-7.77 (m, 1H), 7.01 (d, 1H), 6.98-6.95 (m, 1H), 6.84-6.83 (m, 1H), 6.69-6.65 (m, 1H), 6.19 (t, 1H), 2.39 (s, 3H).

Example 136

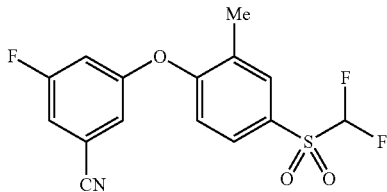 [SMILES: Cc1cc(S(=O)(=O)C(F)F)ccc1Oc1cc(F)cc(C#N)c1]

3-[4-(Difluoromethylsulfonyl)-2-methyl-phenoxy]-5-fluoro-benzonitrile (Compound 136)

Cesium carbonate (8-mg, 0.25 mmol) was added all at once to 4-(difluoromethylsulfonyl)-1-fluoro-2-methyl-benzene (50 mg, 0.22 mmol) and 3-fluoro-5-hydroxy-benzonitrile (34 mg, 0.25 mmol) in 1-methyl-2-pyrrolidone (1.0 mL) at room temperature then the reaction vial was sealed with a threaded cap. The reaction mixture was then warmed to 50° C. and continued to stir at this temperature until completion as judged by LC-MS. The mixture was cooled to room temperature then purified directly on reverse phase column (25+M, 14 CV, 20-100% MeCN/water) affording Compound 136 (27 mg, 0.08 mmol, 34% yield) as a white solid. LCMS ESI (−) m/z 340 (M−H). $^1$HNMR (400 MHz, CDCl$_3$): δ 7.93 (d, 1H), 7.85-7.82 (m, 1H), 7.23-7.20 (m, 1H), 7.11-7.09 (m, 1H), 7.04 (d, 1H), 7.03-6.98 (m, 1H), 6.21 (t, 1H), 2.39 (s, 3H).

Example 137

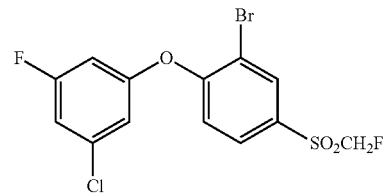

2-Bromo-1-(3-chloro-5-fluorophenoxy)-4-((fluoromethyl)sulfonyl)benzene (Compound 137)

Step A: Preparation of (fluoromethyl)(4-fluorophenyl)sulfane (Diethylamino)sulfur trifluoride (1.46 mL, 11.1 mmol) dissolved in CH$_2$Cl$_2$ (1.8 mL) was added drop-wise to a solution of 1-fluoro-4-(methylsulfinyl)benzene (1.0 g, 6.3 mmol) and SbCl$_3$ (43 mg, 0.190 mmol) in CH$_2$Cl$_2$ (32 mL) at −5° C. under nitrogen then stirred for 14 hours while gradually warming to room temperature. The reaction mixture was carefully quenched by the drop-wise addition of saturated NaHCO$_3$ (10 mL), stirred for 30 minutes, extracted with CH$_2$Cl$_2$ (2×30 mL), washed with brine (30 mL), dried (Na$_2$SO$_4$), filtered and concentrated. The crude product was purified on silica gel (25 g SNAP, 14 CV, 5-50% EtOAc/hexane) affording (fluoromethyl)(4-fluorophenyl)sulfane (748 mg, 74% yield) as a yellow oil.

Step B: Preparation of 1-fluoro-4-((fluoromethyl)sulfonyl)benzene (Fluoromethyl)(4-fluorophenyl)sulfane (748 mg, 4.7 mmol) in MeOH (20.0 mL) was added dropwise to an ice cold solution of Oxone® (6.32 g, 10.3 mmol) in water (20.0 mL) with vigorous stirring. The reaction mixture was then warmed to room temperature and stirred an additional 14 hours. Solids were removed by filtration, the filtrate was diluted with brine (50 mL), extracted with EtOAc (3×50 mL), washed with brine (50 mL), dried (MgSO$_4$), filtered and concentrated. The crude product was purified on reverse phase column (25+M, 14 CV, 20-100% MeCN/water) affording 1-fluoro-4-((fluoromethyl)sulfonyl)benzene as a clear oil.

Step C: Preparation of 2-bromo-1-fluoro-4-((fluoromethyl)sulfonyl)benzene

N-Bromosuccinimide (228 mg, 1.28 mmol) was added in two equal portions over 30 minutes to 1-fluoro-4-((fluoromethyl)sulfonyl)benzene (205 mg, 1.07 mmol) in H$_2$SO$_4$ (1.2 mL) at room temperature then stirred overnight. The reaction mixture was poured onto ice, extracted with dichloromethane (4×10 mL), washed with 3 N NaOH (10 mL), brine (20 mL), dried (Na$_2$SO$_4$), filtered and concentrated. The crude product was purified on reverse phase column (25+M, 14 CV, 20-100% MeCN/water) affording 2-bromo-1-fluoro-4-((fluoromethyl)sulfonyl)benzene (217 mg, 75% yield) as a white solid.

Step D: Preparation of 2-bromo-1-(3-chloro-5-fluorophenoxy)-4-((fluoromethyl)sulfonyl)benzene (Compound 137)

Cesium carbonate (47 mg, 0.144 mmol) was added to 2-bromo-1-fluoro-4-((fluoromethyl)sulfonyl)benzene (30 mg, 0.11 mmol) and 3-chloro-5-fluorophenol (21 mg, 0.144 mmol) in NMP (0.5 mL) then warmed to 100° C. for 1 hour. The mixture was cooled to room temperature then purified on reverse phase column (12+M, 14 CV, 20-100% MeCN/water) affording Compound 137 (31.7 mg, 72% yield). LCMS ESI (−) m/z 395 (M−H). $^1$H-NMR (400 MHz, CDCl$_3$): δ 8.25 (d, 1H), 7.89-7.86 (m, 1H), 7.09 (d, 1H), 7.00-6.97 (m, 1H), 6.87-6.86 (m, 1H), 6.72-6.69 (m, 1H), 5.17 (d, 2H).

Example 138

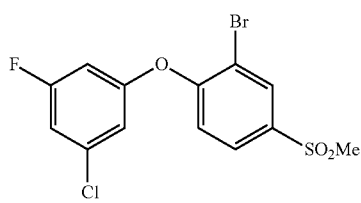 [SMILES: CS(=O)(=O)c1ccc(Oc2cc(F)cc(Cl)c2)c(Br)c1]

2-Bromo-1-(3-chloro-5-fluorophenoxy)-4-(methylsulfonyl)benzene (Compound 138)

Step A: Preparation of 2-bromo-1-fluoro-4-(methylsulfonyl)benzene

N-Bromosuccinimide (579 mg, 3.25 mmol, 1.1 equiv) was added in two equal portions over 30 minutes at room temperature to 1-fluoro-4-(methylsulfonyl)benzene (515 mg, 2.96 mmol) in concentrated H$_2$SO$_4$ (3.0 mL) and stirred for 6 hours. The mixture was carefully poured onto ice and water (10 mL), extracted with CH$_2$Cl$_2$ (4×15 mL), washed with 3 N NaOH (10 mL), brine (20 mL), dried (Na$_2$SO$_4$), filtered and concentrated in vacuo. The residue was purified on silica gel (10 g SNAP, 14 CV, 6-50% EtOAc/hexane) to afford 2-bromo-1-fluoro-4-(methylsulfonyl)benzene (530 mg, 71% yield) as a white solid.

Step B: Preparation of 2-bromo-1-(3-chloro-5-fluorophenoxy)-4-(methylsulfonyl)benzene (Compound 138)

Cesium carbonate (176 mg, 0.54 mmol) was added to 2-bromo-1-fluoro-4-(methylsulfonyl)benzene (114 mg, 0.45 mmol) and 3-chloro-5-fluorophenol (79 mg, 0.54 mmol) in NMP (2.0 mL) then warmed to 50° C. for 20 hours. The crude reaction mixture was purified on reverse phase silica gel (25+M, 14 CV, 20-100% MeCN/water) affording Compound 138 (113 mg, 66% yield) as a white solid. LCMS ESI (−) m/z 377 (M−H).

Example 139

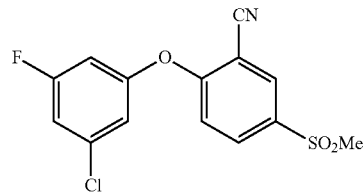 [SMILES: CS(=O)(=O)c1ccc(Oc2cc(F)cc(Cl)c2)c(C#N)c1]

2-(3-Chloro-5-fluorophenoxy)-5-(methylsulfonyl)benzonitrile (Compound 139)

Copper (I) cyanide (11 mg, 0.126 mmol) was added all at once to a solution of 2-bromo-1-(3-chloro-5-fluorophenoxy)-4-(methylsulfonyl)benzene (40 mg, 0.105 mmol) in NMP (0.4 mL) in a microwave vial, sealed then warmed to 190° C. for 30 minutes in a microwave reactor. The mixture was cooled to room temperature then purified directly on reverse phase column (12+M, 20-100% MeCN/water) affording Compound 139 (9 mg, 25% yield). LCMS ESI (−) m/z 370 (M+HCO$_2^-$), $^1$HNMR (400 MHz, CDCl$_3$): δ 8.29-8.28 (m, 1 H), 8.09-8.06 (m, 1H), 7.10-7.06 (m, 2H), 6.97-6.96 (m, 1H), 6.83-6.79 (m, 1H), 3.10 (s, 3H).

Example 140

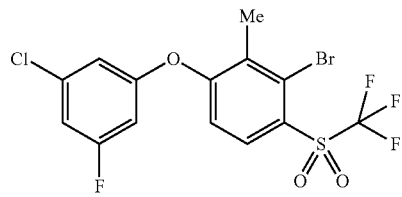 [SMILES: Cc1c(Oc2cc(F)cc(Cl)c2)ccc(S(=O)(=O)C(F)(F)F)c1Br]

3-Bromo-1-(3-chloro-5-fluoro-phenoxy)-2-methyl-4-(trifluoromethylsulfonyl)benzene (Compound 140)

Step A: Preparation of 2,4-dibromo-3-methyl-benzenesulfonyl chloride 1,3-dibromo-2-methyl-benzene (5.5 mL, 40 mmol) was added dropwise by addition funnel over 10 minutes to sulfurochloridic acid (10 mL, 150 mmol) at room temperature and stirred for 2 hours then warmed to 40° C. and stirred for an additional 2 hours. The mixture was carefully poured into water/ice (250 mL) and an off-white solid was collected by filtration, washed with water then dried under vacuum. Crude 2,4-dibromo-3-methyl-benzenesulfonyl chloride (13.3 g, 91%) was used without further purification.

Step B: Preparation of 2,4-dibromo-3-methyl-benzenethiol

A solution of 2,4-dibromo-3-methyl-benzenesulfonyl chloride (5 g, 14.4 mmol) in dichloromethane (20 mL) was added dropwise over 20 minutes to an ice-cold solution of triphenylphosphine (8.28 g, 31.57 mmol) in dichloromethane (20 mL) and DMF (1.2 mL). The reaction mixture was gradually warmed to room temperature over 4 hours. The mixture was quenched with 1 N HCl (30 mL), extracted with CH$_2$Cl$_2$ (3×30 mL), washed with brine (20 mL), dried over Na$_2$SO$_4$, filtered and concentrated in vacuo. Ph$_3$PO was removed by stirring the crude product in MTBE (100 mL) and then filtered. The filtrate was concentrated. The crude product was purified on silica gel (50 g SNAP, 14 CV, 0-20% EtOAc/hexanes) affording 2,4-dibromo-3-methyl-benzenethiol (1.7 g, 5.7 mmol, 40% yield) as a white solid.

Step C: Preparation of 1,3-dibromo-2-methyl-4-(trifluoromethylsulfanyl)benzene

Trifluoromethyl iodide (1.77 g, 9.0 mmol) was condensed into a degassed solution of 2,4-dibromo-3-methyl-benzenethiol (850 mg, 3.0 mmol), triethylamine (1.05 mL, 7.5 mmol) and methyl viologen dichloride hydrate (77.5 mg, 0.3 mmol) in DMF (8.2 mL) at −78° C. in a pressure vessel through a septum vented to a bubbler. The reaction vessel was then quickly sealed with a threaded teflon cap and stirred at room temperature for 24 hours. The mixture was diluted with Et$_2$O (50 mL), washed with saturated NaHCO$_3$ (20 mL), the aqueous phase was back-extracted with Et$_2$O (3×30 mL), washed with brine (20 mL), dried (Na$_2$SO$_4$), filtered and concentrated in vacuo. Crude 1,3-dibromo-2-methyl-4-(trifluoromethylsulfanyl)benzene was used without further purification in the next reaction.

Step D: Preparation of 1,3-dibromo-2-methyl-4-(trifluoromethylsulfonyl)benzene

Sodium periodate (1.34 g, 6.3 mmol) was added all at once to 1,3-dibromo-2-methyl-4-(trifluoromethylsulfanyl)benzene (1 g, 2.9 mmol) and ruthenium(III) chloride (14.8 mg, 0.07 mmol) in acetonitrile (7 mL)/carbon tetrachloride (7 mL)/water (14 mL) at room temperature and stirred for 16 hours. The mixture was filtered, diluted with water (20 mL), washed with CH$_2$Cl$_2$ (3×20 mL), washed with brine (20 mL), dried (Na$_2$SO$_4$), filtered and concentrated in vacuo affording 1,3-dibromo-2-methyl-4-(trifluoromethylsulfonyl)benzene (660 mg, 1.7 mmol, 60% yield) as a white solid.

Step E: Preparation of 3-bromo-1-(3-chloro-5-fluoro-phenoxy)-2-methyl-4-(trifluoromethylsulfonyl)benzene (Compound 140)

Cesium hydrogen carbonate (183 mg, 0.94 mmol) was added all at once to 1,3-dibromo-2-methyl-4-(trifluoromethylsulfonyl)benzene (328 mg, 0.86 mmol) and 3-chloro-5-fluoro-phenol (138 mg, 0.94 mmol) in 1-methyl-2-pyrrolidone (3.5 mL) at room temperature then the reaction vial was sealed with a threaded cap. The reaction mixture was then warmed to 50° C. and continued to stir at this temperature until completion as judged by LC-MS. The mixture was cooled to room temperature then purified directly on reverse phase column (25+M, 14 CV, 20-100% MeCN/water) affording Compound 140 (140 mg, 0.3 mmol, 35% yield). LCMS ESI (−) m/z 445 (M−H); $^1$HNMR (400 MHz, CDCl$_3$): δ 8.07 (d, 1H), 7.03-7.00 (m, 1H), 6.94 (d, 1H), 6.87-6.86 (m, 1H), 6.72-6.68 (m, 1H), 2.52 (s, 3H).

Example 141

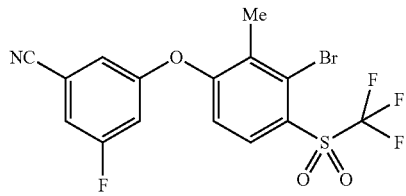

3-[3-Bromo-2-methyl-4-(trifluoromethylsulfonyl)phenoxy]-5-fluoro-benzonitrile (Compound 141)

Cesium carbonate (51.2 mg, 0.16 mmol) was added all at once to 1,3-dibromo-2-methyl-4-(trifluoromethylsulfonyl)benzene (100.0 mg, 0.26 mmol) and 3-fluoro-5-hydroxy-benzonitrile (35.9 mg, 0.26 mmol) in 1-methyl-2-pyrrolidone (1.0 mL) at room temperature then the reaction vial was sealed with a threaded cap. The reaction mixture was then warmed to 50° C. and continued to stir at this temperature until completion as judged by LC-MS (20 hours). The mixture was cooled to room temperature then purified directly on reverse phase column (25+M, 14 CV, 20-100% MeCN/water) affording Compound 141 (71 mg, 0.15 mmol, 59% yield) as a colorless oil. LCMS ESI (+) m/z 438 (M+H).

Example 142

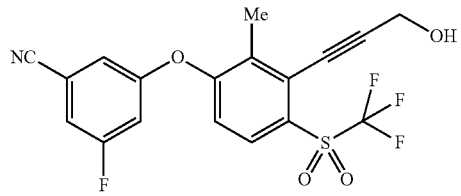 [SMILES: Cc1c(Oc2cc(F)cc(C#N)c2)ccc(S(=O)(=O)C(F)(F)F)c1C#CCO]

3-Fluoro-5-[3-(3-hydroxyprop-1-ynyl)-2-methyl-4-(trifluoromethylsulfonyl)phenoxy]benzonitrile (Compound 142)

Copper (I) iodide (4.4 mg, 0.02 mmol) and dichloropalladium triphenylphosphane (8.2 mg, 0.01 mmol) were added to a degassed mixture of 3-[3-bromo-2-methyl-4-(trifluoromethylsulfonyl)phenoxy]-5-fluoro-benzonitrile (51 mg, 0.12 mmol), triethylamine (0.16 mL, 1.16 mmol) and propargyl alcohol (0.02 mL, 0.30 mmol) in DMF (0.90 mL) under a stream of nitrogen. The septum was quickly replaced with a crimp cap and sealed. The reaction mixture was then warmed to 100° C. for 20 hours. The crude product was purified directly on reverse phase silica gel (12+M, 14 CV, 20-100% MeCN/water) affording Compound 142 (4.7 mg, 0.01 mmol, 10% yield) as a brown oil. LCMS ESI (−) m/z 412 (M−H); $^1$HNMR (400 MHz, CDCl$_3$): δ 8.00 (d, 1H), 7.26-7.23 (m, 1H), 7.12-7.11 (m, 1H), 7.03-6.99 (m, 1H), 6.97 (d, 1H), 4.62 (d, 2H), 2.49 (s, 3H), 1.96-1.91 (m, 1H).

Example 143

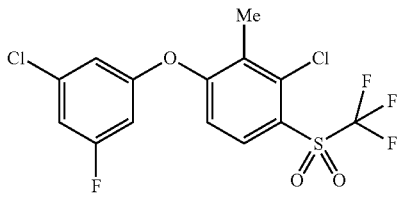 [SMILES: Cc1c(Oc2cc(F)cc(Cl)c2)ccc(S(=O)(=O)C(F)(F)F)c1Cl]

3-Chloro-1-(3-chloro-5-fluoro-phenoxy)-2-methyl-4-(trifluoromethylsulfonyl)benzene (Compound 143)

Step A: Preparation of 1,3-dichloro-2-methyl-4-(trifluoromethylsulfanyl)benzene

Trifluoromethyl iodide (3.6 g, 18.3 mmol) was condensed into a degassed solution of 2,4-dichloro-3-methyl-benzenethiol (1.18 g, 6.1 mmol), triethylamine (2.1 mL, 15.3 mmol) and methyl viologen dichloride hydrate (157 mg, 0.6 mmol) in DMF (8.2 mL) at −78° C. in a pressure vessel. The reaction vessel was then quickly sealed with a threaded teflon cap and stirred at room temperature for 24 hours. The mixture was diluted with Et$_2$O (50 mL), washed with saturated NaHCO$_3$ (20 mL), the aqueous was back-extracted with Et$_2$O (3×30 mL). The combined organic layers were washed with brine (20 mL), dried (Na$_2$SO$_4$), filtered and concentrated in vacuo. 1,3-Dichloro-2-methyl-4-(trifluoromethylsulfanyl)benzene (1.59 g, 6.1 mmol, 99.6% yield) was used without further purification in the next reaction assuming quantitative yield.

Step B: Preparation of 1,3-dichloro-2-methyl-4-(trifluoromethylsulfonyl)benzene

Sodium periodate (3.26 g, 15.2 mmol) was added all at once to 1,3-dichloro-2-methyl-4-(trifluoromethylsulfanyl)benzene (1.59 g, 6.1 mmol) and ruthenium (III) chloride (31.6 mg, 0.15 mmol) in acetonitrile (15 mL)/carbon tetrachloride (15 mL)/water (30 mL) at room temperature and stirred for 16 hours. The reaction mixture was filtered, diluted with water (20 mL), washed with CH$_2$Cl$_2$ (3×20 mL), washed with brine (20 mL), dried (Na$_2$SO$_4$), filtered and concentrated in vacuo affording 1,3-dichloro-2-methyl-4-(trifluoromethylsulfonyl)benzene (1.2 g, 4.1 mmol, 67% yield over 2 steps) as a white solid.

Step C: Preparation of 3-chloro-1-(3-chloro-5-fluoro-phenoxy)-2-methyl-4-(trifluoromethylsulfonyl)benzene (Compound 143)

Cesium carbonate (71 mg, 0.22 mmol) added all at once to a solution of 1,3-dichloro-2-methyl-4-(trifluoromethylsulfonyl)benzene (70 mg, 0.24 mmol) and 3-chloro-5-fluoro-phenol (32 mg, 0.22 mmol) in 1-methyl-2-pyrrolidone (1 mL) at room temperature and stirred for 45 minutes, warmed to 50° C. and stirred for 2 hours. The reaction mixture was cooled to room temperature and purified directly on reverse phase silica gel (25+M, 14 CV, 30-100% MeCN/water) affording Compound 143 (67 mg, 0.16 mmol, 72% yield) as a white solid. LCMS ESI (−) m/z 401 (M−H);

$^1$H-NMR (400 MHz, CDCl$_3$): δ 8.03 (d, 1H), 7.03-7.00 (m, 1H), 6.90 (d, 1H), 6.88-6.86 (m, 1H), 6.72-6.69 (m, 1H), 2.47 (s, 3H).

Example 144

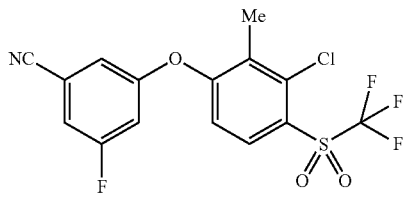 [SMILES: Cc1c(Oc2cc(F)cc(C#N)c2)ccc(S(=O)(=O)C(F)(F)F)c1Cl]

3-Fluoro-5-[3-chloro-2-methyl-4-(trifluoromethylsulfonyl)phenoxy]benzonitrile (Compound 144)

Cesium carbonate (71 mg, 0.22 mmol) was added all at once to a solution of 1,3-dichloro-2-methyl-4-(trifluoromethylsulfonyl)benzene (70 mg, 0.24 mmol) and 3-fluoro-5-hydroxy-benzonitrile (30 mg, 0.22 mmol) in 1-methyl-2-pyrrolidone (1 mL) at room temperature and stirred for 45 minutes, warmed to 50° C. and stirred for 2 hours. The mixture was cooled to room temperature and purified directly on reverse phase column (25+M, 14 CV, 30-100% MeCN/water) affording a slightly impure product which was further purified on silica gel (10 g SNAP, 14 CV, 2-26% EtOAc/hexane) affording Compound 144 (33 mg, 0.08 mmol, 36% yield) as a white solid. LCMS ESI (−) m/z 392 (M−H); $^1$HNMR (400 MHz, CDCl$_3$): δ 8.05 (m, 1H), 7.29-7.26 (m, 1H), 7.14 (s, 1H), 7.05-7.02 (m, 1H), 6.94-6.91 (m, 1H), 2.46 (s, 3H).

Example 145

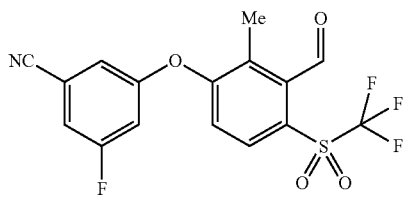 [SMILES: Cc1c(Oc2cc(F)cc(C#N)c2)ccc(S(=O)(=O)C(F)(F)F)c1C=O]

3-Fluoro-5-[3-formyl-2-methyl-4-(trifluoromethylsulfonyl)phenoxy]benzonitrile (Compound 145)

Step A: Preparation of 3-fluoro-5-[2-methyl-4-(trifluoromethylsulfonyl)-3-vinyl-phenoxy]benzonitrile Tributyl(vinyl)stannane (300 μL, 1.0 mmol) was added to a degassed mixture of 3-[3-chloro-2-methyl-4-(trifluoromethylsulfonyl)phenoxy]-5-fluoro-benzonitrile (250 mg, 0.63 mmol) and bis(di-tert-butyl(4-dimethylaminophenyl)phosphine)dichloropalladium(II) (45 mg, 0.06 mmol) in DMF (3.6 mL) at room temperature. The microwave vial was then evacuated and back-filled with nitrogen three times. The septum was quickly replaced with a crimp cap, sealed then the reaction was warmed to 160° C. for 30 minutes in a microwave reactor. Once cooled to room temperature, the reaction mixture was diluted with MTBE (5 mL) and saturated KF (10 mL) followed by stirring for 30 minutes. The aqueous layer was extracted with MTBE (3×10 mL), washed with brine (10 mL), dried over Na₂SO₄, filtered and concentrated in vacuo. The crude product was purified on silica gel (10 g SNAP, 14 CV, 2-50% EtOAc/hexane) affording 3-fluoro-5-[2-methyl-4-(trifluoromethylsulfonyl)-3-vinyl-phenoxy]benzonitrile (179 mg, 0.46 mmol, 73% yield) as a clear, colorless oil.

Step B: Preparation of 3-fluoro-5-[3-formyl-2-methyl-4-(trifluoromethylsulfonyl)phenoxy]benzonitrile (Compound 145)

Tetraoxoosmium (0.07 mL, 0.01 mmol) was added dropwise by syringe to 3-fluoro-5-[2-methyl-4-(trifluoromethylsulfonyl)-3-vinyl-phenoxy]benzonitrile (85 mg, 0.22 mmol) and sodium periodate (142 mg, 0.66 mmol) in tetrahydrofuran (0.9 mL) and water (0.3 mL) at room temperature then stirred overnight. The mixture was diluted with water (5 mL), extracted with EtOAc (3×10 mL), washed with brine (10 mL), dried over MgSO₄, filtered and concentrated. Purified on silica gel (25 g SNAP, 14 CV, % EtOAc/hexane) affording Compound 145 (50 mg, 0.13 mmol, 59% yield). LCMS ESI (−) m/z 386 (M−H); ¹HNMR (400 MHz, CDCl₃): δ 10.62 (s, 1H), 7.97 (d, 1H), 7.30-7.27 (m, 1H), 7.16-7.15 (m, 1H), 7.10 (d, 1H), 7.07-7.03 (m, 1H), 2.40 (s, 3H).

Example 146

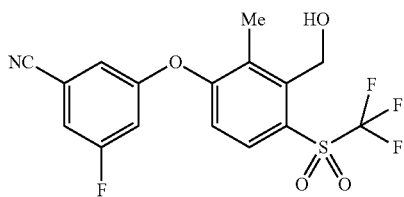 [SMILES: Cc1c(Oc2cc(F)cc(C#N)c2)ccc(S(=O)(=O)C(F)(F)F)c1CO]

3-Fluoro-5-[3-(hydroxymethyl)-2-methyl-4-(trifluoromethylsulfonyl)phenoxy]benzonitrile (Compound 146)

Sodium borohydride (2 mg, 0.05 mmol) was added all at once to crude 3-fluoro-5-[3-formyl-2-methyl-4-(trifluoromethylsulfonyl)phenoxy]benzonitrile (5 mg, 0.01 mmol) in methanol (0.4 mL) at room temperature and stirred for 5 minutes. The reaction was quenched with 1 drop of 1 N HCl, diluted with water (5 mL), extracted with EtOAc (3×5 mL), washed with brine (5 mL), dried over Na₂SO₄, filtered and concentrated. The crude product was purified by preparative TLC (25% EtOAc/hexane) affording Compound 146 (2 mg, 0.005 mmol, 40% yield) as a clear oil. LCMS ESI (−) m/z 434 (M+HCO₂⁻); ¹HNMR (400 MHz, CDCl₃): δ 8.01 (d, 1H), 7.26-7.23 (m, 1H), 7.12-7.11 (m, 1H), 7.03-6.99 (m, 2H), 4.99 (d, 2H), 2.50 (s, 3H).

Example 147

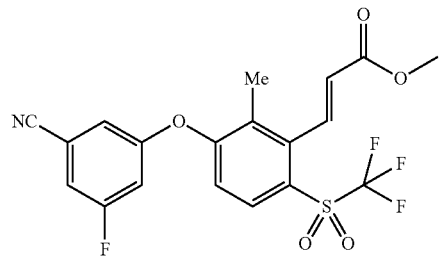 [SMILES: COC(=O)/C=C/c1c(S(=O)(=O)C(F)(F)F)ccc(Oc2cc(F)cc(C#N)c2)c1C]

Methyl (E)-3-[3-(3-cyano-5-fluoro-phenoxy)-2-methyl-6-(trifluoromethylsulfonyl)phenyl]prop-2-enoate (Compound 147)

Triethylamine (0.06 mL, 0.45 mmol) and DMF (1 mL) were added to 3-[3-bromo-2-methyl-4-(trifluoromethylsulfonyl)phenoxy]-5-fluoro-benzonitrile (65 mg, 0.15 mmol) in a reaction vial equipped with a stir bar then evacuated and back-filled with nitrogen three times. Methyl prop-2-enoate (0.07 mL, 0.74 mmol) and di-µ-chlorobis[5-hydroxy-2-[1-(hydroxyimino)ethyl]phenyl]-palladium dimer (8.7 mg, 0.01 mmol) were added. The septum was quickly replaced with a crimp cap and sealed. The reaction mixture was warmed to 120° C. for 16 hours. After cooling to room temperature, the mixture was filtered through a frit, and purified directly on reverse phase silica gel (25+M, 20-100% MeCN/water) affording Compound 147 (38 mg, 0.08 mmol, 54% yield) as a clear oil. LCMS ESI (−) m/z 442 (M−H). ¹H-NMR (400 MHz, CDCl₃): δ 8.02 (s, 1H), 7.99 (d, 1H), 7.28-7.25 (m, 1H), 7.16-7.15 (m, 1H), 7.07-7.05 (m, 1H), 6.98 (d, 1H), 6.03 (d, 1H), 3.85 (s, 3H), 2.34 (s, 3H).

Example 148

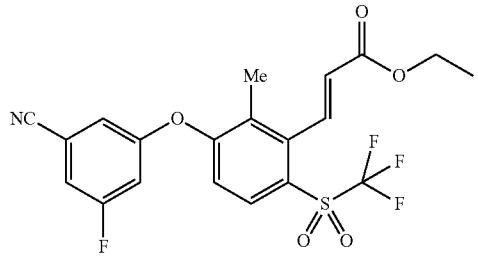 [SMILES: CCOC(=O)/C=C/c1c(S(=O)(=O)C(F)(F)F)ccc(Oc2cc(F)cc(C#N)c2)c1C]

Ethyl (E)-3-(3-(3-cyano-5-fluorophenoxy)-2-methyl-6-((trifluoromethyl)sulfonyl)phenyl)acrylate (Compound 148)

Step A: Preparation of (E)-3-[3-(3-cyano-5-fluorophenoxy)-2-methyl-6-(trifluoromethylsulfonyl)phenyl]prop-2-enoic acid Lithium hydroxide monohydrate (66.31 mg, 1.58 mmol) was added all at once to methyl (E)-3-[3-(3-cyano-5-fluorophenoxy)-2-methyl-6-(trifluoromethylsulfonyl)phenyl]prop-2-enoate (140 mg, 0.32 mmol) in tetrahydrofuran (1 mL) and water (1 mL) at room temperature then stirred for 2 hours. The reaction was quenched with 1 N HCl (1 mL), extracted with EtOAc (3×5 mL), washed with brine (5 mL), dried over Na₂SO₄, filtered and concentrated. Crude (E)-3-[3-(3-cyano-5-fluoro-phenoxy)-2-methyl-6-(trifluoromethylsulfonyl)phenyl]prop-2-enoic acid (120 mg, 0.28 mmol, 88% yield) was used without further purification.

Step B: Preparation of ethyl (E)-3-(3-(3-cyano-5-fluorophenoxy)-2-methyl-6-((trifluoromethyl)sulfonyl)phenyl)acrylate (Compound 148)

[(Dimethylamino)-1H-1,2,3-triazolo-[4,5-b]pyridin-1-yl-methylene]-N-methylmethanaminium hexafluorophosphate N-oxide, (HATU) (14.7 mg, 0.04 mmol) was added all at once to (E)-3-[3-(3-cyano-5-fluoro-phenoxy)-2-methyl-6-(trifluoromethylsulfonyl)phenyl]prop-2-enoic acid (11 mg, 0.03 mmol), N,N-diisopropylethylamine (6.6 mg, 0.05 mmol) and ethanol (5.9 mg, 0.13 mmol) in DMF (0.20 mL) at room temperature. The reaction mixture was stirred for 2 hours then purified directly on reverse phase column (12+M, 14 CV, 20-100% MeCN/water) affording Compound 148 (6.7 mg, 0.015 mmol, 57% yield) as a yellow oil. LCMS ESI (+) m/z 458 (M+H). ¹HNMR (400 MHz, CDCl₃): δ 8.02 (s, 1H), 7.99 (d, 1H), 7.28-7.25 (m, 1H), 7.16-7.15 (m, 1H), 7.07-7.03 (m, 1H), 6.98 (d, 1H), 6.02 (d, 1H), 4.31 (q, 2H), 2.34 (s, 3H), 1.36 (t, 3H).

Example 149

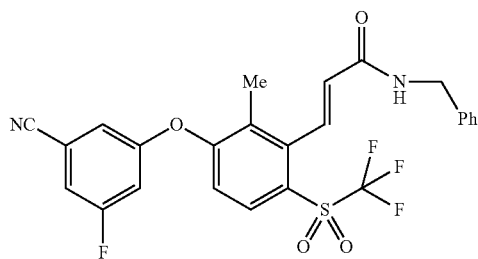 [SMILES: Cc1c(Oc2cc(F)cc(C#N)c2)ccc(S(=O)(=O)C(F)(F)F)c1/C=C/C(=O)NCc1ccccc1]

(E)-N-Benzyl-3-(3-(3-cyano-5-fluorophenoxy)-2-methyl-6-((trifluoromethyl)sulfonyl)phenyl)acrylamide (Compound 149)

[(Dimethylamino)-1H-1,2,3-triazolo-[4,5-b]pyridin-1-yl-methylene]-N-methylmethanaminium hexafluorophosphate N-oxide (HATU, 13.3 mg, 0.03 mmol) was added all at once to (E)-3-[3-(3-cyano-5-fluoro-phenoxy)-2-methyl-6-(trifluoromethylsulfonyl)phenyl]prop-2-enoic acid (10 mg, 0.02 mmol), N,N-diisopropylethylamine (6 mg, 0.05 mmol) and benzylamine (5 mg, 0.05 mmol) in DMF (0.2 mL) at room temperature. The reaction mixture was stirred for 13 hours. The crude product was purified directly on reverse phase column (12+M, 14 CV, 20-100% MeCN/water) affording Compound 149 (5.1 mg, 0.01 mmol, 42% yield). LCMS ESI (+) m/z 519 (M+H). ¹H-NMR (400 MHz, CDCl₃): δ 8.01 (d, 1H), 7.79 (d, 1H), 7.39-7.29 (m, 5H), 7.27-7.24 (m, 1H), 7.14-7.13 (m, 1H), 7.06-7.03 (m, 1H), 6.97 (d, 1H), 6.06-6.02 (m, 2H), 4.60 (d, 2H), 2.33 (s, 3H).

Example 150

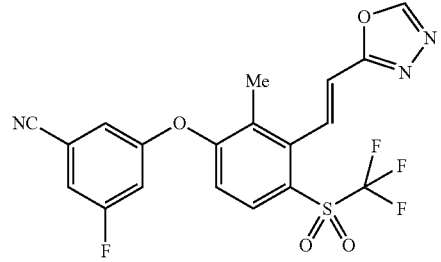 [SMILES: Cc1c(Oc2cc(F)cc(C#N)c2)ccc(S(=O)(=O)C(F)(F)F)c1/C=C/c1nnco1]

3-Fluoro-5-[2-methyl-3-[(E)-2-(1,3,4-oxadiazol-2-yl)vinyl]-4-(trifluoromethylsulfonyl)phenoxy]benzonitrile (Compound 150)

Step A: Preparation of (E)-3-[3-(3-cyano-5-fluoro-phenoxy)-2-methyl-6-(trifluoromethylsulfonyl)phenyl]prop-2-enehydrazide Isobutyl chloroformate (17 μL, 0.13 mmol) added dropwise to (E)-3-[3-(3-cyano-5-fluoro-phenoxy)-2-methyl-6-(trifluoromethylsulfonyl)phenyl]prop-2-enoic acid (50 mg, 0.12 mmol) and triethylamine (49 μL, 0.35 mmol) in tetrahydrofuran (1.2 mL) at 0° C. and stirred for 1 hour. Hydrazine monohydrate (28.25 μL, 0.5800 mmol) was added at 0° C. and stirred an additional 2 hours. The reaction was diluted with water (2 mL), extracted with EtOAc (3×5 mL), washed with brine (5 mL), dried over MgSO₄, filtered and concentrated then the crude product was used without further purification.

Step B: Preparation of 3-fluoro-5-[2-methyl-3-[(E)-2-(1,3,4-oxadiazol-2-yl)vinyl]-4-(trifluoromethylsulfonyl)phenoxy]benzonitrile (Compound 150)

p-Toluenesulfonic acid monohydrate (2 mg, 0.01 mmol) was added to a well stirred solution of (E)-3-[3-(3-cyano-5-fluoro-phenoxy)-2-methyl-6-(trifluoromethylsulfonyl)phenyl]prop-2-enehydrazide (23 mg, 0.05 mmol) in triethyl orthoformate (460 μL, 3.0 mmol) followed by warming the reaction mixture to 90° C. until completion as judged by LC-MS. The mixture was cooled to room temperature then concentrated in vacuo. The reaction mixture was then purified directly on reverse phase silica gel (12+M, 14 CV, 20-100% MeCN/water) affording Compound 150 (21 mg, 0.05 mmol, 89% yield). LCMS ESI (+) m/z 454 (M+H). ¹HNMR (400 MHz, CDCl₃): δ 8.47 (d, 1H), 8.05 (d, 1H), 7.98 (d, 1H), 7.31-7.27 (m, 1H), 7.19-7.18 (m, 1H), 7.10-7.07 (m, 1H), 7.01 (d, 1H), 6.72 (d, 1H), 2.42 (s, 3H).

Example 151

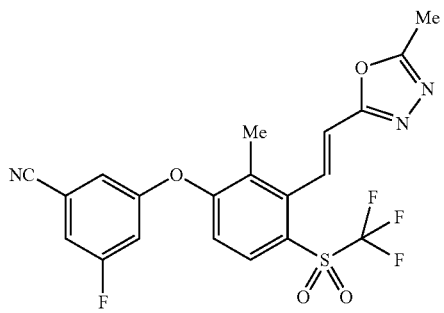 [SMILES: Cc1nnc(/C=C/c2c(S(=O)(=O)C(F)(F)F)ccc(Oc3cc(F)cc(C#N)c3)c2C)o1]

3-Fluoro-5-[2-methyl-3-[(E)-2-(5-methyl-1,3,4-oxadiazol-2-yl)vinyl]-4-(trifluoromethylsulfonyl)phenoxy]benzonitrile (Compound 151)

p-Toluenesulfonic acid monohydrate (1.7 mg, 0.01 mmol) was added to a well stirred solution of (E)-3-[3-(3-cyano-5-fluoro-phenoxy)-2-methyl-6-(trifluoromethylsulfonyl)phenyl]prop-2-enehydrazide (20 mg, 0.05 mmol) in triethyl orthoacetate (400 µL, 2.2 mmol) followed by warming the reaction mixture to 90° C. until completion as judged by LC-MS. The mixture was cooled to room temperature then concentrated in vacuo. The reaction mixture was purified directly on reverse phase silica gel (12+M, 14 CV, 20-100% MeCN/water) affording Compound 151 (1.3 mg, 0.003 mmol, 6% yield). LCMS ESI (+) m/z 468 (M+H); $^1$HNMR (400 MHz, CDCl$_3$): δ 8.03 (d, 1H), 7.85 (d, 1H), 7.30-7.27 (m, 1H), 7.18-7.17 (m, 1H), 7.09-7.05 (m, 1H), 6.99 (d, 1H), 6.62 (d, 1H), 2.63 (s, 3H), 2.40 (s, 3H).

Example 152

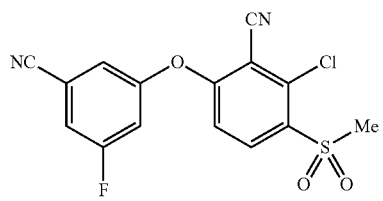 [SMILES: CS(=O)(=O)c1ccc(Oc2cc(F)cc(C#N)c2)c(C#N)c1Cl]

2-chloro-6-(3-cyano-5-fluorophenoxy)-3-(methylsulfonyl)benzonitrile (Compound 152)

Step A: Preparation of 3-bromo-2,4-dichloro-benzenesulfonyl chloride

2-Bromo-1,3-dichloro-benzene (5.0 g, 22.1 mmol) was added to sulfurochloridic acid (6.68 mL, 66 mmol) slowly. After addition, the mixture was stirred at 82° C. for 3 hours. After cooled to ambient temperature, the mixture was added slowly to ice water (200 mL) with vigorous stirring. The solid that formed was collected by filtration and dried to give 3-bromo-2,4-dichloro-benzenesulfonyl chloride (5.9 g, 18.2 mmol, 82% yield) as solid.

Step B: Preparation of 3-bromo-2,4-dichloro-benzenethiol 3-bromo-2,4-dichloro-benzenesulfonyl chloride (24.3 g, 74.9 mmol) in CH$_2$Cl$_2$ (80 mL) was added to triphenylphosphine (58.94 g, 225 mmol) in CH$_2$Cl$_2$ (80 mL) and N,N-dimethylformamide (5.8 mL, 75 mmol) at 0° C. After addition, the mixture was warmed to ambient temperature and stirred for 2 hours. Hydrochloric acid (1 N, 80 mL) and CH$_2$Cl$_2$ (50 mL) were added. The organic layer was separated, washed with brine, dried (sodium sulfate), filtered and concentrated under reduced pressure. The resulting solid was suspended in 1:5 MTBE/hexane (200 mL) and stirred for 30 minutes. The solid was removed by filtration and washed with 100 mL 1:5 hexane/MTBE. The filtrate was extracted with 1 N potassium carbonate solution (3×50 mL). The combined aqueous layers were extracted with MTBE (2×50 mL). The aqueous was acidified with 1 N HCl to pH-5 and extracted with MTBE (200 mL). The organic was washed with brine, dried (sodium sulfate), filtered and concentrated under reduced pressure. The residue was purified by flash chromatography on silica gel eluting with 1:1 hexanes/CH$_2$Cl$_2$ to give 3-bromo-2,4-dichloro-benzenethiol (17.6 g, 68 mmol, 91% yield) as solid.

Step C: Preparation of 2-bromo-1,3-dichloro-4-methylsulfanyl-benzene

Iodomethane (1.45 mL, 23.3 mmol) was added to a mixture of 3-bromo-2,4-dichloro-benzenethiol (2.0 g, 7.8 mmol) and potassium carbonate (2.14 g, 15.5 mmol) in DMF (5 mL) at ambient temperature. The reaction mixture was stirred at ambient temperature for 2 hours. Water (20 mL) and ethyl acetate (30 mL) were added. The organic layer was separated, washed with brine, dried (sodium sulfate), filtered and concentrated under reduced pressure. The residue was purified by flash chromatography on silica gel eluting with 1:1 hexane/ethyl acetate to give 2-bromo-1,3-dichloro-4-methylsulfanyl-benzene (2.08 g, 7.6 mmol, 98% yield) as solid.

Step D: Preparation of 2,6-dichloro-3-methylsulfanyl-benzonitrile

A mixture of 2-bromo-1,3-dichloro-4-methylsulfanyl-benzene (2.08 g, 7.7 mmol) and copper (I) cyanide (0.82 g, 9.2 mmol) in NMP (14 mL) was stirred at 190° C. in a microwave for 30 minutes. After cooling to ambient temperature, water (30 mL) and MTBE (50 mL) were added. The organic layer was separated, washed with brine, dried (sodium sulfate), filtered and concentrated under reduced pressure. The residue was purified by flash chromatography on silica gel eluting with 15:1 hexanes/ethyl acetate to give 2,6-dichloro-3-methylsulfanyl-benzonitrile (1.2 g, 5.5 mmol, 71% yield) as solid.

Step E: Preparation of 2,6-dichloro-3-methylsulfonyl-benzonitrile

Sodium periodate (1.87 g, 8.7 mmol) was added to 2,6-dichloro-3-methylsulfanyl-benzonitrile (0.76 g, 3.5 mmol) and ruthenium (III) chloride (0.02 g, 0.09 mmol) in a mixture of acetonitrile (10 mL), carbon tetrachloride (10 mL) and water (22 mL) at ambient temperature. The reaction mixture was stirred at ambient temperature for 18 hours. The mixture was filtered through a pad of celite and washed with MTBE (30 mL). The organic layer was separated, washed with brine, dried (sodium sulfate), filtered and concentrated under reduced pressure. The residue was purified by flash chromatography on silica gel eluting with 15:1 hexane/ethyl acetate to give 2,6-dichloro-3-methylsulfonyl-benzonitrile (0.3 g, 1.2 mmol, 34% yield) as solid.

Step F: Preparation of 2-chloro-6-(3-cyano-5-fluorophenoxy)-3-(methylsulfonyl)benzonitrile (Compound 152)

A solution of 3-fluoro-5-hydroxy-benzonitrile (27.41 mg, 0.2 mmol) in 1-methyl-2-pyrrolidone (0.5 mL) was added dropwise to an ice cold mixture of 2,6-dichloro-3-methylsulfonyl-benzonitrile (50.0 mg, 0.2 mmol) and cesium carbonate (39 mg, 0.12 mmol) in 1-methyl-2-pyrrolidone (0.5 mL). The reaction mixture was stirred at 0° C. for two hours then warmed to 50° C. for 16 hours. The reaction mixture was cooled to room temperature then directly purified on reverse phase silica gel (25+M, 14 CV, 20-100% MeCN/ water) affording Compound 152 (38 mg, 0.1 mmol, 51% yield) as a white solid. LCMS ESI (−) m/z 349 (M−H); ¹HNMR (400 MHz, CDCl₃): δ 8.32 (d, 1H), 7.38-7.35 (m, 1H), 7.26-7.25 (m, 1H), 7.18-7.15 (m, 1H), 6.97 (d, 1H), 3.30 (s, 3H).

Example 153

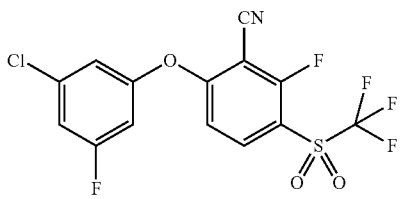 [SMILES: N#Cc1c(Oc2cc(F)cc(Cl)c2)ccc(S(=O)(=O)C(F)(F)F)c1F]

6-(3-chloro-5-fluorophenoxy)-2-fluoro-3-((trifluoromethyl)sulfonyl)benzonitrile (Compound 153)

Step A: Preparation of 3-bromo-2,6-difluorobenzonitrile

A solution of 2,6-difluorobenzonitrile (5.0 g, 36 mmol) in concentrated sulfuric acid (25 mL) was treated with NBS (7.0 g, 29.5 mmol) at 0° C. and stirred at ambient temperature for 24 hours. Ice (about 100 g) was added to the reaction mixture. After melting, the mixture was extracted with MTBE (100 mL). The organic layer was separated, washed with brine, dried (sodium sulfate), filtered and concentrated under reduced pressure. The residue was purified by flash chromatography on silica gel eluting with 5:1 to 1:2 hexanes/ethyl acetate to give both 3-bromo-2,6-difluorobenzonitrile (5.5 g, 70% yield) as solid and 3-bromo-2,6-difluorobenzamide (2.1 g, 25%) as solid.

Step B: Preparation of 2,6-difluoro-3-mercaptobenzonitrile

A mixture of 3-bromo-2,6-difluorobenzonitrile (4.4 g, 20 mmol), potassium ethanethioate (2.88 g, 25 mmol), Pd₂(dba)₃ (0.555 g, 0.61 mmol) and Xantphos (0.70 g, 1.2 mmol) in p-dioxane (30 mL) was stirred at 102° C. for 15 hours. After cooling to ambient temperature, 28% aqueous ammonium hydroxide (12.3 g, 202 mmol) was added. The mixture was stirred at ambient temperature for 1 hour. Water (50 mL) and 2:1 MTBE/hexanes (200 mL) were added. The aqueous layer was separated, acidified with 1 N HCl to pH-5 and extracted with MTBE (50 mL). The organic layer was separated, washed with brine, dried (sodium sulfate), filtered and concentrated under reduced pressure. The residue was purified by flash chromatography on silica gel eluting with 3:1 hexane/CH₂Cl₂ to give 2,6-difluoro-3-mercaptobenzonitrile (0.74 g, 21%) as solid.

Step C: Preparation of 2,6-difluoro-3-((trifluoromethyl)thio)benzonitrile

Trifluoromethyliodide (2.29 g, 11.7 mmol) was condensed into a degassed solution of 2,6-difluoro-3-mercaptobenzonitrile (0.50 g, 2.9 mmol), methyl viologen dichloride (75 mg, 0.29 mmol) and Et₃N (1.0 mL, 7.3 mmol) in DMF (4.0 mL) at −78° C. in a sealed tube. The septum was quickly replaced with a threaded teflon cap and tightly sealed. The reaction mixture was then warmed to room temperature and stirred for 60 hours. The reaction mixture was cooled to −78° C. and opened carefully, poured into brine (10 mL), extracted with Et₂O (5×20 mL), washed with brine (20 mL), dried (Na₂SO₄), filtered through a 4 cm plug of Florisil® and concentrated in vacuo. Crude 2,6-difluoro-3-((trifluoromethyl)thio)benzonitrile (698 mg) was used without purification in the following reaction.

Step D: Preparation of 2,6-difluoro-3-((trifluoromethyl)sulfonyl)benzonitrile

Sodium periodate (1.56 g, 7.3 mmol) was added all at once to crude 2,6-difluoro-3-((trifluoromethyl)thio)benzonitrile (698 mg, 2.92 mmol) and RuCl₃ (15 mg, 0.073 mmol) in MeCN (7 mL)/CCl₄ (7 mL)/water (14 mL) at room temperature then stirred vigorously for 2 hours. The mixture was diluted with water (20 mL), extracted with CH₂Cl₂ (4×25 mL), washed with brine (25 mL), dried over Na₂SO₄, filtered and concentrated in vacuo. The residue was purified on silica gel (25 g SNAP, 14 CV, 20-60% EtOAc/hexanes) afforded 2,6-difluoro-3-((trifluoromethyl)sulfonyl)benzonitrile (560 mg, 71% yield over 2 steps) as a white solid.

Step E: Preparation of 6-(3-chloro-5-fluorophenoxy)-2-fluoro-3-((trifluoromethyl)sulfonyl)benzonitrile (Compound 153)

Sodium bicarbonate (17 mg, 0.2 mmol) was added all at once to 3-chloro-5-fluorophenol (15 mg, 0.1 mmol) and 2,6-difluoro-3-((trifluoromethyl)sulfonyl)benzonitrile (27.6 mg, 0.1 mmol) in MeCN (0.5 mL) then stirred at room temperature for 1.5 hours then warmed to 50° C. and stirred for an additional 7 hours. The mixture was concentrated then purified on reverse phase silica gel (12+M, 14 CV, 20-100% MeCN/water) affording Compound 153 (14 mg, 35% yield) as a white solid. LCMS ESI (−) m/z 396 (M−H). ¹HNMR (400 MHz, CDCl₃): δ 8.01 (d, 1H), 7.22 (d, 1H), 7.09-7.05 (m, 1H), 6.94-6.92 (m, 1H), 6.80-6.77 (m, 1H).

Example 154

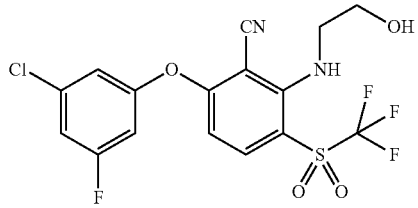 [SMILES: N#Cc1c(Oc2cc(F)cc(Cl)c2)ccc(S(=O)(=O)C(F)(F)F)c1NCCO]

6-(3-Chloro-5-fluoro-phenoxy)-2-(2-hydroxyethylamino)-3-(trifluoromethylsulfonyl)benzonitrile (Compound 154)

To 6-(3-chloro-5-fluoro-phenoxy)-2-fluoro-3-(trifluoromethylsulfonyl)benzonitrile (30 mg, 0.08 mmol) in a reaction vial was added ethanolamine (20 mg, 0.33 mmol) followed by THF (100 µL). The reaction vial was sealed then the reaction mixture was warmed to 50° C. for 18 hours. The reaction mixture was purified directly by preparative TLC eluting with 80% Et₂O/hexane affording Compound 154 (12 mg, 0.026 mmol, 34% yield) as a yellow oil. LCMS ESI (−) m/z 437 (M−H). ¹HNMR (400 MHz, CDCl₃): δ 7.44-7.40

(m, 1H), 7.33 (m, 1H), 7.15 (d, 1H), 6.91-6.88 (m, 1H), 6.74-6.73 (m, 1H), 6.62-6.58 (m, 1H), 3.95-3.91 (m, 2H), 3.44-3.40 (m, 2H), 1.71-1.69 (m, 1H).

Example 155

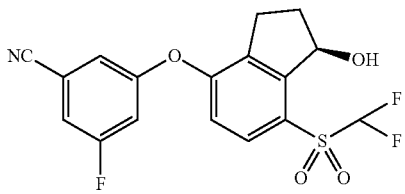 [SMILES: N#Cc1cc(F)cc(Oc2ccc(S(=O)(=O)C(F)F)c3c2CC[C@H]3O)c1]

Preparation of 3-[(1R)-7-(difluoromethylsulfonyl)-1-hydroxy-indan-4-yl]oxy-5-fluoro-benzonitrile (Compound 155)

Prepared similarly as described in Example 1 using 3-fluoro-5-hydroxybenzonitrile in place of 3-chloro-5-fluoro-phenol in Step G. The ee was determined to be 98% by $^{19}F$ NMR analysis of the corresponding Mosher ester. LCMS ESI (−) m/z 428 (M+HCO$_2^-$). $^1$H NMR (400 MHz, CDCl$_3$): δ 7.85 (d, 1H), 7.26-7.24 (m, 1H), 7.17-7.15 (m, 1H), 7.06-7.03 (m, 1H), 6.97 (d, 1H), 6.37 (t, 3H), 5.68-5.65 (m, 1H), 3.20-3.11 (m, 2H), 2.94-2.87 (m, 1H), 2.51-2.41 (m, 1H), 2.31-2.25 (m, 1H).

Example 156

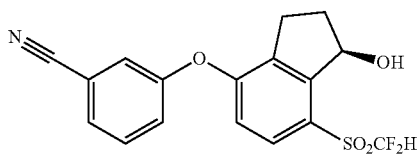

3-[(1R)-7-(Difluoromethylsulfonyl)-1-hydroxy-indan-4-yl]oxybenzonitrile (Compound 156)

Prepared similarly as described in Example 1 using 3-hydroxybenzonitrile in place of 3-chloro-5-fluoro-phenol in Step G. The ee was determined to be 98% by $^{19}F$ NMR analysis of the corresponding Mosher ester. LCMS ESI (−) m/z 410 (M+HCO$_2^-$); $^1$H-NMR (400 MHz, CDCl$_3$): δ 7.80 (d, 1H), 7.56-7.54 (m, 2H), 7.39-7.30 (m, 2H), 6.88-6.84 (m, 1H), 6.38 (t, 1H), 5.68-5.66 (m, 1H), 3.22-3.13 (m, 2H), 2.98-2.90 (m, 1H), 2.50-2.41 (m, 1H), 2.32-2.22 (m, 1H).

Example 157

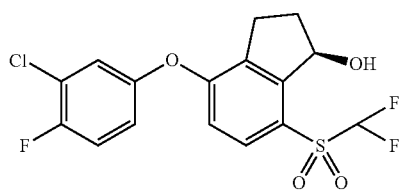 [SMILES: O=S(=O)(c1ccc(Oc2ccc(F)c(Cl)c2)c2c1[C@H](O)CC2)C(F)F]

(1R)-4-(3-Chloro-4-fluoro-phenoxy)-7-(difluoromethylsulfonyl)indan-1-ol (Compound 157)

Prepared similarly as described in Example 1 using 3-chloro-4-fluoro-phenol in place of 3-chloro-5-fluoro-phenol in Step G. The ee was determined to be 98% by $^{19}F$ NMR analysis of the corresponding Mosher ester. LCMS ESI (−) 437 (M+HCO2$^-$).

Example 158

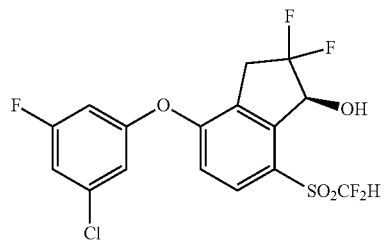

(1S)-4-(3-Chloro-5-fluoro-phenoxy)-7-(difluoromethylsulfonyl)-2,2-difluoro-indan-1-ol (Compound 158)

An ice cold solution of RuCl(p-cymene)[(R,R)-Ts-DPEN] (0.51 mg, 0.08 mmol) in CH$_2$Cl$_2$ (0.20 mL) was added by syringe to an ice cold solution of 4-(3-chloro-5-fluoro-phenoxy)-7-(difluoromethylsulfonyl)-2,2-difluoro-indan-1-one (17 mg, 0.04 mmol), triethylamine (11 µL, 0.08 mmol) and formic acid (4.5 µL, 0.12 mmol) in CH$_2$Cl$_2$ (0.20 mL). The reaction vial was then placed in a 4° C. refrigerator overnight. The crude reaction mixture was purified directly on silca gel (10 g SNAP, 14 CV, 5-50% EtOAc/hexane) affording Compound 158 (8 mg, 0.02 mmol, 46% yield). The ee was determined to be 91% by $^{19}F$ NMR analysis of the corresponding Mosher ester. LCMS ESI (−) 473 (M+HCO2$^-$). $^1$H NMR (400 MHz, CDCl$_3$): δ 7.90 (d, 1H), 7.06-7.03 (m, 1H), 6.99 (d, 1H), 6.94-6.93 (m, 1H), 6.78-6.75 (m, 1H), 6.43 (t, 1H), 5.52-5.48 (m, 1H), 3.64-3.43 (m, 2H), 3.29 (s, 1H).

Example 159

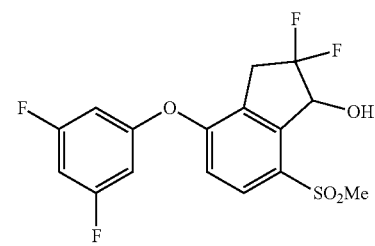 [SMILES: CS(=O)(=O)c1ccc(Oc2cc(F)cc(F)c2)c2c1C(O)C(F)(F)C2]

4-(3,5-Difluorophenoxy)-2,2-difluoro-7-(methylsulfonyl)-2,3-dihydro-1H-inden-1-ol (Compound 159)

Step A: Preparation of 4-fluoro-7-(methylthio)-2,3-dihydro-1H-inden-1-one

A stirred mixture of S-(7-fluoro-3-oxo-indan-4-yl)-N,N-dimethylcarbamothioate (50 g, 199 mmol), 95% ethanol (690 mL) and 3 N NaOH solution (398 mL, 1.6 mol) was heated at reflux for 30 minutes. After cooling, the reaction mixture was cooled to 0° C. using an ice bath. Iodomethane (16 mL, 259 mmol) was added dropwise to the reaction mixture. The reaction mixture was stirred at 0° C. for 1 hour, and then concentrated under reduced pressure to remove EtOH. The residue was partitioned between EtOAc and water. The aqueous layer was extracted with EtOAc. The combined organic layers were washed with brine, dried and concentrated. The crude was used in the next step without further purification. LCMS ESI (+) m/z 197 (M+H).

Step B: Preparation of 4-fluoro-7-(methylsulfonyl)-2,3-dihydro-1H-inden-1-one

A solution of Oxone® (117 g, 191 mmol) in water (580 mL) was added dropwise to a suspension of 4-fluoro-7-(methylthio)-2,3-dihydro-1H-inden-1-one (crude from Step A, 17 g, 86.6 mmol) in methanol (580 mL) at ambient temperature. The temperature slightly increased during the addition. The reaction mixture was stirred at ambient temperature for 5 hours. Residual solids were removed by filtration and washed with EtOAc. The organics were removed from the filtrate in vacuo. The residue was extracted with EtOAc (3×), washed with brine and dried. The aqueous layer was further extracted with dichloromethane (2×). The organic layers were washed with brine, dried over $Na_2SO_4$, and concentrated in vacuo. The resulting solid was triturated with EtOAc/hexane (1:5) to give 4-fluoro-7-(methylsulfonyl)-2,3-dihydro-1H-inden-1-one as a white solid (16.8 g). The mother liquor was concentrated and purified by flash chromatography on silica gel (10-80% EtOAc in hexane) to afford additional 4-fluoro-7-(methylsulfonyl)-2,3-dihydro-1H-inden-1-one (2.30 g, combined 19.1 g, 96%). LCMS ESI (+) m/z 229 (M+H).

Step C: Preparation of 4-fluoro-7-(methylsulfonyl)-2,3-dihydrospiro[indene-1,2'-[1,3]dioxolane]

Trimethylsilyl trifluoromethanesulfonate (4.8 mL, 26.6 mmol) was added dropwise to a solution of 4-fluoro-7-(methylsulfonyl)-2,3-dihydro-1H-inden-1-one (19.1 g, 83.6 mmol) and trimethyl(2-trimethylsilyloxyethoxy)silane (28.5 mL, 116 mmol) in dichloromethane (310 mL) which was cooled to −78° C. under nitrogen. The reaction mixture was allowed to warm to ambient temperature. After 6 hours, the reaction was quenched with triethylamine (46.6 mL, 334 mmol) and evaporated. The residue was partitioned between EtOAc and brine. The organic layer was washed with water and brine, dried over $MgSO_4$, filtered, and evaporated. Dichloromethane was added to the residue which caused a solid to form. The precipitated product was collected by filtration, washed with 50% dichloromethane/hexanes and air-dried to afford 4-fluoro-7-(methylsulfonyl)-2,3-dihydrospiro[indene-1,2'[1,3]dioxolane] (9.95 g). The filtrate was concentrated and purified by flash chromatography on silica gel (20-60% EtOAc/hexane) to give additional 4-fluoro-7-(methylsulfonyl)-2,3-dihydrospiro[indene-1,2' [1,3]dioxolane] (4.58 g, combined 14.5 g, 64%). LCMS ESI (+) m/z 273 (M+H).

Step D: Preparation of 4-(3,5-difluorophenoxy)-2,2-difluoro-7-(methylsulfonyl)-2,3-dihydro-1H-inden-1-ol (Compound 159)

Sodium borohydride (3.03 mg, 0.08 mmol) was added all at once to 4-(3,5-difluorophenoxy)-2,2-difluoro-7-methyl-sulfonyl-indan-1-one (15.0 mg, 0.04 mmol, prepared from 4-fluoro-7-(methylsulfonyl)-2,3-dihydrospiro[indene-1,2'-[1,3]dioxolane] following procedures in Example 8) in methanol (0.5 mL) at room temperature and stirred for 5 minutes. The reaction was quenched with 1 N HCl (1 mL), extracted with EtOAc (3×5 mL), washed with brine (5 ml), dried over MgSO4, filtered and concentrated in vacuo. The crude product was purified on silica gel (10 g SNAP ULTRA, 14 CV, 20-100% EtOAc/hexane) affording Compound 159 (9 mg, 0.024 mmol, 60% yield). LCMS ESI (−) 421 (M+HCO2−); $^1$HNMR (400 MHz, CDCl$_3$): δ 7.89 (d, 1H), 7.01 (d, 1H), 6.74-6.68 (m, 1H), 6.62-6.58 (m, 2H), 5.61-5.57 (m, 1H), 3.54-3.40 (m, 3H), 3.22 (s, 3H).

Example 160

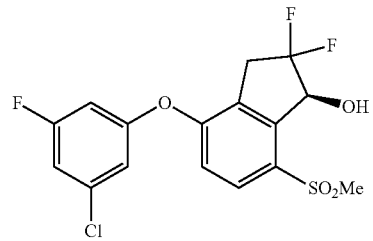 [SMILES: CS(=O)(=O)c1ccc(Oc2cc(F)cc(Cl)c2)c2c1[C@H](O)C(F)(F)C2]

(1S)-4-(3-Chloro-5-fluoro-phenoxy)-2,2-difluoro-7-methylsulfonyl-indan-1-ol (Compound 160)

Step A: Preparation of 4'-(3-chloro-5-fluoro-phenoxy)-7'-methylsulfonyl-spiro[1,3-dioxolane-2,1'-indane]

Cesium hydrogen carbonate (320 mg, 1.65 mmol) was added all at once to 4'-fluoro-7'-methylsulfonyl-spiro[1,3-dioxolane-2,1'-indane] (300 mg, 1.1 mmol) and 3-chloro-5-fluoro-phenol (242 mg, 1.65 mmol) in 1-methyl-2-pyrrolidone (4.4 mL) at room temperature in a microwave reaction vial equipped with a stir bar, flushed with nitrogen then sealed with a crimp cap. The reaction mixture was heated at 160° C. for 2 hours using microwave heating. Additional CsHCO$_3$ (100 mg) was added and the reaction was heated to 160° C. for an additional 30 minutes. The crude product was purified directly on reverse phase silica gel (25+M, 14 CV, 20-100% MeCN/water) affording 4'-(3-chloro-5-fluoro-phenoxy)-7'-methylsulfonyl-spiro[1,3-dioxolane-2,1'-indane] (303 mg, 0.76 mmol, 69% yield).

Step B: Preparation of 4-(3-chloro-5-fluoro-phenoxy)-7-methylsulfonyl-indan-1-one Pyridinium para-toluenesulfonate (191 mg, 0.76 mmol) was added all at once to a solution of 4'-(3-chloro-5-fluoro-phenoxy)-7'-methylsulfonyl-spiro[1,3-dioxolane-2,1'-indane] (303 mg, 0.76 mmol) in acetone (4 mL)/water (1 mL) at room temperature then warmed to reflux for 5 hours. The reaction was concentrated in vacuo then purified on silica gel (10 g SNAP, 14 CV, 20-100% EtOAc/hexanes) affording 4-(3-chloro-5-fluoro-phenoxy)-7-methylsulfonyl-indan-1-one (263 mg, 0.74 mmol, 97% yield).

Step C: Preparation of N-butyl-4-(3-chloro-5-fluoro-phenoxy)-7-methylsulfonyl-indan-1-imine Butan-1-amine (2.93 mL, 29.65 mmol) was added to 4-(3-chloro-5-fluoro-phenoxy)-7-methylsulfonyl-indan-1- one (263 mg, 0.74 mmol) and trifluoroacetic acid (11.35 µL, 0.15 mmol) in benzene (10 mL) at room temperature. The reaction was warmed to reflux with the azeotropic removal of water by a Dean-Stark apparatus for 4 hours, then cooled to room temperature and concentrated in vacuo. The residue was diluted with water (10 mL), extracted with MTBE (3×10 mL), washed with brine, dried over Na₂SO₄, filtered and concentrated. The crude product was used without purification in the next step immediately.

Step D: Preparation of 4-(3-chloro-5-fluoro-phenoxy)-2,2-difluoro-7-methylsulfonyl-indan-1-one Selectfluor® (654 mg, 1.85 mmol) was added to crude N-butyl-4-(3-chloro-5-fluoro-phenoxy)-7-methylsulfonyl-indan-1-imine (303 mg, 0.74 mmol) and sodium sulfate (157 mg, 1.1 mmol) in acetonitrile (8 mL) then warmed to reflux for 6 hours. The reaction was cooled to room temperature, concentrated HCl (1 mL, 12 mmol) was added and the mixture was stirred for 15 minutes. The solution was diluted with water (10 mL), extracted with EtOAc (3×10 mL), washed with brine (10 mL), dried over MgSO₄, filtered and concentrated in vacuo. The crude product was purified on silica gel (25 g SNAP, 14 CV, 20-100% EtOAc/hexane) affording 4-(3-chloro-5-fluoro-phenoxy)-2,2-difluoro-7-methylsulfonyl-indan-1-one (200 mg, 0.5 mmol, 69% yield).

Step E: Preparation of (1S)-4-(3-chloro-5-fluoro-phenoxy)-2,2-difluoro-7-methylsulfonyl-indan-1-ol (Compound 160)

An ice cold solution of RuCl(p-cymene)[(R,R)-Ts-DPEN] (1.1 mg, 0.0017 mmol) in dichloromethane (0.9 mL) was added by syringe to an ice cold solution of 4-(3-chloro-5-fluoro-phenoxy)-2,2-difluoro-7-methylsulfonyl-indan-1-one (68 mg, 0.17 mmol), triethylamine (48.4 µL, 0.35 mmol) and formic acid (19.7 µL, 0.52 mmol) in dichloromethane (0.9 mL). The reactor was sealed then placed in a refrigerator at 4° C. overnight. The crude product was purified directly on silica gel (10 g SNAP ULTRA, 14 CV, 10-60% EtOAc/hexane) affording Compound 160 (60 mg, 0.15 mmol, 87% yield). The ee was determined to be >99% by ¹⁹F NMR analysis of the corresponding Mosher ester. LCMS ESI (+) m/z 393 (M+H). ¹HNMR (400 MHz, CDCl₃): δ 7.90-7.87 (m, 1H), 7.01-6.97 (m, 2H), 6.88-6.87 (m, 1H), 6.73-6.69 (m, 1H), 5.61-5.57 (m, 1H), 3.57-3.37 (m, 3H), 3.22 (s, 3H).

Example 161

(S)-4-(3,5-Difluorophenoxy)-2,2-difluoro-7-(methylsulfonyl)-2,3-dihydro-1H-inden-1-ol (Compound 161)

An ice cold solution of RuCl(p-cymene)[(R,R)-Ts-DPEN] (0.85 mg, 0.01 mmol) in CH₂Cl₂ (0.6 mL) was added by syringe to an ice cold solution of 4-(3,5-difluoro-phenoxy)-2,2-difluoro-7-methylsulfonyl-indan-1-one (50 mg, 0.13 mmol, prepared according to the procedures in Examples 8 and 160), triethylamine (37 µL, 0.27 mmol) and formic acid (15 µL, 0.40 mmol) in CH₂Cl₂ (0.60 mL) then placed in a refrigerator at 4° C. overnight. The crude product was purified directly on silica gel (10 g SNAP ULTRA, 14 CV, 10-60% EtOAc/hexane) affording Compound 161 (37 mg, 0.1 mmol, 73% yield). The ee was determined to be >96% by ¹⁹F NMR analysis of the corresponding Mosher ester. LCMS ESI (-) 421 (M+HCO₂⁻); ¹HNMR (400 MHz, CDCl₃): δ 7.89 (d, 1H), 7.01 (d, 1H), 6.74-6.68 (m, 1H), 6.62-6.58 (m, 2H), 5.61-5.57 (m, 1H), 3.54-3.40 (m, 3H), 3.22 (s, 3H).

Example 162

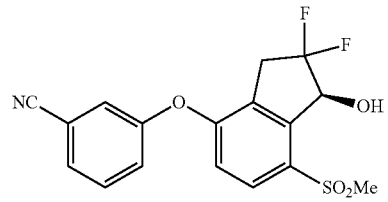

3-[(1S)-2,2-Difluoro-1-hydroxy-7-methylsulfonyl-indan-4-yl]oxybenzonitrile (Compound 162)

An ice cold solution of RuCl(p-cymene)[(R,R)-Ts-DPEN] (1.2 mg, 0.02 mmol) in CH₂Cl₂ (0.9 mL) was added by syringe to an ice cold solution of 3-(2,2-difluoro-7-methylsulfonyl-1-oxo-indan-4-yl)oxybenzonitrile (70 mg, 0.19 mmol, prepared similarly according to the procedures in Examples 8 and 160), triethylamine (53.7 µL, 0.39 mmol) and formic acid (21.8 µL, 0.58 mmol) in CH₂Cl₂ (0.9 mL) then placed in a refrigerator at 4° C. overnight. The crude product was purified directly on silica gel (10 g SNAP ULTRA, 14 CV, 10-60% EtOAc/hexane) affording Compound 162 (56 mg, 0.15 mmol, 78% yield). The ee was determined to be >99% by ¹⁹F NMR analysis of the corresponding Mosher ester. LCMS ESI (-) 410 (M+HCO₂).

Example 163

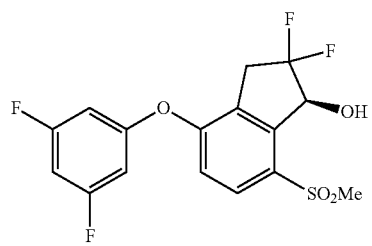 [SMILES: CS(=O)(=O)c1ccc(Oc2cc(F)cc(F)c2)c2c1[C@H](O)C(F)(F)C2]

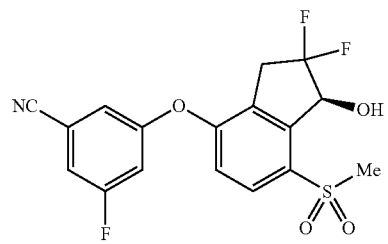 [SMILES: CS(=O)(=O)c1ccc(Oc2cc(F)cc(C#N)c2)c2c1[C@H](O)C(F)(F)C2]

(S)-3-((2,2-Difluoro-1-hydroxy-7-(methylsulfonyl)-2,3-dihydro-1H-inden-4-yl)oxy)-5-fluorobenzonitrile (Compound 163)

Step A: Preparation of 4'-(3-bromo-5-fluoro-phenoxy)-7'-methylsulfonyl-spiro[1,3-dioxolane-2,1'-indane]

Cesium hydrogen carbonate (142 mg, 0.73 mmol) was added all at once to 4'-fluoro-7'-methylsulfonyl-spiro[1,3-dioxolane-2,1'-indane] (100 mg, 0.37 mmol) and 3-bromo-5-fluoro-phenol (105 mg, 0.55 mmol) in 1-methyl-2-pyrrolidone (1.5 mL) at room temperature in a microwave reaction vial equipped with a stir bar. The flask was flushed with nitrogen then sealed with a crimp cap. The reaction was heated to 150° C. for 7 hours, cooled to ambient temperature then purified directly on reverse phase silica gel (25+M, 14 CV, 20-100% MeCN/water) affording 4'-(3-bromo-5-fluoro-phenoxy)-7'-methylsulfonyl-spiro[1,3-dioxolane-2,1'-indane] (118 mg, 0.26 mmol, 72% yield).

Step B: Preparation of 3-fluoro-5-(7'-methylsulfonylspiro[1,3-dioxolane-2,1'-indane]-4'-yl)oxy-benzonitrile Dichloro[1;1'-bis(diphenylphosphino)ferrocene]palladium (II) dichloromethane adduct (784 mg, 0.97 mmol) was quickly added to a degassed mixture of 4'-(3-bromo-5-fluoro-phenoxy)-7'-methylsulfonyl-spiro[1,3-dioxolane-2,1'-indane] (4.3 g, 9.7 mmol), zinc cyanide (1.14 g, 9.7 mmol) and zinc powder (761 mg, 11.6 mmol) in DMF (60 mL) under nitrogen. The reaction mixture was then warmed to 110° C. for 2 hours. After cooling, the mixture was filtered through a pad of celite. The filtrate was diluted with water (100 mL), extracted with MTBE (5×100 mL), washed with brine (100 mL), dried over MgSO$_4$, filtered and concentrated in vacuo. The crude product was purified on silica gel (100 g SNAP, 14 CV, 15-100% EtOAc/hexanes) then purified again on silica gel (25 g Ultra SNAP, 14 CV, 0-20% dichloromethane/EtOAc) affording 3-fluoro-5-(7'-methylsulfonylspiro[1,3-dioxolane-2,1'-indane]-4'-yl)oxy-benzonitrile (3.77 g, 9.7 mmol, 100% yield).

Step C: Preparation of 3-fluoro-5-(7-methylsulfonyl-1-oxo-indan-4-yl)oxy-benzonitrile Pyridinium para-toluenesulfonate (354 mg, 1.4 mmol) was added all at once to a solution of 3-fluoro-5-(7'-methylsulfonylspiro[1,3-dioxolane-2,1'-indane]-4'-yl)oxy-benzonitrile (550 mg, 1.4 mmol) in acetone (6 mL)/water (2 mL) at room temperature and then warmed to reflux until completion. The mixture was concentrated in vacuo then purified on silica gel (10 g SNAP, 14 CV, 20-100% EtOAc/hexane) affording 3-fluoro-5-(7-methylsulfonyl-1-oxo-indan-4-yl)oxy-benzonitrile (450 mg, 1.3 mmol, 92% yield).

Step D: Preparation of 3-[(E,Z)-1-butylimino-7-methylsulfonyl-indan-4-yl]oxy-5-fluoro-benzonitrile Butan-1-amine (5.15 mL, 52 mmol) was added to 3-fluoro-5-(7-methylsulfonyl-1-oxo-indan-4-yl)oxy-benzonitrile (450 mg, 1.3 mmol) and trifluoroacetic acid (19.96 μL, 0.26 mmol) in benzene (10 mL) at room temperature then warmed to reflux with the azeotropic removal of water by a Dean-Stark apparatus. Progress of the reaction was monitored by $^1$H-NMR. When complete, the reaction was cooled to room temperature then concentrated in vacuo. The residue was diluted with water (10 mL), extracted with MTBE (3×10 mL), washed with brine and dried over Na$_2$SO$_4$, filtered and concentrated. Crude 3-[(E,Z)-1-butylimino-7-methylsulfonyl-indan-4-yl]oxy-5-fluoro-benzonitrile was used immediately without purification in the next step.

Step E: Preparation of 3-(2,2-difluoro-7-methylsulfonyl-1-oxo-indan-4-yl)oxy-5-fluoro-benzonitrile Selectfluor® (1.15 g, 3.25 mmol) was added to crude 3-[(E,Z)-1-butylimino-7-methylsulfonyl-indan-4-yl]oxy-5-fluoro-benzonitrile (520 mg, 1.3 mmol) and sodium sulfate (369 mg, 2.6 mmol) in acetonitrile (10 mL) then warmed to reflux for 6 hours. The reaction was cooled to room temperature, concentrated HCl (1.0 mL, 12 mmol) was added and stirred for 15 minutes. The mixture was diluted with water (10 mL), extracted with EtOAc (3×10 mL), washed with brine (10 mL), dried over MgSO$_4$, filtered and concentrated in vacuo. The residue was purified on silica gel (25 g SNAP, 14 CV, 20-100% EtOAc/hexane) afforded 3-(2,2-difluoro-7-methylsulfonyl-1-oxo-indan-4-yl)oxy-5-fluoro-benzonitrile (437 mg, 1.2 mmol, 88% yield).

Step F: Preparation of (S)-3-((2,2-difluoro-1-hydroxy-7-(methylsulfonyl)-2,3-dihydro-1H-inden-4-yl)oxy)-5-fluorobenzonitrile (Compound 163)

An ice cold solution of RuCl(p-cymene)[(R,R)-Ts-DPEN] (40.7 mg, 0.06 mmol) in CH$_2$Cl$_2$ (30 mL) was added by syringe under nitrogen to an ice cold solution of 3-(2,2-difluoro-7-methylsulfonyl-1-oxo-indan-4-yl)oxy-5-fluoro-benzonitrile (2.44 g, 6.4 mmol), triethylamine (1.78 mL, 12.8 mmol) and formic acid (724 μL, 19.2 mmol) in CH$_2$Cl$_2$ (30 mL). The reaction was placed in a refrigerator at 4° C. for 16 hours. The mixture was concentrated to 10 mL then purified directly on silica gel (25 g SNAP ULTRA, 14 CV, 10-50% EtOAc/hexane) affording Compound 163 (2.15 g, 5.6 mmol, 87% yield). Enantiomeric excess (98%) was determined by chiral HPLC. Retention time for (S)-enantiomer: 1.93 minutes; retention time for (R)-enantiomer: 2.32 minutes. LCMS ESI (−) 428 (M+HCO$_2$). $^1$HNMR (400 MHz, CDCl$_3$): δ 7.93 (d, 1H), 7.27-7.24 (m, 1H), 7.15-7.14 (m, 1H), 7.07-7.03 (m, 1H), 7.00 (d, 1H), 5.63-5.58 (m, 1H), 3.56-3.35 (m, 3H), 3.24 (s, 3H).

Alternative protocol for the synthesis of 3-fluoro-5-(7'-methylsulfonylspiro[1,3-dioxolane-2,1'-indane]-4'-yl)oxy-benzonitrile Cesium hydrogen carbonate (320.48 mg, 1.65 mmol) was added all at once to 4'-fluoro-7'-methylsulfonyl-spiro[1,3-dioxolane-2,1'-indane] (300 mg, 1.1 mmol) and 3-fluoro-5-hydroxy-benzonitrile (227 mg, 1.65 mmol) in 1-methyl-2-pyrrolidone (4.4 mL) at room temperature in a microwave reaction vial equipped with a stir bar, flushed with nitrogen then sealed with a crimp cap. The reaction mixture was heated to 160° C. for 2 hours in a microwave reactor. Additional CsHCO$_3$ (100 mg) was added and the mixture was heated at 160° C. for 30 minutes in a microwave reactor. The mixture was purified directly on reverse phase column (25+M, 14 CV, 20-100% MeCN/water) affording 3-fluoro- 5-(7'-methylsulfonylspiro[1,3-dioxolane-2,1'-indane]-4'-yl)oxy-benzonitrile (104 mg, 0.26 mmol, 24% yield).

Alternative preparation of 3-fluoro-5-((7-(methylsulfonyl)-2,3-dihydrospiro[indene-1,2'-[1,3]dioxolan]-4-yl)oxy)benzonitrile

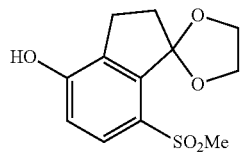 [SMILES: CS(=O)(=O)c1ccc(O)c2c1C1(CC2)OCCO1]

7-(Methylsulfonyl)-2,3-dihydrospiro[indene-1,2'[1,3]dioxolan]-4-ol

Step A: Preparation of 7-(methylsulfonyl)-2,3-dihydrospiro[indene-1,2'-[1,3]dioxolan]-4-ol Sodium hydroxide (3 M, 62.4 mL, 187.3 mmol) was added by syringe to a solution of 4'-fluoro-7'-methylsulfonyl-spiro[1,3-dioxolane-2,1'-indane] (25.5 g, 93.6 mmol) in DMSO (280 mL) under nitrogen then the mixture was warmed to 75° C. until complete as judged by LC-MS (5 hours). The reaction mixture was cooled to room temperature then poured into ice cold 0.7 M $KHSO_4$ (255 mL), adjusted to pH 5-6 with saturated $NaHCO_3$, then extracted with EtOAc (5×300 mL). The combined organic layers were washed with water (100 mL), brine (100 mL), dried over $Na_2SO_4$, filtered and concentrated in vacuo affording 7-(methylsulfonyl)-2,3-dihydrospiro[indene-1,2'-[1,3]dioxolan]-4-ol (24.6 g, 97% yield). LCMS ESI (+) m/z 271 (M+H).

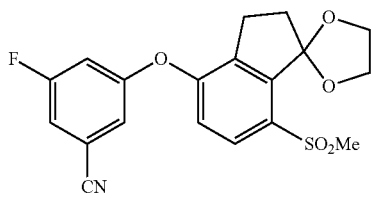 [SMILES: CS(=O)(=O)c1ccc(Oc2cc(F)cc(C#N)c2)c2c1C1(CC2)OCCO1]

3-Fluoro-5-((7-(methylsulfonyl)-2,3-dihydrospiro[indene-1,2'-[1,3]dioxolan]-4-yl)oxy)benzonitrile Step B: Preparation of 3-fluoro-5-((7-(methylsulfonyl)-2,3-dihydrospiro[indene-1,2'-[1,3]dioxolan]-4-yl)oxy)benzonitrile Cesium carbonate (6.33 g, 19.4 mmol) was added all at once to a solution of 3,5-difluorobenzonitrile (5.4 g, 38.85 mmol) and 7'-methylsulfonylspiro[1,3-dioxolane-2,1'-indane]-4'-ol (3.50 g, 13 mmol) in 1-methyl-2-pyrrolidone (45 mL) at room temperature. The reaction mixture was warmed to 110° C. under nitrogen until complete as judged by LC-MS (3 hours). The reaction mixture was diluted with 3 N NaOH (10 mL) and water (20 mL), extracted with EtOAc (5×30 mL). The combined organic layers were washed with brine (30 mL), dried over $MgSO_4$, filtered and concentrated in vacuo. The residue was purified on silica gel (100 g SNAP Ultra, 14 CV, 10-80% EtOAc/hexanes) affording 3-fluoro-5-(7'-methylsulfonylspiro[1,3-dioxolane-2,1'-indane]-4'-yl)oxy-benzonitrile (3.70 g, 9.5 mmol, 73% yield). LCMS ESI (+) m/z 390 (M+H).

Alternative protocol for the synthesis of 3-fluoro-5-(7-methylsulfonyl-1-oxo-indan-4-yl)oxy-benzonitrile Step A: Preparation of 2-hydroxy-5-(methylthio)benzaldehyde To a suspension of 4-methylsulfanylphenol (50 g, 357 mmol), paraformaldehyde (72.3 g, 2407 mmol), and anhydrous magnesium chloride (50.9 g, 535 mmol) in acetonitrile (500 mL) was added triethyl amine (186 mL, 1337 mmol) at ambient temperature. After the addition, the reaction mixture was stirred at 60° C. for 5 hours. After cooling to 0° C., 1 N HCl was added slowly until two phase separated (ca. 1.5 L). MTBE (700 mL) was added. The organic layer was separated, washed with brine, dried (sodium sulfate), filtered and concentrated under reduced pressure. The residue obtained was purified by flash chromatography on silica gel eluting with 1:1 hexane/dichloromethane to give 2-hydroxy-5-methylsulfanyl-benzaldehyde (50.5 g, 300 mmol, 84% yield) as semisolid.

Step B: Preparation of 3-(2-hydroxy-5-(methylthio)phenyl)propanoic acid

Triethylamine (2.5 mL, 17.8 mmol) was added slowly to formic acid (1.55 mL, 41.0 mmol) at 0° C. Then 2,2-dimethyl-1,3-dioxane-4,6-dione (1.84 g, 12.9 mmol) was added, followed by a solution of 2-hydroxy-5-methylsulfanyl-benzaldehyde (2.0 g, 11.9 mmol) in N,N-dimethylacetamide (4 mL). The reaction mixture was stirred at ambient temperature for 1 hour and then it was stirred at 100° C. for 6 hours. After cooling to ambient temperature, water (100 mL) was added and the pH was adjusted with 3N NaOH to pH-9. Ethyl acetate (50 mL) was added. The aqueous layer was separated, then acidified with saturated potassium hydrogen sulfate to pH-3. This aqueous layer was extracted with MTBE (50 mL). The organic layer was separated, washed with brine, dried (sodium sulfate), filtered and concentrated under reduced pressure. The residue obtained was purified by flash chromatography on silica gel with 1:1 hexane/ethyl acetate to give 3-(2-hydroxy-5-methylsulfanyl-phenyl)propanoic acid (1.67 g, 7.9 mmol, 66% yield) as solid.

Step C: Preparation of 3-[2-(3-cyano-5-fluoro-phenoxy)-5-methylsulfanyl-phenyl]propanoic acid A suspension of 3-(2-hydroxy-5-methylsulfanyl-phenyl)propanoic acid (2.14 g, 10 mmol), 3,5-difluorobenzonitrile (3.51 g, 25 mmol), and cesium carbonate (9.85 g, 30 mmol) in sulfolane (36 mL) and s-butanol (4 mL) was stirred at 105° C. for 4 hours. After cooled to ambient temperature, water (100 mL) and MTBE (100 mL) were added. The liquid layer was separated, acidified with saturated potassium hydrogen sulfate to pH-3-4 and extracted with MTBE. The organic layer was washed with brine, dried (sodium sulfate), filtered and concentrated under reduced pressure. Water (50 mL) was added and the mixture was stirred at ambient temperature for 30 minutes. The resulting solid was collected by filtration and dried under vacuum. The filtered solid was suspended in 3:1 hexane/MTBE (~20 mL) and stirred at ambient temperature for 30 minutes. The solid was collected by filtration, washed with hexane and dried to give 3-[2-(3-cyano-5-fluoro-phenoxy)-5-methylsulfanyl-phenyl]propanoic acid (2.9 g, 8.8 mmol, 87% yield) as solid.

Step D: Preparation of 3-fluoro-5-(7-methylsulfanyl-1-oxo-indan-4-yl)oxy-benzonitrile To a solution of 3-[2-(3-cyano-5-fluoro-phenoxy)-5-methylsulfanyl-phenyl]propanoic acid (8.44 g, 25.5 mmol) in dichloromethane (50 mL) was added a drop of DMF, then followed by addition of oxalyl chloride (2.62 mL, 30.6 mmol). The reaction mixture was stirred at ambient temperature for 1 hour. Volatile solvents were removed under reduced pressure. Dichloromethane (20 mL) was added. The resulting mixture was added slowly to a suspension of trichloroalumane (6.79 g, 50.0 mmol) in dichloromethane (50 mL). The mixture was stirred at ambient temperature for 1 hour. The reaction mixture was cooled to 0° C. Aqueous 1 N HCl (20 mL) was added slowly, followed by water (50 mL) and dichloromethane (100 mL). The organic layer was separated, washed with saturated sodium bicarbonate, dried (sodium sulfate), filtered and concentrated under reduced pressure to give 3-fluoro-5-(7-methylsulfanyl-1-oxo-indan-4-yl)oxy-benzonitrile (7.98 g, 25.5 mmol, 100% yield) as solid.

Step E: Preparation of 3-fluoro-5-(7-methylsulfanyl-1-oxo-indan-4-yl)oxy-benzonitrile A suspension of 3-fluoro-5-(7-methylsulfanyl-1-oxo-indan-4-yl)oxy-benzonitrile (7.98 g, 25.5 mmol), Oxone® (53.6 g, 87 mmol) in acetonitrile (40 mL) and water (20 mL) was stirred at ambient temperature for 18 hours. Solid was removed by filtration and washed with dichloromethane (40 mL). The organics was removed under reduced pressure. Acetone (20 mL) and water (40 mL) were added. The resulting suspension was stirred at ambient temperature for 30 minutes. The solid was collected by filtration and dried to give 3-fluoro-5-(7-methylsulfonyl-1-oxo-indan-4-yl)oxy-benzonitrile (7.3 g, 21 mmol, 83% yield) as solid.

Example 164

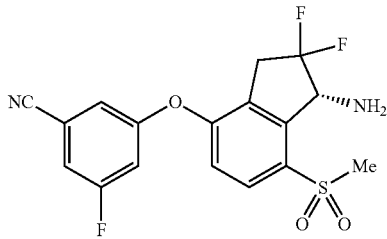 [SMILES: CS(=O)(=O)c1ccc(Oc2cc(F)cc(C#N)c2)c2c1[C@@H](N)C(F)(F)C2]

3-[(1R)-1-Amino-2,2-difluoro-7-methylsulfonyl-indan-4-yl]oxy-5-fluoro-benzonitrile (Compound 164)

Step A: Preparation of (S)—N—((R)-4-(3-cyano-5-fluorophenoxy)-2,2-difluoro-7-(methylsulfonyl)-2,3-dihydro-1H-inden-1-yl)-2-methylpropane-2-sulfinamide Titanium tetraethoxide (54.98 µL, 0.26 mmol) was added dropwise to 3-(2,2-difluoro-7-methylsulfonyl-1-oxo-indan-4-yl)oxy-5-fluoro-benzonitrile (40 mg, 0.1 mmol) and (R)-2-methylpropane-2-sulfinamide (14 mg, 0.12 mmol) in tetrahydrofuran (1 mL) at room temperature under nitrogen then warmed to 45° C. for 8 hours. The reaction mixture was then cooled to 0° C. followed by the addition of sodium borohydride (4 mg, 0.1 mmol). After stirring for 30 minutes the reaction mixture was quenched with water (0.2 mL) at room temperature, the solids were removed by filtration and washed with EtOAc (20 mL) and the filtrate was concentrated in vacuo. The crude product was purified on silica gel (10 g SNAP, 14 CV, 15-100% EtOAc/hexane) affording (S)—N—((R)-4-(3-cyano-5-fluorophenoxy)-2,2-difluoro-7-(methylsulfonyl)-2,3-dihydro-1H-inden-1-yl)-2-methylpropane-2-sulfinamide (24 mg, 0.05 mmol, 47% yield).

Step B: Preparation of 3-[(1R)-1-amino-2,2-difluoro-7-methylsulfonyl-indan-4-yl]oxy-5-fluoro-benzonitrile (Compound 164)

Hydrogen chloride (4.0 M solution in dioxane, 103 µL, 0.41 mmol) was added all at once to a solution of (S)—N—((R)-4-(3-cyano-5-fluorophenoxy)-2,2-difluoro-7-(methylsulfonyl)-2,3-dihydro-1H-inden-1-yl)-2-methylpropane-2-sulfinamide (20 mg, 0.04 mmol) in methanol (0.4 mL) at room temperature then stirred for 30 minutes. The reaction was quenched with saturated NaHCO₃ (1 mL) carefully, extracted with EtOAc (3×5 mL), washed with brine (5 mL), dried over MgSO₄, filtered and concentrated in vacuo. The crude product was purified on silica gel (10 g SNAP, 14 CV, 20-80% EtOAc/hexane) affording Compound 164 (11 mg, 0.03 mmol, 70% yield) as a white foam. LCMS ESI (+) 383 (M+H). ¹H NMR (400 MHz, CDCl₃): δ 7.93-7.91 (m, 1H), 7.25-7.22 (m, 1H), 7.14-7.13 (m, 1H), 7.06-7.02 (m, 1H), 6.96 (d, 1H), 4.97-4.93 (m, 1H), 3.55-3.37 (m, 2H), 3.32 (s, 3H).

Example 165

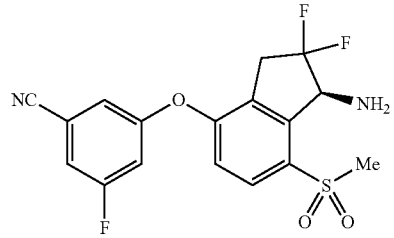 [SMILES: CS(=O)(=O)c1ccc(Oc2cc(F)cc(C#N)c2)c2c1[C@H](N)C(F)(F)C2]

3-[(1S)-1-Amino-2,2-difluoro-7-methylsulfonyl-indan-4-yl]oxy-5-fluoro-benzonitrile (Compound 165)

Step A: Preparation of (R)—N-(4-(3-cyano-5-fluorophenoxy)-2,2-difluoro-7-(methylsulfonyl)-2,3-dihydro-1H-inden-1-ylidene)-2-methylpropane-2-sulfinamide Titanium tetraethoxide (49.5 µL, 0.24 mmol) was added dropwise to 3-(2,2-difluoro-7-methylsulfonyl-1-oxo-indan-4-yl)oxy-5-fluoro-benzonitrile (30 mg, 0.08 mmol) and (S)-(−)-2-methyl-2-propanesulfinamide (11 mg, 0.09 mmol) in tetrahydrofuran (0.8 mL) at room temperature under nitrogen then warmed to 45° C. for 8 hours. The reaction was quenched with water (0.1 mL) at room temperature, the solids were removed by filtration, washed with EtOAc (20 mL) and concentrated in vacuo. The crude product was purified on silica gel (10 g SNAP, 14 CV, 15-100% EtOAc/hexane) affording (R)—N-(4-(3-cyano-5-fluorophenoxy)-2,2-difluoro-7-(methylsulfonyl)-2,3-dihydro-1H-inden-1-ylidene)-2-methylpropane-2-sulfinamide (24 mg, 0.05 mmol, 63% yield).

Step B: Preparation of (R)—N—((S)-4-(3-cyano-5-fluorophenoxy)-2,2-difluoro-7-(methylsulfonyl)-2,3-dihydro-1H-inden-1-yl)-2-methylpropane-2-sulfinamide Sodium borohydride (5.6 mg, 0.15 mmol) was added all at once to an ice cold solution of (R)—N-[4-(3-cyano-5-fluoro-phenoxy)-2,2-difluoro-7-methylsulfonyl-indan-1-ylidene]-2-methyl-propane-2-sulfinamide (24 mg, 0.05 mmol) in tetrahydrofuran (0.5 mL) then stirred until complete as judged by LC-MS. Quenched with water (1 mL), extracted with EtOAc (3×5 mL), washed with brine (5 mL), dried over MgSO$_4$, filtered and concentrated in vacuo. The residue was purified on silica gel (10 g SNAP Ultra, 14 CV, 18-100% EtOAc/hexane) affording (R)—N—((S)-4-(3-cyano-5-fluorophenoxy)-2,2-difluoro-7-(methylsulfonyl)-2,3-dihydro-1H-inden-1-yl)-2-methylpropane-2-sulfinamide (7 mg, 0.01 mmol, 29% yield).

Step C: Preparation of 3-[(1S)-1-amino-2,2-difluoro-7-methylsulfonyl-indan-4-yl]oxy-5-fluoro-benzonitrile (Compound 165)

Hydrogen chloride (4.0 M solution in dioxane, 0.2 mL, 0.8 mmol) was added dropwise to a solution of (R)—N-(4-(3-cyano-5-fluorophenoxy)-2,2-difluoro-7-(methylsulfonyl)-2,3-dihydro-1H-inden-1-ylidene)-2-methylpropane-2-sulfinamide (7 mg, 0.01 mmol) in methanol (0.2 mL) at room temperature then stirred for 30 minutes. The reaction was carefully quenched by dropwise addition of saturated NaHCO$_3$ (2 mL), extracted with EtOAc (3×5 mL), washed with brine (5 mL), dried over Na$_2$SO$_4$, filtered and concentrated in vacuo. The crude product was purified on silica gel (10 g SNAP, 14 CV, 15-100% EtOAc/hexane) affording Compound 165 (2.3 mg, 0.006 mmol, 42% yield). LCMS ESI (+) 383 (M+H). $^1$HNMR (400 MHz, CDCl$_3$): δ 7.93-7.91 (m, 1H), 7.25-7.22 (m, 1H), 7.14-7.13 (m, 1H), 7.06-7.02 (m, 1H), 6.96 (d, 1H), 4.97-4.93 (m, 1H), 3.55-3.37 (m, 2H), 3.32 (s, 3H).

Example 166

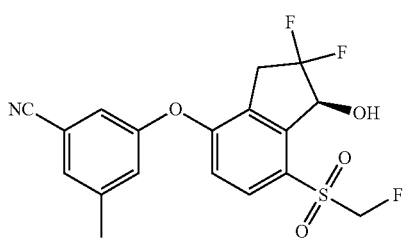 [SMILES: Cc1cc(C#N)cc(Oc2ccc(S(=O)(=O)CF)c3c2CC(F)(F)[C@H]3O)c1]

(S)-3-((2,2-Difluoro-7-((fluoromethyl)sulfonyl)-1-hydroxy-2,3-dihydro-1H-inden-4-yl)oxy)-5-methyl-benzonitrile (Compound 166)

Prepared similarly according to Example 63, Steps B-F, substituting 3-hydroxy-5-methylbenzonitrile for 3-fluoro-5-hydroxy-benzonitrile. m/z (ES-API-neg) [M−H+46]=442; $^1$H NMR (400 MHz, CDCl$_3$) δ 7.87 (d, 1H), 7.38 (br s, 1H), 7.16 (br d, 1H), 6.88 (d, 1H), 5.58-5.12 (m, 3H), 3.59-3.44 (m, 3H). Enantiomeric excess was 95% as determined by Mosher ester analysis.

Example 167

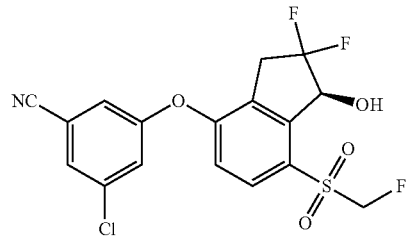

(S)-3-Chloro-5-((2,2-difluoro-7-((fluoromethyl)sulfonyl)-1-hydroxy-2,3-dihydro-1H-inden-4-yl)oxy)benzonitrile (Compound 167)

Prepared similarly according to Example 63, Steps B-F, substituting 3-chloro-5-hydroxybenzonitrile for 3-fluoro-5-hydroxy-benzonitrile. m/z (ES-API-neg) [M−H+46]=462; $^1$H NMR (400 MHz, CDCl$_3$) δ 7.92 (d, 1H), 7.36-7.33 (m, 1H), 7.32-7.27 (m, 1H), 6.97 (d, 1H), 5.58-5.12 (m, 3H), 3.62-3.38 (m, 3H). Enantiomeric excess 95% as determined by Mosher ester analysis.

Example 168

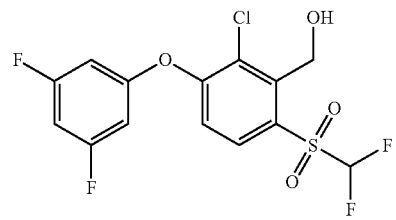 [SMILES: O=S(=O)(c1ccc(Oc2cc(F)cc(F)c2)c(Cl)c1CO)C(F)F]

(2-Chloro-6-((difluoromethyl)sulfonyl)-3-(3,5-difluorophenoxy)phenyl)methanol (Compound 168)

Prepared similarly according to Example 41, Step E, substituting 3,5-difluorophenol for 3-chloro-5-fluoro-phenol. m/z (ES-API-neg) [M−H+46]=429; $^1$HNMR (400 MHz, CDCl$_3$) δ 8.01 (d, 1H), 7.09 (d, 1H), 6.77-6.67 (m, 1H), 6.64-6.61 (m, 2H), 6.47 (t, 1H), 5.21 (d, 2H), 2.70 (t, 1H).

Example 169

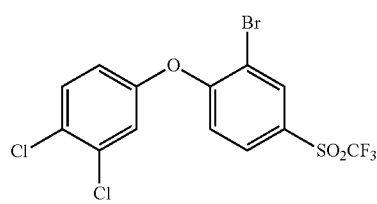

2-Bromo-1-(3,4-dichlorophenoxy)-4-((trifluoromethyl)sulfonyl)benzene (Compound 169)

Prepared similarly as in Example 116 substituting 3-chloro-5-fluorophenol with 3,4-dichlorophenol in step C. ¹HNMR (400 MHz, CDCl₃): δ 8.30 (d, 1H), 7.89 (d, 1H), 7.54 (d, 1H), 7.26 (s, 1H), 6.99 (m, 2H).

Example 170

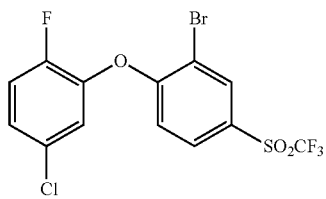

2-Bromo-1-(5-chloro-2-fluorophenoxy)-4-((trifluoromethyl)sulfonyl)benzene (Compound 170)

Prepared similarly as in Example 116 substituting 3-chloro-5-fluorophenol with 5-chloro-2-fluorophenol in step C. ¹HNMR (400 MHz, CDCl₃): δ 8.30 (s, 1H), 7.88 (d, 1H), 7.21-7.31 (m, 3H), 6.90 (d, 1H).

Example 171

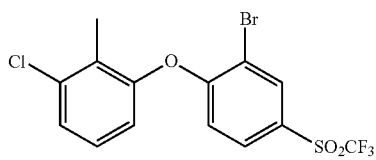

1-(2-Bromo-4-((trifluoromethyl)sulfonyl)phenoxy)-3-chloro-2-methylbenzene (Compound 171)

Prepared similarly as in Example 116 substituting 3-chloro-5-fluorophenol with 3-chloro-2-methylphenol in step C. ¹HNMR (400 MHz, d₆-DMSO): δ 8.40 (d, 1H), 8.02 (d, 1H), 7.45 (d, 1H), 7.35 (t, 1H), 7.20 (d, 1H), 6.95 (d, 1H), 2.13 (s, 3H).

Example 172

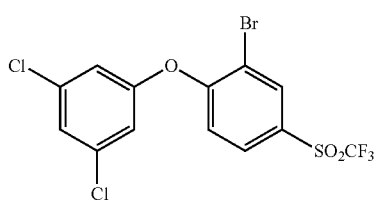

2-Bromo-1-(3,5-dichlorophenoxy)-4-((trifluoromethyl)sulfonyl)benzene (Compound 172)

Prepared similarly as in Example 116 substituting 3-chloro-5-fluorophenol with 3,5-dichlorophenol in step C. ¹HNMR (400 MHz, CDCl₃): δ 8.30 (d, 1H), 7.93 (d, 1H), 7.31 (d, 1H), 7.04 (m, 3H).

Example 173

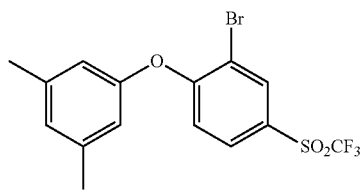

2-Bromo-1-(3,5-dimethylphenoxy)-4-((trifluoromethyl)sulfonyl)benzene (Compound 173)

Prepared similarly as in Example 116 substituting 3-chloro-5-fluorophenol with 3,5-dimethylphenol in step C. ¹HNMR (400 MHz, CDCl₃): δ 8.26 (d, 1H), 7.81 (d, 1H), 6.95 (s, 1H), 6.91 (d, 1H), 6.74 (s, 2H), 2.35 (s, 6H).

Example 174

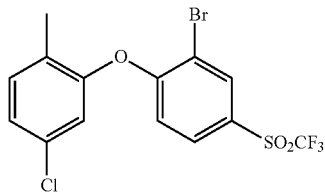

2-Bromo-1-(5-chloro-2-methylphenoxy)-4-((trifluoromethyl)sulfonyl)benzene (Compound 174)

Prepared similarly as in Example 116 substituting 3-chloro-5-fluorophenol with 5-chloro-2-methylphenol in step C. ¹HNMR (400 MHz, CDCl₃): δ 8.29 (d, 1H), 7.84 (d, 1H), 7.22-7.27 (m, 2H), 7.06 (s, 1H), 6.78 (d, 1H), 2.16 (s, 3H).

Example 175

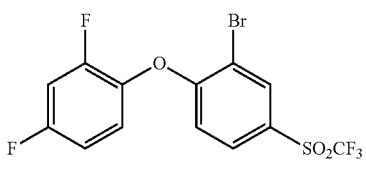

2-(2-Bromo-4-((trifluoromethyl)sulfonyl)phenoxy)-1,3-difluorobenzene (Compound 175)

Prepared similarly as in Example 116 substituting 3-chloro-5-fluorophenol with 3,5-difluorophenol in step C.

¹HNMR (400 MHz, d₆-DMSO): δ 8.40 (s, 1H), 8.03 (d, 1H), 7.58 (m, 2H), 7.23 (m, 1H), 7.11 (d, 1H).

Example 176

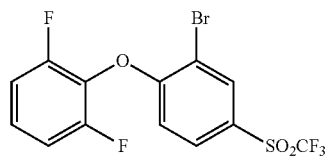

2-Bromo-1-(2,4-difluorophenoxy)-4-((trifluoromethyl)sulfonyl)benzene (Compound 176)

Prepared similarly as in Example 116 substituting 3-chloro-5-fluorophenol with 2,6-difluorophenol in step C. ¹HNMR (400 MHz, d₆-DMSO): δ 8.30 (s, 1H), 7.88 (d, 1H), 7.27-7.32 (m, 1H), 7.08-7.14 (m, 2H), 6.85 (d, 1H).

Example 177

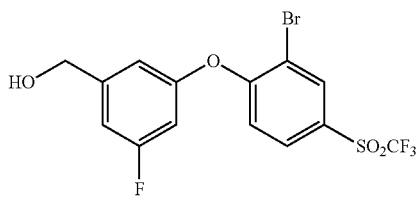

(3-(2-Bromo-4-((trifluoromethyl)sulfonyl)phenoxy)-5-fluorophenyl)methanol (Compound 177)

Prepared similarly as in Example 116 substituting 3-chloro-5-fluorophenol with 5-fluoro-3-(hydroxymethyl)phenol in step C. ¹HNMR (400 MHz, CDCl₃): δ 8.29 (d, 1H), 7.87 (m, 1H), 7.06 (d, 1H), 7.02 (d, 1H), 6.94 (d, 1H), 6.77 (m, 1H), 4.75 (d, 2H), 1.83 (t, 1H).

Example 178

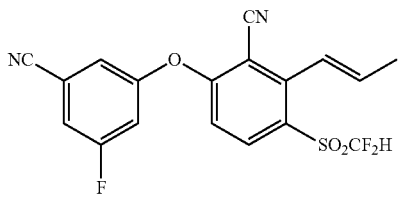

(E)-6-(3-Cyano-5-fluorophenoxy)-3-((difluoromethyl)sulfonyl)-2-(prop-1-en-1-yl)benzonitrile (Compound 178)

Allyl(tributyl)stannane (0.08 mL, 0.25 mmol) was added by syringe to a degassed mixture of 2-chloro-6-(3-cyano-5-fluoro-phenoxy)-3-(difluoromethylsulfonyl)benzonitrile (Compound 30, 48 mg, 0.12 mmol) and tetrakis(triphenylphosphine)palladium(0) (14 mg, 0.01 mmol) in DMF (0.6 mL) at ambient temperature to a microwave vial equipped with a septum under nitrogen. The septa was quickly replaced with a microwave cap and sealed under a blanket of nitrogen. The reaction mixture was then heated at 160° C. for 30 minutes in a microwave reactor. After cooling to ambient temperature, the reaction mixture was filtered through Celite. The filtrate was washed with MTBE (10 mL) and then stirred with saturated KF solution (10 mL) for 30 minutes. The organic phase was separated. The aqueous phase was extracted with MTBE. The combined organics were washed with brine (20 mL), dried (Na₂SO₄), filtered and concentrated in vacuo. The crude product was purified by flash chromatography on silica gel (2-5% EtOAc/hexane) affording Compound 178 (46 mg, 94%) as a white solid. LCMS ESI (−) m/z 391 (M−H); ¹H NMR (400 MHz, CDCl₃): δ 8.18 (d, 1H), 7.38-7.35 (m, 1H), 7.29-7.27 (m, 1H), 7.21-7.18 (m, 1H), 7.07-7.02 (m, 1H), 6.90 (d, 1H), 6.56-6.47 (m, 1H), 6.22 (t, 1H), 2.08-2.06 (m, 1H).

Example 179

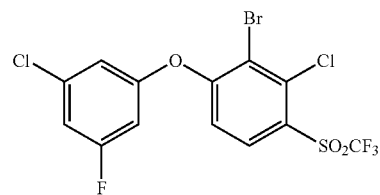

2-Bromo-3-chloro-1-(3-chloro-5-fluorophenoxy)-4-((trifluoromethyl)sulfonyl)benzene (Compound 179)

Prepared analogously to the procedures for Compound 28 omitting Step C. ¹H NMR (400 MHz, CDCl₃): δ 8.13 (d, 1H), 7.08-7.05 (m, 1H), 6.95-6.93 (m, 2H), 6.79-6.76 (m, 1H).

Example 180

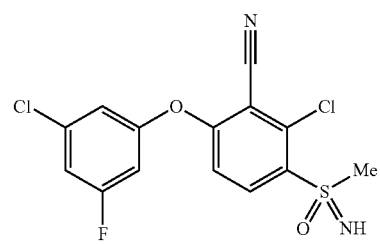 [SMILES: CS(=N)(=O)c1ccc(Oc2cc(F)cc(Cl)c2)c(C#N)c1Cl]

2-Chloro-6-(3-chloro-5-fluorophenoxy)-3-(S-methylsulfonimidoyl)benzonitrile (Compound 180)

Prepared by an analogous set of procedures described for the preparation of Compounds 69 and 152. LCMS ESI (+) m/z 359, 361 (M+H); ¹H NMR (400 MHz, CDCl₃): δ 8.33 (d, 1H), 7.09 (m, 1H), 6.97-6.95 (m, 1H), 6.94 (d, 1H), 6.81 (m, 1H), 3.32 (s, 3H), 2.94 (br s, 1H).

Example 181

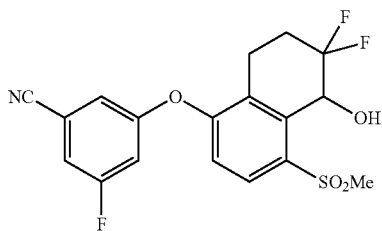 [SMILES: CS(=O)(=O)c1ccc(Oc2cc(F)cc(C#N)c2)c2c1C(O)C(F)(F)CC2]

3-((6,6-Difluoro-5-hydroxy-4-(methyl sulfonyl)-5,6,7,8-tetrahydronaphthalen-1-yl)oxy)-5-fluorobenzonitrile (Compound 181)

Prepared by an analogous set of procedures described for the preparation of Compound 8. LCMS ESI (+) m/z 359, 361 (M+H); $^1$H NMR (400 MHz, CDCl$_3$): δ 8.04 (d, 1H), 7.23 (m, 1H), 7.12-7.10 (m, 1H), 7.03-6.99 (m, 1H), 6.07 (d, 1H), 5.54-5.49 (m, 1H), 3.68 (m, 1H), 3.26 (s, 3H), 3.20 (m, 1H), 2.97-2.86 (m, 1H), 2.63-2.45 (m, 1H), 2.35-2.25 (m, 1H).

Example 182

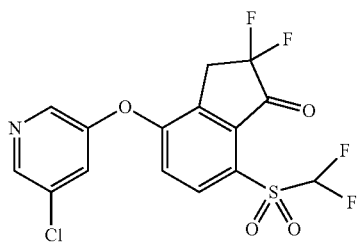 [SMILES: O=C1c2c(S(=O)(=O)C(F)F)ccc(Oc3cncc(Cl)c3)c2CC1(F)F]

4-((5-Chloropyridin-3-yl)oxy)-7-((difluoromethyl)sulfonyl)-2,2-difluoro-2,3-dihydro-1H-inden-1-one (Compound 182)

Prepared in Example 25, Step D.

Example 183

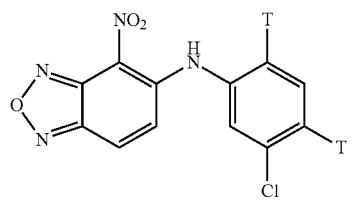

N-(3-Chlorophenyl-4,6-t2)-4-nitrobenzo[c][1,2,5]oxadiazol-5-amine (Compound 183)

Step A: Synthesis of 3-chlorobenzen-4,6-t$_2$-amine

3-Chloro-4,6-diiodoaniline (100 mg.) was dissolved in methanol (3 mL) and added with triethylamine (0.1 mL) and submitted for overnight tritiation using 50 Ci of tritium gas, at room temperature. Labile tritium was removed by dissolving the crude reaction mixture in methanol (3 mL) and bringing to dryness under vacuum. Labile removal was done in dupicate. The crude tritiated material was purified by preparative TLC (Silica gel, 1000μ) using hexane:ethylacetate:AcOH (85:14:1). The product band was eluted with ethylacetate to give 3-chlorobenzen-4,6-t$_2$-amine (yield=600 mCi, radiochemical purity was >98%).

Step B: Synthesis of Compound 183

A stirred mixture of 5-chloro-4-nitro-2,1,3-benzoxadiazole (20 mg, 0.1 mmol), 3-chlorobenzen-4,6-t$_2$-amine (600 mCi) and Cs$_2$CO$_3$ (65 mg, 0.20 mmol) in DMF (1 mL) was heated at 60° C. for 1 h. After cooling, the reaction mixture was partitioned between EtOAc and water. The aqueous layer was extracted with EtOAc. The combined organic layers were washed with water and brine, dried and concentrated. The residue was purified by preparative HPLC on an ACE-5 C18 Semi-prep column, 250×10 mm, 100 Å. Elution was carried out isocratically using 0.1% TFA in water/Acetonitrile (35:65) to give Compound 183 (478 mCi, 80%).

Example 184

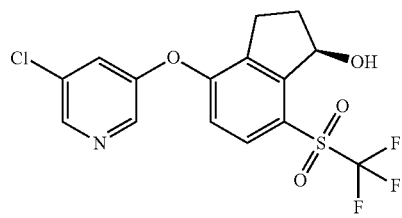 [SMILES: O=S(=O)(c1ccc(Oc2cncc(Cl)c2)c2c1[C@H](O)CC2)C(F)(F)F]

(R)-4-((5-Chloropyridin-3-yl)oxy)-7-((trifluoromethyl)sulfonyl)-2,3-dihydro-1H-inden-1-ol (Compound 184)

Prepared similarly according to Example 55, Step D substituting 3-chloro-5-hydroxypyridine for 3,5-difluorophenol. $^1$H NMR (400 MHz, CDCl$_3$): δ 8.47 (d, 1H), 8.35 (d, 1H), 7.82 (d, 1H), 7.45 (t, 1H), 6.88 (d, 1H), 5.64-5.59 (m, 1H), 3.30-3.15 (m, 2H), 3.02-2.93 (m, 1H) 2.46-2.26 (m, 2H); m/z (ES-API-pos) [M+H]=394.

Example 185

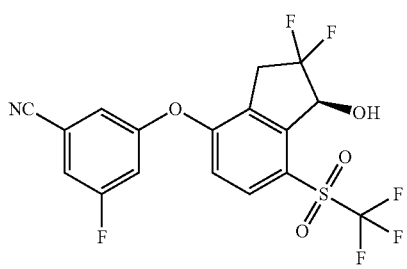 [SMILES: N#Cc1cc(F)cc(Oc2ccc(S(=O)(=O)C(F)(F)F)c3c2CC(F)(F)[C@H]3O)c1]

(S)-3-((2,2-Difluoro-1-hydroxy-7-((trifluoromethyl)
sulfonyl)-2,3-dihydro-1H-inden-4-yl)oxy)-5-fluo-
robenzonitrile (Compound 185)

Step A: 3-Fluoro-5-((1-oxo-7-((trifluoromethyl)sul-
fonyl)-2,3-dihydro-1H-inden-4-yl)oxy)benzonitrile Dess Martin periodinane (192 mg, 0.45 mmol) was added to a solution of 3-fluoro-5-[(1R)-1-hydroxy-7-(trifluoromethylsulfonyl)indan-4-yl]oxy-benzonitrile Compound 57 (121 mg, 0.3 mmol) in dichloromethane (4 mL). The mixture was stirred at ambient temperature. After 1 hour, the reaction mixture was partitioned between EtOAc and water. The EtOAc was washed with brine, dried over MgSO$_4$, filtered, and evaporated. The residue was chromatographed on a Biotage 10 g SNAP column with a 20% to 80% EtOAc:hexane gradient to afford 3-fluoro-5-((1-oxo-7-((trifluoromethyl)sulfonyl)-2,3-dihydro-1H-inden-4-yl)oxy)benzonitrile (102 mg, 0.26 mmol, 85% yield) as a colorless glass. m/z (ES-API-pos) [M+H]=400

Step B: (E,Z)-3-((1-(Butylimino)-7-((trifluorom-
ethyl)sulfonyl)-2,3-dihydro-1H-inden-4-yl)oxy)-5-
fluorobenzonitrile Trifluoroacetic acid (0.0039 mL, 0.05 mmol) was added to a solution of 3-fluoro-5-((1-oxo-7-((trifluoromethyl)sulfonyl)-2,3-dihydro-1H-inden-4-yl)oxy)benzonitrile (102 mg, 0.26 mmol) and butan-1-amine (1.26 mL, 12.8 mmol) in benzene (15 mL). The mixture was heated at reflux with a Hickman still attached. After 6 hours, the reaction mixture was evaporated and the residue was partitioned between EtOAc and saturated aqueous NaHCO$_3$. The EtOAc was washed with brine, dried over MgSO$_4$, filtered, and evaporated to yield (E,Z)-3-((1-(butylimino)-7-((trifluoromethyl)sulfonyl)-2,3-dihydro-1H-inden-4-yl)oxy)-5-fluorobenzonitrile (100 mg, 0.2 mmol, 86% yield) as a green film.

Step C: 3-((2,2-Difluoro-1-oxo-7-((trifluoromethyl)
sulfonyl)-2,3-dihydro-1H-inden-4-yl)oxy)-5-fluo-
robenzonitrile 1-(Chloromethyl)-4-fluoro-1,4-diazoniabicyclo[2.2.2]octane ditetrafluoroborate (195 mg, 0.55 mmol) was added to a mixture of crude (E,Z)-3-((1-(butylimino)-7-((trifluoromethyl)sulfonyl)-2,3-dihydro-1H-inden-4-yl)oxy)-5-fluorobenzonitrile (100 mg, 0.22 mmol) and sodium sulfate (31 mg, 0.22 mmol) in acetonitrile (8 mL). The reaction mixture was heated at 80° C. for 5 hours then stirred at ambient temperature overnight. The reaction mixture was treated with 6 M HCl (1 mL) and water (1 mL) and stirred for 15 minutes. The reaction mixture was partitioned between EtOAc and water. The EtOAc was washed with brine, dried over MgSO$_4$, filtered, and evaporated. The residue was chromatographed on a Biotage 10 g SNAP column with a 10% to 60% EtOAc:hexane gradient to afford 3-((2,2-difluoro-1-oxo-7-((trifluoromethyl)sulfonyl)-2,3-dihydro-1H-inden-4-yl)oxy)-5-fluorobenzonitrile (55 mg, 0.13 mmol, 58% yield) as a colorless oil.

Step D: (S)-3-((2,2-difluoro-1-hydroxy-7-((trifluo-
romethyl)sulfonyl)-2,3-dihydro-1H-inden-4-yl)oxy)-
5-fluorobenzonitrile (Compound 185)

RuCl(p-cymene)[(R,R)-Ts-DPEN] (1.6 mg, 0.0025 mmol) was added to a nitrogen-sparged ice-cold solution of 3-((2,2-difluoro-1-oxo-7-((trifluoromethyl)sulfonyl)-2,3-dihydro-1H-inden-4-yl)oxy)-5-fluorobenzonitrile (55 mg, 0.13 mmol), formic acid (0.006 mL, 0.16 mmol), and triethylamine (0.02 mL, 0.14 mmol) in dichloromethane (5 mL). The vial was sealed and stored at 4° C. overnight. The reaction mixture was evaporated. The residue was chromatographed on a Biotage 10 g SNAP column with a 10% to 60% EtOAc:hexane gradient to afford Compound 185 (45 mg, 0.1 mmol, 81% yield) as a colorless glass that solidified to a white solid. $^1$H NMR (400 MHz, CDCl$_3$): δ 7.95 (d, 1H), 7.35-7.31 (m, 1H), 7.26-7.23 (m, 1H), 7.15-7.11 (m, 1H), 6.99 (d, 1H), 5.46-5.39 (m, 1H), 3.63-3.41 (m, 2H), 3.36 (d, 1H). m/z (ES-API-neg) [M−H]=436.93% e.e. based on the Mosher ester analysis of the trifluoromethyl resonance.

Example 186

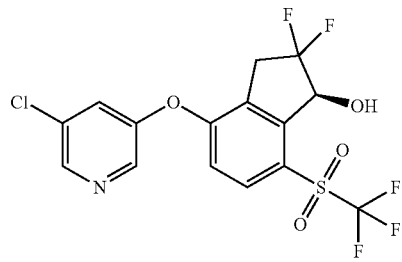 [SMILES: O=S(=O)(c1ccc(Oc2cncc(Cl)c2)c2c1[C@H](O)C(F)(F)C2)C(F)(F)F]

(S)-4-((5-Chloropyridin-3-yl)oxy)-2,2-difluoro-7-
((trifluoromethyl)sulfonyl)-2,3-dihydro-1H-inden-1-
ol (Compound 186)

Prepared similarly according to Example 185, Steps A-D, substituting (R)-4-((5-chloropyridin-3-yl)oxy)-7-((trifluoromethyl)sulfonyl)-2,3-dihydro-1H-inden-1-ol Example 184 for 3-fluoro-5-[(1R)-1-hydroxy-7-(trifluoromethylsulfonyl)indan-4-yl]oxy-benzonitrile Compound 57. $^1$H NMR (400 MHz, CDCl$_3$): δ 8.55 (d, 1H), 8.40 (d, 1H), 7.91 (d, 1H), 7.52 (t, 1H), 6.94 (d, 1H), 5.46-5.40 (m, 1H), 3.85 (d, 1H), 3.66-3.47 (m, 2H). m/z (ES-API-pos) [M+H]=430.95% e.e. based on the Mosher ester analysis of the trifluoromethyl resonance.

Example 187

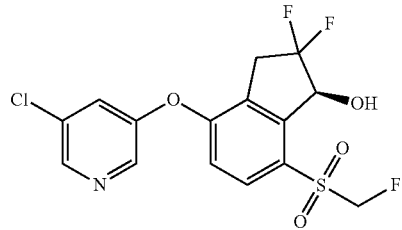 [SMILES: O=S(=O)(CF)c1ccc(Oc2cncc(Cl)c2)c2c1[C@H](O)C(F)(F)C2]

(S)-4-((5-Chloropyridin-3-yl)oxy)-2,2-difluoro-7-
((fluoromethyl)sulfonyl)-2,3-dihydro-1H-inden-1-ol
(Compound 187)

Prepared similarly according to Example 63, Steps B-F, substituting 3-chloro-5-hydroxypyridine for 3-fluoro-5-hydroxy-benzonitrile. ¹H NMR (400 MHz, CDCl₃): δ 8.51 (d, 1H), 8.37 (d, 1H), 7.90 (d, 1H), 7.48 (t, 1H), 6.93 (d, 1H), 5.61-5.11 (m, 3H), 3.94 (d, 1H), 3.62-3.42 (m, 2H). m/z (ES-API-pos) [M+H]=394.88% e.e. based on the Mosher ester analysis of the trifluoromethyl resonance.

Example 188

Compound 188

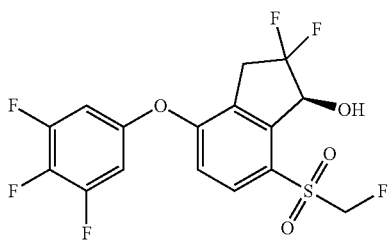

(S)-2,2-Difluoro-7-((fluoromethyl)sulfonyl)-4-(3,4, 5-trifluorophenoxy)-2,3-dihydro-1H-inden-1-ol (Compound 188)

Prepared similarly according to Example 63, Steps B-F, substituting 3,4,5-trifluorophenol for 3-fluoro-5-hydroxy-benzonitrile. ¹H NMR (400 MHz, CDCl₃): δ 7.89 (d, 1H), 6.94 (d, 1H), 6.82-6.71 (m, 2H), 5.59-5.11 (m, 3H), 3.59-3.38 (m, 3H). m/z (ES-API-neg) [M−H+46]=457.89% e.e. based on the Mosher ester analysis of the trifluoromethyl resonance.

Example 189

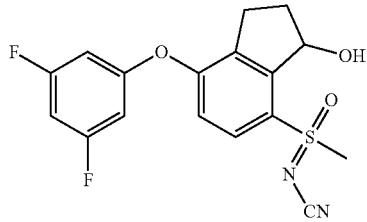 [SMILES: CS(=O)(=NC#N)c1ccc(Oc2cc(F)cc(F)c2)c2c1C(O)CC2]

N-((7-(3,5-Difluorophenoxy)-3-hydroxy-2,3-di-hydro-1H-inden-4-yl)(methyl)(oxo)-λ⁶-sulfa-nylidene)cyanamide (Compound 189)

Step A: N-((7-Fluoro-3-oxo-2,3-dihydro-1H-inden-4-yl)(methyl)λ⁴-sulfanylidene)cyanamide (Diacetoxyiodo)benzene (903 mg, 2.8 mmol) was added to an ice-cold solution of 4-fluoro-7-methylsulfanyl-indan-1-one (500 mg, 2.55 mmol) and cyanamide (128 mg, 3.1 mmol) in acetonitrile (25 mL). The reaction mixture was stirred at ice-bath temperature. After 6 hours, the reaction mixture was evaporated and the residue was partitioned between EtOAc and water. The EtOAc was washed with brine, dried over MgSO₄, filtered, and evaporated to afford N-((7-fluoro-3-oxo-2,3-dihydro-1H-inden-4-yl)(methyl)λ⁴-sulfanylidene)cyanamide (600 mg; 2.5 mmol; 99% yield). m/z (ES-API-pos) [M+H]=237.

Step B: N-((7-fluoro-3-oxo-2,3-dihydro-1H-inden-4-yl)(methyl)(oxo)-λ⁶-sulfanylidene)cyanamide Sodium periodate (1358 mg, 6.4 mmol) was added to a mixture of N-((7-Fluoro-3-oxo-2,3-dihydro-1H-inden-4-yl)(methyl)λ⁴-sulfanylidene)cyanamide and ruthenium (III) chloride (13.2 mg, 0.06 mmol) in carbon tetrachloride (10 mL), acetonitrile (10 mL), and water (20 mL). The mixture was stirred at ambient temperature for 2 hours. The reaction mixture was partitioned between dichloromethane and water. The dichloromethane was washed with brine, dried over MgSO₄, filtered, and evaporated to afford N-((7-fluoro-3-oxo-2,3-dihydro-1H-inden-4-yl)(methyl)(oxo)-λ⁶-sulfa-nylidene)cyanamide (510 mg; 2. mmol; 96% yield). m/z (ES-API-pos) [M+H]=253.

Step C: N-((7-fluoro-3-hydroxy-2,3-dihydro-1H-inden-4-yl)(methyl)(oxo)-λ⁶-sulfanylidene)cyana-mide Sodium borohydride (42 mg, 1.1 mmol) was added to an ice-cold solution of N-((7-fluoro-3-oxo-2,3-dihydro-1H-inden-4-yl)(methyl)(oxo)-λ⁶-sulfanylidene)cyanamide (280 mg, 1.1 mmol) in methanol (10 mL). The mixture was stirred in an icebath. After 15 minutes, the reaction mixture was treated with saturated aqueous NH₄Cl and evaporated. The residue was partitioned between EtOAc and water. The EtOAc was washed with brine, dried over MgSO₄, filtered, and evaporated to yield N-((7-fluoro-3-hydroxy-2,3-di-hydro-1H-inden-4-yl)(methyl)(oxo)-λ⁶-sulfanylidene)cy-anamide (290 mg, 1.14 mmol, 100% yield). m/z (ES-API-pos) [M+H]=255.

Step D: N-((7-(3,5-Difluorophenoxy)-3-hydroxy-2, 3-dihydro-1H-inden-4-yl)(methyl)(oxo)-λ⁶-sulfa-nylidene)cyanamide Sodium hydrogen carbonate (70 mg, 0.83 mmol) was added to a solution of 3,5-difluorophenol (81.2 mg, 0.62 mmol) and N-((7-fluoro-3-hydroxy-2,3-dihydro-1H-inden-4-yl)(methyl)(oxo)-λ⁶-sulfanylidene)cyanamide (100 mg, 0.42 mmol) in DMF (2 mL). The vial was sealed and heated at 110° C. overnight. The reaction mixture was partitioned between EtOAc and saturated aqueous NaHCO₃. The EtOAc was washed with saturated aqueous NaHCO₃, water, brine, dried over MgSO₄, filtered, and evaporated. The residue was chromatographed on a Biotage 10 g SNAP column with a 10% to 60% EtOAc:hexane gradient. Further manual elution with 4:1 EtOAc:hexane afforded Compound 189 (103 mg, 0.28 mmol, 68% yield) as an amber glass that solidified to a tan solid. ¹H NMR (400 MHz, CDCl₃): δ 7.88-7.80 (m, 1H), 6.97 (d, 1H), 6.72-6.65 (m, 1H), 6.63-6.55 (m, 2H), 5.83-5.76 (m, 1H), 3.57 (s, 1H), 3.51 (s, 3H), 3.18-3.07 (m, 1H), 2.93-2.79 (m, 1H), 2.60-2.47 (m, 1H), 2.23-2.11 (m, 1H). m/z (ES-API-pos) [M+H]=365.

Example 190

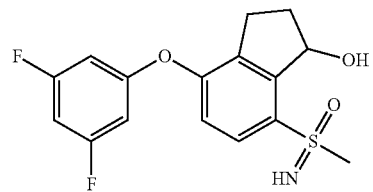 [SMILES: CS(=N)(=O)c1ccc(Oc2cc(F)cc(F)c2)c2c1C(O)CC2]

(7-(3,5-Difluorophenoxy)-3-hydroxy-2,3-dihydro-1H-inden-4-yl)(imino)(methyl)-λ⁶-sulfanone (Compound 190)

Trifluoroacetic anhydride (0.02 mL, 0.16 mmol) was added to an ice-cold solution of N-((7-(3,5-difluorophenoxy)-3-hydroxy-2,3-dihydro-1H-inden-4-yl)(methyl)(oxo)-λ⁶-sulfanylidene)cyanamide (Compound 189, 10 mg, 0.03 mmol) in dichloromethane (0.5 mL). The mixture was allowed to slowly warm to ambient temperature. After 2 hours, the mixture was evaporated, dissolved in methanol (0.5 mL), and treated with potassium carbonate (19 mg, 0.14 mmol) and stirred at ambient temperature overnight. The reaction mixture was evaporated and the residue was partitioned between EtOAc and water. The EtOAc was washed with brine, dried over MgSO₄, filtered, and evaporated. The residue was chromatographed on a Biotage 10 g SNAP column with a 10% to 100% EtOAc:hexane gradient to afford Compound 190 (2.6 mg, 0.008 mmol, 28% yield) as a colorless glass. ¹H NMR (400 MHz, CDCl₃): δ 7.89-7.81 (m, 1H), 6.99-6.94 (m, 1H), 6.66-6.60 (m, 1H), 6.57-6.51 (m, 2H), 5.66-5.59 (m, 1H), 3.28 (s, 3H), 3.24 (s, 1H), 3.15-3.01 (m, 1H), 2.87-2.71 (m, 1H), 2.55-2.41 (m, 1H), 2.27-2.13 (m, 1H). m/z (ES-API-pos) [M+H]=340.

Example 191

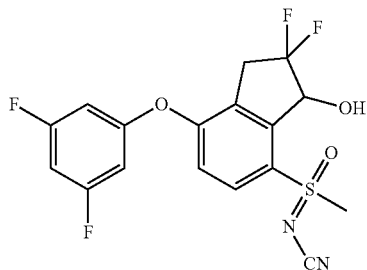 [SMILES: CS(=O)(=NC#N)c1ccc(Oc2cc(F)cc(F)c2)c2c1C(O)C(F)(F)C2]

N-((7-(3,5-difluorophenoxy)-2,2-difluoro-3-hydroxy-2,3-dihydro-1H-inden-4-yl)(methyl)(oxo)-λ⁶-sulfanylidene)cyanamide (Compound 191)

Step A: N-((7-(3,5-difluorophenoxy)-3-oxo-2,3-dihydro-1H-inden-4-yl)(methyl)(oxo)-λ⁶-sulfanylidene)cyanamide Dess-Martin periodinane (192 mg, 0.45 mmol) was added to a solution of N-((7-(3,5-difluorophenoxy)-3-hydroxy-2,3-dihydro-1H-inden-4-yl)(methyl)(oxo)-λ⁶-sulfanylidene)cyanamide (Compound 189, 86 mg, 0.24 mmol) in dichloromethane (5 mL). The mixture was stirred at ambient temperature. After 30 minutes, the reaction mixture was partitioned between EtOAc and water. The EtOAc was washed with brine, dried over MgSO₄, filtered, and evaporated to afford N-((7-(3,5-difluorophenoxy)-3-oxo-2,3-dihydro-1H-inden-4-yl)(methyl)(oxo)-λ⁶-sulfanylidene)cyanamide (95 mg, 0.26 mmol, 100% yield) as a colorless glass. m/z (ES-API-pos) [M+H]=363.

Step B: N-((3-(butylimino)-7-(3,5-difluorophenoxy)-2,3-dihydro-1H-inden-4-yl)(methyl)(oxo)-λ⁶-sulfanylidene)cyanamide Trifluoroacetic acid (0.004 mL, 0.05 mmol) was added to a solution of N-((7-(3,5-difluorophenoxy)-3-oxo-2,3-dihydro-1H-inden-4-yl)(methyl)(oxo)-λ⁶-sulfanylidene)cyanamide (95 mg, 0.26 mmol) and butan-1-amine (1.3 mL, 13 mmol) in benzene (15 mL). This was refluxed with a Hickman still attached for 6 hours and stirred at ambient temperature overnight. The reaction mixture was evaporated and the dark green residue partitioned between EtOAc and saturated aqueous NaHCO₃. The EtOAc was washed with brine, dried over MgSO₄, filtered, and evaporated to afford N-((3-(butylimino)-7-(3,5-difluorophenoxy)-2,3-dihydro-1H-inden-4-yl)(methyl)(oxo)-λ⁶-sulfanylidene)cyanamide (110 mg; 0.26 mmol; 100% yield).

Step C: N-((7-(3,5-difluorophenoxy)-2,2-difluoro-3-oxo-2,3-dihydro-1H-inden-4-yl)(methyl)(oxo)-λ⁶-sulfanylidene)cyanamide 1-(Chloromethyl)-4-fluoro-1,4-diazoniabicyclo[2.2.2]octane ditetrafluoroborate (231 mg, 0.65 mmol) was added to a mixture of N-((3-(butylimino)-7-(3,5-difluorophenoxy)-2,3-dihydro-1H-inden-4-yl)(methyl)(oxo)-λ⁶-sulfanylidene)cyanamide (109 mg, 0.26 mmol) and sodium sulfate (37 mg, 0.26 mmol) in acetonitrile (8 mL). The reaction mixture was heated at 80° C. for 8 hours and treated with 6 M HCl (1 mL) and water (1 mL) and stirred for 15 minutes. The reaction mixture was partitioned between EtOAc and water. The EtOAc was washed with brine, dried over MgSO₄, filtered, and evaporated. The residue was chromatographed on a Biotage 10 g SNAP column with a 20% to 100% EtOAc:hexane gradient to afford N-((7-(3,5-difluorophenoxy)-2,2-difluoro-3-oxo-2,3-dihydro-1H-inden-4-yl)(methyl)(oxo)-λ⁶-sulfanylidene)cyanamide (5.7 mg, 0.014 mmol, 5% yield) as a pale yellow glass. m/z (ES-API-pos) [M+H]=399.

Step D: N-((7-(3,5-difluorophenoxy)-2,2-difluoro-3-hydroxy-2,3-dihydro-1H-inden-4-yl)(methyl)(oxo)-λ⁶-sulfanylidene)cyanamide (Compound 191)

Sodium borohydride (1.08 mg, 0.03 mmol) was added to a solution of N-((7-(3,5-difluorophenoxy)-2,2-difluoro-3-oxo-2,3-dihydro-1H-inden-4-yl)(methyl)(oxo)-λ⁶-sulfanylidene)cyanamide (5.7 mg, 0.01 mmol) in methanol (1 mL). The mixture was stirred at ambient temperature for 10 minutes. The reaction mixture was evaporated and the residue was partitioned between EtOAc and water. The EtOAc was washed with brine, dried over MgSO₄, filtered, and evaporated. The residue was chromatographed on a Biotage 10 g SNAP column with a 20% to 100% EtOAc:hexane gradient to afford Compound 191 (3.5 mg, 0.009 mmol, 61% yield) as a colorless glass. ¹H NMR (400 MHz, CDCl₃): δ 7.98-7.91 (m, 1H), 7.04-7.01 (m, 1H), 6.80-6.73 (m, 1H), 6.69-6.61 (m, 2H), 5.73-5.63 (m, 1H), 3.60 (s, 1H), 3.58-3.40 (m, 5H). m/z (ES-API-pos) [M+H]=401.

Example 192

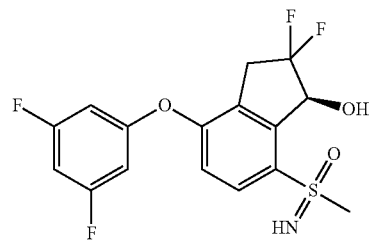 [SMILES: CS(=N)(=O)c1ccc(Oc2cc(F)cc(F)c2)c2c1[C@H](O)C(F)(F)C2]

((S)-7-(3,5-Difluorophenoxy)-2,2-difluoro-3-hydroxy-2,3-dihydro-1H-inden-4-yl)(imino)(methyl)-λ⁶-sulfanone (Compound 192)

Step A: (7-(3,5-Difluorophenoxy)-3-oxo-2,3-dihydro-1H-inden-4-yl)(imino)(methyl)-λ⁶-sulfanone Dess-Martin periodinane (192 mg, 0.452 mmol) was added to a solution of (7-(3,5-Difluorophenoxy)-3-hydroxy-2,3-dihydro-1H-inden-4-yl)(imino)(methyl)-λ⁶-sulfanone (Compound 190, 69 mg, 0.2 mmol) in dichloromethane (10 mL). The mixture was stirred at ambient temperature. After 15 minutes, the reaction mixture was evaporated and the residue was partitioned between EtOAc and a mixture of 1 M sodium thiosulfate and saturated aqueous NaHCO₃. The EtOAc was washed with saturated aqueous NaHCO₃, brine, dried over MgSO₄, filtered, and evaporated. The residue was chromatographed on a Biotage 10 g SNAP column with a 80% to 100% EtOAc:hexane gradient to afford the desired ketone product. An adduct of the desired product and the periodinane (49 mg) was also obtained. The adduct was taken up in methanol (3 mL) and treated with 1 M HCl (10 drops). After 10 minutes, the reaction mixture was evaporated and the residue was partitioned between EtOAc and dilute NaHCO₃. The EtOAc was washed with brine, dried over MgSO₄, filtered, and evaporated. The residue was chromatographed on a Biotage 10 g SNAP column with a 80% to 100% EtOAc:hexane gradient. Desired fractions were evaporated and combined with the previously obtained product to afford (7-(3,5-difluorophenoxy)-3-oxo-2,3-dihydro-1H-inden-4-yl)(imino)(methyl)-λ⁶-sulfanone (36 mg, 0.11 mmol, 53% yield) as a white solid. m/z (ES-API-pos) [M+H]=338.

Step B: (3-(Butylimino)-7-(3,5-difluorophenoxy)-2,3-dihydro-1H-inden-4-yl)(imino)(methyl)-λ⁶-sulfanone Trifluoroacetic acid (0.0013 mL, 0.02 mmol) was added to a solution of (7-(3,5-difluorophenoxy)-3-oxo-2,3-dihydro-1H-inden-4-yl)(imino)(methyl)-λ⁶-sulfanone (27.9 mg, 0.08 mmol) and butan-1-amine (0.41 mL, 4.1 mmol) in benzene (10 mL). The mixture was refluxed with a Hickman still attached. After 6 hours, the reaction mixture was evaporated and the residue was partitioned between EtOAc and saturated aqueous NaHCO₃. The EtOAc was washed with brine, dried over MgSO₄, filtered, and evaporated to afford (3-(butylimino)-7-(3,5-difluorophenoxy)-2,3-dihydro-1H-inden-4-yl)(imino)(methyl)-λ⁶-sulfanone (32 mg, 0.08 mmol, 100% yield) as a yellow film.

Step C: (7-(3,5-Difluorophenoxy)-2,2-difluoro-3-oxo-2,3-dihydro-1H-inden-4-yl)(imino)(methyl)-λ⁶-sulfanone 1-(Chloromethyl)-4-fluoro-1,4-diazoniabicyclo[2.2.2]octane ditetrafluoroborate (72 mg, 0.2 mmol) was added to a mixture of crude (3-(butylimino)-7-(3,5-difluorophenoxy)-2,3-dihydro-1H-inden-4-yl)(imino)(methyl)-λ⁶-sulfanone (32 mg, 0.08 mmol) and sodium sulfate (11.6 mg, 0.08 mmol) in acetonitrile (3 mL). The reaction mixture was heated at 80° C. for 6 hours, then stirred at ambient temperature overnight. The mixture was treated with 6 M HCl (0.5 mL) and water (1 mL), and stirred for 15 minutes. The reaction mixture was partitioned between EtOAc and water. The EtOAc was washed with brine, dried over MgSO₄, filtered, and evaporated. The residue was chromatographed on a Biotage 10 g SNAP column with a 40% to 100% EtOAc:hexane gradient to afford (7-(3,5-difluorophenoxy)-2,2-difluoro-3-oxo-2,3-dihydro-1H-inden-4-yl)(imino)(methyl)-λ⁶-sulfanone (13.7 mg, 0.04 mmol, 45% yield) as a pale yellow glass. m/z (ES-API-pos) [M+H]=374.

Step D: ((S)-7-(3,5-Difluorophenoxy)-2,2-difluoro-3-hydroxy-2,3-dihydro-1H-inden-4-yl)(imino)(methyl)-λ⁶-sulfanone (Compound 192)

RuCl(p-cymene)[(R,R)-Ts-DPEN] (0.47 mg, 0.0007 mmol) was added to a nitrogen-sparged ice-cold solution of (7-(3,5-difluorophenoxy)-2,2-difluoro-3-oxo-2,3-dihydro-1H-inden-4-yl)(imino)(methyl)-λ⁶-sulfanone (13.7 mg, 0.037 mmol), formic acid (0.0035 mL, 0.09 mmol), and triethylamine (0.01 mL, 0.07 mmol) in dichloromethane (5 mL). The mixture was stored at 4° C. overnight. The reaction mixture was evaporated and the residue was chromatographed on a Biotage 10 g SNAP column with a 40% to 100% EtOAc:hexane gradient to afford Compound 192 (10 mg, 0.028 mmol, 76% yield) as a colorless film. ¹H NMR (400 MHz, CDCl₃): δ 7.96-7.89 (m, 1H), 7.03-6.98 (m, 1H), 6.73-6.66 (m, 1H), 6.63-6.55 (m, 2H), 5.62-5.56 (m, 1H), 5.47-5.41 (m, 1H), 3.57-3.30 (m, 2H), 3.28 (s, 3H) 3.24-2.88 (m, 1H). m/z (ES-API-pos) [M+H]=376.

Example 193

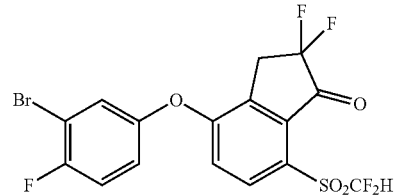

4-(3-Bromo-4-fluorophenoxy)-7-((difluoromethyl)sulfonyl)-2,2-difluoro-2,3-dihydro-1H-inden-1-one (Compound 193)

Prepared similarly according to Example 25, Steps A-D, utilizing 3-bromo-4-fluorophenol. ¹H NMR (400 MHz, CDCl₃) δ 8.18 (d, 1H), 7.41-7.39 (m, 1H), 7.30-7.26 (m, 1H), 7.13-7.05 (m, 2H), 6.91 (t, 1H), 3.67 (t, 2H).

Example 194

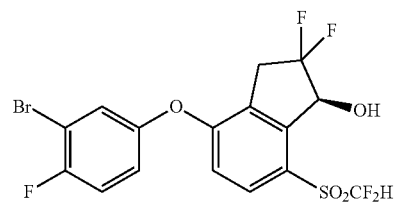

(S)-4-(3-Bromo-4-fluorophenoxy)-7-((difluoromethyl)sulfonyl)-2,2-difluoro-2,3-dihydro-1H-inden-1-ol (Compound 194)

Prepared similarly according to Example 25, Step E, utilizing Compound 193. LCMS ESI (−) m/z (M+HCOOH−

H): 517, 519; ¹H NMR (400 MHz, CDCl₃) δ 7.86 (d, 1H), 7.37-7.35 (m, 1H), 7.25-7.21 (m, 1H), 7.08-7.04 (m, 1H), 6.86 (d, 1H), 6.41 (t, 1H), 5.51-5.47 (m, 1H), 3.63-3.47 (m, 2H), 3.25 (d, 1H).

Example 195

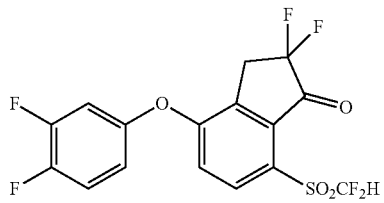

7-((Difluoromethyl)sulfonyl)-4-(3,4-difluorophenoxy)-2,2-difluoro-2,3-dihydro-1H-inden-1-one (Compound 195)

Prepared similarly according to Example 25, Steps A-D, utilizing 3,4-difluorophenol. ¹H NMR (400 MHz, CDCl₃) δ 8.16 (d, 1H), 7.32 (q, 1H), 7.13 (d, 1H), 7.06-7.02 (m, 1H), 6.93-6.91 (m, 1H), 6.90 (t, 1H), 3.67 (t, 2H).

Example 196

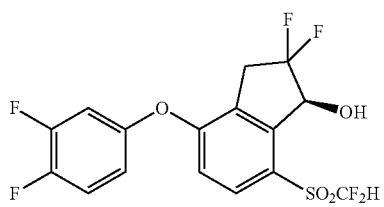

(S)-7-((Difluoromethyl)sulfonyl)-4-(3,4-difluorophenoxy)-2,2-difluoro-2,3-dihydro-1H-inden-1-ol (Compound 196)

Prepared similarly according to Example 25, Step E, utilizing Compound 195. LCMS ESI (−) m/z (M+HCOOH−H) 457; ¹H NMR (400 MHz, CDCl₃) δ 7.86 (d, 1H), 7.30-7.24 (m, 1H), 7.02-6.97 (m, 1H), 6.89-6.86 (m, 2H), 6.41 (t, 1H), 5.51-5.47 (m, 1H), 3.63-3.47 (m, 2H), 3.27 (d, 1H).

Example 197

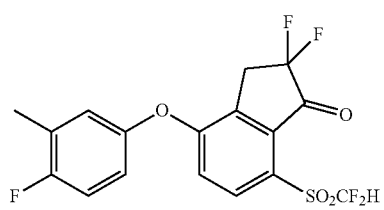

7-((Difluoromethyl)sulfonyl)-2,2-difluoro-4-(4-fluoro-3-methylphenoxy)-2,3-dihydro-1H-inden-1-one (Compound 197)

Prepared similarly according to Example 25, Steps A-D, utilizing 4-fluoro-3-methylphenol. ¹H NMR (400 MHz, CDCl₃) δ 8.14 (d, 1H), 7.15-7.05 (m, 2H), 6.99-6.91 (m, 2H), 6.92 (t, 1H), 3.67 (t, 2H), 2.33 (m, 3H).

Example 198

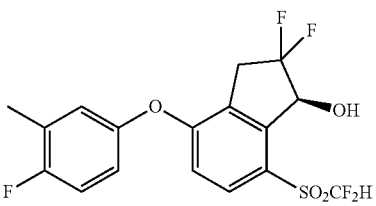

(S)-7-((Difluoromethyl)sulfonyl)-2,2-difluoro-4-(4-fluoro-3-methylphenoxy)-2,3-dihydro-1H-inden-1-ol (Compound 198)

Prepared similarly according to Example 25, Step E, utilizing Compound 197. LCMS ESI (−) m/z (M+HCOOH−H) 452.9; ¹H NMR (400 MHz, CDCl₃) δ 7.82 (d, 1H), 7.09 (t, 1H), 6.93-6.88 (m, 2H), 6.82 (d, 1H), 6.40 (t, 1H), 5.48 (m, 1H), 3.63-3.48 (m, 2H), 3.25 (d, 1H), 2.31 (m, 3H).

Example 199

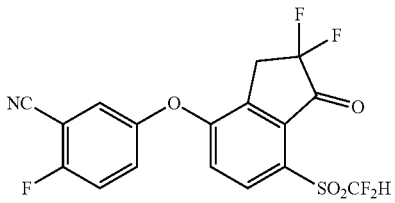

7-((Difluoromethyl)sulfonyl)-2,2-difluoro-4-(4-fluoro-3-methylphenoxy)-2,3-dihydro-1H-inden-1-one (Compound 199)

Prepared similarly according to Example 25, Steps A-D, utilizing 2-fluoro-5-hydroxybenzonitrile. ¹H NMR (400 MHz, CDCl₃) δ 8.20 (d, 1H), 7.47-7.38 (m, 3H), 7.11 (d, 1H), 6.92 (t, 1H), 3.68 (t, 2H).

Example 200

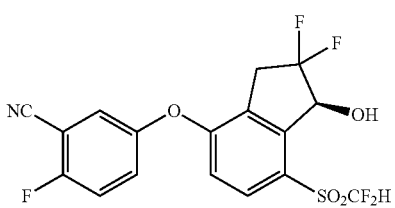

(S)-5-((7-((Difluoromethyl)sulfonyl)-2,2-difluoro-1-hydroxy-2,3-dihydro-1H-inden-4-yl)oxy)-2-fluorobenzonitrile (Compound 200)

Prepared similarly according to Example 25, Step E, utilizing Compound 199. LCMS ESI (−) m/z (M+HCOOH−H) 464; $^1$H NMR (400 MHz, CDCl$_3$) δ 7.89 (d, 1H), 7.41-7.32 (m, 3H), 6.85 (d, 1H), 6.43 (t, 1H), 5.57-5.48 (m, 1H), 3.59-3.49 (m, 2H), 3.29 (d, 1H).

Example 201

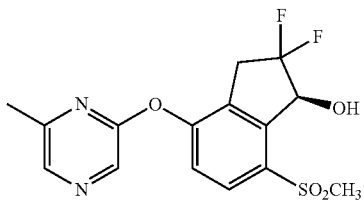 [SMILES: Cc1cncc(Oc2ccc(S(C)(=O)=O)c3c2CC(F)(F)[C@H]3O)n1]

(S)-2,2-Difluoro-4-((6-methylpyrazin-2-yl)oxy)-7-(methylsulfonyl)-2,3-dihydro-1H-inden-1-ol (Compound 201)

Prepared similarly according to procedures outlined in Example 163 utilizing 7-(methylsulfonyl)-2,3-dihydrospiro[indene-1,2'-[1,3]dioxolan]-4-ol and 2-chloro-6-methylpyrazine. LCMS ESI (−) m/z (M+HCOOH−H) 401; $^1$H NMR (400 MHz, CDCl$_3$) δ 8.31 (s, 1H), 8.28 (s, 1H), 7.94 (d, 1H), 7.33 (d, 1H), 5.61-5.58 (m, 1H), 3.57 (d, 1H), 3.51-3.28 (m, 2H), 3.24 (s, 3H), 2.44 (s, 3H).

Example 202

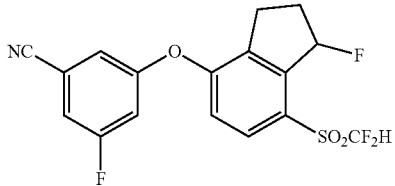

3-((7-((Difluoromethyl)sulfonyl)-1-fluoro-2,3-dihydro-1H-inden-4-yl)oxy)-5-fluorobenzonitrile (Compound 202)

Step A: Preparation of 3-((7-((difluoromethyl)sulfonyl)-1-hydroxy-2,3-dihydro-1H-inden-4-yl)oxy)-5-fluorobenzonitrile 3-((7-((difluoromethyl)sulfonyl)-1-oxo-2,3-dihydro-1H-inden-4-yl)oxy)-5-fluorobenzonitrile (prepared as described for Example 25, Steps A and B) (30 mg, 0.08 mmol) was slurried in 1,2-dichloroethane (0.5 mL), cooled to 0° C. and treated with sodium borohydride (5.9 mg, 0.16 mmol). The mixture was stirred at 0° C. for 2 hours. The reaction mixture was quenched with 10% citric acid and diluted with MTBE. After separation, the aqueous layer was washed with MTBE and the combined organic layers were washed with saturated NaHCO$_3$, saturated NaCl, dried over Na$_2$SO$_4$ and concentrated in vacuo to a colorless film. The crude material was chromatographed on SiO$_2$ eluting with a gradient of ethyl acetate/hexane. 3-((7-((Difluoromethyl)sulfonyl)-1-oxo-2,3-dihydro-1H-inden-4-yl)oxy)-5-fluorobenzonitrile was isolated as a colorless film (14.5 mg). LCMS ESI (−) m/z (M+HCOOH−H) 428.

Step B: Preparation of 3-((7-((difluoromethyl)sulfonyl)-1-fluoro-2,3-dihydro-1H-inden-4-yl)oxy)-5-fluorobenzonitrile 3-((7-((difluoromethyl)sulfonyl)-1-hydroxy-2,3-dihydro-1H-inden-4-yl)oxy)-5-fluorobenzonitrile (14.5 mg, 0.04 mmol) was dissolved in methylene chloride (0.2 mL) and cooled to 0° C. The solution was treated with (diethylamino)sulfur trifluoride (DAST) (7 µL, 0.05 mmol) and stirred at 0° C. for 30 minutes. An additional aliquot of (diethylamino)sulfur trifluoride (3 µL, 0.025 mmol) was added and the mixture was stirred at 0° C. for an additional hour. The reaction was quenched with water, diluted with methylene chloride and separated. The organic layer was washed twice with water, twice with one-half saturated NaHCO$_3$, dried over Na$_2$SO$_4$ and concentrated in vacuo. The crude colorless oil was chromatographed on SiO$_2$ eluting with a gradient of ethyl acetate/hexane to give Compound 202 as a colorless oil (10.3 mg). $^1$H NMR (400 MHz, CDCl$_3$) δ 7.95 (d, 1H), 7.28-7.26 (m, 1H), 7.18 (brd s, 1H), 7.08-7.03 (m, 2H), 6.64-6.47 (m, 1H), 6.34 (t, 1H), 3.23-3.14 (m, 1H), 3.04-2.95 (m, 1H), 2.57-2.42 (m, 2H).

Example 203

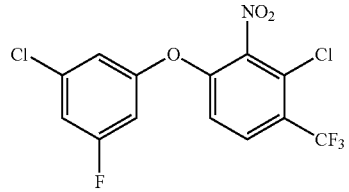 [SMILES: O=[N+]([O-])c1c(Oc2cc(F)cc(Cl)c2)ccc(C(F)(F)F)c1Cl]

2-Chloro-4-(3-chloro-5-fluorophenoxy)-3-nitro-1-(trifluoromethyl)benzene (Compound 203)

1,3-dichloro-2-nitro-4-(trifluoromethyl)benzene (0.15 g, 0.6 mmol) was dissolved in acetonitrile (1.8 mL) and treated with sodium bicarbonate (0.10 g, 1.18 mmol) followed by 3-chloro-5-fluorophenol (0.09 g, 0.6 mmol) and cesium carbonate (383 mg, 1.2 mmol). The mixture was stirred at ambient temperature for 9 days. The reaction mixture was concentrated with a stream of nitrogen gas then redissolved in Et$_2$O and water. After separation, the aqueous was washed with Et$_2$O then the combined organics were washed with 1M Na$_2$CO$_3$, saturated NaHCO$_3$, saturated NaCl, dried over Na$_2$SO$_4$ and concentrated in vacuo to a yellow oil which slowly solidified to a white solid. The crude material was chromatographed on SiO$_2$ eluting with a gradient of ethyl acetate/hexane to give Compound 203 as a colorless oil which solidified, under vacuum overnight, to free-flowing white solid (35 mg). $^1$H NMR (400 MHz, CDCl$_3$) δ 7.78-

7.75 (m, 1H), 7.05-7.02 (m, 1H), 7.00-6.98 (m, 1H), 6.93-6.92 (m, 1H), 6.78-6.75 (m, 1H).

Example 204

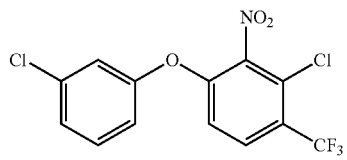 [SMILES: O=[N+]([O-])c1c(Oc2cccc(Cl)c2)ccc(C(F)(F)F)c1Cl]

2-Chloro-4-(3-chlorophenoxy)-3-nitro-1-(trifluoromethyl)benzene 1,3-dichloro-2-nitro-4-(trifluoromethyl)benzene (Compound 204)

Prepared analogously to the procedures for Compound 203 substituting 3-chloro-5-fluorophenol with 3-chlorophenol. LCMS ESI (−) m/z 350, 352, 354 (M−H); $^1$H NMR (400 MHz, CDCl$_3$): δ 7.71 (d, 1H), 7.38 (t, 1H), 7.31-7.26 (m, 1H), 7.14 (t, 1H), 7.03-7.00 (m, 1H), 6.91 (d, 1H).

Example 205

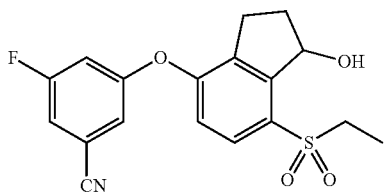 [SMILES: CCS(=O)(=O)c1ccc(Oc2cc(F)cc(C#N)c2)c2c1C(O)CC2]

3-((7-(Ethylsulfonyl)-1-hydroxy-2,3-dihydro-1H-inden-4-yl)oxy)-5-fluorobenzonitrile (Compound 205)

Step A: Preparation of 7-(ethylsulfonyl)-4-fluoro-2,3-dihydrospiro[indene-1,2'[1,3]dioxolane]

Prepared similarly as in Example 159 substituting iodomethane with bromoethane in step A.

Step B: Preparation of 3-((7-(ethylsulfonyl)-1-oxo-2,3-dihydro-1H-inden-4-yl)oxy)-5-fluorobenzonitrile Prepared similarly as in Example 163 substituting 4-fluoro-7-(methylsulfonyl)-2,3-dihydrospiro[indene-1,2'-[1,3]dioxolane] with 7-(ethylsulfonyl)-4-fluoro-2,3-dihydrospiro[indene-1,2'-[1,3]dioxolane].

Step C: Preparation of 3-((7-(ethylsulfonyl)-1-hydroxy-2,3-dihydro-1H-inden-4-yl)oxy)-5-fluorobenzonitrile: To a solution of 3-((7-(ethylsulfonyl)-1-oxo-2,3-dihydro-1H-inden-4-yl)oxy)-5-fluorobenzonitrile (0.03 g, 0.083 mmol) in MeOH (2 mL) was added sodium borohydride (0.003 g, 0.83 mmol) at ambient temperature. The reaction mixture was stirred at ambient temperature for 30 minutes. Water (50 mL) and dichloromethane (20 mL) were added. The organic layer was separated, washed with brine, dried (sodium sulfate), filtered and concentrated under reduced pressure. The residue obtained was purified by flash chromatography on silica gel to give Compound 205 (0.02 g, 67%) as solid. $^1$HNMR (400 MHz, CDCl$_3$): δ 7.79 (d, 1H), 7.18 (d, 1H), 7.09 (s, 1H), 6.98 (m, 2H), 5.65 (m, 1H), 3.69 (d, 1H), 3.29 (m, 2H), 3.08 (m, 1H), 2.83 (m, 1H), 2.45 (m, 1H), 2.24 (m, 1H), 1.36 (t, 3H).

Example 206

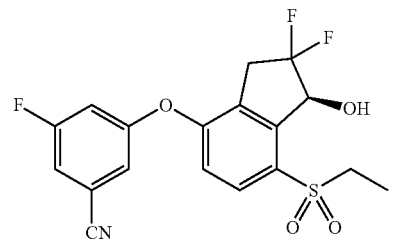 [SMILES: CCS(=O)(=O)c1ccc(Oc2cc(F)cc(C#N)c2)c2c1[C@H](O)C(F)(F)C2]

(S)-3-((7-(Ethylsulfonyl)-2,2-difluoro-1-hydroxy-2,3-dihydro-1H-inden-4-yl)oxy)-5-fluorobenzonitrile (Compound 206)

Prepared similarly as in Example 163 substituting 3-fluoro-5-(7-methylsulfonyl-1-oxo-indan-4-yl)oxy-benzonitrile with 3-((7-(ethylsulfonyl)-1-oxo-2,3-dihydro-1H-inden-4-yl)oxy)-5-fluorobenzonitrile in step D. LC-MS ESI (−) m/z 442 (M+HCO2). $^1$H NMR (400 MHz, CDCl$_3$): δ 7.86 (m, 1H), 7.27-7.24 (m, 1H), 7.16-7.14 (m, 1H), 7.07-7.04 (m, 1H), 6.99 (d, 1H), 5.55-5.51 (m, 1H), 3.61-3.27 (m, 5H), 1.35 (t, 3H).

Example 207

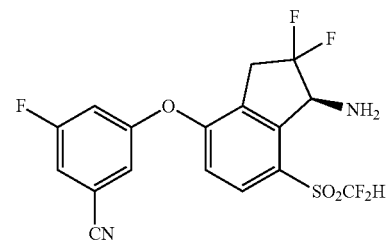

(S)-3-((1-Amino-7-((difluoromethyl)sulfonyl)-2,2-difluoro-2,3-dihydro-1H-inden-4-yl)oxy)-5-fluorobenzonitrile (Compound 207)

Step A: A solution of 3-[7-(difluoromethylsulfonyl)-2,2-difluoro-1-oxo-indan-4-yl]oxy-5-fluoro-benzonitrile (40 mg, 0.1 mmol) and titanium(IV) ethoxide (60 μL, 0.3 mmol) in tetrahydrofuran (1.0 mL) was treated with (R)-2-methylpropane-2-sulfinamide (14 mg, 0.12 mmol) and heated by microwave irradiation to 90° C. for 30 minutes. The reaction mixture was then cooled to ambient temperature, treated with sodium triacetoxyborohydride (31 mg, 0.14 mmol) and allowed to stir for 2 hours. The reaction mixture was quenched with 1 mL of brine and the resulting suspension was vigorously stirred for 10 minutes. The filtrate was rinsed with water and the leftover aqueous phase was extracted with 2×20 mL EtOAc. The combined organics were rinsed with 10 mL of brine, dried with MgSO₄, filtered, and concentrated to dryness. Purification was achieved by chromatography on silica using 0%-40% EtOAc/CHCl₃.(R)—N—((S)-4-(3-cyano-5-fluorophenoxy)-7-((difluoromethyl)sulfonyl)-2,2-difluoro-2,3-dihydro-1H-inden-1-yl)-2-methylpropane-2-sulfinamide was isolated as a slightly impure dark green film (11 mg, 0.02 mmol, 21% yield). LCMS ESI (+) m/z 523 (M+H).

Step B: A solution of N-[(1S)-4-(3-cyano-5-fluoro-phenoxy)-7-(difluoromethylsulfonyl)-2,2-difluoro-indan-1-yl]-2-methyl-propane-2-sulfinamide (11 mg from step A, 0.02 mmol) in methanol (0.4 mL) at 25° C. was treated with hydrogen chloride (4.0 M solution in dioxane, 0.2 mL, 0.81 mmol) and stirred at 25° C. After 3 hours, volatiles were removed by concentration under reduced pressure. The reaction mixture was poured into 10 mL of aqueous saturated NaHCO₃ and extracted with 3×10 mL EtOAc. The combined organics were rinsed with 10 mL of brine, dried with MgSO₄, filtered, and concentrated to dryness. Purification was achieved by chromatography on silica using 10%-35% EtOAc/hexane to give Compound 207 (4.4 mg, 0.01 mmol, 52% yield). ESI (+) m/z 419 (M+H); ¹H NMR (400 MHz, CDCl₃): δ 7.94 (d, 1H), 7.32-7.28 (m, 1H), 7.22-7.19 (m, 1H), 7.12-7.07 (m, 1H), 6.94 (d, 1H), 6.83 (t, 1H), 4.91 (d, 1H), 3.60-3.40 (m, 2H), 1.91 (br s, 2H).

Example 208

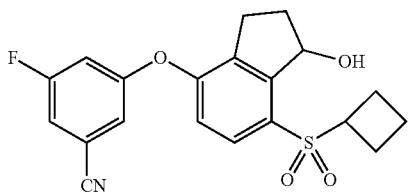 [SMILES: N#Cc1cc(F)cc(Oc2ccc(S(=O)(=O)C3CCC3)c3c2CCC3O)c1]

3-((7-(Cyclobutylsulfonyl)-1-hydroxy-2,3-dihydro-1H-inden-4-yl)oxy)-5-fluorobenzonitrile (Compound 208)

Step A: Preparation of 7-(cyclobutylthio)-4-fluoro-2,3-dihydro-1H-inden-1-one

To a solution of 4-fluoro-7-sulfanyl-indan-1-one (2.5 g, 13.7 mmol) in DMSO (25 mL) was added t-BuOK at ambient temperature and stirred for 10 minutes. Then bromocyclobutane (2.78 g, 20.6 mmol) was added and the mixture was stirred at ambient temperature overnight. The mixture was poured into water and extracted with ethyl acetate. The organic phase was separated, dried (sodium sulfate), filtered and concentrated under reduced pressure to give 7-(cyclobutylthio)-4-fluoro-2,3-dihydro-1H-inden-1-one to be used directly to the next step without purification.

Step B: Preparation of 3-((7-(cyclobutylsulfonyl)-1-hydroxy-2,3-dihydro-1H-inden-4-yl)oxy)-5-fluorobenzonitrile (Compound 208)

Prepared similarly as in Example 205 substituting 4-fluoro-7-(ethylsulfonyl)-2,3-dihydrospiro[indene-1,2'-[1,3]dioxolane] with 7-(cyclobutylthio)-4-fluoro-2,3-dihydro-1H-inden-1-one in step A. ¹HNMR (400 MHz, CDCl₃): δ 7.73 (d, 1H), 7.18 (d, 1H), 7.08 (s, 1H), 6.95 (m, 2H), 5.62 (m, 1H), 4.02 (m, 1H), 3.77 (s, 1H), 3.07 (m, 1H), 2.81 (m, 1H), 2.61 (m, 2H), 2.45 (m 1H), 2.26 (m, 3H), 2.06 (m, 2H).

Example 209

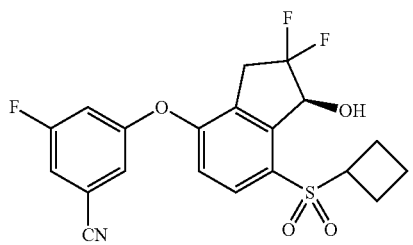 [SMILES: N#Cc1cc(F)cc(Oc2ccc(S(=O)(=O)C3CCC3)c3c2CC(F)(F)[C@H]3O)c1]

(S)-3-((7-(Cyclobutylsulfonyl)-2,2-difluoro-1-hydroxy-2,3-dihydro-1H-inden-4-yl)oxy)-5-fluorobenzonitrile (Compound 209)

Prepared similarly as in Example 163 substituting 3-fluoro-5-(7-methylsulfonyl-1-oxo-indan-4-yl)oxy-benzonitrile with 3-((7-(cyclobutylsulfonyl)-1-oxo-2,3-dihydro-1H-inden-4-yl)oxy)-5-fluorobenzonitrile in step D. LC-MS ESI (−) m/z 468 (M+HCO2). ¹HNMR (400 MHz, CDCl₃): δ 7.81 (d, 1H), 7.27-7.24 (m, 1H), 7.15-7.14 (m, 1H), 7.06-7.03 (m, 1H), 6.96 (d, 1H), 5.50-5.45 (m, 1H), 3.70 (d, 1H), 3.55-3.34 (m, 2H), 2.67-2.50 (m, 2H), 2.29-2.17 (m, 2H), 2.08-2.01 (m, 2H).

Example 210

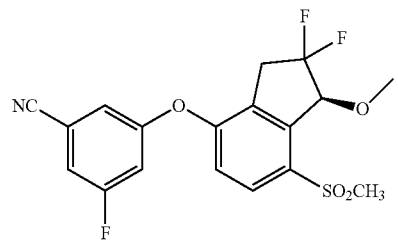 [SMILES: CO[C@H]1c2c(S(C)(=O)=O)ccc(Oc3cc(F)cc(C#N)c3)c2CC1(F)F]

(S)-3-((2,2-Difluoro-1-methoxy-7-(methylsulfonyl)-2,3-dihydro-1H-inden-4-yl)oxy)-5-fluorobenzonitrile (Compound 210)

To a stirred solution (S)-3-((2,2-difluoro-1-hydroxy-7-(methylsulfonyl)-2,3-dihydro-1H-inden-4-yl)oxy)-5-fluorobenzonitrile Compound 163 (20 mg, 0.05 mmol) in DMF (0.5 mL) were added cesium carbonate (34 mg, 0.1 mmol) and MeI (0.02 mL, 0.26 mmol). The reaction mixture was heated at 90° C. under nitrogen for 16 hours. After cooling, the reaction mixture was partitioned between EtOAc and water. The aqueous layer was extracted with EtOAc. The combined organic layers were washed with water and brine, dried and concentrated. The residue was purified by flash chromatography on silica gel (10-35% EtOAc/hexane) affording Compound 210 (6 mg, 29%) as a white solid. LCMS ESI (+) m/z 398 (M+H); ¹H NMR (400 MHz, CDCl₃): δ 7.95 (d, 1H), 7.24 (d, 1H), 7.13 (br s, 1H), 7.05-7.01 (m, 1H), 6.99 (d, 1H), 5.31 (d, 1H), 3.78 (s, 3H), 3.53-3.32 (m, 2H), 3.19 (s, 3H).

Example 211

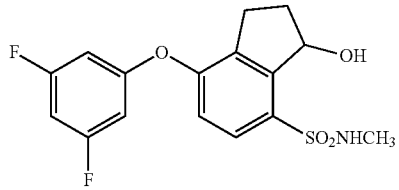

7-(3,5-Difluorophenoxy)-3-hydroxy-N-methyl-2,3-dihydro-1H-indene-4-sulfonamide (Compound 211)

Step A: Preparation of 7-fluoro-3-oxo-indane-4-sulfonyl chloride

To a mixture of N-chlorosuccinimide (2.95 g, 22 mmol), acetonitrile (18 mL) and 2 N HCl (3.6 mL) cooled in an ice-water bath was added O-(7-fluoro-3-oxo-indan-4-yl)-N,N-dimethylcarbamothioate (1.40 g, 5.5 mmol) in small portions to maintain the temperature between 5 to 10° C. The reaction mixture was stirred in the cold-water bath for 3 hours. The reaction mixture was then poured into half-saturated brine and extracted with dichloromethane. The organic layer was washed with saturated aqueous NaHCO₃ solution and brine, dried over Na₂SO₄, filtered, and concentrated. The crude was used in the next step without further purifications. LCMS ESI (+) m/z 249, 251 (M+H).

Step B: Preparation of 7-fluoro-N-methyl-3-oxo-indane-4-sulfonamide

To a stirred mixture of 7-fluoro-3-oxo-indane-4-sulfonyl chloride (520 mg, 2.1 mmol) and methylamine hydrochloride (169 mg, 2.5 mmol) in dichloromethane (21 mL) was added dropwise triethylamine (0.87 mL, 6.27 mmol) at 0° C. under nitrogen. The reaction mixture was stirred at 0° C. for 2 hours. The reaction mixture was then diluted with dichloromethane, washed with saturated aqueous NaHCO₃ solution and brine, dried and concentrated. The residue was purified by flash chromatography on silica gel (10-60% EtOAc/hexane) to give 7-fluoro-N-methyl-3-oxo-indane-4-sulfonamide (102 mg, 20%). LCMS ESI (+) m/z 244 (M+H).

Step C: Preparation of 7-(3,5-difluorophenoxy)-3-hydroxy-N-methyl-2,3-dihydro-1H-indene-4-sulfonamide Prepared analogously to the procedures for Compound 17. LCMS ESI (−) m/z 354 (M−H); ¹H NMR (400 MHz, CDCl₃): δ 7.75 (d, 1H), 6.94 (d, 1H), 6.65-6.60 (m, 1H), 6.54-6.52 (m, 2H), 5.77-5.71 (m, 1H), 5.02-4.95 (m, 1H), 3.23-3.18 (m, 1H), 3.12-3.04 (m, 1H), 2.84-2.70 (m, 1H), 2.65 (d, 3H), 2.57-2.47 (m, 1H), 2.19-2.11 (m, 1H).

Example 212

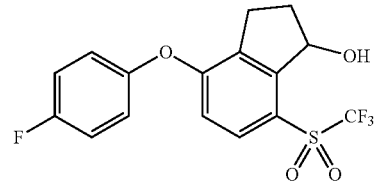 [SMILES: O=S(=O)(c1ccc(Oc2ccc(F)cc2)c2c1C(O)CC2)C(F)(F)F]

4-(4-Fluorophenoxy)-7-((trifluoromethyl)sulfonyl)-2,3-dihydro-1H-inden-1-ol (Compound 212)

Step A: Preparation of 4-fluoro-7-((trifluoromethyl)sulfonyl)-2,3-dihydrospiro[indene-1,2'-[1,3]dioxolane]

Trimethylsily trifluoromethanesulfonate (10.6 g, 47.8 mmol) was added dropwise to a solution of 4-fluoro-7-(trifluoromethylsulfonyl)indan-1-one (27.0 g, 95.7 mmol) and trimethyl(2-trimethylsiilyloxyethoxy)silane (23.7 g, 114.8 mmol) in dichloromethane (500 mL) at −78° C. After addition, the reaction mixture was allowed to warm to ambient temperature. After 2 hours at ambient temperature, the reaction was quenched with triethylamine and the mixture was concentrated under reduced pressure. The residue was dissolved in ethyl acetate (500 mL), washed with water (2×200 mL), brine (500 mL), dried (sodium sulfate), filtered, and concentrated under reduced pressure. The residue was purified by flash column chromatography on silica gel eluting with 20% ethyl acetate in hexane to give 4-fluoro-7-((trifluoromethyl)sulfonyl)-2,3-dihydrospiro[indene-1,2'-[1,3]dioxolane] (25.0 g, 80%) as a white solid.

Step B: Preparation of 4-(4-fluorophenoxy)-7-((trifluoromethyl)sulfonyl)-2,3-dihydrospiro[indene-1,2'-[1,3]dioxolane]

A solution of 4'-fluoro-7'-(trifluoromethylsulfonyl)spiro [1,3-dioxolane-2,1'-indane] (0.16 g, 0.5 mmol) and 4-fluorophenol (0.056 g, 0.5 mmol) in 1-methyl-2-pyrrolidone (10 mL) was treated with cesium carbonate (0.33 g, 1.0 mmol) at ambient temperature. The reaction was stirred at 100° C. for 1 hour. After cooling to ambient temperature, water was added and the resulting mixture was extracted with ethyl acetate. The combined organic layer was washed with water, dried (magnesium sulfate), filtered, and concentrated under reduced pressure. The residue was purified by flash chromatography on silica gel eluting 20% ethyl acetate in hexane to give 4-(4-fluorophenoxy)-7-((trifluoromethyl)sulfonyl)-2,3-dihydrospiro[indene-1,2'-[1,3]dioxolane] (0.12 g, 57%) as oil.

Step C: Preparation of 4-(4-fluorophenoxy)-7-((trifluoromethyl)sulfonyl)-2,3-dihydro-1H-inden-1-one To a solution of 4'-(4-fluorophenoxy)-7'-(trifluoromethylsulfonyl)spiro[1,3-dioxolane-2,1'-indane] (0.12 g, 0.29 mmol) in methanol (5 mL), 2 N HCl (2.0 mL) was added at ambient temperature. The reaction was stirred at ambient temperature for 2 hours. Water (50 mL) and ethyl acetate (25 mL) were added. The organic layer was separated, washed with brine, dried (magnesium sulfate), filtered, and concentrated under reduced pressure. The residue was purified by flash chromatography on silica gel to give 4-(4-fluorophenoxy)-7-((trifluoromethyl)sulfonyl)-2,3-dihydro-1H-inden-1-one (0.09 g, 84%) as solid.

Step D: Preparation of 4-(4-fluorophenoxy)-7-((trifluoromethyl)sulfonyl)-2,3-dihydro-1H-inden-1-ol (Compound 212)

Prepared similarly as described in Example 205 substituting 3-((7-(ethylsulfonyl)-1-oxo-2,3-dihydro-1H-inden-4-yl)oxy)-5-fluorobenzonitrile with 4-(4-fluorophenoxy)-7-((trifluoromethyl)sulfonyl)-2,3-dihydro-1H-inden-1-one in step C. $^1$HNMR (400 MHz, CDCl$_3$): δ 7.77 (d, 1H), 7.05-7.26 (m, 4H), 6.75 (d, 1H), 5.62 (m, 1H), 3.17-3.30 (m, 2H), 2.98-3.07 (m, 1H), 2.40-2.47 (m, 1H), 2.28-2.37 (m, 1H).

Example 213

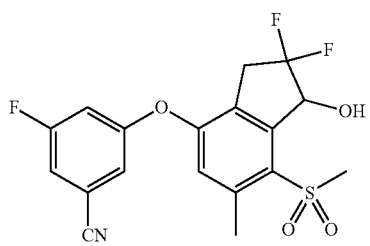 [SMILES: Cc1cc(Oc2cc(F)cc(C#N)c2)c2c(c1S(C)(=O)=O)C(O)C(F)(F)C2]

3-((2,2-Difluoro-1-hydroxy-6-methyl-7-(methyl sulfonyl)-2,3-dihydro-1H-inden-4-yl)oxy)-5-fluorobenzonitrile (Compound 213)

Prepared similarly as Example 163. $^1$HNMR (400 MHz, CDCl$_3$): δ 7.22-7.25 (m, 1H), 7.08 and 7.12 (m 1H), 6.98-7.04 (m 1H), 6.80 (s, 1H), 5.58 and 5.78 (m 1H), 3.69 (d, 1H), 3.20 and 3.23 (s, 3H), 3.08-3.47 (m, 2H), 2.68 (s, 3H).

Example 214

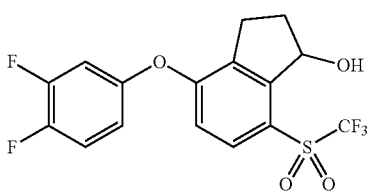 [SMILES: O=S(=O)(c1ccc(Oc2ccc(F)c(F)c2)c2c1C(O)CC2)C(F)(F)F]

4-(3,4-Difluorophenoxy)-7-((trifluoromethyl)sulfonyl)-2,3-dihydro-1H-inden-1-ol (Compound 214)

Prepared similarly as Example 212. $^1$H NMR (400 MHz, d$_6$-DMSO): 7.87 (d, 1H), 7.51-7.64 (m, 2H), 7.11-7.16 (m, 1H), 6.96 (d, 1H), 5.51 (m, 1H), 5.30 (d, 1H), 3.04-3.31 (m, 1H), 2.87-2.95 (m, 1H), 2.11-2.30 (m, 1H), 1.99-2.09 (m, 1H).

Example 215

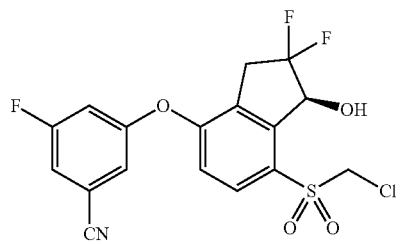 [SMILES: N#Cc1cc(F)cc(Oc2ccc(S(=O)(=O)CCl)c3c2CC(F)(F)[C@H]3O)c1]

(S)-3-((7-((Chloromethyl)sulfonyl)-2,2-difluoro-1-hydroxy-2,3-dihydro-1H-inden-4-yl)oxy)-5-fluorobenzonitrile (Compound 215)

Separated as a minor impurity in the final step for the preparation of Compound 163. $^1$HNMR (400 MHz, CDCl$_3$): 7.92 (d, 1H), 7.27 (m, 2H), 7.08 (d, 1H), 6.99 (d, 1H), 5.63 (dd, 1H), 4.92 (d, 1H), 4.65 (d, 1H), 3.34-3.49 (m, 2H), 3.21 (s, 1H).

Example 216

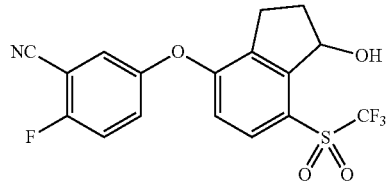 [SMILES: N#Cc1cc(Oc2ccc(S(=O)(=O)C(F)(F)F)c3c2CCC3O)ccc1F]

2-Fluoro-5-((1-hydroxy-7-((trifluoromethyl)sulfonyl)-2,3-dihydro-1H-inden-4-yl)oxy)benzonitrile (Compound 216)

Prepared similarly as Example 212. $^1$HNMR (400 MHz, CDCl$_3$): 7.83 (d, 1H), 7.26-7.38 (m, 3H), 6.81 (d, 1H), 5.64 (dd, 1H), 3.16-3.25 (m, 2H), 3.00-3.04 (m 1H), 2.34-2.42 (m, 2H), Example 217

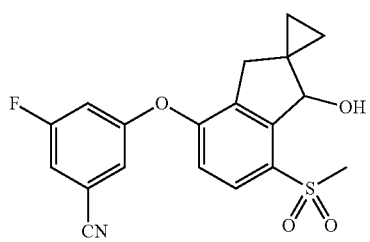 [SMILES: CS(=O)(=O)c1ccc(Oc2cc(F)cc(C#N)c2)c2c1C(O)C1(CC1)C2]

3-Fluoro-5-((1'-hydroxy-7'-(methylsulfonyl)-1',3'-dihydrospiro[cyclopropane-1,2'-inden]-4'-yl)oxy)benzonitrile (Compound 217)

To a solution of 3-fluoro-5-(7-methylsulfonyl-1-oxo-indan-4-yl)oxy-benzonitrile (0.1 g, 0.29 mmol) and 1, 2-dibromoethane (0.04 mL, 0.43 mmol) in N N-dimethylformamide (2 mL) was added 60% NaH (17.34 mg, 0.72 mmol) at ambient temperature. The mixture was stirred at ambient temperature for 2 hours. Methanol (2 mL) was added, followed by sodium borohydride (21.9 mg, 0.58 mmol). The mixture was stirred at ambient temperature for 1 hour. Water (10 mL) and ethyl acetate (20 mL) were added. The organic layer was separated, washed with brine, dried (sodium sulfate), filtered and concentrated under reduced pressure. The residue was purified by flash chromatography on silica gel 2:1 hexane/ethyl acetate to give Compound 217 (0.01 g, 0.025 mmol, 9% yield) as solid. LCMS ESI (−) 418 (M+HCO$_2^-$); $^1$H-NMR (400 MHz, CDCl$_3$): 7.88 (d, 1H), 7.17 (d, 1H), 7.09 (s, 1H), 7.06 (m, 2H), 5.07 (d, 1H), 3.20 (m, 5H), 2.60 (d, 1H), 1.18-1.32 (m, 2H), 0.68-0.87 (m, 2H).

Example 218

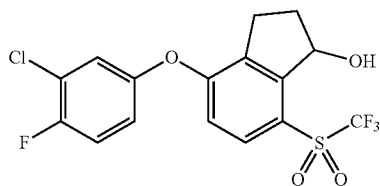 [SMILES: O=S(=O)(c1ccc(Oc2ccc(F)c(Cl)c2)c2c1C(O)CC2)C(F)(F)F]

4-(3-Chloro-4-fluorophenoxy)-7-((trifluoromethyl) sulfonyl)-2,3-dihydro-1H-inden-1-ol (Compound 218)

Prepared similarly as Example 212. $^1$HNMR (400 MHz, CDCl$_3$): 7.80 (d, 1H), 7.18-7.23 (m, 2H), 6.97-7.01 (m, 1H), 6.80 (d, 1H), 5.63 (m 1H), 3.16-3.29 (m, 2H), 2.96-3.05 (m 1H), 2.29-2.46 (m, 2H).

Example 219

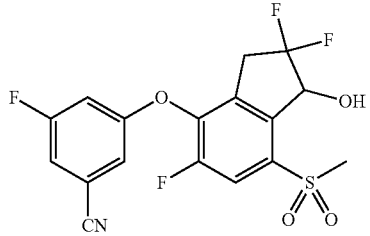 [SMILES: CS(=O)(=O)c1cc(F)c(Oc2cc(F)cc(C#N)c2)c2c1C(O)C(F)(F)C2]

3-Fluoro-5-((2,2,5-trifluoro-1-hydroxy-7-(methylsulfonyl)-2,3-dihydro-1H-inden-4-yl)oxy)benzonitrile (Compound 219)

Step A: Preparation of 5-bromo-3-fluoro-2-hydroxybenzaldehyde

To a solution of 4-bromo-2-fluoro-phenol (10 g, 52.4 mmol) in trifluoroacetic acid (50 mL) was added hexamethylenetetramine (14.7 g, 105 mmol) in three portions over 20 minutes at room temperature. The mixture was stirred at room temperature for 20 minutes, and then heated to 90° C. and stirred at 90° C. for 13 hours. The reaction mixture was cooled to room temperature. Water (60 mL) and a 50% aqueous sulfuric acid solution (30 mL) were sequentially added at room temperature, and the mixture was stirred at room temperature for two hours. The resultant mixture was extracted with ethyl acetate. The organic layer was washed with 1 N hydrochloric acid solution, brine, dried (magnesium sulfate), filtered and concentrated under reduced pressure. Ethanol (20 mL) was added and the mixture was stirred at room temperature for 30 minutes. The resulting mixture was filtered. Solid collected was washed with ethanol and dried to give 5-bromo-3-fluoro-2-hydroxybenzaldehyde (7.0 g, 61%).

Step B: Preparation of 3-(5-bromo-2-(3-cyano-5-fluorophenoxy)-3-fluorophenyl)propanoic acid Prepared similarly as in the synthesis of 3-[2-(3-cyano-5-fluoro-phenoxy)-5-methylsulfanyl-phenyl]propanoic acid in step B.

Step C: Preparation of methyl 3-(5-bromo-2-(3-cyano-5-fluorophenoxy)-3-fluorophenyl)propanoate To a solution of 3-(5-bromo-2-(3-cyano-5-fluorophenoxy)-3-fluorophenyl)propanoic acid (3.0 g, 7.85 mmol) in methanol (50 mL) was added concentrated H$_2$SO$_4$. (0.01 mL) at room temperature. The reaction was heated to 70° C. and stirred at this temperature for 2 hours. After cooling to room temperature, solvents were removed under reduced pressure. The residue was dissolved in ethyl acetate (50 mL), washed with water, brine, dried (MgSO4), filtered and concentrated under reduced pressure. The residue was purified by flash chromatography on silica gel to give methyl 3-(5-bromo-2-(3-cyano-5-fluorophenoxy)-3-fluorophenyl) propanoate (2.2 g, 71%) as solid.

Step D: Preparation of methyl 3-(5-(acetylthio)-2-(3-cyano-5-fluorophenoxy)-3-fluorophenyl)propanoate:

A mixture of methyl 3-[5-bromo-2-(3-cyano-5-fluoro-phenoxy)-3-fluoro-phenyl]propanoate (2.2 g, 5.6 mmol), CH$_3$COSK (0.95 g, 8.3 mmol), Pd$_2$(dba)$_3$ (0.51 g, 0.56 mmol) and Xantphos (0.48 g, 0.83 mmol) in toluene (40 mL) and acetone (20 mL) was stirred at 100° C. in a sealed tube for 5 hours. After cooling to room temperature, the solid was removed by filtration. The filtrate was concentrated under reduced pressure. The residue was purified by flash chromatography on silica gel to give methyl methyl 3-(5-(acetylthio)-2-(3-cyano-5-fluorophenoxy)-3-fluorophenyl)propanoate (1.0 g, 46%).

Step E: Preparation of methyl 3-(2-(3-cyano-5-fluorophenoxy)-3-fluoro-5-(methylthio)phenyl)propanoate To a solution of methyl 3-[5-acetylsulfanyl-2-(3-cyano-5-fluoro-phenoxy)-3-fluoro-phenyl]propanoate (1.0 g, 2.55 mmol) in methanol (50 mL) was added Cs$_2$CO$_3$ (1.25 g, 3.83 mmol) at room temperature. After 1 hour, Met (0.72 g, 5.11 mmol) was added and the reaction was stirred for additional 2 hours at room temperature. Water and dichloromethane were added and the organic layer was separated, washed with water, brine, dried (MgSO4), filtered and concentrated under reduced pressure. The residue obtained was purified by flash chromatography on silica gel to give methyl methyl 3-(2-(3-cyano-5-fluorophenoxy)-3-fluoro-5-(methylthio) phenyl)propanoate (0.6 g, 64%) as solid.

Step F: Preparation of 3-(2-(3-cyano-5-fluorophenoxy)-3-fluoro-5-(methylthio)phenyl)propanoic acid To a solution of methyl 3-[2-(3-cyano-5-fluoro-phenoxy)-3-fluoro-5-methylsulfanyl-phenyl]propanoate (0.60 g, 1.65 mmol) in methanol (10 mL) and water (10 mL), LiOH (0.079 g, 3.3 mmol) was added at room temperature. The reaction was stirred at room temperature overnight. It was acidified by 1N HCl to pH-3 and extracted with ethyl acetate. The organic layer was washed with brine, dried (sodium sulfate), filtered and concentrated under reduced pressure to give 3-(2-(3-cyano-5-fluorophenoxy)-3-fluoro-5-(methylthio)phenyl)propanoic acid (0.4 g, 69%).

Step G: Preparation of 3-fluoro-5-((2,2,5-trifluoro-1-hydroxy-7-(methylsulfonyl)-2,3-dihydro-1H-inden-4-yl)oxy)benzonitrile (Compound 219)

Prepared similarly as Example 163. $^1$HNMR (400 MHz, d$_6$-DMSO): δ 7.85 (d, 1H), 7.67 (m, 1H), 7.46 (d, 1H), 6.85 (d, 1H), 5.38 (dd, 1H), 3.40-3.49 (m, 2H), 3.40 (s, 3H).

Example 220

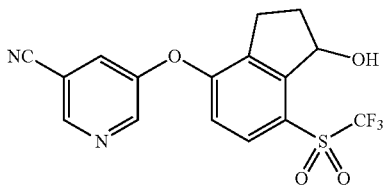 [SMILES: N#Cc1cncc(Oc2ccc(S(=O)(=O)C(F)(F)F)c3c2CCC3O)c1]

5-((1-Hydroxy-7-((trifluoromethyl)sulfonyl)-2,3-dihydro-1H-inden-4-yl)oxy)nicotinonitrile (Compound 220)

Prepared similarly as Example 212.

Example 221

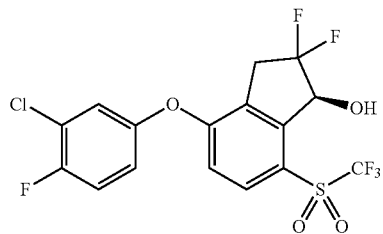 [SMILES: O=S(=O)(c1ccc(Oc2ccc(F)c(Cl)c2)c2c1[C@H](O)C(F)(F)C2)C(F)(F)F]

(S)-4-(3-Chloro-4-fluorophenoxy)-2,2-difluoro-7-((trifluoromethyl)sulfonyl)-2,3-dihydro-1H-inden-1-ol (Compound 221)

Prepared in a similar fashion as in the synthesis of Compound 185. LC-MS ESI (−) m/z 445, 447 (M−H); $^1$H-NMR (400 MHz, CDCl$_3$): δ 7.97 (d, 1H), 7.28-7.22 (m, 2H), 7.02 (d, 1H), 6.87 (d, 1H), 5.43-5.39 (m, 1H), 3.64-3.47 (m, 2H), 3.26 (d, 1H).

Example 222

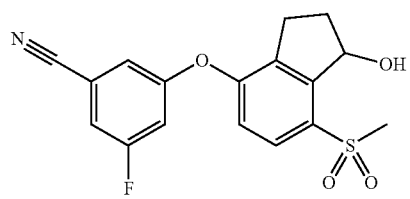 [SMILES: CS(=O)(=O)c1ccc(Oc2cc(F)cc(C#N)c2)c2c1C(O)CC2]

3-Fluoro-5-((1-hydroxy-7-(methylsulfonyl)-2,3-dihydro-1H-inden-4-yl)oxy)benzonitrile (Compound 222)

Sodium borohydride (6.6 mg, 0.17 mmol) was added all at once to a solution of 3-fluoro-5-(7-methylsulfonyl-1-oxo-indan-4-yl)oxy-benzonitrile (20.0 mg, 0.06 mmol) in methanol (1 mL) at room temperature then stirred for 15 minutes. The reaction mixture was quenched with water, extracted with ethyl acetate, washed with brine, dried over MgSO$_4$, filtered and concentrated in vacuo. The residue was purified on silica gel (10 g SNAP, 14 CV, 20-100% ethyl acetate/hexane) to afford Compound 222 (11 mg, 0.032 mmol, 55% yield). LC-MS ESI (−) m/z 392 (M+HCO$_2$$^−$); $^1$HNMR (400 MHz, CDCl$_3$): δ 7.84 (d, 1H), 7.19-7.17 (m, 1H), 7.08 (s, 1H), 7.00-6.97 (m, 2H), 5.71-5.68 (m, 1H), 3.64 (d, 1H), 3.21 (s, 3H), 3.12-3.04 (m, 1H), 2.84-2.76 (m, 1H), 2.52-2.43 (m, 1H), 2.27-2.19 (m, 1H).

Example 223

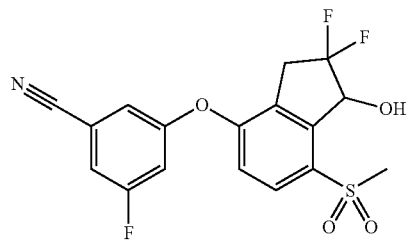 [SMILES: CS(=O)(=O)c1ccc(Oc2cc(F)cc(C#N)c2)c2c1C(O)C(F)(F)C2]

3-((2,2-Difluoro-1-hydroxy-7-(methylsulfonyl)-2,3-dihydro-1H-inden-4-yl)oxy)-5-fluorobenzonitrile (Compound 223)

Sodium borohydride (40 mg, 1.1 mmol) added all at once to 3-(2,2-difluoro-7-methylsulfonyl-1-oxo-indan-4-yl)oxy-5-fluoro-benzonitrile (200 mg, 0.52 mmol) in methanol (5 mL) at room temperature. The reaction mixture was stirred for 10 minutes, quenched with 1 N HCl, extracted with ethyl acetate, washed with brine, dried over MgSO4, filtered and concentrated in vacuo. The residue was purified on silica gel (10 g SNAP, 14 CV, 20-80% ethyl acetate/hexanes) to afford Compound 223 (146 mg, 0.38 mmol, 73% yield) as a white foam. LC-MS ESI (−) m/z 428 (M+HCO$_2$$^−$); $^1$HNMR (400 MHz, CDCl$_3$): δ 7.93 (d, 1H), 7.27-7.24 (m, 1H), 7.15-7.14 (m, 1H), 7.07-7.03 (m, 1H), 7.00 (d, 1H), 5.63-5.58 (m, 1H), 3.56-3.35 (m, 3H), 3.24 (s, 3H).

Example 224

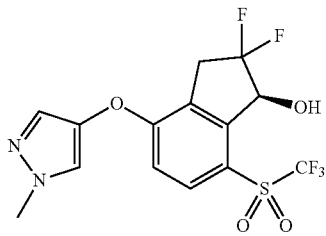 [SMILES: Cn1cc(Oc2ccc(S(=O)(=O)C(F)(F)F)c3c2CC(F)(F)[C@H]3O)cn1]

(S)-2,2-Difluoro-4-((1-methyl-1H-pyrazol-4-yl)oxy)-7-((trifluoromethyl)sulfonyl)-2,3-dihydro-1H-inden-1-ol (Compound 224)

Prepared in a similar fashion as in the synthesis of Compound 185. LC-MS ESI (+) m/z 399 (M+H); $^1$HNMR (400 MHz, CDCl$_3$): δ 7.87 (d, 1H), 7.40 (s, 1H), 7.36 (s, 1H), 7.08 (d, 1H), 5.42-5.38 (m, 1H), 3.94 (s, 3H), 3.59-3.52 (m, 2H), 3.21 (d, 1H).

Example 225

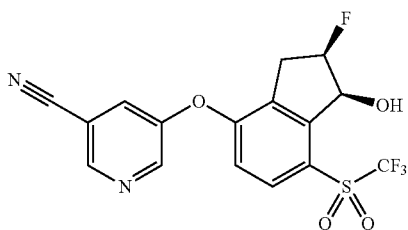 [SMILES: N#Cc1cncc(Oc2ccc(S(=O)(=O)C(F)(F)F)c3c2C[C@@H](F)[C@H]3O)c1]

5-(((1S,2R)-2-Fluoro-1-hydroxy-7-((trifluoromethyl)sulfonyl)-2,3-dihydro-1H-inden-4-yl)oxy)nicotinonitrile (Compound 225)

Step A: Preparation of 5-[7'-(trifluoromethylsulfonyl)spiro[1,3-dioxolane-2,1'-indane]-4'-yl]oxypyridine-3-carbonitrile Cesium carbonate (1.93 g, 5.94 mmol) was added all at once to 4'-fluoro-7'-(trifluoromethylsulfonyl)spiro[1,3-dioxolane-2,1'-indane] (775 mg, 2.38 mmol) and 3-cyano-5-hydroxypyridine (371 mg, 3.1 mmol) in 1-methyl-2-pyrrolidone (15 mL) then warmed to 100° C. for 90 minutes. The reaction mixture was diluted with water, extracted with methyl t-butyl ether, washed with brine, dried over Na$_2$SO$_4$, filtered and concentrated in vacuo. Crude 5-[7'-(trifluoromethylsulfonyl)spiro[1,3-dioxolane-2,1'-indane]-4'-yl]oxypyridine-3-carbonitrile was used without further purification. LC-MS ESI (+) m/z 427 (M+H).

Step B: Preparation of 5-[1-oxo-7-(trifluoromethylsulfonyl)indan-4-yl]oxypyridine-3-carbonitrile Concentrated HCl (3.24 mL, 9.38 mmol) was added to 5-[7'-(trifluoromethylsulfonyl)spiro[1,3-dioxolane-2,1'-indane]-4'-yl]oxypyridine-3-carbonitrile (1.0 g, 2.35 mmol) in acetone (15 mL) at room temperature and stirred for 4 hours. The reaction mixture was quenched with saturated NaHCO$_3$, extracted with ethyl acetate, washed with brine, dried over MgSO$_4$, filtered and concentrated in vacuo. The residue was purified on silica gel (25 g SNAP Ultra, 14 CV, 20-100% ethyl acetate/hexane) affording 5-[1-oxo-7-(trifluoromethylsulfonyl)indan-4-yl]oxypyridine-3-carbonitrile (737 mg, 1.93 mmol, 82% yield). LC-MS ESI (+) m/z 383 (M+H).

Step C: Preparation of 5-[2-fluoro-1-oxo-7-(trifluoromethylsulfonyl)indan-4-yl]oxypyridine-3-carbonitrile 1-Chloromethyl-4-fluoro-1,4-diazoniabicyclo[2.2.2]octane bis(tetrafluoroborate) (499 mg, 1.4 mmol) was added all at once to 5-[1-oxo-7-(trifluoromethylsulfonyl)indan-4-yl]oxypyridine-3-carbonitrile (269 mg, 0.7 mmol) in 2-propanol (10 mL) at room temperature then warmed to reflux until the reaction was complete as judged by LC-MS. The reaction mixture was diluted with water, extracted with ethyl acetate, washed with brine, dried over Na$_2$SO$_4$, filtered and dried in vacuo. The residue was purified on silica gel (10 g SNAP Ultra, 14 CV, 20-100% ethyl acetate/hexane) affording 5-[2-fluoro-1-oxo-7-(trifluoromethylsulfonyl)indan-4-yl]oxypyridine-3-carbonitrile (260 mg, 0.65 mmol, 92% yield). LC-MS ESI (−) m/z 399 (M−H).

Step D: Preparation of 5-[(1S,2R)-2-fluoro-1-hydroxy-7-(trifluoromethylsulfonyl)indan-4-yl]oxypyridine-3-carbonitrile (Compound 225)

Chloro{[(1R,2R)-(+2-amino-1,2-diphenylethyl](4-toluenesulfonyl)amido}(p-cymene)ruthenium(II) (2.1 mg, 0.007 mmol) was added all at once to an ice cold mixture of 5-[2-fluoro-1-oxo-7-(trifluoromethylsulfonyl)indan-4-yl]oxypyridine-3-carbonitrile (130 mg, 0.32 mmol), triethylamine (91 μL, 0.65 mmol) and formic acid (37 μL, 0.97 mmol) in dichloromethane (5 mL) then sealed with a teflon cap and placed in a 4° C. refridgerator overnight. The reaction mixture was purified directly on silica gel (10 g SNAP Ultra, 14 CV, 20-100% ethyl acetate/hexane) affording Compound 225 (112 mg, 0.28 mmol, 86% yield). LC-MS ESI (−) m/z 401 (M−H); $^1$H-NMR (400 MHz, CDCl$_3$): δ 8.82 (d, 1H), 8.70 (d, 1H), 7.95 (d, 1H), 7.71-7.69 (m, 1H), 6.94 (d, 1H), 5.64-5.59 (m, 1H), 5.46-5.31 (m, 1H), 3.36-3.27 (m, 2H), 3.19 (d, 1H).

Example 226

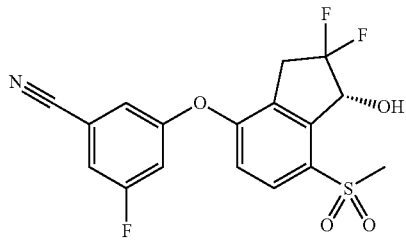 [SMILES: CS(=O)(=O)c1ccc(Oc2cc(F)cc(C#N)c2)c2c1[C@@H](O)C(F)(F)C2]

(R)-3-((2,2-Difluoro-1-hydroxy-7-(methylsulfonyl)-2,3-dihydro-1H-inden-4-yl)oxy)-5-fluorobenzonitrile (Compound 226)

Prepared similarly according to Step F in the synthesis of Compound 163 substituting chloro{[1S, 2S)-(−)-2-amino-1,2-diphenylethyl](4-toluenesulfonyl)amido}(p-cymene)ruthenium(II) for chloro{[(1R,2R)-(+2-amino-1,2-diphenylethyl](4-toluenesulfonyl)amido}(p-cymene)ruthenium(II). LC-MS ESI (−) m/z 428 (M+HCO$_2^-$); $^1$HNMR (400 MHz, CDCl$_3$): δ 7.93 (d, 1H), 7.27-7.24 (m, 1H), 7.15-7.14 (m, 1H), 7.07-7.03 (m, 1H), 7.00 (d, 1H), 5.63-5.58 (m, 1H), 3.56-3.35 (m, 3H), 3.24 (s, 3H).

Example 227

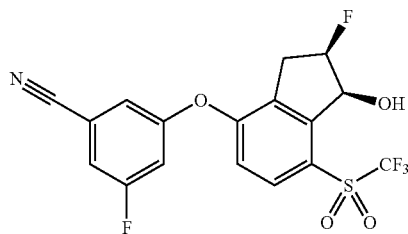 [SMILES: N#Cc1cc(F)cc(Oc2ccc(S(=O)(=O)C(F)(F)F)c3c2C[C@@H](F)[C@H]3O)c1]

3-Fluoro-5-(((1S,2R)-2-fluoro-1-hydroxy-7-((trifluoromethyl)sulfonyl)-2,3-dihydro-1H-inden-4-yl)oxy) benzonitrile (Compound 227)

Prepared similarly according to Compound 225, Steps A-D. LC-MS ESI (−) m/z 464 (M+HCO$_2^-$); $^1$HNMR (400 MHz, CDCl$_3$): δ 7.94 (d, 1H), 7.31-7.29 (m, 1H), 7.21 (s, 1H), 7.11-7.08 (m, 1H), 6.98 (d, 1H), 5.62-5.58 (m, 1H), 5.40-5.27 (m, 1H), 3.40-3.26 (m, 2H), 3.20 (d, 1H).

Example 228

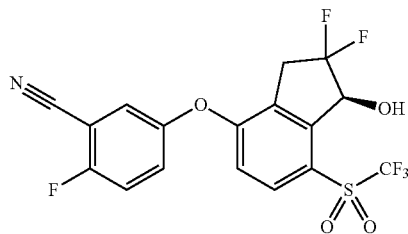 [SMILES: N#Cc1cc(Oc2ccc(S(=O)(=O)C(F)(F)F)c3c2CC(F)(F)[C@H]3O)ccc1F]

(S)-5-((2, 2-Difluoro-1-hydroxy-7-((trifluoromethyl) sulfonyl)-2,3-dihydro-1H-inden-4-yl)oxy)-2-fluorobenzonitrile (Compound 228)

Prepared in a similar fashion as in the synthesis of Compound 185. LC-MS ESI m/z 436 (M−H); $^1$HNMR (400 MHz, CDCl$_3$): δ 7.90 (d, 1H), 7.42-7.30 (m, 3H), 6.86 (d, 1H), 5.42 (dd, 1H), 3.58-3.47 (m, 2H), 3.32 (d, 1H).

Example 229

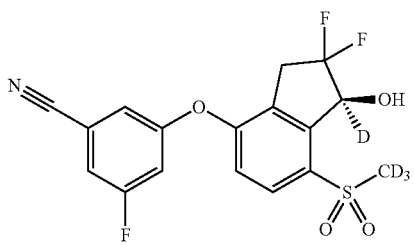 [SMILES: [2H]C([2H])([2H])S(=O)(=O)c1ccc(Oc2cc(F)cc(C#N)c2)c2c1[C@]([2H])(O)C(F)(F)C2]

3-[(1S)-1-Deuterio-2,2-difluoro-1-hydroxy-7-(trideuteriomethylsulfonyl)indan-4-yl]oxy-5-fluorobenzonitrile (Compound 229)

Step A: Preparation of 2-hydroxy-5-(trideuteriomethylsulfanyl)benzaldehyde

To a suspension of 4-(trideuteriomethylsulfanyl)phenol (13.9 g, 77.4 mmol) and paraformaldehyde (13.9 g, 464 mmol) in acetonitrile (55 mL) at 0° C. was added magnesium chloride (11.8 g, 124 mmol) followed by triethylamine (27 mL, 193 mmol). The reaction mixture was then warmed to 68° C. in an oil bath until complete as judged by LC-MS (2.5 hours). The yellow reaction mixture was cooled to 0° C. then quenched by the dropwise addition of 1 N HCl (60 mL), and extracted with methyl t-butyl ether (3×60 mL). Solids was removed by filtration. The organic layer was washed with brine, dried over MgSO$_4$, filtered and concentrated in vacuo. The residue was separated and washed with methyl t-butyl ether and then dried in vacuo affording 2-hydroxy-5-(trideuteriomethylsulfanyl)benzaldehyde. Remaining crude material in the mother liquor was purified on silica gel (100 g SNAP Ultra, 14 CV, 5-100% ethyl acetate/hexane) affording 2-hydroxy-5-(trideuteriomethylsulfanyl)benzaldehyde as a yellow solid.

Step B: Preparation of 2-oxo-6-(trideuteriomethylsulfanyl)chromene-3 carboxylic acid To a solution of 2-hydroxy-5-(trideuteriomethylsulfanyl) benzaldehyde (4.65 g, 27 mmol) and 2,2-dimethyl-1,3-dioxane-4,6-dione (3.91 g, 27 mmol) in 95% ethanol (70 mL) was added potassium phosphate tribasic (0.58 g, 2.7 mmol) in water (210 mL) at ambient temperature. The mixture was stirred at ambient temperature for 1 hour (slightly exothermic). The reaction mixture was acidified with 1 N HCl to pH ~3-4. The solid was collected by filtration, washed with water and then 5:1 hexane/methyl t-butyl ether and dried to give 2-oxo-6-(trideuteriomethylsulfanyl)chromene-3-carboxylic acid (5.95 g, 25 mmol, 92% yield) as yellow solid.

Step C: Preparation of 3-[2-hydroxy-5-(trideuteriomethylsulfanyl)phenyl]propanoic acid Triethylamine (8.3 mL, 60 mmol) was added slowly to formic acid (5.6 mL, 149 mmol) in N, N-dimethylformamide (12 mL) at 0° C. The mixture was warmed to 100° C. (internal) then 2-oxo-6-(trideuteriomethylsulfanyl) chromene-3-carboxylic acid (5.95 g, 24.9 mmol) was added in 5 portions (~1.2 g per 5 minutes). After the addition (ca. 30 minutes), the reaction mixture was stirred at 100° C. (internal) for 1 hour. After cooling to ambient temperature, 6N NaOH (49.74 mL, 149.2 mmol) was added. The reaction mixture was stirred at ambient temperature for 30 minutes. Methyl t-butyl ether (40 mL) was added. The aqueous layer was separated, acidified with concentrated HCl to pH ~3-4 and extracted with methyl t-butyl ether (3×50 mL). The combined organic layer was washed with brine, dried (sodium sulfate), filtered and concentrated under reduced pressure to give 3-[2-hydroxy-5-(trideuteriomethylsulfanyl)phenyl]propanoic acid (4.8 g, 22.4 mmol, 90% yield), which was used directly in the next step without purification.

Step D: Preparation of 3-[2-(3-cyano-5-fluoro-phenoxy)-5 (trideuteriomethylsulfanyl)phenyl]propanoic acid A suspension of 3-[2-hydroxy-5-(trideuteriomethylsulfanyl)phenyl]propanoic acid (4.82 g, 22.4 mmol), 3,5-difluorobenzonitrile (6.23 g, 44.8 mmol), and cesium carbonate (16.1 g, 49.3 mmol) in dimethyl sulfoxide (22 mL) was stirred at 72.6° C. (internal) for 7 h. After cooling to ambient temperature, water (50 mL) and MTBE (50 mL) were added. The organic layer was separated, the aqueous layer was acidified with 1 N HCl to pH-3-4 with stirring and extracted with ethyl acetate (3×50 mL). The organic layers were combined and washed with brine (30 mL), dried over $Na_2SO_4$, filtered and concentrated in vacuo affording 3-[2-(3-cyano-5-fluoro-phenoxy)-5-(trideuteriomethylsulfanyl) phenyl]propanoic acid, which was used in the next step without further purification. LC-MS ESI (−) m/z 333 (M−H).

Step E: Preparation of 3-fluoro-5-[1-oxo-7-(trideuteriomethylsulfanyl)indan-4-yl]oxy-benzonitrile DMF (10 µL) was added to 3-[2-(3-cyano-5-fluoro-phenoxy)-5-(trideuteriomethylsulfanyl)phenyl]propanoic acid (7.48 g, 22.4 mmol) in dichloromethane (40 mL) at room temperature followed by oxalyl chloride (2.1 mL, 24.6 mmol). The reaction mixture was stirred for 2.5 hours then added dropwise to trichloroalumane (5.97 g, 44.7 mmol) in dichloromethane (40 mL) and stirred for 1 hour. The reaction mixture was then cooled to 0° C., quenched dropwise with 1 N HCl (20 mL), and extracted with dichloromethane (3×50 mL). The organic layer was washed with saturated $NaHCO_3$ (50 mL), brine (30 mL), dried over $MgSO_4$, filtered through a pad of silica gel, washed with 1:1 dichloromethane/methyl t-butyl ether and concentrated in vacuo. The residue was suspended in 2:1 acetonitrile/water (35 mL) and stirred for 30 minutes, filtered, washed with 2:1 MeCN/water (10 mL) and then dried in vacuo affording 3-fluoro-5-[1-oxo-7-(trideuteriomethylsulfanyl)indan-4-yl]oxy-benzonitrile (5.0 g, 15.8 mmol, 71% yield over two steps). LC-MS ESI (+) m/z 317 (M+H).

Step F: Preparation of 3-fluoro-5-[1-oxo-7-(trideuteriomethylsulfonyl)indan-4-yl]oxy-benzonitrile Oxone® (21.4 g, 34.8 mmol) was added all at once to a suspension of 3-fluoro-5-[1-oxo-7 (trideuteriomethylsulfanyl)indan-4-yl]oxy-benzonitrile (5.0 g, 15.8 mmol) in a mixture of acetonitrile (50 mL) and water (25 mL) at room temperature. The reaction mixture was stirred overnight. Solids were removed by filtration then the acetonitrile was removed in vacuo. The residue was suspended in water (25 mL) and stirred for 30 minutes. The resulting solid was rinsed with water (100 mL), washed with methyl t-butyl ether (50 mL), and then dried in vacuo affording 3-fluoro-5-[1-oxo-7-(trideuteriomethylsulfonyl)indan-4-yl]oxy-benzonitrile (4.8 g, 13.8 mmol, 87% yield) as a yellow solid. LC-MS ESI (+) m/z 349 (M+H).

Step G: Preparation of 3-[2,2-difluoro-1-oxo-7-(trideuteriomethylsulfonyl)indan-4-yl]oxy-5-fluoro-benzonitrile:

3-Methoxypropan-1-amine (913 µL, 9.0 mmol) was added to 3-fluoro-5-[1-oxo-7-(trideuteriomethylsulfonyl)indan-4-yl]oxy-benzonitrile (2.6 g, 7.5 mmol) and 2,2-dimethylpropanoic acid (76 mg, 0.75 mmol) in a mixture of cyclohexane (40 mL) and toluene (40 mL) at room temperature and then warmed to reflux with the azeotropic removal of water via a Dean-Stark trap for 3 hours. The reaction mixture was cooled to room temperature, filtered through a frit, and then concentrated in vacuo to give crude 3-fluoro-5-[(1E/Z)-1-(3-methoxypropylimino)-7-(trideuteriomethylsulfonyl)indan-4-yl]oxy-benzonitrile. A solution of 3-fluoro-5-[(1E/Z)-1-(3-methoxypropylimino)-7-(trideuteriomethylsulfonyl) indan-4-yl]oxy-benzonitrile (3.13 g, 7.5 mmol) in acetonitrile (10 mL) was added dropwise by syringe to Selectfluor® (6.6 g, 18.7 mmol) and sodium sulfate (2.12 g, 14.9 mmol) in acetonitrile (40 mL) at 60° C. then stirred until complete as judged by LC-MS (1 hour). The reaction mixture was cooled to room temperature, and diluted with 50 mL of water. Concentrated HCl (2.5 mL, 30 mmol) was added and the reaction mixture was stirred for 1 hour. Acetonitrile was removed in vacuo then solids were filtered, washed with water, methyl t-butyl ether and then dried in vacuo affording 3-[2,2-difluoro-1-oxo-7-(trideuteriomethylsulfonyl)indan-4-yl]oxy-5-fluoro-benzonitrile (2.2 g, 5.7 mmol, 77% yield). LC-MS ESI (+) m/z 402 (M+$NH_4^+$).

Step H: Preparation of 3-[(1S)-1-deuterio-2,2-difluoro-1-hydroxy-7-(trideuteriomethylsulfonyl)indan-4-yl]oxy-5-fluoro-benzonitrile (Compound 229)

RuCl(p-cymene)[(R,R)-Ts-DPEN] (58 mg, 0.09 mmol) was added all at once to an ice cold solution of 3-[2,2-difluoro-1-oxo-7-(trideuteriomethylsulfonyl)indan-4-yl]oxy-5-fluoro-benzonitrile (3.53 g, 9.17 mmol), triethylamine (2.56 mL, 18.4 mmol) and deuterio deuterioformate (1.09 mL, 27.6 mmol). The reaction flask was sealed with a rubber septum with a limp balloon and placed in a 4° C. refridgerator overnight. The reaction mixture was concentrated in vacuo until ~10 mL of solvent remained then purified directly on silica gel (25 g SNAP Ultra, 14 CV, 10-60% EtOAc/hexane) affording Compound 229, which was further purified by dissolving in refluxing 95% ethanol (10 mL) then slowly cooled to room temperature with stirring to give a white crystalline solid (2.44 g, 6.3 mmol, 69% yield). LC-MS ESI (−) m/z 432 (M+$HCO_2^-$); $^1$HNMR (400 MHz, $CDCl_3$): δ 7.92 (d, 1H), 7.26-7.24 (m, 1H), 7.15 (s, 1H), 7.06-7.03 (m, 1H), 7.01 (d, 1H), 3.56-3.35 (m, 3H).

Example 230

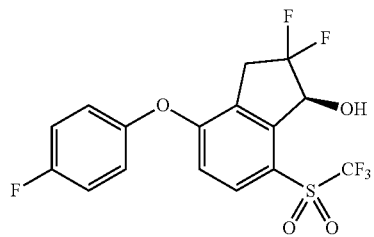 [SMILES: O=S(=O)(c1ccc(Oc2ccc(F)cc2)c2c1[C@H](O)C(F)(F)C2)C(F)(F)F]

(S)-2,2-Difluoro-4-(4-fluorophenoxy)-7-((trifluoromethyl)sulfonyl)-2,3-dihydro-1H-inden-1-ol (Compound 230)

Prepared in a similar fashion as for the synthesis of Compound 185. LC-MS ESI (−) m/z 411 (M−H); $^1$HNMR (400 MHz, CDCl$_3$): δ 7.85 (d, 1H), 7.19-7.08 (m, 4H), 6.83 (d, 1H), 5.42 (dd, 1H), 3.65-3.49 (m, 2H), 3.25 (dd, 1H).

Example 231

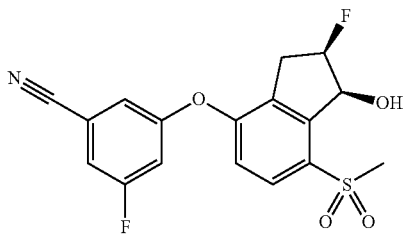 [SMILES: CS(=O)(=O)c1ccc(Oc2cc(F)cc(C#N)c2)c2c1[C@H](O)[C@H](F)C2]

3-Fluoro-5-4(1S,2R)-2-fluoro-1-hydroxy-7-(methylsulfonyl)-2,3-dihydro-1H-inden-4-yl)oxy)benzonitrile (Compound 231)

Step A: Preparation of 3-fluoro-5-((2-fluoro-7-(methylsulfonyl)-1-oxo-2,3-dihydro-1H-inden-4-yl)oxy)benzonitrile Selectfluor® (18.1 g, 51 mmol) was added all at once to 3-fluoro-5-(7-methylsulfonyl-1-oxo-indan-4-yl)oxy-benzonitrile (11 g, 31.9 mmol) in methanol (300 mL) at room temperature and then warmed to reflux for 24 hours. The reaction mixture was cooled to room temperature, and filtered. The solids was washed with ethyl acetate then the filtrate was concentrated in vacuo. The residue was dissolved in ethyl acetate, washed with 1 N HCl and brine, dried over Na$_2$SO$_4$, filtered and concentrated in vacuo affording 3-fluoro-5-(2-fluoro-7-methylsulfonyl-1-oxo-indan-4-yl)oxy-benzonitrile as a light yellow foam which was used without further purification. LC-MS ESI (+) m/z 364 (M+H).

Step B: Preparation of 3-fluoro-5-(((1S,2R)-2-fluoro-1-hydroxy-7-(methylsulfonyl)-2,3-dihydro-1H-inden-4-yl)oxy)benzonitrile (Compound 231)

RuCl(p-cymene)[(R,R)-Ts-DPEN] (203 mg, 0.32 mmol) was added all at once to an ice cold solution of 3-fluoro-5-(2-fluoro-7-methylsulfonyl-1-oxo-indan-4-yl)oxy-benzonitrile (11.6 g, 31.8 mmol), triethylamine (8.9 mL, 63.7 mmol) and formic acid (3.6 mL, 95.5 mmol) in dichloromethane (200 mL). The reaction flask was sealed with a septum equipped with a limp balloon and placed in a 4° C. refridgerator overnight. The reaction mixture was poured into saturated NaHCO$_3$, extracted with dichloromethane, washed with brine, dried over Na$_2$SO$_4$, filtered and concentrated in vacuo until ~25 mL of solvent remained. Approximately 50% of the material precipitated on top of the column (100 g SNAP Ultra, 14 CV, 15-80% ethyl acetate/hexanes). The solid was removed and the material absorbed on the column was purified. The precipitated material was dissolved in 250-300 mL of warm dichloromethane then purified on a plug of silica gel eluting with 50% then 60% ethyl acetate/hexane affording Compound 231 (9.65 g, 26.4 mmol, 83% yield over two steps) as an off-white solid. Enantiomeric excess was determined by chiral HPLC (>99% ee). LC-MS ESI (+) m/z 383 (M+NH$_4^+$); $^1$HNMR (400 MHz, CDCl$_3$): δ 7.92 (d, 1H), 7.21-7.20 (m, 1H), 7.12-7.11 (m, 1H), 7.03-6.98 (m, 2H), 5.71-5.65 (m, 1H), 5.46-5.33 (m, 1H), 3.66 (dd, 1H), 3.31 (s, 3H), 3.27-3.05 (m, 2H).

Example 232

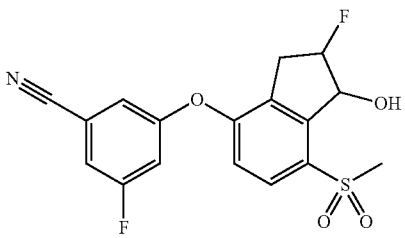 [SMILES: CS(=O)(=O)c1ccc(Oc2cc(F)cc(C#N)c2)c2c1C(O)C(F)C2]

3-Fluoro-5-((2-fluoro-1-hydroxy-7-(methylsulfonyl)-2,3-dihydro-1H-inden-4-yl)oxy)benzonitrile (Compound 232)

Sodium borohydride (5.2 mg, 0.14 mmol) was added all at once to 3-fluoro-5-(2-fluoro-7-methylsulfonyl-1-oxo-indan-4-yl)oxy-benzonitrile (25 mg, 0.07 mmol) in methanol (0.5 mL) at room temperature and stirred until complete as judged by LC-MS. The reaction mixture was concentrated in vacuo, diluted with water, extracted with methyl t-butyl ether, washed with brine, dried over MgSO4, filtered and concentrated in vacuo. The residue was purified on silica gel (10 g SNAP Ultra, 14 CV, 20-100% ethyl acetate/hexane) affording Compound 232 (14 mg, 0.04 mmol, 56% yield) as the cis isomer. LC-MS ESI (+) m/z 383 (M+NH$_4^+$). $^1$HNMR (400 MHz, CDCl$_3$): δ 7.92 (d, 1H), 7.21-7.20 (m, 1H), 7.12-7.11 (m, 1H), 7.03-6.98 (m, 2H), 5.71-5.65 (m, 1H), 5.46-5.33 (m, 1H), 3.66 (dd, 1H), 3.31 (s, 3H), 3.27-3.05 (m, 2H).

Example 233

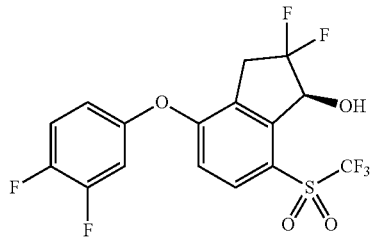 [SMILES: O=S(=O)(c1ccc(Oc2ccc(F)c(F)c2)c2c1[C@H](O)C(F)(F)C2)C(F)(F)F]

(S)-4-(3,4-Difluorophenoxy)-2,2-difluoro-7-((trifluoromethyl)sulfonyl)-2,3-dihydro-1H-inden-1-ol (Compound 233)

Prepared in a similar fashion as in the synthesis of Compound 185. LC-MS ESI (−) m/z 429 (M−H); $^1$HNMR (400 MHz, CDCl$_3$): δ 7.88 (d, 1H), 7.32-7.25 (m, 1H), 7.03-6.98 (m, 1H), 6.91-6.86 (m, 2H), 5.42 (dd, 1H), 3.64-3.47 (m, 2H), 3.22 (d, 1H).

Example 234

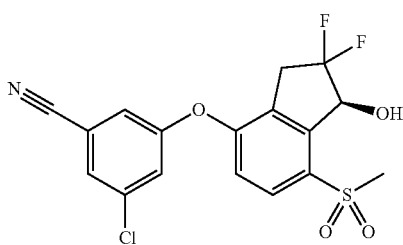 [SMILES: CS(=O)(=O)c1ccc(Oc2cc(Cl)cc(C#N)c2)c2c1[C@H](O)C(F)(F)C2]

(S)-3-Chloro-5-((2,2-difluoro-1-hydroxy-7-(methylsulfonyl)-2,3-dihydro-1H-inden-4-yl)oxy)benzonitrile (Compound 234)

prepared similarly according to Steps A-F in the synthesis for Compound 163. LC-MS ESI (−) m/z 444 (M+HCO$_2^-$). $^1$HNMR (400 MHz, CDCl$_3$): δ 7.92 (d, 1H), 7.52-7.51 (m, 1H), 7.32-7.31 (m, 1H), 7.25-7.24 (m, 1H), 6.98 (d, 1H), 5.62-5.58 (m, 1H), 3.56-3.35 (m, 3H), 3.24 (s, 3H).

Example 235

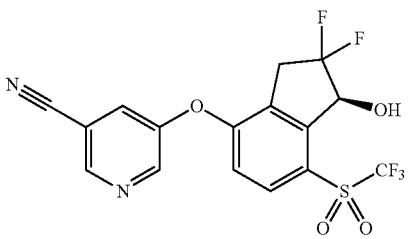 [SMILES: N#Cc1cncc(Oc2ccc(S(=O)(=O)C(F)(F)F)c3c2CC(F)(F)[C@H]3O)c1]

(S)-5-((2,2-Difluoro-1-hydroxy-7-((trifluoromethyl)sulfonyl)-2,3-dihydro-1H-inden-4-yl)oxy)nicotinonitrile (Compound 235)

Prepared in a similar fashion as in the synthesis of Compound 163. LC-MS ESI (−) m/z 419 (M−H). $^1$HNMR (400 MHz, CDCl$_3$): δ 8.84 (d, 1H), 8.73 (d, 1H), 7.96 (d, 1H), 7.75-7.74 (m, 1H), 6.95 (d, 1H), 5.45 (dd, 1H), 3.64-3.48 (m, 2H), 3.31 (d, 1H).

Example 236

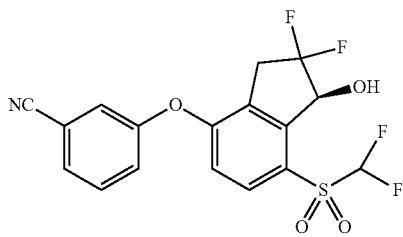 [SMILES: N#Cc1cccc(Oc2ccc(S(=O)(=O)C(F)F)c3c2CC(F)(F)[C@H]3O)c1]

(S)-3-((7-((difluoromethyl)sulfonyl)-2,2-difluoro-1-hydroxy-2,3-dihydro-1H-inden-4-yl)oxy)benzonitrile (Compound 236): Prepared similarly as in the synthesis of Compound 15. LCMS ESI (+) m/z 419 (M+NH4); $^1$HNMR (400 MHz, CDCl$_3$): δ 7.89 (d, 1H), 7.62-7.57 (m, 2H), 7.42 (s, 1H), 7.39-7.34 (m, 1H), 6.90 (d, 1H), 6.44 (t, 1H), 5.51 (dd, 1H), 5.63-5.45 (m, 2H), 3.37 (d, 1H).

Example 237

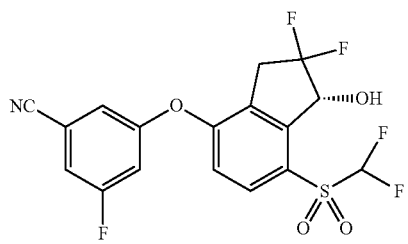 [SMILES: N#Cc1cc(F)cc(Oc2ccc(S(=O)(=O)C(F)F)c3c2CC(F)(F)[C@@H]3O)c1]

(R)-3-((7-((difluoromethyl)sulfonyl)-2,2-difluoro-1-hydroxy-2,3-dihydro-1H-inden-4-yl)oxy)-5-fluorobenzonitrile (Compound 237)

Prepared similarly as in the synthesis of Compound 15 except by replacing RuCl(p-cymene)[(R,R)-Ts-DPEN] with RuCl(p-cymene)[(S,S)-Ts-DPEN]. Chiral HPLC retention time: 2.19 minutes.

Example 238

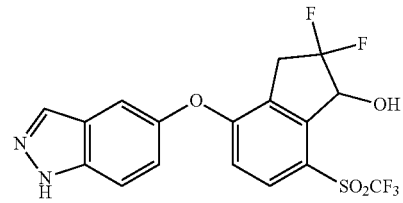

4-((1H-Indazol-5-yl)oxy)-2,2-difluoro-7-((trifluoromethyl)sulfonyl)-2,3-dihydro-1H-inden-1-ol (Compound 238)

Step A: 4-Fluoro-7-((trifluoromethyl)sulfonyl)-2,3-dihydrospiro[indene-1,2'-[1,3]dioxolane]

Trimethylsily trifluoromethanesulfonate (10.6 g, 47.8 mmol) was added dropwise to a solution of 4-fluoro-7-(trifluoromethylsulfonyl)indan-1-one (27 g, 95.7 mmol) and trimethyl(2-trimethylsilyloxyethoxy)silane (23.7 g, 115 mmol) in dichloromethane (500 mL) at −78° C. The reaction mixture was allowed to warm to room temperature. After 2 hours, the reaction was then quenched with triethylamine and evaporated. The residue was taken up in EtOAc (500 mL) and the organic layer was washed with 2×200 mL water then 1×500 mL saturated brine solution. The organic layer was separated, dried (NaSO$_4$), and concentrated to dryness. The crude was purified by flash column chromatography eluting with 20% EtOAc in hexane to give 4-fluoro-7-((trifluoromethyl)sulfonyl)-2,3-dihydrospiro[indene-1,2'-[1,3]dioxolane] (2.1 g, 6.4 mmol, 55% yield) as a white solid.

Step B: 5-((7-((Trifluoromethyl)sulfonyl)-2,3-dihydrospiro[indene-1,2'-[1,3]dioxolan]-4-yl)oxy)-1H-indazole Sodium hydrogen carbonate (64.4 mg, 0.77 mmol) was added to a vial containing 4-fluoro-7-((trifluoromethyl)sulfonyl)-2,3-dihydrospiro[indene-1,2'[1,3]dioxolane] (100 mg, 0.31 mmol) and 1H-indazol-5-ol (61.7 mg, 0.46 mmol) in DMF (2.5 mL). The sealed vial was heated at 80° C. for a total of 10.5 hours. The reaction mixture was diluted with water and the resulting solid was collected by vacuum filtration. The solid was chromatographed on a Biotage 10 g SNAP column with a 10% to 80% EtOAc:hexane gradient to afford 5-((7-((trifluoromethyl)sulfonyl)-2,3-dihydrospiro[indene-1,2'-[1,3]dioxolan]-4-yl)oxy)-1H-indazole (59 mg, 0.133 mmol, 43% yield. m/z (ES-API-pos) [M+1]=441.

Step C: 4-((1H-indazol-5-yl)oxy)-7-((trifluoromethyl)sulfonyl)-2,3-dihydro-1H-inden-1-one Hydrochloric acid (6 M, 0.066 mL, 0.4 mmol) was added to a solution of 5-((7-((trifluoromethyl)sulfonyl)-2,3-dihydrospiro[indene-1,2'[1,3]dioxolan]-4-yl)oxy)-1H-indazole (59 mg, 0.13 mmol) in acetone (3.0 mL) and water (0.50 mL). The mixture was stirred at 50° C. After 3.5 hours, the reaction mixture was evaporated and the residue was partitioned between EtOAc and dilute aqueous NaHCO$_3$. The EtOAc was washed with brine, dried over MgSO$_4$, filtered, and evaporated to afford 4-((1H-indazol-5-yl)oxy)-7-((trifluoromethyl)sulfonyl)-2,3-dihydro-1H-inden-1-one (48 mg, 0.12 mmol, 91% yield as a pale yellow film. m/z (ES-API-pos) [M+H]=397.

Step D: (E/Z)-4-((1H-Indazol-5-yl)oxy)-N-(3-methoxypropyl)-7-((trifluoromethyl)sulfonyl)-2,3-dihydro-1H-inden-1-imine 2,2-dimethylpropanoic acid (2.5 mg, 0.024 mmol) was added to a mixture of 4-((1H-indazol-5-yl)oxy)-7-((trifluoromethyl)sulfonyl)-2,3-dihydro-1H-inden-1-one (48 mg, 0.12 mmol) and 3-methoxypropan-1-amine (0.03 mL, 0.3 mmol) in toluene (4 mL) and cyclohexane (4 mL). The reaction mixture was refluxed with a Hickman still attached. After 5 hours, the cooled reaction mixture was evaporated and the residue was used as is in the next step.

Step E: 4-((1H-Indazol-5-yl)oxy)-2,2-difluoro-7-((trifluoromethyl)sulfonyl)-2,3-dihydro-1H-inden-1-one 1-(Chloromethyl)-4-fluoro-1,4-diazoniabicyclo[2.2.2]octane ditetrafluoroborate (Selectfluor®, 106 mg, 0.3 mmol) was added to a flask containing (/ZE)-4-((1H-indazol-5-yl)oxy)-N-(3-methoxypropyl)-7-((trifluoromethyl)sulfonyl)-2,3-dihydro-1H-inden-1-imine (56 mg, 0.12 mmol) and sodium sulfate (43 mg, 0.30 mmol) in acetonitrile (5 mL). This was heated at 60° C. After 30 minutes, 1M hydrochloric acid (0.36 mL, 0.36 mmol) was added. The reaction mixture was stirred for 20 minutes, and then partitioned between EtOAc and water. The EtOAc layer was washed with brine, dried over MgSO$_4$, filtered, and evaporated. The residue was chromatographed on a Biotage 10 g SNAP column with a 10% to 60% EtOAc:hexane gradient to afford 4-((1H-indazol-5-yl)oxy)-2,2-difluoro-7-((trifluoromethyl)sulfonyl)-2,3-dihydro-1H-inden-1-one (31 mg, 0.073 mmol, 61% yield). m/z (ES-API-pos) [M+H]=433.

Step F: 4-((1H-Indazol-5-yl)oxy)-2,2-difluoro-7-((trifluoromethyl)sulfonyl)-2,3-dihydro-1H-inden-1-ol (Compound 238)

Sodium borohydride (1.6 mg, 0.043 mmol) was added to a solution of 4-((1H-indazol-5-yl)oxy)-2,2-difluoro-7-((trifluoromethyl)sulfonyl)-2,3-dihydro-1H-inden-1-one (18 mg, 0.043 mmol) in methanol (3 mL). After 10 minutes, the reaction mixture was evaporated and the residue was partitioned between EtOAc and water. The EtOAc layer was washed with brine, dried over MgSO$_4$, filtered, and evaporated to afford Compound 238 (18 mg, 0.042 mmol, 98% yield) as a colorless film. $^1$H NMR (400 MHz, CDCl$_3$): δ 10.35 (br s, 1H), 8.14 (s, 1H), 7.82 (d, 1H), 7.61 (d, 1H), 7.51 (d, 1H), 7.21-7.17 (m, 1H), 6.82 (d, 1H), 5.44 (d, 1H), 3.70-3.57 (m, 2H), 3.40 (br s, 1H). m/z (ES-API-pos) [M+H]=435.

Example 239

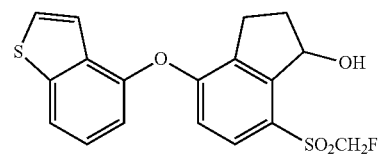

4-(Benzo[b]thiophen-4-yloxy)-7-((fluoromethyl)sulfonyl)-2,3-dihydro-1H-inden-1-ol (Compound 239)

Sodium borohydride (0.45 mg, 0.01 mmol) was added to a solution of 4-(benzo[b]thiophen-4-yloxy)-7-((fluoromethyl)sulfonyl)-2,3-dihydro-1H-inden-1-one (4.1 mg, 0.01 mmol) (Example 242, Step B) in methanol (2 mL). After 20 minutes, the reaction mixture was evaporated and the residue was partitioned between EtOAc and water. The EtOAc layer was washed with brine, dried over MgSO$_4$, filtered, and evaporated to afford Compound 239 (3.6 mg, 0.009 mmol, 87% yield). $^1$H NMR (400 MHz, CDCl$_3$): δ 7.78 (d, 1H), 7.68 (d, 1H), 7.44 (d, 1H), 7.37 (t, 1H), 7.23 (d, 1H), 7.00 (d, 1H), 6.71 (d, 1H), 5.73-5.68 (m, 1H), 5.38-5.12 (m, 2H), 3.37-3.33 (m, 1H), 3.32-3.22 (m, 1H) 3.07-2.99 (m, 1H), 2.56-2.46 (m, 1H), 2.35-2.24 (m, 1H). m/z (ES-API-pos) [M+formic acid]=459.

Example 240

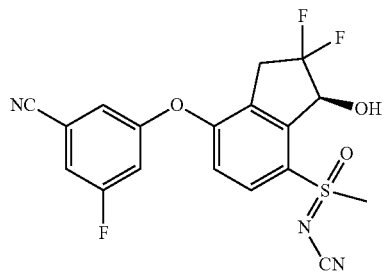 [SMILES: CS(=O)(=NC#N)c1ccc(Oc2cc(F)cc(C#N)c2)c2c1[C@H](O)C(F)(F)C2]

Isomer 1 of N—((S)-7-(3-Cyano-5-fluorophenoxy)-2,2-difluoro-3-hydroxy-2,3-dihydro-1H-inden-4-yl)(methyl)(oxo)-λ⁶-sulfanylidene)cyanamide (Compound 240)

Step A: N-((7-(3-cyano-5-fluorophenoxy)-3-hydroxy-2,3-dihydro-1H-inden-4-yl)(methyl)(oxo)-λ⁶-sulfanylidene)cyanamide Sodium hydrogen carbonate (79.3 mg, 0.94 mmol) was added to a solution of 3-fluoro-5-hydroxy-benzonitrile (86.27 mg, 0.63 mmol) and N-((7-fluoro-3-hydroxy-2,3-dihydro-1H-inden-4-yl)(methyl)(oxo)-λ⁶-sulfanylidene)cyanamide (80 mg, 0.31 mmol) (Example 189, Step C) in DMF (3 mL). The vial was sealed and heated at 100° C. over a weekend. The reaction mixture was partitioned between EtOAc and dilute aqueous NaOH. The EtOAc was washed with water, two portions of brine, dried over MgSO₄, filtered, and evaporated. The residue was chromatographed on a Biotage 25M reverse phase column with a 20% to 90% ACN:water gradient to afford N-((7-(3-cyano-5-fluorophenoxy)-3-hydroxy-2,3-dihydro-1H-inden-4-yl)(methyl)(oxo)-λ⁶-sulfanylidene)cyanamide (80 mg, 0.21 mmol, 69% yield). m/z (ES-API-pos) [M+H]=372.

Step B: N-((7-(3-cyano-5-fluorophenoxy)-3-oxo-2,3-dihydro-1H-inden-4-yl)(methyl)(oxo)-λ⁶-sulfanylidene)cyanamide Dess-Martin periodinane (192 mg, 0.45 mmol) was added to a solution of N-((7-(3-cyano-5-fluorophenoxy)-3-hydroxy-2,3-dihydro-1H-inden-4-yl)(methyl)(oxo)-λ⁶-sulfanylidene)cyanamide (200 mg, 0.54 mmol) in dichloromethane (50 mL). After 10 minutes, the reaction mixture was evaporated and the residue was partitioned between EtOAc and aqueous sodium thiosulfate and saturated aqueous NaHCO₃. The EtOAc layer was washed with water, brine, dried over MgSO₄, filtered, and evaporated to afford N-((7-(3-cyano-5-fluorophenoxy)-3-oxo-2,3-dihydro-1H-inden-4-yl)(methyl)(oxo)-λ⁶-sulfanylidene)cyanamide (174 mg, 0.47 mmol, 88% yield) as a colorless film. m/z (ES-API-pos) [M+H]=370.

Step C: (E/Z)—N-((7-(3-cyano-5-fluorophenoxy)-3-((3-methoxypropyl)imino)-2,3-dihydro-1H-inden-4-yl)(methyl)(oxo)-λ⁶-sulfanylidene)cyanamide Pivalic acid (9.4 mg, 0.09 mmol) was added to a mixture of N-((7-(3-cyano-5-fluorophenoxy)-3-oxo-2,3-dihydro-1H-inden-4-yl)(methyl)(oxo)-λ⁶-sulfanylidene)cyanamide (170 mg, 0.46 mmol) and 3-methoxypropylamine (0.12 mL, 1.2 mmol) in cyclohexane (7 mL) and toluene (7 mL). The mixture was heated at reflux with a Hickman still attached. After 1 hour, the reaction mixture was evaporated and the residue was used as is in the next step.

Step D: N-((7-(3-cyano-5-fluorophenoxy)-2,2-difluoro-3-oxo-2,3-dihydro-1H-inden-4-yl)(methyl)(oxo)-λ⁶-sulfanylidene)cyanamide 1-Chloromethyl-4-fluoro-1,4-diazoniabicyclo[2.2.2]octane bis(tetrafluoroborate) (406 mg, 1.15 mmol) was added to a mixture of (E/Z)—N-((7-(3-cyano-5-fluorophenoxy)-3-((3-methoxypropyl)imino)-2,3-dihydro-1H-inden-4-yl)(methyl)(oxo)-λ⁶-sulfanylidene)cyanamide (202 mg, 0.46 mmol) and sodium sulfate (162 mg, 1.15 mmol) in acetonitrile (5 mL). The mixture was heated at 70° C. After 3.5 hours, the reaction mixture was evaporated and the residue was partitioned between EtOAc and water. The EtOAc was washed with brine, dried over MgSO₄, filtered, and evaporated. The residue was taken up in EtOAc, absorbed on silica gel, and chromatographed on a Biotage 25 g SNAP column with a 50% to 100% EtOAc:hexane gradient to afford N-((7-(3-cyano-5-fluorophenoxy)-2,2-difluoro-3-oxo-2,3-dihydro-1H-inden-4-yl)(methyl)(oxo)-λ⁶-sulfanylidene)cyanamide (48 mg, 0.118 mmol, 26% yield. m/z (ES-API-pos) [M+H]=406.

Step E: N—(((S)-7-(3-cyano-5-fluorophenoxy)-2,2-difluoro-3-hydroxy-2,3-dihydro-1H-inden-4-yl)(methyl)(oxo)-λ⁶-sulfanylidene)cyanamide (Compound 240)

RuCl(p-cymene)[(R,R)-Ts-DPEN] (1.5 mg, 0.020 mmol) was added to a nitrogen-sparged, ice-cold solution of N-((7-(3-cyano-5-fluorophenoxy)-2,2-difluoro-3-oxo-2,3-dihydro-1H-inden-4-yl)(methyl)(oxo)-λ⁶-sulfanylidene)cyanamide (49 mg, 0.120 mmol), triethylamine (0.022 mL, 0.16 mmol), and formic acid (0.01 mL, 0.24 mmol) in dichloromethane (5 mL). The flask was placed in a 4° C. refrigerator over a weekend. The reaction mixture was evaporated and the residue was chromatographed on a Biotage 10 g SNAP Ultra column with a 20% to 80% EtOAc:hexane gradient to afford a solid, which was triturated twice with chloroform to afford Compound 240 (8.6 mg, 0.021 mmol, 18% yield) as a single diastereomer in 93% d.e. by chiral chromatography. ¹H NMR (400 MHz, CD₃OD): δ 8.01 (d, 1H), 7.54-7.49 (m, 1H), 7.46-7.44 (m, 1H), 7.40-7.36 (m, 1H), 7.20-7.14 (m, 1H), 5.56 (d, 1H), 3.78-3.61 (m, 1H), 3.62 (s, 3H), 3.55-3.47 (m, 1H). m/z (ES-API-pos) [M+H]=408.

Example 241

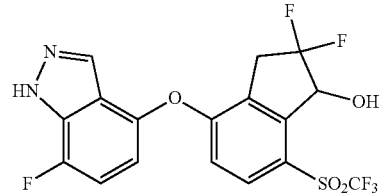

2,2-Difluoro-4-((7-fluoro-1H-indazol-4-yl)oxy)-7-((trifluoromethyl)sulfonyl)-2,3-dihydro-1H-inden-1-ol (Compound 241)

Step A: 2,2-difluoro-4-((7-fluoro-1H-indazol-4-yl)oxy)-7-((trifluoromethyl)sulfonyl)-2,3-dihydro-1H-inden-1-one 1-(Chloromethyl)-4-fluoro-1,4-diazoniabicyclo[2.2.2]octane ditetrafluoroborate (129 mg, 0.36 mmol) was added to a flask containing (E/Z)-4-((1H-indazol-4-yl)oxy)-N-(3-methoxypropyl)-7-((trifluoromethyl)sulfonyl)-2,3-dihydro-1H-inden-1-imine (68 mg, 0.15 mmol) (Example 243, Step C) and sodium sulfate (52 mg, 0.36 mmol) in acetonitrile (5 mL). The reaction mixture was heated at 70° C. for 6 hour, then stirred at room temperature overnight. Hydrochloric acid (1 M, 0.44 mL, 0.440 mmol) was added. The resulting mixture was stirred for 20 minutes, and partitioned between EtOAc and water. The EtOAc layer was washed with brine, dried over MgSO$_4$, filtered, and evaporated. The residue was chromatographed on a Biotage 10 g SNAP column with a 10% to 60% EtOAc:hexane gradient to afford 2,2-difluoro-4-((7-fluoro-1H-indazol-4-yl)oxy)-7-((trifluoromethyl)sulfonyl)-2,3-dihydro-1H-inden-1-one (9 mg, 0.02 mmol, 14% yield); m/z (ES-API-neg) [M–H]=449; 4-((1H-indazol-4-yl)oxy)-2,2-difluoro-7-((trifluoromethyl)sulfonyl)-2,3-dihydro-1H-inden-1-one (12 mg, 0.03 mmol, 19% yield), m/z (ES-API-neg) [M–H]=431; and 2,2-difluoro-4-((5-fluoro-1H-indazol-4-yl)oxy)-7-((trifluoromethyl)sulfonyl)-2,3-dihydro-1H-inden-1-one (10 mg, 0.023 mmol, 16% yield); m/z (ES-API-neg) [M–H]=449.

Step B: 2,2-Difluoro-4-((7-fluoro-1H-indazol-4-yl)oxy)-7-((trifluoromethyl)sulfonyl)-2,3-dihydro-1H-inden-1-ol (Compound 241)

Sodium borohydride (0.76 mg, 0.020 mmol) was added to a solution of 2,2-difluoro-4-((7-fluoro-1H-indazol-4-yl)oxy)-7-((trifluoromethyl)sulfonyl)-2,3-dihydro-1H-inden-1-one (9 mg, 0.02 mmol) in methanol (3 mL). After 1 hour, the reaction mixture was evaporated and the residue was partitioned between EtOAc and water. The EtOAc was washed with brine, dried over MgSO$_4$, filtered, and evaporated. The residue was chromatographed on a Biotage 10 g SNAP Ultra column with a 0% to 50% EtOAc:dichloromethane gradient to afford Compound 241 (3.4 mg, 0.0075 mmol, 38% yield) as a colorless film. $^1$H NMR (400 MHz, CDCl$_3$): δ 10.55 (br s, 1H), 7.94 (d, 1H), 7.83 (d, 1H), 7.16-7.10 (m, 1H), 6.86 (d, 1H), 6.83-6.78 (m, 1H), 5.46 (d, 1H), 3.72-3.59 (m, 2H), 3.34 (br s, 1H); m/z (ES-API-pos) [M+1]=453.

Example 242

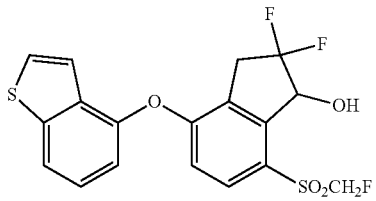

4-(Benzo[b]thiophen-4-yloxy)-2,2-difluoro-7-((fluoromethyl)sulfonyl)-2,3-dihydro-1H-inden-1-ol (Compound 242)

Step A: 4-(Benzo[b]thiophen-4-yloxy)-7-((fluoromethyl)sulfonyl)-2,3-dihydrospiro[indene-1,2'-[1,3]dioxolane]

Sodium hydrogen carbonate (51 mg, 0.6 mmol) was added to a vial containing 4'-fluoro-7'-(fluoromethylsulfonyl)spiro[1,3-dioxolane-2,1'-indane] (70 mg, 0.24 mmol) (Example 63, Step A) and benzothiophen-4-ol (65 mg, 0.43 mmol) in DMF (1.5 mL). The vial was sealed and heated at 110° C. for 9.5 hours, then stirred at room temperature. The reaction mixture was partitioned between EtOAc and water. The EtOAc was washed with 2 portions of brine, dried over MgSO$_4$, filtered, and evaporated. The residue was chromatographed on a Biotage 10 g SNAP column with a 10% to 80% EtOAc:hexane gradient to afford 4-(benzo[b]thiophen-4-yloxy)-7-((fluoromethyl)sulfonyl)-2,3-dihydrospiro[indene-1,2'[1,3]dioxolane] (62 mg, 0.15 mmol, 61% yield).

Step B: 4-(Benzo[b]thiophen-4-yloxy)-7-((fluoromethyl)sulfonyl)-2,3-dihydro-1H-inden-1-one Pyridin-1-ium-4-methylbenzenesulfonate (43 mg, 0.17 mmol) was added to a solution of 4-(benzo[b]thiophen-4-yloxy)-7-((fluoromethyl)sulfonyl)-2,3-dihydrospiro[indene-1,2'[1,3]dioxolane] (62 mg, 0.15 mmol) in acetone (4 mL) and water (0.50 mL) in a vial. The vial was sealed and heated at 80° C. for 5 hours. The reaction mixture was evaporated and the residue was partitioned between EtOAc and water. The EtOAc was washed with brine, dried over MgSO$_4$, filtered, and evaporated. The residue was chromatographed on a Biotage 12+M reverse phase column with a 20% to 80% ACN:water gradient to afford 4-(benzo[b]thiophen-4-yloxy)-7-((fluoromethyl)sulfonyl)-2,3-dihydro-1H-inden-1-one (27 mg, 0.072 mmol, 49% yield). m/z (ES-API-pos) [M+H]=377.

Step C: (E/Z)-4-(Benzo[b]thiophen-4-yloxy)-7-((fluoromethyl)sulfonyl)-N-(3-methoxypropyl)-2,3-dihydro-1H-inden-1-imine 2,2-Dimethylpropanoic acid (2.21 mg, 0.02 mmol) was added to a flask containing a suspension of 4-(benzo[b]thiophen-4-yloxy)-7-((fluoromethyl)sulfonyl)-2,3-dihydro-1H-inden-1-one (27 mg, 0.072 mmol) and 3-methoxypropan-1-amine (0.01 mL, 0.11 mmol) in a mixture of toluene (3 mL) and cyclohexane (3 mL). This was refluxed with a Hickman still attached. After 5 hours, the reaction mixture was evaporated and the crude product was used as is in the next step.

Step D: 4-(Benzo[b]thiophen-4-yloxy)-2,2-difluoro-7-((fluoromethyl)sulfonyl)-2,3-dihydro-1H-inden-1-one 1-(Chloromethyl)-4-fluoro-1,4-diazoniabicyclo[2.2.2]octane ditetrafluoroborate (63 mg, 0.18 mmol) was added to a vial containing crude (E/Z)-4-(benzo[b]thiophen-4-yloxy)-7-((fluoromethyl)sulfonyl)-N-(3-methoxypropyl)-2,3-dihydro-1H-inden-1-imine (32 mg, 0.07 mmol) and sodium sulfate (25 mg, 0.18 mmol) in acetonitrile (3 mL). The vial was sealed and heated at 80° C. overnight. The reaction mixture was treated with water (1 mL) and HCl (6 M, 0.5 mL), stirred for 15 minutes, and the reaction mixture was partitioned between EtOAc and water. The EtOAc layer was washed with brine, dried over MgSO$_4$, filtered, and evaporated. The residue was chromatographed on a Biotage 10 g SNAP Ultra column with a 20% to 80% EtOAc:hexane gradient to afford 4-(benzo[b]thiophen-4-yloxy)-2,2-difluoro-7-((fluoromethyl)sulfonyl)-2,3-dihydro-1H-inden-1-one (4 mg, 0.01 mmol, 14% yield). m/z (ES-API-pos) [M+H+H$_2$O]=430.

Step E: 4-(Benzo[b]thiophen-4-yloxy)-2,2-difluoro-7-((fluoromethyl)sulfonyl)-2,3-dihydro-1H-inden-1-ol (Compound 242)

Sodium borohydride (0.5 mg, 0.012 mmol) was added to a solution of 4-(benzo[b]thiophen-4-yloxy)-2,2-difluoro-7-((fluoromethyl)sulfonyl)-2,3-dihydro-1H-inden-1-one (4 mg, 0.012 mmol) in methanol (2 mL). After 20 minutes, the reaction mixture was evaporated and the residue was partitioned between EtOAc and water. The EtOAc layer was washed with brine, dried over MgSO₄, filtered, and evaporated to afford Compound 242 (3.6 mg, 0.009 mmol, 87% yield). ¹H NMR (400 MHz, CDCl₃): δ 7.83-7.76 (m, 2H), 7.47 (d, 1H), 7.40 (t, 1H), 7.21-7.19 (m, 1H), 7.05 (d, 1H), 6.76 (d, 1H), 5.61-5.11 (m, 3H), 3.71-3.57 (m, 2H), 3.30 (br s, 1H). m/z (ES-API-pos) [M+formic acid]=459.

Example 243

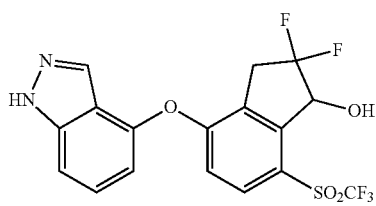

4-((1H-Indazol-4-yl)oxy)-2,2-difluoro-7-((trifluoromethyl)sulfonyl)-2,3-dihydro-1H-inden-1-one (Compound 243)

Prepared similarly as described for Compound 241. ¹H NMR (400 MHz, CDCl₃): δ 10.45 (br s, 1H), 7.93 (s, 1H), 7.84 (d, 1H), 7.48-7.41 (m, 2H), 6.92 (d, 1H), 6.86 (dd, 1H), 5.46 (d, 1H), 3.72-3.59 (m, 2H), 3.44 (br s, 1H). m/z (ES-API-pos) [M+H]=435.

Example 244

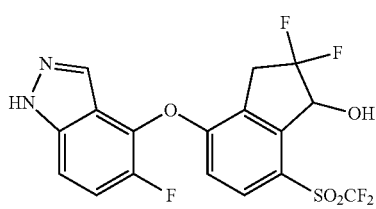

2,2-Difluoro-4-((5-fluoro-1H-indazol-4-yl)oxy)-7-((trifluoromethyl)sulfonyl)-2,3-dihydro-1H-inden-1-ol (Compound 244)

Prepared similarly as described for Compound 241. ¹H NMR (400 MHz, CDCl₃): δ 10.35 (br s, 1H), 7.96 (s, 1H), 7.84 (d, 1H), 7.47-7.43 (m, 1H), 7.39-7.33 (m, 1H), 6.81 (dd, 1H), 5.46 (d, 1H), 3.74-3.59 (m, 2H), 3.36 (br s, 1H). m/z (ES-API-pos) [M+H]=453.

Example 245

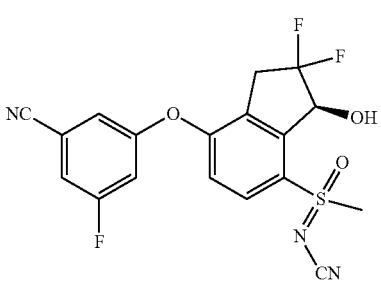 [SMILES: CS(=O)(=NC#N)c1ccc(Oc2cc(F)cc(C#N)c2)c2c1[C@H](O)C(F)(F)C2]

Isomer 2 of N—((S)-7-(3-cyano-5-fluorophenoxy)-2,2-difluoro-3-hydroxy-2,3-dihydro-1H-inden-4-yl)(methyl)(oxo)-λ⁶-sulfanylidene)cyanamide (Compound 245)

Isolated in 69% purity judged by chiral chromatography (contaminated by Compound 240). ¹H NMR (400 MHz, CDCl₃): δ 8.01 (d, 1H), 7.32-7.28 (m, 1H), 7.22-7.20 (m, 1H), 7.14-7.09 (m, 1H), 7.02 (d, 1H), 5.67 (d, 1H), 4.22 (br s, 1H), 3.65 (s, 3H), 3.60-3.40 (m, 2H). m/z (ES-API-pos) [M+H]=408.

Example 246

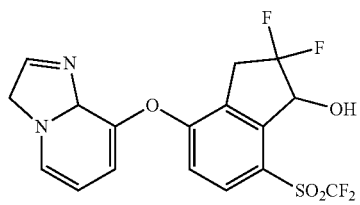

4-((3,8a-Dihydroimidazo[1,2-a]pyridin-8-yl)oxy)-2,2-difluoro-7-((trifluoromethyl)sulfonyl)-2,3-dihydro-1H-inden-1-ol (Compound 246)

Prepared similarly as described in Example 238, substituting 3,8a-dihydroimidazo[1,2-a]pyridin-8-ol for 1H-indazol-5-ol in Step B. ¹H NMR (400 MHz, CDCl₃): δ 8.15 (d, 1H), 7.82 (d, 1H), 7.72 (s, 1H), 7.65 (s, 1H), 6.99 (d, 1H), 6.88-6.81 (m, 2H), 5.43 (d, 1H), 3.76-3.63 (m, 2H), 3.51 (br s, 1H). m/z (ES-API-pos) [M+H]=435.

Example 247

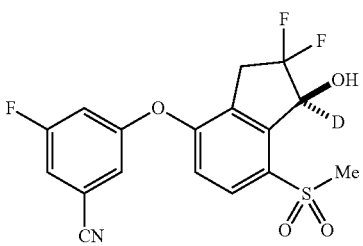 [SMILES: [2H][C@]1(O)c2c(S(C)(=O)=O)ccc(Oc3cc(F)cc(C#N)c3)c2CC1(F)F]

(S)-3-((2,2-Difluoro-1-hydroxy-7-(methylsulfonyl)-2,3-dihydro-1H-inden-4-yl-1-d)oxy)-5-fluorobenzonitrile (Compound 247)

Prepared similarly according to Example 229. The ee was determined to be >99% by ¹⁹F NMR analysis of the corresponding Mosher ester. Retention time on chiral HPLC column: 2.05 min. LCMS ESI (+) (M+H) m/z 385; ¹H NMR (400 MHz, CDCl₃): δ 7.93 (d, 1H), 7.27-7.23 (m, 1H), 7.16-7.13 (m, 1H), 7.07-6.98 (m, 2H), 3.56-3.34 (m, 3H), 3.24 (s, 3H).

Example 248

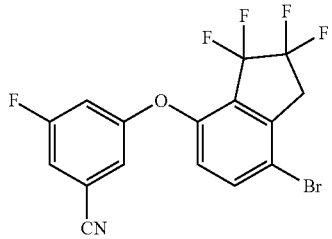 [SMILES: N#Cc1cc(F)cc(Oc2ccc(Br)c3c2C(F)(F)C(F)(F)C3)c1]

3-((7-Bromo-2,2,3,3-tetrafluoro-2,3-dihydro-1H-inden-4-yl)oxy)-5-fluorobenzonitrile (Compound 248)

Step A: Preparation of 3-(4-bromo-3-formylphenoxy)-5-fluorobenzonitrile

A solution of 2-bromo-5-hydroxy-benzaldehyde (1.50 g, 7.46 mmol) and 3,5-difluorobenzonitrile (3.11 g, 22.4 mmol) in dimethyl sulfoxide (15.5 mL) was treated with potassium phosphate tribasic (1.90 g, 8.95 mmol) and stirred at 100° C. overnight. The reaction mixture was poured into 150 mL of water and extracted with 3×30 mL Et$_2$O. The combined organics were rinsed with 20 mL of brine, dried with MgSO$_4$, filtered, and concentrated to dryness. Purification was achieved by chromatography on silica using 5-10% EtOAc/hexane to afford 3-(4-bromo-3-formylphenoxy)-5-fluorobenzonitrile (1.06 g, 44%). LCMS ESI (+) (M+H) m/z 320, 322.

Step B: Preparation of 3-(4-bromo-3-(2,2-difluorovinyl)phenoxy)-5-fluorobenzonitrile A solution of 3-(4-bromo-3-formyl-phenoxy)-5-fluorobenzonitrile (317.0 mg, 0.99 mmol), sodium chlorodifluoroacetate (452.9 mg, 2.97 mmol), and triphenylphosphine (259.7 mg, 0.99 mmol) in DMF (4.95 mL) was heated to 90° C. for 30 minutes. The reaction mixture was cooled to room temperature and poured into 30 mL of water and extracted with 3×20 mL Et$_2$O. The combined organics were rinsed with 20 mL of brine, dried with MgSO$_4$, filtered, and concentrated to dryness. Purification was achieved by chromatography on silica using 5-15% EtOAc/hexane to afford 3-(4-bromo-3-(2,2-difluorovinyl)phenoxy)-5-fluorobenzonitrile as a faint yellow oil (273 mg, 78%). $^1$H NMR (400 MHz, CDCl$_3$): δ 7.62 (d, 1H), 7.24 (d, 1H), 7.11-7.08 (m, 1H), 7.04-7.01 (m, 1H), 6.93 (dt, 1H), 6.82 (dd, 1H), 5.70 (dd, 1H).

Step C: Preparation of 3-((7-bromo-2,2,3,3-tetrafluoro-2,3-dihydro-1H-inden-4-yl)oxy)-5-fluorobenzonitrile A solution of 3-[4-bromo-3-(2,2-difluorovinyl)phenoxy]-5-fluoro-benzonitrile (273 mg, 0.77 mmol) in diglyme (anhydrous, 0.8 mL) at 180° C. was treated with sodium chlorodifluoroacetate (353 mg, 2.3 mmol) as a solution in diglyme (anhydrous, 1.2 mL) by dropwise addition over 30 minutes. The reaction mixture was heated for 12 hours at 180° C. The reaction mixture was cooled to room temperature, poured into 20 mL of water, and extracted with 3×20 mL Et$_2$O. The combined organics were rinsed with 10 mL of brine, dried with MgSO$_4$, filtered, and concentrated to dryness. Purification was achieved by chromatography on silica using 5-15% EtOAc/hexane to afford Compound 248 as a clear oil (34.4 mg, 11%). LCMS ESI (−) (M−H) m/z 402, 404; $^1$H NMR (400 MHz, CDCl$_3$): δ 7.70 (d, 1H), 7.20-7.15 (m, 1H), 7.10-7.08 (m, 1H), 7.02 (dt, 1H), 6.86 (d, 1H), 3.50 (t, 2H).

Example 249

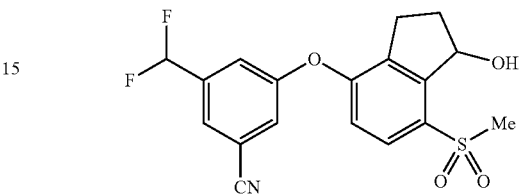

3-(Difluoromethyl)-5-((1-hydroxy-7-(methylsulfonyl)-2,3-dihydro-1H-inden-4-yl)oxy)benzonitrile (Compound 249)

Step A: Preparation of 3-(difluoromethyl)-5-((7-(methylsulfonyl)-1-oxo-2,3-dihydro-1H-inden-4-yl)oxy)benzonitrile 3-(Difluoromethyl)-5-(7'-methylsulfonylspiro[1,3-dioxolane-2,1'-indane]-4'-yl)oxy-benzonitrile (prepared similarly according to Example 162 (18 mg, 0.043 mmol) was dissolved in 2 mL of THF and treated with 1 mL of 1 M HCl. The resulting solution was stirred for 2 hours at room temperature. Volatiles were removed by concentration under reduced pressure. The remaining reaction mixture was poured into 20 mL of saturated aqueous NaHCO$_3$ and extracted with 3×10 mL EtOAc. The combined organic layer was rinsed with 10 mL of brine, dried with MgSO$_4$, filtered, and concentrated to dryness. Purification was achieved by chromatography on silica using 20-60% EtOAc/hexane to afford 3-(difluoromethyl)-5-((7-(methylsulfonyl)-1-oxo-2,3-dihydro-1H-inden-4-yl)oxy)benzonitrile (11.1 mg, 69%). LCMS ESI (+) (M+H) m/z 378.

Step B: Preparation of 3-(difluoromethyl)-5-((1-hydroxy-7-(methylsulfonyl)-2,3-dihydro-1H-inden-4-yl)oxy)benzonitrile (Compound 249)

A solution of 3-(difluoromethyl)-5-((7-(methylsulfonyl)-1-oxo-2,3-dihydro-1H-inden-4-yl)oxy)benzonitrile (11 mg, 0.03 mmol) in methanol (1 mL) at 0° C. was treated with sodium borohydride (1 mg, 0.03 mmol) and stirred at 0° C. for 1 hour. The reaction mixture was quenched by the addition of 0.5 mL of water and 0.25 mL of saturated NH$_4$Cl. Volatiles were removed by concentration under reduced pressure. The reaction mixture was poured into 10 mL of 0.5 M NaOH and extracted with 3×15 mL EtOAc. The combined organics were rinsed with 10 mL of brine, dried with MgSO$_4$, filtered, and concentrated to dryness. Purification with silica chromatography using 25-70% EtOAc/hexane followed by C18 reverse phase flash chromatography (Biotage Isolera One unit, C18 Flash 12+M column, 20-70% CH$_3$CN/water) gave Compound 249 as a white solid (5.4 mg, 48%). LCMS ESI (+) (M+NH$_4$) m/z 397; $^1$H NMR (400 MHz, CDCl$_3$): δ 7.83 (d, 1H), 7.60 (s, 1H), 7.41 (s, 1H), 7.37

(s, 1H), 6.94 (d, 1H), 6.65 (t, 1H), 5.72-5.68 (m, 1H), 3.64 (br d, 1H), 3.22 (s, 3H), 3.14-3.04 (m, 1H), 2.81 (ddd, 1H), 2.54-2.43 (m, 1H), 2.28-2.19 (m, 1H).

Example 250

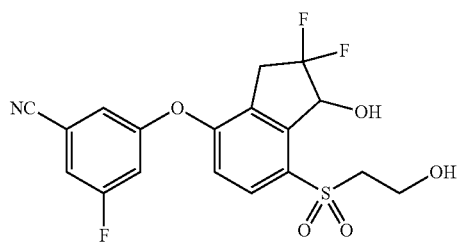 [SMILES: N#Cc1cc(F)cc(Oc2ccc(S(=O)(=O)CCO)c3c2CC(F)(F)C3O)c1]

3-((2,2-Difluoro-1-hydroxy-7-((2-hydroxyethyl)sulfonyl)-2,3-dihydro-1H-inden-4-yl)oxy)-5-fluorobenzonitrile (Compound 250)

Step A: 3-fluoro-5-(7-methylsulfinyl-1-oxo-indan-4-yl)oxy-benzonitrile

To a suspension of 3-fluoro-5-(7-methylsulfanyl-1-oxo-indan-4-yl)oxy-benzonitrile (16.0 g, 51.1 mmol) in formic acid (68 mL) was added dropwise 30% hydrogen peroxide solution in water (3.6 mL, 56.2 mmol). The reaction mixture was stirred at ambient temperature for 1 hour. Water (300 mL) was added, and the reaction mixture was stirred for 15 minutes. The precipitated solid was collected by filtration, washed with water, and dried in vacuo to give 3-fluoro-5-(7-methylsulfinyl-1-oxo-indan-4-yl)oxy-benzonitrile (16.1 g, 96%). LCMS ESI (+) m/z 330 (M+H).

Step B: 3-fluoro-5-(1-oxo-7-sulfanyl-indan-4-yl)oxy-benzonitrile

Trifluoroacetic anhydride (57.8 mL, 416 mmol) was added dropwise to a solution of 3-fluoro-5-(7-methylsulfinyl-1-oxo-indan-4-yl)oxy-benzonitrile (16.1 g, 48.9 mmol) in dichloromethane (400 mL) at ambient temperature under nitrogen. The reaction mixture was stirred for 5 hours. The reaction mixture was then concentrated under reduced pressure. The residue was dissolved in MeOH (50 mL) and Et$_3$N (50 mL), and stirred at ambient temperature for 30 minutes. The solvents were evaporated in vacuo. The residue was partitioned between methyl t-butyl ether and 1 N NaOH. The aqueous layer was separated and pH was adjusted to 3-4 by dropwise addition of 3 N HCl. The mixture was extracted with EtOAc. The combined organic layers were washed with water and brine, dried and concentrated to give 3-fluoro-5-(1-oxo-7-sulfanyl-indan-4-yl)oxy-benzonitrile (8.6 g, 59%), which was used in the next step without further purification. LCMS ESI (−) m/z 298 (M−H).

Step C: 3-[7-[2-[tert-butyl(dimethyl)silyl]oxyethylsulfanyl]-1-oxo-indan-4-yl]oxy-5-fluoro-benzonitrile A mixture of 3-fluoro-5-(1-oxo-7-sulfanyl-indan-4-yl)oxy-benzonitrile (300 mg, 1.00 mmol), cesium carbonate (653 mg, 2.00 mmol), 2-bromoethoxy-tert-butyl-dimethyl-silane (0.32 mL, 1.5 mmol) and 1-methyl-2-pyrrolidone (10 mL) was stirred at ambient temperature for 30 minutes. The mixture was then partitioned between methyl t-butyl ether and water. The aqueous layer was extracted with methyl t-butyl ether. The combined organic layers were washed with water and brine, dried and concentrated. The residue was purified by flash chromatography on silica gel (5-20% EtOAc/hexane) to afford 3-[7-[2-[tert-butyl(dimethyl)silyl]oxyethylsulfanyl]-1-oxo-indan-4-yl]oxy-5-fluoro-benzonitrile (272 mg, 59%). LCMS ESI (+) m/z 458 (M+H).

Step D: 3-[7-[2-[tert-butyl(dimethyl)silyl]oxyethylsulfonyl]-1-oxo-indan-4-yl]oxy-5-fluoro-benzonitrile Sodium periodate (259 mg, 1.21 mmol) was added to a stirred solution of 3-[7-[2-[tert-butyl(dimethyl)silyl]oxyethylsulfanyl]-1-oxo-indan-4-yl]oxy-5-fluoro-benzonitrile (222 mg, 0.49 mmol) and ruthenium (III) chloride (2.5 mg, 0.01 mmol) in acetonitrile (0.30 mL)/carbon tetrachloride (0.30 mL)/water (0.60 mL). The reaction mixture was stirred at ambient temperature for 30 minutes. Solids were removed by filtration and rinsed with EtOAc. The organic layer was separated. The aqueous layer was extracted with EtOAc. The combined organics were washed with brine, dried over Na$_2$SO$_4$, filtered and concentrated in vacuo. The crude product was purified by flash chromatography on silica gel (10-35% EtOAc/hexane) to afford 3-[7-[2-[tert-butyl(dimethyl)silyl]oxyethylsulfonyl]-1-oxo-indan-4-yl]oxy-5-fluoro-benzonitrile (202 mg, 85%) as a white solid. LCMS ESI (+) m/z 490 (M+H).

Step E: 3-[2,2-difluoro-7-(2-hydroxyethylsulfonyl)-1-oxo-indan-4-yl]oxy-5-fluoro-benzonitrile A mixture of 3-[7-[2-[tert-butyl(dimethyl)silyl]oxyethylsulfonyl]-1-oxo-indan-4-yl]oxy-5-fluoro-benzonitrile (111 mg, 0.230 mmol), 3-methoxypropan-1-amine (0.070 mL, 0.68 mmol), 2,2-dimethylpropanoic acid (2.3 mg, 0.020 mmol), toluene (0.7 mL) and cyclohexane (0.7 mL) was heated at reflux with the azeotropic removal of water via a Dean-Stark trap for 4 hours. After cooling to ambient temperature, the solvents were evaporated under reduced pressure. The residue was dissolved in acetonitrile (2 mL). Sodium sulfate (64 mg, 0.45 mmol) and Selectfluor® (211 mg, 0.570 mmol) was sequentially added. The reaction mixture was heated at reflux for 1 hour. After cooling to ambient temperature, 1 N HCl (0.91 mL, 0.91 mmol) was added to the reaction. The reaction mixture was stirred at ambient temperature overnight. The reaction was then partitioned between EtOAc and water. The aqueous layer was extracted with EtOAc. The combined organic layers were washed with water and brine, dried and concentrated. The residue was purified by flash chromatography on silica gel (20-60% EtOAc/hexanes) to give 3-[2,2-difluoro-7-(2-hydroxyethylsulfonyl)-1-oxo-indan-4-yl]oxy-5-fluoro-benzonitrile (68 mg, 73%). LCMS ESI (−) m/z 410 (M−H).

Step F: 3-((2,2-difluoro-1-hydroxy-7-((2-hydroxyethyl)sulfonyl)-2,3-dihydro-1H-inden-4-yl)oxy)-5-fluorobenzonitrile (Compound 250)

To a solution of 3-[2,2-difluoro-7-(2-hydroxyethylsulfonyl)-1-oxo-indan-4-yl]oxy-5-fluoro-benzonitrile (10 mg, 0.020 mmol) in methanol (0.4 mL) was added sodium borohydride (1.4 mg, 0.040 mmol) at ambient temperature. After stirring for 30 minutes, the reaction was quenched by water. The mixture was partitioned between EtOAc and water. The aqueous layer was extracted with EtOAc. The combined organic layers were washed with brine, dried and concentrated. The residue was purified by flash chromatography on silica gel (30-70% EtOAc/hexanes) to give Compound 250 (5 mg, 50%). LCMS ESI (+) m/z 414 (M+H); $^1$H NMR (400 MHz, CDCl$_3$): δ 7.90 (d, 1H), 7.27-7.24 (m, 1H), 7.16 (br s, 1H), 7.06 (d, 1H), 7.00 (d, 1H), 5.62 (d, 1H), 4.00-4.16 (m, 2H), 3.30-3.74 (m, 4H).

Example 251

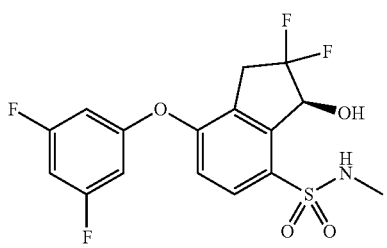 [SMILES: CNS(=O)(=O)c1ccc(Oc2cc(F)cc(F)c2)c2c1[C@H](O)C(F)(F)C2]

(S)-7-(3,5-Difluorophenoxy)-2,2-difluoro-3-hydroxy-N-methyl-2,3-dihydro-1H-indene-4-sulfonamide (Compound 251)

Step A: 7-(3,5-difluorophenoxy)-N-methyl-3-oxo-indane-4-sulfonamide

Prepared similarly as described in Example 18 using 7-(3,5-difluorophenoxy)-3-hydroxy-N-methyl-2,3-dihydro-1H-indene-4-sulfonamide (Compound 11) in place of 4-(3-chloro-5-fluoro-phenoxy)-7-(difluoromethylsulfonyl)indan-1-ol (Compound 17). LCMS ESI (+) m/z 354 (M+H).

Step B: (S)-7-(3,5-difluorophenoxy)-2,2-difluoro-3-hydroxy-N-methyl-2,3-dihydro-1H-indene-4-sulfonamide (Compound 251)

Prepared similarly as described in Example 163 substituting 3-fluoro-5-(7-methylsulfonyl-1-oxo-indan-4-yl)oxy-benzonitrile with 7-(3,5-difluorophenoxy)-N-methyl-3-oxo-indane-4-sulfonamide in step D. LCMS ESI (+) m/z 392 (M+H); $^1$H NMR (400 MHz, CDCl$_3$): δ 7.82 (d, 1H), 6.97 (d, 1H), 6.69 (t, 1H), 6.64-6.54 (m, 2H), 5.62 (d, 1H), 5.04-4.96 (m, 1H), 3.50-3.30 (m, 2H), 2.64 (d, 3H).

Example 252

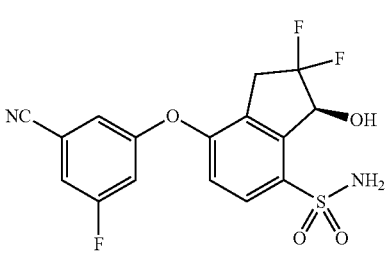 [SMILES: N#Cc1cc(F)cc(Oc2ccc(S(N)(=O)=O)c3c2CC(F)(F)[C@H]3O)c1]

(S)-7-(3-Cyano-5-fluorophenoxy)-2,2-difluoro-3-hydroxy-2,3-dihydro-1H-indene-4-sulfonamide (Compound 252)

Step A: 7-fluoro-3-oxo-indane-4-sulfonamide

Prepared similarly as described in Example 211 substituting methylamine hydrochloride with ammonia solution in dioxane in Step B. LCMS ESI (+) m/z 230 (M+H).

Step B: 7'-fluorospiro[1,3-dioxolane-2,3'-indane]-4'-sulfonamide

Prepared similarly as described in Example 8 substituting 7-(difluoromethylsulfonyl)-4-fluoro-indan-1-one with 7-fluoro-3-oxo-indane-4-sulfonamide in Step A. LCMS ESI (+) m/z 274 (M+H).

Step C: (S)-7-(3-cyano-5-fluorophenoxy)-2,2-difluoro-3-hydroxy-2,3-dihydro-1H-indene-4-sulfonamide (Compound 252)

Prepared similarly as described in Example 163 substituting 4'-fluoro-7'-methylsulfonyl-spiro[1,3-dioxolane-2,1'-indane] with 7'-fluorospiro[1,3-dioxolane-2,3'-indane]-4'-sulfonamide in step A. LCMS ESI (−) m/z 383 (M−H); $^1$H NMR (400 MHz, CDCl$_3$): δ 7.93 (d, 1H), 7.26-7.20 (m, 1H), 7.12 (br s, 1H), 7.04-6.96 (m, 2H), 5.74-5.66 (m, 1H), 5.28 (br s, 2H), 3.50-3.32 (m, 2H).

Example 253

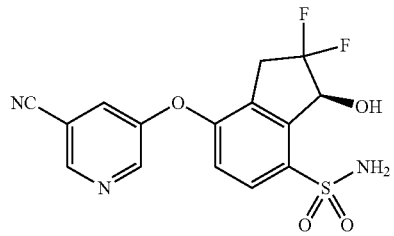 [SMILES: N#Cc1cncc(Oc2ccc(S(N)(=O)=O)c3c2CC(F)(F)[C@H]3O)c1]

(S)-7-((5-Cyanopyridin-3-yl)oxy)-2,2-difluoro-3-hydroxy-2,3-dihydro-1H-indene-4-sulfonamide (Compound 253)

Prepared similarly as described in Example 15 substituting 7'-(difluoromethylsulfonyl)-4'-fluoro-spiro[1,3-dioxolane-2,1'-indane] with 7'-fluorospiro[1,3-dioxolane-2,3'-indane]-4'-sulfonamide, and substituting 3-fluoro-5-hydroxy-benzonitrile with 5-hydroxynicotinonitrile in Step A. LCMS ESI (+) m/z 368 (M+H); $^1$H NMR (400 MHz, CDCl$_3$): δ 8.67 (s, 1H), 8.58 (s, 1H), 7.85 (d, 1H), 7.58 (s, 1H), 6.89 (d, 1H), 5.54 (d, 2H), 3.50-3.24 (m, 2H).

Example 254

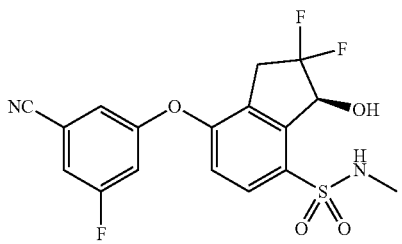 [SMILES: CNS(=O)(=O)c1ccc(Oc2cc(F)cc(C#N)c2)c2c1[C@H](O)C(F)(F)C2]

(S)-7-(3-Cyano-5-fluorophenoxy)-2,2-difluoro-3-hydroxy-N-methyl-2,3-dihydro-1H-indene-4-sulfonamide (Compound 254)

Step A: 7-(3-cyano-5-fluoro-phenoxy)-3-oxo-indane-4-sulfonyl chloride

A solution of 3-fluoro-5-(1-oxo-7-sulfanyl-indan-4-yl)oxy-benzonitrile (0.91 g, 3.0 mmol) in acetonitrile (4 mL) was added dropwise to a suspension of N-chlorosuccinimide (1.62 g, 12.2 mmol) in acetonitrile (4 mL) and 2 M HCl (2 mL) while maintaining the internal temperature below 15° C. using an ice bath. The reaction mixture was stirred at ambient temperature for 2 hours, and then partitioned between EtOAc and water. The aqueous layer was extracted with EtOAc. The combined organic layers were washed with saturated aqueous NaHCO₃ and brine, dried, and concentrated in vacuo to give crude 7-(3-cyano-5-fluoro-phenoxy)-3-oxo-indane-4-sulfonyl chloride, which was used in the next step without further purification. LCMS ESI (+) m/z 366 (M+H).

Step B: 7-(3-cyano-5-fluoro-phenoxy)-N-methyl-3-oxo-indane-4-sulfonamide

Prepared similarly as described in Example 211 substituting 7-fluoro-3-oxo-indane-4-sulfonyl chloride with 7-(3-cyano-5-fluoro-phenoxy)-3-oxo-indane-4-sulfonyl chloride in Step B. LCMS ESI (+) m/z 361 (M+H).

Step C: (S)-7-(3-cyano-5-fluorophenoxy)-2,2-difluoro-3-hydroxy-N-methyl-2,3-dihydro-1H-indene-4-sulfonamide (Compound 254)

Prepared similarly as described in Example 163 substituting 3-fluoro-5-(7-methylsulfonyl-1-oxo-indan-4-yl)oxy-benzonitrile with 7-(3-cyano-5-fluoro-phenoxy)-N-methyl-3-oxo-indane-4-sulfonamide in Step D. LCMS ESI (+) m/z 399 (M+H); ¹H NMR (400 MHz, CDCl₃): δ 7.85 (d, 1H), 7.25-7.18 (m, 1H), 7.13 (brs, 1H), 7.08-6.92 (m, 2H), 5.68-5.56 (m, 1H), 5.05 (br s, 1H), 3.58-3.30 (m, 2H), 2.65 (s, 3H).

Example 255

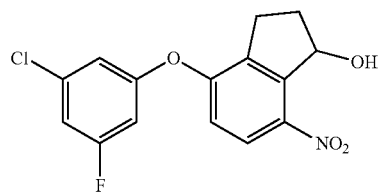 [SMILES: O=[N+]([O-])c1ccc(Oc2cc(F)cc(Cl)c2)c2c1C(O)CC2]

4-(3-Chloro-5-fluorophenoxy)-7-nitro-2,3-dihydro-1H-inden-1-ol (Compound 255)

Step A: 7-nitroindane-1,4-diol

Prepared similarly as described in Example 17 substituting 7-(difluoromethylsulfonyl)-4-fluoro-indan-1-one with 4-hydroxy-7-nitro-indan-1-one in Step A. LCMS ESI (−) m/z 194 (M−H).

Step B: 4-(3-chloro-5-fluorophenoxy)-7-nitro-2,3-dihydro-1H-inden-1-ol (Compound 255)

A mixture of (3-chloro-5-fluoro-phenyl)boronic acid (670 mg, 3.84 mmol), 4 Å molecular sieves (1 g), 7-nitroindane-1,4-diol (250 mg, 1.28 mmol) and copper acetate (233 mg, 1.28 mmol) in anhydrous dichloromethane (10 mL) was stirred for 5 minutes. Triethylamine (0.45 mL, 3.2 mmol) was added dropwise and the reaction mixture was stirred for 36 hours at ambient temperature under air atmosphere. The reaction mixture was filtered. The filtrate was concentrated to dryness. The product was purified by flash chromatography on silica gel (5-25% EtOAc/hexane) to give Compound 255 (72 mg, 17%). LCMS ESI (−) m/z 322 (M−H); ¹H NMR (400 MHz, CDCl₃): δ 8.06 (d, 1H), 6.97-6.93 (m, 1H), 6.85-6.83 (m, 1H), 6.69-6.66 (m, 1H), 3.37 (d, 1H), 3.20-3.12 (m, 1H), 2.93-2.85 (m, 1H), 2.52-2.43 (m, 1H), 2.32-2.25 (m, 1H).

Example 256

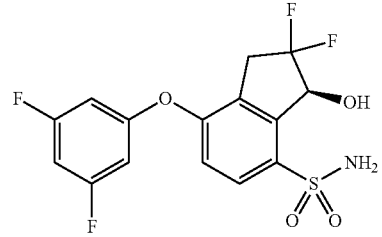 [SMILES: NS(=O)(=O)c1ccc(Oc2cc(F)cc(F)c2)c2c1[C@H](O)C(F)(F)C2]

(S)-7-(3,5-Difluorophenoxy)-2,2-difluoro-3-hydroxy-2,3-dihydro-1H-indene-4-sulfonamide (Compound 256)

Step A: 7-(3,5-difluorophenoxy)-3-oxo-indane-4-sulfonamide

Prepared similarly as described in Example 15 Steps A to B substituting 7'-(difluoromethylsulfonyl)-4'-fluoro-spiro[1,3-dioxolane-2,1'-indane] with 7'-fluorospiro[1,3-dioxolane-2,3'-indane]-4'-sulfonamide, and substituting 3-fluoro-5-hydroxy-benzonitrile with 3,5-difluorophenol. LCMS ESI (+) m/z 340 (M+H).

Step B: (S)-7-(3,5-difluorophenoxy)-2,2-difluoro-3-hydroxy-2,3-dihydro-1H-indene-4-sulfonamide (Compound 256)

Prepared similarly as described in Example 163 substituting 3-fluoro-5-(7-methylsulfonyl-1-oxo-indan-4-yl)oxy-benzonitrile with 7-(3,5-difluorophenoxy)-3-oxo-indane-4-sulfonamide in Step D. LCMS ESI (+) m/z 378 (M+H); ¹H NMR (400 MHz, CDCl₃): δ 7.89 (d, 1H), 6.98 (d, 1H), 6.72-6.60 (m, 1H), 6.62-6.52 (m, 2H), 5.72-5.64 (m, 1H), 5.29 (br s, 2H), 3.56-3.34 (m, 2H).

Example 257

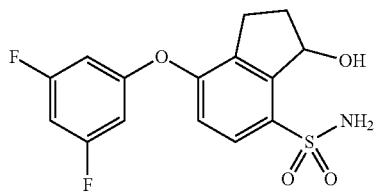 [SMILES: NS(=O)(=O)c1ccc(Oc2cc(F)cc(F)c2)c2c1C(O)CC2]

7-(3,5-Difluorophenoxy)-3-hydroxy-2,3-dihydro-1H-indene-4-sulfonamide (Compound 257)

Prepared similarly as described in Example 25 substituting 3-[2,2-difluoro-7-(2-hydroxy ethylsulfonyl)-1-oxo-indan-4-yl]oxy-5-fluoro-benzonitrile with 7-(3,5-difluorophenoxy)-3-oxo-indane-4-sulfonamide in Step F. LCMS ESI (−) m/z 340 (M−H); $^1$H NMR (400 MHz, CDCl$_3$): δ 7.82 (d, 1H), 6.95 (d, 1H), 6.62 (t, 1H), 6.55-6.50 (m, 2H), 5.84-5.80 (m, 1H), 5.34 (br s, 2H), 3.11-3.03 (m, 1H), 2.83-2.75 (m, 1H), 2.61-2.52 (m, 1H), 2.19-2.10 (m, 1H).

Example 258

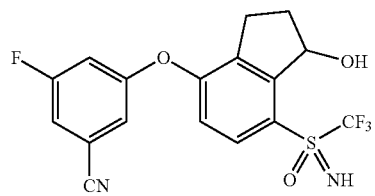 [SMILES: N#Cc1cc(F)cc(Oc2ccc(S(=N)(=O)C(F)(F)F)c3c2CCC3O)c1]

3-Fluoro-5-((1-hydroxy-7-(S-(trifluoromethyl)sulfonimidoyl)-2,3-dihydro-1H-inden-4-yl)oxy)benzonitrile (Compound 258)

Step A: Preparation of 4-fluoro-7-(((trifluoromethyl)sulfinyl)-2,3-dihydro-1H-inden-1-one A solution of 4-fluoro-7-(trifluoromethylsulfanyl)indan-1-one (350 mg, 1.4 mmol) in methanol (7.0 mL) and water (5.6 mL) was treated with Oxone® (430 mg, 0.70 mmol). The resulting suspension was heated to 60° C. for 18 hours. After 6 hours, an additional portion of Oxone® (215 mg, 0.35 mmol) was added. Once complete, volatiles were removed by concentration under reduced pressure. The reaction mixture was poured into 40 mL of water and extracted with 3×20 mL 30% isopropyl alcohol/CHCl$_3$. The combined organics were rinsed with 10 mL of brine, dried with MgSO$_4$, filtered, and concentrated to dryness. The product was used without further purification (360 mg, 96%). LCMS ESI (+) (M+H) m/z 267.

Step B: Preparation of N-((7-fluoro-3-oxo-2,3-dihydro-1H-inden-4-yl)(trifluoromethyl)λ$^4$-sulfanylidene)acetamide A suspension of 4-fluoro-7-(trifluoromethylsulfinyl)indan-1-one (60 mg, 0.23 mmol) and 2,6-bis(1,1-dimethylethyl)-4-methyl-pyridine (23.1 mg, 0.11 mmol) in acetonitrile (0.29 mL, 5.63 mmol) at −20° C. was treated with trifluoromethanesulfonic anhydride (57 μL, 0.34 mmol) and kept at −20° C. overnight (by storing in the freezer). The reaction mixture was then pulled from the freezer and immediately quenched by the addition of 0.5 mL of water. The resulting mixture was allowed to stir for 30 minutes. The reaction mixture was poured into 30 mL of water and extracted with 3×10 mL EtOAc. The combined organics were rinsed with 10 mL of brine, dried with MgSO$_4$, filtered, and concentrated to dryness. Purification was achieved by chromatography on silica using 20-70% EtOAc/hexane to afford N-((7-fluoro-3-oxo-2,3-dihydro-1H-inden-4-yl)(trifluoromethyl)λ$^4$-sulfanylidene)acetamide as an off-white solid (33 mg, 48%). LCMS ESI (+) (M+H) m/z 308.

Step C: Preparation of N-((7-fluoro-3-oxo-2,3-dihydro-1H-inden-4-yl)(oxo)(trifluoromethyl)-λ$^6$-sulfanylidene)acetamide A solution of N-((7-fluoro-3-oxo-2,3-dihydro-1H-inden-4-yl)(trifluoromethyl)λ$^4$-sulfanylidene)acetamide (33 mg, 0.11 mmol) and ruthenium(III) chloride (0.6 mg, 0.0027 mmol) in a mixture of water (1.0 mL), carbon tetrachloride (1.0 mL), and acetonitrile (1.0 mL) was treated with sodium periodate (57 mg, 0.27 mmol) and stirred at 60° C. for 2 days. The reaction mixture was cooled to room temperature and quenched by the addition of 10 mL of saturated Na$_2$S$_2$O$_3$ solution. The mixture stirred for 10 minutes and was then poured into 20 mL of water and extracted with 3×20 mL EtOAc. The combined organics were rinsed with 10 mL of brine, dried with MgSO$_4$, filtered, and concentrated to dryness. Purification was achieved by chromatography on silica using 10-70% EtOAc/hexane to afford N-((7-fluoro-3-oxo-2,3-dihydro-1H-inden-4-yl)(oxo)(trifluoromethyl)-λ$^6$-sulfanylidene)acetamide as a white solid (20 mg, 58%). LCMS ESI (+) (M+H) m/z 324.

Step D: Preparation of 4-fluoro-7-(S-(trifluoromethyl)sulfonimidoyl)-2,3-dihydro-1H-inden-1-yl acetate and N-((7-fluoro-3-hydroxy-2,3-dihydro-1H-inden-4-yl)(oxo)(trifluoromethyl)-λ$^6$-sulfanylidene)acetamide A solution of N-((7-fluoro-3-oxo-2,3-dihydro-1H-inden-4-yl)(oxo)(trifluoromethyl)-λ$^6$-sulfanylidene)acetamide (20 mg, 0.062 mmol) in methanol (1.0 mL) at 0° C. was treated with sodium borohydride (1.2 mg, 0.031 mmol) and stirred at 0° C. for 1 hour. The reaction mixture was quenched by the addition of 0.5 mL of water and 0.5 mL of saturated aqueous NH$_4$Cl. Volatiles were removed by concentration under reduced pressure. The reaction mixture was poured into 10 mL of water and extracted with 3×10 mL EtOAc. The combined organics were rinsed with 10 mL of brine, dried with MgSO$_4$, filtered, and concentrated to dryness. Purification was achieved by chromatography on silica using 10-50% EtOAc/hexane to afford 4-fluoro-7-(S-(trifluoromethyl)sulfonimidoyl)-2,3-dihydro-1H-inden-1-yl acetate as a white solid (9.0 mg, 45%) and N-((7-fluoro-3-hydroxy-2,3-dihydro-1H-inden-4-yl)(oxo)(trifluoromethyl)-λ$^6$-sulfanylidene)acetamide as a white solid (6.7 mg, 33%). Data for 4-fluoro-7-(S-(trifluoromethyl)sulfonimidoyl)-2,3-dihydro-1H-inden-1-yl acetate: LCMS ESI (+) (M+H) m/z 326; $^1$H NMR (400 MHz, CDCl$_3$): δ 8.07 (dd, 1H), 7.30-7.24 (m, 1H), 6.69 (d, 1H), 3.66 (br s, 1H), 3.15 (dt, 1H), 3.05 (m, 1H), 2.50-2.34 (m, 1H), 2.33-2.25 (m, 1H), 2.02 (s, 3H). Data for N-((7-fluoro-3-hydroxy-2,3-dihydro-1H-inden-4- yl)(oxo)(trifluoromethyl)-λ⁶-sulfanylidene)acetamide: LCMS ESI (+) (M+H) m/z 326; ¹H NMR (400 MHz, CDCl₃): δ 7.83 (dd, 1H), 7.22 (t, 1H), 5.70-5.64 (m, 1H), 3.30-3.19 (m, 2H), 3.06-2.97 (dd, 1H), 2.44-2.32 (m, 2H), 2.27 (s, 3H).

Step E: Preparation of 3-fluoro-5-((1-hydroxy-7-(S-(trifluoromethyl)sulfonimidoyl)-2,3-dihydro-1H-inden-4-yl)oxy)benzonitrile (Compound 258)

A solution of 4-fluoro-7-(S-(trifluoromethyl)sulfonimidoyl)-2,3-dihydro-1H-inden-1-yl acetate (9.0 mg, 0.028 mmol), 3-fluoro-5-hydroxy-benzonitrile (3.8 mg, 0.028 mmol), and cesium bicarbonate (5.4 mg, 0.028 mmol) in DMF (0.5 mL) was stirred at 90° C. for 3 hours. The reaction mixture was poured into 50 mL of water and extracted with 3×20 mL Et₂O. The combined organics were rinsed with 10 mL of brine, dried with MgSO₄, filtered, and concentrated to dryness. Purification was achieved by chromatography on silica using 5-25% EtOAc/hexane to afford an intermediate acetate derivative: LCMS ESI (+) (M+H) m/z 443. The product residue was dissolved in 0.5 mL of acetonitrile and treated with 1.0 mL of 22.5% HCl in water. The reaction mixture was left to stir overnight. Volatiles were removed by concentration under reduced pressure. The reaction mixture was poured into 10 mL of water and extracted with 3×10 mL EtOAc. The combined organics were rinsed with 10 mL of brine, dried with MgSO₄, filtered, and concentrated to dryness. Purification was achieved by chromatography on silica using 10-30% EtOAc/hexane to afford Compound 258 as a white solid (3.7 mg, 33%). LCMS ESI (−) (M−H) m/z 399; ¹H NMR (400 MHz, CDCl₃): δ 7.96 (d, 1H), 7.27-7.22 (m, 1H), 7.18-7.15 (m, 1H), 7.07-7.03 (m, 1H), 6.97 (d, 1H), 5.59 (d, 1H), 4.59 (s, 1H), 3.89 (s, 1H), 3.18 (dt, 1H), 2.96 (ddd, 1H), 2.43-2.27 (m, 2H). Retention time=5.55 min (long HPLC method).

Example 259

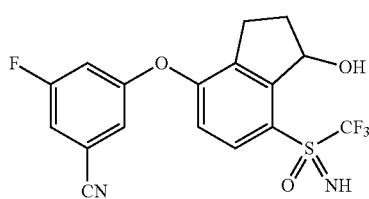

3-Fluoro-5-((1-hydroxy-7-(S-(trifluoromethyl)sulfonimidoyl)-2,3-dihydro-1H-inden-4-yl)oxy)benzonitrile (Compound 259)

3-Fluoro-5-((1-hydroxy-7-(S-(trifluoromethyl)sulfonimidoyl)-2,3-dihydro-1H-inden-4-yl)oxy)benzonitrile was prepared similarly according to Example 258 Step E, substituting N-((7-fluoro-3-hydroxy-2,3-dihydro-1H-inden-4-yl)(oxo)(trifluoromethyl)-λ⁶-sulfanylidene)acetamide (prepared in Example 258 Step D) for 4-fluoro-7-(S-(trifluoromethyl)sulfonimidoyl)-2,3-dihydro-1H-inden-1-yl acetate. Purification of the intermediate acetate was achieved by chromatography on silica using 5-30% EtOAc/hexane: LCMS ESI (+) (M+H) m/z 443. Purification was achieved by chromatography on silica using 5-25% EtOAc/hexane to afford Compound 259 as a white solid (0.6 mg, 7%). LCMS ESI (−) (M−H) m/z 399; ¹H NMR (400 MHz, CDCl₃): δ 8.01 (d, 1H), 7.25-7.21 (m, 1H), 7.17-7.14 (m, 1H), 7.06-7.01 (m, 1H), 6.96 (d, 1H), 5.78-5.73 (m, 1H), 3.96-3.93 (m, 1H), 3.73 (s, 1H), 3.13 (dt, 1H), 2.87 (ddd, 1H), 2.52-2.41 (m, 1H), 2.31-2.23 (m, 1H). Retention time=5.27 min (long HPLC method).

Example 260

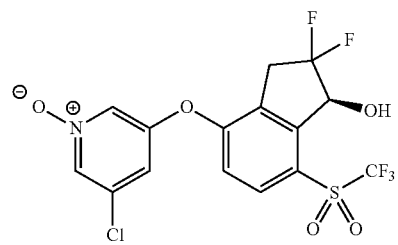 [SMILES: O=S(=O)(c1ccc(Oc2cc(Cl)c[n+]([O-])c2)c2c1[C@H](O)C(F)(F)C2)C(F)(F)F]

(S)-3-Chloro-5-((2,2-difluoro-1-hydroxy-7-((trifluoromethyl)sulfonyl)-2,3-dihydro-1H-inden-4-yl)oxy) pyridine 1-oxide (Compound 260)

A solution of (S)-4-((5-chloropyridin-3-yl)oxy)-2,2-difluoro-7-((trifluoromethyl)sulfonyl)-2,3-dihydro-1H-inden-1-ol (14 mg, 0.032 mmol) in dichloromethane (1.0 mL) was treated with 3-chloroperbenzoic acid (77%, 9.8 mg, 0.040 mmol) and stirred at 45° C. for 8 hours. A further portion of 3-chloroperbenzoic acid (77%, 4.9 mg, 0.020 mmol) was added and the reaction mixture left to stir for 2 days at room temperature. The reaction mixture was poured into 20 mL of a 1:1 mixture of saturated aqueous NaHCO₃ and saturated aqueous Na₂S₂O₃ and extracted with 3×10 mL 30% isopropyl alcohol/CHCl₃. The combined organics were rinsed with 10 mL of brine, dried with MgSO₄, filtered, and concentrated to dryness. Purification was achieved by chromatography on silica using 50-100% EtOAc/hexane to yield Compound 260 as a white solid (8.5 mg, 60%). LCMS ESI (+) (M+H) m/z 446, 448; ¹H NMR (400 MHz, CDCl₃): δ 8.17 (s, 1H), 8.03 (s, 1H), 7.99 (d, 1H), 7.11 (d, 1H), 7.08 (s, 1H), 5.44 (dd, 1H), 3.64-3.42 (m, 3H).

Example 261

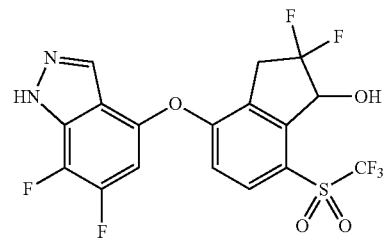 [SMILES: O=S(=O)(c1ccc(Oc2cc(F)c(F)c3[nH]ncc23)c2c1C(O)C(F)(F)C2)C(F)(F)F]

4-((6,7-Difluoro-1H-indazol-4-yl)oxy)-2,2-difluoro-7-((trifluoromethyl)sulfonyl)-2,3-dihydro-1H-inden-1-ol (Compound 261)

Step A: Preparation of 6-fluoro-4-((7-((trifluoromethyl)sulfonyl)-2,3-dihydrospiro[indene-1,2'[1,3] dioxolan]-4-yl)oxy)-1H-indazole A mixture of 4'-fluoro-7'-(trifluoromethylsulfonyl)spiro[1,3-dioxolane-2,1'-indane] (151 mg, 0.46 mmol), 6-fluoro- 1H-indazol-4-ol (47 mg, 0.31 mmol) and cesium carbonate (150 mg, 0.77 mmol) in DMF (4 mL) was stirred at 90° C. for 1 hour. The reaction mixture was diluted with EtOAc, washed with brine, dried over MgSO4, filtered, and concentrated. The residue was purified by flash column chromatography with EtOAc/hexane (0% to 60%) to give 6-fluoro-4-((7-((trifluoromethyl)sulfonyl)-2,3-dihydrospiro[indene-1,2'-[1,3]dioxolan]-4-yl)oxy)-1H-indazole (141 mg, 0.31 mmol, quantative yield). LCMS ESI (+) (M+H) m/z 459.

Step B: Preparation of 4-((6-fluoro-1H-indazol-4-yl)oxy)-7-((trifluoromethyl)sulfonyl)-2,3-dihydro-1H-inden-1-one To a solution of 6-fluoro-4-((7-((trifluoromethyl)sulfonyl)-2,3-dihydrospiro[indene-1,2'-[1,3]dioxolan]-4-yl)oxy)-1H-indazole (141 mg, 0.31 mmol) in acetone (3 mL) and water (0.5 mL) at room temperature was treated with concentrated HCl (37%, 0.06 mL, 0.31 mmol). The reaction mixture was heated at 55° C. for 2 hours. The reaction mixture was diluted with EtOAc, washed with saturated aqueous NaHCO$_3$ and brine. The organic layer was dried over Na$_2$SO$_4$, filtered, and concentrated. The residue was purified by flash column chromatography with EtOAc/hexane (0% to 80%) to yield 4-((6-fluoro-1H-indazol-4-yl)oxy)-7-((trifluoromethyl)sulfonyl)-2,3-dihydro-1H-inden-1-one (16 mg, 0.039 mmol, 12% yield). LCMS ESI (+) (M+H) m/z 415.

Step C: Preparation of (E,Z)—N-butyl-4-((6-fluoro-1H-indazol-4-yl)oxy)-7-((trifluoromethyl)sulfonyl)-2,3-dihydro-1H-inden-1-imine To a solution of 4-((6-fluoro-1H-indazol-4-yl)oxy)-7-((trifluoromethyl)sulfonyl)-2,3-dihydro-1H-inden-1-one (16 mg, 0.04 mmol) in benzene (15 mL) was added butylamine (0.5 mL) and then trifluoroacetic acid (0.1 mL). The reaction was refluxed with removal of water with a Dean-Stark trap. After about 1.5 hours, additional butylamine (0.5 mL) and trifluoroacetic acid (0.1 mL) were added. The reaction was refluxed for an additional 2 hours. The reaction mixture was concentrated under reduced pressure, diluted with EtOAc, washed with saturated aqueous NaHCO$_3$ and brine, dried over Na$_2$SO$_4$, filtered, and concentrated. The crude product was used in the next step without further purification.

Step D: Preparation of 4-((6,7-difluoro-1H-indazol-4-yl)oxy)-2, 2-difluoro-7-((trifluoromethyl)sulfonyl)-2,3-dihydro-1H-inden-1-one and 2,2-difluoro-4-((6-fluoro-1H-indazol-4-yl)oxy)-7-((trifluoromethyl)sulfonyl)-2,3-dihydro-1H-inden-1-one A mixture of (E,Z)—N-butyl-4-((6-fluoro-1H-indazol-4-yl)oxy)-7-((trifluoromethyl)sulfonyl)-2,3-dihydro-1H-inden-1-imine (crude from Step C), sodium sulfate (100 mg) and SelectFluor® (34 mg, 0.1 mmol) in acetonitrile (4 mL) was stirred at 80° C. for 4 hours. After cooling to room temperature, concentrated HCl (0.15 mL) was added. The resulting mixture was stirred for 20 minutes. The reaction mixture was concentrated under reduced pressure, diluted with EtOAc and water. The mixture was washed with saturated aqueous NaHCO$_3$ and brine. The organic layer was dried over Na$_2$SO$_4$, filtered, and concentrated. The residue was purified by flash column chromatography with EtOAc/hexane (30%) to give 2,2-difluoro-4-((6-fluoro-1H-indazol-4-yl)oxy)-7-((trifluoromethyl)sulfonyl)-2,3-dihydro-1H-inden-1-one (1 mg, 0.002 mmol, 12% yield), LCMS ESI (+) (M+H) m/z 451 and 4-((6,7-difluoro-1H-indazol-4-yl)oxy)-2, 2-difluoro-7-((trifluoromethyl)sulfonyl)-2,3-dihydro-1H-inden-1-one (2 mg, 0.004 mmol, 6% yield), LCMS ESI (+) (M+H) m/z 469.

Step E: Preparation of 4-((6,7-difluoro-1H-indazol-4-yl)oxy)-2,2-difluoro-7-((trifluoromethyl)sulfonyl)-2,3-dihydro-1H-inden-1-ol (Compound 261)

To a solution of 4-((6,7-difluoro-1H-indazol-4-yl)oxy)-2, 2-difluoro-7-((trifluoromethyl)sulfonyl)-2,3-dihydro-1H-inden-1-one (2 mg, 0.004 mmol) in tetrahydrofuran (2 mL) at room temperature was added sodium triacetoxyborohydride (10 mg, 0.47 mmol). The reaction was stirred at room temperature overnight. The reaction mixture was directly purified by preparative TLC with EtOAc/hexane (60%) to give Compound 261 (0.6 mg, 0.001 mmol, 30% yield). LCMS ESI (+) (M+H) m/z 471; $^1$H NMR (400 MHz, CDCl$_3$): δ 7.95-7.87 (m, 2H), 6.95 (d, 1H), 6.77 (dd, 1H), 5.46 (d, 1H), 3.66-3.58 (m, 2H), 3.25 (m, 1H).

Example 262

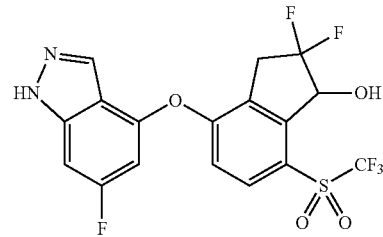 [SMILES: O=S(=O)(c1ccc(Oc2cc(F)cc3[nH]ncc23)c2c1C(O)C(F)(F)C2)C(F)(F)F]

2,2-Difluoro-4-((6-fluoro-1H-indazol-4-yl)oxy)-7-((trifluoromethyl)sulfonyl)-2,3-dihydro-1H-inden-1-ol (Compound 262)

Prepared similarly as described in the Step E of Example 261. LCMS ESI (+) (M+H) m/z 453; $^1$H NMR (400 MHz, CDCl$_3$): δ 7.91-7.88 (m, 2H), 7.12 (d, 1H), 7.03 (d, 1H), 6.66 (d, 1H), 6.46 (d, 1H), 3.66-3.56 (m, 2H), 3.26 (br s, 1H).

Example 263

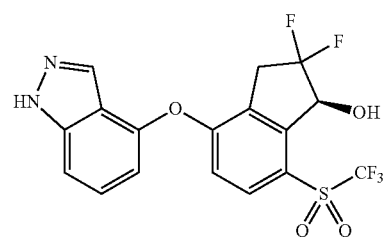 [SMILES: O=S(=O)(c1ccc(Oc2cccc3[nH]ncc23)c2c1[C@H](O)C(F)(F)C2)C(F)(F)F]

(S)-4-((1H-Indazol-4-yl)oxy)-2,2-difluoro-7-((trifluoromethyl)sulfonyl)-2,3-dihydro-1H-inden-1-ol (Compound 263)

To a solution of 2,2-difluoro-4-(1H-indazol-4-yloxy)-7-(trifluoromethylsulfonyl)indan-1-one (43 mg, 0.1 mmol) in dichloromethane (1.5 mL) at 0° C. were added triethylamine (55 µL, 0.39 mmol), formic acid (22 µL, 0.58 mmol) and RuCl(p-cymene)[(R,R)-Ts-DPEN] (20 mg, 0.32 mmol). The reaction mixture was stirred at room temperature overnight. The reaction mixture was purified by preparative TLC with 60% EtOAc/hexane (60%) followed by reverse phase column chromatography with acetonitrile/water (20% to 80%) to give Compound 263 (2.5 mg, 0.006 mmol, 6% yield). Chiral HPLC retention time: 1.82 minutes. LCMS ESI (+) (M+H) m/z 435; $^1$H NMR (400 MHz, CDCl$_3$): δ 7.92 (s, 1H), 7.84 (d, 1H), 7.48-7.42 (m, 2H), 6.92 (d, 1H), 6.86 (d, 1H), 5.46 (d, 1H), 3.68-3.59 (m, 2H), 3.28 (br s, 1H).

Example 264

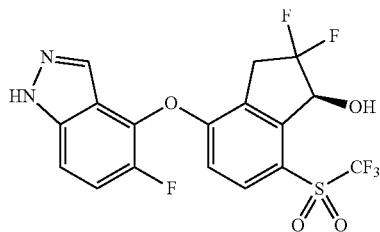 [SMILES: O=S(=O)(c1ccc(Oc2c(F)ccc3[nH]ncc23)c2c1[C@H](O)C(F)(F)C2)C(F)(F)F]

(S)-2,2-Difluoro-4-((5-fluoro-1H-indazol-4-yl)oxy)-7-((trifluoromethyl)sulfonyl)-2,3-dihydro-1H-inden-1-ol (Compound 264)

Prepared similarly as described for Compound 263. Chiral HPLC retention time: 1.78 minutes. LCMS ESI (+) (M+H) m/z 453; $^1$H NMR (400 MHz, CDCl$_3$): δ 7.93 (d, 1H), 7.84 (d, 1H), 7.13 (t, 1H), 6.81 (d, 1H), 6.86 (d, 1H), 5.46 (d, 1H), 3.68-3.69 (m, 2H), 3.29 (br s, 1H).

Example 265

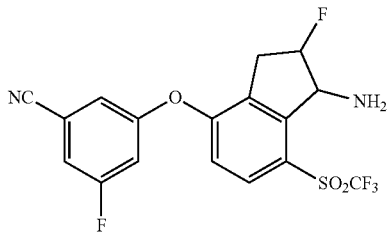

Diastereomer 1 of 3-((1-amino-2-fluoro-7-((trifluoromethyl)sulfonyl)-2,3-dihydro-1H-inden-4-yl)oxy)-5-fluorobenzonitrile (Compound 265)

Step A: Diastereomer 1 of N-(4-(3-cyano-5-fluorophenoxy)-2-fluoro-7-((trifluoromethyl)sulfonyl)-2,3-dihydro-1H-inden-1-ylidene)-2-methylpropane-2-sulfinamide To a stirred mixture of 3-fluoro-5-[2-fluoro-1-oxo-7-(trifluoromethylsulfonyl)indan-4-yl]oxy-benzonitrile (150 mg, 0.36 mmol) and (S)-(−)-2-methyl-2-propanesulfinamide (52 mg, 0.43 mmol) in tetrahydrofuran (3.6 mL), titanium ethoxide (226 µL, 1.08 mmol) was added dropwise at ambient temperature under nitrogen. The reaction mixture was warmed to 60° C. and stirred overnight. After cooling to ambient temperature, water was added. Solids were removed by filtration and washed with EtOAc. The organic phase of the filtrate was separated, washed with brine, dried and concentrated in vacuo. The residue was purified by flash chromatography on silica gel (10-20% EtOAc/hexane) to give the desired product, which was further purified by C18 reverse phase flash chromatography (Biotage Isolera One unit, C18 Flash, 25+M column, 10-95% CH$_3$CN/water) to afford diastereomer 1 of N-(4-(3-cyano-5-fluorophenoxy)-2-fluoro-7-((trifluoromethyl)sulfonyl)-2,3-dihydro-1H-inden-1-ylidene)-2-methylpropane-2-sulfinamide (74 mg, 40%). LCMS ESI (+) m/z 521 (M+H).

Step B: (S)—N-(4-(3-cyano-5-fluorophenoxy)-2-fluoro-7-((trifluoromethyl)sulfonyl)-2,3-dihydro-1H-inden-1-yl)-2-methylpropane-2-sulfinamide To a stirred solution of the diastereomer 1 of N-(4-(3-cyano-5-fluorophenoxy)-2-fluoro-7-((trifluoromethyl)sulfonyl)-2,3-dihydro-1H-inden-1-ylidene)-2-methylpropane-2-sulfinamide (59 mg, 0.11 mmol) in tetrahydrofuran (1 mL) was added sodium borohydride (17 mg, 0.45 mmol) at −78° C. under nitrogen. The reaction mixture was stirred at −78° C. for 10 minutes and then quenched by the addition of water. The reaction mixture was partitioned between EtOAc and water. The aqueous layer was extracted with EtOAc. The combined organic layers were washed with brine, dried and concentrated. The residue was purified by flash chromatography on silica gel (5-50% EtOAc/hexane) to give (S)—N-(4-(3-cyano-5-fluorophenoxy)-2-fluoro-7-((trifluoromethyl)sulfonyl)-2,3-dihydro-1H-inden-1-yl)-2-methylpropane-2-sulfinamide (46 mg, 78%) as a mixture of two diastereomers. LCMS ESI (+) m/z 521 (M+H).

Step C: Diasteromer 1 of 3-((1-amino-2-fluoro-7-((trifluoromethyl)sulfonyl)-2,3-dihydro-1H-inden-4-yl)oxy)-5-fluorobenzonitrile (Compound 265)

To a stirred solution of (S)—N-(4-(3-cyano-5-fluorophenoxy)-2-fluoro-7-((trifluoromethyl)sulfonyl)-2,3-dihydro-1H-inden-1-yl)-2-methylpropane-2-sulfinamide from Example 265 Step B (46 mg, 0.09 mmol) in methanol (0.6 mL), 4 N HCl in dioxane (0.44 mL, 1.8 mmol) was added at ambient temperature. The reaction mixture was stirred for 30 minutes, and then evaporated under reduced pressure. The residue was dissolved in EtOAc, washed with saturated aqueous NaHCO$_3$ solution and brine, dried and concentrated. The residue was purified by flash chromatography on silica gel (10-30% EtOAc/hexanes) to give Compound 265 (33 mg, 90%) as the major product. LCMS ESI (+) m/z 419 (M+H); $^1$H NMR (400 MHz, CDCl$_3$): δ 7.90 (d, 1H), 7.30-7.28 (m, 1H), 7.19 (br s, 1H), 7.10-7.06 (m, 1H), 6.92 (d, 1H), 5.44-5.26 (m, 1H), 4.93 (t, 1H), 3.40-3.24 (m, 2H), 1.95 (br s, 2H).

Example 266

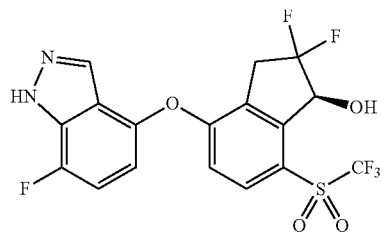 [SMILES: O=S(=O)(c1ccc(Oc2ccc(F)c3[nH]ncc23)c2c1[C@H](O)C(F)(F)C2)C(F)(F)F]

(S)-2,2-difluoro-4-((7-fluoro-1H-indazol-4-yl)oxy)-7-((trifluoromethyl)sulfonyl)-2,3-dihydro-1H-inden-1-ol (Compound 266)

Prepared similarly as Compound 263. Chiral HPLC retention time: 1.81 minutes. LCMS ESI (+) (M+H) m/z 453; $^1$H NMR (400 MHz, CDCl$_3$): δ 7.96 (s, 1H), 7.83 (d, 1H), 7.36 (t, 1H), 6.81 (d, 1H), 6.68 (d, 1H), 5.47 (d, 1H), 3.74-3.65 (m, 2H), 3.28 (br s, 1H).

Example 267

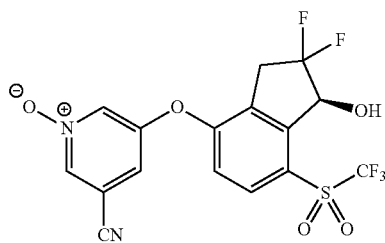 [SMILES: N#Cc1cc(Oc2ccc(S(=O)(=O)C(F)(F)F)c3c2CC(F)(F)[C@H]3O)c[n+]([O-])c1]

(S)-3-cyano-5-((2,2-difluoro-1-hydroxy-7-((trifluoromethyl)sulfonyl)-2,3-dihydro-1H-inden-4-yl)oxy) pyridine 1-oxide (Compound 267)

Prepared similarly as Compound 260. Purification was achieved by chromatography on silica using 40-90% EtOAc/hexane to afford Compound 267 as a beige solid (1.4 mg, 9%). LCMS ESI (−) (M−H) m/z 435; $^1$H NMR (400 MHz, CDCl$_3$): δ 8.32 (s, 1H), 8.23 (s, 1H), 8.03 (d, 1H), 7.23 (s, 1H), 7.13 (d, 1H), 5.46 (dd, 1H), 3.64-3.42 (m, 2H), 3.25 (d, 1H).

Example 268

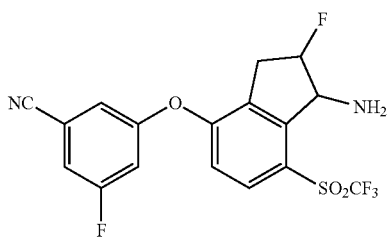

Diasteromer 2 of 3-((1-amino-2-fluoro-7-((trifluoromethyl)sulfonyl)-2,3-dihydro-1H-inden-4-yl)oxy)-5-fluorobenzonitrile (Compound 268)

Step A: Diastereomer 2 of N-(4-(3-cyano-5-fluorophenoxy)-2-fluoro-7-((trifluoromethyl)sulfonyl)-2,3-dihydro-1H-inden-1-ylidene)-2-methylpropane-2-sulfinamide To a stirred mixture of 3-fluoro-5-[2-fluoro-1-oxo-7-(trifluoromethylsulfonyl)indan-4-yl]oxy-benzonitrile (150 mg, 0.36 mmol) and (R)-(−)-2-Methyl-2-propanesulfinamide (65 mg, 0.54 mmol) in toluene (3.6 mL), titanium ethoxide (301 μL, 1.44 mmol) was added dropwise at ambient temperature under nitrogen. The reaction mixture was warmed to 60° C. and stirred overnight. After cooling to ambient temperature, water was added. Solids were removed by filtration and washed with EtOAc. The organic phase of the filtrate was separated, washed with brine, dried and concentrated in vacuo. The residue was purified by flash chromatography on silica gel (10-20% EtOAc/hexane) to afford diastereomer 2 of N-(4-(3-cyano-5-fluorophenoxy)-2-fluoro-7-((trifluoromethyl)sulfonyl)-2,3-dihydro-1H-inden-1-ylidene)-2-methylpropane-2-sulfinamide (102 mg, 54%) as the less polar diastereomer. LCMS ESI (+) m/z 521 (M+H).

Step B: Diasteromer 2 of 3-((1-amino-2-fluoro-7-((trifluoromethyl)sulfonyl)-2,3-dihydro-1H-inden-4-yl)oxy)-5-fluorobenzonitrile (Compound 268)

To a stirred solution of diastereomer 2 of N-(4-(3-cyano-5-fluorophenoxy)-2-fluoro-7-((trifluoromethyl)sulfonyl)-2,3-dihydro-1H-inden-1-ylidene)-2-methylpropane-2-sulfinamide (102 mg, 0.2 mmol) in tetrahydrofuran (2 mL), sodium borohydride (30 mg, 0.78 mmol) was added at ambient temperature under nitrogen. The reaction mixture was stirred for 10 minutes and then quenched by the addition of water. The reaction mixture was partitioned between EtOAc and water. The aqueous layer was extracted with EtOAc. The combined organic layers were washed with brine, dried and concentrated. The residue was dissolved in MeOH (1.3 mL) and 4 N HCl in dioxane (0.98 mL, 3.9 mmol) was added dropwise to the reaction mixture at ambient temperature. The reaction was stirred for 30 minutes, and then evaporated under reduced pressure. The residue was taken up in EtOAc, washed with saturated aqueous NaHCO$_3$ solution and brine, dried and concentrated. The residue was purified by flash chromatography on silica gel (10-50% EtOAc/hexane) to give Compound 268 (15 mg, 18%). LCMS ESI (+) m/z 419 (M+H); $^1$H NMR (400 MHz, CDCl$_3$): δ 7.90 (d, 1H), 7.30-7.28 (m, 1H), 7.22 (br s, 1H), 7.12-7.08 (m, 1H), 6.95 (d, 1H), 5.25-5.12 (m, 1H), 4.95 (d, 1H), 3.52-3.46 (m, 1H), 3.29-3.18 (m, 1H), 1.73 (br s, 2H).

Example 269

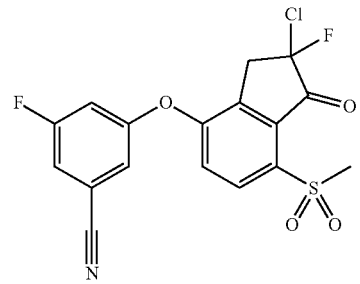 [SMILES: CS(=O)(=O)c1ccc(Oc2cc(F)cc(C#N)c2)c2c1C(=O)C(F)(Cl)C2]

3-((2-chloro-2-fluoro-7-(methylsulfonyl)-1-oxo-2,3-dihydro-1H-inden-4-yl)oxy)-5-fluorobenzonitrile (Compound 269)

Trimethylsilyl trifluoromethanesulfonate (60 μL, 0.33 mmol) was added to an ice cold solution of 3-fluoro-5-(2-fluoro-7-methylsulfonyl-1-oxo-indan-4-yl)oxy-benzonitrile (from Step A, Compound 231) (100 mg, 0.28 mmol) and triethylamine (46 μL, 0.33 mmol) in dichloromethane (1.0 mL) under nitrogen then stirred for 1.5 h. N-Chlorosuccinimide (44 mg, 0.33 mmol) was added all at once as a solid and the reaction mixture was stirred until complete as judged by LC-MS (1 hour). The reaction mixture was quenched with water, extracted with ethyl acetate, washed with brine and dried over sodium sulfate. The residue was purified on silica gel (10 g SNAP Ultra, 14 CV, 20-100% ethyl acetate/hexanes) affording Compound 269 (54 mg, 0.14 mmol, 42% yield). LC-MS ESI (+) m/z 398/400 (M+NH$_4^+$); $^1$H-NMR (400 MHz, CDCl$_3$): δ 8.23-8.21 (m, 1H), 7.35-7.32 (m, 1H), 7.26-7.24 (m, 1H), 7.23-7.21 (m, 1H), 7.14-7.10 (m, 1H), 3.97-3.78 (m, 2H), 3.43 (s, 3H).

Example 270

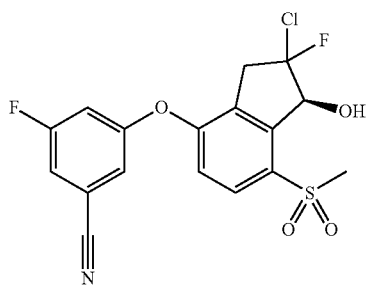 [SMILES: CS(=O)(=O)c1ccc(Oc2cc(F)cc(C#N)c2)c2c1[C@H](O)C(F)(Cl)C2]

3-(((1S)-2-chloro-2-fluoro-1-hydroxy-7-(methylsulfonyl)-2,3-dihydro-1H-inden-4-yl)oxy)-5-fluorobenzonitrile (Compound 270)

Prepared in a similar fashion as in the synthesis of Compound 163. Compound 270 was isolated as an inseparable mixture of diastereomers. ESI (+) m/z 417/419 (M+NH$_4^+$); $^1$H-NMR (400 MHz, CDCl$_3$): δ 7.95-7.91 (m, 1H), 7.26-7.23 (m, 1H), 7.14-7.13 (m, 1H), 7.06-7.00 (m, 2H), 5.80-5.78 (m, 0.5H), 5.65-5.61 (m, 0.5H), 3.81-3.55 (m, 3.5H), 3.25 (s, 1.5H), 3.24 (s, 1.5H).

Example 271

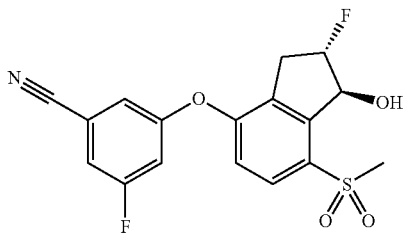 [SMILES: CS(=O)(=O)c1ccc(Oc2cc(F)cc(C#N)c2)c2c1[C@H](O)[C@@H](F)C2]

3-fluoro-5-(((1S,2S)-2-fluoro-1-hydroxy-7-(methylsulfonyl)-2,3-dihydro-1H-inden-4-yl)oxy)benzonitrile (Compound 271)

Isolated as a minor product from the preparation of Compound 231, Step B. LC-MS ESI (+) m/z 383 (M+NH$_4^+$); $^1$HNMR (400 MHz, CDCl$_3$): δ 7.87 (d, 1H), 7.23-7.21 (m, 1H), 7.13-7.12 (m, 1H), 7.05-7.00 (m, 2 H), 5.62-5.56 (m, 1H), 5.44-5.29 (m, 1H), 3.66 (dd, 1H), 3.49-3.35 (m, 1H), 3.20 (s, 3H), 3.17-3.06 (m, 1H).

Example 272

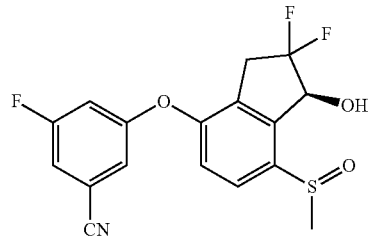 [SMILES: CS(=O)c1ccc(Oc2cc(F)cc(C#N)c2)c2c1[C@H](O)C(F)(F)C2]

3-[(1S)-2,2-Difluoro-1-hydroxy-7-methylsulfinyl-indan-4-yl]oxy-5-fluoro-benzonitrile (Compound 272)

Step A: 3-Fluoro-5-(7-methylsulfinyl-1-oxo-indan-4-yl)oxy-benzonitrile

3-Chloroperbenzoic acid (734 mg, 3.19 mmol) was added to an ice-cold solution of 3-fluoro-5-(7-methylsulfanyl-1-oxo-indan-4-yl)oxy-benzonitrile (1000 mg, 3.19 mmol) (Example 163) in dichloromethane (30 mL). After 5 minutes, the reaction mixture was diluted with DCM and was washed with 2 portions of saturated aqueous NaHCO$_3$/Na$_2$S$_2$O$_3$ mixture, brine, dried over MgSO$_4$, filtered, and evaporated to afford 3-fluoro-5-(7-methylsulfinyl-1-oxo-indan-4-yl)oxy-benzonitrile (1030 mg, 3.13 mmol, 98% yield) as a pale yellow solid. (ES-API-pos) [M+H]=330.

Step B: (E,Z)-3-Fluoro-5-[1-(3-methoxypropylimino)-7-methylsulfinyl-indan-4-yl]oxy-benzonitrile Pivalic acid (64 mg, 0.63 mmol) was added to a suspension of 3-fluoro-5-(7-methylsulfinyl-1-oxo-indan-4-yl)oxy-benzonitrile (1030 mg, 3.13 mmol) and 3-methoxypropylamine (1.6 mL, 15.6 mmol) in toluene (30 mL) and cyclohexane (20 mL). The mixture was heated at reflux with a Dean-Stark trap attached. After 5 hours, the reaction mixture was evaporated and the residue was used as is.

Step C: 3-(2,2-Difluoro-7-methylsulfinyl-1-oxo-indan-4-yl)oxy-5-fluoro-benzonitrile 1-Chloromethyl-4-fluoro-1,4-diazoniabicyclo[2.2.2]octane bis(tetrafluoroborate) (2769 mg, 7.82 mmol) was added to a solution of crude (E,Z)-3-fluoro-5-[1-(3-methoxypropylimino)-7-methylsulfinyl-indan-4-yl]oxy-benzonitrile (1252 mg, 3.13 mmol) in acetonitrile (50 mL). The reaction mixture was stirred at 70° C. After 1 h, the cooled reaction mixture was treated with 1M HCl (9.38 mL, 9.38 mmol), stirred for 15 minutes, and evaporated. The residue was partitioned between EtOAc and water. The EtOAc layer was washed with brine, dried over MgSO$_4$, filtered, and evaporated. The residue was chromatographed on a Biotage 50 g SNAP column with a 30% to 100% EtOAc:hexane gradient to afford 3-(2,2-difluoro-7-methylsulfinyl-1-oxo-indan-4-yl)oxy-5-fluoro-benzonitrile (430 mg, 1.18 mmol, 38% yield). (ES-API-pos) [M+H]=366.

Step D: 3-[(1S)-2,2-Difluoro-1-hydroxy-7-methylsulfinyl-indan-4-yl]oxy-5-fluoro-benzonitrile (Compound 272)

RuCl(p-cymene)[(R,R)-Ts-DPEN] (5.2 mg, 0.01 mmol) was added to a nitrogen-sparged, ice cold solution of 3-(2, 2-difluoro-7-methylsulfinyl-1-oxo-indan-4-yl)oxy-5-fluoro-benzonitrile (108 mg, 0.27 mmol), formic acid (0.04 mL, 1.09 mmol), and triethylamine (0.1 mL, 0.68 mmol) in dichloromethane (5 mL). The flask was sealed and kept in a 4° C. refrigerator overnight. The reaction mixture was evaporated and the residue was chromatographed on a Biotage 10 g ultra SNAP column with a 60% to 100% EtOAc:hexane gradient to afford Compound 272 (85 mg, 0.23 mmol, 85% yield). $^1$H NMR (400 MHz, CDCl$_3$): δ 7.84-7.80 (m, 1H), 7.19-7.16 (m, 1H), 7.10 (d, 1H), 7.08-7.06 (m, 1H), 7.00-6.96 (m, 1H), 5.40 (d, 1H), 4.48-4.36 (m, 1H), 3.49-3.27 (m, 2H), 2.93 (s, 3H). (ES-API-pos) [M+1]= 368.

Example 273

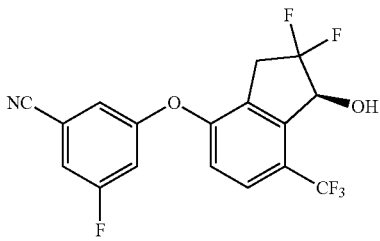 [SMILES: N#Cc1cc(F)cc(Oc2ccc(C(F)(F)F)c3c2CC(F)(F)[C@H]3O)c1]

3-[(1S)-2,2-Difluoro-1-hydroxy-7-(trifluoromethyl) indan-4-yl]oxy-5-fluoro-benzonitrile (Compound 273)

Step A: 7-Iodo-4-methoxy-indan-1-one

1-Chloromethyl-4-fluoro-1,4-diazoniabicyclo[2.2.2]octane bis(tetrafluoroborate) (1970 mg, 5.6 mmol) was added to an ice-cold solution of iodine (1721 mg, 6.8 mmol) in acetonitrile (100 mL). The resulting solution was stirred at 0° C. for a few minutes, then 4-methoxyindanone (1000 mg, 6.17 mmol) was added. The resulting mixture was stirred at ambient temperature. After 3 hours, the reaction mixture was evaporated and the residue was partitioned between EtOAc and dilute aqueous sodium thiosulfate. The EtOAc was washed with saturated aqueous sodium thiosulfate, brine, dried over MgSO$_4$, filtered, and evaporated to afford 7-iodo-4-methoxy-indan-1-one (1310 mg, 4.6 mmol, 74% yield). (ES-API-pos) [M+H]=289.

Step B: 4-Hydroxy-7-iodo-indan-1-one

Trimethylammonium chloride (1260 mg, 13.2 mmol) was added to an ice-cold suspension of aluminium chloride (3638 mg, 27.3 mmol) in DCM (10 mL). This yellow suspension was stirred in ice. After 3 hours of warming slowly to room temperature, the resulting liquid was added to a solution of 7-iodo-4-methoxy-indan-1-one (1310 mg, 4.55 mmol) in DCM (40 mL). The reaction mixture turned a dark brown color. The flask was heated at 50° C. overnight. The mixture was pipetted into 40 mL 1M HCl with stirring. The tan suspension was extracted with two portions of EtOAc. The EtOAc was washed with brine, dried over MgSO$_4$, filtered, and evaporated to yield 4-hydroxy-7-iodo-indan-1-one (1260 mg, 4.6 mmol, quantitative yield). (ES-API-neg) [M−H]=273.

Step C: 7-Iodoindane-1,4-diol

Sodium borohydride (345 mg, 9.1 mmol) was added to an ice-cold solution of 4-hydroxy-7-iodo-indan-1-one (1250 mg, 4.6 mmol) in methanol (100 mL). Additional sodium borohydride was added until LC/MS showed complete reduction. The reaction mixture was evaporated and the residue was partitioned between EtOAc and dilute HCl. The EtOAc was washed with brine, dried over MgSO$_4$, filtered, and evaporated to afford 7-iodoindane-1,4-diol (1230 mg, 4.5 mmol, 98% yield). (ES-API-neg) [M−H]=275, 311.

Step D: 3-Fluoro-5-(1-hydroxy-7-iodo-indan-4-yl) oxy-benzonitrile

Potassium carbonate (300 mg, 2.2 mmol) was added to a vial containing a solution of 7-iodoindane-1,4-diol (200 mg, 0.72 mmol) and 3,5-difluorobenzonitrile (151 mg, 1.1 mmol) in DMF (5 mL). The sealed vial was heated overnight at 110° C. The cooled reaction mixture was treated with dilute aqueous NaCl and extracted with 2 portions of EtOAc. The EtOAc was washed with 2 portions of brine, dried over MgSO$_4$, filtered, and evaporated. The residue was chromatographed on a Biotage 25 g SNAP column with a 10% to 60% EtOAc:hexane to afford 3-fluoro-5-(1-hydroxy-7-iodo-indan-4-yl)oxy-benzonitrile (180 mg, 0.46 mmol, 63% yield). (ES-API-pos) [M+H]=378.

Step E: 3-Fluoro-5-(7-iodo-1-oxo-indan-4-yl)oxy-benzonitrile

Dess-Martin periodinane (192 mg, 0.45 mmol) was added to a solution of 3-fluoro-5-(1-hydroxy-7-iodo-indan-4-yl) oxy-benzonitrile (180 mg, 0.46 mmol) in dichloromethane (20 mL). After 15 minutes, the reaction mixture was evaporated and the residue was partitioned between EtOAc and aqueous sodium thiosulfate and saturated aqueous NaHCO$_3$. The EtOAc was washed with water, brine, dried over MgSO$_4$, filtered, and evaporated to afford 3-fluoro-5-(7-iodo-1-oxo-indan-4-yl)oxy-benzonitrile (170 mg, 0.43 mmol, 95% yield) as a colorless film. (ES-API-pos) [M+H]= 394.

Step F: (E,Z)-3-Fluoro-5-[7-iodo-1-(3-methoxypropylimino)indan-4-yl]oxy-benzonitrile Pivalic acid (8.83 mg, 0.090 mmol) was added to a suspension of 3-fluoro-5-(7-iodo-1-oxo-indan-4-yl)oxy-benzonitrile (170 mg, 0.430 mmol) and 3-methoxypropylamine (0.22 mL, 2.16 mmol) in toluene (10 mL) and cyclohexane (5 mL). The mixture was heated at reflux overnight with a Dean-Stark trap attached. The reaction mixture was evaporated and the residue was used as is in the next step.

Step G: 3-(2,2-Difluoro-7-iodo-1-oxo-indan-4-yl) oxy-5-fluoro-benzonitrile

A solution of 1-chloromethyl-4-fluoro-1,4-diazoniabicyclo[2.2.2]octane bis(tetrafluoroborate) (381 mg, 1.1 mmol) in acetonitrile (5 mL) was treated with sodium sulfate (122 mg, 0.86 mmol) and heated to 70° C. To this was added dropwise, a solution of crude (E,Z)-3-fluoro-5-[7-iodo-1-(3-methoxypropylimino)indan-4-yl]oxy-benzonitrile (200 mg, 0.43 mmol) in acetonitrile (5 mL). After 1 hour, the cooled reaction mixture was treated with 1M HCl (1.29 mL, 1.29 mmol) and stirred for 10 minutes at ambient temperature.

The reaction mixture was concentrated and the residue was partitioned between EtOAc and water. The EtOAc was washed with brine, dried over MgSO$_4$, filtered, and evaporated. The residue was chromatographed on a Biotage 25 g ultra SNAP column with a 5% to 50% EtOAc:DCM to afford 3-(2,2-difluoro-7-iodo-1-oxo-indan-4-yl)oxy-5-fluoro-benzonitrile (73 mg, 0.17 mmol, 39% yield). (ES-API-pos) [M+H]=430.

Step H: 3-[2,2-Difluoro-1-oxo-7-(trifluoromethyl) indan-4-yl]oxy-5-fluoro-benzonitrile Methyl 2,2-difluoro-2-fluorosulfonyl-acetate (0.089 mL, 0.7 mmol) was added to a vial (equipped with a nitrogen-filled balloon) containing 3-(2,2-difluoro-7-iodo-1-oxo-indan-4-yl)oxy-5-fluoro-benzonitrile (60 mg, 0.14 mmol) and copper(I) iodide (53 mg, 0.28 mmol) in DMF (3 mL). The sealed vial was heated at 100° C. for 4 hours. The reaction mixture was partitioned between EtOAc and dilute aqueous NaCl. The EtOAc was washed with 2 portions of brine, dried over MgSO$_4$, filtered, and evaporated. The residue was chromatographed on a Biotage 10 g ultraSNAP column with a 5% to 50% EtOAc:hexane to afford 3-[2,2-difluoro-1-oxo-7-(trifluoromethyl)indan-4-yl]oxy-5-fluoro-benzonitrile (29 mg, 0.078 mmol, 56% yield). (ES-API-pos) [M+H]=372.

Step I: 3-[(1S)-2,2-Difluoro-1-hydroxy-7-(trifluoromethyl)indan-4-yl]oxy-5-fluoro-benzonitrile (Compound 273)

RuCl(p-cymene)[(R,R)-Ts-DPEN] (1.5 mg, 0.0082 mmol) was added to a nitrogen-sparged, ice-cold solution of 3-[2,2-difluoro-1-oxo-7-(trifluoromethyl)indan-4-yl]oxy-5-fluoro-benzonitrile (29 mg, 0.078 mmol), formic acid (0.0117 mL, 0.31 mmol), and triethylamine (0.027 mL, 0.195 mmol) in dichloromethane (2 mL). The flask was sealed and kept in a 4° C. refrigerator overnight. The reaction mixture was evaporated and the residue was chromatographed on a Biotage 10 g ultraSNAP column with a 5% to 60% EtOAc:hexane gradient to afford Compound 273 (25 mg, 0.066 mmol, 85% yield) in 98% e.e. by chiral HPLC analysis. $^1$H NMR (400 MHz, CDCl$_3$): δ 7.63 (d, 1H), 7.21-7.18 (m, 1H), 7.11-7.09 (m, 1H), 7.03-6.97 (m, 2H), 5.29 (d, 1H), 3.51-3.28 (m, 2H), 2.76 (br s, 1H). m/z (ES-API-neg) [M+formate-H]=418.

Examples 274 and 275

Compound 274

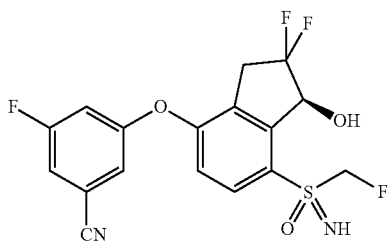

Compound 275

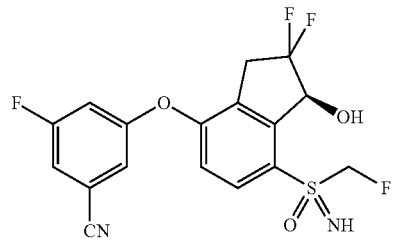

Isomer 1 of 3-(((1S)-2,2-difluoro-7-(S-(fluoromethyl)sulfonimidoyl)-1-hydroxy-2,3-dihydro-1H-inden-4-yl)oxy)-5-fluorobenzonitrile (Compound 274) and isomer 2 of 3-(((1S)-2,2-difluoro-7-(S-(fluoromethyl)sulfonimidoyl)-1-hydroxy-2,3-dihydro-1H-inden-4-yl)oxy)-5-fluorobenzonitrile (Compound 275)

Step A: Preparation of (N-((7-(3-cyano-5-fluorophenoxy)-3-oxo-2,3-dihydro-1H-inden-4-yl)(fluoromethyl)λ$^4$-sulfanylidene)cyanamide: 3-fluoro-5-((7-((fluoromethyl)thio)-1-oxo-2,3-dihydro-1H-inden-4-yl)oxy)benzonitrile was prepared similarly according to Examples 272 and 59. A solution of 3-fluoro-5-((7-((fluoromethyl)thio)-1-oxo-2,3-dihydro-1H-inden-4-yl)oxy)benzonitrile (620 mg, 1.87 mmol), bis(tert-butylcarbonyloxy)iodobenzene (1140 mg, 2.8 mmol), magnesium oxide (302 mg, 7.48 mmol), and cyanamide (157 mg, 3.74 mmol) in dichloromethane (25 mL) was treated with bis[rhodium(α,α,α',α'-tetramethyl-1, 3-benzenedipropionic acid)] (14.3 mg, 0.019 mmol). The vessel was sealed and left to stir at 25° C. for 3 h. The reaction mixture was filtered through celite, concentrated, and used without further purification. LCMS ESI (+) (M+H) m/z 372.

Step B: Preparation of N-((7-(3-cyano-5-fluorophenoxy)-3-oxo-2,3-dihydro-1H-inden-4-yl)(fluoromethyl)(oxo)-λ$^6$-sulfanylidene)cyanamide A solution of (N-((7-(3-cyano-5-fluorophenoxy)-3-oxo-2,3-dihydro-1H-inden-4-yl)(fluoromethyl)-λ$^4$-sulfanylidene) cyanamide (691 mg, 1.87 mmol) and ruthenium(III) chloride (9.7 mg, 0.047 mmol) in a mixture of water (18.6 mL), carbon tetrachloride (18.6 mL), and acetonitrile (18.6 mL) was treated with sodium periodate (1.19 g, 5.58 mmol) and stirred at 25° C. for 2 days. The reaction mixture was cooled to room temperature and quenched by the addition of 20 mL of saturated Na$_2$S$_2$O$_3$ solution. The mixture was stirred for 10 minutes and then poured into 40 mL of water and extracted with 3×30 mL EtOAc. The combined organics were rinsed with 10 mL of brine, dried with MgSO$_4$, filtered, and concentrated to dryness. Purification was achieved by chromatography on silica using 10-55% EtOAc/hexane to afford N-((7-(3-cyano-5-fluorophenoxy)-3-oxo-2,3-dihydro-1H-inden-4-yl)(fluoromethyl)(oxo)-λ$^6$-sulfanylidene)cyanamide (630 mg, 87%). LCMS ESI (+) (M+H) m/z 388.

Step C: Preparation of N-((7-(3-cyano-5-fluorophenoxy)-3-oxo-2,3-dihydro-1H-inden-4-yl)(fluoromethyl)(oxo)-λ$^6$-sulfanylidene)-2,2,2-trifluoroacetamide A solution of N-((7-(3-cyano-5-fluorophenoxy)-3-oxo-2, 3-dihydro-1H-inden-4-yl)(fluoromethyl)(oxo)-λ$^6$-sulfanylidene)cyanamide (94 mg, 0.24 mmol) in dichloromethane (4.9 mL) at 25° C. was treated with trifluoroacetic anhydride (0.10 mL, 0.73 mmol) and stirred overnight. Volatiles were removed by concentration under reduced pressure and the resulting solid was used without further purification after drying for 1 hour under high vacuum. LCMS ESI (−) (M−H) m/z 457.

Step D: Preparation of (E,Z)-3-fluoro-5-((7-(S-(fluoromethyl)sulfonimidoyl)-1-((3-methoxypropyl)imino)-2,3-dihydro-1H-inden-4-yl)oxy)benzonitrile A solution of N-((7-(3-cyano-5-fluorophenoxy)-3-oxo-2,3-dihydro-1H-inden-4-yl)(fluoromethyl)(oxo)-$\lambda^6$-sulfanylidene)-2,2,2-trifluoroacetamide (110 mg, 0.24 mmol) and 2,2-dimethylpropanoic acid (4.9 mg, 0.048 mmol) in a mixture of toluene (2.4 mL) and cyclohexane (2.4 mL) was treated with 3-methoxypropan-1-amine (74 µL, 0.72 mmol). The reaction vessel was equipped with a Hickman still and a reflux condenser and heated at 104° C. for 2.5 h. LCMS analysis was achieved by taking an aliquot of the reaction mixture and adding it to a solution of MeOH containing excess NaBH$_4$. LCMS indicated formation of the amine via imine reduction. Once complete, volatiles were removed by concentration under reduced pressure. The residue was used without further purification. LCMS ESI (+) (M+H) m/z 436.

Step E: Preparation of 3-((2,2-difluoro-7-(S-(fluoromethyl)sulfonimidoyl)-1-oxo-2,3-dihydro-1H-inden-4-yl)oxy)-5-fluorobenzonitrile A solution of (E,Z)-3-fluoro-5-((7-(S-(fluoromethyl)sulfonimidoyl)-1-((3-methoxypropyl)imino)-2,3-dihydro-1H-inden-4-yl)oxy)benzonitrile (104 mg, 0.24 mmol) and sodium sulfate (85 mg, 0.60 mmol) in acetonitrile (2.4 mL) was treated with 1-(chloromethyl)-4-fluoro-1,4-diazoniabicyclo[2.2.2]octane ditetrafluoroborate (213 mg, 0.60 mmol) and stirred at 70° C. for 2 h. The reaction mixture was treated with 1 mL of 10% aqueous HCl solution and stirred for 20 minutes. The reaction mixture was poured into 30 mL of water and extracted with 3×20 mL EtOAc. The combined organics were rinsed with 10 mL of brine, dried with MgSO4, filtered, and concentrated to dryness. Purification was achieved by chromatography on silica using 20-65% EtOAc/hexane to give 3-((2,2-difluoro-7-(S-(fluoromethyl)sulfonimidoyl)-1-oxo-2,3-dihydro-1H-inden-4-yl)oxy)-5-fluorobenzonitrile as a beige solid (21 mg, 21%). LCMS ESI (+) (M+H) m/z 399.

Step F: Preparation of 3-(((1S)-2,2-difluoro-7-(S-(fluoromethyl)sulfonimidoyl)-1-hydroxy-2,3-dihydro-1H-inden-4-yl)oxy)-5-fluorobenzonitrile A solution of 3-((2,2-difluoro-7-(S-(fluoromethyl)sulfonimidoyl)-1-oxo-2,3-dihydro-1H-inden-4-yl)oxy)-5-fluorobenzonitrile (20.5 mg, 0.052 mmol) in dichloromethane (2.1 mL) was cooled to 0° C. and sparged with nitrogen for 5 minutes. During this time formic acid (5.8 µL, 0.15 mmol) and triethylamine (14.3 µL, 0.10 mmol) were sequentially added. Once sparging was complete, RuCl(p-cymene)[(R,R)-Ts-DPEN] (1.0 mg, 3 mol %) was added to the reaction mixture under a continuous stream of nitrogen. The reaction vessel was sealed and stored at 4° C. overnight. The reaction mixture was poured into 10 mL of saturated aqueous NaHCO$_3$ and extracted with 3×15 mL CH$_2$Cl$_2$. The combined organics were rinsed with 10 mL of brine, dried with MgSO$_4$, filtered, and concentrated to dryness. Purification was achieved by chromatography on silica using 10-55% EtOAc/hexane to afford two isomers.

Data for Isomer 1 (Compound 274):
3.7 mg (18% yield); HPLC Retention time (long method)=4.28 min; LCMS ESI (+) (M+H) m/z 401; $^1$H NMR (400 MHz, CDCl$_3$): δ 7.95 (d, 1H), 7.28-7.25 (m, 1H), 7.17-7.15 (m, 1H), 7.06 (dt, 1H), 7.00 (d, 1H), 5.62-5.56 (m, 1H), 5.37 (dd, 1H), 5.24 (dd, 1H), 4.26 (d, 1H), 3.57-3.34 (m, 2H), 3.20 (br d, 1H).

Data for Isomer 2 (Compound 275):
8.4 mg (41% yield); HPLC Retention time (long method)=4.39 min; LCMS ESI (+) (M+H) m/z 401; $^1$H NMR (400 MHz, CDCl$_3$): δ 7.96 (d, 1H), 7.28-7.25 (m, 1H), 7.18-7.16 (m, 1H), 7.06 (dt, 1H), 7.01 (d, 1H), 5.42 (dd, 1H), 5.27 (dd, 1H), 5.15 (dd, 1H), 5.04-5.02 (m, 1H), 3.62-3.38 (m, 2H), 3.33 (br s, 1H).

Example 276 and 277

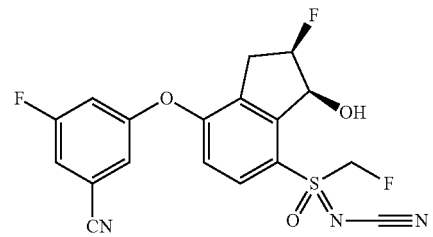

Compound 276

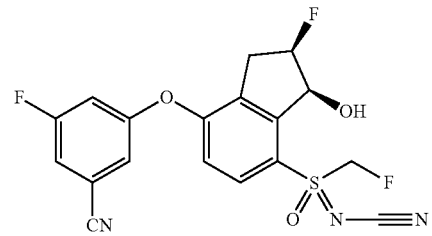

Compound 277

Isomer 1 of N-(((2R,3S)-7-(3-cyano-5-fluorophenoxy)-2-fluoro-3-hydroxy-2,3-dihydro-1H-inden-4-yl)(fluoromethyl)(oxo)-$\lambda^6$-sulfanylidene)cyanamide (Compound 276) and isomer 2 of N-(((2R,3S)-7-(3-cyano-5-fluorophenoxy)-2-fluoro-3-hydroxy-2,3-dihydro-1H-inden-4-yl)(fluoromethyl)(oxo)-$\lambda^6$-sulfanylidene)cyanamide (Compound 277)

Step A: Preparation of N-((7-(3-cyano-5-fluorophenoxy)-2-fluoro-3-oxo-2,3-dihydro-1H-inden-4-yl)(fluoromethyl)(oxo)-$\lambda^6$-sulfanylidene)cyanamide A solution of N-((7-(3-cyano-5-fluorophenoxy)-3-oxo-2,3-dihydro-1H-inden-4-yl)(fluoromethyl)(oxo)-$\lambda^6$-sulfanylidene)cyanamide (103 mg, 0.27 mmol) in acetonitrile (3.0 mL) was treated with Accufluor® (171 mg, 0.27 mmol) and heated to 84° C. for 3 hours. An additional portion of Accufluor® (171 mg, 0.27 mmol) was added and the reaction mixture was heated for an additional 3 hours. The reaction mixture was poured into 40 mL of water and extracted with 3×15 mL EtOAc. The combined organics were rinsed with 10 mL of brine, dried with MgSO$_4$, filtered, and concentrated to dryness. The residue was purified by chromatography on silica using 20-55% EtOAc/hexane to afford N-((7-(3-cyano-5-fluorophenoxy)-2-fluoro-3-oxo-2,3-dihydro-1H-inden-4-yl)(fluoromethyl)(oxo)-$\lambda^6$-sulfanylidene)cyanamide (51 mg, 47%). LCMS ESI (+) (M+H) m/z 406.

Step B: Preparation of N-(((2R,3S)-7-(3-cyano-5-fluorophenoxy)-2-fluoro-3-hydroxy-2,3-dihydro-1H-inden-4-yl)(fluoromethyl)(oxo)-$\lambda^6$-sulfanylidene)cyanamide A solution of N-((7-(3-cyano-5-fluorophenoxy)-2-fluoro-3-oxo-2,3-dihydro-1H-inden-4-yl)(fluoromethyl)(oxo)-$\lambda^6$-sulfanylidene)cyanamide (50.6 mg, 0.125 mmol) in dichloromethane (4.0 mL) was cooled to 0° C. and sparged with nitrogen for 5 minutes. During this time formic acid (14.1 µL, 0.375 mmol) and triethylamine (34.6 µL, 0.250 mmol) were sequentially added. Once the sparging was complete, RuCl(p-cymene)[(R,R)-Ts-DPEN] (2.4 mg, 3 mol %) was added under a continuous stream of nitrogen. The reaction vessel was sealed and kept at 4° C. overnight. The reaction mixture was poured into 10 mL of saturated aqueous NaHCO$_3$ and extracted with 3×15 mL CH$_2$Cl$_2$. The combined organics were rinsed with 10 mL of brine, dried with MgSO$_4$, filtered, and concentrated to dryness. Purification by chromatography on silica using 15-55% EtOAc/hexane (25 g Biotage Ultra) afforded two isomers.

Data for isomer 1 (Compound 276):
5.8 mg (11% yield); HPLC retention time (long method)=4.46 min; LCMS ESI (+) (M+H) m/z 408; $^1$H NMR (400 MHz, CDCl$_3$): δ 8.00 (d, 1H), 7.30 (ddd, 1H), 7.21-7.19 (m, 1H), 7.09 (dt, 1H), 6.99 (d, 1H), 5.92 (dd, 1H), 5.76-5.69 (m, 1H), 5.65 (dd, 1H), 5.55-5.37 (m, 1H), 3.43-3.18 (m, 2H), 3.22 (dd, 1H).

Data for isomer 2 (Compound 277):
7.8 mg (15% yield); HPLC retention time (long method)=4.58 min; LCMS ESI (+) (M+H) m/z 408; $^1$H NMR (400 MHz, CDCl$_3$): δ 8.04 (d, 1H), 7.31 (ddd, 1H), 7.24-7.22 (m, 1H), 7.11 (dt, 1H), 7.00 (d, 1H), 6.27 (dd, 1H), 5.75-5.69 (m, 1H), 5.55 (dd, 1H), 5.56-5.39 (m, 1H), 3.45-3.22 (m, 2H), 3.12 (t, 1H).

Example 278

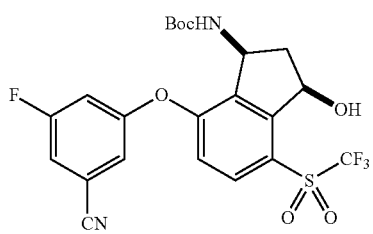 [SMILES: CC(C)(C)OC(=O)N[C@H]1C[C@@H](O)c2c(S(=O)(=O)C(F)(F)F)ccc(Oc3cc(F)cc(C#N)c3)c21]

tert-butyl (cis-7-(3-cyano-5-fluorophenoxy)-3-hydroxy-4-((trifluoromethyl)sulfonyl)-2,3-dihydro-1H-inden-1-yl)carbamate (Compound 278)

Step A: Preparation of 3-bromo-4-(3-bromo-5-fluorophenoxy)-7-((trifluoromethyl)sulfonyl)-2,3-dihydrospiro[indene-1,2'-[1,3]dioxolane]

The diaryl ether starting material, 4-(3-bromo-5-fluorophenoxy)-7-((trifluoromethyl)sulfonyl)-2,3-dihydrospiro[indene-1,2'[1,3]dioxolane], was prepared similarly according to Example 212, Steps A-B, substituting 3-bromo-5-fluorophenol for 4-fluorophenol. A solution of 4'-(3-bromo-5-fluoro-phenoxy)-7'-(trifluoromethylsulfonyl)spiro[1,3-dioxolane-2,1'-indane] (930 mg, 1.87 mmol) and N-bromosuccinimide (399 mg, 2.24 mmol) in carbon tetrachloride (12.5 mL) was sparged with nitrogen for 5 minutes and treated with benzoyl peroxide (91 mg, 0.37 mmol). The reaction vessel was fitted with a reflux condenser. The condenser was flushed with nitrogen for 5 minutes. The vessel was then sealed, placed under nitrogen atmosphere and stirred at 88° C. for 1 day. An additional portion of benzoyl peroxide (91 mg, 0.37 mmol) was added and the reaction was heated for an additional day. The reaction mixture was poured into 10 mL of 1 M NaOH and extracted with 3×20 mL CH$_2$Cl$_2$. The combined organics were rinsed with 10 mL of brine, dried with MgSO$_4$, filtered, and concentrated to dryness. Purification was achieved by chromatography on silica using 20-70% CH$_2$Cl$_2$/hexane to afford 3-bromo-4-(3-bromo-5-fluorophenoxy)-7-((trifluoromethyl)sulfonyl)-2,3-dihydrospiro[indene-1,2'-[1,3]dioxolane] (448 mg, 42%). LCMS ESI (+) (M+H) m/z: 575, 577, 579.

Step B: Preparation of 3-azido-4-(3-bromo-5-fluorophenoxy)-7-((trifluoromethyl)sulfonyl)-2,3-dihydrospiro[indene-1,2'-[1,3]dioxolane]

A solution of 3-bromo-4-(3-bromo-5-fluorophenoxy)-7-((trifluoromethyl)sulfonyl)-2,3-dihydrospiro[indene-1,2'[1,3]dioxolane] (448 mg, 0.78 mmol) in DMF (4.0 mL) at 25° C. was treated with sodium azide (50.6 mg, 0.78 mmol) and stirred at 25° C. for 1 hour. The reaction mixture was poured into 40 mL of water and extracted with 3×15 mL Et$_2$O. The combined organics were rinsed with 10 mL of brine, dried with MgSO$_4$, filtered, and concentrated to dryness. The residue was used without further purification. LCMS ESI (+) (M-N$_2$+H) m/z: 510, 512.

Step C: Preparation of 4-(3-bromo-5-fluorophenoxy)-7-((trifluoromethyl)sulfonyl)-2,3-dihydrospiro[indene-1,2'-[1,3]dioxolan]-3-amine A solution of 3-azido-4-(3-bromo-5-fluorophenoxy)-7-((trifluoromethyl)sulfonyl)-2,3-dihydrospiro[indene-1,2'-[1,3]dioxolane] (675 mg, 1.25 mmol) in a mixture of tetrahydrofuran (6.0 mL) and water (0.4 mL) at 25° C. was treated with trimethylphosphine solution (~1.0 M in THF, 1.5 mL, 1.5 mmol) and stirred for 30 minutes. Gas evolution was observed during this time. The reaction mixture was heated to 60° C. for 2 h. Volatiles were removed by concentration under reduced pressure. The resulting residue was dried under high vacuum overnight. Purification was achieved by chromatography on silica using 1-9% MeOH/CH$_2$Cl$_2$+1% NH$_4$OH to afford 4-(3-bromo-5-fluorophenoxy)-7-((trifluoromethyl)sulfonyl)-2,3-dihydrospiro[indene-1,2'[1,3]dioxolan]-3-amine (630 mg, 98%). LCMS ESI (+) (M+H) m/z: 512, 514.

Step D: Preparation of tert-butyl (4-(3-bromo-5-fluorophenoxy)-7-((trifluoromethyl)sulfonyl)-2,3-dihydrospiro[indene-1,2'-[1,3]dioxolan]-3-yl)carbamate A solution of 4-(3-bromo-5-fluorophenoxy)-7-((trifluoromethyl)sulfonyl)-2,3-dihydrospiro[indene-1,2'-[1,3]dioxolan]-3-amine (65 mg, 0.13 mmol) in dichloromethane (2.0 mL) at 25° C. was treated with di-tert-butyl pyrocarbonate (30.5 mg, 0.14 mmol) and stirred overnight. Volatiles were removed by concentration under reduced pressure. The product residue was used without further purification. LCMS ESI (−) (M−H) m/z: 610, 612.

Step E: Preparation of tert-butyl (7-(3-bromo-5-fluorophenoxy)-3-oxo-4-((trifluoromethyl)sulfonyl)-2,3-dihydro-1H-inden-1-yl)carbamate In a pressure tube, a sample of tert-butyl (4-(3-bromo-5-fluorophenoxy)-7-((trifluoromethyl)sulfonyl)-2,3-dihydrospiro[indene-1,2'[1,3]dioxolan]-3-yl)carbamate (77 mg, 0.13 mmol) was dissolved in a mixture of acetic acid (1.0 mL), tetrahydrofuran (0.5 mL), and water (0.5 mL). The reaction mixture was sealed and heated to 80° C. for 14 hours. LCMS analysis indicates a relatively clean reaction with formation of the desired product, unreacted starting material, and the corresponding Boc deprotected materials predominating. Volatiles were removed by concentration under reduced pressure. The leftover residue was poured into 20 mL of saturated NaHCO₃ and extracted with 3×15 mL EtOAc. The combined organics were rinsed with 10 mL of brine, dried with MgSO₄, filtered, and concentrated to dryness. The residue was dissolved in 3 mL of $CH_2Cl_2$ and treated with di-tert-butyl pyrocarbonate (13.8 mg, 0.063 mmol). The mixture was left to stir overnight. Volatiles were removed by concentration under reduced pressure. Purification was achieved by chromatography on silica using 5-35% EtOAc/hexane to afford tert-butyl (7-(3-bromo-5-fluorophenoxy)-3-oxo-4-((trifluoromethyl)sulfonyl)-2,3-dihydro-1H-inden-1-yl)carbamate (50 mg, 70%). LCMS ESI (−) (M−H) m/z: 566, 568.

Step F: Preparation of tert-butyl (cis-7-(3-bromo-5-fluorophenoxy)-3-hydroxy-4-((trifluoromethyl)sulfonyl)-2,3-dihydro-1H-inden-1-yl)carbamate A solution of tert-butyl (7-(3-bromo-5-fluorophenoxy)-3-oxo-4-((trifluoromethyl)sulfonyl)-2,3-dihydro-1H-inden-1-yl)carbamate (50 mg, 0.088 mmol) in methanol (2.0 mL) at 25° C. was treated with sodium borohydride (3.3 mg, 0.088 mmol) and stirred at 25° C. for 1 hour. The reaction mixture was quenched by the addition of 0.5 mL of aqueous saturated NH₄Cl and stirred for 5 minutes. Volatiles were removed by concentration under reduced pressure. The reaction mixture was poured into 10 mL of water and extracted with 3×10 mL EtOAc. The combined organics were rinsed with 10 mL of brine, dried with MgSO₄, filtered, and concentrated to dryness. Purification was achieved by chromatography on silica using 10-35% EtOAc/hexane to afford tert-butyl (cis-7-(3-bromo-5-fluorophenoxy)-3-hydroxy-4-((trifluoromethyl)sulfonyl)-2,3-dihydro-1H-inden-1-yl)carbamate (25 mg, 50%) as a clear solid film. LCMS ESI (−) (M−H) m/z: 568, 570.

Step G: Preparation of tert-butyl (cis-7-(3-cyano-5-fluorophenoxy)-3-hydroxy-4-((trifluoromethyl)sulfonyl)-2,3-dihydro-1H-inden-1-yl)carbamate (Compound 278)

A solution of tert-butyl (cis-7-(3-bromo-5-fluorophenoxy)-3-hydroxy-4-((trifluoromethyl)sulfonyl)-2,3-dihydro-1H-inden-1-yl)carbamate (20.5 mg, 0.036 mmol) and zinc cyanide (4.6 mg, 0.04 mmol) in DMF (0.36 mL) was sparged with nitrogen for 3 minutes. The reaction mixture was then treated sequentially with dichloro[1;1'-bis(diphenylphosphino)ferrocene]palladium(II) dichloromethane adduct (2.9 mg, 10 mol %) and zinc powder (2.8 mg, 0.043 mmol) under continuous nitrogen stream. The vessel was sealed and heated to 110° C. for 4 hours. The reaction mixture was poured into 30 mL of water and extracted with 3×10 mL Et₂O. The combined organics were rinsed with 10 mL of brine, dried with MgSO₄, filtered, and concentrated to dryness. Purification was achieved by chromatography on silica using 5-30% EtOAc/hexane to afford Compound 278 as a white solid (13.4 mg, 72%). LCMS ESI (−) (M+Cl⁻) m/z: 551, 553; ¹H NMR (400 MHz, CDCl₃): δ 7.97 (d, 1H), 7.27-7.23 (m, 1H), 7.17-7.13 (m, 1H), 7.07 (dt, 1H), 7.02 (d, 1H), 5.54 (dd, 1H), 5.49-5.41 (m, 1H), 5.12 (br d, 1H), 3.33 (br s, 1H), 2.73-2.64 (m, 1H), 2.22 (d, 1H), 1.35 (s, 9H).

Example 279

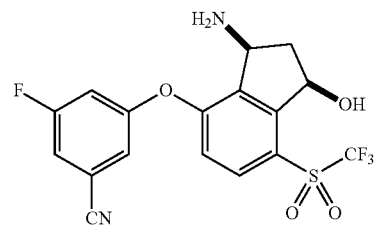 [SMILES: N#Cc1cc(F)cc(Oc2ccc(S(=O)(=O)C(F)(F)F)c3c2[C@@H](N)C[C@H]3O)c1]

3-((cis-3-amino-1-hydroxy-7-((trifluoromethyl)sulfonyl)-2,3-dihydro-1H-inden-4-yl)oxy)-5-fluorobenzonitrile (Compound 279)

A solution of tert-butyl (cis-7-(3-cyano-5-fluorophenoxy)-3-hydroxy-4-((trifluoromethyl)sulfonyl)-2,3-dihydro-1H-inden-1-yl)carbamate (10.5 mg, 0.020 mmol) in dichloromethane (0.5 mL) at 25° C. was treated with trifluoroacetic acid (0.5 mL) and stirred at 25° C. for 1 hour. Volatiles were removed by concentration under reduced pressure. The reaction mixture was poured into 10 mL of saturated aqueous NaHCO₃ and extracted with 3×10 mL 30% isopropyl alcohol in CHCl₃. The combined organics were rinsed with 10 mL of brine, dried with MgSO₄, filtered, and concentrated to dryness to afford Compound 279 (6.5 mg, 77%). LCMS ESI (+) (M+H) m/z 417; ¹H NMR (400 MHz, CDCl₃): δ 7.93 (d, 1H), 7.31 (ddd, 1H), 7.26-7.24 (m, 1H), 7.16 (dt, 1H), 6.94 (d, 1H), 5.53 (d, 1H), 4.59 (d, 1H), 2.69-2.61 (m, 1H), 2.35-1.95 (m, 4H).

Examples 280 and 281

Compound 280

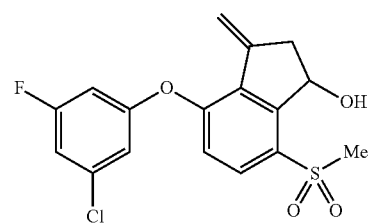

Compound 281

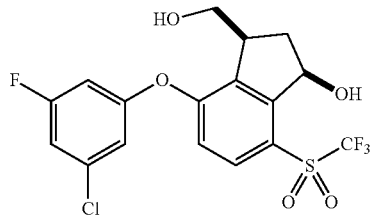

4-(3-chloro-5-fluorophenoxy)-3-methylene-7-(methylsulfonyl)-2,3-dihydro-1H-inden-1-ol (Compound 280) and (1R,3S)-4-(3-chloro-5-fluorophenoxy)-3-(hydroxymethyl)-7-((trifluoromethyl)sulfonyl)-2,3-dihydro-1H-inden-1-ol (Compound 281)

Step A: Preparation of 3,7-dibromo-4-fluoro-2,3-dihydrospiro[indene-1,2'[1,3]dioxolane]

A solution of 7'-bromo-4'-fluoro-spiro[1,3-dioxolane-2,1'-indane] (2.55 g, 9.34 mmol) and AIBN (23 mg, 0.14 mmol) in carbon tetrachloride (65 mL) was treated with N-bromosuccinimide (1.99 g, 11.2 mmol). The resulting mixture was sparged with nitrogen for 5 minutes. The reaction vessel was sealed and heated to 80° C. for 3 hours. The reaction mixture was poured into 50 mL of water and extracted with 3×30 mL $CH_2Cl_2$. The combined organics were rinsed with 10 mL of brine, dried with $MgSO_4$, filtered, and concentrated to dryness. The product was used without further purification. $^1$H NMR (400 MHz, $CDCl_3$): δ 7.52 (dd, 1H), 6.98 (dt, 1H), 5.41 (dd, 1H), 4.47-4.33 (m, 2H), 4.19-4.08 (m, 2H), 2.91-2.88 (dd, 1H), 2.76 (dd, 1H).

Step B: Preparation of 7-bromo-4-fluoro-2,3-dihydrospiro[indene-1,2'-[1,3]dioxolane]-3-carbonitrile A solution of 3,7-dibromo-4-fluoro-2,3-dihydrospiro[indene-1,2'[1,3]dioxolane] (3.27 g, 9.3 mmol) in DMF (9.3 mL) was treated with sodium cyanide (501 mg, 10.2 mmol) and stirred at 60° C. overnight. The reaction mixture was poured into 150 mL of water and extracted with 3×50 mL $Et_2O$. The combined organics were rinsed with 10 mL of brine, dried with $MgSO_4$, filtered, and concentrated to dryness. Purification was achieved by chromatography on silica using 10-40% EtOAc/hexane to afford 7-bromo-4-fluoro-2,3-dihydrospiro[indene-1,2'-[1,3]dioxolane]-3-carbonitrile (750 mg, 27%). LCMS ESI (+) (M+H) m/z: 298, 300.

Step C: Preparation of 4-bromo-7-fluoro-3-oxo-2,3-dihydro-1H-indene-1-carboxylic acid A solution of 7-bromo-4-fluoro-2,3-dihydrospiro[indene-1,2'-[1,3]dioxolane]-3-carbonitrile (166 mg, 0.56 mmol) in 1,4-Dioxane (2.5 mL) was treated with concentrated aqueous HCl solution (1.9 mL) and stirred at 105° C. for 1 hour. Volatiles were removed by concentration under reduced pressure. The remaining reaction mixture was poured into 20 mL of water and extracted with 3×15 mL EtOAc. The combined organics were rinsed with 10 mL of brine, dried with $MgSO_4$, filtered, and concentrated to dryness. The product was used without further purification. LCMS ESI (+) (M+H) m/z: 273, 275.

Step D: Preparation of cis-7-bromo-4-fluoro-3-(hydroxymethyl)-2,3-dihydro-1H-inden-1-ol A solution of 4-bromo-7-fluoro-3-oxo-2,3-dihydro-1H-indene-1-carboxylic acid (581 mg, 2.1 mmol) in tetrahydrofuran (10.6 mL) was treated with borane dimethyl sulfide complex (504 μL, 5.3 mmol). The resulting mixture was stirred at 70° C. for 1 hour. The reaction mixture was cooled and an additional portion of borane dimethyl sulfide complex (504 μL, 5.3 mmol) was added. The reaction mixture was heated to 80° C. for 2 hours. After cooling to room temperature, the reaction mixture was quenched by the careful dropwise addition of water. Once effervescence had ceased, the reaction mixture was poured into 20 mL of saturated aqueous $NaHCO_3$ and extracted with 4×10 mL 30% isopropyl alcohol in $CHCl_3$. The combined organics were rinsed with 10 mL of brine, dried with $MgSO_4$, filtered, and concentrated to dryness. Purification was achieved by chromatography on silica using 15-80% EtOAc/hexane to afford cis-7-bromo-4-fluoro-3-(hydroxymethyl)-2,3-dihydro-1H-inden-1-ol (210 mg, 38%). $^1$H NMR (400 MHz, $CDCl_3$): δ 7.36 (dd, 1H), 6.87 (dt, 1H), 5.13-5.06 (m, 1H), 4.00 (dd, 1H), 3.91-3.83 (m, 1H), 3.81 (dd, 1H), 3.66-3.60 (m, 1H), 2.68-2.58 (m, 1H), 2.60 (ddd, 1H), 2.00 (d, 1H).

Step E: Preparation of cis-4-fluoro-3-(hydroxymethyl)-7-(methylthio)-2,3-dihydro-1H-inden-1-ol A solution of cis-7-bromo-4-fluoro-3-(hydroxymethyl)-2,3-dihydro-1H-inden-1-ol (195 mg, 0.75 mmol) and palladium diacetate (5.0 mg, 0.022 mmol) and (R)-Josiphos (12.3 mg, 0.022 mmol) in 1,2-dimethoxyethane (2.0 mL) was sparged with nitrogen for 3 minutes. The reaction mixture was then treated with sodium thiomethoxide (78.5 mg, 1.12 mmol) under continuous nitrogen stream. The vessel was sealed and heated to 110° C. over 2 days. The reaction mixture was poured into 20 mL of water and extracted with 3×10 mL 30% isopropyl alcohol in $CHCl_3$. The combined organics were rinsed with 10 mL of brine, dried with $MgSO_4$, filtered, and concentrated to dryness. Purification was achieved by chromatography on silica using 20-60% EtOAc/hexane to afford cis-4-fluoro-3-(hydroxymethyl)-7-(methylthio)-2,3-dihydro-1H-inden-1-ol (31 mg, 18%). LCMS ESI (+) (M+Na) m/z 251.

Step F: Preparation of cis-4-fluoro-3-(hydroxymethyl)-7-(methylsulfonyl)-2,3-dihydro-1H-inden-1-ol A solution of cis-4-fluoro-3-(hydroxymethyl)-7-(methylthio)-2,3-dihydro-1H-inden-1-ol (31 mg, 0.13 mmol) in dichloromethane (2.7 mL) at 25° C. was treated with 3-chloroperbenzoic acid (82 mg, 0.33 mmol) and stirred at 25° C. overnight. The reaction mixture was poured into 10 mL of 1M aqueous NaOH solution and extracted with 3×10 mL 30% isopropyl alcohol in $CHCl_3$. The combined organics were rinsed with 10 mL of brine, dried with $MgSO_4$, filtered, and concentrated to dryness. Purification was achieved by chromatography on silica using 40-100% EtOAc/hexane to afford cis-4-fluoro-3-(hydroxymethyl)-7-(methylsulfonyl)-2,3-dihydro-1H-inden-1-ol (23 mg, 66%). LCMS ESI (+) (M+H) m/z: 261.

Step G: Preparation of 4-(3-chloro-5-fluorophenoxy)-3-methylene-7-(methylsulfonyl)-2,3-dihydro-1H-inden-1-ol (Compound 280) and cis-4-(3-chloro-5-fluorophenoxy)-3-(hydroxymethyl)-7-((trifluoromethyl)sulfonyl)-2,3-dihydro-1H-inden-1-ol (Compound 281)

A solution of cis-4-fluoro-3-(hydroxymethyl)-7-(methylsulfonyl)-2,3-dihydro-1H-inden-1-ol (23 mg, 0.089 mmol)

and 3-chloro-5-fluorophenol (13 mg, 0.089 mmol) in 1-methyl-2-pyrrolidone (0.9 mL) was treated with cesium bicarbonate (21 mg, 0.11 mmol) and stirred at 145° C. for 4 hours. The reaction mixture was poured into 30 mL of water and extracted with 3×10 mL Et$_2$O. The combined organics were rinsed with 10 mL of brine, dried with MgSO$_4$, filtered, and concentrated to dryness. Purification was achieved by chromatography on silica using 30-100% EtOAc/hexane to afford Compound 280 as a white solid (1.3 mg, 4%) Compound 281 as a thin film (3.2 mg, 9%).

Data for 4-(3-chloro-5-fluorophenoxy)-3-methylene-7-(methylsulfonyl)-2,3-dihydro-1H-inden-1-ol (Compound 280)

LCMS ESI (+) (M+H) m/z: 369, 371; $^1$H NMR (400 MHz, CDCl$_3$): δ 7.79 (d, 1H), 6.98 (ddd, 1H), 6.91 (d, 1H), 6.91-6.89 (m, 1H), 6.74 (dt, 1H), 5.97 (t, 1H), 5.68 (dt, 1H), 5.41 (t, 1H), 3.75 (d, 1H), 3.26-3.17 (m, 1H), 3.20 (s, 3H), 2.91-2.84 (m, 1H).

Data for cis-4-(3-chloro-5-fluorophenoxy)-3-(hydroxymethyl)-7-((trifluoromethyl)sulfonyl)-2,3-dihydro-1H-inden-1-ol (Compound 281)

LCMS ESI (+) (M+H) m/z: 387, 389; $^1$H NMR (400 MHz, CDCl$_3$): δ 7.85 (d, 1H), 6.95 (ddd, 1H), 6.92 (d, 1H), 6.88-6.85 (m, 1H), 6.70 (dt, 1H), 5.65 (d, 1H), 4.24-4.06 (br m, 1H), 4.08 (dd, 1H), 3.88 (dd, 1H), 3.64-3.59 (m, 1H), 3.26 (s, 3H), 2.69 (ddd, 1H), 2.66-2.48 (br m, 1H), 2.12 (d, 1H).

Examples 282 and 283

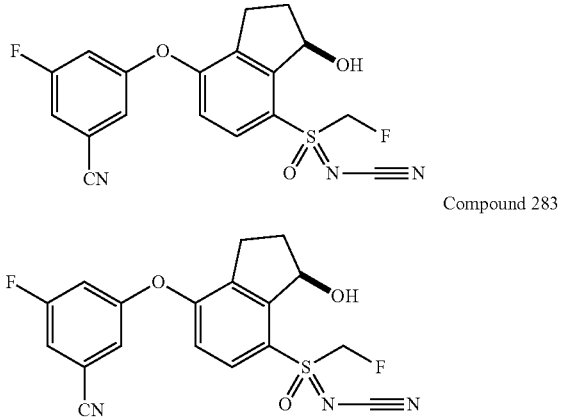

Compound 282

Compound 283

Isomer 1 of N—(((R)-7-(3-cyano-5-fluorophenoxy)-3-hydroxy-2,3-dihydro-1H-inden-4-yl)(fluoromethyl)(oxo)-λ$^6$-sulfanylidene)cyanamide (Compound 282) and isomer 2 of N—(((R)-7-(3-cyano-5-fluorophenoxy)-3-hydroxy-2,3-dihydro-1H-inden-4-yl)(fluoromethyl)(oxo)-λ$^6$-sulfanylidene)cyanamide (Compound 283)

A solution of N-((7-(3-cyano-5-fluorophenoxy)-3-oxo-2,3-dihydro-1H-inden-4-yl)(fluoromethyl)(oxo)-λ$^6$-sulfanylidene)cyanamide (85 mg, 0.22 mmol) in dichloromethane (2.2 mL) was cooled to 0° C. and sparged with nitrogen for 5 minutes. During this time formic acid (25 μL, 0.66 mmol) and triethylamine (31 μL, 0.44 mmol) were sequentially added. Once sparging was complete, RuCl(p-cymene)[(R,R)-Ts-DPEN] (4.2 mg, 3 mol %) was added under a continuous stream of nitrogen. The reaction vessel was sealed and stored at 4° C. overnight. The reaction mixture was poured into 10 mL of saturated aqueous NaHCO$_3$ and extracted with 3×15 mL CH$_2$Cl$_2$. The combined organics were rinsed with 10 mL of brine, dried with MgSO$_4$, filtered, and concentrated to dryness. Purification was achieved by chromatography on silica using 10-45% EtOAc/CH$_2$Cl$_2$ to afford two isomers.

Data for isomer 1 (Compound 282):

17.9 mg (21%); HPLC Retention time (long method)=4.75 min; LCMS ESI (+) (M+H) m/z 390; $^1$H NMR (400 MHz, CDCl$_3$): δ 7.93 (d, 1H), 7.27 (ddd, 1H), 7.20-7.18 (m, 1H), 7.08 (dt, 1H), 7.00 (d, 1H), 5.98 (dd, 1H), 5.80-5.75 (m, 1H), 5.49 (dd, 1H), 3.17 (dt, 1H), 2.94 (ddd, 1H), 2.86 (d, 1H), 2.62-2.51 (m, 1H), 2.29-2.20 (m, 1H).

Data for isomer 2 (Compound 283):

14 mg (16%); HPLC Retention time (long method)=4.69 min; LCMS ESI (+) (M+H) m/z 390; $^1$H NMR (400 MHz, CDCl$_3$): δ 7.91 (d, 1H), 7.27 (ddd, 1H), 7.19-7.16 (m, 1H), 7.06 (dt, 1H), 6.98 (d, 1H), 5.85-5.79 (m, 1H), 5.72 (dd, 1H), 5.61 (dd, 1H), 3.15 (ddd, 1H), 2.97 (d, 1H), 2.89 (ddd, 1H), 2.62-2.52 (m, 1H), 2.27-2.18 (m, 1H).

Example 284

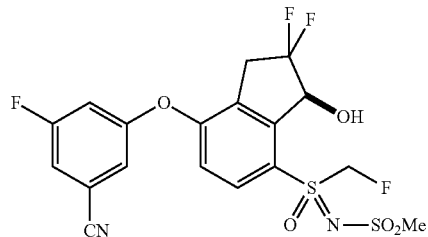 [SMILES: CS(=O)(=O)N=S(=O)(CF)c1ccc(Oc2cc(F)cc(C#N)c2)c2c1[C@H](O)C(F)(F)C2]

N—(((S)-7-(3-cyano-5-fluorophenoxy)-2,2-difluoro-3-hydroxy-2,3-dihydro-1H-inden-4-yl)(fluoromethyl)(oxo)-λ$^6$-sulfanylidene)methanesulfonamide (Compound 284)

Step A: Preparation of N-((7-(3-cyano-5-fluorophenoxy)-3-oxo-2,3-dihydro-1H-inden-4-yl)(fluoromethyl)λ$^4$-sulfanylidene)methanesulfonamide 3-fluoro-5-((7-((fluoromethyl)thio)-1-oxo-2,3-dihydro-1H-inden-4-yl)oxy)benzonitrile was prepared similarly according to Examples 272 and 59. A solution of 3-fluoro-5-((7-((fluoromethyl)thio)-1-oxo-2,3-dihydro-1H-inden-4-yl)oxy)benzonitrile (106 mg, 0.32 mmol), bis(tert-butylcarbonyloxy)iodobenzene (196 mg, 0.48 mmol), magnesium oxide (52 mg, 1.28 mmol), and methanesulfonamide (61 mg, 0.64 mmol) in dichloromethane (3.0 mL) was treated with bis[rhodium(α,α,α',α'-tetramethyl-1,3-benzenedipropionic acid)] (12 mg, 5 mol %). The vessel was sealed and stirred at 25° C. overnight. The reaction mixture was filtered through celite, concentrated, and used without further purification. LCMS ESI (+) (M+H) m/z 425.

Step B: Preparation of N-((7-(3-cyano-5-fluorophenoxy)-3-oxo-2,3-dihydro-1H-inden-4-yl)(fluoromethyl)(oxo)-λ⁶-sulfanylidene)methanesulfonamide A solution of N-((7-(3-cyano-5-fluorophenoxy)-3-oxo-2,3-dihydro-1H-inden-4-yl)(fluoromethyl)λ⁴-sulfanylidene)methanesulfonamide (170 mg, 0.4 mmol) and ruthenium (III) chloride (2.1 mg, 0.01 mmol) in a mixture of water (2.0 mL), carbon tetrachloride (2.0 mL), and acetonitrile (2.0 mL) was treated with sodium periodate (257 mg, 1.2 mmol) and stirred at 60° C. for overnight. The reaction mixture was cooled to room temperature and quenched by the addition of 10 mL of saturated $Na_2S_2O_3$ solution. The mixture was stirred for 10 minutes and then poured into 20 mL of water and extracted with 3×20 mL $CH_2Cl_2$. The combined organics were rinsed with 10 mL of brine, dried with $MgSO_4$, filtered, and concentrated to dryness. Purification was achieved by chromatography on silica using 20-65% EtOAc/hexane to afford N-((7-(3-cyano-5-fluorophenoxy)-3-oxo-2,3-dihydro-1H-inden-4-yl)(fluoromethyl)(oxo)-λ⁶-sulfanylidene)methanesulfonamide (110 mg, 62%). LCMS ESI (+) (M+H) m/z 441.

Step C: Preparation of (E,Z)—N-((7-(3-cyano-5-fluorophenoxy)-3-((3-methoxypropyl)imino)-2,3-dihydro-1H-inden-4-yl)(fluoromethyl)(oxo)-λ⁶-sulfanylidene)methanesulfonamide Performed similarly as described in step D of Example 274, except that 1.5 equivalents of 3-methoxypropyl amine were used. LCMS analysis was achieved by taking an aliquot of the reaction mixture and adding it to a solution of MeOH containing excess $NaBH_4$. LCMS indicated the formation of the amine via imine reduction. LCMS ESI (+) (M+H) m/z 514.

Step D: Preparation of N-((7-(3-cyano-5-fluorophenoxy)-2,2-difluoro-3-oxo-2,3-dihydro-1H-inden-4-yl)(fluoromethyl)(oxo)-λ⁶-sulfanylidene)methanesulfonamide Performed similarly as described in step E of Example 274. Purification was achieved by chromatography on silica using 25-55% EtOAc/hexane to afford N-((7-(3-cyano-5-fluorophenoxy)-2,2-difluoro-3-oxo-2,3-dihydro-1H-inden-4-yl)(fluoromethyl)(oxo)-λ⁶-sulfanylidene)methanesulfonamide (54 mg, 47%). LCMS ESI (+) (M+H) m/z 477.

Step E: Preparation of N—(((S)-7-(3-cyano-5-fluorophenoxy)-2,2-difluoro-3-hydroxy-2,3-dihydro-1H-inden-4-yl)(fluoromethyl)(oxo)-λ⁶-sulfanylidene)methanesulfonamide (Compound 284)

Performed similarly as described in step F of Example 274. Purification was achieved by chromatography on silica using 20-55% EtOAc/hexane to afford Compound 284 as thin film (24 mg, 44%). HPLC retention time (long method)=4.82 min; LCMS ESI (+) (M+H) m/z 479; ¹H NMR (400 MHz, CDCl₃): δ 8.04 (d, 1H), 7.30 (ddd, 1H), 7.22-7.19 (m, 1H), 7.10 (dt, 1H), 7.01 (d, 1H), 5.97 (dd, 1H), 5.70 (dd, 1H), 5.60 (dd, 1H), 3.68 (d, 1H), 3.61-3.39 (m, 2H), 3.23 (s, 3H).

Examples 285 and 286

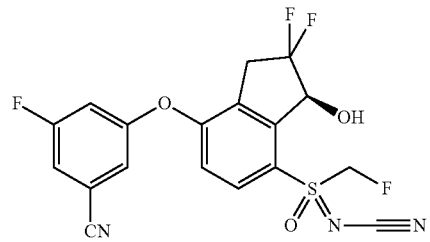

Compound 285

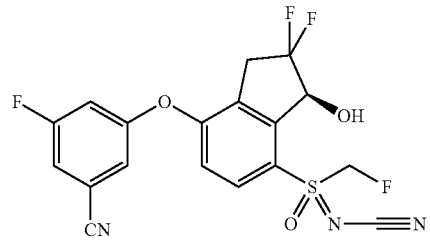

Compound 286

Isomer 1 of N—(((S)-7-(3-cyano-5-fluorophenoxy)-2,2-difluoro-3-hydroxy-2,3-dihydro-1H-inden-4-yl)(fluoromethyl)(oxo)-λ⁶-sulfanylidene)cyanamide (Compound 285) and isomer 2 of N-q(S)-7-(3-cyano-5-fluorophenoxy)-2,2-difluoro-3-hydroxy-2,3-dihydro-1H-inden-4-yl)(fluoromethyl)(oxo)-λ⁶-sulfanylidene)cyanamide (Compound 286)

Preparation of N-q(S)-7-(3-cyano-5-fluorophenoxy)-2,2-difluoro-3-hydroxy-2,3-dihydro-1H-inden-4-yl)(fluoromethyl)(oxo)-λ⁶-sulfanylidene)cyanamide Small amounts of two isomers were isolated during the purification from Example 275, Step B.

Data for isomer 1 (Compound 285):
1.1 mg (2% yield); HPLC retention time (long method)=4.91 min; LCMS ESI (+) (M+H) m/z 426; ¹H NMR (400 MHz, CDCl₃): δ 8.01 (d, 1H), 7.34 (ddd, 1H), 7.25-7.22 (m, 1H), 7.12 (dt, 1H), 7.01 (d, 1H), 5.75 (dd, 1H), 5.71-5.65 (m, 1H), 5.61 (dd, 1H), 3.64-3.45 (m, 2H), 3.14 (dd, 1H).

Data for isomer 2 (Compound 286):
1.0 mg (2% yield); HPLC retention time (long method)=4.89 min; LCMS ESI (+) (M+H) m/z 426; ¹H NMR (400 MHz, CDCl₃): δ 8.03 (d, 1H), 7.34 (ddd, 1H), 7.26-7.24 (m, 1H), 7.14 (dt, 1H), 7.02 (d, 1H), 6.02 (dd, 1H), 5.65-5.59 (m, 1H), 5.54 (dd, 1H), 3.66-3.48 (m, 2H), 3.30 (dd, 1H).

Example 287

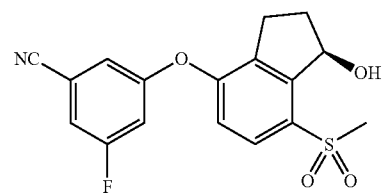 [SMILES: CS(=O)(=O)c1ccc(Oc2cc(F)cc(C#N)c2)c2c1[C@H](O)CC2]

3-fluoro-5-[(1R)-1-hydroxy-7-methylsulfonyl-indan-4-yl]oxy-benzonitrile (Compound 287)

Prepared similarly as described in Example 163 substituting 3-fluoro-5-(7-methylsulfonyl-1-oxo-indan-4-yl)oxy-benzonitrile with 3-fluoro-5-((7-(methylsulfonyl)-1-oxo-2,3-dihydro-1H-inden-4-yl)oxy)benzonitrile in step D. LCMS ESI (−) m/z 392 (M+HCO$_2$−); $^1$H NMR (400 MHz, CDCl$_3$): δ 7.83 (d, 1H), 7.19-7.16 (m, 1H), 7.09-7.07 (m, 1H), 7.01-6.96 (m, 2H), 5.71-5.67 (m, 1H), 3.64 (d, 1H), 3.21 (s, 3H), 3.12-3.02 (m, 1H), 2.84-2.75 (m, 1H), 2.52-2.42 (m, 1H), 2.27-2.18 (m, 1H).

Example 288

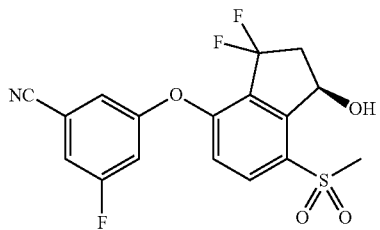 [SMILES: CS(=O)(=O)c1ccc(Oc2cc(F)cc(C#N)c2)c2c1[C@H](O)CC2(F)F]

3-[(1R)-3,3-difluoro-1-hydroxy-7-methylsulfonyl-indan-4-yl]oxy-5-fluoro-benzonitrile (Compound 288)

Step A: [(1R)-4-(3-cyano-5-fluoro-phenoxy)-7-methylsulfonyl-indan-1-yl] acetate

To a stirred solution of 3-fluoro-5-[(1R)-1-hydroxy-7-methylsulfonyl-indan-4-yl]oxy-benzonitrile (1.05 g, 3.0 mmol) in DCM (29 mL) was added 4-(dimethylamino)pyridine (0.369 g, 3.0 mmol) and triethylamine (0.84 mL, 6.1 mmol). Acetyl chloride (0.43 mL, 6.1 mmol) was added dropwise at 0° C. under nitrogen. The reaction mixture was stirred at ambient temperature for 2 hours. The reaction mixture was diluted with DCM, washed with saturated aqueous NaHCO$_3$ and brine, dried and concentrated. The residue was purified by flash chromatography on silica gel (20-50% EtOAc/hexane) to give [(1R)-4-(3-cyano-5-fluoro-phenoxy)-7-methylsulfonyl-indan-1-yl] acetate (0.72 g, 61%). LCMS ESI (−) m/z 434 (M+HCO$_2$−).

Step B: [(1R,3R)-3-bromo-4-(3-cyano-5-fluoro-phenoxy)-7-methylsulfonyl-indan-1-yl] acetate To a stirred solution of [(1R)-4-(3-cyano-5-fluoro-phenoxy)-7-methylsulfonyl-indan-1-yl] acetate (720 mg, 1.85 mmol) in carbon tetrachloride (18 mL) was added N-bromosuccinimide (362 mg, 2.0 mmol) and 2,2'-azobisisobutyronitrile (3 mg, 0.02 mmol). The reaction mixture was heated at 80° C. for 2 hours. After cooling, the reaction mixture was diluted with DCM, washed with saturated aqueous NaHCO$_3$ and brine, dried and concentrated. The residue was purified by column chromatography on silica gel (10-40% EtOAc/hexanes) to give [(1R,3R)-3-bromo-4-(3-cyano-5-fluoro-phenoxy)-7-methylsulfonyl-indan-1-yl] acetate (514 mg, 59%) and a 1:2 mixture of (1R,3R)-3-bromo-4-(3-cyano-5-fluoro-phenoxy)-7-methylsulfonyl-indan-1-yl] acetate and [(1R,3S)-3-bromo-4-(3-cyano-5-fluoro-phenoxy)-7-methylsulfonyl-indan-1-yl] acetate (360 mg, 41%). LCMS ESI (−) m/z: 512, 514 (M+HCO$_2$−).

Step C: [(1R,3S)-4-(3-cyano-5-fluoro-phenoxy)-3-hydroxy-7-methylsulfonyl-indan-1-yl] acetate To a stirred solution of [(1R,3R)-3-bromo-4-(3-cyano-5-fluoro-phenoxy)-7-methylsulfonyl-indan-1-yl] acetate (423 mg, 0.9 mmol) in 1,2-dimethoxyethane (5 mL) and water (2 mL) was added silver carbonate (374 mg, 1.35 mmol). The reaction mixture was stirred at ambient temperature overnight. The mixture was diluted with EtOAc and filtered through Celite. The filtrate was washed with water and brine, dried and concentrated. The crude was used in the next step without further purification. LCMS ESI (−) m/z 450 (M+HCO$_2$−).

Step D: [(1R)-4-(3-cyano-5-fluoro-phenoxy)-7-methylsulfonyl-3-oxo-indan-1-yl] acetate To a stirred solution of [(1R,3S)-4-(3-cyano-5-fluoro-phenoxy)-3-hydroxy-7-methylsulfonyl-indan-1-yl]acetate (366 mg, 0.9 mmol) in DCM (9 mL) was added Dess-Martin periodinane (574 mg, 1.35 mmol). The reaction mixture was stirred at ambient temperature for 1 hour. The reaction mixture was partitioned between EtOAc and saturated aqueous NaHCO$_3$. The aqueous layer was extracted with EtOAc. The combined organic layers were washed with water and brine, dried and concentrated. The crude was purified by flash chromatography on silica gel (10-50% EtOAc/hexane) to give [(1R)-4-(3-cyano-5-fluoro-phenoxy)-7-methylsulfonyl-3-oxo-indan-1-yl]acetate (320 mg, 88%). LCMS ESI (−) m/z 402 (M−H).

Step E: [(1R)-4-(3-cyano-5-fluoro-phenoxy)-3,3-difluoro-7-methylsulfonyl-indan-1-yl] acetate To a plastic tube containing [(1R)-4-(3-cyano-5-fluoro-phenoxy)-7-methylsulfonyl-3-oxo-indan-1-yl] acetate (109 mg, 0.27 mmol) and DCM (1.2 mL) was added 4-(tert-butyl)-2,6-dimethylphenyl sulfur trifluoride (115 mg, 0.46 mmol) under nitrogen. Hydrogen fluoride pyridine (70%, 0.02 mL, 0.27 mmol) was added, and the mixture was stirred at ambient temperature for 4 hours. The solvent was removed under reduced pressure. The residue was taken up in EtOAc, washed with saturated aqueous NaHCO$_3$ and brine, dried and concentrated. The residue was purified by flash chromatography on silica gel (10-50% EtOAc/hexane) to give [(1R)-4-(3-cyano-5-fluoro-phenoxy)-3,3-difluoro-7-methylsulfonyl-indan-1-yl] acetate (97 mg, 84%). LCMS ESI (+) m/z 426 (M+H).

Step F: [(1R)-3,3-difluoro-1-hydroxy-7-methylsulfonyl-indan-4-yl]oxy-5-fluoro-benzonitrile (Compound 288)

To a stirred solution of [(1R)-4-(3-cyano-5-fluoro-phenoxy)-3,3-difluoro-7-methylsulfonyl-indan-1-yl] acetate (97 mg, 0.23 mmol) in tetrahydrofuran (1.5 mL) was added 0.5 N LiOH solution (0.68 mL, 0.34 mmol) at 0° C. under nitrogen. The reaction mixture was stirred at 0° C. for 1 hour. The reaction was then partitioned between EtOAc and water. The aqueous layer was extracted with EtOAc. The combined organic layers were washed with water and brine, dried and concentrated. The residue was purified by flash chromatography on silica gel (30-70% EtOAc/hexane) to give Compound 288 (75 mg, 86%). LCMS ESI (−) m/z 428 (M+HCO$_2$⁻); $^1$H NMR (400 MHz, CDCl$_3$): δ 8.08 (d, 1H), 7.29-7.23 (m, 1H), 7.19 (brs, 1H), 7.15-7.08 (m, 1H), 7.02 (d, 1H), 5.78-5.70 (m, 1H), 3.89 (d, 1H), 3.23 (s, 3H), 3.17-3.02 (m, 1H), 2.80-2.64 (m, 1H).

Example 289

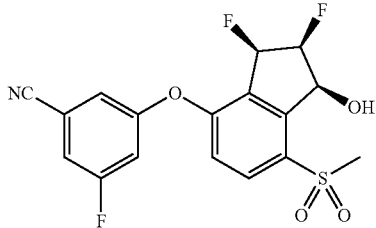 [SMILES: CS(=O)(=O)c1ccc(Oc2cc(F)cc(C#N)c2)c2c1[C@H](O)[C@H](F)[C@@H]2F]

3-[(1S,2S,3R)-2,3-difluoro-1-hydroxy-7-methylsulfonyl-indan-4-yl]oxy-5-fluoro-benzonitrile (Compound 289)

Step A: [(1S,2R)-4-(3-cyano-5-fluoro-phenoxy)-2-fluoro-7-methylsulfonyl-indan-1-yl] acetate To a stirred solution of 3-fluoro-5-[(1S,2R)-2-fluoro-1-hydroxy-7-methylsulfonyl-indan-4-yl]oxy-benzonitrile (2.00 g, 5.47 mmol) in DCM (27 mL) was added 4-(dimethylamino)pyridine (0.2 g, 1.64 mmol) and triethylamine (1.53 mL, 10.9 mmol). Acetic anhydride (1.00 mL, 10.9 mmol) was added dropwise at 0° C. under nitrogen. The reaction mixture was stirred at ambient temperature overnight. The reaction mixture was diluted with DCM, washed with saturated aqueous NaHCO$_3$ and brine, dried and concentrated. The residue was purified by flash chromatography on silica gel (20-40% EtOAc/hexane) to give [(1S,2R)-4-(3-cyano-5-fluoro-phenoxy)-2-fluoro-7-methylsulfonyl-indan-1-yl] acetate (1.95 g, 87%). LCMS ESI (+) m/z 408 (M+H).

Step B: [(1S,2S,3S)-3-bromo-4-(3-cyano-5-fluoro-phenoxy)-2-fluoro-7-methylsulfonyl-indan-1-yl] acetate and [(1S,2S,3R)-3-bromo-4-(3-cyano-5-fluoro-phenoxy)-2-fluoro-7-methylsulfonyl-indan-1-yl] acetate To a stirred solution of [(1S,2R)-4-(3-cyano-5-fluoro-phenoxy)-2-fluoro-7-methylsulfonyl-indan-1-yl] acetate (1.95 g, 4.79 mmol) in 1,2-dichloroethane (24 mL) was added N-bromosuccinimide (0.94 g, 5.27 mmol) and 2,2'-azobisisobutyronitrile (8 mg, 0.05 mmol). The reaction mixture was heated at 80° C. for 3 hours. After cooling, the reaction mixture was diluted with DCM, washed with saturated aqueous NaHCO$_3$ and brine, dried and concentrated. The residue was purified by column chromatography on silica gel (20-30% EtOAc/hexane) to give [(1S,2S,3S)-3-bromo-4-(3-cyano-5-fluoro-phenoxy)-2-fluoro-7-methylsulfonyl-indan-1-yl] acetate (1.52 g, 65%). LCMS ESI (+) m/z 486, 488 (M+H). Further elution with 30-50% EtOAc/hexane gave the more polar product [(1S,2S,3R)-3-bromo-4-(3-cyano-5-fluoro-phenoxy)-2-fluoro-7-methylsulfonyl-indan-1-yl] acetate (0.583 g, 25%). LCMS ESI (+) m/z 486, 488 (M+H).

Step C: [(1S,2R,3S)-4-(3-cyano-5-fluoro-phenoxy)-2-fluoro-3-hydroxy-7-methylsulfonyl-indan-1-yl] acetate To a combined mixture of [(1S,2S,3S)-3-bromo-4-(3-cyano-5-fluoro-phenoxy)-2-fluoro-7-methylsulfonyl-indan-1-yl] acetate and [(1S,2S,3R)-3-bromo-4-(3-cyano-5-fluoro-phenoxy)-2-fluoro-7-methylsulfonyl-indan-1-yl] acetate prepared in Step B (2.05 g, 4.22 mmol) were added 1,2-dimethoxyethane (28 mL) and water (0.050 mL) followed by silver perchlorate hydrate (1.42 g, 6.32 mmol). The reaction mixture was heated at 70° C. for 2 hours. After cooling, the reaction mixture was diluted with EtOAc and filtered through Celite. The filtrate was washed with water and brine, dried and concentrated. The residue was purified by flash chromatography on silica gel (20-50%) to give [(1S,2R,3S)-4-(3-cyano-5-fluoro-phenoxy)-2-fluoro-3-hydroxy-7-methylsulfonyl-indan-1-yl] acetate (0.416 g, 23%) as the less polar product. LCMS ESI (+) m/z 441 (M+NH$_4$⁺). Further elution with 60% EtOAc/hexane gave [(1S,2R,3R)-4-(3-cyano-5-fluoro-phenoxy)-2-fluoro-3-hydroxy-7-methylsulfonyl-indan-1-yl] acetate (0.58 g, 32%). LCMS ESI (+) m/z 441 (M+NH$_4$⁺).

Step D: [(1S,2S,3R)-4-(3-cyano-5-fluoro-phenoxy)-2,3-difluoro-7-methylsulfonyl-indan-1-yl] acetate To a stirred solution of [(1S,2R,3S)-4-(3-cyano-5-fluoro-phenoxy)-2-fluoro-3-hydroxy-7-methylsulfonyl-indan-1-yl] acetate (416 mg, 0.98 mmol) in DCM (10 mL) was added (diethylamino)sulfur trifluoride (DAST) (0.26 mL, 2.0 mmol) at −78° C. under nitrogen. The reaction mixture was allowed to warm to 0° C. and stirred for 15 minutes. The reaction was quenched by saturated aqueous NaHCO$_3$. The mixture was partitioned between EtOAc and water. The aqueous layer was extracted with EtOAc. The combined organic layers were washed with brine, dried and concentrated. The residue was purified by flash chromatography on silica gel (20-40% EtOAc/hexane) to give [(1S,2S,3R)-4-(3-cyano-5-fluoro-phenoxy)-2,3-difluoro-7-methylsulfonyl-indan-1-yl] acetate (310 mg, 74%). LCMS ESI (+) m/z 426 (M+H).

Step E: 3-[(1S,2S,3R)-2,3-difluoro-1-hydroxy-7-methylsulfonyl-indan-4-yl]oxy-5-fluoro-benzonitrile (Compound 289)

Prepared as described in Example 288 Step F substituting [(1R)-4-(3-cyano-5-fluoro-phenoxy)-3,3-difluoro-7-methylsulfonyl-indan-1-yl] acetate with [(1S,2S,3R)-4-(3-cyano-5-fluoro-phenoxy)-2,3-difluoro-7-methylsulfonyl-indan-1-yl] acetate. LCMS ESI (+) m/z 384 (M+H); $^1$H NMR (400 MHz, CDCl$_3$): δ 8.13 (d, 1H), 7.31-7.25 (m, 1H), 7.23-7.19 (m, 1H), 7.14-7.09 (m, 1H), 7.04 (d, 1H), 6.09-5.91 (m, 1H), 5.87-5.80 (m, 1H), 5.25-5.05 (m, 1H), 3.32 (s, 3H), 2.95 (d, 1H).

Example 290

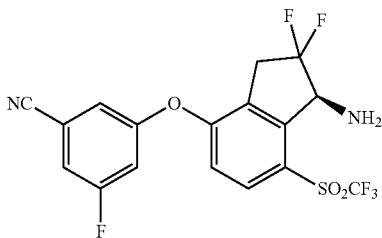

3-[(1S)-1-amino-2,2-difluoro-7-(trifluoromethylsulfonyl)indan-4-yl]oxy-5-fluoro-benzonitrile (Compound 290)

Prepared as described in Example 165 using 3-[2,2-difluoro-1-oxo-7-(trifluoromethylsulfonyl)indan-4-yl]oxy-5-fluoro-benzonitrile in place of 3-(2,2-difluoro-7-methylsulfonyl-1-oxo-indan-4-yl)oxy-5-fluoro-benzonitrile in Step A. LCMS ESI (+) m/z 437 (M+H); $^1$H NMR (400 MHz, CDCl$_3$): δ 7.92 (d, 1H), 7.34-7.30 (m, 1H), 7.24-7.22 (m, 1H), 7.14-7.10 (m, 1H), 6.94 (d, 1H), 4.85 (d, 1H), 3.65-3.41 (m, 2H).

Example 291

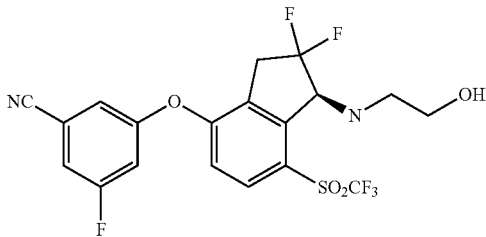

3-[(1S)-2,2-difluoro-1-(2-hydroxyethylamino)-7-(trifluoromethylsulfonyl)indan-4-yl]oxy-5-fluoro-benzonitrile (Compound 291)

Step A: 3-[(1S)-1-[2-[tert-butyl(dimethyl)silyl]oxyethylamino]-2,2-difluoro-7-(trifluoromethylsulfonyl)indan-4-yl]oxy-5-fluoro-benzonitrile To a stirred solution of 3-[(1S)-1-amino-2,2-difluoro-7-(trifluoromethylsulfonyl)indan-4-yl]oxy-5-fluoro-benzonitrile (18 mg, 0.04 mmol) and 2[tert-butyl(dimethyl)silyl]oxyacetaldehyde (36 mg, 0.21 mmol) in 1,2-dichloroethane (0.4 mL) was added NaB(OAc)$_3$H (306 mg, 1.44 mmol). The reaction mixture was stirred at ambient temperature for 2 hours. The reaction was partitioned between EtOAc and water. The aqueous layer was extracted with EtOAc. The combined organic layers were washed with brine, dried and concentrated. The residue was purified by flash chromatography on silica gel (5-20% EtOAc/hexane) to give 3-[(1S)-1-[2-[tert-butyl(dimethyl)silyl]oxyethylamino]-2,2-difluoro-7-(trifluoromethylsulfonyl)indan-4-yl]oxy-5-fluoro-benzonitrile (7 mg, 29%). LCMS ESI (+) m/z 595 (M+H).

Step B: 3-[(1S)-2,2-difluoro-1-(2-hydroxyethylamino)-7-(trifluoromethylsulfonyl)indan-4-yl]oxy-5-fluoro-benzonitrile (Compound 291)

A mixture of 3-[(1S)-1-[2-[tert-butyl(dimethyl)silyl]oxyethylamino]-2,2-difluoro-7-(trifluoromethylsulfonyl)indan-4-yl]oxy-5-fluoro-benzonitrile (7 mg, 0.01 mmol) in DCM (0.2 mL) was treated with 5 N HCl in isopropanol (0.07 mL, 0.35 mmol) for 1 hour. The solvent was evaporated. The residue was taken up in EtOAc, washed with saturated aqueous NaHCO$_3$ and brine, dried and concentrated. The residue was purified by flash chromatography (20-50% EtOAc/hexane) to give Compound 291 (5 mg, 88%). LCMS ESI (+) m/z 481 (M+H); $^1$H NMR (400 MHz, CDCl$_3$): δ 7.95 (d, 1H), 7.35-7.31 (m, 1H), 7.24-7.22 (m, 1H), 7.14-7.10 (m, 1H), 6.95 (d, 1H), 4.59 (d, 1H), 3.77-3.52 (m, 2H), 3.42 (t, 2H), 3.06 (t, 2H).

Example 292

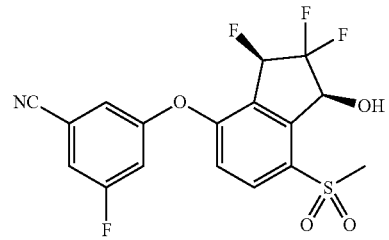 [SMILES: CS(=O)(=O)c1ccc(Oc2cc(F)cc(C#N)c2)c2c1[C@H](O)C(F)(F)[C@@H]2F]

3-fluoro-5-[(1S,3R)-2,2,3-trifluoro-1-hydroxy-7-methylsulfonyl-indan-4-yl]oxy-benzonitrile (Compound 292)

Step A: [(1S,3S)-4-(3-cyano-5-fluoro-phenoxy)-2,2-difluoro-3-hydroxy-7-methylsulfonyl-indan-1-yl] acetate and [(1S,3R)-4-(3-cyano-5-fluoro-phenoxy)-2,2-difluoro-3-hydroxy-7-methylsulfonyl-indan-1-yl] acetate To a stirred solution of [(1S)-4-(3-cyano-5-fluoro-phenoxy)-2,2-difluoro-7-methylsulfonyl-indan-1-yl] acetate (1.0 g, 2.35 mmol) in DCE (24 mL) were added N-bromosuccinimide (0.46 g, 2.59 mmol) and 2,2'-azobisisobutyronitrile (4 mg, 0.02 mmol). The reaction mixture was heated at 80° C. overnight. After cooling, the reaction mixture was diluted with DCM, washed with saturated aqueous NaHCO$_3$ and brine, dried and concentrated. The crude product was dissolved in 1,2-dimethoxyethane (11 mL) and water (0.11 mL). Silver perchlorate hydrate (0.35 g, 1.55 mmol) was added. The reaction mixture was heated at 70° C. overnight. After cooling, the reaction mixture was diluted with EtOAc and filtered through Celite. The filtrate was washed with water and brine, dried and concentrated. The residue was purified by flash chromatography on silica gel (20-60% EtOAc/hexane) to give [(1S,3S)-4-(3-cyano-5-fluoro-phenoxy)-2,2-difluoro-3-hydroxy-7-methylsulfonyl-indan-1-yl] acetate (39 mg, 9% yield) as the less polar product. LCMS ESI (+) m/z 459 (M+NH$_4^+$). Further elution gave [(1S,3R)-4-(3-cyano-5-fluoro-phenoxy)-2,2-difluoro-3-hydroxy-7-methylsulfonyl-indan-1-yl] acetate (80 mg, 18%). LCMS ESI (+) m/z 459 (M+NH$_4^+$).

Step B: [(1S,3R)-4-(3-cyano-5-fluoro-phenoxy)-2,2,3-trifluoro-7-methylsulfonyl-indan-1-yl] acetate Prepared as described in Example 289 Step D substituting [(1S,2R,3S)-4-(3-cyano-5-fluoro-phenoxy)-2-fluoro-3-hydroxy-7-methylsulfonyl-indan-1-yl] acetate with [(1S,3S)-4-(3-cyano-5-fluoro-phenoxy)-2,2-difluoro-3-hydroxy-7-methylsulfonyl-indan-1-yl] acetate. LCMS ESI (+) m/z 444 (M+H).

Step C: 3-fluoro-5-[(1S,3R)-2,2,3-trifluoro-1-hydroxy-7-methylsulfonyl-indan-4-yl]oxy-benzonitrile Prepared as described in Example 288 Step F substituting [(1R)-4-(3-cyano-5-fluoro-phenoxy)-3,3-difluoro-7-methylsulfonyl-indan-1-yl] acetate with [(1S,3R)-4-(3-cyano-5-fluoro-phenoxy)-2,2,3-trifluoro-7-methylsulfonyl-indan-1-yl] acetate. LCMS ESI (+) m/z 419 (M+NH$_4^+$); $^1$H NMR (400 MHz, CDCl$_3$): δ 8.14-8.11 (m, 1H), 7.33-7.29 (m, 1H), 7.25-7.23 (m, 1H), 7.16-7.12 (m, 1H), 7.05 (d, 1H), 5.91-5.75 (m, 1H), 5.71-5.65 (m, 1H), 3.39 (d, 1H), 3.25 (s, 3H).

Alternative synthesis 1 of 3-fluoro-5-[(1S,3R)-2,2,3-trifluoro-1-hydroxy-7-methylsulfonyl-indan-4-yl]oxy-benzonitrile (Compound 292)

Step A: 3-fluoro-5-(2'-fluoro-7'-methylsulfonyl-3'-oxo-spiro[1,3-dioxolane-2,1'-indane]-4'-yl)oxy-benzonitrile To a stirred solution of 3-fluoro-5-(7'-methylsulfonyl-3'-oxo-spiro[1,3-dioxolane-2,1'-indane]-4'-yl)oxy-benzonitrile (1.0 g, 2.48 mmol) and triethylamine (2.07 mL, 14.9 mmol) in DCM (24.8 mL) was added dropwise [tert-butyl(dimethyl)silyl] trifluoromethanesulfonate (0.85 mL, 3.7 mmol) at 0° C. under nitrogen. The reaction was allowed to warm to ambient temperature and stir overnight. The reaction was diluted with EtOAc, washed with saturated aqueous NaHCO$_3$ solution and brine, dried and concentrated. The crude was dissolved in acetonitrile (25 mL). Selectfluor® (1.14 g, 3.2 mmol) was added to the reaction mixture. The reaction was stirred at ambient temperature for 1 hour. The solvent was evaporated under reduced pressure. The residue was taken up in DCM, washed with water and brine, dried over Na$_2$SO$_4$, filtered, and concentrated to dryness. The residue was purified by flash chromatography on silica gel (20-50% EtOAc/hexane) to give 3-fluoro-5-(2'-fluoro-7'-methylsulfonyl-3'-oxo-spiro[1,3-dioxolane-2,1'-indane]-4'-yl)oxy-benzonitrile (0.81 g, 78%). LCMS ESI (+) m/z 422 (M+H).

Step B: 3-(2',2'-difluoro-7'-methylsulfonyl-3'-oxo-spiro[1,3-dioxolane-2,1'-indane]-4'-yl)oxy-5-fluoro-benzonitrile To a stirred solution of 3-fluoro-5-(2'-fluoro-7'-methylsulfonyl-3'-oxo-spiro[1,3-dioxolane-2,1'-indane]-4'-yl)oxy-benzonitrile (455 mg, 1.08 mmol) and triethylamine (0.90 mL, 6.5 mmol) in DCM (11 mL) was added dropwise [tert-butyl(dimethyl)silyl] trifluoromethanesulfonate (0.37 mL, 1.6 mmol) at 0° C. under nitrogen. The reaction was allowed to warm to ambient temperature and stir overnight. The reaction was diluted with EtOAc, washed with saturated aqueous NaHCO$_3$ solution and brine, dried and concentrated. The crude was dissolved in acetonitrile (11 mL). Selectfluor® (612 mg, 1.73 mmol) was added and the reaction mixture was stirred at ambient temperature for 2 hours. The solvent was evaporated under reduced pressure. The residue was taken up in DCM, washed with water and brine, dried over Na$_2$SO$_4$, filtered, and concentrated. The residue was purified by flash chromatography on silica gel (20-50% EtOAc/hexane) to give 3-(2',2'-difluoro-7'-methylsulfonyl-3'-oxo-spiro[1,3-dioxolane-2,1'-indane]-4'-yl)oxy-5-fluoro-benzonitrile (337 mg, 71%). LCMS ESI (+) m/z 440 (M+H).

Step C: 3-[(3'S)-2',2'-difluoro-3'-hydroxy-7'-methylsulfonyl-spiro[1,3-dioxolane-2,1'-indane]-4'-yl]oxy-5-fluoro-benzonitrile Formic acid (0.087 mL, 2.3 mmol) was added slowly to a solution of triethylamine (0.21 mL, 1.5 mmol) in DCM (8 mL) at 0° C. 3-(2',2'-difluoro-7'-methylsulfonyl-3'-oxo-spiro[1,3-dioxolane-2,1'-indane]-4'-yl)oxy-5-fluoro-benzonitrile (337 mg, 0.77 mmol) was then added followed by the addition of RuCl(p-cymene)[(R,R)-Ts-DPEN] (5.5 mg, 0.01 mmol) under nitrogen. The flask was then placed in a 4° C. refrigerator overnight. The reaction mixture was diluted with DCM, washed with saturated aqueous NaHCO$_3$ and brine, dried and concentrated. The residue was purified by flash chromatography on silica gel (20-60% EtOAc/hexanes) to give 3-[(3'S)-2',2'-difluoro-3'-hydroxy-7'-methylsulfonyl-spiro[1,3-dioxolane-2,1'-indane]-4'-yl]oxy-5-fluoro-benzonitrile (335 mg, 99%). LCMS ESI (+) m/z 424 (M+H).

Step D: 3-fluoro-5-[(3'R)-2',2',3'-trifluoro-7'-methylsulfonyl-spiro[1,3-dioxolane-2,1'-indane]-4'-yl]oxy-benzonitrile To a stirred solution of 3-[(3'S)-2',2'-difluoro-3'-hydroxy-7'-methylsulfonyl-spiro[1,3-dioxolane-2,1'-indane]-4'-yl]oxy-5-fluoro-benzonitrile (285 mg, 0.650 mmol) in DCM (6 mL) was added (diethylamino)sulfur trifluoride (DAST) (0.17 mL, 1.3 mmol) at −78° C. under nitrogen. The reaction mixture was allowed to warm to 0° C. and stirred for 30 minutes. The reaction was quenched by the addition of saturated aqueous NaHCO$_3$. The mixture was partitioned between EtOAc and water. The aqueous layer was extracted with EtOAc. The combined organic layers were washed with brine, dried and concentrated. The residue was purified by flash chromatography on silica gel (20-60% EtOAc/hexane) to give 3-fluoro-5-[(3'R)-2',2',3'-trifluoro-7'-methylsulfonyl-spiro[1,3-dioxolane-2,1'-indane]-4'-yl]oxy-benzonitrile (248 mg, 87%). LCMS ESI (+) m/z 444 (M+H).

Step E: 3-fluoro-5-[(3R)-2,2,3-trifluoro-7-methylsulfonyl-1-oxo-indan-4-yl]oxy-benzonitrile To a stirred solution of 3-fluoro-5-[(3'R)-2',2',3'-trifluoro-7'-methylsulfonyl-spiro[1,3-dioxolane-2,1'-indane]-4'-yl]oxy-benzonitrile (286 mg, 0.65 mmol) in DCM (6 mL) was added 70% perchloric acid (2 mL). The reaction mixture was stirred at ambient temperature for 3 days. The reaction was diluted with EtOAc, washed with water, saturated aqueous NaHCO$_3$ and brine, dried and concentrated. The residue was purified by flash chromatography on silica gel (30-60% EtOAc/hexanes) to give 3-fluoro-5-[(3R)-2,2,3-trifluoro-7-methylsulfonyl-1-oxo-indan-4-yl]oxy-benzonitrile (145 mg, 56%). LCMS ESI (+) m/z 400 (M+H).

Step F: 3-fluoro-5-[(1S,3R)-2,2,3-trifluoro-1-hydroxy-7-methylsulfonyl-indan-4-yl]oxy-benzonitrile (Compound 292)

To a stirred solution of 3-fluoro-5-[(3R)-2,2,3-trifluoro-7-methylsulfonyl-1-oxo-indan-4-yl]oxy-benzonitrile (144 mg, 0.36 mmol) in DCM (3.6 mL) was added formic acid (0.041 mL, 1.1 mmol) followed by triethylamine (0.1 mL, 0.72 mmol). The reaction mixture was purged with nitrogen. RuCl(p-cymene)[(R,R)-Ts-DPEN] (1.1 mg) was added under nitrogen. The reaction vial was then placed in a 4° C. refrigerator overnight. The solvents were evaporated. The residue was purified by flash chromatography on silica gel (20-60% EtOAc/hexane) to give Compound 292 (92 mg, 64%).

Alternative synthesis 2 of 3-fluoro-5-[(1S,3R)-2,2,3-trifluoro-1-hydroxy-7-methylsulfonyl-indan-4-yl]oxy-benzonitrile (Compound 292)

Step A: 3-fluoro-5-(7-methylsulfonyl-1,3-dioxo-indan-4-yl)oxy-benzonitrile

To a stirred solution of 3-fluoro-5-(7'-methylsulfonyl-3'-oxo-spiro[1,3-dioxolane-2,1'-indane]-4'-yl)oxy-benzonitrile (500 mg, 1.24 mmol) in tetrahydrofuran (6 mL) was added 4N HCl (3.1 mL, 12 mmol). The reaction was heated at reflux for 2 hours. After cooling, the reaction mixture was partitioned between EtOAc and water. The aqueous layer was extracted with EtOAc. The combined organic layers were washed with water and brine, dried and concentrated. The crude was used in the next step without further purification. LCMS ESI (+) m/z 360 (M+H).

Step B: 3-(2,2-difluoro-7-methylsulfonyl-1,3-dioxo-indan-4-yl)oxy-5-fluoro-benzonitrile To a stirred solution of 3-fluoro-5-(7-methylsulfonyl-1,3-dioxo-indan-4-yl)oxy-benzonitrile (crude product from Step A, 445 mg, 1.24 mmol) in acetonitrile (12 mL) at 25° C. was added anhydrous sodium carbonate (289 mg, 2.72 mmol) under nitrogen. Selectfluor® (965 mg, 2.72 mmol) was added and the reaction mixture was stirred at 25° C. for 2 hours. The reaction mixture was partitioned between EtOAc and water. The aqueous layer was extracted with EtOAc. The combined organic layers were washed with water and brine, dried and concentrated. The residue was purified by flash chromatography on silica gel (20-60% EtOAc/hexane) to give 3-(2,2-difluoro-7-methylsulfonyl-1,3-dioxo-indan-4-yl)oxy-5-fluoro-benzonitrile (230 mg, 47%). LCMS ESI (+) m/z 396 (M+H).

Step C: 3-[(1S,3S)-2,2-difluoro-1,3-dihydroxy-7-methylsulfonyl-indan-4-yl]oxy-5-fluoro-benzonitrile Formic acid (0.049 mL, 1.3 mmol) was added slowly to a solution of triethylamine (0.12 mL, 0.86 mmol) in DCM (4 mL) at 0° C. 3-(2,2-Difluoro-7-methylsulfonyl-1,3-dioxo-indan-4-yl)oxy-5-fluoro-benzonitrile (170 mg, 0.43 mmol) was then added followed by the addition of RuCl(p-cymene)[(R,R)-Ts-DPEN] (5.5 mg, 0.01 mmol) under nitrogen. The flask was then placed in a 4° C. refrigerator overnight. The reaction mixture was diluted with DCM, washed with saturated aqueous NaHCO₃ and brine, dried and concentrated. The residue was purified by flash chromatography on silica gel (20-60% EtOAc/hexane) to give 3-[(1S,3S)-2,2-difluoro-1,3-dihydroxy-7-methylsulfonyl-indan-4-yl]oxy-5-fluoro-benzonitrile (70 mg, 41%) and 3-[(1S,3R)-2,2-difluoro-1,3-dihydroxy-7-methylsulfonyl-indan-4-yl]oxy-5-fluoro-benzonitrile (65 mg, 38%). LCMS ESI (+) m/z 400 (M+H).

Step D: 3-fluoro-5-[(1S,3R)-2,2,3-trifluoro-1-hydroxy-7-methylsulfonyl-indan-4-yl]oxy-benzonitrile (Compound 292)

To a stirred solution of 3-[(1S,3S)-2,2-difluoro-1,3-dihydroxy-7-methylsulfonyl-indan-4-yl]oxy-5-fluoro-benzonitrile (70 mg, 0.18 mmol) in DCM (2 mL) was added (diethylamino)sulfur trifluoride (DAST) (0.058 mL, 0.44 mmol) at −78° C. under nitrogen. The reaction mixture was allowed to warm to −20° C. and stirred for 1 hour. The reaction was quenched by the addition of saturated aqueous NaHCO₃. The mixture was partitioned between EtOAc and water. The aqueous layer was extracted with EtOAc. The combined organic layers were washed with brine, dried and concentrated. The residue was purified by flash chromatography on silica gel (20-60% EtOAc/hexane) to give Compound 292 (31 mg, 44%).

Example 293

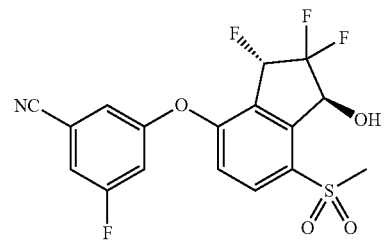 [SMILES: CS(=O)(=O)c1ccc(Oc2cc(F)cc(C#N)c2)c2c1[C@H](O)C(F)(F)[C@H]2F]

3-fluoro-5-[(1S,3S)-2,2,3-trifluoro-1-hydroxy-7-methylsulfonyl-indan-4-yl]oxy-benzonitrile (Compound 293)

Prepared similarly as described in Example 292 Step B to C substituting [(1S,3S)-4-(3-cyano-5-fluoro-phenoxy)-2,2-difluoro-3-hydroxy-7-methylsulfonyl-indan-1-yl] acetate with [(1S,3R)-4-(3-cyano-5-fluoro-phenoxy)-2,2-difluoro-3-hydroxy-7-methylsulfonyl-indan-1-yl] acetate in Step B. LCMS ESI (+) m/z 419 (M+NH₄⁺); ¹H NMR (400 MHz, CDCl₃): δ 8.10-8.07 (m, 1H), 7.32-7.28 (m, 1H), 7.23-7.20 (m, 1H), 7.15-7.10 (m, 1H), 7.02 (d, 1H), 6.07-5.90 (m, 1H), 5.87-5.80 (m, 1H), 3.95 (d, 1H), 3.26 (s, 3H).

Example 294

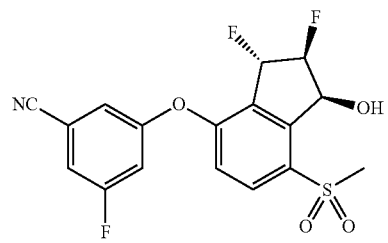 [SMILES: CS(=O)(=O)c1ccc(Oc2cc(F)cc(C#N)c2)c2c1[C@H](O)[C@H](F)[C@H]2F]

3-[(1S,2S,3S)-2,3-difluoro-1-hydroxy-7-methylsulfonyl-indan-4-yl]oxy-5-fluoro-benzonitrile (Compound 294)

Prepared similarly as described in Example 289 substituting [(1S,2R,3S)-4-(3-cyano-5-fluoro-phenoxy)-2-fluoro- 3-hydroxy-7-methylsulfonyl-indan-1-yl] acetate with [(1S,2R,3R)-4-(3-cyano-5-fluoro-phenoxy)-2-fluoro-3-hydroxy-7-methylsulfonyl-indan-1-yl] acetate in Step D. LCMS ESI (+) m/z 384 (M+H); $^1$H NMR (400 MHz, CDCl$_3$): δ 8.09-8.06 (m, 1H), 7.27-7.24 (m, 1H), 7.19-7.17 (m, 1H), 7.10-7.07 (m, 1H), 7.04 (d, 1H), 6.30-6.12 (m, 1H), 5.96-5.89 (m, 1H), 5.46-5.27 (m, 1H), 3.53-3.51 (m, 1H), 3.27 (s, 3H).

Example 295

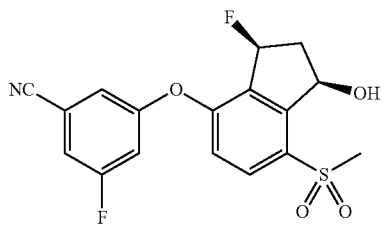 [SMILES: CS(=O)(=O)c1ccc(Oc2cc(F)cc(C#N)c2)c2c1[C@H](O)C[C@@H]2F]

3-fluoro-5-[(1R,3S)-3-fluoro-1-hydroxy-7-methyl-sulfonyl-indan-4-yl]oxy-benzonitrile (Compound 295)

Step A: [(1R)-4-(3-cyano-5-fluoro-phenoxy)-3-hydroxy-7-methylsulfonyl-indan-1-yl] acetate Prepared as described in Example 288 Step C substituting [(1R,3R)-3-bromo-4-(3-cyano-5-fluoro-phenoxy)-7-methylsulfonyl-indan-1-yl] acetate with [(1R)-3-bromo-4-(3-cyano-5-fluoro-phenoxy)-7-methylsulfonyl-indan-1-yl] acetate. LCMS ESI (−) m/z 450 (M+HCO$_2$).

Step B: [(1R,3S)-4-(3-cyano-5-fluoro-phenoxy)-3-fluoro-7-methylsulfonyl-indan-1-yl] acetate To a stirred solution of [(1R)-4-(3-cyano-5-fluoro-phenoxy)-3-hydroxy-7-methylsulfonyl-indan-1-yl] acetate (306 mg, 0.75 mmol) in DCM (8 mL) was added (diethylamino)sulfur trifluoride (DAST) (0.2 mL, 1.5 mmol) at 0° C. under nitrogen. The reaction mixture was stirred at 0° C. for 30 minutes. The reaction was quenched by the addition of saturated aqueous NaHCO$_3$. The mixture was partitioned between EtOAc and water. The aqueous layer was extracted with EtOAc. The combined organic layers were washed with brine, dried and concentrated. The residue was purified by column chromatography on silica gel (20-40% EtOAc/hexane) to give [(1R,3S)-4-(3-cyano-5-fluoro-phenoxy)-3-fluoro-7-methylsulfonyl-indan-1-yl] acetate (144 mg, 47%) as the less polar product and [(1R,3R)-4-(3-cyano-5-fluoro-phenoxy)-3-fluoro-7-methylsulfonyl-indan-1-yl] acetate (82 mg, 27%) as the more polar product.

Step C: 3-fluoro-5-[(1R,3S)-3-fluoro-1-hydroxy-7-methylsulfonyl-indan-4-yl]oxy-benzonitrile (Compound 295)

Prepared as described in Example 288 Step F substituting [(1R)-4-(3-cyano-5-fluoro-phenoxy)-3,3-difluoro-7-methylsulfonyl-indan-1-yl] acetate with [(1R,3S)-4-(3-cyano-5-fluoro-phenoxy)-3-fluoro-7-methylsulfonyl-indan-1-yl] acetate. LCMS ESI (+) m/z 383 (M+NH$_4$$^+$); $^1$H NMR (400 MHz, CDCl$_3$): δ 8.04-8.01 (m, 1H), 7.25-7.22 (m, 1H), 7.18-7.16 (m, 1H), 7.11-7.06 (m, 1H), 7.00 (d, 1H), 6.09-5.79 (m, 1H), 5.69-5.61 (m, 1H), 3.54 (d, 1H), 3.23 (s, 3H), 2.94-2.80 (m, 1H), 2.52-2.41 (m, 1H).

Example 296

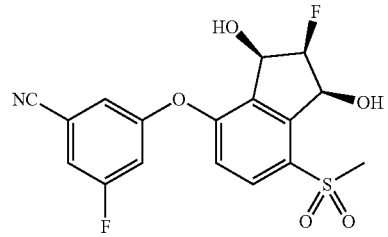 [SMILES: CS(=O)(=O)c1ccc(Oc2cc(F)cc(C#N)c2)c2c1[C@H](O)[C@H](F)[C@@H]2O]

3-fluoro-5-[(1S,2R,3R)-2-fluoro-1,3-dihydroxy-7-methylsulfonyl-indan-4-yl]oxy-benzonitrile (Compound 296)

Prepared similarly as described in Example 288 Step F substituting [(1R)-4-(3-cyano-5-fluoro-phenoxy)-3,3-difluoro-7-methylsulfonyl-indan-1-yl] acetate with [(1S,2R,3R)-4-(3-cyano-5-fluoro-phenoxy)-2-fluoro-3-hydroxy-7-methylsulfonyl-indan-1-yl] acetate. LCMS ESI (+) m/z 399 (M+NH$_4$$^+$); $^1$H NMR (400 MHz, CDCl$_3$): δ 8.05 (d, 1H), 7.26-7.22 (m, 1H), 7.19-7.17 (m, 1H), 7.12-7.07 (m, 1H), 7.05 (d, 1H), 5.76-5.70 (m, 1H), 5.30-5.24 (m, 1H), 5.18-5.01 (m, 1H), 3.29 (s, 3H).

Example 297

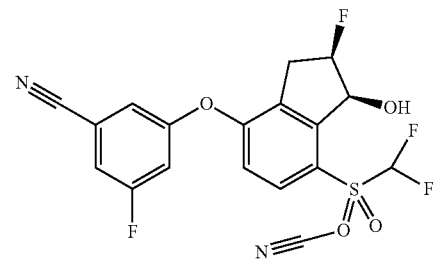

Isomer 1 of N-(((2R,3S)-7-(3-cyano-5-fluorophenoxy)-2-fluoro-3-hydroxy-2,3-dihydro-1H-inden-4-yl)(difluoromethyl)(oxo)-λ$^6$-sulfanylidene)cyanamide (Compound 297)

Step A: Preparation of 3-fluoro-5-((7-mercapto-1-oxo-2,3-dihydro-1H-inden-4-yl)oxy)benzonitrile A mixture of 3-fluoro-5-((7-(methylsulfonyl)-1-oxo-2,3-dihydro-1H-inden-4-yl)oxy)benzonitrile and 3-fluoro-5-((7-(methylsulfinyl)-1-oxo-2,3-dihydro-1H-inden-4-yl)oxy)benzonitrile (ca. 1:2 ratio) was dissolved in methylene chloride (100 mL) under nitrogen. Trifluoroacetic anhydride (21.1 mL, 152 mmol) was added dropwise at ambient temperature. After about two hours, the reaction mixture was concentrated in vacuo. The residue was dissolved in MeOH (25 mL). Triethylamine (25 mL, 179 mmol) was added slowly under nitrogen. The reaction mixture was stirred at ambient temperature for 30 minutes then concentrated in vacuo. The residue was partitioned between 1 N NaOH and MTBE and the aqueous layer was separated. The aqueous was cooled to 0° C. and the pH was adjusted to 3-4 using 10% KHSO$_4$. The aqueous layer was extracted twice with ethyl acetate. The combined organic layers were washed with saturated NaCl, dried over Na$_2$SO$_4$ and concentrated in vacuo. The crude product was used in the subsequent alkylation without delay. LCMS ESI (+) m/z 300 (M+H).

Step B: Preparation of 3-((7-((difluoromethyl)thio)-1-oxo-2,3-dihydro-1H-inden-4-yl)oxy)-5-fluorobenzonitrile 3-Fluoro-5-(1-oxo-7-sulfanyl-indan-4-yl)oxy-benzonitrile (4.54 g, 15.2 mmol) was dissolved in acetonitrile (54 mL) and treated with a solution of KOH (17.0 g, 303 mmol) in water (54 mL). The mixture was purged with argon, cooled to −20° C. then treated with bromodifluoromethyl-diethylphosphonate (5.4 mL, 30.4 mmol). The resulting mixture was allowed to warm to ambient temperature and stirred for 2 hours. The mixture was concentrated gently to remove MeCN, then MTBE and water were added (ca. 50-70 mL each). The layers were separated. The aqueous layer was cooled in an ice bath and adjusted to pH 3-4 with 10% KHSO$_4$. The aqueous was treated with MTBE/ethyl acetate (1:1, ca. 200 mL) and separated. The aqueous was extracted with ethyl acetate then the combined organics were washed with water, saturated NaHCO$_3$, water, saturated NaCl, saturated NaHCO$_3$, saturated NaCl, dried over Na$_2$SO$_4$, and then concentrated in vacuo. The residue was chromatographed on SiO$_2$ (Biotage SNAP 10 g) and eluted with a gradient of ethyl acetate/hexane to give the desired product as a pinkish solid (ca. 650 mg). The mixed fractions were re-chromatographed on SiO$_2$ (Biotage SNAP 50 g) with chloroform to give the desired product (0.87 g, combined yield of 29%). LCMS ESI (+) m/z 350 (M+H).

Step C: Preparation of N-((7-(3-cyano-5-fluorophenoxy)-3-oxo-2,3-dihydro-1H-inden-4-yl)(difluoromethyl)-λ$^4$-sulfanylidene)cyanamide A solution of 3-((7-((difluoromethyl)thio)-1-oxo-2,3-dihydro-1H-inden-4-yl)oxy)-5-fluorobenzonitrile (573 mg, 1.64 mmol), bis(tert-butylcarbonyloxy)iodobenzene (1330 mg, 3.28 mmol), magnesium oxide (264 mg, 6.56 mmol), and cyanamide (138 mg, 3.28 mmol) in dichloromethane (22 mL) was treated with bis[rhodium(α,α,α',α'-tetramethyl-1,3-benzenepropionic acid)] (100 mg, 0.13 mmol). The reaction was stirred at ambient temperature for 90 minutes. The reaction was filtered through celite, washed with dichloromethane and concentrated in vacuo. The residue was used without further purification. LCMS ESI (+) m/z 390 (M+H).

Step D: Preparation of N-((7-(3-cyano-5-fluorophenoxy)-3-oxo-2,3-dihydro-1H-inden-4-yl)(difluoromethyl)(oxo)-λ$^6$-sulfanylidene)cyanamide

[[7-(3-cyano-5-fluoro-phenoxy)-3-oxo-indan-4-yl]-(difluoromethyl)λ$^4$-sulfanylidene]cyanamide (638 mg, 1.64 mmol) was dissolved in a mixture of carbon tetrachloride (4 mL), acetonitrile (4 mL) and water (8 mL). This solution was treated with ruthenium (III) trichloride (6.8 mg, 0.03 mmol) followed by sodium periodate (1.05 g, 4.92 mmol). The mixture was stirred at ambient temperature for 14 hours. Additional ruthenium (III) trichloride (6.8 mg, 0.03 mmol) and sodium periodate (1.05 g, 4.92 mmol) were added and stirring was continued for an additional 24 hours. The heterogeneous mixture was diluted with methylene chloride and one-half saturated sodium thiosulfate solution and stirred for 1 hour then filtered through a pad of celite. The aqueous layer was washed with methylene chloride. The combined organic layers were washed with dilute sodium thiosulfate, water, then dried over Na$_2$SO$_4$ and concentrated in vacuo. The crude material was chromatographed on SiO$_2$ (Biotage SNAP 25 g) with a gradient of ethyl acetate/hexane to afford the desired product (304 mg). LCMS ESI (+) m/z 406 (M+H).

Step E: Preparation of N—(((R)-7-(3-cyano-5-fluorophenoxy)-2-fluoro-3-oxo-2,3-dihydro-1H-inden-4-yl)(difluoromethyl)(oxo)-λ$^6$-sulfanylidene)cyanamide A solution of cyano-[[7-(3-cyano-5-fluoro-phenoxy)-3-oxo-indan-4-yl]-(difluoromethyl)-oxo-λ$^6$-sulfanylidene] ammonium (136 mg, 0.33 mmol) in acetonitrile (3.8 mL) was treated with [1-fluoro-4-hydroxy-1,4-diazoniabicyclo[2,2,2]octane bis(tetrafluoroborate) on aluminum oxide (Accufluor® 50 wt %) and stirred at reflux for 9 hours then allowed to cool with the bath and stirred overnight. The solvent was removed with a stream of nitrogen gas. The crude material was chromatographed on SiO$_2$ (Biotage SNAP 10 g) with a gradient of ethyl acetate/hexane to afford the desired product (78 mg). LCMS ESI (+) m/z 424 (M+H).

Step F: Preparation of N-(((2R,3S)-7-(3-cyano-5-fluorophenoxy)-2-fluoro-3-hydroxy-2,3-dihydro-1H-inden-4-yl)(difluoromethyl)(oxo)-λ$^6$-sulfanylidene) cyanamide (Compound 297)

N—(((R)-7-(3-cyano-5-fluorophenoxy)-2-fluoro-3-oxo-2,3-dihydro-1H-inden-4-yl)(difluoromethyl)(oxo)-λ$^6$-sulfanylidene)cyanamide (78 mg, 0.18 mmol) (containing some N-((7-(3-cyano-5-fluorophenoxy)-3-oxo-2,3-dihydro-1H-inden-4-yl)(difluoromethyl)(oxo)-λ$^6$-sulfanylidene)cyanamide from the previous reaction) was dissolved in isopropanol (0.9 mL) and treated with triethylamine (0.05 mL, 0.37 mmol), formic acid (0.02 mL, 0.55 mmol) and RuCl (p-cymene)[(R,R)-Ts-DPEN] (1.2 mg, 0.002 mmol). The reaction mixture was stirred at ambient temperature for 14 hours. The reaction mixture was concentrated in a stream of nitrogen then chromatographed on SiO$_2$ (Biotage SNAP 10 g) with a gradient of ethyl acetate/hexane. A second purification on SiO$_2$ (Biotage SNAP 25 g Ultra) with a gradient of ethyl acetate/hexane afforded Compound 297 (2.7 mg). LCMS ESI (+) m/z 426 (M+H); $^1$H NMR (400 MHz, CDCl$_3$): δ 8.04 (d, 1H), 7.34-7.30 (m, 1H), 7.25-7.22 (m, 1H), 7.23 (t, J=54 Hz, 1H), 7.14-7.10 (m, 1H), 7.00 (d, 1H), 5.71-5.63 (m, 1H), 5.56-5.52 (m, 0.5H), 5.43-5.39 (m, 0.5H), 3.59 (t, 1H), 3.46-3.18 (m, 2H).

Example 298

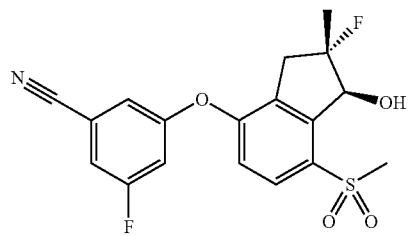

3-fluoro-5-(((1S,2S)-2-fluoro-1-hydroxy-2-methyl-7-(methylsulfonyl)-2,3-dihydro-1H-inden-4-yl)oxy)benzonitrile (Compound 298)

Step A: Preparation of 3-fluoro-5-((2-fluoro-2-methyl-7-(methylsulfonyl)-1-oxo-2,3-dihydro-1H-inden-4-yl)oxy)benzonitrile 3-fluoro-5-(2-fluoro-7-methylsulfonyl-1-oxo-indan-4-yl)oxy-benzonitrile (192 mg, 0.53 mmol) was dissolved in DMF (1.5 mL) and treated with cesium carbonate (343 mg, 1.06 mmol). Iodomethane (0.16 mL, 2.6 mmol) was added. The mixture was stirred at ambient temperature for 60 hours. The reaction mixture was sparged with nitrogen gas for several minutes then diluted with methylene chloride/ethyl acetate (1:1). The suspension was filtered through paper and then the filtrate was diluted with water and mixed gently. After the slow separation, the organic layer was washed twice with water, saturated NaCl, dried over $Na_2SO_4$ and concentrated in vacuo (315 mg). The crude material was chromatographed on $SiO_2$ (Biotage SNAP Ultra 10 g) with a gradient of ethyl acetate/hexane to give the desired product as colorless oil (61 mg). LCMS ESI (+) m/z 378 (M+H)

Step B: Preparation of 3-fluoro-5-(((1S,2S)-2-fluoro-1-hydroxy-2-methyl-7-(methylsulfonyl)-2,3-dihydro-1H-inden-4-yl)oxy)benzonitrile (Compound 298)

3-Fluoro-5-(2-fluoro-2-methyl-7-methylsulfonyl-1-oxo-indan-4-yl)oxy-benzonitrile (61 mg, 0.16 mmol) was suspended in methylene chloride (1.2 mL), cooled to 0° C. and treated with triethylamine (0.05 mL, 0.32 mmol), formic acid (0.02 mL, 0.48 mmol) and RuCl(p-cymene)[(R,R)-Ts-DPEN] (1.03 mg, 0.002 mmol). The reaction mixture was stirred at 0° C. for 20 hours. The solvent was removed by exposure to a stream of nitrogen gas. The residue was purified by preparative TLC with 2% MeOH/methylene chloride to give Compound 298 (8.6 mg). LCMS ESI (+) m/z 397 (M+NH$_4$); $^1$H NMR (400 MHz, CDCl$_3$): δ 7.85 (d, 1H), 7.22-7.19 (m, 1H), 7.12-7.09 (m, 1H), 7.03-6.98 (m, 2H), 5.29-5.23 (m, 1H), 3.57-3.53 (m, 1H), 3.26-3.04 (m, 2H), 3.19 (s, 3H), 1.70 (d, J=22 Hz, 3H)

Example 299

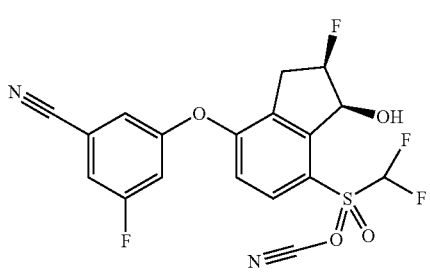

Isomer 2 of N-(((2R,3S)-7-(3-cyano-5-fluorophenoxy)-2-fluoro-3-hydroxy-2,3-dihydro-1H-inden-4-yl)(difluoromethyl)(oxo)-λ$^6$-sulfanylidene)cyanamide (Compound 299)

Prepared as described in Example 297 (2.2 mg). LCMS ESI (+) m/z 426 (M+H); $^1$H NMR (400 MHz, CDCl$_3$): δ 8.03 (d, 1H), 7.34-7.30 (m, 1H), 7.23-7.21 (m, 1H), 7.13-7.09 (m, 1H), 7.01 (t, J=53 Hz, 1H), 6.99 (d, 1H), 5.73-5.66 (m, 1H), 5.56-5.52 (m, 0.5H), 5.43-5.39 (m, 0.5H), 3.45-3.34 (m, 1H), 3.35-3.19 (m, 2H)

Example 300

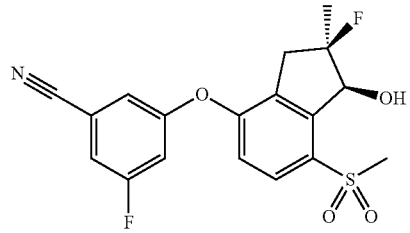 [SMILES: C[C@@]1(F)Cc2c(Oc3cc(F)cc(C#N)c3)ccc(S(C)(=O)=O)c2[C@@H]1O]

3-fluoro-5-(((1S,2R)-2-fluoro-1-hydroxy-2-methyl-7-(methylsulfonyl)-2,3-dihydro-1H-inden-4-yl)oxy)benzonitrile (Compound 300)

Prepared as described in Example 298. LCMS ESI (+) m/z 397 (M+NH$_4$); $^1$H NMR (400 MHz, CDCl$_3$): δ 7.90 (d, 1H), 7.21-7.19 (m, 1H), 7.10-7.08 (m, 1H), 6.99 (dt, 1H), 6.98 (d, 1H), 5.40-5.35 (m, 1H), 3.79-3.77 (m, 1H), 3.36-3.27 (m, 1H), 3.32 (s, 3H), 2.95-2.84 (m, 1H), 1.70 (d, 3H)

Example 301

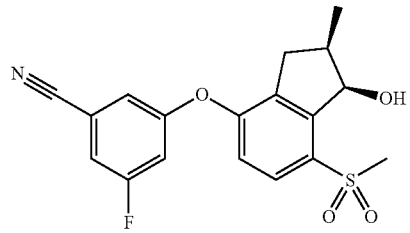 [SMILES: C[C@@H]1Cc2c(Oc3cc(F)cc(C#N)c3)ccc(S(C)(=O)=O)c2[C@@H]1O]

3-fluoro-5-4(1R,2R)-1-hydroxy-2-methyl-7-(methylsulfonyl)-2,3-dihydro-1H-inden-4-yl)oxy)benzonitrile (Compound 301)

Step A: Preparation of 3-fluoro-5-((2-methyl-7-(methylsulfonyl)-1-oxo-2,3-dihydro-1H-inden-4-yl)oxy)benzonitrile A solution of diisopropylamine (0.28 mL, 2.0 mmol) in THF (2 mL) was cooled to 0° C. and treated with n-BuLi (2.26 M in hexanes, 0.83 mL, 1.9 mmol) then stirred for 15 minutes. The solvents were removed from the mixture under high vacuum while maintaining the flask at 0° C. The resulting white solid was dissolved in fresh THF (1.8 mL). This solution was added dropwise to a flask containing a solution of 3-fluoro-5-(7-methylsulfonyl-1-oxo-indan-4-yl)oxy-benzonitrile (500 mg, 1.45 mmol) dissolved in a mixture of THF (2 mL) and 1,3-dimethyl-3,4,5,6-tetrahydro-2 (1H)-pyrimidinone (1 mL) which was cooled to −40° C. The dark solution was stirred for 30 minutes at −40° C. then iodomethane (0.13 mL, 2.0 mmol) was added. The mixture was allowed to warm to ambient temperature with the bath and stirred for 10 hours. The dark reaction mixture was cooled to 0° C. and poured into cold 10% KHSO$_4$ and stirred for several minutes. Ethyl acetate was added. The pH of the aqueous was adjusted to about 8 with solid NaHCO$_3$ and the layers were separated. The aqueous layer was washed with ethyl acetate and the combined organics were washed with saturated NaHCO$_3$, saturated NaCl, dried over Na$_2$SO$_4$ and concentrated in vacuo. The crude material was chromatographed on SiO$_2$ (Biotage SNAP 25 g) with a gradient of ethyl acetate/hexane. The desired material was isolated as a white solid (55 mg). LCMS ESI (+) m/z 360 (M+H).

Step B: Preparation of 3-fluoro-5-4(1R,2R)-1-hydroxy-2-methyl-7-(methylsulfonyl)-2,3-dihydro-1H-inden-4-yl)oxy)benzonitrile (Compound 301)

3-Fluoro-5-(2-methyl-7-methylsulfonyl-1-oxo-indan-4-yl)oxy-benzonitrile (26 mg, 0.07 mmol) was suspended in isopropanol (0.2 mL) and treated with triethylamine (0.02 mL, 0.14 mmol), formic acid (0.01 mL, 0.22 mmol) and RuCl(p-cymene)[(R,R)-Ts-DPEN] (0.46 mg, 0.001 mmol). The reaction mixture was stirred at ambient temperature for 14 hours. Additional methylene chloride (about 100 µL) was added. The reaction mixture was treated with fresh triethylamine (0.02 mL, 0.14 mmol), formic acid (0.01 mL, 0.22 mmol), and RuCl(p-cymene)[(R,R)-Ts-DPEN] (0.46 mg, 0.001 mmol) and stirring was continued at ambient temperature for 4 hours. The reaction mixture was concentrated in a stream of nitrogen gas and then chromatographed on SiO$_2$ (Biotage SNAP 10 g) with a gradient of ethyl acetate/hexane to give Compound 301 (19 mg). LCMS ESI (+) m/z 379 (M+NH$_4$); $^1$H NMR (400 MHz, CDCl$_3$): δ 7.84 (d, 1H), 7.19-7.15 (m, 1H), 7.07-7.06 (m, 1H), 6.98 (d, 1H), 6.97 (dt, 1H), 5.46-5.43 (m, 1H), 3.12 (s, 3H), 3.08 (d, 1H), 2.97-2.91 (m, 1H), 2.68-2.53 (m, 2H), 1.25 (d, 3H).

Example 302

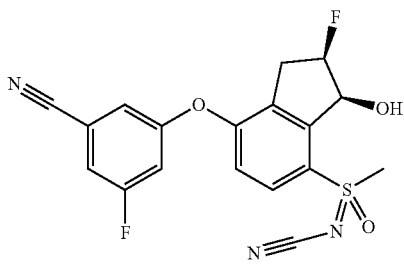 [SMILES: CS(=O)(=NC#N)c1ccc(Oc2cc(F)cc(C#N)c2)c2c1[C@H](O)[C@H](F)C2]

N-(((2R,3S)-7-(3-cyano-5-fluorophenoxy)-2-fluoro-3-hydroxy-2,3-dihydro-1H-inden-4-yl)(methyl)(oxo)-λ$^6$-sulfanylidene)cyanamide (Compound 302)

Step A: Preparation of [[7-(3-cyano-5-fluoro-phenoxy)-2-fluoro-3-oxo-indan-4-yl]-methyl-oxo-λ$^6$-sulfanylidene]cyanamide

[[7-(3-cyano-5-fluoro-phenoxy)-3-oxo-indan-4-yl]-methyl-oxo-λ$^6$-sulfanylidene]cyanamide (250 mg, 0.69 mmol) was dissolved in MeOH (3 mL) and treated with Selectfluor® (365 mg, 1.03 mmol). The mixture was heated to reflux for 24 hours. Additional fresh MeOH (3 mL) was added followed by Selectfluor® (365 mg, 1.03 mmol) and the mixture was heated for an additional 30 hours. The mixture was diluted with ethyl acetate and water and then separated. The organic layer was washed with water, saturated NaHCO$_3$, saturated NaCl, dried over Na$_2$SO$_4$ and concentrated in vacuo to give a brown solid (297 mg). The crude material was chromatographed on SiO$_2$ (Biotage SNAP 10 g) with a gradient of 10% ethyl acetate in methylene chloride to give the desired product as a mixture of isomers (17 mg). LCMS ESI (−) m/z 432 (M+HCOO$^-$).

Step B: Preparation of N-(((2R,3S)-7-(3-cyano-5-fluorophenoxy)-2-fluoro-3-hydroxy-2,3-dihydro-1H-inden-4-yl)(methyl)(oxo)-λ$^6$-sulfanylidene)cyanamide (Compound 302)

[[7-(3-cyano-5-fluoro-phenoxy)-2-fluoro-3-oxo-indan-4-yl]-methyl-oxo-λ$^6$-sulfanylidene]cyanamide (17 mg, 0.04 mmol) was dissolved in methylene chloride (0.14 mL), cooled to 0° C., and treated with triethylamine (12 µL, 0.09 mmol) and formic acid (5 µL, 0.13 mmol). A separate solution containing RuCl(p-cymene)[(R,R)-Ts-DPEN] (0.28 mg, 0.0004 mmol) dissolved in dichloromethane (0.14 mL) was chilled to 0° C. and then added to the first solution. The reaction mixture was transferred to a refrigerator (4° C.) and allowed to stand for 120 hours. The reaction mixture was concentrated in a stream of nitrogen gas and then chromatographed on SiO$_2$ with a stepped-gradient of hexane/ethyl acetate (3:1, 3:2, 1:1, 2:3) to give Compound 302 (8.8 mg) as a mixture of isomers at sulfur. LCMS ESI (+) m/z 390 (M+H); $^1$H NMR (400 MHz, CDCl$_3$): δ 8.00 (d, J=8.7 Hz, 0.5H), 7.95 (d, J=8.7 Hz, 0.5H), 7.29-7.25 (m, 1H), 7.19-7.16 (m, 1H), 7.10-7.05 (m, 1H), 7.01 (d, 1H), 5.78-5.69 (m, 1H), 5.54-5.50 (m, 0.5H), 5.40-5.37 (m, 0.5H), 3.50 (d, J=42 Hz, 3H), 3.39-3.11 (m, 3H).

Example 303

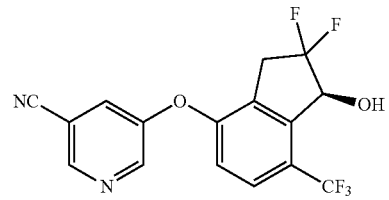

5-[(1S)-2,2-difluoro-1-hydroxy-7-(trifluoromethyl)indan-4-yl]oxypyridine-3-carbonitrile (Compound 303)

Prepared similarly as described for Compound 273, substituting 5-fluoronicotinonitrile for 3,5-difluorobenzonitrile in Step D. The product was determined to have 98% e.e. by chiral HPLC analysis. $^1$H NMR (400 MHz, CDCl$_3$): δ 8.72 (s, 1H), 8.64 (s, 1H), 7.64 (d, 1H), 7.59-7.57 (m, 1H), 6.97 (d, 1H), 5.33-5.28 (m, 1H), 3.55-3.32 (m, 2H), 2.86-2.82 (m, 1H). m/z (ES-API-pos) [M+H]=357.

Example 304

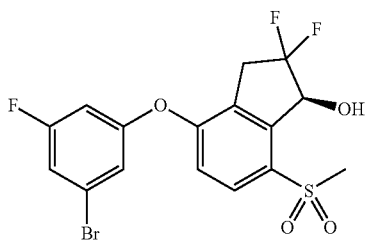 [SMILES: CS(=O)(=O)c1ccc(Oc2cc(F)cc(Br)c2)c2c1[C@H](O)C(F)(F)C2]

(S)-4-(3-bromo-5-fluorophenoxy)-2,2-difluoro-7-(methylsulfonyl)-2,3-dihydro-1H-inden-1-ol (Compound 304)

Prepared in a similar fashion as in the synthesis of Compound 163. LC-MS ESI (+) m/z 437, 439 (M+H$^+$); $^1$H-NMR (400 MHz, CDCl$_3$): δ 7.88 (d, 1H), 7.17-7.13 (m, 1H), 7.04-7.02 (m, 1H), 6.98 (d, 1H), 6.77-6.74 (m, 1H), 5.61-5.56 (m, 1H), 3.57-3.36 (m 3H), 3.22 (s, 3H).

Examples 305 and 306

Compound 305

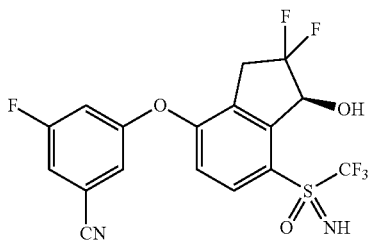

Compound 306

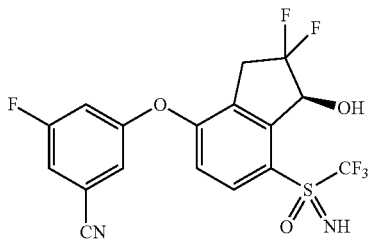

Isomer 1 of 3-(((1S)-2,2-difluoro-1-hydroxy-7-(S-(trifluoromethyl)sulfonimidoyl)-2,3-dihydro-1H-inden-4-yl)oxy)-5-fluorobenzonitrile (Compound 305) and isomer 2 of 3-(41S)-2,2-difluoro-1-hydroxy-7-(S-(trifluoromethyl)sulfonimidoyl)-2,3-dihydro-1H-inden-4-yl)oxy)-5-fluorobenzonitrile (Compound 306)

Step A: Preparation of (7-fluoro-3-hydroxy-2,3-dihydro-1H-inden-4-yl)(imino)(trifluoromethyl)-λ$^6$-sulfanone A mixture of N-((7-fluoro-3-hydroxy-2,3-dihydro-1H-inden-4-yl)(oxo)(trifluoromethyl)-λ$^6$-sulfanylidene)acetamide and 4-fluoro-7-(S-(trifluoromethyl)sulfonimidoyl)-2,3-dihydro-1H-inden-1-yl acetate (469 mg, 1.44 mmol) in acetonitrile (7.2 mL) at 25° C. was treated with 22.5% aqueous HCl solution (3.6 mL) and stirred at 25° C. overnight. Volatiles were removed by concentration under reduced pressure. The reaction mixture was poured into 30 mL of water and extracted with 3×20 mL 30% isopropyl alcohol in CHCl$_3$. The combined organics were rinsed with 10 mL of brine, dried with MgSO$_4$, filtered, and concentrated to dryness. The product residue was used without further purification. LCMS ESI (+) (M+H) m/z 284.

Step B: Preparation of 3-fluoro-5-((1-hydroxy-7-(S-(trifluoromethyl)sulfonimidoyl)-2,3-dihydro-1H-inden-4-yl)oxy)benzonitrile A solution of (7-fluoro-3-hydroxy-2,3-dihydro-1H-inden-4-yl)(imino)(trifluoromethyl)-λ$^6$-sulfanone (428 mg, 1.5 mmol), 3-fluoro-5-hydroxy-benzonitrile (207 mg, 1.5 mmol), and cesium bicarbonate (322 mg, 1.66 mmol) in DMF (6.0 mL) was stirred at 90° C. for 4.5 hours. An additional 40 mg of cesium bicarbonate was added and the reaction mixture heated for an additional hour. The reaction mixture was poured into 60 mL of water and extracted with 3×20 mL Et$_2$O. The combined organics were rinsed with 20 mL of brine, dried with MgSO$_4$, filtered, and concentrated to dryness. Purification was achieved by chromatography on silica using 10-35% EtOAc/hexane to afford 3-fluoro-5-((1-hydroxy-7-(S-(trifluoromethyl)sulfonimidoyl)-2,3-dihydro-1H-inden-4-yl)oxy)benzonitrile (171 mg, 28%). LCMS ESI (+) (M+H) m/z 401.

Step C: Preparation of 3-fluoro-5-((1-oxo-7-(S-(trifluoromethyl)sulfonimidoyl)-2,3-dihydro-1H-inden-4-yl)oxy)benzonitrile A solution of 3-fluoro-5-((1-hydroxy-7-(S-(trifluoromethyl)sulfonimidoyl)-2,3-dihydro-1H-inden-4-yl)oxy)benzonitrile (171 mg, 0.43 mmol) in dichloromethane (8.5 mL) at 0° C. was treated with Dess-Martin periodinane (217 mg, 0.51 mmol). The reaction mixture was allowed to warm to room temperature for 2 hours. An additional 40 mg of Dess-Martin periodinane was added to drive the reaction to completion. After stirring for an additional 2 hours, the reaction mixture was quenched by the addition of 10 mL of saturated aqueous Na$_2$S$_2$O$_3$ and 10 mL of saturated aqueous NaHCO$_3$. The resulting biphase was stirred for 10 minutes. The reaction mixture was poured into 20 mL of water and extracted with 3×20 mL CH$_2$Cl$_2$. The combined organics were rinsed with 10 mL of brine, dried with MgSO$_4$, filtered, and concentrated to dryness. Purification was achieved by chromatography on silica using 10-40% EtOAc/hexane to afford 3-fluoro-5-((1-oxo-7-(S-(trifluoromethyl)sulfonimidoyl)-2,3-dihydro-1H-inden-4-yl)oxy)benzonitrile (123 mg, 72%). LCMS ESI (+) (M+H) m/z 399.

Step D: Preparation of (E,Z)-3-fluoro-5-((1-((3-methoxypropyl)imino)-7-(S-(trifluoromethyl)sulfonimidoyl)-2,3-dihydro-1H-inden-4-yl)oxy)benzonitrile A solution of 3-fluoro-5-((1-oxo-7-(S-(trifluoromethyl)sulfonimidoyl)-2,3-dihydro-1H-inden-4-yl)oxy)benzonitrile (52.5 mg, 0.13 mmol) and 3-methoxypropan-1-amine (61 µL, 0.59 mmol) in a mixture of toluene (2.6 mL) and cyclohexane (2.6 mL) was treated with 2,2-dimethylpropanoic acid (8 mg, 0.08 mmol). The reaction vessel was equipped with a Hickman still and a reflux condenser and heated to 104° C. for 2.5 h. LCMS analysis was achieved by taking an aliquot of the reaction mixture and adding it to a solution of MeOH containing NaBH$_4$. LCMS indicated the formation of the amine via imine reduction. LCMS ESI (+) (M+H) m/z 472. Once complete, volatiles were removed by concentration under reduced pressure. The product residue was used without further purification.

Step E: Preparation of 3-((2,2-difluoro-1-oxo-7-(S-(trifluoromethyl)sulfonimidoyl)-2,3-dihydro-1H-inden-4-yl)oxy)-5-fluorobenzonitrile A similar procedure as described in Step E of Example 274 was followed. Purification was achieved by chromatography on silica using 10-35% EtOAc/hexane to give 3-((2,2-difluoro-1-oxo-7-(S-(trifluoromethyl)sulfonimidoyl)-2,3-dihydro-1H-inden-4-yl)oxy)-5-fluorobenzonitrile (32 mg, 56%). LCMS ESI (+) (M+H) m/z 435.

Step F: Preparation of 3-(((1S)-2,2-difluoro-1-hydroxy-7-(S-(trifluoromethyl)sulfonimidoyl)-2,3-dihydro-1H-inden-4-yl)oxy)-5-fluorobenzonitrile A solution of 3-((2,2-difluoro-1-oxo-7-(S-(trifluoromethyl)sulfonimidoyl)-2,3-dihydro-1H-inden-4-yl)oxy)-5-fluorobenzonitrile (32 mg, 0.074 mmol) in dichloromethane (1.5 mL) was cooled to 0° C. and sparged with nitrogen for 5 minutes. During this time formic acid (8.3 μL, 0.22 mmol) and triethylamine (20.4 μL, 0.15 mmol) were sequentially added. Once the sparging was complete, RuCl(p-cymene) [(R,R)-Ts-DPEN] (1.4 mg, 3 mol %) was added under a continuous stream of nitrogen. The reaction vessel was sealed and kept at 4° C. overnight. The reaction mixture was poured into 10 mL of saturated aqueous NaHCO$_3$ and extracted with 3×20 mL CH$_2$Cl$_2$. The combined organics were rinsed with 10 mL of brine, dried with MgSO$_4$, filtered, and concentrated to dryness. Purification was achieved by chromatography on silica using 5-40% EtOAc/hexane as eluent to afford two isomers.

Data for isomer 1 (Compound 305):
12 mg (38% yield); chiral HPLC Retention time=2.25 min; LCMS ESI (+) (M+H) m/z 437; $^1$H NMR (400 MHz, CDCl$_3$): δ 8.01 (d, 1H), 7.32 (ddd, 1H), 7.24-7.22 (m, 1H), 7.12 (dt, 1H), 6.99 (d, 1H), 5.35 (dd, 1H), 4.73-4.71 (m, 1H), 3.97 (br s, 1H), 3.63-3.46 (m, 2H).

Data for isomer 2 (Compound 306):
17 mg (52%); chiral HPLC Retention time=2.08 min; LCMS ESI (+) (M+H) m/z 437; $^1$H NMR (400 MHz, CDCl$_3$): δ 8.07 (d, 1H), 7.30 (ddd, 1H), 7.23-7.21 (m, 1H), 7.11 (dt, 1H), 6.98 (d, 1H), 5.59 (ddd, 1H), 3.97 (d, 1H), 3.81 (br s, 1H), 3.61-3.39 (m, 2H).

Examples 307 and 308

Compound 307

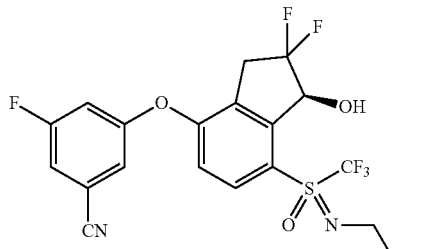

Compound 308

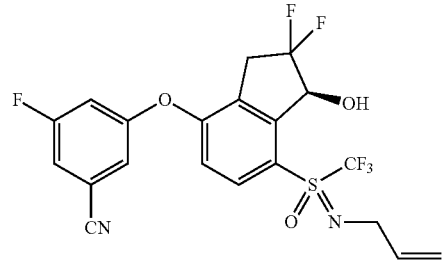

Isomer 1 of 3-(((1S)-7-(N-allyl-S-(trifluoromethyl) sulfonimidoyl)-2,2-difluoro-1-hydroxy-2,3-dihydro-1H-inden-4-yl)oxy)-5-fluorobenzonitrile (Compound 307) and isomer 2 of 3-4(1S)-7-(N-allyl-S-(trifluoromethyl)sulfonimidoyl)-2,2-difluoro-1-hydroxy-2,3-dihydro-1H-inden-4-yl)oxy)-5-fluorobenzonitrile (Compound 308)

Step A: Preparation of 3-((7-(N-allyl-S-(trifluoromethyl)sulfonimidoyl)-2,2-difluoro-1-oxo-2,3-dihydro-1H-inden-4-yl)oxy)-5-fluorobenzonitrile A solution of 3-fluoro-5-((1-oxo-7-(S-(trifluoromethyl)sulfonimidoyl)-2,3-dihydro-1H-inden-4-yl)oxy)benzonitrile (25.7 mg, 0.064 mmol) and Selectfluor® (50.3 mg, 0.14 mmol) in DMF (3.0 mL) at 25° C. was treated with cesium carbonate (46.3 mg, 0.14 mmol) and stirred at 25° C. After 1 hour, allyl iodide (7.1 μL, 0.077 mmol) and cesium carbonate (23.1 mg, 0.071 mmol) were added to the reaction mixture. The resulting mixture stirred for 1 hour and was then poured into 30 mL of water and extracted with 3×10 mL Et$_2$O. The combined organics were rinsed with 10 mL of brine, dried with MgSO$_4$, filtered, and concentrated to dryness. Purification was achieved by chromatography on silica using 5%→35% EtOAc/hexane to afford 3-((7-(N-allyl-S-(trifluoromethyl)sulfonimidoyl)-2,2-difluoro-1-oxo-2,3-dihydro-1H-inden-4-yl)oxy)-5-fluorobenzonitrile (4.5 mg, 16%). LCMS ESI (+) (M+H) m/z 475.

Step B: Preparation of 3-4(1S)-7-(N-allyl-S-(trifluoromethyl)sulfonimidoyl)-2,2-difluoro-1-hydroxy-2,3-dihydro-1H-inden-4-yl)oxy)-5-fluorobenzonitrile A solution of 3-((7-(N-allyl-S-(trifluoromethyl)sulfonimidoyl)-2,2-difluoro-1-oxo-2,3-dihydro-1H-inden-4-yl)oxy)-5-fluorobenzonitrile (4.5 mg, 0.01 mmol) in dichloromethane (1.0 mL) was cooled to 0° C. and sparged with nitrogen for 5 minutes. During this time formic acid (1.1 μL, 0.029 mmol) and triethylamine (2.6 μL, 0.019 mmol) were sequentially added. Once the sparging was complete, RuCl(p-cymene)[(R,R)-Ts-DPEN] (0.2 mg, 3 mol %) was added under a continuous stream of nitrogen. The reaction vessel was stored at 4° C. overnight. The reaction mixture was poured into 10 mL of saturated aqueous NaHCO$_3$ and extracted with 3×10 mL CH$_2$Cl$_2$. The combined organics were rinsed with 10 mL of brine, dried with MgSO$_4$, filtered, and concentrated to dryness. Purification was achieved by chromatography on silica using 5-25% EtOAc/hexane to afford two isomers.

Data for isomer 1 (Compound 307):
Retention time (Chiral HPLC)=3.50 min; LCMS ESI (+) (M+H) m/z 477; $^1$H NMR (400 MHz, CDCl$_3$): δ 7.99 (d, 1H), 7.30 (ddd, 1H), 7.23-7.20 (m, 1H), 7.10 (dt, 1H), 6.98 (d, 1H), 6.04-5.93 (m, 1H), 5.35-5.28 (m, 2H), 5.21 (dq, 1H), 4.87 (br s, 1H), 4.16-4.09 (m, 1H), 4.04-3.96 (m, 1H), 3.61-3.44 (m, 2H).

Data for isomer 2 (Compound 308):

Retention time (chiral HPLC)=3.05 min; LCMS ESI (+) (M+H) m/z 477; $^1$H NMR (400 MHz, CDCl$_3$): δ 8.04 (d, 1H), 7.29 (ddd, 1H), 7.21-7.19 (m, 1H), 7.09 (dt, 1H), 6.97 (d, 1H), 5.98 (ddt, 1H), 5.58 (dd, 1H), 5.34 (dq, 1H), 5.19 (dq, 1H), 4.13-4.05 (m, 1H), 4.03-3.95 (m, 1H), 3.59-3.33 (m, 3H).

Example 309

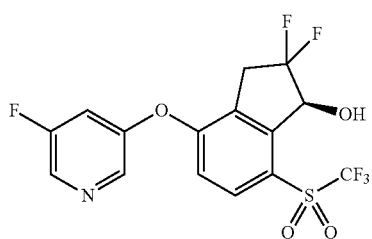 [SMILES: O=S(=O)(c1ccc(Oc2cncc(F)c2)c2c1[C@H](O)C(F)(F)C2)C(F)(F)F]

(S)-2,2-difluoro-4-((5-fluoropyridin-3-yl)oxy)-7-((trifluoromethyl)sulfonyl)-2,3-dihydro-1H-inden-1-ol (Compound 309)

Prepared similarly as described in Example 212. Purification was achieved by chromatography on silica using 5-35% EtOAc/hexane to afford Compound 309 as a beige oil (430 mg, 99%). LCMS ESI (+) (M+H) m/z 414; $^1$H NMR (400 MHz, CDCl$_3$): δ 8.49 (d, 1H), 8.37 (d, 1H), 7.93 (d, 1H), 7.26 (dt, 1H), 6.95 (d, 1H), 5.44 (dd, 1H), 3.67-3.48 (m, 2H), 3.42 (d, 1H).

Example 310

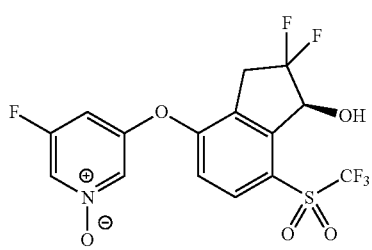 [SMILES: O=S(=O)(c1ccc(Oc2cc(F)c[n+]([O-])c2)c2c1[C@H](O)C(F)(F)C2)C(F)(F)F]

(S)-3-((2,2-difluoro-1-hydroxy-7-((trifluoromethyl)sulfonyl)-2,3-dihydro-1H-inden-4-yl)oxonio)-5-fluoropyridine 1-oxide (Compound 310)

A solution of (S)-2,2-difluoro-4-((5-fluoropyridin-3-yl)oxy)-7-((trifluoromethyl)sulfonyl)-2,3-dihydro-1H-inden-1-ol (324 mg, 0.78 mmol) and urea hydrogen peroxide (155 mg, 1.65 mmol) in acetonitrile (7.9 mL) was cooled to 0° C. and treated with trifluoroacetic anhydride (217 μL, 1.57 mmol). After 15 minutes, the ice bath was removed and the reaction left to stir for 1 hour. The reaction was quenched by the addition of 3 mL of saturated aqueous Na$_2$S$_2$O$_3$. The resulting biphasic mixture stirred for 15 minutes and was then poured into 20 mL of water and extracted with 4×15 mL 30% isopropyl alcohol in CHCl$_3$. The combined organics were rinsed with 10 mL of brine, dried with MgSO$_4$, filtered, and concentrated to dryness. Purification was achieved by chromatography on silica using 70-100% EtOAc/hexane to afford Compound 310 as a white solid (310 mg, 92%). LCMS ESI (+) (M+H) m/z 430; $^1$H NMR (400 MHz, CDCl$_3$): δ 8.11-8.08 (m, 1H), 8.01-7.97 (m, 2H), 7.14 (d, 1H), 6.90 (dt, 1H), 5.43 (dd, 1H), 3.95 (d, 1H), 3.62-3.41 (m, 2H).

Example 311

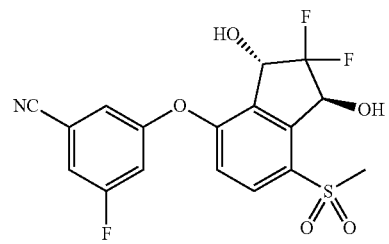 [SMILES: CS(=O)(=O)c1ccc(Oc2cc(F)cc(C#N)c2)c2c1[C@H](O)C(F)(F)[C@H]2O]

3-[(1S,3S)-2,2-difluoro-1,3-dihydroxy-7-methylsulfonyl-indan-4-yl]oxy-5-fluoro-benzonitrile (Compound 311)

Prepared as described in Example 292 alternative Synthesis 2 Step C. LCMS ESI (+) m/z 400 (M+H); $^1$H NMR (400 MHz, CDCl$_3$): δ 8.00 (d, 1H), 7.27-7.25 (m, 1H), 7.20-7.18 (m, 1H), 7.12-7.07 (m, 1H), 7.03 (d, 1H), 5.81-5.74 (m, 1H), 5.43-5.36 (m, 1H), 3.81 (d, 1H), 3.25 (s, 3H), 2.71 (m, 1H).

Example 312

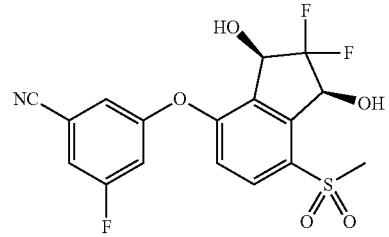 [SMILES: CS(=O)(=O)c1ccc(Oc2cc(F)cc(C#N)c2)c2c1[C@H](O)C(F)(F)[C@@H]2O]

3-[(1S,3R)-2,2-difluoro-1,3-dihydroxy-7-methylsulfonyl-indan-4-yl]oxy-5-fluoro-benzonitrile (Compound 312)

Prepared as described in Example 292 alternative Synthesis 2 Step C. LCMS ESI (+) m/z 400 (M+H); $^1$H NMR (400 MHz, CDCl$_3$): δ 8.05 (d, 1H), 7.29-7.20 (m, 2H), 7.15-7.10 (m, 1H), 7.05 (d, 1H), 5.63-5.57 (m, 1H), 5.22-5.15 (m, 1H), 3.53-3.48 (m, 1H), 3.24 (s, 3H), 2.73 (d, 1H).

Example 313

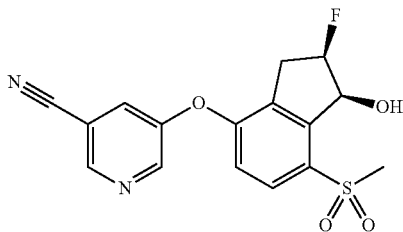 [SMILES: CS(=O)(=O)c1ccc(Oc2cncc(C#N)c2)c2c1[C@H](O)[C@H](F)C2]

5-(((1S,2R)-2-fluoro-1-hydroxy-7-(methylsulfonyl)-
2,3-dihydro-1H-inden-4-yl)oxy)nicotinonitrile
(Compound 313)

Step A: Preparation of 4-fluoro-7-(methylthio)-2,3-dihydro-1H-inden-1-one

S-(7-Fluoro-3-oxo-indan-4-yl) N,N-dimethylcarbamothioate (10 g, 37 mmol) was suspended in 95% ethanol (140 mL) and treated with 4 M aqueous sodium hydroxide (79 mL, 320 mmol) then the mixture was heated to reflux for 30 minutes. The reaction was cooled to 0° C. and treated dropwise with iodomethane (3.2 mL, 51.5 mmol) and the mixture was stirred for 1 hour at 0° C. The mixture was concentrated in vacuo, and then the residue was partitioned between ethyl acetate and water. After separation, the aqueous was washed with ethyl acetate and the organic layers were combined. The ethyl acetate was washed three times with water, saturated NaHCO$_3$, saturated NaCl, dried over Na$_2$SO$_4$ and concentrated in vacuo to a dark solid (7.1 g). The crude material was chromatographed on SiO$_2$ eluting with a gradient of ethyl acetate/hexane to give a dark solid (5.9 g). LCMS ESI (+) m/z 197 (M+H).

Step B: Preparation of 4-fluoro-7-(methylsulfonyl)-2,3-dihydro-1H-inden-1-one 4-Fluoro-7-methylsulfanyl-indan-1-one (5.9 g, 30 mmol) was dissolved in MeOH (200 mL) and the reaction was treated dropwise with a solution of Oxone® (40.8 g, 66.3 mmol) which had been dissolved in water (200 mL). The mixture was stirred at ambient temperature for 20 hours. The reaction mixture was filtered, the solids were washed with ethyl acetate and the filtrate was concentrated in vacuo. The aqueous filtrate was extracted three times with ethyl acetate then the combined organics were washed with saturated NaCl, dried over Na$_2$SO$_4$ and concentrated in vacuo to a tan solid (9.43 g). LCMS ESI (+) m/z 229 (M+H).

Step C: Preparation of 4-fluoro-7-(methylsulfonyl)-2,3-dihydrospiro[indene-1,2'-[1,3]dioxolane]

4-Fluoro-7-methylsulfonyl-indan-1-one (6.58 g, 28.8 mmol) and trimethyl(2-trimethylsilyloxyethoxy)silane (9.9 mL, 40.4 mmol) were dissolved in dichloromethane (105 mL), cooled to −78° C. then the reaction was treated dropwise with trimethylsilyl trifluoromethanesulfonate (1.67 mL, 9.23 mmol). After the addition, the reaction mixture was allowed to warm to ambient temperature without the bath and stirred for 4.5 hours. The reaction was quenched by addition of triethylamine (16.1 mL, 115 mmol) at ambient temperature and the reaction mixture was concentrated in vacuo. The dark residue was dissolved in ethyl acetate and washed with half-saturated NaCl. The aqueous was washed with ethyl acetate and the combined organics were washed with water, saturated NaCl, dried over Na$_2$SO$_4$ and concentrated in vacuo to give a dark residue. The sticky semi-solid was suspended in 3:1 hexane/ethyl acetate (250 mL) and stirred for one hour. The dark solids were collected by filtration, washed with 3:1 hexane/ethyl acetate and air-dried to a greenish solid (4.66 g). The filtrate was concentrated and triturated with acetone (ca. 25 mL) and stirred for 20 minutes. The mixture was diluted with approximately an equal portion of hexanes then filtered. The solid was washed with 9:1 hexane/ethyl acetate and air-dried to give additional product as a lighter green solid (1.1 g). LCMS ESI (+) m/z 273 (M+H).

Step D: Preparation of 5-((7-(methylsulfonyl)-2,3-dihydrospiro[indene-1,2'-[1,3]dioxolan]-4-yl)oxy)nicotinonitrile 4'-Fluoro-7'-methylsulfonyl-spiro[1,3-dioxolane-2,1'-indane] (2.0 g, 7.4 mmol) was combined with 3-cyano-5-hydroxypyridine (1.06 g, 8.8 mmol) in NMP (14 mL) and the solution was treated with potassium phosphate tribasic (4.68 g, 22 mmol) in a single portion. The reaction was heated to 120° C. for 14 hours. The mixture was cooled to ambient temperature then diluted with ethyl acetate (50-70 mL) and the undissolved solids were removed by filtration through a frit and washed with additional ethyl acetate. The filtrate was diluted with an equal volume of water. This caused some dark solids to form in the mixture. Addition of 25% isopropanol/methylene chloride redissolved the solids and the layers were separated. The organic layer was washed five times with water, saturated NaCl, dried over Na$_2$SO$_4$ then concentrated to a dark solid (1.15 g). The crude material was chromatographed on SiO$_2$ (Biotage SNAP 50 g) and eluted with a gradient of ethyl acetate/hexane. The desired product was concentrated to a light pink solid (0.50 g). LCMS ESI (+) m/z 373 (M+H)

Step E: Preparation of 5-((7-(methylsulfonyl)-1-oxo-2,3-dihydro-1H-inden-4-yl)oxy)nicotinonitrile 5-(7'-Methylsulfonylspiro[1,3-dioxolane-2,1'-indane]-4'-yl)oxypyridine-3-carbonitrile (0.5 g, 1.3 mmol) was slurried in acetone (6 mL) and treated with 10% aqueous HCl (2.3 mL, 6.7 mmol). The solution was stirred at ambient temperature for 1 hour. The reaction mixture was adjusted to pH 8 with saturated NaHCO$_3$ then concentrated in vacuo to remove acetone. The resulting solids were collected by filtration and air-dried (0.44 g). LCMS ESI (+) m/z 329.1 (M+H).

Step F: Preparation of 5-((2-fluoro-7-(methylsulfonyl)-1-oxo-2,3-dihydro-1H-inden-4-yl)oxy)nicotinonitrile 5-(7-Methylsulfonyl-1-oxo-indan-4-yl)oxypyridine-3-carbonitrile (0.44 g, 1.3 mmol) was dissolved in MeOH (4 mL) and treated with Selectfluor® (760 mg, 2.2 mmol). The mixture was heated to reflux for 40 hours. Acetonitrile (2 mL) was added and heating continued for 7 additional hours. The mixture was stirred overnight at ambient temperature then diluted with water, ethyl acetate and methylene chloride. The suspension was filtered and the solids were washed with ethyl acetate. The filtrate was concentrated in vacuo then the residual water was treated with acetone (2 mL) and 10% HCl (2 mL) and warmed to 50° C. for 30 minutes. The mixture was adjusted to pH 8 with solid NaHCO₃ then concentrated in vacuo. The resulting aqueous was washed twice with ethyl acetate and the combined organics were washed with saturated NaHCO₃, saturated NaCl, dried over Na₂SO₄ and concentrated in vacuo to a light yellow oil (447 mg). The crude material was chromatographed on SiO₂ (Biotage SNAP 25 g) and eluted with a gradient of MeOH/methylene chloride. The desired material was concentrated to a yellow film (274 mg). LCMS ESI (−) m/z 345.0 (M−H).

Step G: Preparation of 54(1S,2R)-2-fluoro-1-hydroxy-7-(methylsulfonyl)-2,3-dihydro-1H-inden-4-yl)oxy)nicotinonitrile (Compound 313)

5-(2-Fluoro-7-methylsulfonyl-1-oxo-indan-4-yl)oxypyridine-3-carbonitrile (274 mg, 0.79 mmol) was suspended in methylene chloride (3 mL), cooled to 0° C., then treated with triethylamine (0.22 mL, 1.6 mmol), formic acid (0.09 mL, 2.4 mmol) and RuCl(p-cymene)[(R,R)-Ts-DPEN] (5 mg, 0.01 mmol). The reaction mixture was allowed to stand at 0° C. for 15 hours. The mixture was concentrated and chromatographed on SiO₂ (Biotage SNAP 10 g) and eluted with a gradient of ethyl acetate/hexane to give Compound 313 as a white solid (120 mg). LCMS ESI (+) m/z 349 (M+H); ¹H NMR (400 MHz, CDCl₃): δ 8.75-8.72 (m, 1H), 8.66-8.64 (m, 1H), 7.92 (d, 1H), 7.61-7.59 (m, 1H), 6.95 (d, 1H), 5.73-5.65 (m, 1H), 5.51-5.47 (m, 0.5H), 5.38-5.34 (m, 0.5H), 3.71-3.68 (m, 1H), 3.36-3.38 (m, 2H), 3.31 (s, 3H).

Examples 314 and 315

Compound 314

Compound 315

5-(((1S)-2,2-difluoro-1-hydroxy-7-(S-(trifluoromethyl)sulfonimidoyl)-2,3-dihydro-1H-inden-4-yl)oxy)nicotinonitrile (Compound 314) and 5-(((1S)-2,2-difluoro-1-hydroxy-7-(S-(trifluoromethyl)sulfonimidoyl)-2,3-dihydro-1H-inden-4-yl)oxy)nicotinonitrile (Compound 315)

Prepared in a similar manner to that described in Example 163, Step F, substituting 5-((2,2-difluoro-1-oxo-7-(S-(trifluoromethyl)sulfonimidoyl)-2,3-dihydro-1H-inden-4-yl)oxy)nicotinonitrile for 3-(2,2-difluoro-7-methylsulfonyl-1-oxo-indan-4-yl)oxy-5-fluoro-benzonitrile. 5-((2,2-Difluoro-1-oxo-7-(S-(trifluoromethyl)sulfonimidoyl)-2,3-dihydro-1H-inden-4-yl)oxy)nicotinonitrile was prepared similarly according to Examples 305 and 306.

Data for 5#(1S)-2,2-difluoro-1-hydroxy-7-(S-(trifluoromethyl)sulfonimidoyl)-2,3-dihydro-1H-inden-4-yl)oxy)nicotinonitrile (Compound 314)

Retention time HPLC (long method)=4.46 min; LCMS ESI (+) (M+H) m/z 420; ¹H NMR (400 MHz, CDCl₃): δ 8.83 (d, 1H), 8.72 (d, 1H), 8.02 (d, 1H), 7.73 (dd, 1H), 6.95 (d, 1H), 5.35 (dd, 1H), 4.73-4.70 (m s, 1H), 3.99 (br s, 1H), 3.67-3.49 (m, 2H).

Data for 5-(((1S)-2,2-difluoro-1-hydroxy-7-(S-(trifluoromethyl)sulfonimidoyl)-2,3-dihydro-1H-inden-4-yl)oxy)nicotinonitrile (Compound 315)

Retention time HPLC (long method)=4.17 min; LCMS ESI (+) (M+H) m/z 420; ¹H NMR (400 MHz, CDCl₃): δ 8.82 (d, 1H), 8.71 (d, 1H), 8.08 (d, 1H), 7.72 (dd, 1H), 6.93 (d, 1H), 5.63-5.57 (m, 1H), 3.97 (d, 1H), 3.82 (br s, 1H), 3.65-3.43 (m, 2H).

Examples 316, 317, and 318

Compound 316

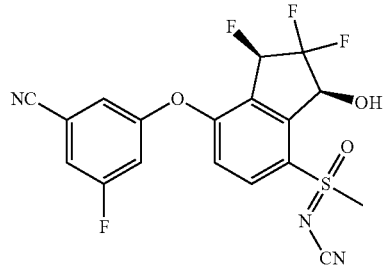

Compound 317

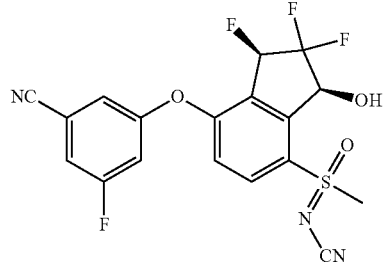

Compound 318

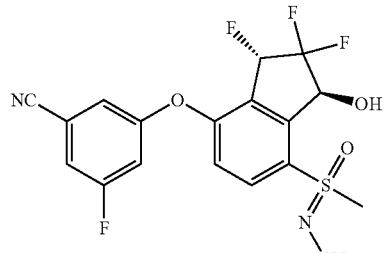

Isomer 1 of [[(1R,3S)-7-(3-cyano-5-fluoro-phenoxy)-1,2,2-trifluoro-3-hydroxy-indan-4-yl]-methyl-oxo-λ⁶-sulfanylidene]cyanamide (Compound 316), isomer 2 of [[(1R,3S)-7-(3-cyano-5-fluoro-phenoxy)-1,2,2-trifluoro-3-hydroxy-indan-4-yl]-methyl-oxo-λ⁶-sulfanylidene]cyanamide (Compound 317), and isomer 1 of [[(1S,3S)-7-(3-cyano-5-fluoro-phenoxy)-1,2,2-trifluoro-3-hydroxy-indan-4-yl]-methyl-oxo-λ⁶-sulfanylidene]cyanamide (Compound 318)

Step A: Preparation of 2,2,3,4-tetrafluoro-7-methylsulfanyl-indan-1-one

Diethylaminosulfur trifluoride (0.089 mL, 0.67 mmol) was added to an ice-cold solution of 2,2,4-trifluoro-3-hydroxy-7-methylsulfanyl-indan-1-one (139 mg, 0.56 mmol) in dichloromethane (10 mL). The reaction mixture was allowed to warm to ambient temperature. Additional diethylaminosulfur trifluoride was added after 1 hour to allow the reaction to go to completion. The mixture was treated carefully with aqueous NaHCO₃ and partitioned between EtOAc and water. The EtOAc was washed with brine, dried over MgSO₄, filtered, and evaporated to afford 2,2,3,4-tetrafluoro-7-methylsulfanyl-indan-1-one (120 mg, 0.48 mmol, 86% yield) as an orange oil. m/z (ES-API-pos) [M+H]=250.

Step B: Preparation of [methyl-[(1R)-1,2,2,7-tetrafluoro-3-oxo-indan-4-yl]-λ⁴-sulfanylidene]cyanamide (Diacetoxyiodo)benzene (170 mg, 0.53 mmol) was added to an ice-cold solution of 2,2,3,4-tetrafluoro-7-methylsulfanyl-indan-1-one (120 mg, 0.48 mmol) and cyanamide (24 mg, 0.58 mmol) in dichloromethane (10 mL). The reaction mixture was treated with bis[rhodium(α,α,α',α'-tetramethyl-1,3-benzenedipropionic acid)] (3.6 mg, 0.0048 mmol) and allowed to warm to ambient temperature. After 1 hour, the reaction mixture was evaporated and the residue was partitioned between EtOAc and dilute aqueous sodium thiosulfate. The EtOAc was washed with brine, dried over MgSO₄, filtered, and evaporated to afford [methyl-[1,2,2,7-tetrafluoro-3-oxo-indan-4-yl]-λ⁴-sulfanylidene]cyanamide (100 mg, 0.35 mmol, 72% yield) as a brown foam. m/z (ES-API-pos) [M+H+18]=309.

Step C: Preparation of [methyl-oxo-[1,2,2,7-tetrafluoro-3-oxo-indan-4-yl]-λ⁶-sulfanylidene]cyanamide Ruthenium(III) chloride (1.4 mg, 0.007 mmol) was added to an ice-cold mixture of [methyl-[1,2,2,7-tetrafluoro-3-oxo-indan-4-yl]-λ⁴-sulfanylidene]cyanamide (100 mg, 0.34 mmol) and sodium periodate (221 mg, 1.0 mmol) in a mixture of carbon tetrachloride (4 mL), acetonitrile (4 mL), and water (8 mL). The mixture was stirred vigorously in an ice bath. After 45 minutes, the reaction mixture was diluted with dichloromethane and was washed with dilute aqueous sodium thiosulfate solution. The dichloromethane was washed with brine, dried over MgSO₄, filtered, and evaporated to afford [methyl-oxo-[1,2,2,7-tetrafluoro-3-oxo-indan-4-yl]-λ⁶-sulfanylidene]cyanamide (70 mg, 0.23 mmol, 66% yield). m/z (ES-API-pos) [M+H+18]=325.

Step D: Preparation of [[7-(3-cyano-5-fluoro-phenoxy)-1,2,2-trifluoro-3-oxo-indan-4-yl]-methyl-oxo-λ⁶-sulfanylidene]cyanamide Cesium bicarbonate (88.6 mg, 0.46 mmol) was added to a solution of 3-fluoro-5-hydroxy-benzonitrile (40.7 mg, 0.3 mmol) and [methyl-oxo-[1,2,2,7-tetrafluoro-3-oxo-indan-4-yl]-λ⁶-sulfanylidene]cyanamide (70 mg, 0.23 mmol) in N,N-dimethylformamide (3 mL). The mixture was stirred at ambient temperature. After 25 minutes, the reaction mixture was partitioned between EtOAc and dilute aqueous NaCl. The EtOAc was washed with 2 portions of brine, dried over MgSO₄, filtered, and evaporated.

The residue was chromatographed on a Biotage 10 g ultra SNAP column with a 20% to 80% EtOAc:hexane gradient to afford [[7-(3-cyano-5-fluoro-phenoxy)-1,2,2-trifluoro-3-oxo-indan-4-yl]-methyl-oxo-λ⁶-sulfanylidene]cyanamide (35.5 mg, 0.084 mmol, 37% yield) as a diastereomeric mixture. m/z (ES-API-pos) [M+H+18]=442.

Step E: Preparation of isomer 1 of [[(1R,3S)-7-(3-cyano-5-fluoro-phenoxy)-1,2,2-trifluoro-3-hydroxy-indan-4-yl]-methyl-oxo-λ⁶-sulfanylidene]cyanamide (Compound 316), isomer 2 of [[(1R,3S)-7-(3-cyano-5-fluoro-phenoxy)-1,2,2-trifluoro-3-hydroxy-indan-4-yl]-methyl-oxo-λ⁶-sulfanylidene]cyanamide (Compound 317), and isomer 1 of [[(1S,3S)-7-(3-cyano-5-fluoro-phenoxy)-1,2,2-trifluoro-3-hydroxy-indan-4-yl]-methyl-oxo-λ⁶-sulfanylidene]cyanamide (Compound 318)

RuCl(p-cymene)[(R,R)-Ts-DPEN] (1.6 mg, 0.0025 mmol) was added to a nitrogen-sparged, ice-cold solution of [[7-(3-cyano-5-fluoro-phenoxy)-1,2,2-trifluoro-3-oxo-indan-4-yl]-methyl-oxo-λ⁶-sulfanylidene]cyanamide (35.5 mg, 0.084 mmol), formic acid (0.013 mL, 0.34 mmol), and triethylamine (0.029 mL, 0.21 mmol) in dichloromethane (5 mL). The flask was sealed and kept at 4° C. overnight. The reaction mixture was evaporated and the residue was purified by chromatography on Biotage ultra SNAP columns with EtOAc:hexane gradients to afford 3 isomers.

Data for isomer 1 [[(1R,3S)-7-(3-cyano-5-fluoro-phenoxy)-1,2,2-trifluoro-3-hydroxy-indan-4-yl]-methyl-oxo-λ⁶-sulfanylidene]cyanamide (Compound 316; 1.9 mg; 0.0045 mmol; 5% yield)

¹H NMR (400 MHz, CD₃OD): δ 8.21 (dd, 1H), 7.59-7.56 (m, 1H), 7.54-7.53 (m, 1H), 7.46 (dt, 1H), 7.25 (d, 1H), 6.00 (dd, 1H), 5.60-5.56 (m, 1H), 3.64 (s, 3H); m/z (ES-API-pos) [M+H]=426.

Data for isomer 2 [[(1R,3S)-7-(3-cyano-5-fluoro-phenoxy)-1,2,2-trifluoro-3-hydroxy-indan-4-yl]-methyl-oxo-λ⁶-sulfanylidene]cyanamide (Compound 317; 3.4 mg; 0.008 mmol; 10% yield)

¹H NMR (400 MHz, CDCl₃): δ 8.23-8.20 (m, 1H), 7.38-7.34 (m, 1H), 7.30-7.28 (m, 1H), 7.21-7.17 (m, 1H), 7.09 (d, 1H), 5.90 (dd, 1H), 5.71-5.66 (m, 1H), 3.90-3.88 (m, 1H), 3.64 (s, 3H); m/z (ES-API-pos) [M+H]=426.

Data for isomer 1 of [[(1S,3S)-7-(3-cyano-5-fluoro-phenoxy)-1,2,2-trifluoro-3-hydroxy-indan-4-yl]-methyl-oxo-$\lambda^6$-sulfanylidene]cyanamide (Compound 318; 3.4 mg; 0.008 mmol; 10% yield)

$^1$H NMR (400 MHz, CDCl$_3$): δ 8.13 (dd, 1H), 7.37-7.33 (m, 1H), 7.28-7.27 (m, 1H), 7.19-7.15 (m, 1H), 7.05 (d, 1H), 6.08-5.84 (m, 2H), 4.08 (d, 1H), 3.54 (s, 3H); m/z (ES-API-pos) [M+H]=426.

Examples 319, 320, 321, and 322

Compound 319

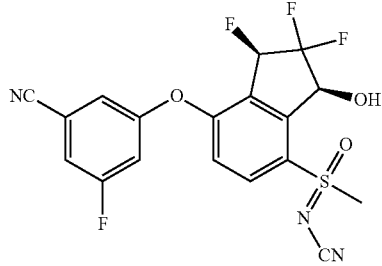

Compound 320

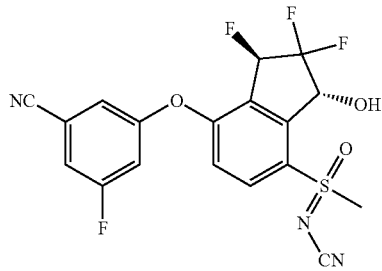

Compound 321

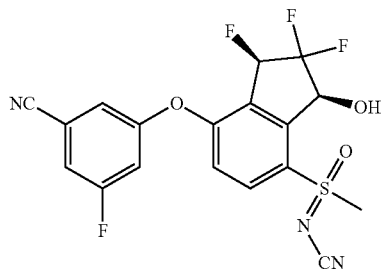

Compound 322

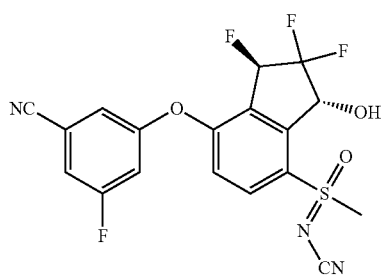

Isomer 1 of [[(1R,3S)-7-[(5-Cyano-3-pyridyl)oxy]-1,2,2-trifluoro-3-hydroxy-indan-4-yl]-methyl-oxo-$\lambda^6$-sulfanylidene]cyanamide (Compound 319); isomer 1 of [[(1R,3R)-7-(3-cyano-5-fluoro-phenoxy)-1,2,2-trifluoro-3-hydroxy-indan-4-yl]-methyl-oxo-$\lambda^6$-sulfanylidene]cyanamide (Compound 320); isomer 2 of [[(1R,3S)-7-[(5-cyano-3-pyridyl)oxy]-1,2,2-trifluoro-3-hydroxy-indan-4-yl]-methyl-oxo-$\lambda^6$-sulfanylidene]cyanamide (Compound 321); and isomer 2 of [[(1R,3R)-7-(3-cyano-5-fluoro-phenoxy)-1,2,2-trifluoro-3-hydroxy-indan-4-yl]-methyl-oxo-$\lambda^6$-sulfanylidene]cyanamide (Compound 322)

Step A: Preparation of (3S)-2,2,4-trifluoro-3-hydroxy-7-methylsulfanyl-indan-1-one A solution of (3S)-2,2,4,7-tetrafluoro-3-hydroxy-indan-1-one (966 mg, 4.39 mmol) in acetonitrile (40 mL) at 0° C. was sparged with nitrogen for 5 minutes and treated with sodium thiomethoxide (354 mg, 5.05 mmol). The ice bath was removed and the reaction mixture was stirred at ambient temperature. After 2 hours, the reaction mixture was evaporated and the residue was partitioned between EtOAc and water. The aqueous layer was extracted with 2 additional portions of EtOAc. The combined EtOAc extracts were washed with brine, dried over MgSO$_4$, filtered, and evaporated. The residue was chromatographed on a Biotage 100 g SNAP column with a 10% to 60% EtOAc:hexane to afford (3S)-2,2,4-trifluoro-3-hydroxy-7-methylsulfanyl-indan-1-one (870 mg, 3.51 mmol, 80% yield) as a yellow solid. m/z (ES-API-pos) [M+H]=249.

Step B: Preparation of (3R)-2,2,3,4-tetrafluoro-7-methylsulfanyl-indan-1-one

Diethylaminosulfur trifluoride (0.08 mL, 0.6 mmol) was added to an ice-cold solution of (3S)-2,2,4-trifluoro-3-hydroxy-7-methylsulfanyl-indan-1-one (100 mg, 0.4 mmol) in dichloromethane (10 mL). The reaction mixture was stirred overnight at ambient temperature. A small amount of additional diethylaminosulfur trifluoride was added and stirring continued. After 1 hour, the mixture was treated carefully with aqueous NaHCO$_3$, stirred for 10 minutes, and concentrated. The aqueous slurry was partitioned between EtOAc and dilute aqueous NaHCO$_3$. The aqueous layer was extracted with another portion of EtOAc. The combined EtOAc was washed with brine, dried over MgSO$_4$, filtered, and evaporated to afford (3R)-2,2,3,4-tetrafluoro-7-methylsulfanyl-indan-1-one (99 mg, 0.4 mmol, 98% yield) as a yellow semi-crystalline solid. m/z (ES-API-pos) [M+H]=250.

Step C: Preparation of [methyl-[(1R)-1,2,2,7-tetrafluoro-3-oxo-indan-4-yl]-$\lambda^4$-sulfanylidene]cyanamide diastereomers Bis[rhodium(α,α,α',α'-tetramethyl-1, 3-benzenedipropionic acid)] (3.05 mg, 0.004 mmol) was added to an ice-cold solution of (3R)-2,2,3,4-tetrafluoro-7-methylsulfanyl-indan-1-one (100 mg, 0.4 mmol), cyanamide (33.6 mg, 0.8 mmol), and (diacetoxyiodo)benzene (155 mg, 0.48 mmol) in dichloromethane (10 mL). The reaction mixture was allowed to warm to ambient temperature. After 1 hour, the reaction mixture was evaporated and the residue was chromatographed on a Biotage 25 g ultra SNAP column with a 50% to 100% EtOAc:hexane to afford two isomers of [methyl-[(1R)-1,2,2,7-tetrafluoro-3-oxo-indan-4-yl]-$\lambda^4$-sulfanylidene]cyanamide (isomer A: 59.5 mg, 0.21 mmol, 51% yield, m/z (ES-API-pos) [M+H+18]=309; isomer B: 39.2 mg, 0.135 mmol, 34% yield, m/z (ES-API-pos) [M+H+18]=309).

Step D: Preparation of [methyl-oxo-[(1R)-1,2,2,7-tetrafluoro-3-oxo-indan-4-yl]-$\lambda^6$-sulfanylidene]cyanamide (Parallel reactions with separated isomers from Step C) Ruthenium(III) chloride (0.85 mg, 0.004 mmol) was added to an ice-cold mixture of isomer A of [methyl-[(1R)-1,2,2,7-tetrafluoro-3-oxo-indan-4-yl]-$\lambda^4$-sulfanylidene]cyanamide (59.5 mg, 0.21 mmol) and sodium periodate (131 mg, 0.62 mmol) in carbon tetrachloride (3 mL), acetonitrile (3 mL), and water (6 mL). The mixture was stirred vigorously in ice. The ice bath was removed and the mixture was allowed to warm to ambient temperature. After 1.5 hours, the reaction mixture was diluted with EtOAc and was washed with dilute sodium thiosulfate solution. The aqueous layer was extracted with another portion of EtOAc. The EtOAc was washed with brine, dried over MgSO$_4$, filtered, and evaporated to afford isomer A of [methyl-oxo-[(1R)-1,2,2,7-tetrafluoro-3-oxo-indan-4-yl]-$\lambda^6$-sulfanylidene]cyanamide (55.2 mg, 0.18 mmol, 88% yield). m/z (ES-API-pos) [M+H+18]=325. Isomer B of [methyl-oxo-[(1R)-1,2,2,7-tetrafluoro-3-oxo-indan-4-yl]-$\lambda^6$-sulfanylidene]cyanamide was prepared in a similar fashion. m/z (ES-API-pos) [M+H+18]=325.

Step E: Preparation of [[(1R)-7-[(5-cyano-3-pyridyl)oxy]-1,2,2-trifluoro-3-oxo-indan-4-yl]-methyl-oxo-$\lambda^6$-sulfanylidene]cyanamide (Parallel reactions with each isomer from Step D) Isomer A of [methyl-oxo-[(1R)-1,2,2,7-tetrafluoro-3-oxo-indan-4-yl]-$\lambda^6$-sulfanylidene]cyanamide (47.7 mg, 0.16 mmol) was added to a solution of cesium bicarbonate (45 mg, 0.23 mmol) in tetrahydrofuran (5 mL) at ambient temperature. The mixture was stirred for 10 minutes, then added to a solution of 3-cyano-5-hydroxypyridine (24.3 mg, 0.2 mmol) in tetrahydrofuran (5 mL). The reaction mixture was stirred overnight at ambient temperature. The reaction mixture was evaporated, and the residue was partitioned between EtOAc and dilute aqueous NaCl. The aqueous layer was extracted with another portion of EtOAc. The combined EtOAc was washed with brine, dried over MgSO$_4$, filtered, and evaporated. The residue was chromatographed on a Biotage 10 g ultra SNAP column with a 50% to 100% EtOAc:hexane to afford isomer A of [[(1R)-7-[(5-cyano-3-pyridyl)oxy]-1,2,2-trifluoro-3-oxo-indan-4-yl]-methyl-oxo-$\lambda^6$-sulfanylidene]cyanamide (52 mg, 0.13 mmol, 82% yield) as a white solid. m/z (ES-API-pos) [M+H+18]=425. Isomer B of [[(1R)-7-[(5-cyano-3-pyridyl)oxy]-1,2,2-trifluoro-3-oxo-indan-4-yl]-methyl-oxo-$\lambda^6$-sulfanylidene]cyanamide was prepared in a similar fashion. m/z (ES-API-pos) [M+H+18]=425.

Step F: Preparation of [[(1R,3S)-7-[(5-cyano-3-pyridyl)oxy]-1,2,2-trifluoro-3-hydroxy-indan-4-yl]-methyl-oxo-$\lambda^6$-sulfanylidene]cyanamide (Compound 319); [[(1R,3R)-7-(3-cyano-5-fluoro-phenoxy)-1,2,2-trifluoro-3-hydroxy-indan-4-yl]-methyl-oxo-$\lambda^6$-sulfanylidene]cyanamide (Compound 320); [[(1R,3S)-7-[(5-cyano-3-pyridyl)oxy]-1,2,2-trifluoro-3-hydroxy-indan-4-yl]-methyl-oxo-$\lambda^6$-sulfanylidene cyanamide (Compound 321); and [[(1R,3R)-7-(3-cyano-5-fluoro-phenoxy)-1,2,2-trifluoro-3-hydroxy-indan-4-yl]-methyl-oxo-$\lambda^6$-sulfanylidene]cyanamide (Compound 322)

(Parallel reactions with each isomer from Step E) RuCl(p-cymene)[(R,R)-Ts-DPEN] (2.44 mg, 0.0038 mmol) was added to an ice-cold nitrogen-sparged solution of isomer A of [[(1R)-7-[(5-cyano-3-pyridyl)oxy]-1,2,2-trifluoro-3-oxo-indan-4-yl]-methyl-oxo-$\lambda^6$-sulfanylidene]cyanamide (52 mg, 0.13 mmol), formic acid (0.019 mL, 0.51 mmol), and triethylamine (0.045 mL, 0.32 mmol) in dichloromethane (10 mL). The flask was sealed and stored at 4° C. overnight. The reaction mixture was evaporated and the residue was chromatographed on a Biotage 25 g SNAP ultra column with a 50% to 100% EtOAc:hexane gradient to afford 2 isomeric products.

Data for isomer 1 of [(1R,3S)-7-[(5-cyano-3-pyridyl)oxy]-1,2,2-trifluoro-3-hydroxy-indan-4-yl]-methyl-oxo-$\lambda^6$-sulfanylidene]cyanamide (Compound 319)

(25.5 mg, 0.062 mmol, 49% yield); $^1$H NMR (400 MHz, CD$_3$COCD$_3$): δ 8.95 (d, 1H), 8.94 (d, 1H), 8.34-8.32 (m, 1H), 8.23-8.20 (m, 1H), 7.45 (d, 1H), 6.43-6.40 (m, 1H), 6.15 (dd, 1H), 5.72-5.66 (m, 1H), 3.69 (s, 3H); m/z (ES-API-pos) [M+H]=409.

Data for isomer 1 of [[(1R,3R)-7-(3-cyano-5-fluoro-phenoxy)-1,2,2-trifluoro-3-hydroxy-indan-4-yl]-methyl-oxo-$\lambda^6$-sulfanylidene]cyanamide (Compound 320)

(8.1 mg, 0.02 mmol, 16% yield); $^1$H NMR (400 MHz, CD$_3$COCD$_3$): δ 8.96-8.95 (m, 1H), 8.94-8.92 (m, 1H), 8.34-8.32 (m, 1H), 8.24-8.20 (m, 1H), 7.44-7.41 (m, 1H), 6.51-6.31 (m, 2H), 5.90-5.83 (m, 1H), 3.81 (s, 3H); m/z (ES-API-pos) [M+H]=409.

Compounds 321 and 322 were Synthesized in a Similar Fashion.

Data for isomer 2 of [[(1R,3S)-7-[(5-cyano-3-pyridyl)oxy]-1,2,2-trifluoro-3-hydroxy-indan-4-yl]-methyl-oxo-$\lambda^6$-sulfanylidene]cyanamide (Compound 321)

(12.1 mg, 0.03 mmol, 40% yield); $^1$H NMR (400 MHz, CD$_3$COCD$_3$): δ 8.97-8.96 (m, 1H), 8.96-8.94 (m, 1H), 8.35 (dd, 1H), 8.25 (dd, 1H), 7.45 (d, 1H), 6.50 (brs, 1H), 6.16 (dd, 1H), 5.68-5.30 (m, 1H), 3.80 (s, 3H); m/z (ES-API-pos) [M+H]=409.

Data for isomer 2 of [[(1R,3R)-7-(3-cyano-5-fluoro-phenoxy)-1,2,2-trifluoro-3-hydroxy-indan-4-yl]-methyl-oxo-$\lambda^6$-sulfanylidene]cyanamide (Compound 322)

(4.9 mg, 0.012 mmol, 16% yield); $^1$H NMR (400 MHz, CD$_3$COCD$_3$): δ 8.95-8.94 (m, 1H), 8.94-8.92 (m, 1H), 8.33 (dd, 1H), 8.19 (dd, 1H), 7.41 (d, 1H), 6.50-6.28 (m, 2H), 5.90-5.85 (m, 1H), 3.70 (s, 3H); m/z (ES-API-pos) [M+H]=409.

Example 323

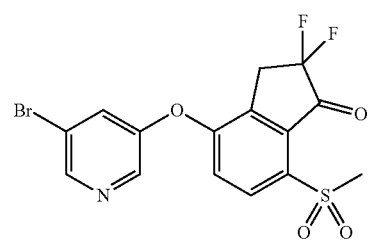 [SMILES: CS(=O)(=O)c1ccc(Oc2cncc(Br)c2)c2c1C(=O)C(F)(F)C2]

4-((5-Bromopyridin-3-yl)oxy)-2,2-difluoro-7-(methylsulfonyl)-2,3-dihydro-1H-inden-1-one (Compound 323)

Step A: Preparation of 4-((5-bromopyridin-3-yl)oxy)-7-(methylsulfonyl)-2,3-dihydro-1H-inden-1-one Prepared in a similar manner to that described in Example 313, Step D and E, substituting 5-bromopyridin-3-ol for 3-cyano-5-hydroxypyridine. LCMS ESI (−) m/z 380, 382 (M−H).

Step B: Preparation of 4-((5-bromopyridin-3-yl)oxy)-2,2-difluoro-7-(methylsulfonyl)-2,3-dihydro-1H-inden-1-one Prepared in a similar manner to that described in Example 163, Step D and E, substituting 4-((5-bromopyridin-3-yl)oxy)-7-(methylsulfonyl)-2,3-dihydro-1H-inden-1-one for 3-fluoro-5-(7-methylsulfonyl-1-oxo-indan-4-yl)oxy-benzonitrile. LCMS ESI (+) m/z 418, 420 (M+H); $^1$H NMR (400 MHz, CD$_3$COCD$_3$): δ 8.65-8.63 (m, 1H), 8.60-8.59 (m, 1H), 8.15-8.12 (m, 1H), 8.02-8.00 (m, 1H), 7.60-7.57 (m, 1H), 3.86-3.79 (m, 2H), 3.39 (s, 3H).

Example 324

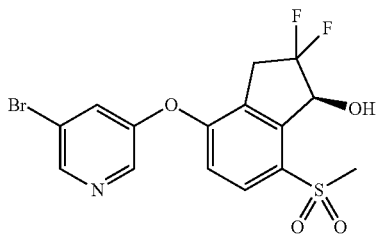 [SMILES: CS(=O)(=O)c1ccc(Oc2cncc(Br)c2)c2c1[C@H](O)C(F)(F)C2]

(S)-4-((5-Bromopyridin-3-yl)oxy)-2,2-difluoro-7-(methylsulfonyl)-2,3-dihydro-1H-inden-1-ol (Compound 324)

Prepared in a similar manner to that described in Example 163, Step F, substituting 4-((5-bromopyridin-3-yl)oxy)-2,2-difluoro-7-(methylsulfonyl)-2,3-dihydro-1H-inden-1-one for 3-(2,2-difluoro-7-methylsulfonyl-1-oxo-indan-4-yl)oxy-5-fluoro-benzonitrile. LCMS ESI (+) m/z 420, 422 (M+H); $^1$H NMR (400 MHz, CDCl$_3$): δ 8.61-8.59 (m, 1H), 8.41-8.39 (m, 1H), 7.91-7.87 (d, 1H), 7.61-7.58 (m, 1H), 6.95-6.9' (d, 1H), 5.63-5.57 (m, 1H), 3.61-3.40 (m, 3H), 3.23 (s, 3H).

Example 325

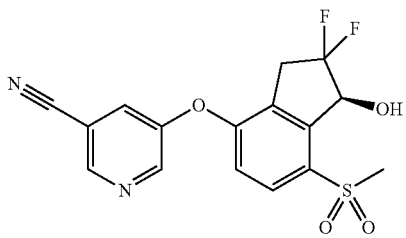 [SMILES: CS(=O)(=O)c1ccc(Oc2cncc(C#N)c2)c2c1[C@H](O)C(F)(F)C2]

(S)-5-((2,2-Difluoro-1-hydroxy-7-(methylsulfonyl)-2,3-dihydro-1H-inden-4-yl)oxy)nicotinonitrile (Compound 325)

(1S)-4-[(5-bromo-3-pyridyl)oxy]-2,2-difluoro-7-methylsulfonyl-indan-1-ol (0.028 g, 0.066 mmol) was combined with zinc powder (7.3 mg, 0.11 mmol) and zinc cyanide (11 mg, 0.093 mmol) in dry DMF (0.25 mL) then the suspension was sparged with argon for several minutes. The solution was treated with dichloro[1,1'-bis(diphenylphosphino)ferrocene]palladium (II) dichloromethane adduct (2.7 mg, 0.003 mmol) and the mixture was sparged again for several minutes then heated to 100° C. for 3 hours in the microwave reactor, then allowed to stand overnight at ambient temperature. The reaction was filtered through celite and the filtered solids were washed with DMF then with ethyl acetate. The filtrate was concentrated in a stream of nitrogen gas to an orange residue. The crude material was chromatographed on SiO$_2$ (Biotage SNAP 10 g) and eluted with a gradient of ethyl acetate/hexane to give Compound 325 as a white solid (17 mg). LCMS ESI (+) m/z 367 (M+H); $^1$H NMR (400 MHz, CDCl$_3$): δ 8.76-8.75 (m, 1H), 8.67-8.66 (m, 1H), 7.95 (d, 1H), 7.70-7.68 (m, 1H), 6.98 (d, 1H), 5.60 (d, 1H), 3.57-3.35 (m, 3H), 3.22 (s, 3H).

Example 326

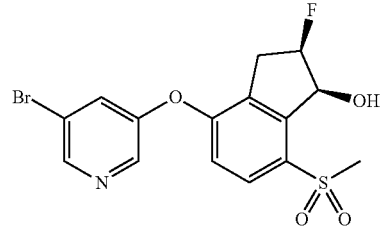 [SMILES: CS(=O)(=O)c1ccc(Oc2cncc(Br)c2)c2c1[C@H](O)[C@H](F)C2]

(1S,2R)-4-((5-Bromopyridin-3-yl)oxy)-2-fluoro-7-(methylsulfonyl)-2,3-dihydro-1H-inden-1-ol (Compound 326)

Prepared in a similar manner to that described in Example 231, substituting 4-((5-bromopyridin-3-yl)oxy)-7-(methylsulfonyl)-2,3-dihydro-1H-inden-1-one for 3-fluoro-5-(7-methylsulfonyl-1-oxo-indan-4-yl)oxy-benzonitrile to provide Compound 326. LCMS ESI (+) m/z 402, 404 (M+H); $^1$H NMR (400 MHz, CDCl$_3$): δ 8.57-8.56 (m, 1H), 8.39-8.38 (m, 1H), 7.88 (d, 1H), 7.56-7.54 (m, 1H), 6.91 (d, 1H), 5.72-5.65 (m, 1H), 5.51-5.47 (m, 0.5H), 5.38-5.34 (m, 0.5H), 3.71-3.69 (m, 1H), 3.38-3.09 (m, 3H), 3.29 (s, 3H)

Example 327

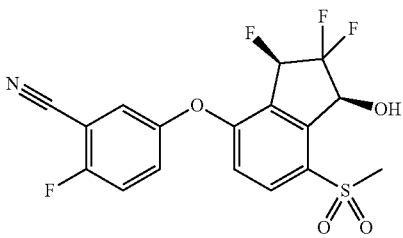 [SMILES: CS(=O)(=O)c1ccc(Oc2ccc(F)c(C#N)c2)c2c1[C@H](O)C(F)(F)[C@@H]2F]

2-Fluoro-5-(((1S,3R)-2,2,3-trifluoro-1-hydroxy-7-(methylsulfonyl)-2,3-dihydro-1H-inden-4-yl)oxy)benzonitrile (Compound 327)

Step A: Preparation of 4,7-difluoro-1H-indene-1,3(2H)-dione

A solution of 3,6 difluorophthalic anhydride (4.25 g, 23.1 mmol), tert-butyl 3-oxobutanoate (4.29 mL, 25.9 mmol) and acetic anhydride (21.0 mL, 221.6 mmol) at 25° C. was treated with triethylamine (11.7 mL, 84.3 mmol) and stirred at ambient temperature for 18 hours. The reaction mixture was cooled to 0° C. and treated with 10% hydrochloric acid (65 mL, 211 mmol) by dropwise addition. Once the addition was complete, the ice bath was removed and the mixture stirred at ambient for 10 minutes. The mixture was then heated to 75° C. for 10 minutes. During this time gas evolution was observed. The suspension slowly broke up to form a clear red mixture. The reaction mixture was poured into 100 mL of water and extracted with 3×50 mL $CH_2Cl_2$. The combined organics were dried with $MgSO_4$, filtered, and concentrated to dryness. The product was used without further purification.

Step B: Preparation of 2,2,4,7-tetrafluoro-1H-indene-1,3(2H)-dione

A solution of the unpurified 4,7-difluoro-1H-indene-1,3(2H)-dione (4.2 g, 23.1 mmol) in acetonitrile (100 mL) cooled in a 25° C. water bath was treated with sodium carbonate (5.38 g, 50.7 mmol). Selectfluor® (17.97 g, 50.7 mmol) was added and the reaction mixture was stirred at ambient temperature for 1 hour. Volatiles were removed under reduced pressure and the residue was poured into 100 mL of 0.1% HCl and extracted with 3×50 mL EtOAc. The combined organics were rinsed with 40 mL of brine, dried with $MgSO_4$, filtered, and concentrated to dryness. The residue was purified by flash chromatography on silica gel 1:1 hexane/ethyl acetate to give 2,2,4,7-tetrafluoro-1H-indene-1,3(2H)-dione (3.5 g, 70%) as a solid. $^1$H NMR (400 MHz, $CDCl_3$): δ 7.70 (t, 2H).

Step C: Preparation of (S)-2,2,4,7-tetrafluoro-3-hydroxy-2,3-dihydro-1H-inden-1-one To a solution of 2,2,4,7-tetrafluoro-1H-indene-1,3(2H)-dione (3.48 g, 16.0 mmol) in dichloromethane (150 mL) at 0° C. was added formic acid (600 μL, 16.0 mmol) and triethylamine (1.55 mL, 11.2 mmol). The resulting mixture was sparged with nitrogen for 5 minutes and then RuCl(p-cymene)[(S,S)-Ts-DPEN] (203.6 mg, 0.32 mmol) was added. The reaction vessel was sealed and put into a 4° C. refrigerator to stand for 18 hours. The reaction mixture was poured into 40 mL 1 N HCl. The $CH_2Cl_2$ layer was separated and the aqueous layer extracted with ethyl acetate (2×50 mL). The combined organics were dried with $Na_2SO_4$, filtered and concentrated under reduced pressure. The residue was purified by flash chromatography on silica gel using 25% EtOAc/hexane to give (S)-2,2,4,7-tetrafluoro-3-hydroxy-2,3-dihydro-1H-inden-1-one (2.9 g, 83%) as an oil. $^1$H NMR (400 MHz, $CDCl_3$): δ 7.51 (ddd, 1H), 7.29-7.23 (m, 1H), 5.44 (dd, 1H), 2.79 (dd, 1H).

Step D: Preparation of (S)-2,2,4-trifluoro-3-hydroxy-7-(methylthio)-2,3-dihydro-1H-inden-1-one A solution of (S)-2,2,4,7-tetrafluoro-3-hydroxy-2,3-dihydro-1H-inden-1-one (966 mg, 4.39 mmol) in acetonitrile (40 mL) at 0° C. was sparged with nitrogen for 5 minutes and treated with sodium thiomethoxide (353.7 mg, 5.05 mmol). The ice bath was removed and the reaction mixture was allowed to stir at ambient temperature for 2 hours. The reaction mixture was evaporated and the residue partitioned between 40 mL of EtOAc and 40 mL of water. The aqueous layer was further extracted with 2×40 mL of EtOAc. The combined organic extracts were washed with brine, dried over $MgSO_4$, filtered, and evaporated. The residue was chromatographed on silica using 10-60% EtOAc/hexane to afford (S)-2,2,4-trifluoro-3-hydroxy-7-(methylthio)-2,3-dihydro-1H-inden-1-one (870 mg, 80%) as a yellow solid. LCMS ESI (+) m/z 249 (M+H).

Step E: Preparation of (S)-2,2,4-trifluoro-3-hydroxy-7-(methylsulfonyl)-2,3-dihydro-1H-inden-1-one (S)-2,2,4-trifluoro-3-hydroxy-7-(methylthio)-2,3-dihydro-1H-inden-1-one (400 mg, 1.6 mmol) was dissolved in MeOH (10 mL) and the reaction was treated dropwise with a solution of Oxone® (2.18 g, 3.55 mmol) dissolved in water (10 mL). The mixture was stirred at ambient temperature for 14 hours. The reaction mixture was filtered, the solids were washed with ethyl acetate and the filtrate was concentrated in vacuo. The aqueous filtrate was extracted 3×30 mL of EtOAc and then the combined organics were washed with saturated NaCl, dried over $Na_2SO_4$ and concentrated in vacuo to a yellow solid that was used without further purification (467 mg). LCMS ESI (+) m/z 281.1 (M+H).

Step F: Preparation of (R)-2,2,3,4-tetrafluoro-7-(methylsulfonyl)-2,3-dihydro-1H-inden-1-one (S)-2,2,4-trifluoro-3-hydroxy-7-(methylsulfonyl)-2,3-dihydro-1H-inden-1-one (450 mg, 1.6 mmol) was dissolved in dichloromethane (16 mL), cooled to 0° C. and treated dropwise with diethylaminosulfur trifluoride (0.32 mL, 2.4 mmol) and the mixture was stirred at 0° C. for 2 hours, then the whole homogeneous reaction mixture was placed into the refrigerator overnight. The reaction was treated with additional diethylaminosulfur trifluoride (0.32 mL, 2.4 mmol) and stirring continued for 6 hours at 0° C. The cold reaction was treated with saturated $NaHCO_3$ (10 mL) and stirred vigorously for 20 minutes. The mixture was diluted with additional methylene chloride and the layers were separated. The aqueous was re-extracted with methylene chloride and the combined organic layers were dried over $Na_2SO_4$ and concentrated in vacuo to a yellow solid. The crude material was chromatographed on $SiO_2$ (Biotage SNAP Ultra) and eluted with a gradient of ethyl acetate/hexanes. The desired material was concentrated to a pale yellow solid (258 mg). LCMS ESI (+) m/z 283 (M+H).

Step G: Preparation of (R)-2-fluoro-5-((2,2,3-trifluoro-7-(methylsulfonyl)-1-oxo-2,3-dihydro-1H-inden-4-yl)oxy)benzonitrile (3R)-2,2,3,4-Tetrafluoro-7-methylsulfonyl-indan-1-one (0.066 g, 0.24 mmol) and 2-fluoro-5-hydroxybenzenecarbonitrile (35 mg, 0.26 mmol) were dissolved in DMF (1 mL) and treated with cesium bicarbonate (59 mg, 0.31 mmol). The mixture was stirred at ambient temperature for 3 hours. The reaction was concentrated in a stream of nitrogen to remove most of the DMF then redissolved in dichloromethane. The crude material was chromatographed on $SiO_2$ (Biotage SNAP) and eluted with a gradient of ethyl acetate/ hexane. The product was concentrated to colorless oil (97 mg). LCMS ESI (+) m/z 400.1 (M+H).

Step H: Preparation of 2-fluoro-5-(((1S,3R)-2,2,3-trifluoro-1-hydroxy-7-(methylsulfonyl)-2,3-dihydro-1H-inden-4-yl)oxy)benzonitrile Compound 327):

2-Fluoro-5-[(3R)-2,2,3-trifluoro-7-methylsulfonyl-1-oxo-indan-4-yl]oxy-benzonitrile (0.097 g, 0.24 mmol) was suspended in methylene chloride (1.6 mL), cooled to 0° C. and treated with triethylamine (0.068 mL, 0.49 mmol), formic acid (0.027 mL, 0.73 mmol) and RuCl(p-cymene)(R,R)-Ts-DPEN] (1.5 mg, 0.002 mmol). The reaction mixture was stirred at 0° C. in the refrigerator for 14 hours. The mixture was concentrated in a stream of nitrogen gas then chromatographed on $SiO_2$ (Biotage SNAP) and eluted with a gradient of ethyl acetate/hexane to provide Compound 327 as off-white solid (26 mg). LCMS ESI (+) m/z 402 (M+H); $^1$H NMR (400 MHz, $CDCl_3$): δ 8.10-8.06 (m, 1H), 7.44-7.32 (m, 3H), 6.91 (d, 1H), 5.95-5.91 (m, 0.5H), 5.81-5.78 (m, 0.5H), 5.70-5.64 (m, 1H), 4.00-3.97 (m, 1H), 3.24 (s, 3H).

Example 328

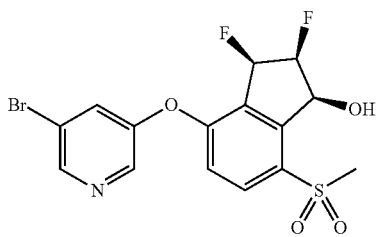 [SMILES: CS(=O)(=O)c1ccc(Oc2cncc(Br)c2)c2c1[C@H](O)[C@H](F)[C@@H]2F]

(1S,2S,3R)-4-((5-Bromopyridin-3-yl)oxy)-2,3-difluoro-7-(methylsulfonyl)-2,3-dihydro-1H-inden-1-ol (Compound 328)

Step A: Preparation of (1S,2R)-4-((5-bromopyridin-3-yl)oxy)-2-fluoro-7-(methylsulfonyl)-2,3-dihydro-1H-inden-1-ol Prepared in a similar manner to that described in Example 313, Steps D-G substituting 5-bromopyridin-3-ol for 3-cyano-5-hydroxypyridine in Step D. LCMS ESI (+) m/z 402, 404 (M+H).

Step B: Preparation of (1S,2R)-4-((5-bromopyridin-3-yl)oxy)-2-fluoro-7-(methylsulfonyl)-2,3-dihydro-1H-inden-1-yl acetate (1S,2R)-4-[(5-Bromo-3-pyridyl)oxy]-2-fluoro-7-methylsulfonyl-indan-1-ol (0.88 g, 2.2 mmol) was dissolved in dichloromethane (21 mL), treated with 4-dimethylaminopyridine (80 mg, 0.66 mmol) and triethylamine (0.61 mL, 4.4 mmol) then cooled to 0° C. The mixture was treated dropwise with acetic anhydride (0.41 mL, 4.4 mmol) then allowed to warm to ambient temperature and stirred for 2 hours. The mixture was diluted with additional methylene chloride and washed with water, 1N $KHSO_4$, water, one-half saturated $NaHCO_3$, dried over $Na_2SO_4$ and concentrated in vacuo to white solid (0.97 g). LCMS ESI (+) m/z 444, 446 (M+H).

Step C: Preparation of (1S,2S)-3-bromo-4-((5-bromopyridin-3-yl)oxy)-2-fluoro-7-(methylsulfonyl)-2,3-dihydro-1H-inden-1-yl acetate

[(1S,2R)-4-[(5-Bromo-3-pyridyl)oxy]-2-fluoro-7-methylsulfonyl-indan-1-yl] acetate (0.97 g, 2.2 mmol) was dissolved in 1,2-dichloroethane (13 mL) and treated with freshly-recrystallized N-bromosuccinimide (427 mg, 2.4 mmol) and azobisisobutyronitrile (36 mg, 0.22 mmol). The reaction mixture was placed under an argon atmosphere and heated to 80° C. for 30 minutes. Two additional portions of fresh azobisisobutyronitrile (36 mg, 0.22 mmol) were added at 30 minute intervals. After 100 minutes, the reaction was cooled and concentrated in vacuo. The residue was dissolved with methylene chloride, washed with saturated $NaHCO_3$, saturated NaCl, dried over $Na_2SO_4$ and concentrated in vacuo to orange residue. This crude mixture isomers (1.1 g), was used without further purification. LCMS ESI (+) m/z 522, 524, 526 (M+H).

Step D: Preparation of (1S,2R,3S)-4-((5-bromopyridin-3-yl)oxy)-2-fluoro-3-hydroxy-7-(methylsulfonyl)-2,3-dihydro-1H-inden-1-yl acetate

[(1S,2S)-3-Bromo-4-[(5-bromo-3-pyridyl)oxy]-2-fluoro-7-methylsulfonyl-indan-1-yl] acetate (1.1 g, 2.1 mmol) was dissolved in 1,2-dimethoxyethane (15 mL) and water (0.07 mL) and the solution was treated with silver perchlorate hydrate (710 mg, 3.2 mmol). The mixture was heated to 70° C. for 1.5 hours. The reaction was cooled, diluted with hexane then with ethyl acetate and filtered through celite. The filtrate was concentrated in vacuo to an insoluble residue. The oily solid was dissolved in ethyl acetate/methylene chloride and concentrated onto powdered $Na_2SO_4$. The dry load was placed atop a column pre-equilibrated with 20% ethyl acetate/hexane and chromatographed on $SiO_2$ (Biotage SNAP Ultra 100 g) eluting with a gradient of MeOH/methylene chloride. The mixed fractions from the first column were concentrated to a yellow oil and re-chromatographed on $SiO_2$ (Biotage SNAP Ultra 25 g) and eluted with a gradient of ethyl acetate/hexane to give a colorless oil (33 mg). LCMS ESI (+) m/z 460, 462 (M+H).

Step E: Preparation of (1S,2S,3R)-4-((5-bromopyridin-3-yl)oxy)-2,3-difluoro-7-(methylsulfonyl)-2,3-dihydro-1H-inden-1-yl acetate

[(1S,2R,3S)-4-[(5-Bromo-3-pyridyl)oxy]-2-fluoro-3-hydroxy-7-methylsulfonyl-indan-1-yl] acetate (0.053 g, 0.12 mmol) was dissolved in dichloromethane (1.2 mL), cooled to 0° C. and treated dropwise with diethylaminosulfur trifluoride (0.023 mL, 0.17 mmol) then stirred at 0° C. for 1 hour. The mixture was removed from the ice bath and allowed to warm to ambient temperature for 30 minutes, then the reaction was recooled to 0° C., treated with saturated $NaHCO_3$ (5 mL) and stirred vigorously for 20 minutes. The mixture was diluted with additional dichloromethane and separated. The aqueous was washed twice with dichloromethane and the combined organic layers were dried over $Na_2SO_4$ and concentrated in vacuo. The crude product was chromatographed on $SiO_2$ (Biotage SNAP Ultra 10 g) and eluted with a gradient of ethyl acetate/hexane to give a colorless film (47 mg). LCMS ESI (+) m/z 462, 464 (M+H).

Step F: Preparation of (1S,2S,3R)-4-((5-bromopyridin-3-yl)oxy)-2,3-difluoro-7-(methylsulfonyl)-2,3-dihydro-1H-inden-1-ol (Compound 328)

[(1S,2S,3R)-4-[(5-bromo-3-pyridyl)oxy]-2,3-difluoro-7-methylsulfonyl-indan-1-yl] acetate (0.046 g, 0.10 mmol) was dissolved in THF/MeOH (1:1, 1.25 mL), cooled to 0° C., and treated with a solution containing lithium hydroxide hydrate (7.9 mg, 0.20 mmol) in water (0.65 mL). The reaction was stirred at 0° C. for 90 minutes. The reaction was quenched at 0° C. with 10% citric acid to pH 4 then saturated NaHCO₃ was added to pH 8. The aqueous was extracted three times with ethyl acetate and the combined organics were washed with saturated NaHCO₃, saturated NaCl, dried over Na₂SO₄ and concentrated in vacuo. The crude material was chromatographed on SiO₂ (Biotage SNAP 10 g) and eluted with a gradient of ethyl acetate/hexane. The fractions were assayed by LCMS and those containing pure product were combined and concentrated in vacuo to give Compound 328 as white film (28 mg). LCMS ESI (+) m/z 420, 422 (M+H); ¹H NMR (400 MHz, CDCl₃): δ 8.63-8.61 (m, 1H), 8.45-8.43 (m, 1H), 8.11-8.07 (m, 1H), 7.66-7.64 (m, 1H), 6.96 (d, 1H), 6.13-6.11 (m, 0.5H), 5.99-5.97 (m, 0.5H), 5.86-5.82 (m, 1H), 5.24-5.04 (m, 1H), 3.30 (s, 3H), 3.03-3.00 (m, 1H).

Example 329

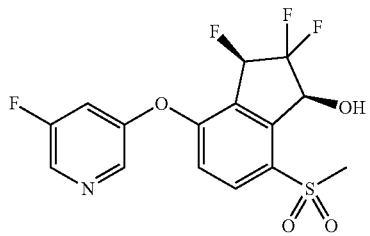 [SMILES: CS(=O)(=O)c1ccc(Oc2cncc(F)c2)c2c1[C@H](O)C(F)(F)[C@@H]2F]

(1S,3R)-2,2,3-trifluoro-4-((5-fluoropyridin-3-yl)oxy)-7-(methylsulfonyl)-2,3-dihydro-1H-inden-1-ol (Compound 329)

Prepared in a similar manner to that described in Example 327 substituting 5-fluoropyridin-3-ol for 2-fluoro-5-hydroxybenzenecarbonitrile in Step C. LCMS ESI (+) m/z 378 (M+H); ¹H NMR (400 MHz, CDCl₃): δ 8.49-8.47 (m, 1H), 8.39-8.37 (m, 1H), 8.11-8.07 (m, 1H), 7.29-7.25 (m, 1H), 7.00 (d, 1H), 5.96-5.93 (m, 0.5H), 5.83-5.79 (m, 0.5H), 5.71-5.65 (m, 1H), 3.65-3.63 (m, 1H), 3.24 (s, 3H).

Example 330

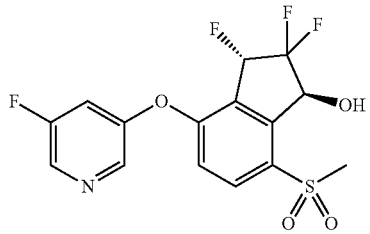 [SMILES: CS(=O)(=O)c1ccc(Oc2cncc(F)c2)c2c1[C@H](O)C(F)(F)[C@H]2F]

(1S,3S)-2,2,3-trifluoro-4-((5-fluoropyridin-3-yl)oxy)-7-(methylsulfonyl)-2,3-dihydro-1H-inden-1-ol (Compound 330)

Prepared in a similar manner to that described in Example 327 substituting 5-fluoropyridin-3-ol for 2-fluoro-5-hydroxybenzenecarbonitrile in Step C. LCMS ESI (+) m/z 378 (M+H); ¹H NMR (400 MHz, CDCl₃): δ 8.49-8.46 (m, 1H), 8.39-8.36 (m, 1H), 8.08-8.04 (m, 1H), 8.28-8.24 (m, 1H), 6.98 (d, 1H), 6.12-6.08 (m, 0.5H), 5.99-5.95 (m, 0.5H), 5.88-5.81 (m, 1H), 4.10-4.06 (m, 1H), 3.26 (s, 3H).

Example 331

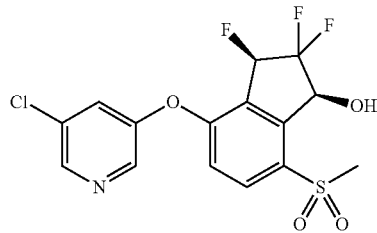 [SMILES: CS(=O)(=O)c1ccc(Oc2cncc(Cl)c2)c2c1[C@H](O)C(F)(F)[C@@H]2F]

(1S,3R)-4-((5-chloropyridin-3-yl)oxy)-2,2,3-trifluoro-7-(methylsulfonyl)-2,3-dihydro-1H-inden-1-ol (Compound 331)

Prepared in a similar manner to that described in Example 327 substituting 5-chloropyridin-3-ol for 2-fluoro-5-hydroxybenzenecarbonitrile in Step C. LCMS ESI (+) m/z 394, 396 (M+H); ¹H NMR (400 MHz, CDCl₃): δ 8.56-8.55 (m, 1H), 8.44-8.43 (m, 1H), 8.11-8.08 (m, 1H), 7.54-7.52 (m, 1H), 6.99 (d, 1H), 5.96-5.92 (m, 0.5H), 5.83-5.79 (m, 0.5H), 5.71-5.65 (m, 1H), 3.66-3.64 (m, 1H), 3.25 (s, 3H).

Example 332

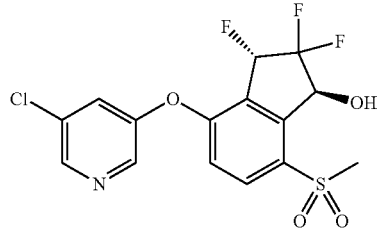 [SMILES: CS(=O)(=O)c1ccc(Oc2cncc(Cl)c2)c2c1[C@H](O)C(F)(F)[C@H]2F]

(1S,3S)-4-((5-chloropyridin-3-yl)oxy)-2,2,3-trifluoro-7-(methylsulfonyl)-2,3-dihydro-1H-inden-1-ol (Compound 332)

Prepared in a similar manner to that described in Example 327 substituting 5-chloropyridin-3-ol for 2-fluoro-5-hydroxybenzenecarbonitrile in Step C. LCMS ESI (+) m/z 394, 396 (M+H); ¹H NMR (400 MHz, CDCl₃): δ 8.56-8.54 (m, 1H), 8.43-8.41 (m, 1H), 8.08-8.04 (m, 1H), 7.52-7.50 (m, 1H), 6.96 (d, 1H), 6.12-6.08 (m, 0.5H), 5.98-5.94 (m, 0.5H), 5.88-5.81 (m, 1H), 4.02-3.99 (m, 1H), 3.26 (s, 3H).

Example 333

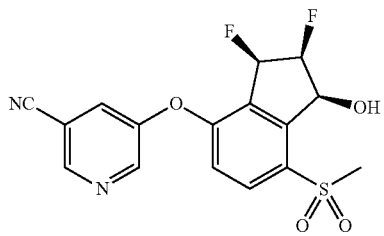 [SMILES: CS(=O)(=O)c1ccc(Oc2cncc(C#N)c2)c2c1[C@H](O)[C@H](F)[C@@H]2F]

5-(((1S,2S,3R)-2,3-difluoro-1-hydroxy-7-(methylsulfonyl)-2,3-dihydro-1H-inden-4-yl)oxy)nicotinonitrile (Compound 333)

(1S,2S,3R)-4-[(5-Bromo-3-pyridyl)oxy]-2,3-difluoro-7-methylsulfonyl-indan-1-ol (0.015 g, 0.035 mmol) was combined with zinc powder (4.0 mg, 0.06 mmol) and zinc cyanide (5.9 mg, 0.05 mmol) in dry DMF (0.25 mL) then the suspension was sparged with argon for several minutes. The solution was treated with dichloro[1,1'-bis(diphenylphosphino)ferrocene]palladium (II) dichloromethane adduct (1.4 mg, 0.0018 mmol) and the mixture was sparged again for several minutes then heated to 150° C. for 2 hours in the microwave reactor. The solvent was removed in a stream of nitrogen gas. The residue was chromatographed on $SiO_2$ (Biotage SNAP 10) and eluted with a gradient of ethyl acetate/hexane. The desired material was concentrated to afford Compound 333 as white solid (8.5 mg). LCMS ESI (+) m/z 367 (M+H); $^1$H NMR (400 MHz, $CD_3COCD_3$): δ 8.88-8.86 (m, 1H), 8.82-8.80 (m, 1H), 8.13-8.08 (m, 2H), 7.33 (d, 1H), 6.21-6.18 (m, 0.5H), 6.07-6.04 (m, 0.5H), 5.83-5.79 (m, 1H), 5.36-5.29 (m, 0.5H), 5.25-5.16 (m, 0.5H), 5.07-5.04 (m, 1H), 3.33 (s, 3H).

Example 334

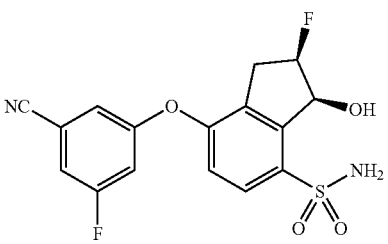 [SMILES: N#Cc1cc(F)cc(Oc2ccc(S(N)(=O)=O)c3c2C[C@@H](F)[C@H]3O)c1]

(2R,3S)-7-(3-cyano-5-fluoro-phenoxy)-2-fluoro-3-hydroxy-indane-4-sulfonamide (Compound 334)

Prepared similarly as described in Example 231 substituting 3-fluoro-5-(7-methylsulfonyl-1-oxo-indan-4-yl)oxybenzonitrile with 7-(3-cyano-5-fluoro-phenoxy)-3-oxo-indane-4-sulfonamide in step A. LCMS ESI (−) m/z 365 (M−H); $^1$H NMR (400 MHz, $CD_3OD$): δ 7.87 (d, 1H), 7.42-7.35 (m, 1H), 7.26-7.13 (m, 2H), 7.08 (d, 1H), 5.63-5.51 (m, 1H), 5.40-5.18 (m, 1H), 3.20-3.15 (m, 2H).

Example 335

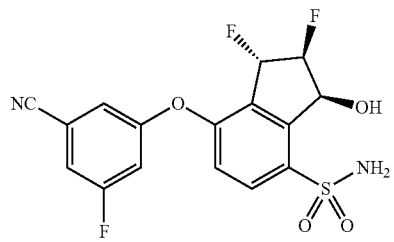 [SMILES: N#Cc1cc(F)cc(Oc2ccc(S(N)(=O)=O)c3c2[C@H](F)[C@@H](F)[C@H]3O)c1]

(1S,2S,3S)-7-(3-cyano-5-fluoro-phenoxy)-1,2-difluoro-3-hydroxy-indane-4-sulfonamide (Compound 335)

Step A: [(1S,2R)-7-(acetylsulfamoyl)-4-(3-cyano-5-fluoro-phenoxy)-2-fluoro-indan-1-yl] acetate To a stirred solution of (2R,3S)-7-(3-cyano-5-fluoro-phenoxy)-2-fluoro-3-hydroxy-indane-4-sulfonamide (0.115 g, 0.32 mmol) in DCM (3 mL) was added 4-(dimethylamino)pyridine (0.012 g, 0.097 mmol) and triethylamine (0.090 mL, 0.64 mmol). Acetic anhydride (0.061 mL, 0.64 mmol) was added dropwise at 0° C. under nitrogen. The reaction mixture was allowed to warm to ambient temperature and stirred overnight. The reaction mixture was diluted with DCM, washed with saturated aqueous $NaHCO_3$ and brine, dried and concentrated. The residue was purified by column chromatography on silica gel (20-50% EtOAc/hexane) to give [(1S,2R)-7-(acetylsulfamoyl)-4-(3-cyano-5-fluoro-phenoxy)-2-fluoro-indan-1-yl] acetate (0.111 g, 77%). LCMS ESI (−) m/z 449 (M−H).

Step B: [(1S,2S)-7-(acetylsulfamoyl)-3-bromo-4-(3-cyano-5-fluoro-phenoxy)-2-fluoro-indan-1-yl] acetate To a stirred solution of [(1S,2R)-7-(acetylsulfamoyl)-4-(3-cyano-5-fluoro-phenoxy)-2-fluoro-indan-1-yl] acetate (111 mg, 0.25 mmol) in DCE (2.7 mL) was added N-bromosuccinimide (66 mg, 0.37 mmol) and 2,2'-azobisisobutyronitrile (0.8 mg, 0.005 mmol). The reaction mixture was heated at 80° C. for 3 hours. After cooling, the reaction mixture was diluted with DCM, washed with saturated aqueous $NaHCO_3$ and brine, dried and concentrated. The residue was purified by column chromatography on silica gel (30-75% EtOAc/hexane) to give [(1S,2S)-7-(acetylsulfamoyl)-3-bromo-4-(3-cyano-5-fluoro-phenoxy)-2-fluoro-indan-1-yl] acetate (144 mg). LCMS ESI (−) m/z 527/529 (M−H).

Step C: [(1S,2R,3R)-7-(acetylsulfamoyl)-4-(3-cyano-5-fluoro-phenoxy)-2-fluoro-3-hydroxy-indan-1-yl] acetate and [(1S,2R,3S)-7-(acetylsulfamoyl)-4-(3-cyano-5-fluoro-phenoxy)-2-fluoro-3-hydroxy-indan-1-yl] acetate To a stirred solution of [(1S,2S)-7-(acetylsulfamoyl)-3-bromo-4-(3-cyano-5-fluoro-phenoxy)-2-fluoro-indan-1-yl] acetate (0.144 g, 0.272 mmol) in 1,2-dimethoxyethane (0.90 mL) and water (0.090 mL) was added silver perchlorate hydrate (0.092 g, 0.41 mmol). The reaction mixture was heated at 70° C. for 30 minutes. After cooling, the reaction mixture was diluted with EtOAc and filtered through Celite. The filtrate was washed with water and brine, dried and concentrated. The residue was purified by column chromatography on silica gel (30-60% EtOAc/hexane) to give [(1S,2R,3S)-7-(acetylsulfamoyl)-4-(3-cyano-5-fluoro-phenoxy)-2-fluoro-3-hydroxy-indan-1-yl] acetate, which were further purified by C18 reverse phase flash chromatography (Biotage Isolera One unit, C18 Flash) with 20-60% CH$_3$CN/water affording [(1S,2R,3S)-7-(acetylsulfamoyl)-4-(3-cyano-5-fluoro-phenoxy)-2-fluoro-3-hydroxy-indan-1-yl] acetate (0.032 g, 25%). LCMS ESI (−) m/z 465 (M−H). Further elution of the silica gel column with 60-80% EtOAc/hexane gave [(1S,2R,3R)-7-(acetylsulfamoyl)-4-(3-cyano-5-fluoro-phenoxy)-2-fluoro-3-hydroxy-indan-1-yl] acetate (0.023 g, 18%). LCMS ESI (−) m/z 465 (M−H).

Step D: [(1S,2S,3S)-7-(acetylsulfamoyl)-4-(3-cyano-5-fluoro-phenoxy)-2,3-difluoro-indan-1-yl] acetate To a stirred solution of [(1S,2R,3R)-7-(acetylsulfamoyl)-4-(3-cyano-5-fluoro-phenoxy)-2-fluoro-3-hydroxy-indan-1-yl] acetate (23 mg, 0.050 mmol) in DCM (0.5 mL) was added (diethylamino)sulfur trifluoride (DAST) (0.013 mL, 0.099 mmol) at −78° C. under nitrogen. The reaction mixture was allowed to warm to 0° C. and stirred for 15 minutes. The reaction was quenched by saturated aqueous NaHCO$_3$ solution. The mixture was partitioned between EtOAc and water. The aqueous layer was extracted with EtOAc. The combined organic layers were washed with brine, dried and concentrated. The residue was purified by flash chromatography on silica gel (20-50% EtOAc/hexanes) to give [(1S,2S,3S)-7-(acetylsulfamoyl)-4-(3-cyano-5-fluoro-phenoxy)-2,3-difluoro-indan-1-yl] acetate (20 mg, 87%). LCMS ESI (−) m/z 467 (M−H).

Step E: N-[(1S,2S,3S)-7-(3-cyano-5-fluoro-phenoxy)-1,2-difluoro-3-hydroxy-indan-4-yl]sulfonylacetamide To a stirred solution of (1S,2S,3S)-7-(acetylsulfamoyl)-4-(3-cyano-5-fluoro-phenoxy)-2,3-difluoro-indan-1-yl] acetate (20 mg, 0.043 mmol) in tetrahydrofuran (0.3 mL) was added 0.5 N LiOH solution (0.26 mL, 0.13 mmol) at 0° C. under nitrogen. The reaction mixture was allowed to warm to ambient temperature and stirred for 3 hours. The reaction was partitioned between EtOAc and water. The aqueous layer was extracted with EtOAc. The combined organic layers were washed with water and brine, dried and concentrated. The crude was used in the next step without further purification. LCMS ESI (+) m/z 425 (M+H).

Step F: (1S,2S,3S)-7-(3-cyano-5-fluoro-phenoxy)-1,2-difluoro-3-hydroxy-indane-4-sulfonamide (Compound 335)

To a stirred solution of N-[(1S,2S,3S)-7-(3-cyano-5-fluoro-phenoxy)-1,2-difluoro-3-hydroxy-indan-4-yl]sulfonylacetamide (18 mg, 0.042 mmol) in tetrahydrofuran (0.3 mL) was added 3 NHCl (0.084 mL, 9.2 mmol). The reaction mixture was heated at reflux for 12 hours. After cooling, the reaction was partitioned between EtOAc and water. The aqueous layer was extracted with EtOAc. The combined organic layers were washed with water and brine, dried and concentrated. The residue was purified by flash chromatography on silica gel (20-50% EtOAc/hexane) to give Compound 335 (8 mg, 49%). LCMS ESI (−) m/z 383 (M−H); $^1$H NMR (400 MHz, CD$_3$OD): δ 8.04 (d, 1H), 7.45-7.41 (m, 1H), 7.31-7.29 (m, 1H), 7.26-7.21 (m, 1H), 7.18 (d, 1H), 6.30-6.11 (m, 1H), 5.80 (t, 1H), 5.37-5.17 (m, 1H).

Example 336

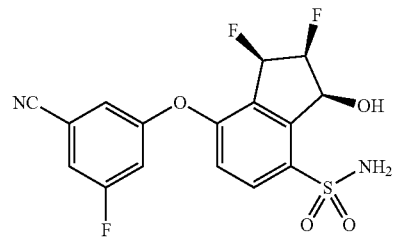 [SMILES: N#Cc1cc(F)cc(Oc2ccc(S(N)(=O)=O)c3c2[C@@H](F)[C@@H](F)[C@H]3O)c1]

(1R,2S,3S)-7-(3-cyano-5-fluoro-phenoxy)-1,2-difluoro-3-hydroxy-indane-4-sulfonamide (Compound 336)

Prepared similarly as described in Example 323 using [(1S,2R,3S)-7-(acetylsulfamoyl)-4-(3-cyano-5-fluoro-phenoxy)-2-fluoro-3-hydroxy-indan-1-yl] acetate in place of [(1S,2R,3R)-7-(acetylsulfamoyl)-4-(3-cyano-5-fluoro-phenoxy)-2-fluoro-3-hydroxy-indan-1-yl] acetate in Step D. LCMS ESI (−) m/z 383 (M−H).

Example 337

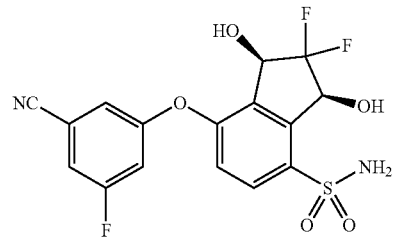 [SMILES: N#Cc1cc(F)cc(Oc2ccc(S(N)(=O)=O)c3c2[C@@H](O)C(F)(F)[C@H]3O)c1]

(1R,3S)-7-(3-cyano-5-fluoro-phenoxy)-2,2-difluoro-1,3-dihydroxy-indane-4-sulfonamide (Compound 337)

Step A: 7'-(3-cyano-5-fluoro-phenoxy)spiro[1,3-dioxolane-2,3'-indane]-4'-sulfonamide To a stirred solution of 7-(3-cyano-5-fluoro-phenoxy)-3-oxo-indane-4-sulfonamide (2.80 g, 8.1 mmol) in DCM (54 mL) was added trimethyl(2-trimethylsilyloxyethoxy)silane (2.78 mL, 11.3 mmol). The reaction mixture was cooled to −78° C. Trimethylsilyl trifluoromethanesulfonate (0.58 mL, 3.2 mmol) was added dropwise under nitrogen. The reaction mixture was allowed to warm to ambient temperature. After stirring for 2 hours, additional trimethyl(2-trimethylsilyloxyethoxy)silane (1.40 mL, 5.60 mmol) was added, and the reaction was stirred at ambient temperature for additional 1 hour. Triethylamine (3.38 mL, 24.3 mmol) was added dropwise. After stirring for 10 minutes, the reaction was concentrated under reduced pressure. The residue was purified by flash chromatography on silica gel (20-50% EtOAc/ hexane) to give 7'-(3-cyano-5-fluoro-phenoxy)spiro 1,3-dioxolane-2,3'-indane]-4'-sulfonamide (1.41 g, 45%). LCMS ESI (−) m/z 389 (M−H).

Step B: 1'-bromo-7'-(3-cyano-5-fluoro-phenoxy) spiro[1,3-dioxolane-2,3'-indane]-4'-sulfonamide To a stirred solution of 7'-(3-cyano-5-fluoro-phenoxy)spiro[1,3-dioxolane-2,3'-indane]-4'-sulfonamide (1.41 g, 3.61 mmol) in DCE (24 mL) was added N-bromosuccinimide (0.707 g, 3.97 mmol) and 2,2'-azobisisobutyronitrile (0.006 g, 0.04 mmol). The reaction mixture was heated at 80° C. for 30 minutes. After cooling, the reaction mixture was diluted with DCM, washed with saturated aqueous NaHCO$_3$ and brine, dried and concentrated. The residue was purified by column chromatography on silica gel (20-50% EtOAc/hexane) to give 1'-bromo-7'-(3-cyano-5-fluoro-phenoxy)spiro[1,3-dioxolane-2,3'-indane]-4'-sulfonamide (1.19 g, 70%). LCMS ESI (+) m/z 467, 469 (M−H).

Step C: 7'-(3-cyano-5-fluoro-phenoxy)-1'-hydroxy-spiro[1,3-dioxolane-2,3'-indane]-4'-sulfonamide To a stirred solution of 1'-bromo-7'-(3-cyano-5-fluoro-phenoxy)spiro[1,3-dioxolane-2,3'-indane]-4'-sulfonamide (1.19 g, 2.54 mmol) in 1,2-dimethoxyethane (21 mL) and water (7 mL) was added disilver carbonate (1.05 g, 3.8 mmol). The reaction mixture was stirred at ambient temperature overnight. The mixture was diluted with EtOAc and filtered through Celite. The filtrate was washed with water and brine, dried and concentrated. The crude was used in the next step without further purification. LCMS ESI (−) m/z 405 (M−H).

Step D: 7'-(3-cyano-5-fluoro-phenoxy)-1'-oxo-spiro[1,3-dioxolane-2,3'-indane]-4'-sulfonamide To a stirred solution of 7'-(3-cyano-5-fluoro-phenoxy)-1'-hydroxy-spiro[1,3-dioxolane-2,3'-indane]-4'-sulfonamide (1.03 g, 2.53 mmol) in DCM (25 mL) was added Dess-Martin periodinane (1.61 g, 3.80 mmol). The reaction mixture was stirred at ambient temperature for 1 hour. The reaction mixture was partitioned between EtOAc and saturated aqueous NaHCO$_3$. The aqueous layer was extracted with EtOAc. The combined organic layers were washed with water and brine, dried and concentrated. The crude was purified by flash chromatography on silica gel (20-60% EtOAc/hexane) to give 7'-(3-cyano-5-fluoro-phenoxy)-1'-oxo-spiro[1,3-dioxolane-2,3'-indane]-4'-sulfonamide (0.460 g, 45%). LCMS ESI (−) m/z 403 (M−H).

Step E: 7-(3-cyano-5-fluoro-phenoxy)-1,3-dioxo-indane-4-sulfonamide

To a stirred solution of 7'-(3-cyano-5-fluoro-phenoxy)-1'-oxo-spiro[1,3-dioxolane-2,3'-indane]-4'-sulfonamide (250 mg, 0.620 mmol) in tetrahydrofuran (3 mL) was added 4 NHCl (1.55 mL, 6.18 mmol). The reaction was heated at 60° C. for 1 hour. After cooling, the reaction mixture was partitioned between EtOAc and water. The aqueous layer was extracted with EtOAc. The combined organic layers were washed with water and brine, dried and concentrated. The crude was used in the next step without further purification. LCMS ESI (−) m/z 359 (M−H).

Step F: 7-(3-cyano-5-fluoro-phenoxy)-2,2-difluoro-1,3-dioxo-indane-4-sulfonamide To a stirred solution of 7-(3-cyano-5-fluoro-phenoxy)-1,3-dioxo-indane-4-sulfonamide (223 mg, 0.620 mmol) in acetonitrile (6 mL) was added sodium carbonate (144 mg, 1.36 mmol) at ambient temperature under nitrogen. Selectfluor® (482 mg, 1.36 mmol) was added and the reaction mixture was stirred at 25° C. for 30 minutes. The reaction mixture was partitioned between EtOAc and water. The aqueous layer was extracted with EtOAc. The combined organic layers were washed with water and brine, dried and concentrated. The residue was purified by flash chromatography on silica gel (20-50% EtOAc/hexanes) to give 7-(3-cyano-5-fluoro-phenoxy)-2,2-difluoro-1,3-dioxo-indane-4-sulfonamide (161 mg, 66%). LCMS ESI (−) m/z 395 (M−H).

Step G: (1R,3S)-7-(3-cyano-5-fluoro-phenoxy)-2,2-difluoro-1,3-dihydroxy-indane-4-sulfonamide (Compound 337)

Formic acid (0.092 mL, 2.4 mmol) was added slowly to a solution of triethylamine (0.227 mL, 1.63 mmol) in DCM (4 mL) at 0° C. 7-(3-cyano-5-fluoro-phenoxy)-2,2-difluoro-1,3-dioxo-indane-4-sulfonamide (161 mg, 0.410 mmol) was then added followed by the addition of RuCl(p-cymene)[(R, R)-Ts-DPEN] (7.8 mg, 0.012 mmol) under nitrogen. The flask was placed in a 4° C. refrigerator overnight. The reaction mixture was diluted with DCM, washed with saturated aqueous NaHCO$_3$ and brine, dried, and concentrated. The residue was purified by flash chromatography on silica gel (20-60% EtOAc/hexane) to give (1S,3S)-7-(3-cyano-5-fluoro-phenoxy)-2,2-difluoro-1,3-dihydroxy-indane-4-sulfonamide (43 mg, 26%). LCMS ESI (−) m/z 399 (M−H). Further elution afforded Compound 337 (26 mg, 16%). LCMS ESI (−) m/z 399 (M−H). $^1$H NMR (400 MHz, CD$_3$OD): δ 8.00 (d, 1H), 7.44-7.41 (m, 1H), 7.35-7.32 (m, 1H), 7.29-7.24 (m, 1H), 7.14 (d, 1H), 5.46 (d, 1H), 5.06 (d, 1H).

Example 338

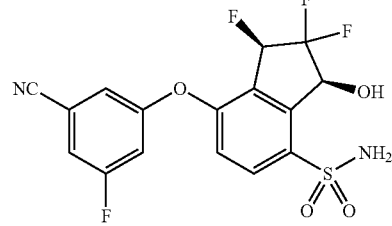

(1R,3S)-7-(3-cyano-5-fluoro-phenoxy)-1,2,2-trifluoro-3-hydroxy-indane-4-sulfonamide (Compound 338)

To a stirred solution of (1S,3S)-7-(3-cyano-5-fluoro-phenoxy)-2,2-difluoro-1,3-dihydroxy-indane-4-sulfonamide (43 mg, 0.11 mmol) in DCM (1 mL) was added (diethylamino)sulfur trifluoride (DAST) (0.028 mL, 0.21 mmol) at −78° C. under nitrogen. The reaction mixture was allowed to warm to 0° C. and stirred for 1 hour. The reaction was quenched by the addition of saturated aqueous NaHCO$_3$. The mixture was partitioned between EtOAc and water. The aqueous layer was extracted with EtOAc. The combined organic layers were washed with brine, dried and concentrated. The residue was dissolved in DCM (1 mL). 5 NHCl in isopropanol (0.3 mL) was added. The reaction mixture was stirred for 15 minutes and then concentrated under reduced pressure. The residue was purified by flash chromatography on silica gel (20-50% EtOAc/hexane) to give Compound 338 (16 mg, 37%). LCMS ESI (−) m/z 401 (M−H); $^1$H NMR (400 MHz, CD$_3$OD): δ 8.03-8.00 (m, 1H), 7.24-7.20 (m, 1H), 7.17-7.15 (m, 1H), 7.08-7.04 (m, 1H), 6.96 (d, 1H), 5.82-5.65 (m, 1H), 5.54-5.48 (m, 1H).

Example 339

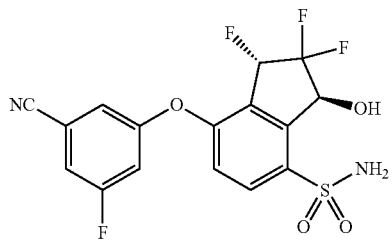 [SMILES: N#Cc1cc(F)cc(Oc2ccc(S(N)(=O)=O)c3c2[C@H](F)C(F)(F)[C@H]3O)c1]

(1S,3S)-7-(3-cyano-5-fluoro-phenoxy)-1,2,2-trifluoro-3-hydroxy-indane-4-sulfonamide (Compound 339)

The title compound was prepared similarly as described in Example 338 from (1R,3S)-7-(3-cyano-5-fluoro-phenoxy)-2,2-difluoro-1,3-dihydroxy-indane-4-sulfonamide. LCMS ESI (−) m/z 401 (M−H); $^1$H NMR (400 MHz, CD$_3$OD): δ 8.09-8.05 (m, 1H), 7.50-7.46 (m, 1H), 7.39-7.38 (m, 1H), 7.33-7.29 (m, 1H), 7.14 (d, 1H), 6.19-6.02 (m, 1H), 5.72-5.65 (m, 1H).

Example 340

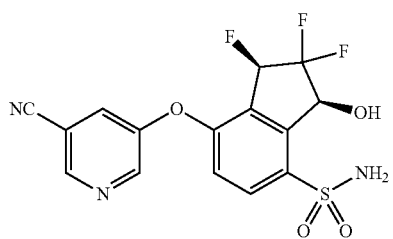 [SMILES: N#Cc1cncc(Oc2ccc(S(N)(=O)=O)c3c2[C@@H](F)C(F)(F)[C@H]3O)c1]

(1R,3S)-7-[(5-cyano-3-pyridyl)oxy]-1,2,2-trifluoro-3-hydroxy-indane-4-sulfonamide (Compound 340)

Step A: (3S)-7-benzylsulfanyl-2,2,4-trifluoro-3-hydroxy-indan-1-one

To a stirred mixture of (3S)-2,2,4,7-tetrafluoro-3-hydroxy-indan-1-one (250 mg, 1.14 mmol) and cesium carbonate (555 mg, 1.7 mmol) in DMF (8 mL) was added dropwise benzyl mercaptan (0.15 mL, 1.3 mmol) at 0° C. under nitrogen. The reaction mixture was stirred at 0° C. for 30 minutes. The reaction was partitioned between EtOAc and water. The aqueous layer was extracted with EtOAc. The combined organic layers were washed with water and brine, dried and concentrated. The residue was purified by flash chromatography on silica gel (20-40% EtOAc/hexane) to give (3S)-7-benzylsulfanyl-2,2,4-trifluoro-3-hydroxy-indan-1-one (350 mg, 95%). LCMS ESI (+) m/z 342 (M+NH$_4^+$).

Step B: (3R)-7-benzylsulfanyl-2,2,3,4-tetrafluoro-indan-1-one

To a stirred solution of (3S)-7-benzylsulfanyl-2,2,4-trifluoro-3-hydroxy-indan-1-one (350 mg, 1.08 mmol) in DCM (10 mL) was added dropwise (diethylamino)sulfur trifluoride (DAST) (0.228 mL, 1.73 mmol) at 0° C. under nitrogen. The reaction mixture was stirred at 0° C. for 5 hours. The reaction was quenched by the addition of saturated aqueous NaHCO$_3$. The mixture was partitioned between EtOAc and water. The aqueous layer was extracted with EtOAc. The combined organic layers were washed with brine, dried and concentrated. The residue was purified by flash chromatography on silica gel (5-20% EtOAc/hexane) to give (3R)-7-benzylsulfanyl-2,2,3,4-tetrafluoro-indan-1-one (210 mg, 60%). LCMS ESI (−) m/z 325 (M−H).

Step C: (1R)-1,2,2,7-tetrafluoro-3-oxo-indane-4-sulfonamide

To a stirred suspension of (3R)-7-benzylsulfanyl-2,2,3,4-tetrafluoro-indan-1-one (290 mg, 0.89 mmol) in acetic acid (9 mL) and water (1 mL) was added N-chlorosuccinimide (356 mg, 2.67 mmol) at 0° C. The reaction mixture was allowed to warm to ambient temperature and stirred for 2 hours. The reaction was partitioned between EtOAc and water. The aqueous layer was extracted with EtOAc. The combined organic layers were washed with water and brine, dried and concentrated. The crude was used in the next step without further purification. The crude was dissolved in DCM (3 mL) and added dropwise to a stirred solution of 0.5 N ammonia in dioxane (8.9 mL, 4.4 mmol) 0° C. under nitrogen. The reaction mixture was stirred for 15 minutes and then concentrated under reduced pressure. The residue was partitioned between EtOAc and water. The organic layer was washed successively with saturated aqueous NaHCO$_3$, water and brine, dried and concentrated. The residue was purified by flash chromatography on silica gel (20-50% EtOAc/hexanes) to give (1R)-1,2,2,7-tetrafluoro-3-oxo-indane-4-sulfonamide (142 mg, 56%). LCMS ESI (+) m/z 284 (M+H).

Step D: (1R)-7-[(5-cyano-3-pyridyl)oxy]-1,2,2-trifluoro-3-oxo-indane-4-sulfonamide A mixture of (1R)-1,2,2,7-tetrafluoro-3-oxo-indane-4-sulfonamide (66 mg, 0.23 mmol), 3-cyano-5-hydroxypyridine (42 mg, 0.35 mmol) and cesium bicarbonate (59 mg, 0.3 mmol) in NMP (2.3 mL) was heated at 60° C. for 1 hour. After cooling, the reaction mixture was partitioned between EtOAc and water. The aqueous layer was extracted with EtOAc. The combined organic layers were washed with water and brine, dried and concentrated. The residue was purified by flash chromatography on silica gel (30-80% EtOAc/hexane) to give (1R)-7-[(5-cyano-3-pyridyl)oxy]-1,2,2-trifluoro-3-oxo-indane-4-sulfonamide (19 mg, 21%). LCMS ESI (−) m/z 382 (M−H).

Step E: (1R,3S)-7-[(5-cyano-3-pyridyl)oxy]-1,2,2-trifluoro-3-hydroxy-indane-4-sulfonamide (Compound 340)

To a stirred solution of (1R)-7-[(5-cyano-3-pyridyl)oxy]-1,2,2-trifluoro-3-oxo-indane-4-sulfonamide (19 mg, 0.05 mmol) in DCM (0.5 mL) were added formic acid (0.0056 mL, 0.15 mmol) and triethylamine (0.014 mL, 0.10 mmol) followed by RuCl(p-cymene)[(R,R)-Ts-DPEN] (0.6 mg, 0.001 mmol) under nitrogen. The flask was then placed in a 4° C. refrigerator overnight. The reaction mixture was concentrated in vacuo. The residue was purified by flash chromatography on silica gel (20-60% EtOAc/hexane) to give Compound 340 (7 mg, 37%). LCMS ESI (−) m/z 384 (M−H); $^1$H NMR (400 MHz, CD$_3$OD): δ 8.81 (d, 1H), 8.73 (d, 1H), 8.11-8.07 (m, 1H), 8.06-8.04 (m, 1H), 7.18 (d, 1H), 6.04-5.86 (m, 1H), 5.57-5.51 (m, 1H).

Example 341

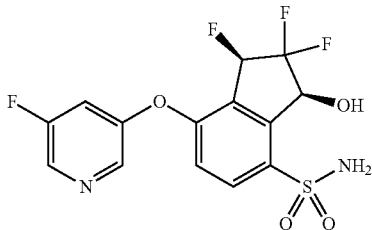 [SMILES: NS(=O)(=O)c1ccc(Oc2cncc(F)c2)c2c1[C@H](O)C(F)(F)[C@@H]2F]

(1R,3S)-1,2,2-trifluoro-7-[(5-fluoro-3-pyridyl)oxy]-3-hydroxy-indane-4-sulfonamide (Compound 341)

Step A: (1R)-1,2,2-trifluoro-7-[(5-fluoro-3-pyridyl)oxy]-3-oxo-indane-4-sulfonamide A mixture of (1R)-1,2,2,7-tetrafluoro-3-oxo-indane-4-sulfonamide (70 mg, 0.25 mmol), 3-fluoro-5-hydroxypyridine (42 mg, 0.37 mmol) and cesium bicarbonate (62 mg, 0.32 mmol) in NMP (1.2 mL) was heated at 60° C. for 8 hours. After cooling, the reaction mixture was partitioned between EtOAc and water. The aqueous layer was extracted with EtOAc. The combined organic layers were washed with water and brine, dried and concentrated. The residue was purified by flash chromatography on silica gel (30-70% EtOAc/hexane) to give (1R)-1,2,2-trifluoro-7-[(5-fluoro-3-pyridyl)oxy]-3-oxo-indane-4-sulfonamide (28 mg, 30%). LCMS ESI (−) m/z 375 (M−H).

Step B: (1R,3S)-1,2,2-trifluoro-7-[(5-fluoro-3-pyridyl)oxy]-3-hydroxy-indane-4-sulfonamide (Compound 341)

To a stirred solution of (1R)-1,2,2-trifluoro-7-[(5-fluoro-3-pyridyl)oxy]-3-oxo-indane-4-sulfonamide (28 mg, 0.070 mmol) in DCM (0.7 mL) were added formic acid (0.0084 mL, 0.22 mmol) and triethylamine (0.021 mL, 0.15 mmol) followed by RuCl(p-cymene)[(R,R)-Ts-DPEN] (1 mg, 0.002 mmol) under nitrogen. The flask was then placed in a 4° C. refrigerator overnight. The reaction mixture was concentrated in vacuo. The residue was purified by flash chromatography on silica gel (20-60% EtOAc/hexane) to give Compound 341 (12 mg, 43%). LCMS ESI (−) m/z 377 (M−H); $^1$H NMR (400 MHz, CD$_3$OD): δ 8.43 (d, 1H), 8.35 (d, 1H), 8.10-8.06 (m, 1H), 7.59-7.54 (m, 1H), 7.15 (d, 1H), 6.03-5.85 (m, 1H), 5.56-5.50 (m, 1H).

Examples 342 and 343

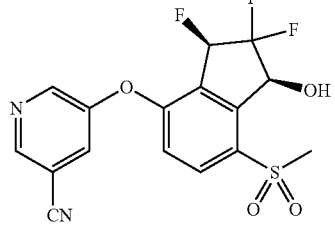

Compound 342

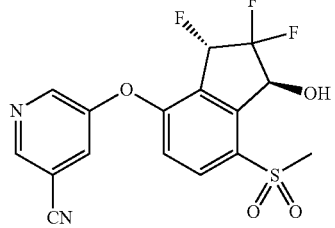

Compound 343

5-(((1S,3R)-2,2,3-trifluoro-1-hydroxy-7-(methylsulfonyl)-2,3-dihydro-1H-inden-4-yl)oxy)nicotinonitrile (Compound 342) and 5-(((1S,3S)-2,2,3-trifluoro-1-hydroxy-7-(methylsulfonyl)-2,3-dihydro-1H-inden-4-yl)oxy)nicotinonitrile (Compound 343)

Prepared similarly according to Example 327, steps C-H, substituting RuCl(p-cymene) (R,R)-Ts-DPEN] for RuCl(p-cymene)[(S,S)-Ts-DPEN] in step C and 3-cyano-5-hydroxypyridine for 2-fluoro-5-hydroxybenzenecarbonitrile in step G.

Data for 5-(((1S,3R)-2,2,3-trifluoro-1-hydroxy-7-(methylsulfonyl)-2,3-dihydro-1H-inden-4-yl)oxy)nicotinonitrile (Compound 342)

LCMS ESI (+) (M+H) m/z 385; $^1$H NMR (400 MHz, CDCl$_3$): δ 8.82 (d, 1H), 8.74 (d, 1H), 8.14 (dd, 1H), 7.74 (dd, 1H), 7.02 (d, 1H), 5.87 (dd, 1H), 5.73-5.66 (m, 1H), 3.58 (d, 1H), 3.26 (s, 3H).

Data for 5 #(1S,3S)-2,2,3-trifluoro-1-hydroxy-7-(methylsulfonyl)-2,3-dihydro-1H-inden-4-yl)oxy)nicotinonitrile (Compound 343)

LCMS ESI (+) (M+H) m/z 385; $^1$H NMR (400 MHz, (CD$_3$)$_2$CO): δ 8.89 (dd, 1H), 8.86 (d, 1H), 8.21 (dd, 1H), 8.11 (dd, 1H), 7.36 (d, 1H), 6.36 (ddd, 1H), 6.10 (d, 1H), 5.87-5.80 (m, 1H), 3.31 (s, 3H).

Examples 344 and 345

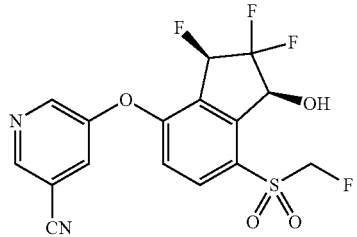

Compound 344

Compound 345

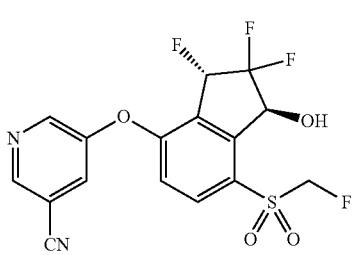

5-(((1S,3R)-2,2,3-trifluoro-7-((fluoromethyl)sulfonyl)-1-hydroxy-2,3-dihydro-1H-inden-4-yl)oxy)nicotinonitrile (Compound 344) and 5-(((1S,3S)-2,2,3-trifluoro-7-((fluoromethyl)sulfonyl)-1-hydroxy-2,3-dihydro-1H-inden-4-yl)oxy)nicotinonitrile (Compound 345)

Step A: Preparation of (R)-2,2,3,4-tetrafluoro-7-(methylthio)-2,3-dihydro-1H-inden-1-one A solution of (S)-2,2,4-trifluoro-3-hydroxy-7-(methylthio)-2,3-dihydro-1H-inden-1-one (402 mg, 1.62 mmol) in dichloromethane (16.2 mL) at 0° C. was treated with diethylaminosulfur trifluoride (390 μL, 2.92 mmol). The ice bath was removed from the resulting reaction mixture and the reaction mixture was stirred for 2 hours at room temperature. Volatiles were removed by concentration under reduced pressure. The residue was suspended in 30 mL of EtOAc, cooled to 0° C., and quenched by the addition of 20 mL of saturated aqueous NaHCO₃. The reaction mixture was vigorously stirred for 30 minutes and then extracted with 3×20 mL EtOAc. The combined organics were rinsed with 10 mL of brine, dried with MgSO₄, filtered, and concentrated to dryness. The product was used without further purification. LCMS ESI (+) (M+H) m/z 251.

Step B: Preparation of (R)-2,2,3,4-tetrafluoro-7-((fluoromethyl)thio)-2,3-dihydro-1H-inden-1-one A solution of (R)-2,2,3,4-tetrafluoro-7-(methylthio)-2,3-dihydro-1H-inden-1-one (393 mg, 1.57 mmol) in acetonitrile (15.7 mL) at 0° C. was treated with Selectfluor® (584.3 mg, 1.65 mmol) and stirred at 0° C. for 2 hours. Volatiles were removed by concentration under reduced pressure. The reaction mixture was poured into 30 mL of water and extracted with 3×20 mL EtOAc. The combined organics were rinsed with 10 mL of brine, dried with MgSO₄, filtered, and concentrated to dryness. Purification was achieved by chromatography on silica using 10-30% EtOAc/hexane to afford (R)-2,2,3,4-tetrafluoro-7-((fluoromethyl)thio)-2,3-dihydro-1H-inden-1-one (153 mg, 36%) as a yellow oil. LCMS ESI (+) (M-F) m/z 249.

Step C: Preparation of (R)-2,2,3,4-tetrafluoro-7-((fluoromethyl)sulfonyl)-2,3-dihydro-1H-inden-1-one A solution of (R)-2,2,3,4-tetrafluoro-7-((fluoromethyl)thio)-2,3-dihydro-1H-inden-1-one (91.8 mg, 0.34 mmol) in a mixture of methanol (3.4 mL) and water (3.4 mL) was treated with Oxone® (252.5 mg, 0.41 mmol). The resulting suspension was heated to 60° C. overnight. Additional Oxone® (252.5 mg, 0.41 mmol) was added and the reaction mixture heated for an additional 6 hours. Volatiles were removed by concentration under reduced pressure. The reaction mixture was poured into 100 mL of water and extracted with 3×25 mL EtOAc. The combined organics were rinsed with 10 mL of brine, dried with MgSO₄, filtered, and concentrated to dryness. Purification was achieved by chromatography on silica using 10-40% EtOAc/hexane to afford (R)-2,2,3,4-tetrafluoro-7-((fluoromethyl)sulfonyl)-2,3-dihydro-1H-inden-1-one as a white solid (73 mg, 71%). LCMS ESI (+) (M+H) m/z 301.

Step D: Preparation of (R)-5 #2,2,3-trifluoro-7-((fluoromethyl)sulfonyl)-1-oxo-2,3-dihydro-1H-inden-4-yl)oxy)nicotinonitrile A solution of (R)-2,2,3,4-tetrafluoro-7-((fluoromethyl)sulfonyl)-2,3-dihydro-1H-inden-1-one (36.9 mg, 0.12 mmol) and 3-cyano-5-hydroxypyridine (14.8 mg, 0.12 mmol) in DMF (1.2 mL) was treated with cesium bicarbonate (28.6 mg, 0.15 mmol) and stirred at 35° C. for 3 hours. The reaction mixture was poured into 30 mL of water and extracted with 3×10 mL Et₂O. The combined organics were rinsed with 10 mL of brine, dried with MgSO₄, filtered, and concentrated to dryness. Purification was achieved by chromatography on silica using 20-60% EtOAc/hexane to afford (R)-5-((2,2,3-trifluoro-7-((fluoromethyl)sulfonyl)-1-oxo-2,3-dihydro-1H-inden-4-yl)oxy)nicotinonitrile (43.4 mg, 88%) as a solid. LCMS ESI (+) m/z 419 (M+H+H₂O).

Step E: Preparation of 54(1S,3R)-2,2,3-trifluoro-7-((fluoromethyl)sulfonyl)-1-hydroxy-2,3-dihydro-1H-inden-4-yl)oxy)nicotinonitrile (Compound 344) and 5-(41S,3S)-2,2,3-trifluoro-7-((fluoromethyl)sulfonyl)-1-hydroxy-2,3-dihydro-1H-inden-4-yl)oxy)nicotinonitrile (Compound 345)

Prepared similarly according to Example 327, step H. Purification was achieved by chromatography on silica using 20-45% EtOAc/hexane to afford Compound 344 (27.3 mg, 59%) and Compound 345 (4.2 mg, 9%).

Data for Compound 344: LCMS ESI (+) (M+H) m/z 403; ¹H NMR (400 MHz, CDCl₃): δ 8.84 (d, 1H), 8.75 (d, 1H), 8.15 (dd, 1H), 7.77 (dd, 1H), 7.02 (d, 1H), 5.83 (dd, 1H), 5.68-5.62 (m, 1H), 5.43 (dd, 1H), 5.31 (dd, 1H), 3.43 (dd, 1H).

Data for Compound 345: LCMS ESI (+) (M+H) m/z 403; ¹HNMR (400 MHz, (CD₃)₂CO): δ 8.93 (dd, 1H), 8.90 (dd, 1H), 8.26 (dd, 1H), 8.13 (dd, 1H), 7.38 (d, 1H), 6.39 (ddd, 1H), 5.73 (dd, 1H), 5.80 (ddd, 1H), 5.61 (dd, 1H).

Example 346

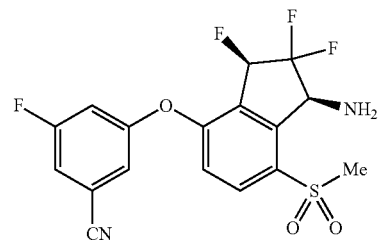 [SMILES: CS(=O)(=O)c1ccc(Oc2cc(F)cc(C#N)c2)c2c1[C@H](N)C(F)(F)[C@@H]2F]

(1S,3R)-2,2,3-trifluoro-4-(3-fluoro-5-(iminomethyl)phenoxy)-7-(methylsulfonyl)-2,3-dihydro-1H-inden-1-amine (Compound 346)

Prepared similarly according to Example 265. Purification was achieved by chromatography on silica using 10-65% EtOAc/hexane to afford Compound 346 as a white solid (10.2 mg, 86%). LCMS ESI (+) (M+H) m/z 401; $^1$H NMR (400 MHz, CDCl$_3$): δ 8.14 (dd, 1H), 7.30 (ddd, 1H), 7.24-7.22 (m, 1H), 7.14 (dt, 1H), 6.98 (d, 1H), 5.77 (dd, 1H), 5.10-5.01 (m, 1H), 3.45 (s, 3H), 1.82 (br d, 2H).

Example 347: Mosher Ester Analysis

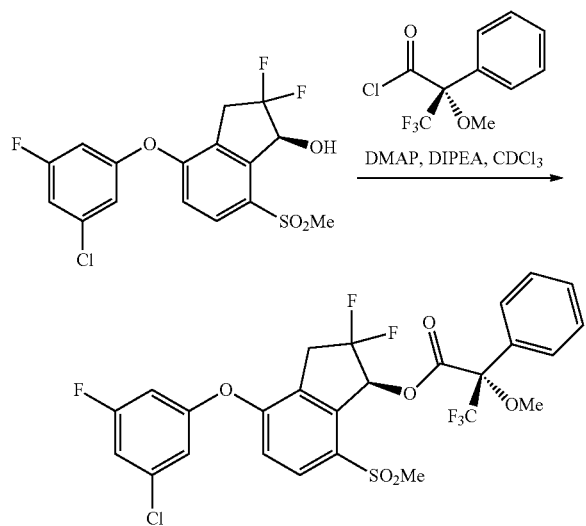

Mosher ester analysis was typically carried out by preparation of the diastereomeric esters in an NMR tube. A typical example: 4-(Dimethylamino)pyridine (0.56 mg, 0.0046 mmol) was added to (1S)-4-(3-chloro-5-fluoro-phenoxy)-2,2-difluoro-7-methylsulfonyl-indan-1-ol (1.8 mg, 0.0046 mmol) and (2R)-3,3,3-trifluoro-2-methoxy-2-phenyl-propanoyl chloride (1.74 mg, 0.0069 mmol) in CDCl$_3$ (0.5 mL) in a NMR tube followed by N,N-diisopropylethylamine (1.18 mg, 0.0092 mmol). The reaction mixture was slightly shaken for 2 minutes then analyzed by $^{19}$FNMR and/or $^1$H NMR to determine the ee of the corresponding alcohol. Diagnostic peaks are between 5.70-5.50 ppm for $^1$H-NMR and −68 to −75 ppm for $^{19}$F-NMR. Compounds that are greater than 95% ee generally had one set of peaks observed corresponding to the Mosher ester as well as a peak corresponding to excess (2R)-3,3,3-trifluoro-2-methoxy-2-phenyl-propanoyl chloride.

An alternative procedure: To a reaction vial equipped with a stir bar was added (1S)-4-(3-chloro-5-fluoro-phenoxy)-2,2-difluoro-7-methylsulfonyl-indan-1-ol (3.6 mg, 0.0092 mmol), DMAP (1.12 mg, 0.0092 mmol), CDCl$_3$ (1.0 mL), (2R)-3,3,3-trifluoro-2-methoxy-2-phenyl-propanoyl chloride (3.48 mg, 0.0138 mmol) and N,N-diisopropylethylamine (2.36 mg, 0.0184 mmol) in that order, then the mixture was stirred up to 24 hours. An aliquot may be taken for analysis by $^{19}$FNMR and/or $^1$H NMR to determine the ee of the corresponding alcohol or the reaction mixture may be diluted with water, extracted with dichloromethane (2×3 mL), washed with saturated NaHCO$_3$ (2 ml), dried over MgSO$_4$, filtered and concentrated in vacuum. The crude mixture is then analyzed by $^{19}$FNMR and/or $^1$H NMR to determine the ee of the corresponding alcohol.

Example 348: HIF-2α Scintillation Proximity Assay (SPA)

The total assay volume was about 100 µL in the following configuration: 2 µL compound in 100% DMSO, 88 µL buffer with protein and probe and 10 µL of SPA beads. The compound was diluted in a master plate consisting of a 10-point dose response with a 3-fold compound dilution from 100 µM to 5 nM. Assays were run on a 96-well plate in which one column, designated as the high signal control, contained DMSO with no compound and another column, designated as the low signal control, contained no protein. Prior to plating out of compound, a buffer solution, consisting of 25 mM TRIS pH 7.5 (Sigma), 150 mM NaCl (Sigma), 15% Glycerol (Sigma), 0.15% BSA (Sigma), 0.001% Tween-20 (Sigma), 150 nM Compound 183 and 100 nM HIF-2α HIS TAG-PASB Domain, was made and allowed to equilibrate for 30 minutes. Compounds that were to be tested were then plated in to a 96-well white clear bottom Isoplate-96 SPA plate (Perkin Elmer). To the compounds, 88 µL of the buffer solution was then added, the plate was covered with a plastic cover and then aluminum foil, placed onto a shaker and equilibrated for 1 hour. After equilibration, 10 µL of a 2 mg/mL solution of YSi Cu His tagged SPA beads (Perkin Elmer) were then added to each well of the plate, covered and equilibrated for another 2 hours. The plates were then removed from the shaker, placed into a 1450 LSC and luminescence counter MicroBeta Trilux (Perkin Elmer) to measure the extent of probe displacement. The percent inhibition was determined and IC$_{50}$ values were calculated using the Dotmatics system based on the following equation: % inhibition=[(high control−sample)/(high control−low control)]×100.

Table 1 shows IC$_{50}$s of Compounds in Scintillation Proximity Assay (SPA).

TABLE 1

Compound IC$_{50}$s in SPA

| Compound Number | Mean SPA IC$_{50}$ (µM) | SD |
|---|---|---|
| 1 | 0.005 | N/A |
| 2 | <0.005 | N/A |
| 3 | 0.34 | 0.03 |
| 4 | 3.3 | N/A |
| 5 | 0.90 | 0.08 |
| 6 | <0.005 | N/A |
| 7b | 3.8 | N/A |
| 7a | 0.047 | N/A |
| 8 | <0.005 | N/A |
| 9 | <0.005 | N/A |
| 11 | <0.005 | N/A |
| 12 | 9.8 | N/A |
| 13 | 6.6 | N/A |
| 14 | 5.2 | N/A |
| 15 | 0.008 | 0.003 |
| 16 | 0.98 | N/A |
| 17 | 0.058 | 0.059 |
| 18 | 0.12 | N/A |
| 19 | 3.8 | N/A |
| 20 | 1.1 | 1.04 |
| 21 | 0.14 | 0.023 |
| 22 | 0.49 | N/A |
| 23 | 6.6 | N/A |
| 24 | 0.92 | N/A |
| 25 | 0.029 | 0.02 |
| 26 | <0.005 | N/A |

TABLE 1-continued

Compound IC$_{50}$s in SPA

| Compound Number | Mean SPA IC$_{50}$ (μM) | SD |
|---|---|---|
| 27 | 0.25 | 0.05 |
| 28 | 49.9 | 71 |
| 29 | 0.022 | N/A |
| 30 | 0.018 | N/A |
| 31 | 0.33 | N/A |
| 32 | 0.018 | N/A |
| 33 | 0.157 | N/A |
| 34 | <0.005 | N/A |
| 35 | 5.7 | 2.3 |
| 36 | 17 | N/A |
| 37 | 6.7 | N/A |
| 38 | 0.071 | N/A |
| 39 | 0.23 | N/A |
| 40 | 0.52 | N/A |
| 41 | 0.067 | N/A |
| 42 | 0.28 | N/A |
| 43 | 0.42 | N/A |
| 44 | 6.8 | 3.8 |
| 45 | 6.1 | 1.4 |
| 46 | 0.4 | 0.16 |
| 47 | 9 | N/A |
| 48 | 0.92 | N/A |
| 49 | 13 | N/A |
| 50 | 0.078 | N/A |
| 51 | 2 | N/A |
| 52 | 0.046 | N/A |
| 53 | 0.33 | N/A |
| 54 | 0.15 | N/A |
| 55 | <0.005 | N/A |
| 56 | <0.005 | N/A |
| 57 | 0.015 | N/A |
| 58 | <0.005 | N/A |
| 59 | <0.005 | N/A |
| 60 | <0.005 | N/A |
| 61 | 0.039 | 0.02 |
| 62 | <0.005 | N/A |
| 63 | <0.005 | N/A |
| 64 | <0.005 | N/A |
| 65 | <0.005 | N/A |
| 66 | 5 | 0.2 |
| 67 | 0.035 | N/A |
| 68 | 3.1 | N/A |
| 69 | 1.3 | N/A |
| 70 | 0.77 | N/A |
| 71 | 0.64 | N/A |
| 72 | 0.51 | N/A |
| 73 | 1.4 | N/A |
| 74 | 0.15 | N/A |
| 75 | 0.24 | N/A |
| 76 | 0.88 | N/A |
| 77 | 1.9 | N/A |
| 78 | 0.88 | N/A |
| 79 | 1.3 | N/A |
| 80 | 0.022 | N/A |
| 81 | 0.29 | N/A |
| 82 | 15 | N/A |
| 83 | 3.2 | N/A |
| 84 | 2.8 | 1.1 |
| 85 | 2.9 | N/A |
| 86 | 71 | 0.0003 |
| 87 | 8.8 | N/A |
| 88 | 14 | N/A |
| 89 | 1.4 | 0.02 |
| 90 | 0.23 | N/A |
| 91 | 0.28 | N/A |
| 92 | 0.037 | N/A |
| 93 | 0.17 | N/A |
| 94 | 0.13 | 0.011 |
| 95 | 3.6 | N/A |
| 96 | 3.1 | N/A |
| 97 | 2.2 | N/A |
| 98 | 0.015 | 0.011 |
| 99 | 0.17 | N/A |
| 100 | 0.094 | N/A |
| 101 | 0.026 | N/A |
| 102 | 0.12 | N/A |
| 103 | 0.30 | N/A |
| 104 | 0.27 | N/A |
| 105 | 12 | N/A |
| 106 | 1.0 | N/A |
| 107 | 0.16 | N/A |
| 108 | 5.8 | 2.7 |
| 109 | 2.1 | 0.012 |
| 110 | 1.6 | 0.32 |
| 111 | 0.015 | 0.008 |
| 112 | 0.04 | 0.007 |
| 113 | 2.3 | N/A |
| 114 | 1.1 | N/A |
| 115 | 0.35 | N/A |
| 116 | 0.15 | N/A |
| 117 | 0.21 | N/A |
| 118 | 0.16 | N/A |
| 119 | 0.071 | N/A |
| 120 | 0.34 | N/A |
| 121 | 16 | N/A |
| 122 | 1.7 | N/A |
| 123 | 0.032 | N/A |
| 124 | 0.038 | N/A |
| 125 | 8 | N/A |
| 126 | 5.8 | N/A |
| 127 | 2.8 | N/A |
| 128 | 0.15 | N/A |
| 129 | 2.2 | N/A |
| 130 | 5.5 | N/A |
| 131 | 0.31 | N/A |
| 132 | 0.31 | N/A |
| 133 | 0.50 | N/A |
| 134 | 0.45 | 0.17 |
| 135 | 0.37 | N/A |
| 136 | 0.23 | N/A |
| 137 | 0.56 | N/A |
| 138 | 4.0 | N/A |
| 139 | 2.6 | N/A |
| 140 | 0.029 | 0.019 |
| 141 | 0.065 | N/A |
| 142 | 13 | 1.3 |
| 143 | 0.02 | N/A |
| 144 | 0.044 | N/A |
| 145 | 0.074 | N/A |
| 146 | 0.073 | 0.06 |
| 147 | 0.11 | 0.07 |
| 148 | 0.22 | N/A |
| 149 | 5.7 | N/A |
| 150 | 1.3 | N/A |
| 151 | 1.1 | N/A |
| 152 | 0.32 | 0.25 |
| 153 | 0.23 | N/A |
| 154 | 11.7 | 0.54 |
| 155 | 0.02 | N/A |
| 156 | 0.073 | N/A |
| 157 | 0.29 | N/A |
| 158 | <0.005 | N/A |
| 159 | <0.005 | N/A |
| 160 | <0.005 | N/A |
| 161 | <0.005 | N/A |
| 162 | 0.084 | N/A |
| 163 | 0.0085 | 0.002 |
| 164 | 11 | N/A |
| 165 | 0.17 | N/A |
| 166 | <0.005 | N/A |
| 167 | 0.015 | N/A |
| 168 | <0.015 | N/A |
| 169 | 1.9 | N/A |
| 170 | 1.8 | N/A |
| 171 | 1.2 | N/A |
| 172 | 0.31 | N/A |
| 173 | 2.0 | N/A |
| 174 | 1.2 | N/A |
| 175 | 2.5 | N/A |
| 176 | 3.4 | N/A |

TABLE 1-continued

Compound IC$_{50}$s in SPA

| Compound Number | Mean SPA IC$_{50}$ (μM) | SD |
|---|---|---|
| 177 | 18 | 0.59 |
| 178 | 0.92 | N/A |
| 179 | 0.023 | N/A |
| 180 | 9.4 | N/A |
| 181 | 3.7 | N/A |
| 182 | 0.38 | 0.13 |
| 184 | 0.72 | N/A |
| 185 | <0.005 | N/A |
| 186 | <0.005 | N/A |
| 187 | 0.079 | N/A |
| 188 | <0.005 | N/A |
| 189 | 3.2 | N/A |
| 190 | 0.58 | N/A |
| 191 | <0.005 | N/A |
| 192 | 0.18 | N/A |
| 193 | 0.90 | N/A |
| 194 | <0.005 | N/A |
| 195 | 0.11 | N/A |
| 196 | <0.005 | N/A |
| 197 | 0.77 | N/A |
| 198 | 0.03 | N/A |
| 199 | 11.2 | N/A |
| 200 | <0.005 | N/A |
| 201 | <0.005 | N/A |
| 202 | 0.68 | N/A |
| 203 | 0.077 | 0.04 |
| 204 | 0.21 | N/A |
| 205 | 2.4 | N/A |
| 206 | 0.038 | N/A |
| 207 | 0.5 | 0.15 |
| 208 | >100 | N/A |
| 209 | 0.81 | N/A |
| 210 | 17 | 8.87 |
| 211 | 2.1 | 0.61 |
| 212 | 0.67 | N/A |
| 213 | 0.80 | N/A |
| 214 | 0.23 | N/A |
| 215 | 0.017 | N/A |
| 216 | 2.7 | N/A |
| 217 | 3.2 | N/A |
| 218 | 0.81 | N/A |
| 219 | 17 | N/A |
| 220 | 0.7 | N/A |
| 221 | 0.029 | N/A |
| 222 | 1.2 | N/A |
| 223 | 0.011 | .0008 |
| 224 | 0.083 | N/A |
| 225 | <0.005 | N/A |
| 226 | 3.1 | 1.54 |
| 227 | 0.013 | N/A |
| 228 | 0.04 | N/A |
| 229 | 0.017 | N/A |
| 230 | 0.028 | N/A |
| 231 | 0.045 | .016 |
| 232 | 0.016 | N/A |
| 233 | <0.005 | N/A |
| 234 | 0.026 | N/A |
| 235 | 0.038 | .015 |
| 236 | <0.005 | N/A |
| 237 | 0.10 | N/A |
| 238 | 4.9 | N/A |
| 239 | 1.8 | N/A |
| 240 | 0.026 | N/A |
| 241 | 0.068 | N/A |
| 242 | 0.23 | N/A |
| 243 | 0.25 | N/A |
| 244 | 1.0 | N/A |
| 245 | 0.032 | N/A |
| 246 | 21 | N/A |
| 247 | <0.005 | N/A |
| 248 | 17 | N/A |
| 249 | 0.88 | N/A |
| 250 | 1.3 | N/A |
| 251 | 0.031 | N/A |
| 252 | 0.076 | .021 |
| 253 | 18 | N/A |
| 254 | 0.1 | N/A |
| 255 | 1.4 | N/A |
| 256 | 0.015 | N/A |
| 257 | 1.9 | N/A |
| 258 | 0.41 | N/A |
| 259 | 1.2 | N/A |
| 260 | 0.066 | N/A |
| 261 | 0.64 | .52 |
| 262 | 4.9 | N/A |
| 263 | 0.025 | N/A |
| 264 | 0.38 | N/A |
| 265 | .09 | N/A |
| 266 | 0.019 | N/A |
| 267 | 0.092 | N/A |
| 268 | 3.5 | N/A |
| 269 | 0.31 | N/A |
| 270 | 0.097 | N/A |
| 271 | 0.34 | 0.15 |
| 272 | 2.0 | N/A |
| 273 | <0.005 | N/A |
| 274 | 0.094 | N/A |
| 275 | 0.076 | N/A |
| 276 | 0.058 | N/A |
| 277 | 0.135 | N/A |
| 278 | 2.2 | N/A |
| 279 | 5.1 | N/A |
| 280 | 3.4 | 0.42 |
| 281 | 0.73 | N/A |
| 282 | 7.2 | N/A |
| 283 | 1.4 | N/A |
| 284 | 5.6 | N/A |
| 285 | 0.071 | N/A |
| 286 | 0.024 | N/A |
| 287 | 0.55 | N/A |
| 288 | 6.5 | N/A |
| 289 | 0.01 | N/A |
| 290 | 0.018 | N/A |
| 291 | 4.9 | N/A |
| 292 | <0.005 | N/A |
| 293 | 0.72 | 0.37 |
| 294 | 1.1 | N/A |
| 295 | 0.23 | N/A |
| 296 | 1.3 | N/A |
| 297 | 12.4 | N/A |
| 298 | 16.1 | N/A |
| 299 | 16.1 | N/A |
| 300 | 2.03 | N/A |
| 301 | 1.9 | N/A |
| 302 | 0.063 | N/A |
| 303 | 0.037 | N/A |
| 304 | <0.005 | N/A |
| 305 | <0.005 | N/A |
| 306 | <0.005 | N/A |
| 307 | 0.37 | N/A |
| 308 | 0.068 | N/A |
| 309 | <0.005 | N/A |
| 310 | 0.016 | N/A |
| 311 | 8.7 | N/A |
| 312 | 0.15 | N/A |
| 313 | 1.8 | N/A |
| 314 | 0.025 | N/A |
| 315 | 0.0232 | N/A |
| 316 | <0.005 | N/A |
| 317 | <0.005 | N/A |
| 318 | 2.38 | N/A |
| 319 | 0.014 | N/A |
| 320 | 1.57 | N/A |
| 321 | 0.032 | N/A |
| 322 | 9.8 | N/A |
| 323 | 5.25 | N/A |
| 324 | 0.054 | N/A |
| 325 | 0.18 | N/A |
| 326 | 1.28 | N/A |
| 327 | 0.028 | N/A |

TABLE 1-continued

Compound IC$_{50}$s in SPA

| Compound Number | Mean SPA IC$_{50}$ (μM) | SD |
|---|---|---|
| 328 | 0.032 | N/A |
| 329 | <0.005 | N/A |
| 330 | 2.09 | N/A |
| 331 | 0.007 | N/A |
| 332 | 2.33 | N/A |
| 333 | 0.074 | N/A |
| 334 | 0.073 | N/A |
| 335 | 8.1 | N/A |
| 336 | 0.063 | N/A |
| 337 | 3.67 | N/A |
| 338 | 0.013 | N/A |
| 339 | 0.28 | N/A |
| 340 | 0.024 | N/A |
| 341 | 0.018 | N/A |
| 342 | 0.04 | N/A |
| 343 | 23.9 | N/A |
| 344 | 0.0067 | N/A |
| 345 | 2.1824 | N/A |
| 346 | 0.515 | N/A |

SD: standard deviation. SDs and Means were calculated using the python programming language version 2.7.5 with numpy library 1.7.1. When a compound was tested multiple times, any number less than 5 nM or more than 100 μM was excluded from the standard deviation or EC$_{50}$ calculation. N/A: SD is not calculated for compounds with IC$_{50}$ less than 5 nM or having a single data point.

The following compounds were synthesized and tested in SPA, and were found to have an IC$_{50}$ value of greater than 100 μM:

| Structure | IUPAC Name |
|---|---|
| 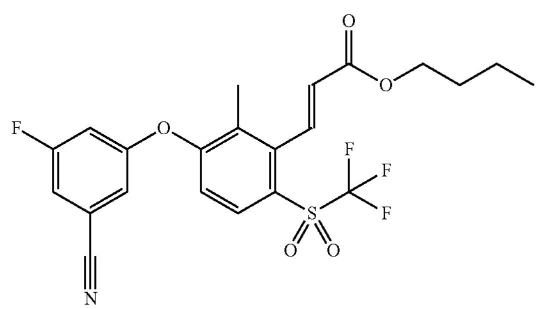 [SMILES: CCCCOC(=O)/C=C/c1c(S(=O)(=O)C(F)(F)F)ccc(Oc2cc(F)cc(C#N)c2)c1C] | butyl (E)-3-[3-(3-cyano-5-fluoro-phenoxy)-2-methyl-6-(trifluoromethylsulfonyl)phenyl]prop-2-enoate |
| 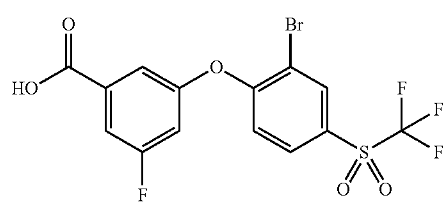 [SMILES: O=C(O)c1cc(F)cc(Oc2ccc(S(=O)(=O)C(F)(F)F)cc2Br)c1] | 3-[2-bromo-4-(trifluoromethylsulfonyl)phenoxy]-5-fluoro-benzoic acid |
| 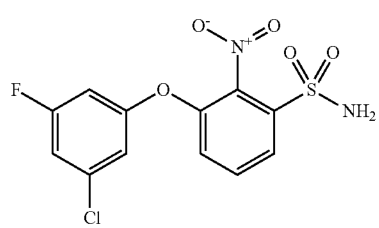 [SMILES: NS(=O)(=O)c1cccc(Oc2cc(F)cc(Cl)c2)c1[N+](=O)[O-]] | 3-(3-chloro-5-fluoro-phenoxy)-2-nitro-benzenesulfonamide |
| 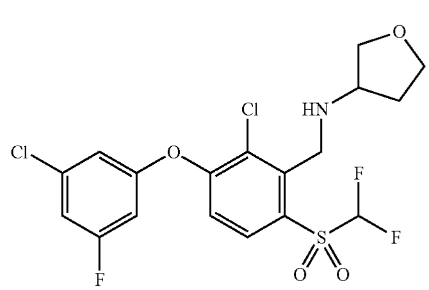 [SMILES: O=S(=O)(c1ccc(Oc2cc(F)cc(Cl)c2)c(Cl)c1CNC1CCOC1)C(F)F] | N-[[2-chloro-3-(3-chloro-5-fluoro-phenoxy)-6-(difluoromethylsulfonyl)phenyl]methyl]tetrahydro-furan-3-amine |

| Structure | IUPAC Name |
|---|---|
| 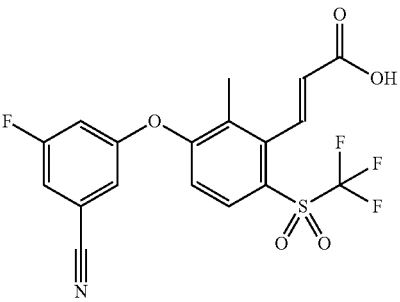 [SMILES: Cc1c(Oc2cc(F)cc(C#N)c2)ccc(S(=O)(=O)C(F)(F)F)c1/C=C/C(=O)O] | (E)-3-[3-(3-cyano-5-fluoro-phenoxy)-2-methyl-6-(trifluoromethylsulfonyl)phenyl]propyl-2-enoic acid |
| 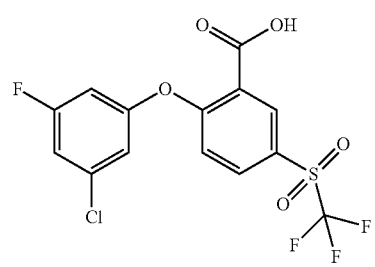 [SMILES: O=C(O)c1cc(S(=O)(=O)C(F)(F)F)ccc1Oc1cc(F)cc(Cl)c1] | 2-(3-chloro-5-fluoro-phenoxy)-5-(trifluoromethylsulfonyl)benzoic acid |
| 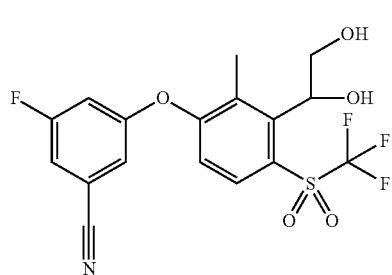 [SMILES: Cc1c(Oc2cc(F)cc(C#N)c2)ccc(S(=O)(=O)C(F)(F)F)c1C(O)CO] | 3-[3-(1,2-dihydroxyethyl)-2-methyl-4-(trifluoromethylsulfonyl)phenoxy]-5-fluoro-benzonitrile |
| 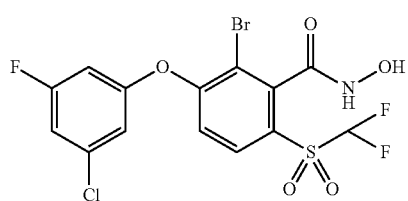 [SMILES: O=C(NO)c1c(S(=O)(=O)C(F)F)ccc(Oc2cc(F)cc(Cl)c2)c1Br] | 2-bromo-3-(3-chloro-5-fluoro-phenoxy)-6-(difluoromethylsulfonyl)benzenecarbohydroxamic acid |
| 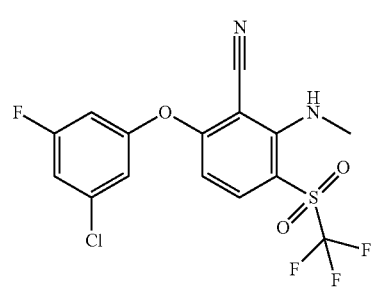 [SMILES: CNc1c(S(=O)(=O)C(F)(F)F)ccc(Oc2cc(F)cc(Cl)c2)c1C#N] | 6-(3-chloro-5-fluoro-phenoxy)-2-(methylamino)-3-(trifluoromethylsulfonyl)benzonitrile |
| 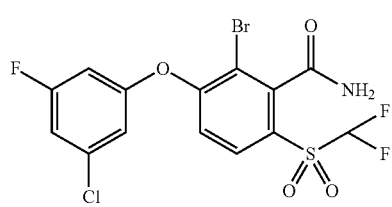 [SMILES: NC(=O)c1c(S(=O)(=O)C(F)F)ccc(Oc2cc(F)cc(Cl)c2)c1Br] | 2-bromo-3-(3-chloro-5-fluoro-phenoxy)-6-(difluoromethylsulfonyl)benzamide |

-continued

| Structure | IUPAC Name |
|---|---|
| 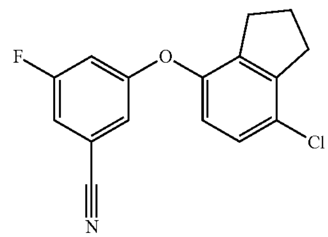 [SMILES: N#Cc1cc(F)cc(Oc2ccc(Cl)c3c2CCC3)c1] | 3-(7-chloroindan-4-yl)oxy-5-fluoro-benzonitrile |
| 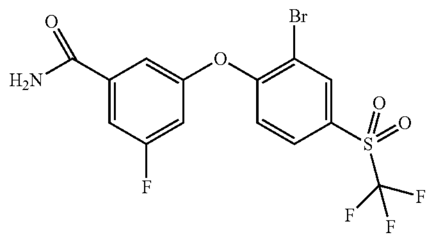 [SMILES: NC(=O)c1cc(F)cc(Oc2ccc(S(=O)(=O)C(F)(F)F)cc2Br)c1] | 3-[2-bromo-4-(trifluoromethylsulfonyl)phenoxy]-5-fluoro-benzamide |
| 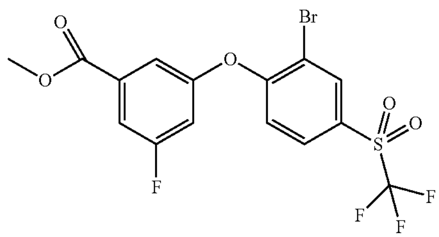 [SMILES: COC(=O)c1cc(F)cc(Oc2ccc(S(=O)(=O)C(F)(F)F)cc2Br)c1] | methyl 3-[2-bromo-4-(trifluoromethylsulfonyl)phenoxy]-5-fluoro-benzoate |
| 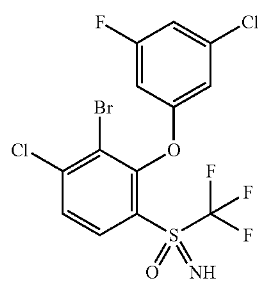 [SMILES: N=S(=O)(c1ccc(Cl)c(Br)c1Oc1cc(F)cc(Cl)c1)C(F)(F)F] | [3-bromo-4-chloro-2-(3-chloro-5-fluoro-phenoxy)phenyl]-imino-oxo-(trifluoromethyl)-$\lambda^6$-sulfane |
| 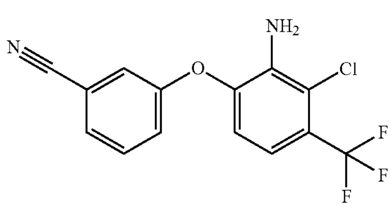 [SMILES: N#Cc1cccc(Oc2ccc(C(F)(F)F)c(Cl)c2N)c1] | 3-[2-amino-3-chloro-4-(trifluoromethyl)phenoxy]benzonitrile |
| 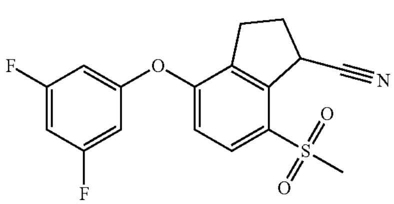 [SMILES: CS(=O)(=O)c1ccc(Oc2cc(F)cc(F)c2)c2c1C(C#N)CC2] | 4-(3,5-difluorophenoxy)-7-methylsulfonyl-indane-1-carbonitrile |

-continued

| Structure | IUPAC Name |
|---|---|
| | 3-(7-cyclobutylsulfonyl-1-hydroxy-indan-4-yl)oxy-5-fluoro-benzonitrile |
| 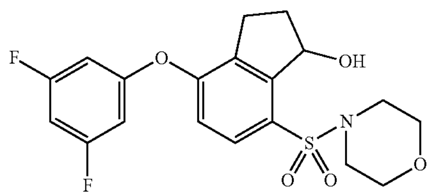 [SMILES: O=S(=O)(c1ccc(Oc2cc(F)cc(F)c2)c2c1C(O)CC2)N1CCOCC1] | 4-(3,5-difluorophenoxy)-7-morpholinosulfonyl-indan-1-ol |
| 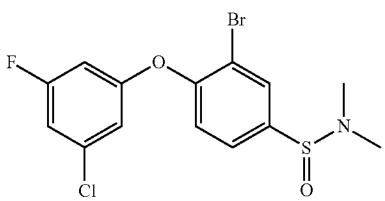 [SMILES: CN(C)S(=O)c1ccc(Oc2cc(F)cc(Cl)c2)c(Br)c1] | 3-bromo-4-(3-chloro-5-fluoro-phenoxy)-N,N-dimethyl-benzenesulfinamide |
| 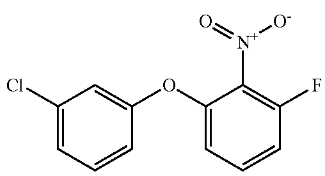 [SMILES: O=[N+]([O-])c1c(F)cccc1Oc1cccc(Cl)c1] | 1-(3-chlorophenoxy)-3-fluoro-2-nitro-benzene |
| 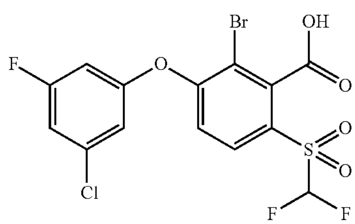 [SMILES: O=C(O)c1c(S(=O)(=O)C(F)F)ccc(Oc2cc(F)cc(Cl)c2)c1Br] | 2-bromo-3-(3-chloro-5-fluoro-phenoxy)-6-(difluoromethylsulfonyl)benzoic acid |
| 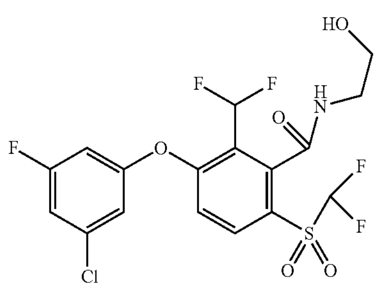 [SMILES: O=C(NCCO)c1c(S(=O)(=O)C(F)F)ccc(Oc2cc(F)cc(Cl)c2)c1C(F)F] | 3-(3-chloro-5-fluoro-phenoxy)-2-(difluoromethyl)-6-(difluoromethylsulfonyl)-N-(2-hydroxyethyl)benzamide |
| 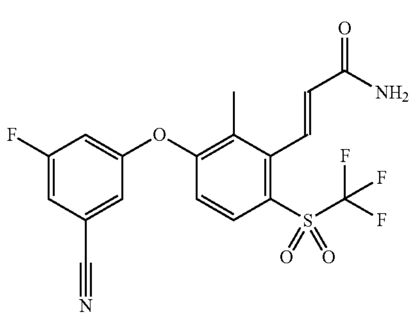 [SMILES: Cc1c(Oc2cc(F)cc(C#N)c2)ccc(S(=O)(=O)C(F)(F)F)c1/C=C/C(N)=O] | (E)-3-[3-(3-cyano-5-fluoro-phenoxy)-2-methyl-6-(trifluoromethylsulfonyl)phenyl]prop-2-enamide |

| Structure | IUPAC Name |
|---|---|
| 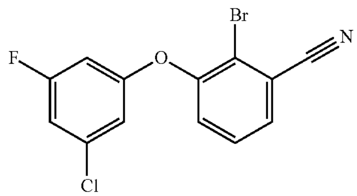 [SMILES: N#Cc1cccc(Oc2cc(F)cc(Cl)c2)c1Br] | 2-bromo-3-(3-chloro-5-fluoro-phenoxy)benzonitrile |
| 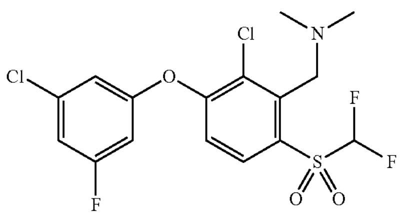 [SMILES: CN(C)Cc1c(S(=O)(=O)C(F)F)ccc(Oc2cc(F)cc(Cl)c2)c1Cl] | 1-[2-chloro-3-(3-chloro-5-fluoro-phenoxy)-6-(difluoromethylsulfonyl)phenyl]-N,N-dimethyl-methanamine |
| 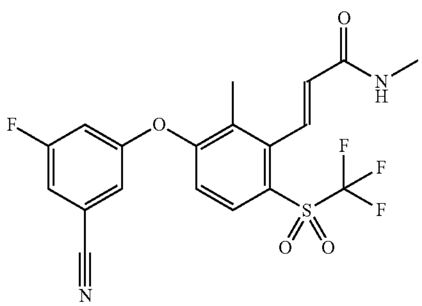 [SMILES: CNC(=O)/C=C/c1c(S(=O)(=O)C(F)(F)F)ccc(Oc2cc(F)cc(C#N)c2)c1C] | (E)-3-[3-(3-cyano-5-fluoro-phenoxy)-2-methyl-6-(trifluoromethylsulfonyl)phenyl]-N-methyl-prop-2-enamide |
| 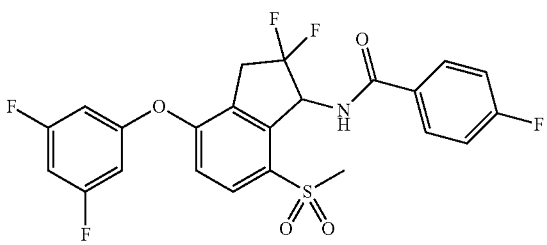 [SMILES: CS(=O)(=O)c1ccc(Oc2cc(F)cc(F)c2)c2c1C(NC(=O)c1ccc(F)cc1)C(F)(F)C2] | N-[4-(3,5-difluorophenoxy)-2,2-difluoro-7-methylsulfonyl-indan-1-yl]-4-fluoro-benzamide |
| 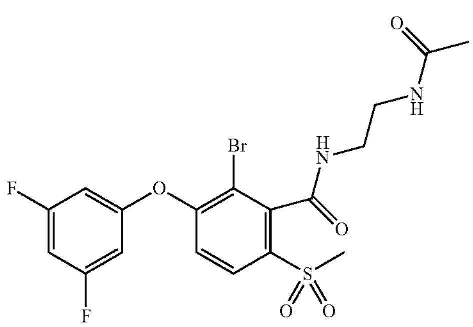 [SMILES: CC(=O)NCCNC(=O)c1c(S(C)(=O)=O)ccc(Oc2cc(F)cc(F)c2)c1Br] | N-(2-acetamidoethyl)-2-bromo-3-(3,5-difluorophenoxy)-6-methylsulfonyl-benzamide |
| 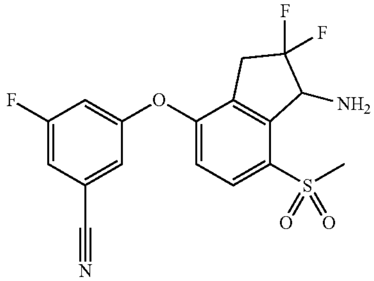 [SMILES: CS(=O)(=O)c1ccc(Oc2cc(F)cc(C#N)c2)c2c1C(N)C(F)(F)C2] | 3-(1-amino-2,2-difluoro-7-methylsulfonyl-indan-4-yl)oxy-5-fluoro-benzonitrile |

-continued

| Structure | IUPAC Name |
|---|---|
| 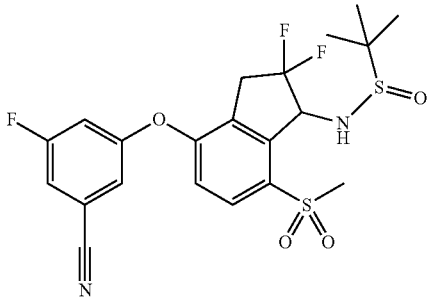 [SMILES: CC(C)(C)S(=O)NC1c2c(S(C)(=O)=O)ccc(Oc3cc(F)cc(C#N)c3)c2CC1(F)F] | N-[4-(3-cyano-5-fluoro-phenoxy)-2,2-difluoro-7-methylsulfonyl-indan-1-yl]-2-methyl-propane-2-sulfinamide |
| 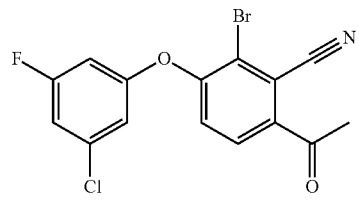 [SMILES: CC(=O)c1ccc(Oc2cc(F)cc(Cl)c2)c(Br)c1C#N] | 6-acetyl-2-bromo-3-(3-chloro-5-fluoro-phenoxy)benzonitrile |
| 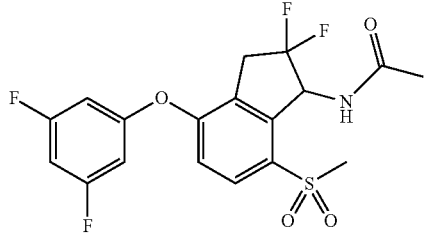 [SMILES: CC(=O)NC1c2c(S(C)(=O)=O)ccc(Oc3cc(F)cc(F)c3)c2CC1(F)F] | N-[4-(3,5-difluorophenoxy)-2,2-difluoro-7-methylsulfonyl-indan-1-yl]acetamide |
| 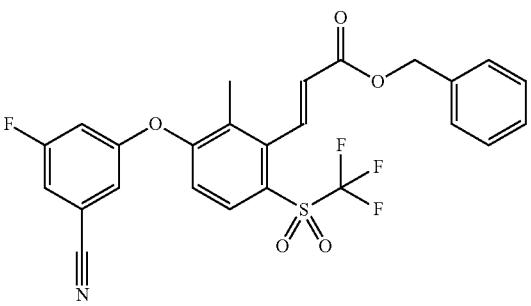 [SMILES: Cc1c(Oc2cc(F)cc(C#N)c2)ccc(S(=O)(=O)C(F)(F)F)c1/C=C/C(=O)OCc1ccccc1] | benzyl (E)-3-[3-(3-cyano-5-fluoro-phenoxy)-2-methyl-6-(trifluoromethylsulfonyl)phenyl]prop-2-enoate |
| 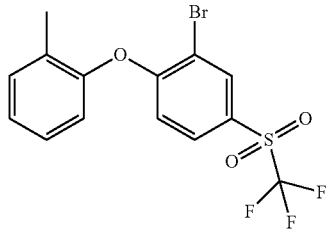 [SMILES: Cc1ccccc1Oc1ccc(S(=O)(=O)C(F)(F)F)cc1Br] | 2-bromo-1-(2-methylphenoxy)-4-(trifluoromethylsulfonyl)benzene |
| 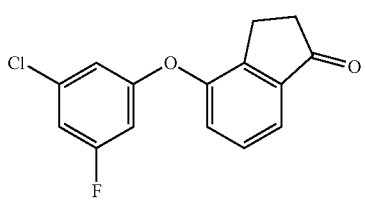 [SMILES: O=C1CCc2c(Oc3cc(F)cc(Cl)c3)cccc21] | 4-(3-chloro-5-fluoro-phenoxy)indan-1-one |

-continued

| Structure | IUPAC Name |
|---|---|
| 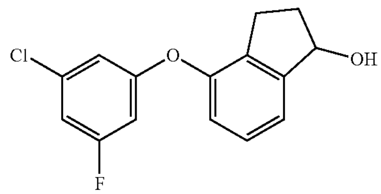 [SMILES: OC1CCc2c(Oc3cc(F)cc(Cl)c3)cccc21] | 4-(3-chloro-5-fluoro-phenoxy)indan-1-ol |
| 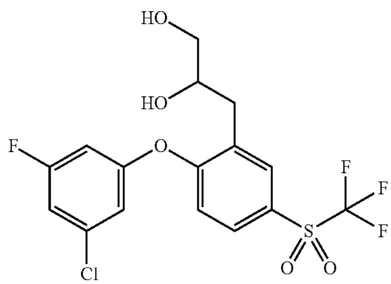 [SMILES: O=S(=O)(c1ccc(Oc2cc(F)cc(Cl)c2)c(CC(O)CO)c1)C(F)(F)F] | 3-[2-(3-chloro-5-fluoro-phenoxy)-5-(trifluoromethylsulfonyl)phenyl]propane-1,2-diol |
| 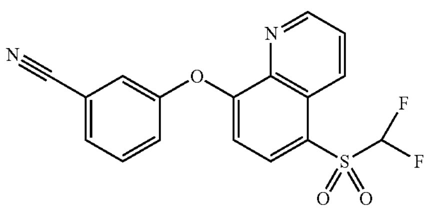 [SMILES: N#Cc1cccc(Oc2ccc(S(=O)(=O)C(F)F)c3cccnc23)c1] | 3-[[5-(difluoromethylsulfonyl)-8-quinolyl]oxy]benzonitrile |
| 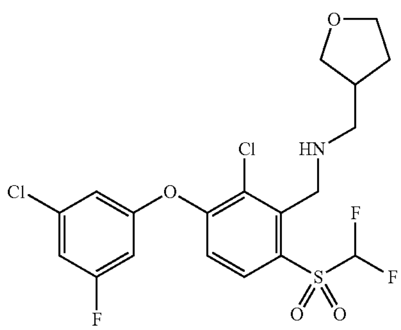 [SMILES: O=S(=O)(c1ccc(Oc2cc(F)cc(Cl)c2)c(Cl)c1CNCC1CCOC1)C(F)F] | 1-[2-chloro-3-(3-chloro-5-fluoro-phenoxy)-6-(difluoromethylsulfonyl)phenyl]-N-(tetrahydrofuran-3-ylmethyl)methanamine |
| 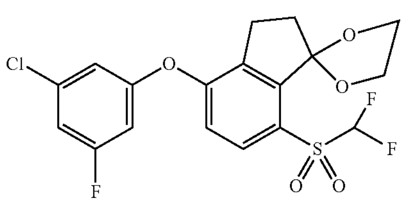 [SMILES: O=S(=O)(c1ccc(Oc2cc(F)cc(Cl)c2)c2c1C1(CC2)OCCO1)C(F)F] | 4'-(3-chloro-5-fluoro-phenoxy)-7'-(difluoromethylsulfonyl)spiro[1,3-dioxalane-2,1'-indane] |
| 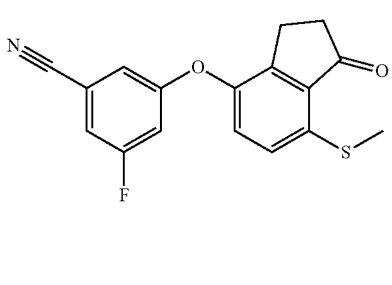 [SMILES: CSc1ccc(Oc2cc(F)cc(C#N)c2)c2c1C(=O)CC2] | 3-fluoro-5-(7-methylsulfanyl-1-oxo-indan-4-yl)oxy-benzonitrile |

-continued

| Structure | IUPAC Name |
|---|---|
| 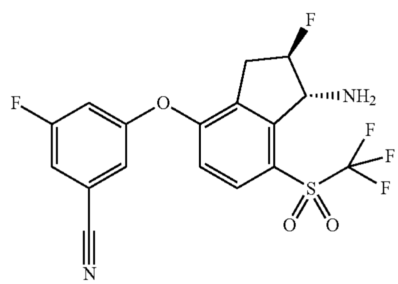 [SMILES: N#Cc1cc(F)cc(Oc2ccc(S(=O)(=O)C(F)(F)F)c3c2C[C@@H](F)[C@@H]3N)c1] | 3-[(1R,2R)-1-amino-2-fluoro-7-(trifluoromethylsulfonyl)indan-4-yl]oxy-5-fluoro-benzonitrile |
| | (1R)-4-([1,2,4]triazolo[4,3-a]pyridin-8-yloxy)-7-(trifluoromethyl-sulfonyl)indan-1-ol |
| 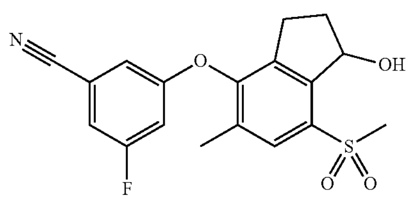 [SMILES: Cc1cc(S(C)(=O)=O)c2c(c1Oc1cc(F)cc(C#N)c1)CCC2O] | 3-fluoro-5-(1-hydroxy-5-methyl-7-methylsulfonyl-indan-4-yl)oxy-benzonitrile |
| 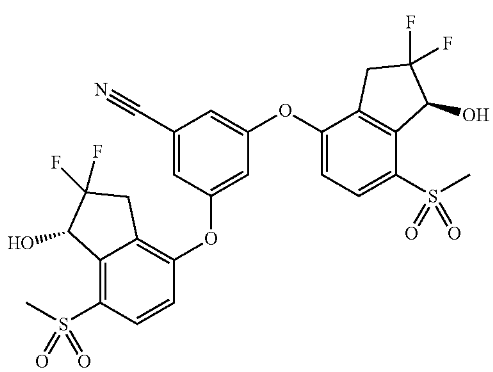 | 3,5-bis[[(1S)-2,2-difluoro-1-hydroxy-7-methylsulfonyl-indan-4-yl]oxy]benzonitrile |
| 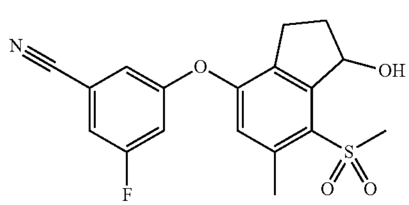 [SMILES: Cc1cc(Oc2cc(F)cc(C#N)c2)c2c(c1S(C)(=O)=O)C(O)CC2] | 3-fluoro-5-(1-hydroxy-6-methyl-7-methylsulfonyl-indan-4-yl)oxy-benzonitrile |
| 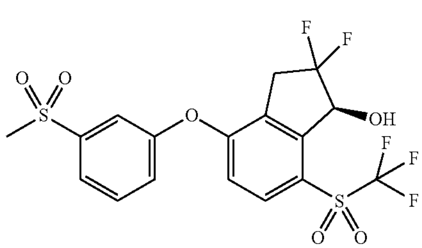 [SMILES: CS(=O)(=O)c1cccc(Oc2ccc(S(=O)(=O)C(F)(F)F)c3c2CC(F)(F)[C@H]3O)c1] | (1S)-2,2-difluoro-4-(3-methylsulfonylphenoxy)-7-(trifluoromethylsulfonyl)indan-1-ol |

-continued

| Structure | IUPAC Name |
|---|---|
| 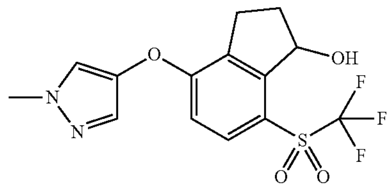 [SMILES: Cn1cc(Oc2ccc(S(=O)(=O)C(F)(F)F)c3c2CCC3O)cn1] | 4-(1-methylpyrazol-4-yl)oxy-7-(trifluoromethylsulfonyl)indan-1-ol |
| 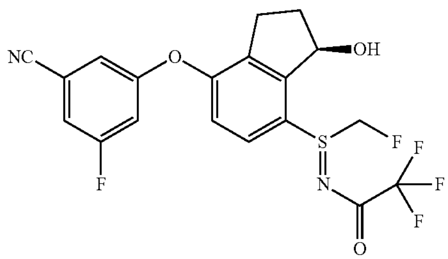 [SMILES: N#Cc1cc(F)cc(Oc2ccc(/S(CF)=N/C(=O)C(F)(F)F)c3c2CC[C@H]3O)c1] | N-((R)-7-(3-cyano-5-fluorophenoxy)-3-hydroxy-2,3-dihydro-1H-inden-4-yl)(fluoromethyl)-$\lambda^4$-sulfanylidene)-2,2,2-trifluoroacetamide |
| 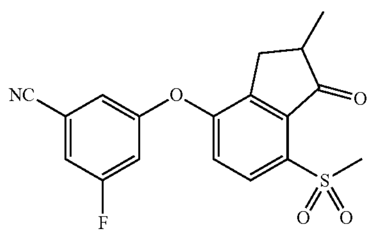 [SMILES: CC1Cc2c(Oc3cc(F)cc(C#N)c3)ccc(S(C)(=O)=O)c2C1=O] | 3-fluoro-5-((2-methyl-7-(methylsulfonyl)-1-oxo-2,3-dihydro-1H-inden-4-yl)oxy)benzonitrile |
| 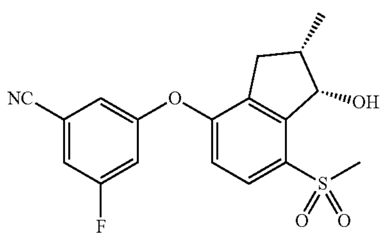 [SMILES: C[C@H]1Cc2c(Oc3cc(F)cc(C#N)c3)ccc(S(C)(=O)=O)c2[C@H]1O] | 3-fluoro-5-(((1S,2S)-1-hydroxy-2-methyl-7-(methylsulfonyl)-2,3-dihydro-1H-inden-4-yl)oxy)benzonitrile |

The following compounds were synthesized and tested in SPA, and were found to have an IC$_{50}$ value between 25 and 100 μM:

| Structure | IUPAC Name |
|---|---|
| 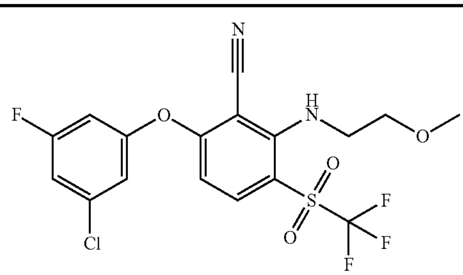 | 6-(3-chloro-5-fluoro-phenoxy)-2-(2-methoxyethylamino)-3-(trifluoromethylsulfonyl)benzonitrile |
| 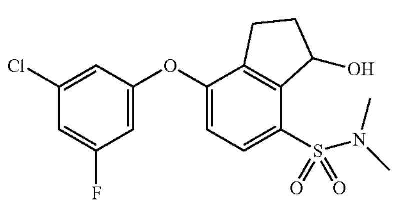 [SMILES: CN(C)S(=O)(=O)c1ccc(Oc2cc(F)cc(Cl)c2)c2c1C(O)CC2] | 7-(3-chloro-5-fluoro-phenoxy)-3-hydroxy-N,N-dimethyl-indane-4-sulfonamide |

| Structure | IUPAC Name |
|---|---|
| 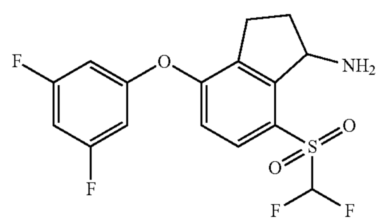 [SMILES: NC1CCc2c(Oc3cc(F)cc(F)c3)ccc(S(=O)(=O)C(F)F)c21] | 7-(difluoromethylsulfonyl)-4-(3,5-difluorophenoxy)indan-1-amine |
| 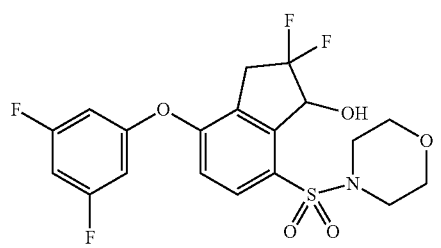 [SMILES: O=S(=O)(c1ccc(Oc2cc(F)cc(F)c2)c2c1C(O)C(F)(F)C2)N1CCOCC1] | 4-(3,5-difluorophenoxy)-2,2-difluoro-7-morpholino-sulfonyl-indan-1-ol |
| 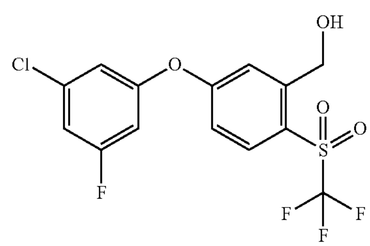 [SMILES: O=S(=O)(c1ccc(Oc2cc(F)cc(Cl)c2)cc1CO)C(F)(F)F] | [5-(3-chloro-5-fluoro-phenoxy)-2-(trifluoromethylsulfonyl)phenyl]methanol |
| 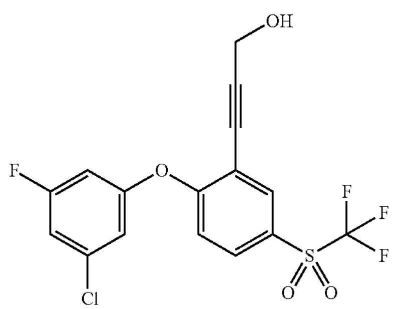 [SMILES: O=S(=O)(c1ccc(Oc2cc(F)cc(Cl)c2)c(C#CCO)c1)C(F)(F)F] | 3-[2-(3-chloro-5-fluoro-phenoxy)-5-(trifluoromethylsulfonyl)phenyl]prop-2-yn-1-ol |
| 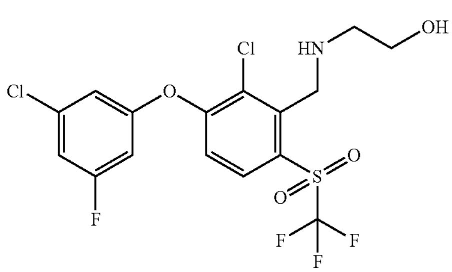 [SMILES: O=S(=O)(c1ccc(Oc2cc(F)cc(Cl)c2)c(Cl)c1CNCCO)C(F)(F)F] | 2-[[2-chloro-3-(3-chloro-5-fluoro-phenoxy)-6-(trifluoromethylsulfonyl)phenyl]methylamino]ethanol |
| 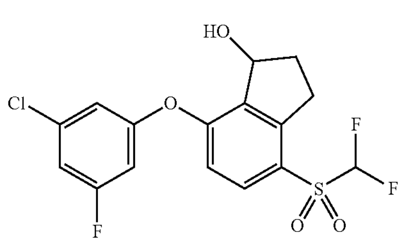 [SMILES: O=S(=O)(c1ccc(Oc2cc(F)cc(Cl)c2)c2c1CCC2O)C(F)F] | 7-(3-chloro-5-fluoro-phenoxy)-4-(difluoromethylsulfonyl)indan-1-ol |

| Structure | IUPAC Name |
|---|---|
| 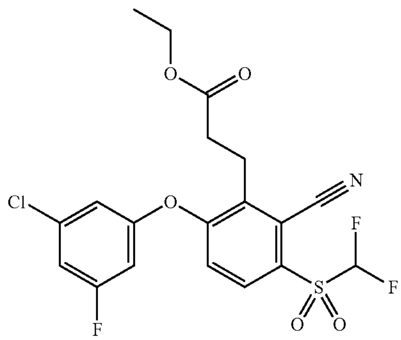 [SMILES: CCOC(=O)CCc1c(Oc2cc(F)cc(Cl)c2)ccc(S(=O)(=O)C(F)F)c1C#N] | ethyl 3-[6-(3-chloro-5-fluoro-phenoxy)-2-cyano-3-(difluoromethylsulfonyl)phenyl]propanoate |
| 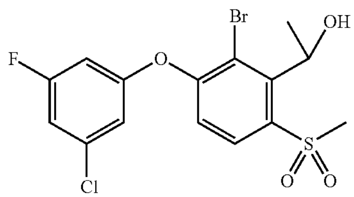 [SMILES: CC(O)c1c(S(C)(=O)=O)ccc(Oc2cc(F)cc(Cl)c2)c1Br] | 1-[2-bromo-3-(3-chloro-5-fluoro-phenoxy)-6-methylsulfonyl-phenyl]ethanol |
| 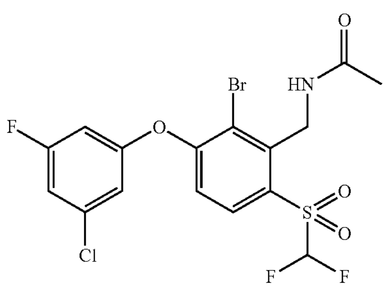 [SMILES: CC(=O)NCc1c(S(=O)(=O)C(F)F)ccc(Oc2cc(F)cc(Cl)c2)c1Br] | N-[[2-bromo-3-(3-chloro-5-fluoro-phenoxy)-6-(difluoromethylsulfonyl)phenyl]methyl]acetamide |
| | 2-chloro-6-(3-chloro-5-fluoro-phenoxy)-3-(trifluoromethyl-sulfonyl)benzonitrile |
| 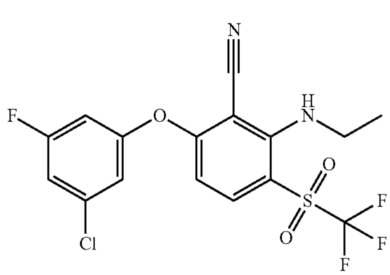 [SMILES: CCNc1c(S(=O)(=O)C(F)(F)F)ccc(Oc2cc(F)cc(Cl)c2)c1C#N] | 6-(3-chloro-5-fluoro-phenoxy)-2-(ethylamino)-3-(trifluoromethylsulfonyl)benzonitrile |

-continued

| Structure | IUPAC Name |
|---|---|
| 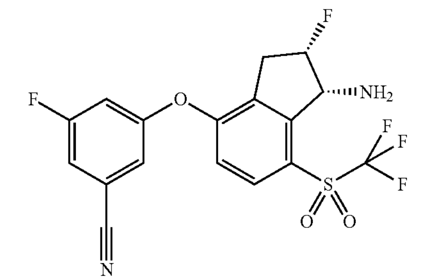 [SMILES: N#Cc1cc(F)cc(Oc2ccc(S(=O)(=O)C(F)(F)F)c3c2C[C@H](F)[C@@H]3N)c1] | 3-[(1R,2S)-1-amino-2-fluoro-7-(trifluoromethylsulfonyl)indan-4-yl]oxy-5-fluoro-benzonitrile |
| 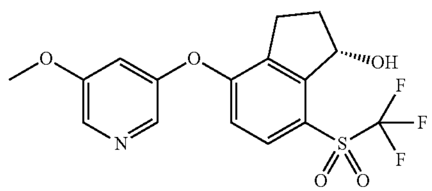 [SMILES: COc1cncc(Oc2ccc(S(=O)(=O)C(F)(F)F)c3c2CC[C@@H]3O)c1] | 4-[(5-methoxy-3-pyridyl)oxy]-7-(trifluoromethylsulfonyl)indan-1-ol |
| 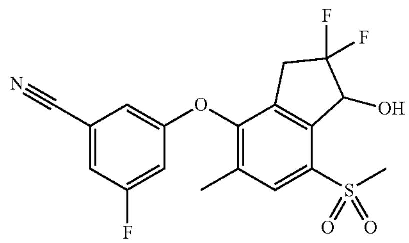 [SMILES: Cc1cc(S(C)(=O)=O)c2c(c1Oc1cc(F)cc(C#N)c1)CC(F)(F)C2O] | 3-(2,2-difluoro-1-hydroxy-5-methyl-7-methylsulfonyl-indan-4-yl)oxy)-5-fluoro-benzonitrile |
| 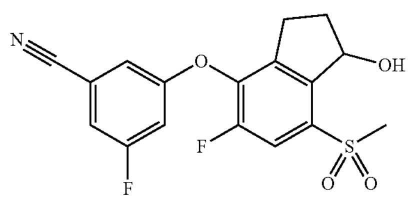 [SMILES: CS(=O)(=O)c1cc(F)c(Oc2cc(F)cc(C#N)c2)c2c1C(O)CC2] | 3-fluoro-5-(5-fluoro-1-hydroxy-7-methylsulfonyl-indan-4-yl)oxy-benzonitrile |
| 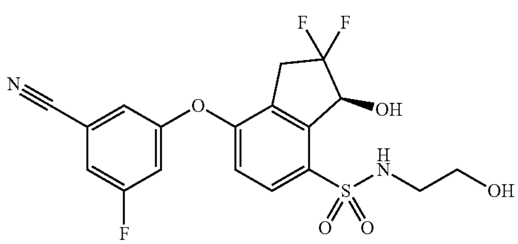 [SMILES: N#Cc1cc(F)cc(Oc2ccc(S(=O)(=O)NCCO)c3c2CC(F)(F)[C@H]3O)c1] | (3S)-7-(3-cyano-5-fluoro-phenoxy)-2,2-difluoro-3-hydroxy-N-(2-hydroxyethyl)indane-4-sulfonamide |
| 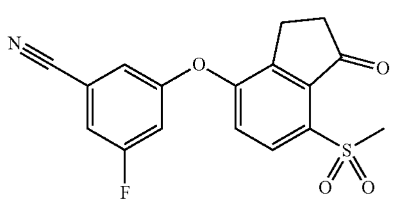 [SMILES: CS(=O)(=O)c1ccc(Oc2cc(F)cc(C#N)c2)c2c1C(=O)CC2] | 3-fluoro-5-(7-methylsulfonyl-1-oxo-indan-4-yl)oxy-benzonitrile |
| 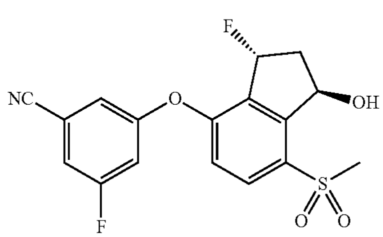 [SMILES: CS(=O)(=O)c1ccc(Oc2cc(F)cc(C#N)c2)c2c1[C@H](O)C[C@H]2F] | 3-fluoro-5-(((1R,3R)-3-fluoro-1-hydroxy-7-(methylsulfonyl)-2,3-dihydro-1H-inden-4-yl)oxy)benzonitrile |

-continued

| Structure | IUPAC Name |
|---|---|
| 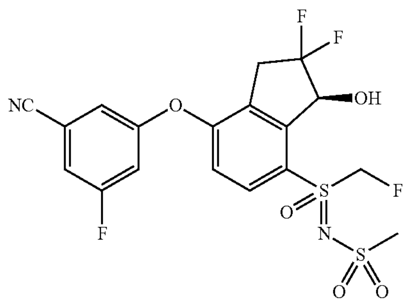 [SMILES: CS(=O)(=O)N=S(=O)(CF)c1ccc(Oc2cc(F)cc(C#N)c2)c2c1[C@H](O)C(F)(F)C2] | N-(((S)-7-(3-cyano-5-fluorophenoxy)-2,2-difluoro-3-hydroxy-2,3-dihydro-1H-inden-4-yl)(fluoromethyl)(oxo)-$\lambda^6$-sulfanylidene)methanesulfonamide |
| 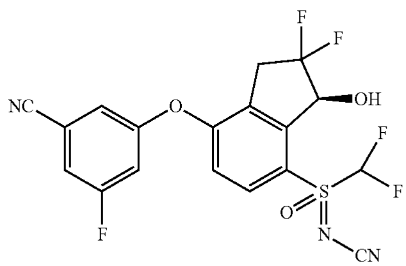 [SMILES: N#CN=S(=O)(c1ccc(Oc2cc(F)cc(C#N)c2)c2c1[C@H](O)C(F)(F)C2)C(F)F] | N-(((S)-7-(3-cyano-5-fluorophenoxy)-2,2-difluoro-3-hydroxy-2,3-dihydro-1H-inden-4-yl)(difluoromethyl)(oxo)-$\lambda^6$-sulfanylidene)cyanamide |
| 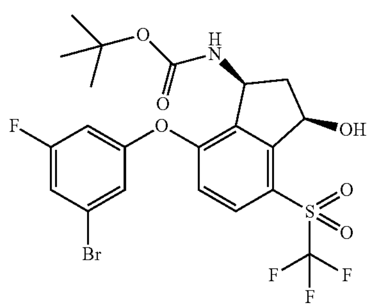 [SMILES: CC(C)(C)OC(=O)N[C@H]1C[C@@H](O)c2c(S(=O)(=O)C(F)(F)F)ccc(Oc3cc(F)cc(Br)c3)c21] | tert-butyl N-[(1S,3R)-7-(3-bromo-5-fluoro-phenoxy)-3-hydroxy-4-(trifluoromethylsulfonyl)indan-1-yl]carbamate |

Example 349: VEGF ELISA Assay

Figure 9:
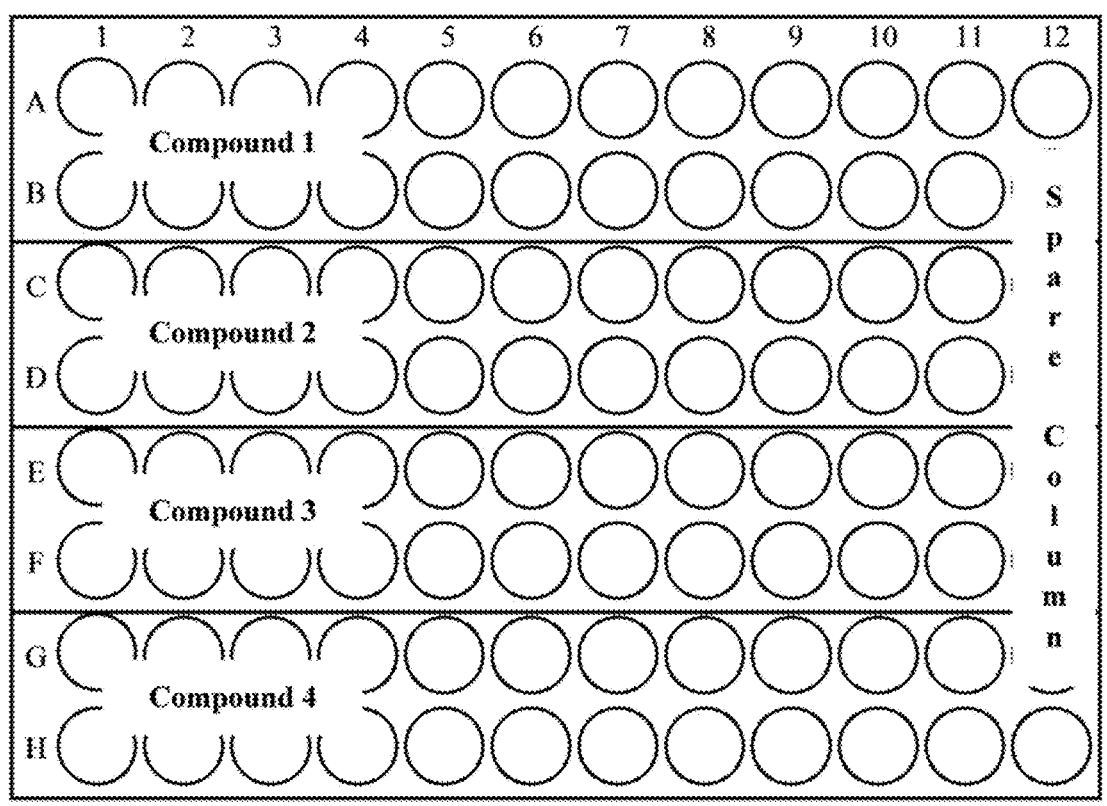
FIG. 9 depicts a 96-well plate layout of an ELISA assay.

About 7500 of 786-O cells in 180 µL of growth medium were seeded into each well of a 96 well plate with white clear bottom on the first day (07-200-566, Fisher scientific) in the layout presented in FIG. 9.

Four hours later, serial dilutions of 10× compound stocks were made in growth medium from 500×DMSO stocks, and 20 µL of those 10× stocks were added to each well to make final concentrations as follows (04): 20, 6.67, 2.22, 0.74, 0.25, 0.082, 0.027, 0.009, 0.003, 0.001, and 0. Each concentration had duplicated wells. About 20 hours later, medium was removed by suction and each well was supplied with 180 µL of growth medium. About 20 µl freshly-made 10× compound stocks were added to each well. About 24 hours later, cell culture medium was removed for the determination of VEGFA concentration using an ELISA kit purchased from R&D systems by following the manufacturer's suggested method. The $EC_{50}$ was calculated by GraphPad Prism using the dose-response-inhibition (four parameter) equation. The cell seeded plate was then subjected to CellTiter-Glo luminescence cell viability assay (Promega) by adding 50 µL of Celltiter Glo reagent into each well and shaking the plate for 8 minutes at 550 rpm (Thermomixer R, Eppendorf) then read luminescence signal in plate reader (3 second delay, 0.5 second/well integration time, Synergy 2 multi Detection Microplate reader) immediately.

Table 2 shows $EC_{50}$s of selected compounds in VEGF ELISA Assay.

TABLE 2

$EC_{50}$s of Selected Compounds in VEGF ELISA Assay

| Compound Number | Mean VEGF ELISA $EC_{50}$ (µM) | SD |
|---|---|---|
| 1 | 0.25 | 0.16 |
| 2 | 0.062 | N/A |
| 8 | 0.033 | N/A |
| 9 | 0.006 | N/A |
| 11 | 0.015 | N/A |
| 15 | 0.013 | 0.004 |
| 17 | 0.16 | N/A |
| 25 | 0.037 | 0.024 |
| 34 | 0.46 | N/A |
| 41 | 0.57 | N/A |
| 55 | 0.035 | N/A |
| 60 | 0.04 | N/A |
| 63 | 0.02 | 0.005 |
| 64 | 0.001 | N/A |
| 67 | 0.22 | 0.09 |
| 74 | 0.32 | 0.19 |
| 78 | 0.75 | N/A |
| 80 | 0.63 | N/A |
| 98 | 1.58 | 1.54 |
| 99 | 0.55 | 0.065 |

TABLE 2-continued

EC$_{50}$s of Selected Compounds in VEGF ELISA Assay

| Compound Number | Mean VEGF ELISA EC$_{50}$ (μM) | SD |
|---|---|---|
| 102 | 0.64 | N/A |
| 124 | 0.40 | N/A |
| 132 | 0.68 | N/A |
| 133 | 1.87 | N/A |
| 155 | 0.14 | N/A |
| 158 | 0.006 | N/A |
| 159 | 0.007 | N/A |
| 161 | 0.011 | N/A |
| 163 | 0.042 | 0.002 |
| 165 | 0.56 | N/A |
| 166 | 0.07 | N/A |
| 167 | 0.038 | N/A |
| 179 | 1.6 | N/A |
| 185 | 0.004 | N/A |
| 186 | 0.013 | N/A |
| 188 | 0.088 | N/A |
| 191 | 0.13 | N/A |
| 196 | 0.047 | 0.001 |
| 203 | 0.7 | 0.41 |
| 225 | 0.069 | N/A |
| 228 | 0.028 | N/A |
| 230 | 0.029 | N/A |
| 231 | 0.067 | N/A |
| 233 | 0.015 | N/A |
| 234 | 0.05 | N/A |
| 235 | 0.028 | N/A |
| 236 | 0.016 | N/A |
| 240 | 0.081 | N/A |
| 245 | 0.16 | N/A |
| 251 | 0.048 | N/A |
| 252 | 0.13 | N/A |
| 254 | 0.18 | N/A |
| 256 | 0.065 | N/A |
| 267 | 0.83 | N/A |
| 274 | 1.44 | N/A |
| 289 | 0.018 | N/A |
| 292 | 0.0062 | N/A |
| 273 | 0.0062 | N/A |
| 304 | 0.062 | N/A |
| 305 | 0.0195 | N/A |
| 306 | 0.0192 | N/A |
| 303 | 0.064 | N/A |
| 309 | 0.026 | N/A |
| 310 | 0.14 | N/A |
| 325 | 0.15 | N/A |
| 316 | 0.017 | N/A |
| 317 | 0.014 | N/A |
| 342 | 0.052 | N/A |

SD: standard deviation. SDs and Means were calculated using the python programming language version 2.7.5 with numpy library 1.7.1. When a compound was tested multiple times, any number less than 5 nM or more than 100 μM was excluded from the standard deviation or EC$_{50}$ calculation. N/A: SD is not calculated for compounds with EC$_{50}$ less than 5 nM or having a single data point.

Example 350: Luciferase Assay

Figure 10:
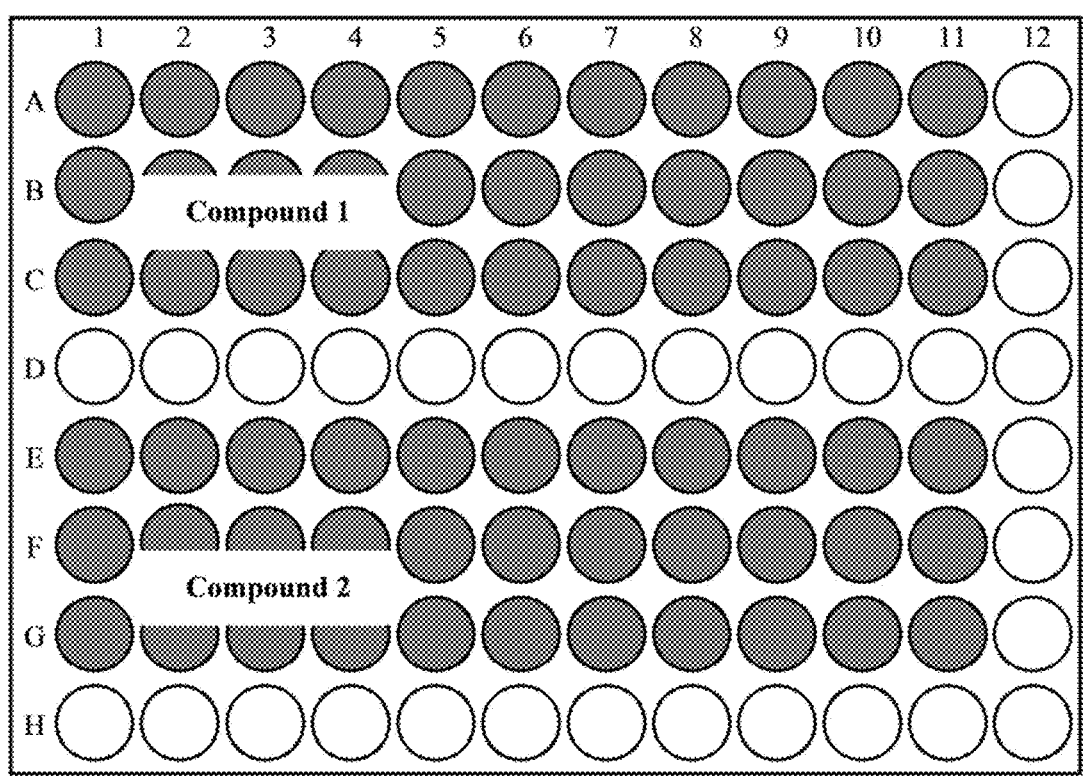
FIG. 10 depicts a 96-well plate layout of a luciferase assay.

The 786-O-Hif-Luc single clone cells were obtained by infecting 786-O cells (ATCC® CRL-1932™) with commercial lentivirus that delivers a luciferase gene driven by multiple HIF responsive elements (Cignal Lenti HIF Reporter (luc): CLS-007L, Qiagen) at Multiplicity of Infection (MOI) of 25 for 24 hours and then the cells were replenished with fresh medium (Dulbecco's Modified Eagle's Medium (DMEM, D5796, Sigma) and supplemented with 10% FBS (F6178, Sigma), 100 units penicillin and 100 μg streptomycin/mL (P4333, Sigma)) for another 24 hours. A pool of infected cells were then selected against 2 μg/mL of puromycin (P8833, Sigma) for 10 days followed by limited dilution to select single clones. The clones were tested for their response to HIF2 inhibitors and the ones that showed the biggest dynamic range (786-0-Hif-Luc) were expanded and used for the luciferase assay. For luciferase assay, about 7500 of 786-O-Hif-Luc cells in 90 μL growth medium were seeded into each well of a 96 well white opaque plate (08-771-26, Fisher scientific) a day before treatment with the layout presented in FIG. 10.

On treatment day, serial dilutions of 10× compound stocks were made in growth medium from 500×DMSO stocks, and 10 μL of the 10× stocks were added to each well to make final concentrations as follows (04): 20, 6.67, 2.22, 0.74, 0.25, 0.08, 0.027, 0.009, 0.003, 0.001, and 0. Each concentration was tested in triplicate. After about 24 hours, luciferase activity was determined using ONE-Glo Luciferase Assay Reagent (E6110, Promega) following the manufacturer's recommended procedure. EC$_{50}$ were calculated by using Dotmatics software.

Table 3 shows EC$_{50}$s of selected compounds in Luciferase Assay.

TABLE 3

EC$_{50}$s of Selected Compounds in Luciferase Assay

| Compound Number | Mean Luciferease EC$_{50}$ (μM) | SD |
|---|---|---|
| 1 | 0.11 | 0.01 |
| 2 | 0.07 | N/A |
| 3 | 0.96 | N/A |
| 5 | 0.42 | N/A |
| 6 | 0.075 | N/A |
| 7a | 1.0 | 0.09 |
| 8 | 0.017 | N/A |
| 9 | 0.009 | N/A |
| 11 | 0.016 | N/A |
| 15 | 0.007 | 0.001 |
| 16 | 3.2 | N/A |
| 17 | 0.18 | 0.06 |
| 18 | 2.67 | N/A |
| 20 | 1.91 | N/A |
| 21 | 1.54 | 0.84 |
| 22 | 1.29 | 0.76 |
| 25 | 0.018 | 0.03 |
| 26 | 0.068 | N/A |
| 27 | 0.16 | N/A |
| 31 | 2.7 | N/A |
| 32 | 1.9 | N/A |
| 33 | 2.9 | N/A |
| 34 | 0.52 | N/A |
| 35 | >20 | N/A |
| 38 | 0.39 | N/A |
| 39 | 0.6 | N/A |
| 40 | 1.2 | N/A |
| 41 | 0.40 | 0.08 |
| 42 | 0.45 | 0.036 |
| 43 | 0.79 | N/A |
| 46 | 8.1 | N/A |
| 50 | 1.6 | N/A |
| 52 | 1.0 | N/A |
| 53 | 3.3 | N/A |
| 54 | 0.35 | N/A |
| SS | 0.032 | N/A |
| 56 | 0.068 | N/A |
| 57 | 0.11 | N/A |
| 58 | 0.16 | N/A |
| 59 | 0.09 | 0.08 |
| 60 | 0.066 | N/A |
| 61 | 0.11 | N/A |
| 62 | 0.18 | N/A |
| 63 | 0.007 | 0.002 |
| 64 | 0.005 | N/A |

TABLE 3-continued

EC$_{50}$s of Selected Compounds in Luciferase Assay

| Compound Number | Mean Luciferease EC$_{50}$ (μM) | SD |
|---|---|---|
| 65 | 0.006 | N/A |
| 67 | 0.074 | N/A |
| 74 | 0.49 | N/A |
| 75 | 8.8 | N/A |
| 80 | 0.31 | 0.06 |
| 81 | 0.85 | N/A |
| 85 | 11.8 | N/A |
| 90 | 0.85 | 0.09 |
| 91 | 2.3 | N/A |
| 92 | 0.49 | N/A |
| 93 | 0.68 | N/A |
| 94 | 0.76 | N/A |
| 98 | 3.3 | 1.1 |
| 99 | 0.42 | N/A |
| 100 | 7.6 | 3.1 |
| 101 | 0.32 | N/A |
| 103 | 3.3 | 0.36 |
| 104 | 12.1 | N/A |
| 107 | 0.52 | N/A |
| 110 | 6.5 | N/A |
| 111 | 1.38 | 0.5 |
| 112 | 0.34 | N/A |
| 114 | 9.0 | N/A |
| 115 | 0.3 | N/A |
| 116 | 3.5 | N/A |
| 117 | 3.0 | N/A |
| 118 | 1.5 | N/A |
| 119 | 6.9 | N/A |
| 120 | 7.4 | N/A |
| 124 | 0.33 | N/A |
| 128 | 3.0 | N/A |
| 131 | 2.0 | N/A |
| 132 | 1.4 | N/A |
| 134 | 2.3 | N/A |
| 135 | 5.4 | N/A |
| 136 | 2.4 | N/A |
| 140 | 2.4 | N/A |
| 143 | 1.2 | N/A |
| 144 | 0.39 | N/A |
| 145 | 0.43 | N/A |
| 146 | 0.48 | 0.04 |
| 147 | 7.6 | 0.52 |
| 148 | 5.6 | N/A |
| 151 | 8.9 | N/A |
| 152 | 2.1 | N/A |
| 155 | 0.13 | N/A |
| 156 | 0.35 | N/A |
| 157 | 2.5 | N/A |
| 158 | 0.005 | N/A |
| 159 | 0.005 | 0.005 |
| 160 | 0.01 | N/A |
| 161 | 0.004 | N/A |
| 162 | 0.063 | N/A |
| 163 | 0.023 | 0.006 |
| 165 | 0.24 | N/A |
| 166 | 0.034 | N/A |
| 167 | 0.016 | N/A |
| 168 | 0.31 | N/A |
| 172 | 3.41 | N/A |
| 181 | 2.0 | N/A |
| 182 | 4.0 | N/A |
| 185 | 0.003 | N/A |
| 186 | 0.011 | N/A |
| 187 | 0.098 | N/A |
| 188 | 0.051 | N/A |
| 190 | 12.7 | N/A |
| 191 | 0.053 | N/A |
| 192 | 0.28 | N/A |
| 194 | 0.33 | N/A |
| 195 | 2.56 | N/A |
| 196 | 0.046 | N/A |
| 198 | 0.29 | N/A |
| 200 | 0.13 | N/A |
| 201 | 13.5 | N/A |
| 202 | 3.6 | N/A |
| 203 | 0.63 | 0.26 |
| 206 | 0.062 | N/A |
| 207 | 0.83 | N/A |
| 209 | 1.9 | N/A |
| 212 | 1.6 | N/A |
| 213 | 0.77 | N/A |
| 214 | 1.27 | N/A |
| 215 | 0.022 | N/A |
| 218 | 3.5 | N/A |
| 220 | 2.1 | N/A |
| 221 | 0.026 | N/A |
| 222 | 1.8 | N/A |
| 223 | 0.063 | N/A |
| 224 | 0.18 | N/A |
| 225 | 0.025 | N/A |
| 226 | 3.5 | 1.2 |
| 227 | 0.003 | N/A |
| 228 | 0.033 | N/A |
| 229 | 0.024 | N/A |
| 230 | 0.016 | N/A |
| 231 | 0.036 | 0.02 |
| 232 | 0.035 | N/A |
| 233 | 0.013 | N/A |
| 234 | 0.041 | N/A |
| 235 | 0.015 | N/A |
| 236 | 0.011 | N/A |
| 237 | 0.12 | N/A |
| 240 | 0.028 | N/A |
| 241 | 0.14 | N/A |
| 242 | 0.51 | N/A |
| 243 | 0.92 | N/A |
| 244 | 1.71 | N/A |
| 245 | 0.061 | N/A |
| 247 | 0.024 | N/A |
| 249 | 1.47 | N/A |
| 250 | 2.95 | N/A |
| 251 | 0.053 | N/A |
| 252 | 0.097 | N/A |
| 253 | 1.08 | N/A |
| 254 | 0.12 | N/A |
| 255 | 1.39 | N/A |
| 256 | 0.049 | N/A |
| 258 | 2.1 | N/A |
| 259 | 2.0 | N/A |
| 260 | 0.17 | N/A |
| 261 | 1.65 | 0.41 |
| 263 | 0.78 | N/A |
| 264 | 2.73 | N/A |
| 265 | 0.90 | N/A |
| 266 | 0.03 | N/A |
| 267 | 0.16 | N/A |
| 268 | 2.45 | N/A |
| 269 | 19.4 | N/A |
| 270 | 0.10 | N/A |
| 271 | 0.47 | N/A |
| 272 | 2.28 | N/A |
| 273 | 0.0046 | N/A |
| 274 | 0.19 | N/A |
| 275 | 0.26 | N/A |
| 276 | 0.15 | N/A |
| 277 | 0.074 | N/A |
| 279 | 5.9 | N/A |
| 285 | 0.1 | N/A |
| 286 | 0.14 | N/A |
| 287 | 0.65 | N/A |
| 289 | 0.0042 | N/A |
| 290 | 0.17 | 0.41 |
| 291 | 3.1 | N/A |
| 292 | 0.0031 | N/A |
| 293 | 0.78 | N/A |
| 294 | 1.0 | N/A |
| 295 | 0.39 | N/A |
| 296 | 1.3 | N/A |

TABLE 3-continued

EC$_{50}$s of Selected Compounds
in Luciferase Assay

| Compound Number | Mean Luciferease EC$_{50}$ (µM) | SD |
| --- | --- | --- |
| 300 | 2.8 | N/A |
| 301 | 2.1 | N/A |
| 302 | 0.11 | N/A |
| 303 | 0.035 | N/A |
| 304 | 0.022 | 0.41 |
| 305 | 0.013 | N/A |
| 306 | 0.03 | N/A |
| 307 | 1.7 | N/A |
| 308 | 0.69 | N/A |
| 309 | 0.009 | N/A |
| 310 | 0.11 | N/A |
| 312 | 0.63 | N/A |
| 313 | 1.1 | N/A |
| 314 | 0.15 | N/A |
| 315 | 0.11 | N/A |
| 316 | 0.012 | N/A |
| 317 | 0.012 | N/A |
| 324 | 0.48 | N/A |
| 325 | 0.49 | N/A |
| 334 | 0.22 | N/A |
| 336 | 0.067 | N/A |
| 338 | 0.0061 | N/A |
| 339 | 0.25 | N/A |
| 342 | 0.091 | N/A |

SD: standard deviation. SDs and Means were calculated using the python programming language version 2.7.5 with numpy library 1.7.1. When a compound was tested multiple times, any number less than 5 nM or more than 100 µM was excluded from the standard deviation or EC$_{50}$ calculation. N/A: SD is not calculated for compounds with EC$_{50}$ less than 5 nM or having a single data point.

Example 351: In Vivo PK/PD Study

PK/PD study for Compound 15: Compound 15 was formulated with 10% absolute ethanol, 30% PEG400, 60% water containing 0.5% methyl cellulose and 0.5% Tween80®. About 5×10$^6$ renal cell carcinoma 786-O tumor cells (ATCC® CRL-1932, VHL and HIF-1α null cell line) in PBS and Matrigel (1:1 in volume) were injected subcutaneously at the right flanks of SCID/Biege mice at 6-7 weeks of age for xenograft development. When the xenografts reached about 450 mm$^3$ in size, the tumor bearing mice were randomly divided into 4 groups (n=4). Plasma was collected prior to treatment by retro-orbital bleeding. The animals were treated with either vehicle or Compound 15 at indicated dose (10, 30, or 100 mg/kg) by oral gavage (three times at 12 hour intervals). All animals were sacrificed at 12 hours post last dose. Tumor, kidney, and plasma were collected from each animal. Total RNA was extracted from the tumors and kidneys. The mRNA levels of HIF-1α, HIF-2α and their respective target genes were determined by qRT-PCR (FIG. 1).

Figure 2:
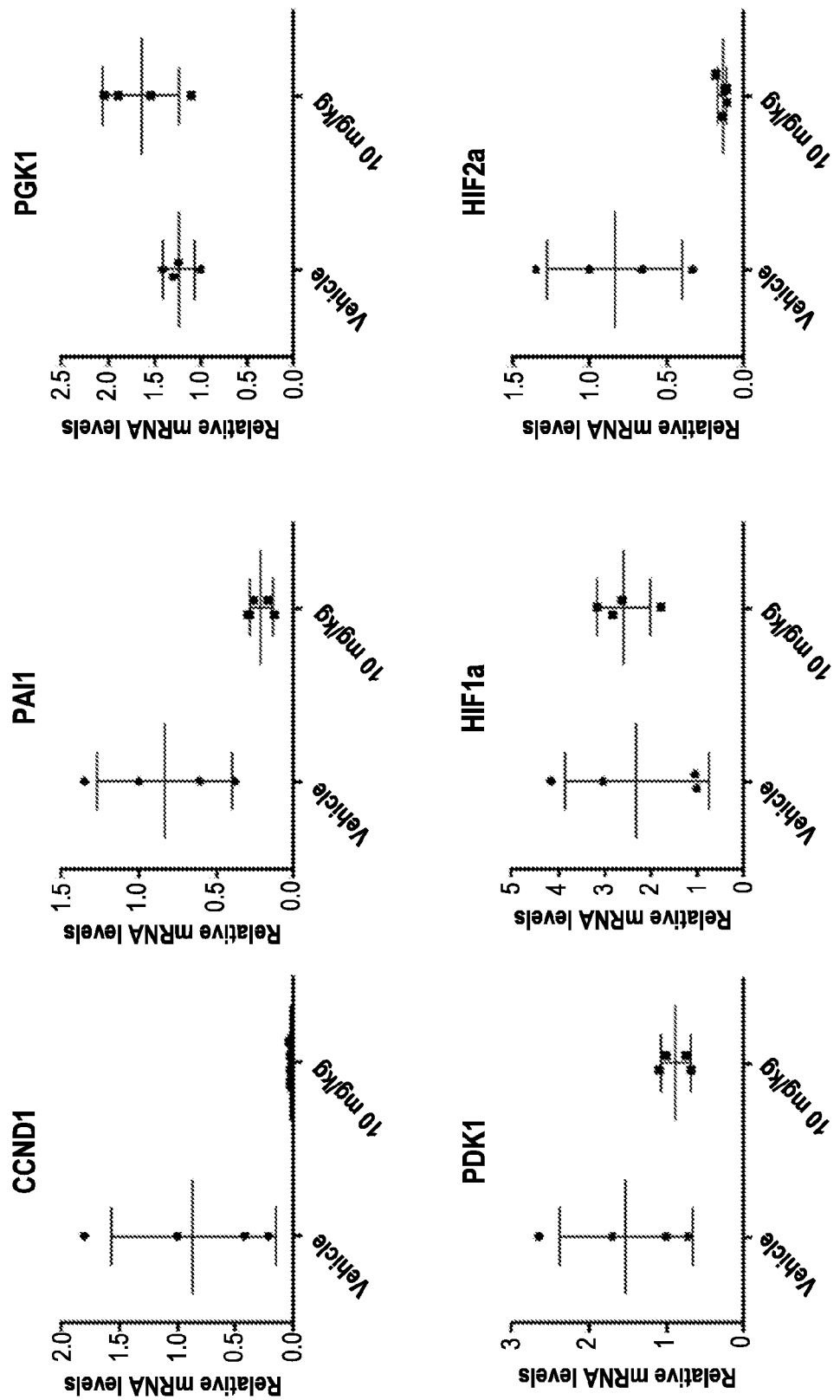
FIG. 2 shows treatment of renal cell carcinoma 786-O xenograft bearing mice at 0 mg/kg (denoted as "Vehicle") and 10 mg/kg of Compound 163 three times each at 12 hour intervals.

PK/PD study for Compound 163: The protocol for Compound 15 was followed. Animals were treated with either vehicle or Compound 163 at 10 mg/kg by oral gavage (three times at 12 hour intervals) and mRNA levels of target genes were determined by qRT-PCR (FIG. 2).

Figure 3:
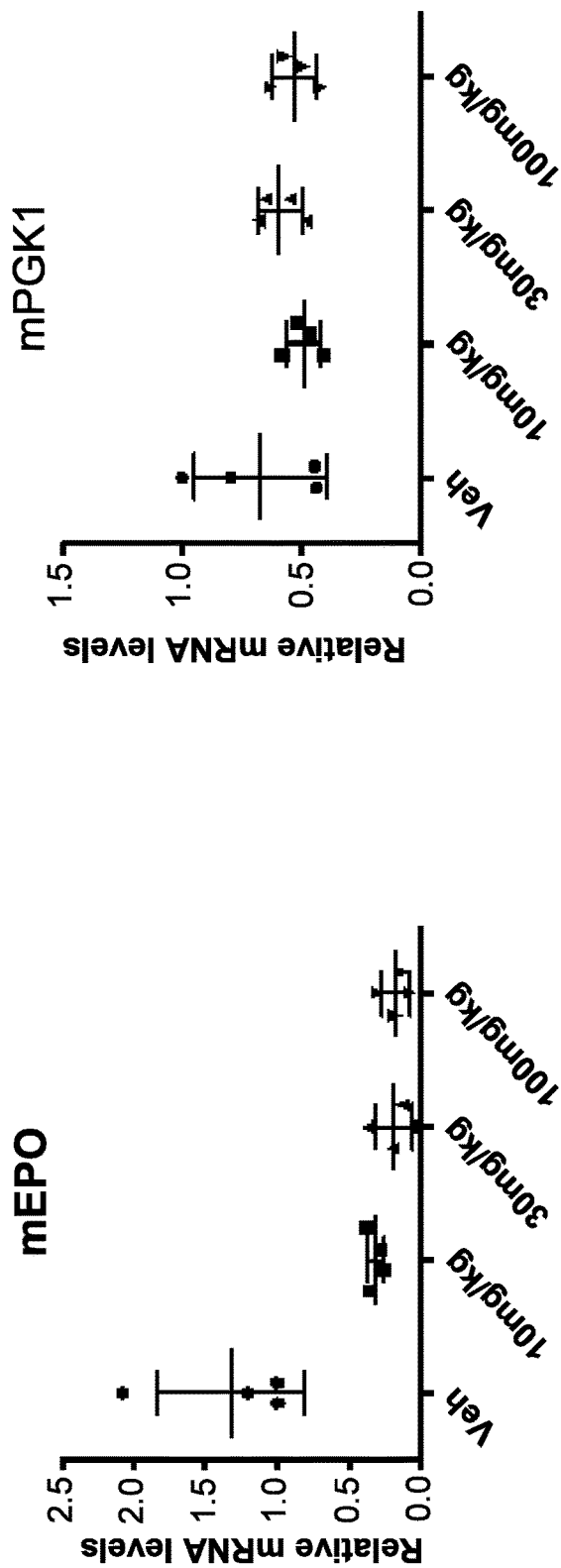
FIG. 3 shows treatment of 786-O xenograft bearing mice at 0 mg/kg (denoted as "Veh"), 10 mg/kg, 30 mg/kg, and 100 mg/kg of Compound 15 three times each at 12 hour intervals.

Tumor mRNA for HIF-2a, two HIF-2α specific target genes (PAI-1 and CCND1) and two genes regulated by both HIF-1α and HIF-2α (VEGFA and GLUT1) displayed a significant reduction in response to Compound 15 (FIG. 1) treatment. The levels of mRNA for two HIF-1α specific target genes (PGK1 and PDK1) exhibited no significant changes in response to Compound 15 treatment. Similarly, Compound 163 (FIG. 2) treatment led to a significant reduction of mRNA for PAI-1, CCND1 and HIF-2a while no significant change was observed for HIF-1α, PGK1 and PDK1. These data indicated that Compound 15 and Compound 163 selectively inhibited the expressions of genes regulated by HIF-2α in the 786-O xenograft. In mouse kidney, the level of EPO mRNA, a transcription product of a HIF-2α specifically regulated gene, was reduced with Compound 15 treatment, whereas mRNA level of PGK1, a HIF-1α targeted gene, remained unchanged (FIG. 3).

Figure 4:
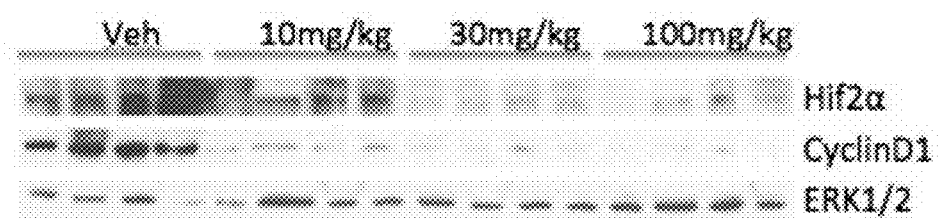
FIG. 4 shows treatment of 786-O xenograft bearing mice at 0 mg/kg (denoted as "Veh"), 10 mg/kg, 30 mg/kg, and 100 mg/kg of Compound 15 three times each at 12 hour intervals.

FIG. 4 shows protein levels for Compound 15 treated animals. Total protein was extracted from the tumors, and levels of HIF-2α and CyclinD1 proteins were determined by western-blot with ERK1/2 as protein loading control. The tumor samples were cut into small pieces and homogenized in RIPA buffer (50 mM Tris-HCl, pH 7.4, 150 mM NaCl, 1% Igepal CA-630, 0.25% sodium deoxycholate, and 0.1% SDS) supplemented with protease inhibitor cocktail (cOmplete, EDTA free, Roche Applied Science), and lysed in 4° C. with agitation for 10 minutes. The sample lysates were then subjected to centrifuge (Centrifuge 5424R, Eppendorf) at 13000 rpm for 10 minutes at 4° C. The clear supernatants were taken and protein concentration was measured by BCA protein assay (Thermo Scientific). About 80 µg of total protein per sample was loaded into 4-15% gradient gel (4-15% Criterion TGX precast gel, Bio-Rad Laboratories) and transferred to PVDF membrane (Bio-Rad Laboratories). The membrane was then blocked in 5% non-fat milk in TBST (Tris-based saline with 0.1% Tween 20®) for 1 hour at room temperature and then probed with primary antibody in either 5% non-fat milk in TBST (for HIF-2a, 1:500 dilution, NB100-122, Novus Biologicals) or in 5% BSA (Bovine Serum Albumin) in TBST (for total ERK1/2 (4695S) and cyclinD1 (2978S), both use 1:1000 dilution. Cell Signaling Technology, Inc) overnight at 4° C. The membrane was then washed three times with TBST (15, 5, and 5 minutes interval) and then probed with secondary antibody (Perox-AffiniPure Donkey Anti-Rabbit IgG (H+L), Jackson ImmunoResearch Laboratories, Inc) in 5% non-fat milk in TBST for 1 hour at room temperature. The membrane was then washed three times with TBST and incubated with Pierce ECL 2 Western Blotting Substrate (Thermo Scientific). Both HIF-2α and CyclinD1 protein levels were reduced by Compound 15 treatment in a dose dependent manner.

Figure 5:
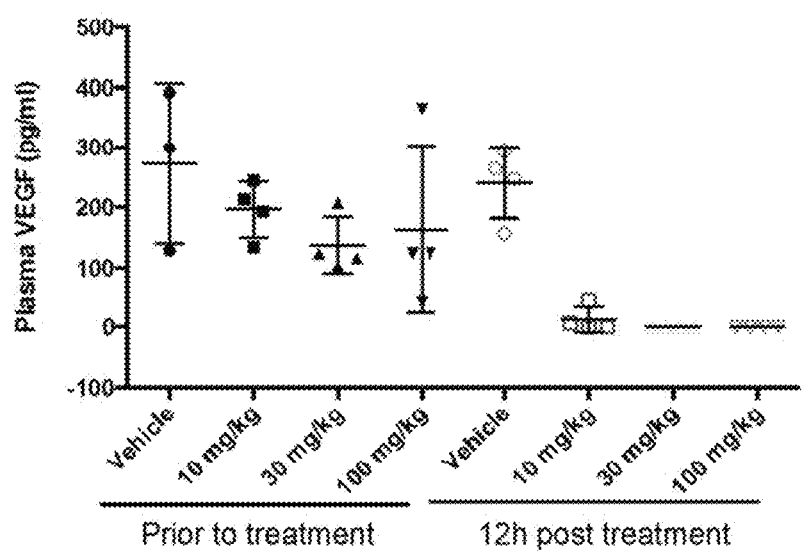
FIG. 5 shows human VEGF levels of 786-O xenograft bearing mice before (denoted as "Prior to treatment") and after treatment (denoted as "12 h post treatment") at 0 mg/kg (denoted as "Vehicle"), 10 mg/kg, 30 mg/kg, and 100 mg/kg of Compound 15 three times each at 12 hour intervals.
Figure 6:
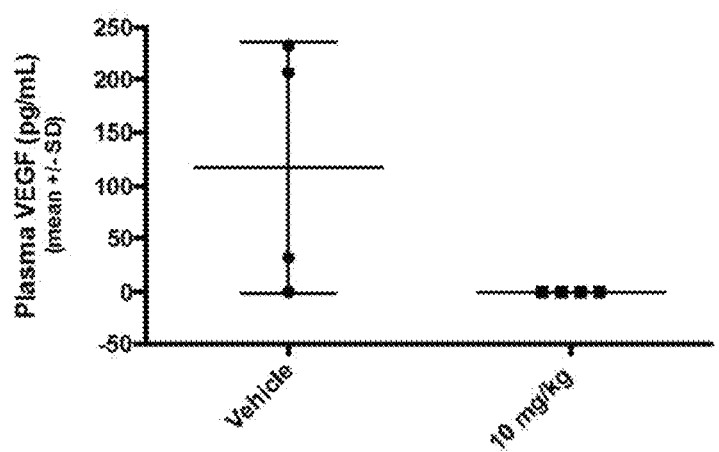
FIG. 6 shows treatment of 786-O xenograft bearing mice at 0 mg/kg (denoted as "Vehicle") and 10 mg/kg of Compound 163 three times each at 12 hour intervals.

FIG. 5 and FIG. 6 showed the plasma level of human VEGFA for vehicle, Compound 15 or Compound 163 treated animals determined by ELISA assay. Both Compound 15 (FIG. 5) and Compound 163 (FIG. 6) treatment led to a significant reduction of human VEGFA in the plasma of 786-O tumor-bearing mice.

Example 352: In Vivo Efficacy Study

Efficacy study for Compound 15: Compound 15 and Sutent® were formulated with 10% absolute ethanol, 30% PEG400, 60% water containing 0.5% methyl cellulose and 0.5% Tween 80®. About 5×10$^6$ 786-O renal cell carcinoma cells (ATCC® CRL-1932™) in PBS and Matrigel (1:1 in volume) were inoculated subcutaneously in the right flank for SCID/Biege mice at 6-7 weeks of age for tumor development. When the xenografts reached about 200 mm$^3$ in size, the tumor bearing mice were randomly grouped into six groups (n=8) and treated by oral gavage with vehicle (BID), Compound 15 (3, 10, 30 and 100 mg/kg, BID), and Sutent (40 mg/kg, QD), respectively, for 20 days. Tumor sizes were measured twice weekly in two dimensions using a caliper and the volume were expressed in mm$^3$ using the formula V=0.5×a×b$^2$ wherein a and b were the long and short diameters of the tumor, respectively.

Efficacy study for Compound 163: The same protocol for Compound 15 was followed except all animals were treated with either Compound 163 (10 mg/kg BID) or vehicle for 28 days.

Figure 7:
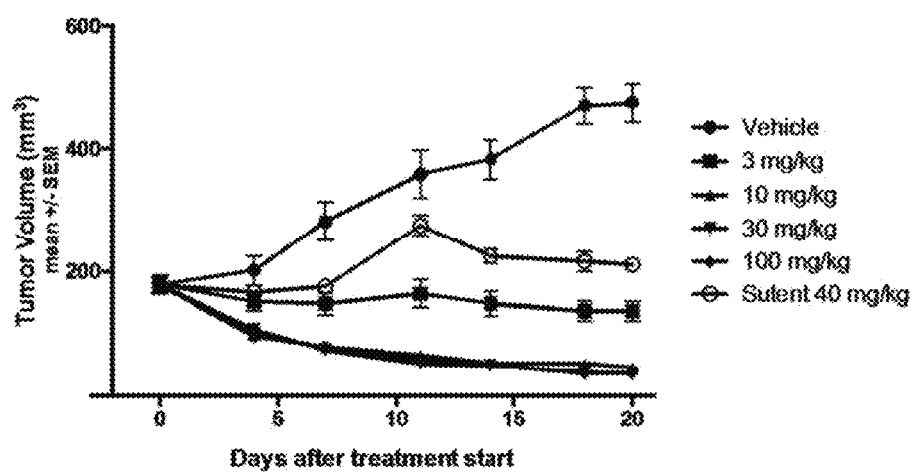
FIG. 7 shows treatment of 786-O xenograft bearing mice at 0 mg/kg (denoted as "Vehicle"), 3 mg/kg, 10 mg/kg, 30 mg/kg, and 100 mg/kg of Compound 15 BID and 40 mg/kg of sutent QD, respectively, for 20 days.
Figure 8:
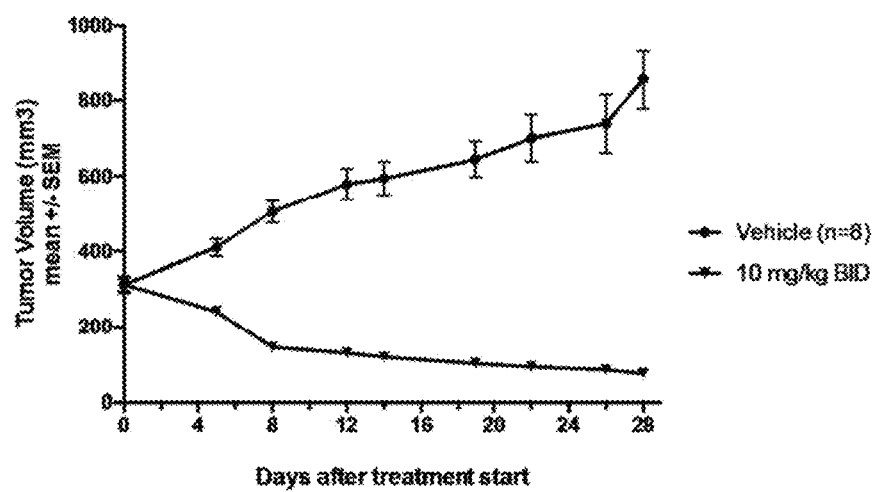
FIG. 8 shows that Compound 163 treatment of 786-O xenograft bearing mice at 0 mg/kg (denoted as "Vehicle") and 10 mg/kg BID of Compound 163 BID for 28 days.

The efficacy studies showed that Compound 15 (FIG. 7 and Table 4) and Compound 163 (FIG. 8 and Table 5) treatment led to a statistically significant reduction of tumor size for all treatment groups in this renal cell carcinoma 786-O xenograft model (all data displayed as Mean with the standard error of the mean (SEM). The t-Test was used for data analysis).

TABLE 4

Compound 15 786-O Xenograft Study: Tumor sizes after 20 days of dosing

| Treatment groups | Vehicle | Compound 15 | | | | Sutent 40 mg/kg QD |
|---|---|---|---|---|---|---|
| | | 3 mg/kg BID | 10 mg/kg BID | 30 mg/kg BID | 100 mg/kg BID | |
| Tumor size (mm$^3$) Mean ± SEM | 475.72 ± 31.85 | 136.29 ± 15.77 | 45.36 ± 2.22 | 35.63 ± 2.26 | 37.11 ± .6 | 211.59 ± 10.36 |

TABLE 5

Compound 163 786-O Xenograft Study: Tumor sizes after 28 days of dosing

| Treatment groups | Vehicle | Compound 163 (10 mg/kg BID) |
|---|---|---|
| Tumor size (mm$^3$) Mean ± SEM | 855.7 ± 78.43 | 74.66 ± 7.08 |

What is claimed is:

1. A compound of Formula Vd:

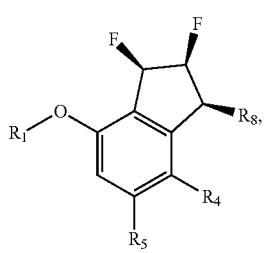

Vd or a pharmaceutically acceptable salt thereof, wherein:
 $R_1$ is aryl or heteroaryl;
 $R_4$ is halo, cyano, alkyl, sulfonamide, sulfinyl, sulfonyl or sulfoximinyl;
 $R_5$ is hydrogen, halo or alkyl; and
 $R_8$ is hydroxy, alkylamino, alkoxy or amino.

2. The compound of claim 1, wherein $R_1$ is phenyl or pyridyl.

3. The compound of claim 2, wherein said phenyl or pyridyl is substituted with at least one substituent selected from the group consisting of halo, C1-C4 alkyl, C1-C4 alkoxy, and cyano.

4. The compound of claim 1, wherein $R_4$ is cyano, fluoroalkyl, sulfonamide, sulfinyl, sulfonyl or sulfoximinyl.

5. The compound of claim 4, wherein $R_4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$, and —S(=O)(=N—CN)CF$_3$.

6. The compound of claim 1, wherein $R_5$ is hydrogen.

7. The compound of claim 6, wherein $R_1$ is phenyl, monocyclic heteroaryl or bicyclic heteroaryl.

8. The compound of claim 7, wherein $R_4$ is cyano, fluoroalkyl, sulfonamide, sulfinyl, sulfonyl or sulfoximinyl.

9. The compound of claim 8, wherein $R_4$ is selected from the group consisting of —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=N—CN)CH$_3$, —S(=O)(=N—CN)CH$_2$F, —S(=O)(=N—CN)CHF$_2$, and —S(=O)(=N—CN)CF$_3$.

10. The compound of claim 8, wherein $R_8$ is hydroxy or amino.

11. The compound of claim 1, wherein $R_8$ is hydroxy or amino.

12. The compound of claim 11, wherein $R_8$ is hydroxy.

13. The compound of claim 1, wherein the enantiomeric excess of said compound is at least 80%.

14. A compound selected from the group consisting of:

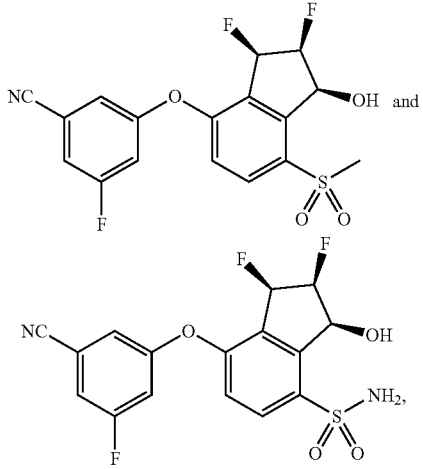

or a pharmaceutically acceptable salt thereof.

15. A pharmaceutical composition comprising a therapeutically effective amount of a compound or pharmaceutically acceptable salt according to claim 1 and a pharmaceutically acceptable carrier.

16. A method of treating von Hippel-Lindau (VHL) disease, comprising administering to a subject in need thereof an effective amount of the compound or pharmaceutically acceptable salt according to claim 1.

17. The method of claim 16, wherein said subject also suffers from a hemangioblastoma, a pheochromocytoma, a pancreatic neuroendocrine tumor or a renal cell carcinoma.

18. The method of claim 17, wherein said subject suffers from renal cell carcinoma.

19. The method of claim 18, wherein said renal cell carcinoma is clear cell renal cell carcinoma.

20. A method of treating renal cell carcinoma in a subject, comprising administering to said subject a therapeutically effective amount of the compound or pharmaceutically acceptable salt according to claim 1.

* * * * *